(12) United States Patent
Ahrens et al.

(10) Patent No.: US 11,390,589 B2
(45) Date of Patent: Jul. 19, 2022

(54) HERBICIDALLY ACTIVE SUBSTITUTED PHENYLPYRIMIDINES

(71) Applicant: Bayer Aktiengesellschaft, Leverkusen (DE)

(72) Inventors: Hartmut Ahrens, Langen (DE); Birgit Kuhn, Kelkheim (DE); Stefan Schnatterer, Hattersheim (DE); Dirk Schmutzler, Hattersheim (DE); Hansjoerg Dietrich, Liederbach am Taunus (DE); Anu Bheemaiah Machettira, Frankfurt am Main (DE); Elisabeth Asmus, Hoesbach (DE); Elmar Gatzweiler, Bad Nauheim (DE)

(73) Assignee: BAYER Aktiengesellschaft, Leverkusen (DE)

( * ) Notice: Subject to any disclaimer, the term of this patent is extended or adjusted under 35 U.S.C. 154(b) by 0 days.

(21) Appl. No.: 15/734,511

(22) PCT Filed: May 29, 2019

(86) PCT No.: PCT/EP2019/064006
§ 371 (c)(1),
(2) Date: Dec. 2, 2020

(87) PCT Pub. No.: WO2019/233862
PCT Pub. Date: Dec. 12, 2019

(65) Prior Publication Data
US 2021/0317089 A1 Oct. 14, 2021

(30) Foreign Application Priority Data
Jun. 4, 2018 (EP) ..................... 18175675

(51) Int. Cl.
*C07D 239/26* (2006.01)
*A01N 43/54* (2006.01)

(52) U.S. Cl.
CPC ........... *C07D 239/26* (2013.01); *A01N 43/54* (2013.01)

(58) Field of Classification Search
None
See application file for complete search history.

(56) References Cited

FOREIGN PATENT DOCUMENTS

| WO | 2016120355 A2 | 8/2016 |
|---|---|---|
| WO | 2018019555 A1 | 2/2018 |

OTHER PUBLICATIONS

PCT International Search Report for PCT/EP2019/064006, dated Jul. 23, 2019.

*Primary Examiner* — Alton N Pryor
(74) *Attorney, Agent, or Firm* — McBee Moore & Vanik IP, LLC

(57) ABSTRACT

The invention relates to substituted phenylpyrimidines of general formula (I), to their agrochemically acceptable salts (I), and to the use thereof in the field of plant protection.

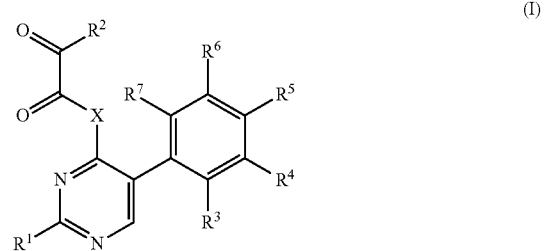

(I)

11 Claims, No Drawings

HERBICIDALLY ACTIVE SUBSTITUTED PHENYLPYRIMIDINES

CROSS-REFERENCE TO RELATED APPLICATIONS

This application is the National Stage entry of International Application No. PCT/EP2019/064006, filed May 29, 2019, which claims priority to European Patent Application No. 18175675.0, filed Jun. 4, 2018.

BACKGROUND

Field

The invention relates to the technical field of the herbicides, especially that of the herbicides for selective control of weeds and weed grasses in crops of useful plants.

Specifically, it relates to substituted phenylpyrimidines, to processes for their preparation and to their use as herbicides.

Description of Related Art

WO 2016/120355 describes substituted phenylpyrimidines bearing a directly bonded carbonyl group at the 4 position of the pyrimidine. WO 2018/019555 describes substituted phenylpyrimidinecarboxylic acid derivatives having an extended side chain in the 4 position. The herbicidal activity of these known compounds, in particular at low application rates, and/or their compatibility with crop plants remain in need of improvement.

For the reasons stated, there is still a need for potent herbicides and/or plant growth regulators for the selective use in crop plants or the use on non-crop land, where these active ingredients preferably should have further advantageous properties in application, for example an improved compatibility with crop plants.

SUMMARY

Accordingly, it is an object of the present invention to provide compounds having herbicidal activity (herbicides) which are highly effective against economically important harmful plants even at relatively low application rates and can be used selectively in crop plants, preferably with good activity against harmful plants, and at the same time preferably have good compatibility with crop plants. Preferably, these herbicidal compounds should be particularly effective and efficient against a broad spectrum of weed grasses and preferably also have good activity against a large number of weeds.

It has now been found that the compounds of the formula (I) below and their salts have excellent herbicidal activity against a broad spectrum of economically important mono- and dicotyledonous annual harmful plants.

The present invention therefore provides compounds of the general formula (I)

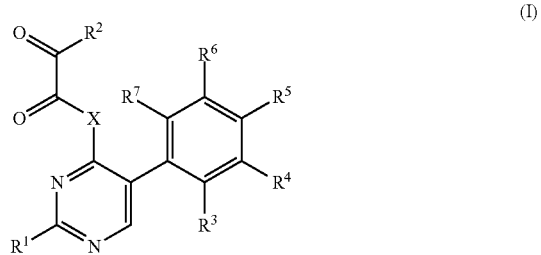

(I)

and agrochemically acceptable salts thereof, in which the symbols and indices have the following meanings:

X represents $C(R^{13})(R^{14})$ $R^1$ represents $(C_3-C_6)$-cycloalkyl, $(C_3-C_6)$-cycloalkenyl or heterocyclyl, where these three aforementioned radicals are each substituted by s radicals from the group consisting of halogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkyl-$(C_1-C_6)$-alkyl, halo-$(C_3-C_6)$-cycloalkenyl-$(C_1-C_6)$-alkyl, $R^8(O)C$, $R^8O(O)C$, $(R^8)_2N(O)C$, $R^8O$, $(R^8)_2N$, $R^9(O)_nS$, phenyl, heteroaryl, heterocyclyl, phenyl-$(C_1-C_6)$-alkyl, heteroaryl-$(C_1-C_6)$-alkyl and heterocyclyl-$(C_1-C_6)$-alkyl, where the six latter radicals are substituted by m radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where cycloalkyl, cycloalkenyl and heterocyclyl each independently bear n oxo groups, $R^2$ represents hydroxy, $(C_1-C_6)$-alkoxy, $(C_2-C_6)$-alkenyloxy, $(C_2-C_6)$-alkynyloxy, $(C_1-C_6)$-haloalkoxy, $(C_2-C_6)$-haloalkenyloxy, $(C_2-C_6)$-haloalkynyloxy, where the 6 latter radicals are each substituted by s radicals from the group consisting of cyano, $(C_3-C_6)$-cycloalkyl, $(C_3-C_6)$-cycloalkenyl, halo-$(C_3-C_6)$-cycloalkyl, halo-$(C_3-C_6)$-cycloalkenyl, $R^8(O)C$, $R^8(R^8ON=)C$, $R^8O(O)C$, $R^9S(O)C$, $(R^8)_2N(O)C$, $R^8(R^8O)N(O)C$, $(R^8)_2N(R^8)N(O)C$, $R^8(O)C(R^8)N(O)C$, $R^9O(O)C(R^8)N(O)C$, $(R^8)_2N(O)C(R^8)N(O)C$, $R^9(O)_2S(R^8)N(O)C$, $R^8O(O)_2S(R^8)N(O)C$, $(R^8)_2N(O)_2S(R^8)N(O)C$, $R^8O$, $R^8(O)CO$, $R^9(O)_2SO$, $R^9O(O)CO$, $(R^8)_2N(O)CO$, $(R^8)_2N$, $R^8(O)C(R^8)N$, $R^9(O)_2S(R^8)N$, $R^9O(O)C(R^8)N$, $(R^8)_2N(O)C(R^8)N$, $R^8O(O)_2S(R^8)N$, $(R^8)_2N(O)_2S(R^8)N$, $R^9(O)_nS$, $R^8O(O)_2S$, $(R^8)_2N(O)_2S$, $R^8(O)C(R^8)N(O)_2S$, $R^9O(O)C(R^8)N(O)_2S$, $(R^8)_2N(O)C(R^8)N(O)_2S$, $R^{11}_3Si$, $(R^{12}O)_2(O)P$, phenyl, heteroaryl and heterocyclyl, where the three latter radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl, or $R^2$ represents $(C_3-C_6)$-cycloalkoxy, $(C_3-C_6)$-cycloalkenyloxy, phenyloxy, heteroaryloxy or heterocyclyloxy, where these five aforementioned radicals are each substituted by s radicals from the group consisting of halogen, cyano, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, halo-$(C_3-C_6)$-cycloalkyl, halo-$(C_3-C_6)$-cycloalkenyl, $R^8(O)C$, $R^8(R^8ON=)C$, $R^8O(O)C$, $R^9S(O)C$, $(R^8)_2N(O)C$, $R^8(R^8O)N(O)C$, $(R^8)_2N(R^8)N(O)C$, $R^8(O)C(R^8)N(O)C$, $R^9O(O)C(R^8)N(O)C$, $(R^8)_2N(O)C(R^8)N(O)C$, $R^9(O)_2S(R^8)N(O)C$, $R^8O(O)_2S(R^8)N(O)C$, $(R^8)_2N(O)_2S(R^8)N(O)C$, $R^8O$, $R^8(O)CO$, $R^9(O)_2SO$, $R^9O(O)CO$, $(R^8)_2N(O)CO$, $(R^8)_2N$, $R^8(O)C(R^8)N$, $R^9(O)_2S(R^8)N$, $R^9O(O)C(R^8)N$, $(R^8)_2N(O)C(R^8)N$, $R^8O(O)_2S(R^8)N$, $(R^8)_2N(O)_2S(R^8)N$, $R^9(O)_nS$, $R^8O(O)_2S$, $(R^8)_2N(O)_2S$, $R^8(O)C(R^8)N(O)_2S$, $R^9O(O)C(R^8)N(O)_2S$, $(R^8)_2N(O)C(R^8)N(O)_2S$, $R^{11}_3Si$, $(R^{12}O)_2(O)P$, phenyl, heteroaryl and heterocyclyl, where the three latter radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl, and where $(C_3-C_6)$- cycloalkyl, $(C_3-C_6)$-cycloalkenyl, heterocyclyl, $(C_3-C_6)$-cycloalkoxy, $(C_3-C_6)$-cycloalkenyloxy and heterocyclyloxy each independently bear n oxo groups, or $R^2$ represents $R^8(O)CO$, $R^9(O)_2SO$ or $R^{15}R^{16}C=N-O$ or $(R^8)_2N-O$, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})(R^{18})N(R^{19})N$, or $R^2$ represents $R^{17}R^{18}C=N-(R^{19})N-$ $R^3$, $R^4$, $R^5$, $R^6$ and $R^7$ each independently represent hydrogen, nitro, halogen, cyano, thiocyano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^8(O)C$, $R^8(R^8ON=)C$, $R^8O(O)C$, $(R^8)_2N(O)C$, $R^8(R^8O)N(O)C$, $(R^8)_2N(R^8)N(O)C$, $R^8O(O)C(R^8)N(O)C$, $R^9O(O)C(R^8)N(O)C$, $(R^8)_2N(O)C(R^8)N(O)C$, $R^9(O)_2S(R^8)N(O)C$, $R^8O(O)_2S(R^8)N(O)C$, $(R^8)_2N(O)_2S(R^8)N(O)C$, $R^8O$, $R^8(O)CO$, $R^9(O)_2SO$, $R^9O(O)CO$, $(R^8)_2N(O)CO$, $(R^8)_2N$, $R^8(O)C(R^8)N$, $R^9(O)_2S(R^8)N$, $R^9O(O)C(R^8)N$, $(R^8)_2N(O)C(R^8)N$, $R^8O(O)_2S(R^8)N$, $(R^8)_2N(O)_2S(R^8)N$, $R^9(O)_nS$, $R^8O(O)_2S$, $(R^8)_2N(O)_2S$, $R^8(O)C(R^8)N(O)_2S$, $R^9O(O)C(R^8)N(O)_2S$, $(R^8)_2N(O)C(R^8)N(O)_2S$, $(R^{12}O)_2(O)P$, $R^8(O)C-(C_1-C_6)$-alkyl, $R^8O(O)C-(C_1-C_6)$-alkyl, $(R^8)_2N(O)C-(C_1-C_6)$-alkyl, $(R^8O)(R^8)N(O)C-(C_1-C_6)$-alkyl, $(R^8)_2N(R^8)N(O)C-(C_1-C_6)$-alkyl, $R^8(O)C(R^8)N(O)C-(C_1-C_6)$-alkyl, $R^9O(O)C(R^8)N(O)C-(C_1-C_6)$-alkyl, $(R^8)_2N(O)C(R^8)N(O)C-(C_1-C_6)$-alkyl, $R^9(O)_2S(R^8)N(O)C-(C_1-C_6)$-alkyl, $R^8O(O)_2S(R^8)N(O)C-(C_1-C_6)$-alkyl, $(R^8)_2N(O)_2S(R^8)N(O)C-(C_1-C_6)$-alkyl, $NC-(C_1-C_6)$-alkyl, $R^8O-(C_1-C_6)$-alkyl, $R^8(O)CO-(C_1-C_6)$-alkyl, $R^9(O)_2SO-(C_1-C_6)$-alkyl, $R^9O(O)CO-(C_1-C_6)$-alkyl, $(R^8)_2N(O)CO-(C_1-C_6)$-alkyl, $(R^8)_2N-(C_1-C_6)$-alkyl, $R^8(O)C(R^8)N-(C_1-C_6)$-alkyl, $R^9(O)_2S(R^8)N-(C_1-C_6)$-alkyl, $R^9O(O)C(R^8)N-(C_1-C_6)$-alkyl, $(R^8)_2N(O)C(R^8)N-(C_1-C_6)$-alkyl, $R^8O(O)_2S(R^8)N-(C_1-C_6)$-alkyl, $(R^8)_2N(O)_2S(R^8)N-(C_1-C_6)$-alkyl, $R^9(O)_nS-(C_1-C_6)$-alkyl, $R^8O(O)_2S-(C_1-C_6)$-alkyl, $(R^8)_2N(O)_2S-(C_1-C_6)$-alkyl, $R^8(O)C(R^8)N(O)_2S-(C_1-C_6)$-alkyl, $R^9O(O)C(R^8)N(O)_2S-(C_1-C_6)$-alkyl, $(R^8)_2N(O)C(R^8)N(O)_2S-(C_1-C_6)$-alkyl, $(R^{12}O)_2(O)P-(C_1-C_6)$-alkyl, phenyl, heteroaryl, heterocyclyl, phenyl-$(C_1-C_6)$-alkyl, heteroaryl-$(C_1-C_6)$-alkyl or heterocyclyl-$(C_1-C_6)$-alkyl, where the six latter radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $R^8O(O)C$, $(R^8)_2N(O)C$, $R^8O$, $(R^8)_2N$, $R^9(O)_nS$, $R^8O(O)_2S$, $(R^8)_2N(O)_2S$ and $R^8O-(C_1-C_6)$-alkyl, and where cycloalkyl and heterocyclyl each independently bear n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, $(C_1-C_6)$-alkyl-O-$(C_1-C_6)$-alkyl, $(C_1-C_6)$-alkyl-O-$(C_1-C_6)$-alkyl-O-$(C_1-C_6)$-alkyl, $(C_3-C_6)$-cycloalkyl-$(C_1-C_6)$-alkyl-O-$(C_1-C_6)$-alkyl, $(C_3-C_6)$-cycloalkenyl-$(C_1-C_6)$-alkyl-O-$(C_1-C_6)$-alkyl or $(C_1-C_6)$-alkylthio-$(C_1-C_6)$-alkyl, where the twelve latter radicals bear s halogen atoms, or $R^8$ represents phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O-$(C_1-C_6)$-alkyl, heteroaryl-O-$(C_1-C_6)$-alkyl, heterocyclyl-O-$(C_1-C_6)$-alkyl, phenyl-N$(R^{10})$-$(C_1-C_6)$-alkyl, heteroaryl-N$(R^{10})$-$(C_1-C_6)$-alkyl, heterocyclyl-N$(R^{10})$-$(C_1-C_6)$-alkyl, phenyl-S$(O)_n$-$(C_1-C_6)$-alkyl, heteroaryl-S$(O)_n$-$(C_1-C_6)$-alkyl or heterocyclyl-S$(O)_n$-$(C_1-C_6)$-alkyl, where the radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl, and where $(C_3-C_6)$-cycloalkyl, $(C_3-C_6)$-cycloalkenyl and heterocyclyl each independently bear n oxo groups, or the $R^8$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl and oxo, $R^9$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, $(C_1-C_6)$-alkyl-O-$(C_1-C_6)$-alkyl, $(C_1-C_6)$-alkyl-O-$(C_1-C_6)$-alkyl-O-$(C_1-C_6)$-alkyl, $(C_3-C_6)$-cycloalkyl-$(C_1-C_6)$-alkyl-O-$(C_1-C_6)$-alkyl, $(C_3-C_6)$-cycloalkenyl-$(C_1-C_6)$-alkyl-O-$(C_1-C_6)$-alkyl or $(C_1-C_6)$-alkylthio-$(C_1-C_6)$-alkyl, where the radicals bear s halogen atoms, or $R^9$ represents phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O-$(C_1-C_6)$-alkyl, heteroaryl-O-$(C_1-C_6)$-alkyl, heterocyclyl-O-$(C_1-C_6)$-alkyl, phenyl-N$(R^{10})$-$(C_1-C_6)$-alkyl, heteroaryl-N$(R^{10})$-$(C_1-C_6)$-alkyl, heterocyclyl-N$(R^{10})$-$(C_1-C_6)$-alkyl, phenyl-S$(O)_n$-$(C_1-C_6)$-alkyl, heteroaryl-S$(O)_n$-$(C_1-C_6)$-alkyl or heterocyclyl-S$(O)_n$-$(C_1-C_6)$-alkyl, where the radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl, and where $(C_3-C_6)$-cycloalkyl, $(C_3-C_6)$-cycloalkenyl and heterocyclyl each independently bear n oxo groups, $R^{10}$ represents hydrogen, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{11}$ represents $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{12}$ represents hydrogen or $(C_1-C_4)$-alkyl, $R^{13}$ and $R^{14}$ each independently represent hydrogen, $(C_1-C_6)$-alkyl, hydroxy, $(C_1-C_6)$-alkoxy, $(R^8)_2N$, halo-$(C_1-C_6)$-alkoxy, halogen, halo-$(C_1-C_6)$-alkyl, cyano, $R^8O(O)C$ or $(R^8)_2N(O)C$, or
 $R^{11}$ and $R^{14}$ together with the carbon atom to which they are bonded form a $(C_3$-$C_8)$-cycloalkyl group,
 $R^{15}$ and $R^{16}$ each independently represent $(C_1$-$C_6)$-alkyl, phenyl, $(C_3$-$C_6)$-cycloalkyl, heteroaryl or heterocyclyl,
 $R^{17}$ and $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$,
 or the ($R^{17}$ and $R^{18}$) or ($R^{17}$ and $R^{19}$) radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, thiocyano, $(C_1$-$C_6)$-alkyl, halo-$(C_1$-$C_6)$-alkyl, $(C_3$-$C_6)$-cycloalkyl, $(C_3$-$C_6)$-cycloalkenyl, $R^{10}O(O)C$, $(R^{10})_2N(O)C$, $R^{10}O$, $(R^{10})_2N$, $R''(O)S$, $R^{10}O(O)_2S$, $(R^{10})_2N(O)_2S$ and $R^{10}O$—$(C_1$-$C_6)$-alkyl and oxo,
 m represents 0, 1, 2, 3, 4 or 5,
 n represents 0, 1 or 2,
 s represents 0, 1, 2, 3, 4, 5, 6, 7, 8, 9, 10 or 11.

DETAILED DESCRIPTION OF A PREFERRED EMBODIMENT

The compounds of the formula (I) are capable of forming salts. Salts may be formed by the action of a base on those compounds of the formula (I) that bear an acidic hydrogen atom. Suitable bases are, for example, organic amines such as trialkylamines, morpholine, piperidine or pyridine, and the hydroxides, carbonates and bicarbonates of ammonium, alkali metals or alkaline earth metals, especially sodium hydroxide, potassium hydroxide, sodium carbonate, potassium carbonate, sodium bicarbonate and potassium bicarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula [NRR'R''R''']$^+$ in which R to R''' each independently of one another represent an organic radical, in particular alkyl, aryl, aralkyl or alkylaryl. Also suitable are alkylsulfonium and alkylsulfoxonium salts, such as $(C_1$-$C_4)$-trialkylsulfonium and $(C_1$-$C_4)$-trialkylsulfoxonium salts.

The compounds of the formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts comprise the conjugated base of the acid as the anion.

Suitable substituents present in deprotonated form, such as, for example, sulfonic acids or carboxylic acids, may form inner salts with groups which for their part can be protonated, such as amino groups.

Alkyl means saturated straight-chain or branched hydrocarbyl radicals having the number of carbon atoms specified in each case, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkenyl represents unsaturated straight-chain or branched hydrocarbyl radicals having the number of carbon atoms stated in each case and one double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbyl radicals having the number of carbon atoms specified in each case and one triple bond in any position, e.g. $C_2$-$C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Cycloalkyl means a carbocyclic saturated ring system having preferably 3-8 ring carbon atoms, for example cyclopropyl, cyclobutyl, cyclopentyl or cyclohexyl. In the case of optionally substituted cycloalkyl, cyclic systems with substituents are included, also including substituents with a double bond on the cycloalkyl radical, for example an alkylidene group such as methylidene.

In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of substituted cycloalkyl, spirocyclic aliphatic systems are also included, for example spiro[2.2]pent-1-yl, spiro[2.3]hex-1-yl and spiro[2.3]hex-4-yl, 3-spiro[2.3]hex-5-yl.

Cycloalkenyl means a carbocyclic, nonaromatic, partially unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

Alkoxy means saturated straight-chain or branched alkoxy radicals having the number of carbon atoms specified in each case, for example $C_1$-$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-1,2-difluoroethoxy, 2,2-dichloro-2-fluoroethoxy, 2,2,2-trichloroethoxy, pentafluoroethoxy and 1,1,1-trifluoroprop-2-oxy.

Aryl means phenyl which is optionally substituted by 0-5 radicals from the group consisting of fluorine, chlorine, bromine, iodine, cyano, hydroxy, ($C_1$-$C_3$)-alkyl, ($C_1$-$C_3$)-alkoxy, ($C_3$-$C_4$)-cycloalkyl, ($C_2$-$C_3$)-alkenyl or ($C_2$-$C_3$)-alkynyl.

A heterocyclic radical (heterocyclyl) contains at least one heterocyclic ring (=carbocyclic ring in which at least one carbon atom has been replaced by a heteroatom, preferably by a heteroatom from the group of N, O, S, P) which is saturated, unsaturated, partially saturated or heteroaromatic and may be unsubstituted or substituted, in which case the bonding site is localized on a ring atom. If the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. Optionally substituted heterocyclyl also includes spirocyclic systems, such as, for example, 1-oxa-5-azaspiro[2.3]hexyl. Unless defined differently, the heterocyclic ring preferably contains 3 to 9 ring atoms, especially 3 to 6 ring atoms, and one or more, preferably 1 to 4, especially 1, 2 or 3, heteroatoms in the heterocyclic ring, preferably from the group of N, O and S, but no two oxygen atoms should be directly adjacent, for example with one heteroatom from the group of N, O and S: 1- or 2- or 3-pyrrolidinyl, 3,4-dihydro-2H-pyrrol-2- or -3-yl, 2,3-dihydro-1H-pyrrol-1- or -2- or -3- or -4- or -5-yl; 2,5-dihydro-1H-pyrrol-1- or -2- or -3-yl, 1- or 2- or 3- or 4-piperidinyl; 2,3,4,5-tetrahydropyridin-2- or -3- or -4- or -5-yl or -6-yl; 1,2,3,6-tetrahydropyridin-1- or -2- or -3- or -4- or -5- or -6-yl; 1,2,3,4-tetrahydropyridin-1- or -2- or -3- or -4- or -5- or -6-yl; 1,4-dihydropyridin-1- or -2- or -3- or -4-yl; 2,3-dihydropyridin-2- or -3- or -4- or -5- or -6-yl; 2,5-dihydropyridin-2- or -3- or -4- or -5- or -6-yl, 1- or 2- or 3- or 4-azepanyl; 2,3,4,5-tetrahydro-1H-azepin-1- or -2- or -3- or -4- or -5- or -6- or -7-yl; 2,3,4,7-tetrahydro-1H-azepin-1- or -2- or -3- or -4- or -5- or -6- or -7-yl; 2,3,6,7-tetrahydro-1H-azepin-1- or -2- or -3- or -4-yl; 3,4,5,6-tetrahydro-2H-azepin-2- or -3- or -4- or -5- or -6- or -7-yl; 4,5-dihydro-1H-azepin-1- or -2- or -3- or -4-yl; 2,5-dihydro-1H-azepin-1- or -2- or -3- or -4- or -5- or -6- or -7-yl; 2,7-dihydro-1H-azepin-1- or -2- or -3- or -4-yl; 2,3-dihydro-1H-azepin-1- or -2- or -3- or -4- or -5- or -6- or -7-yl; 3,4-dihydro-2H-azepin-2- or -3- or -4- or -5- or -6- or -7-yl; 3,6-dihydro-2H-azepin-2- or -3- or -4- or -5- or -6- or -7-yl; 5,6-dihydro-2H-azepin-2- or -3- or -4- or -5- or -6- or -7-yl; 4,5-dihydro-3H-azepin-2- or -3- or -4- or -5- or -6- or -7-yl; 1H-azepin-1- or -2- or -3- or -4- or -5- or -6- or -7-yl; 2H-azepin-2- or -3- or -4- or -5- or -6- or -7-yl; 3H-azepin-2- or -3- or -4- or -5- or -6- or -7-yl; 4H-azepin-2- or -3- or -4- or -5- or -6- or -7-yl, 2- or 3-oxolanyl (=2- or 3-tetrahydrofuranyl); 2,3-dihydrofuran-2- or -3- or -4- or -5-yl; 2,5-dihydrofuran-2- or -3-yl, 2- or 3- or 4-oxanyl (=2- or 3- or 4-tetrahydropyranyl); 3,4-dihydro-2H-pyran-2- or -3- or -4- or -5- or -6-yl; 3,6-dihydro-2H-pyran-2- or -3- or -4- or -5- or -6-yl; 2H-pyran-2- or -3- or -4- or -5- or -6-yl; 4H-pyran-2- or -3- or -4-yl, 2- or 3- or 4-oxepanyl; 2,3,4,5-tetrahydrooxepin-2- or -3- or -4- or -5- or -6- or -7-yl; 2,3,4,7-tetrahydrooxepin-2- or -3- or -4- or -5- or -6- or -7-yl; 2,3,6,7-tetrahydrooxepin-2- or -3- or -4-yl; 2,3-dihydrooxepin-2- or -3- or -4- or -5- or -6- or -7-yl; 4,5-dihydrooxepin-2- or -3- or -4-yl; 2,5-dihydrooxepin-2- or -3- or -4- or -5- or -6- or -7-yl; oxepin-2- or -3- or -4- or -5- or -6- or -7-yl; 2- or 3-tetrahydrothiophenyl; 2,3-dihydrothiophen-2- or -3- or -4- or -5-yl; 2,5-dihydrothiophen-2- or -3-yl; tetrahydro-2H-thiopyran-2- or -3- or -4-yl; 3,4-dihydro-2H-thiopyran-2- or -3- or -4- or -5- or -6-yl; 3,6-dihydro-2H-thiopyran-2- or -3- or -4- or -5- or -6-yl; 2H-thiopyran-2- or -3- or -4- or -5- or -6-yl; 4H-thiopyran-2- or -3- or -4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partly or fully hydrogenated heterocyclic radical having two heteroatoms from the group of N, O and S, for example 1- or 2- or 3- or 4-pyrazolidinyl; 4,5-dihydro-3H-pyrazol-3- or 4- or 5-yl; 4,5-dihydro-1H-pyrazol-1- or 3- or 4- or 5-yl; 2,3-dihydro-1H-pyrazol-1- or 2- or 3- or 4- or 5-yl; 1- or 2- or 3- or 4-imidazolidinyl; 2,3-dihydro-1H-imidazol-1- or 2- or 3- or 4-yl; 2,5-dihydro-1H-imidazol-1- or 2- or 4- or 5-yl; 4,5-dihydro-1H-imidazol-1- or 2- or 4- or 5-yl; hexahydropyridazin-1- or 2- or 3- or 4-yl; 1,2,3,4-tetrahydropyridazin-1- or 2- or 3- or 4- or 5- or 6-yl; 1,2,3,6-tetrahydropyridazin-1- or 3- or 4- or 5- or 6-yl; 1,4,5,6-tetrahydropyridazin-1- or 3- or 4- or 5- or 6-yl; 3,4,5,6-tetrahydropyridazin-3- or 4- or 5-yl; 4,5-dihydropyridazin-3- or 4-yl; 3,4-dihydropyridazin-3- or 4- or 5- or 6-yl; 3,6-dihydropyridazin-3- or 4-yl; 1,6-dihydropyriazin-1- or 3- or 4- or 5- or 6-yl; hexahydropyrimidin-1- or 2- or 3- or 4-yl; 1,4,5,6-tetrahydropyrimidin-1- or 2- or 4- or 5- or 6-yl; 1,2,5,6-tetrahydropyrimidin-1- or 2- or 4- or 5- or 6-yl; 1,2,3,4-tetrahydropyrimidin-1- or 2- or 3- or 4- or 5- or 6-yl; 1,6-dihydropyrimidin-1- or 2- or 4- or 5- or 6-yl; 1,2-dihydropyrimidin-1- or 2- or 4- or 5- or 6-yl; 2,5-dihydropyrimidin-2- or 4- or 5-yl; 4,5-dihydropyrimidin-4- or 5- or 6-yl; 1,4-dihydropyrimidin-1- or 2- or 4- or 5- or 6-yl; 1- or 2- or 3-piperazinyl; 1,2,3,6-tetrahydropyrazin-1- or 2- or 3- or 5- or 6-yl; 1,2,3,4-tetrahydropyrazin-1- or 2- or 3- or 4- or 5- or 6-yl; 1,2-dihydropyrazin-1- or 2- or 3- or 5- or 6-yl; 1,4-dihydropyrazin-1- or 2- or 3-yl; 2,3-dihydropyrazin-2- or 3- or 5- or 6-yl; 2,5-dihydropyrazin-2- or 3-yl; 1,3-dioxolan-2- or 4- or 5-yl; 1,3-dioxol-2- or 4-yl; 1,3-dioxan-2- or 4- or 5-yl; 4H-1,3-dioxin-2- or 4- or 5- or 6-yl; 1,4-dioxan-2- or 3- or 5- or 6-yl; 2,3-dihydro-1,4-dioxin-2- or 3- or 5- or 6-yl; 1,4-dioxin-2- or 3-yl; 1,2-dithiolan-3- or 4-yl; 3H-1,2-dithiol-3- or 4- or 5-yl; 1,3-dithiolan-2- or 4-yl; 1,3-dithiol-2- or 4-yl; 1,2-dithian-3- or 4-yl; 3,4-dihydro-1,2-dithiin-3- or 4- or 5- or 6-yl; 3,6-dihydro-1,2-dithiin-3- or 4-yl; 1,2-dithiin-3- or 4-yl; 1,3-dithian-2- or 4- or 5-yl; 4H-1,3-dithiin-2- or 4- or 5- or 6-yl; isoxazolidin-2- or 3- or 4- or 5-yl; 2,3-dihydroisoxazol-2- or 3- or 4- or 5-yl; 2,5-dihydroisoxazol-2- or 3- or 4- or 5-yl; 4,5-dihydroisoxazol-3- or 4- or 5-yl; 1,3-oxazolidin-2- or 3- or 4- or 5-yl; 2,3-dihydro-1,3-oxazol-2- or 3- or 4- or 5-yl; 2,5-dihydro-1,3-oxazol-2- or 4- or 5-yl; 4,5-dihydro-1,3-oxazol-2- or 4- or 5-yl; 1,2-oxazinan-2- or 3- or 4- or 5- or 6-yl; 3,4-dihydro-2H-1,2-oxazin-2- or 3- or 4- or 5- or 6-yl; 3,6-dihydro-2H-1,2-oxazin-2- or 3- or 4- or 5- or 6-yl; 5,6-dihydro-2H-1,2-oxazin-2- or 3- or 4- or 5- or 6-yl; 5,6-dihydro-4H-1,2-oxazin-3- or 4- or 5- or 6-yl; 2H-1,2-oxazin-2- or 3- or 4- or 5- or 6-yl; 6H-1,2-oxazin-3- or 4- or 5- or 6-yl; 4H-1,2-oxazin-3- or 4- or 5- or 6-yl; 1,3-oxazinan-2- or 3- or 4- or 5- or 6-yl; 3,4-dihydro-2H-1,3-oxazin-2- or 3- or 4- or 5- or 6-yl; 3,6-dihydro-2H-1,3-oxazin-2- or 3- or 4- or 5- or 6-yl; 5,6-dihydro-2H-1,3-oxazin-2- or 4- or 5- or 6-yl; 5,6-dihydro-4H-1,3-oxazin-2- or 4- or 5- or 6-yl; 2H-1,3-oxazin-2- or 4- or 5- or 6-yl; 6H-1,3-oxazin-2- or 4- or 5- or 6-yl; 4H-1,3-oxazin-2- or 4- or 5- or 6-yl; morpholin-2- or 3- or 4-yl; 3,4-dihydro-2H-1,4-oxazin-2- or 3- or 4- or 5- or 6-yl; 3,6-dihydro-2H-1,4-oxazin-2- or 3- or 5- or 6-yl; 2H-1,4-oxazin-2- or 3- or 5- or 6-yl; 4H-1,4-oxazin-2- or 3-yl; 1,2-oxazepan-2- or 3- or 4- or 5- or 6- or 7-yl; 2,3,4,5-tetrahydro-1,2-oxazepin-2- or 3- or 4- or 5- or 6- or 7-yl; 2,3,4,7-tetrahydro-1,2-oxazepin-2- or 3- or 4- or 5- or 6- or 7-yl; 2,3,6,7-tetrahydro-1,2-oxazepin-2- or 3- or 4- or 5- or 6- or 7-yl; 2,5,6,7-tetrahydro-1,2-oxazepin-2- or 3- or 4- or 5- or 6- or 7-yl; 4,5,6,7-tetrahydro-1,2-oxazepin-3- or 4- or 5- or 6- or 7-yl; 2,3-dihydro-1,2-oxazepin-2- or 3- or 4- or 5- or 6- or 7-yl; 2,5-dihydro-1,2-oxazepin-2- or 3- or 4- or 5- or 6- or 7-yl; 2,7-dihydro-1,2-oxazepin-2- or 3- or 4- or 5- or 6- or 7-yl; 4,5-dihydro-1,2-oxazepin-3- or 4- or 5- or 6- or 7-yl; 4,7-dihydro-1,2-oxazepin-3- or 4- or 5- or 6- or 7-yl; 6,7-dihydro-1,2-oxazepin-3- or 4- or 5- or 6- or 7-yl; 1,2-oxazepin-3- or 4- or 5- or 6- or 7-yl; 1,3-oxazepan-2- or 3- or 4- or 5- or 6- or 7-yl; 2,3,4,5-tetrahydro-1,3-oxazepin-2- or 3- or 4- or 5- or 6- or 7-yl; 2,3,4,7-tetrahydro-1,3-oxazepin-2- or 3- or 4- or 5- or 6- or 7-yl; 2,3,6,7-tetrahydro-1,3-oxazepin-2- or 3- or 4- or 5- or 6- or 7-yl; 2,5,6,7-tetrahydro-1,3-oxazepin-2- or 4- or 5- or 6- or 7-yl; 4,5,6,7-tetrahydro-1,3-oxazepin-2- or 4- or 5- or 6- or 7-yl; 2,3-dihydro-1,3-oxazepin-2- or 3- or 4- or 5- or 6- or 7-yl; 2,5-dihydro-1,3-oxazepin-2- or 4- or 5- or 6- or 7-yl; 2,7-dihydro-1,3-oxazepin-2- or 4- or 5- or 6- or 7-yl; 4,5-dihydro-1,3-oxazepin-2- or 4- or 5- or 6- or 7-yl; 4,7-dihydro-1,3-oxazepin-2- or 4- or 5- or 6- or 7-yl; 6,7-dihydro-1,3-oxazepin-2- or 4- or 5- or 6- or 7-yl; 1,3-oxazepin-2- or 4- or 5- or 6- or 7-yl; 1,4-oxazepan-2- or 3- or 5- or 6- or 7-yl; 2,3,4,5-tetrahydro-1,4-oxazepin-2- or 3- or 4- or 5- or 6- or 7-yl; 2,3,4,7-tetrahydro-1,4-oxazepin-2- or 3- or 4- or 5- or 6- or 7-yl; 2,3,6,7-tetrahydro-1,4-oxazepin-2- or 3- or 5- or 6- or 7-yl; 2,5,6,7-tetrahydro-1,4-oxazepin-2- or 3- or 5- or 6- or 7-yl; 4,5,6,7-tetrahydro-1,4-oxazepin-2- or 3- or 4- or 5- or 6- or 7-yl; 2,3-dihydro-1,4-oxazepin-2- or 3- or 5- or 6- or 7-yl; 2,5-dihydro-1,4-oxazepin-2- or 3- or 5- or 6- or 7-yl; 2,7-dihydro-1,4-oxazepin-2- or 3- or 5- or 6- or 7-yl; 4,5-dihydro-1,4-oxazepin-2- or 3- or 4- or 5- or 6- or 7-yl; 4,7-dihydro-1,4-oxazepin-2- or 3- or 4- or 5- or 6- or 7-yl; 6,7-dihydro-1,4-oxazepin-2- or 3- or 5- or 6- or 7-yl; 1,4-oxazepin-2- or 3- or 5- or 6- or 7-yl; isothiazolidin-2- or 3- or 4- or 5-yl; 2,3-dihydroisothiazol-2- or 3- or 4- or 5-yl; 2,5-dihydroisothiazol-2- or 3- or 4- or 5-yl; 4,5-dihydroisothiazol-3- or 4- or 5-yl; 1,3-thiazolidin-2- or 3- or 4- or 5-yl; 2,3-dihydro-1,3-thiazol-2- or 3- or 4- or 5-yl; 2,5-dihydro-1,3-thiazol-2- or 4- or 5-yl; 4,5-dihydro-1,3-thiazol-2- or 4- or 5-yl; 1,3-thiazinan-2- or 3- or 4- or 5- or 6-yl; 3,4-dihydro-2H-1,3-thiazin-2- or 3- or 4- or 5- or 6-yl; 3,6-dihydro-2H-1,3-thiazin-2- or 3- or 4- or 5- or 6-yl; 5,6-dihydro-2H-1,3-thiazin-2- or 4- or 5- or 6-yl; 5,6-dihydro-4H-1,3-thiazin-2- or 4- or 5- or 6-yl; 2H-1,3-thiazin-2- or 4- or 5- or 6-yl; 6H-1,3-thiazin-2- or 4- or 5- or 6-yl; 4H-1,3-thiazin-2- or 4- or 5- or 6-yl. Further examples of "heterocyclyl" are a partially or fully hydrogenated heterocyclic radical having 3 heteroatoms from the group of N, O and S, for example 1,4,2-dioxazolidin-2- or -3- or -5-yl; 1,4,2-dioxazol-3- or -5-yl; 1,4,2-dioxazinan-2- or -3- or -5- or -6-yl; 5,6-dihydro-1,4,2-dioxazin-3- or -5- or -6-yl; 1,4,2-dioxazin-3- or -5- or -6-yl; 1,4,2-dioxazepan-2- or -3- or -5- or -6- or -7-yl; 6,7-dihydro-5H-1,4,2-dioxazepin-3- or -5- or -6- or -7-yl; 2,3-dihydro-7H-1,4,2-dioxazepin-2- or -3- or -5- or -6- or -7-yl; 2,3-dihydro-5H-1,4,2-dioxazepin-2- or -3- or -5- or -6- or -7-yl; 5H-1,4,2-dioxazepin-3- or -5- or -6- or -7-yl; 7H-1,4,2-dioxazepin-3- or -5- or -6- or -7-yl. Structural examples of heterocycles which are optionally substituted further are also listed below:

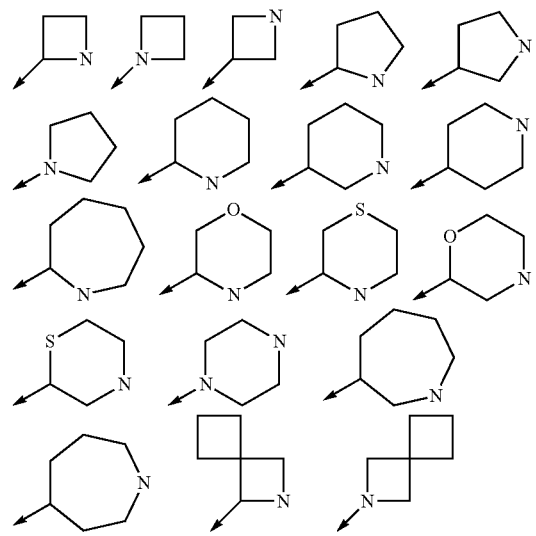

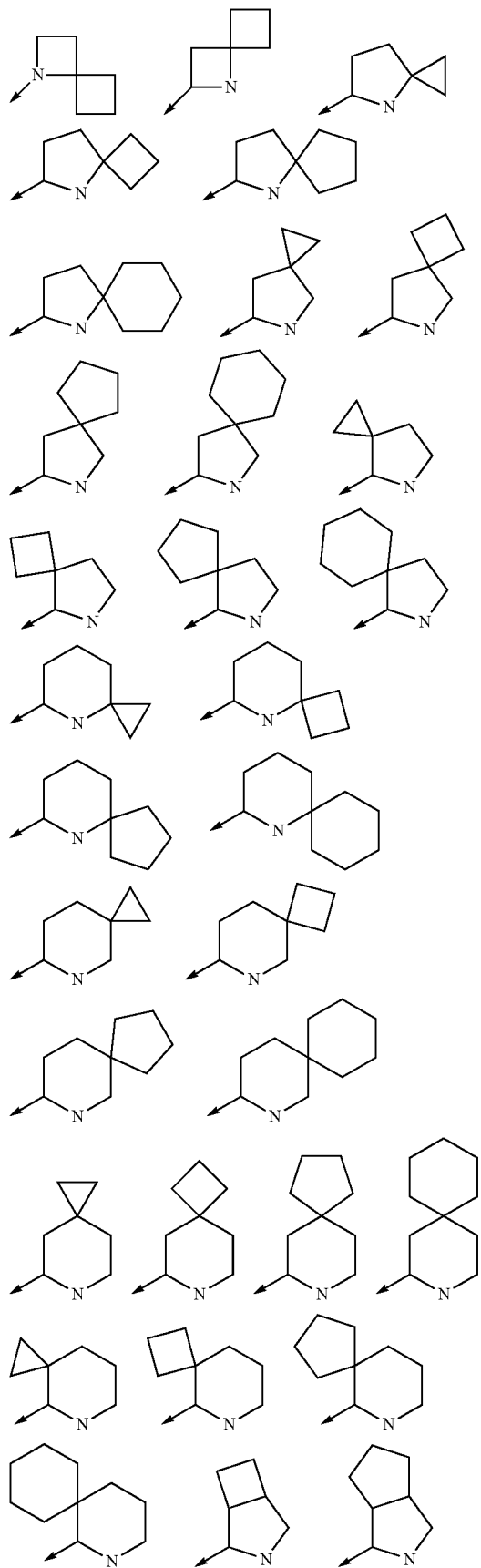
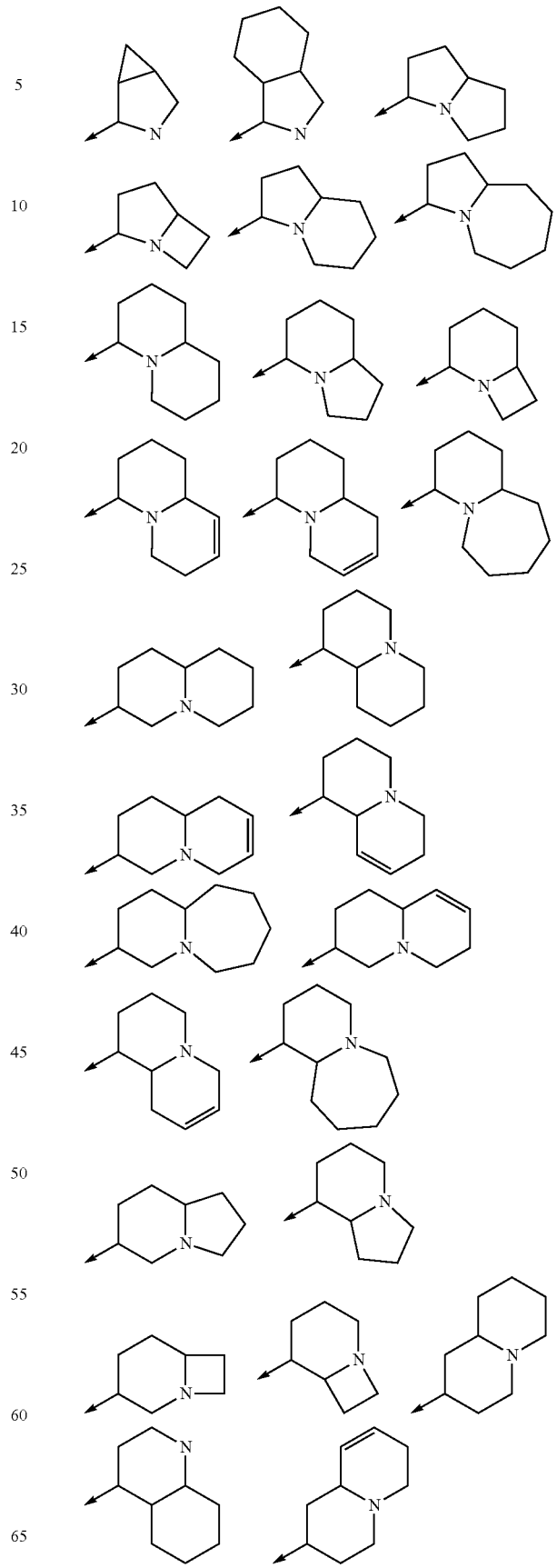

-continued

The heterocycles listed above are preferably substituted, for example, by hydrogen, halogen, alkyl, haloalkyl, hydroxyl, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkoxy, haloalkylthio, alkylthio, hydrothio, hydroxyalkyl, oxo, heteroarylalkoxy, arylalkoxy, heterocyclylalkoxy, heterocyclylalkylthio, heterocyclyloxy, heterocyclylthio, heteroaryloxy, bisalkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, bisalkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

"Arylheterocyclenyl" represents an aryl bonded to a heterocyclenyl, where the bonding site is localized on a ring atom. It is particularly preferable when aryl represents phenyl and the heterocyclenyl ring consists of 5 to 6 ring atoms. The arylheterocyclenyl is bonded via any atom of heterocyclenyl capable of doing so. The prefix aza, oxa or thio before the heterocyclenyl unit of the arylheterocyclenyl defines at least one nitrogen, oxygen or sulfur atom present as ring atom. The nitrogen of an arylheterocyclenyl may be a basic nitrogen atom. The nitrogen or sulfur ring atom of the arylheterocyclenyl may optionally be oxidized to the corresponding N-oxide, S-oxide or S,S-dioxide. Examples of arylheterocyclenyl include 3H-indolinyl, 1H-2-oxoquinolyl, 2H-1-oxoisoquinolyl or 1,2-dihydroisoquinolyl.

"Arylheterocyclyl" represents an aryl bonded to a heterocyclyl, where the bonding site is localized on a ring atom. It is particularly preferable when aryl represents phenyl and the heterocyclyl ring consists of 5 to 6 ring atoms. The arylheterocyclyl is bonded via any atom of heterocyclyl capable of doing so. The prefix aza, oxa or thio before the heterocyclyl unit of the arylheterocyclyl defines at least one nitrogen, oxygen or sulfur atom present as ring atom. The nitrogen of an arylheterocyclyl may be a basic nitrogen atom. The nitrogen or sulfur ring atom of the arylheterocyclyl may optionally be oxidized to the corresponding N-oxide, S-oxide or S,S-dioxide. Examples of arylheterocyclyl include indolinyl, 1,2,3,4-tetrahydroquinolinyl or 1,2,3,4-tetrahydroisoquinolinyl.

Cyclenyl represents a nonaromatic mono- or polycyclic ring system composed, for instance, of 3 to 10 carbon atoms, preferably of 5 to 10 carbon atoms, which contains at least one carbon-carbon double bond. Preference is given to 5- and 6-membered rings in the ring system. Examples of monocyclic cycloalkenyl include cyclopentenyl, cyclohexenyl and cycloheptenyl.

"Cycloalkenylaryl" represents an aryl bonded to a cycloalkenyl, where the bonding site is localized on a ring atom. It is particularly preferable when aryl represents phenyl and the cycloalkenyl consists of 5 to 6 ring atoms. The cycloalkenylaryl is bonded via any atom of cycloalkenyl capable of doing so.

"Cycloalkenylheteroaryl" represents a heteroaryl bonded to a cycloalkenyl, where the bonding site is localized on a ring atom. It is particularly preferable when heteroaryl consists of 5 to 6 ring atoms and cycloalkenyl consists of 5 to 6 ring atoms. The cycloalkenylaryl is bonded via any atom of cycloalkenyl capable of doing so. The nitrogen of a heteroaryl may be a basic nitrogen atom.

The prefix aza, oxa or thio before the heteroaryl unit of the cycloalkenylheteroaryl defines at least one nitrogen, oxygen or sulfur atom present as ring atom. The nitrogen ring atom of the heteroaryl may optionally have been oxidized to the corresponding N-oxide.

When a base structure is substituted "by one or more radicals" from a list of radicals (=group) or a generically defined group of radicals, this in each case includes simultaneous substitution by a plurality of identical and/or structurally different radicals.

In the case of a partially or fully saturated nitrogen heterocycle, this may be joined to the remainder of the molecule either via carbon or via the nitrogen.

Suitable substituents for a substituted heterocyclic radical are the substituents specified further down, and additionally also oxo and thioxo. The oxo group as a substituent on a ring carbon atom is then, for example, a carbonyl group in the heterocyclic ring. As a result, lactones and lactams are preferably also included. The oxo group may also occur on the ring heteroatoms, which may exist in different oxidation states, for example in the case of N and S, and in that case form, for example, the divalent —N(O)—, —S(O)— (also SO for short) and —S(O)$_2$— (also SO$_2$ for short) groups in the heterocyclic ring. In the case of N(O) and S(O) groups, both enantiomers in each case are included.

According to the invention, the expression "heteroaryl" refers to heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups of the invention may also be substituted by one or more identical or different radicals. If two adjacent carbon atoms are part of a further aromatic ring, the systems are fused heteroaromatic systems, such as benzofused or polyannelated heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" means fluorine, chlorine, bromine or iodine. If the term is used for a radical, "halogen" means a fluorine, chlorine, bromine or iodine atom.

According to the nature of the substituents and the way in which they are joined, the compounds of the formula (I) may be present as stereoisomers. If, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries.

The invention also relates to all stereoisomers and mixtures thereof which are encompassed by the formula (I) but not defined specifically. However, the following text will, for the sake of simplicity, always mention compounds of the formula (I), even though this is understood as meaning not only the pure compounds, but also, if appropriate, mixtures with various amounts of isomeric compounds. This also means tautomeric structures of the compounds (I), which result from at least one $R^{13}$ or $R^{14}$ radical being hydrogen.

In all the formulae specified hereinafter, the substituents and symbols have the same meaning as described in formula (I), unless defined differently. Arrows in a chemical formula denote the points at which it is joined to the rest of the molecule.

Preference is given to compounds of the formula (I)

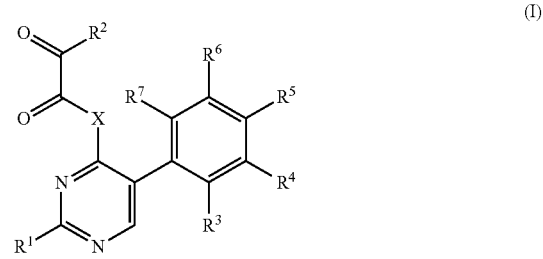

(I)

in which

X represents $C(R^{13})(R^{14})$, $R^1$ represents $(C_3-C_6)$-cycloalkyl, $(C_3-C_6)$-cycloalkenyl or heterocyclyl, where these three radicals are each substituted by s radicals from the group consisting of halogen, $(C_1-C_6)$-alkyl and halo-$(C_1-C_6)$-alkyl and where cycloalkyl, cycloalkenyl and heterocyclyl each independently bear n oxo groups, $R^2$ represents hydroxy, $(C_1-C_6)$-alkoxy, $(C_2-C_6)$-alkenyloxy, $(C_2-C_6)$-alkynyloxy, $(C_1-C_6)$-haloalkoxy, $(C_2-C_6)$-haloalkenyloxy, $(C_2-C_6)$-haloalkynyloxy, where the 6 latter radicals are substituted by s radicals from the group consisting of cyano, $R^8(O)C$, $R^8O(O)C$, $(R^8)_2N(O)C$, $R^8(R^8O)N(O)C$, $(R^8)_2N(R^8)N(O)C$, $R^8O$, $R^8(O)CO$, $R^9(O)_2SO$, $(R^8)_2N$, $R^9(O)_nS$, phenyl, heteroaryl and heterocyclyl, where the three latter radicals are each substituted by m radicals from the group consisting of nitro, halogen, cyano, $(C_1-C_6)$-alkyl, halo-$(C_1-C_6)$-alkyl, $(C_3-C_6)$-cycloalkyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl, and where $(C_3-C_6)$-cycloalkyl and heterocyclyl each independently bear n oxo groups, or $R^2$ represents $(C_3-C_6)$-cycloalkoxy, $(C_3-C_6)$-cycloalkenyloxy, phenyloxy, heteroaryloxy or heterocyclyloxy, where these five aforementioned radicals are each substituted by s radicals from the group consisting of halogen, cyano, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, halo-$(C_3-C_6)$-cycloalkyl, halo-$(C_3-C_6)$-cycloalkenyl, $R^8(O)C$, $R^8O(O)C$, $(R^8)_2N(O)C$, $R^8(R^8O)N(O)C$, $(R^8)_2N(R^8)N(O)C$, $R^8O$, $R^8(O)CO$, $R^9(O)_2SO$, $(R^8)_2N$, $R^9(O)_nS$, phenyl, heteroaryl and heterocyclyl, where the three latter radicals are each substituted by m radicals from the group consisting of nitro, halogen, cyano, $(C_1-C_6)$-alkyl, halo-$(C_1-C_6)$-alkyl, $(C_3-C_6)$-cycloalkyl, $R^{10}O(O)C$, $(R^{10})_2N(O)C$, $R^{10}O$, $(e)_2N$, $R^{11}(O)_nS$, $R^{10}O(O)_2S$, $(R^{10})_2N(O)_2S$ and $R^{10}O$—$(C_1-C_6)$-alkyl, and where $(C_3-C_6)$-cycloalkoxy, $(C_3-C_6)$-cycloalkyl and heterocyclyl each independently bear n oxo groups, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})(R^{18})N(R^{19})N$, or $R^2$ represents $R^{17}R^{18}C=N-(R^{19})N-$ $R^3$, $R^4$, $R^5$, $R^6$ and $R^7$ each independently represent hydrogen, nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^8(O)C$, $R^8(R^8ON=)C$, $R^8O(O)C$, $(R^8)_2N(O)C$, $R^8O$, $(R^8)_2N$, $R^8(O)C(R^8)N$, $R^9(O)_2S(R^8)N$, $R^9O(O)C(R^8)N$, $(R^8)_2N(O)C(R^8)N$, $R^9(O)_nS$, $R^8O(O)_2S$, $(R^8)_2N(O)_2S$, $(R^{12}O)_2(O)P$, $R^8(O)C$—$(C_1-C_6)$-alkyl, $R^8O(O)C$—$(C_1-C_6)$-alkyl, $(R^8)_2N(O)C$—$(C_1-C_6)$-alkyl, NC—$(C_1-C_6)$-alkyl, $R^8O$—$(C_1-C_6)$-alkyl, $(R^8)_2N$—$(C_1-C_6)$-alkyl, $R^8(O)C(R^8)N$—$(C_1-C_6)$-alkyl, $R^9(O)_2S(R^8)N$—$(C_1-C_6)$-alkyl, $R^9O(O)C(R^8)N$—$(C_1-C_6)$-alkyl, $(R^8)_2N(O)C(R^8)N$—$(C_1-C_6)$-alkyl, $R^9(O)_nS$—$(C_1-C_6)$-alkyl, $R^8O(O)_2S$—$(C_1-C_6)$-alkyl, $(R^8)_2N(O)_2S$—$(C_1-C_6)$-alkyl, $(R^{12}O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl, heterocyclyl-$(C_1-C_6)$-alkyl, where the six latter radicals are each substituted by m radicals from the group consisting of nitro, halogen, cyano, $(C_1-C_6)$-alkyl, halo-$(C_1-C_6)$-alkyl, $R^8O$, $(R^8)_2N$, $R^9(O)_nS$, $R^8O(O)_2S$, $(R^8)_2N(O)_2S$ and $R^8O$—$(C_1-C_6)$-alkyl, and where heterocyclyl bears n oxo groups, $R^8$ is hydrogen, $(C_1-C_6)$-alkyl, $(C_3-C_6)$-cycloalkyl-$(C_1-C_6)$-alkyl, $(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl or heterocyclyl-O—$(C_1-C_6)$-alkyl, where the nine latter radicals are each substituted by m radicals from the group consisting of nitro, halogen, $(C_1-C_6)$-alkyl, halo-$(C_1-C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1-C_6)$-alkyl, and where heterocyclyl bears n oxo groups, or the two $R^8$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl and oxo, $R^9$ represents $(C_1-C_6)$-alkyl, $(C_3-C_6)$-cycloalkyl-$(C_1-C_6)$-alkyl, $(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl or heterocyclyl-O—$(C_1-C_6)$-alkyl, where the nine latter radicals are each substituted by m radicals from the group consisting of nitro, halogen, $(C_1-C_6)$-alkyl, halo-$(C_1-C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1-C_6)$-alkyl, and where heterocyclyl bears n oxo groups, $R^{10}$ represents hydrogen or $(C_1-C_6)$-alkyl, $R^{11}$ represents $(C_1-C_6)$-alkyl, $R^{12}$ represents $(C_1-C_4)$-alkyl, $R^{13}$ and $R^{14}$ each independently represent hydrogen, $(C_1-C_6)$-alkyl, hydroxy, $(C_1-C_6)$-alkoxy, $(R^8)_2N$, halo-$(C_1-C_6)$-alkoxy, halogen, halo-$(C_1-C_6)$-alkyl, cyano, $R^8O(O)C$ or $(R^8)_2N(O)C$, or $R^{13}$ and $R^{14}$ together with the carbon atom to which they are bonded form a $(C_3-C_8)$-cycloalkyl group, $R^{15}$ and $R^{16}$ each independently represent $(C_1-C_6)$-alkyl, phenyl, $(C_3-C_6)$-cycloalkyl, heteroaryl or heterocyclyl, $R^{17}$, $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$ or the $(R^{17}$ and $R^{18})$ or $(R^{17}$ and $R^{19})$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl and oxo, m represents 0, 1, 2, 3, 4 or 5, n represents 0, 1 or 2, s represents 0, 1, 2, 3, 4, 5, 6, 7, 8, 9, 10 or 11.

Particular preference is given to compounds of the formula (I)

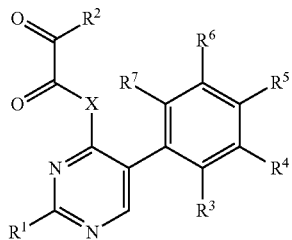

in which

X represents $C(R^{13})(R^{14})$, $R^1$ represents $(C_3-C_6)$-cycloalkyl, where this cycloalkyl group is substituted by s radicals from the group consisting of halogen, $(C_1-C_6)$-alkyl and halo-$(C_1-C_6)$-alkyl, $R^2$ represents hydroxy, $(C_1-C_6)$-alkoxy, $(C_1-C_6)$-haloalkoxy, $(C_2-C_6)$-alkenyloxy, $(C_2-C_6)$-haloalkenyloxy, $(C_2-C_6)$-alkynyloxy, where the five latter radicals are each substituted by a radical from the group of $R^8(O)C$, $R^8O(O)C$, $(R^8)_2N(O)C$, $R^8(R^8O)N(O)C$, $(R^8)_2N(R^8)N(O)C$, $R^8O$ and phenyl, where the latter radical is substituted in each case by m radicals from the group consisting of nitro, halogen, cyano, $(C_1-C_6)$-alkyl, halo-$(C_1-C_6)$-alkyl and $(C_3-C_6)$-cycloalkyl, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})(R^{18})N(R^{19})N$, or $R^2$ represents $R^{17}R^{18}C=N-(R^{19})N-$ $R^3$, $R^4$, $R^5$, $R^6$ and $R^7$ each independently represent hydrogen, nitro, halogen, cyano, $(C_1-C_6)$-alkyl, halo-$(C_1-C_6)$-alkyl, $(C_3-C_6)$-cycloalkyl, $R^8O(O)C$, $R^8O$ or $R^9(O)_nS$, $R^8$ represents hydrogen, $(C_1-C_6)$-alkyl, $(C_3-C_6)$-cycloalkyl-$(C_1-C_6)$-alkyl, $(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl or heterocyclyl-O—$(C_1-C_6)$-alkyl, where the nine latter radicals are each substituted by m radicals from the group consisting of nitro, halogen, $(C_1-C_6)$-alkyl, halo-$(C_1-C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1-C_6)$-alkyl, and where heterocyclyl bears n oxo groups, or the two $R^8$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl and oxo, $R^9$ represents $(C_1-C_6)$-alkyl, $(C_3-C_6)$-cycloalkyl-$(C_1-C_6)$-alkyl, $(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl or heterocyclyl-O—$(C_1-C_6)$-alkyl, where the nine latter radicals are each substituted by m radicals from the group consisting of nitro, halogen, $(C_1-C_6)$-alkyl, halo-$(C_1-C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1-C_6)$-alkyl, and where heterocyclyl bears n oxo groups, $R^{10}$ represents hydrogen or $(C_1-C_6)$-alkyl, $R^{11}$ represents $(C_1-C_6)$-alkyl, $R^{12}$ represents $(C_1-C_4)$-alkyl, $R^{13}$ and $R^{14}$ each independently represent hydrogen, $(C_1-C_6)$-alkyl, cyano, $R^8O(O)C$ or $(R^8)_2N(O)C$, $R^{15}$ and $R^{16}$ each independently represent $(C_1-C_6)$-alkyl, phenyl, $(C_3-C_6)$-cycloalkyl, heteroaryl or heterocyclyl, $R^{17}$, $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$, or or the ($R^{17}$ and $R^{18}$) or ($R^{17}$ and $R^{19}$) radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl and oxo, m represents 0 or 1, 2, 3, 4 or 5, n represents 0, 1 or 2, s represents 0, 1, 2, 3, 4, 5, 6, 7, 8, 9, 10 or 11.

Very particular preference is given to compounds of the formula (I)

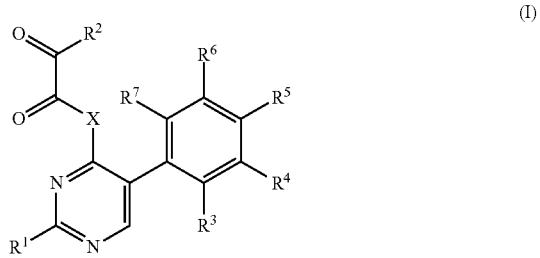

in which

X represents $CH_2$, $R^1$ represents cyclopropyl, where the cyclopropyl group is substituted by s radicals from the group consisting of halogen, $(C_1-C_6)$-alkyl and halo-$(C_1-C_6)$-alkyl, $R^2$ represents hydroxy, $(C_1-C_6)$-alkoxy, $(C_1-C_6)$-haloalkoxy, $(C_2-C_6)$-alkenyloxy, $(C_2-C_6)$-haloalkenyloxy, $(C_2-C_6)$-alkynyloxy, or $R^2$ represents $(R^8)_2N$, $R^8(O)C(R^8)N$, $R^9O(O)C(R^8)N$, $(R^8)_2(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})$ (V) $N(R^{19})N$, or $R^2$ represents $R^{17}R^{18}C=N-(R^{19})N-$ or or the $(R^{17}$ and $R^{18})$ or $(R^{17}$ and $R^{19})$ radicals form a ring with the heteroatom or the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl and oxo, $R^3$ represents cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methylsulfonyl, $R^4$, $R^5$, $R^6$ and $R^7$ each independently represent hydrogen, cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methylsulfonyl, $R^8$ represents hydrogen, $(C_1-C_6)$-alkyl, $(C_3-C_6)$-cycloalkyl-$(C_1-C_6)$-alkyl, $(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl or heterocyclyl-O—$(C_1-C_6)$-alkyl, where the nine latter radicals are each substituted by m radicals from the group consisting of nitro, halogen, $(C_1-C_6)$-alkyl, halo-$(C_1-C_6)$-alkyl, $R^{10}O(O)C$, $(R^{10})_2N(O)C$, $R^{10}O$, $(R^{10})_2N$, $R^{11}(O)_nS$ and $R^{10}O-(C_1-C_6)$-alkyl, and where heterocyclyl bears n oxo groups, or the two $R^8$ radicals form a ring with the heteroatom or the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(e)_2N(O)_2S$ and $R^{10}O-(C_1-C_6)$-alkyl and oxo, $R^9$ represents $(C_1-C_6)$-alkyl, $(C_3-C_6)$-cycloalkyl-$(C_1-C_6)$-alkyl, $(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl or heterocyclyl-O—$(C_1-C_6)$-alkyl, where the nine latter radicals are each substituted by m radicals from the group consisting of nitro, halogen, $(C_1-C_6)$-alkyl, halo-$(C_1-C_6)$-alkyl, $R^{10}O(O)C$, $(R^{10})_2N(O)C$, $R^{10}O$, $(R^{10})_2N$, $R^{11}(O)_nS$ and $R^{10}O-(C_1-C_6)$-alkyl, and where heterocyclyl bears n oxo groups, $R^{10}$ represents hydrogen or $(C_1-C_6)$-alkyl, $R^{11}$ represents $(C_1-C_6)$-alkyl, $R^{12}$ represents $(C_1-C_4)$-alkyl, $R^{13}$ and $R^{14}$ each independently represent hydrogen, $(C_1-C_6)$-alkyl, cyano, $R^8O(O)C$ or $(R^8)_2N(O)C$, $R^{15}$ and $R^{16}$ each independently represent $(C_1-C_6)$-alkyl, phenyl, $(C_3-C_6)$-cycloalkyl, heteroaryl or heterocyclyl, $R^{17}$, $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$, or the $(R^{15}$ and $R^{18})$ or $(R^{15}$ and V) radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of halogen, cyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(e)_2N(O)C$, $R^{10}O$, $(R^{10})_2N$, $R^{11}(O)_nS$, $R^{10}O(O)_2S$, $(R^{10})_2N(O)_2S$ and $R^{10}O-(C_1-C_6)$-alkyl and oxo, m represents 0, 1, 2 or 3, n represents 0, 1 or 2, s represents 0, 1, 2, 3, 4 or 5.

Exceedingly preferred are compounds of the formula (I)

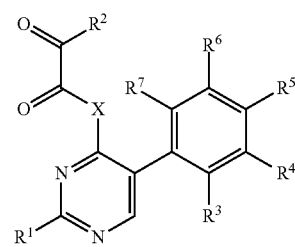

in which

X represents $CH_2$, $R^1$ represents cyclopropyl, where the cycicyclopropyl oalkyl group is substituted by s radicals from the group consisting of halogen, $(C_1-C_6)$-alkyl and halo-$(C_1-C_6)$-alkyl, $R^2$ represents hydroxy, $(C_1-C_6)$-alkoxy, $(C_1-C_6)$-haloalkoxy, $(C_2-C_6)$-alkenyloxy, $(C_2-C_6)$-haloalkenyloxy, $(C_2-C_6)$-alkynyloxy, $R^3$ represents cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methylsulfonyl, $R^4$, $R^5$, $R^6$ and $R^7$ each independently represent hydrogen, cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methylsulfonyl, m represents 0, 1, 2 or 3, n represents 0, 1 or 2, s represents 0, 1, 2, 3, 4 or 5.

In the context of the present invention, it is possible to arbitrarily combine the individual preferred, particularly preferred and very particularly preferred definitions of the substituents X, Z, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and those of the indices n, m and s. This means that the present invention encompasses compounds of the general formula (I) in which, for example, the substituent $R^1$ has a preferred definition and the substituents $R^2$ to $R^7$ have the general definition or else the substituent $R^1$ has a preferred definition, the substituent $R^{10}$ has a particularly preferred or very particularly preferred definition and the remaining substituents have a general definition.

The inventive compounds of the formula (I) listed in tables 1 to 4 below are likewise very particularly preferred. The abbreviations for chemical radicals that are used therein follow the nomenclature known to the person skilled in the art and mean, for example

| Bu = butyl | Et = ethyl | Me = methyl |
| Ph = phenyl | Pr = propyl | c = cyclo |
| i = iso | Ac = acetyl | |
| Bn = benzyl | | |

TABLE 1

Inventive compounds of the formula (I) in which X represents $C(R^{13})(R^{14})$

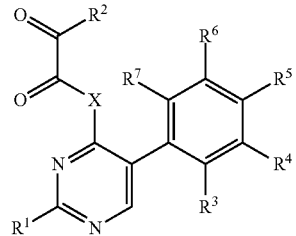

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-001 | c-Pr | $NH_2$ | H | H | H | H | H | H | H |
| I-002 | c-Pr | MeNH | H | H | H | H | H | H | H |
| I-003 | c-Pr | $Me_2N$ | H | H | H | H | H | H | H |
| I-004 | c-Pr | cyclopentyl-NH | H | H | H | H | H | H | H |
| I-005 | c-Pr | Ph—NH | H | H | H | H | H | H | H |
| I-006 | c-Pr | Ph—(Bn)N | H | H | H | H | H | H | H |
| I-007 | c-Pr | (Pyridin-3-yl)amino | H | H | H | H | H | H | H |
| I-008 | c-Pr | Allylamino | H | H | H | H | H | H | H |
| I-009 | c-Pr | Propargylamino | H | H | H | H | H | H | H |
| I-010 | c-Pr | (Pyrrolidin-1-yl) | H | H | H | H | H | H | H |
| I-011 | c-Pr | $F_3CCH_2NH$ | H | H | H | H | H | H | H |
| I-012 | c-Pr | Acetylamino | H | H | H | H | H | H | H |
| I-013 | c-Pr | Benzoylamino | H | H | H | H | H | H | H |
| I-014 | c-Pr | (Ethoxycarbonyl)amino | H | H | H | H | H | H | H |
| I-015 | c-Pr | (N,N-Dimethyl-amino)carbonyl-amino | H | H | H | H | H | H | H |
| I-016 | c-Pr | (N,N-Dimethylamino)(thio-carbonyl)amino | H | H | H | H | H | H | H |
| I-017 | c-Pr | (Methylsulfonyl)amino | H | H | H | H | H | H | H |
| I-018 | 1-Me-c-Pr | $NH_2$ | H | H | H | H | H | H | H |
| I-019 | 1-Me-c-Pr | MeNH | H | H | H | H | H | H | H |
| I-020 | 1-Me-c-Pr | $Me_2N$ | H | H | H | H | H | H | H |
| I-021 | 1-Me-c-Pr | cyclopentyl-NH | H | H | H | H | H | H | H |
| I-022 | 1-Me-c-Pr | Ph—NH | H | H | H | H | H | H | H |
| I-023 | 1-Me-c-Pr | Ph—(Bn)N | H | H | H | H | H | H | H |
| I-024 | 1-Me-c-Pr | (Pyridin-3-yl)amino | H | H | H | H | H | H | H |
| I-025 | 1-Me-c-Pr | Allylamino | H | H | H | H | H | H | H |
| I-026 | 1-Me-c-Pr | Propargylamino | H | H | H | H | H | H | H |
| I-027 | 1-Me-c-Pr | (Pyrrolidin-1-yl) | H | H | H | H | H | H | H |
| I-028 | 1-Me-c-Pr | $F_3CCH_2NH$ | H | H | H | H | H | H | H |
| I-029 | 1-Me-c-Pr | Acetylamino | H | H | H | H | H | H | H |
| I-030 | 1-Me-c-Pr | Benzoylamino | H | H | H | H | H | H | H |
| I-031 | 1-Me-c-Pr | (Ethoxycarbonyl)amino | H | H | H | H | H | H | H |
| I-032 | 1-Me-c-Pr | (N,N-Dimethyl-amino)carbonyl-amino | H | H | H | H | H | H | H |
| I-033 | 1-Me-c-Pr | (N,N-Dimethylamino)(thio-carbonyl)amino | H | H | H | H | H | H | H |
| I-034 | 1-Me-c-Pr | (Methylsulfonyl)amino | H | H | H | H | H | H | H |
| I-035 | 2-Me-c-Pr | $NH_2$ | H | H | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-036 | 2-Me-c-Pr | MeNH | H | H | H | H | H | H | H |
| I-037 | 2-Me-c-Pr | Me$_2$N | H | H | H | H | H | H | H |
| I-038 | 2-Me-c-Pr | cyclopentyl-NH | H | H | H | H | H | H | H |
| I-039 | 2-Me-c-Pr | Ph—NH | H | H | H | H | H | H | H |
| I-040 | 2-Me-c-Pr | Ph—(Bn)N | H | H | H | H | H | H | H |
| I-041 | 2-Me-c-Pr | (Pyridin-3-yl)amino | H | H | H | H | H | H | H |
| I-042 | 2-Me-c-Pr | Allylamino | H | H | H | H | H | H | H |
| I-043 | 2-Me-c-Pr | Propargylamino | H | H | H | H | H | H | H |
| I-044 | 2-Me-c-Pr | (Pyrrolidin-1-yl) | H | H | H | H | H | H | H |
| I-045 | 2-Me-c-Pr | F$_3$CCH$_2$NH | H | H | H | H | H | H | H |
| I-046 | 2-Me-c-Pr | Acetylamino | H | H | H | H | H | H | H |
| I-047 | 2-Me-c-Pr | Benzoylamino | H | H | H | H | H | H | H |
| I-048 | 2-Me-c-Pr | (Ethoxycarbonyl)amino | H | H | H | H | H | H | H |
| I-049 | 2-Me-c-Pr | (N,N-Dimethyl-amino)carbonyl-amino | H | H | H | H | H | H | H |
| I-050 | 2-Me-c-Pr | (N,N-Dimethylamino)(thio-carbonyl)amino | H | H | H | H | H | H | H |
| I-051 | 2-Me-c-Pr | (Methylsulfonyl)amino | H | H | H | H | H | H | H |
| I-052 | c-Pr | NH$_2$ | F | H | H | H | H | H | H |
| I-053 | c-Pr | MeNH | F | H | H | H | H | H | H |
| I-054 | c-Pr | Me$_2$N | F | H | H | H | H | H | H |
| I-055 | c-Pr | cyclopentyl-NH | F | H | H | H | H | H | H |
| I-056 | c-Pr | Ph—NH | F | H | H | H | H | H | H |
| I-057 | c-Pr | Ph—(Bn)N | F | H | H | H | H | H | H |
| I-058 | c-Pr | (Pyridin-3-yl)amino | F | H | H | H | H | H | H |
| I-059 | c-Pr | Allylamino | F | H | H | H | H | H | H |
| I-060 | c-Pr | Propargylamino | F | H | H | H | H | H | H |
| I-061 | c-Pr | (Pyrrolidin-1-yl) | F | H | H | H | H | H | H |
| I-062 | c-Pr | F$_3$CCH$_2$NH | F | H | H | H | H | H | H |
| I-063 | c-Pr | Acetylamino | F | H | H | H | H | H | H |
| I-064 | c-Pr | Benzoylamino | F | H | H | H | H | H | H |
| I-065 | c-Pr | (Ethoxycarbonyl)amino | F | H | H | H | H | H | H |
| I-066 | c-Pr | (N,N-Dimethyl-amino)carbonyl-amino | F | H | H | H | H | H | H |
| I-067 | c-Pr | (N,N-Dimethylamino)(thio-carbonyl)amino | F | H | H | H | H | H | H |
| I-068 | c-Pr | (Methylsulfonyl)amino | F | H | H | H | H | H | H |
| I-069 | 1-Me-c-Pr | NH$_2$ | F | H | H | H | H | H | H |
| I-070 | 1-Me-c-Pr | MeNH | F | H | H | H | H | H | H |
| I-071 | 1-Me-c-Pr | Me$_2$N | F | H | H | H | H | H | H |
| I-072 | 1-Me-c-Pr | cyclopentyl-NH | F | H | H | H | H | H | H |
| I-073 | 1-Me-c-Pr | Ph—NH | F | H | H | H | H | H | H |
| I-074 | 1-Me-c-Pr | Ph—(Bn)N | F | H | H | H | H | H | H |
| I-075 | 1-Me-c-Pr | (Pyridin-3-yl)amino | F | H | H | H | H | H | H |
| I-076 | 1-Me-c-Pr | Allylamino | F | H | H | H | H | H | H |
| I-077 | 1-Me-c-Pr | Propargylamino | F | H | H | H | H | H | H |
| I-078 | 1-Me-c-Pr | (Pyrrolidin-1-yl) | F | H | H | H | H | H | H |
| I-079 | 1-Me-c-Pr | F$_3$CCH$_2$NH | F | H | H | H | H | H | H |
| I-080 | 1-Me-c-Pr | Acetylamino | F | H | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-081 | 1-Me-c-Pr | Benzoylamino | F | H | H | H | H | H | H |
| I-082 | 1-Me-c-Pr | (Ethoxycarbonyl)amino | F | H | H | H | H | H | H |
| I-083 | 1-Me-c-Pr | (N,N-Dimethyl-amino)carbonyl-amino | F | H | H | H | H | H | H |
| I-084 | 1-Me-c-Pr | (N,N-Dimethylamino)(thio-carbonyl)amino | F | H | H | H | H | H | H |
| I-085 | 1-Me-c-Pr | (Methylsulfonyl)amino | F | H | H | H | H | H | H |
| I-086 | 2-Me-c-Pr | $NH_2$ | F | H | H | H | H | H | H |
| I-087 | 2-Me-c-Pr | MeNH | F | H | H | H | H | H | H |
| I-088 | 2-Me-c-Pr | $Me_2N$ | F | H | H | H | H | H | H |
| I-089 | 2-Me-c-Pr | cyclopentyl-NH | F | H | H | H | H | H | H |
| I-090 | 2-Me-c-Pr | Ph—NH | F | H | H | H | H | H | H |
| I-091 | 2-Me-c-Pr | Ph—(Bn)N | F | H | H | H | H | H | H |
| I-092 | 2-Me-c-Pr | (Pyridin-3-yl)amino | F | H | H | H | H | H | H |
| I-093 | 2-Me-c-Pr | Allylamino | F | H | H | H | H | H | H |
| I-094 | 2-Me-c-Pr | Propargylamino | F | H | H | H | H | H | H |
| I-095 | 2-Me-c-Pr | (Pyrrolidin-1-yl) | F | H | H | H | H | H | H |
| I-096 | 2-Me-c-Pr | $F_3CCH_2NH$ | F | H | H | H | H | H | H |
| I-097 | 2-Me-c-Pr | Acetylamino | F | H | H | H | H | H | H |
| I-098 | 2-Me-c-Pr | Benzoylamino | F | H | H | H | H | H | H |
| I-099 | 2-Me-c-Pr | (Ethoxycarbonyl)amino | F | H | H | H | H | H | H |
| I-100 | 2-Me-c-Pr | (N,N-Dimethyl-amino)carbonyl-amino | F | H | H | H | H | H | H |
| I-101 | 2-Me-c-Pr | (N,N-Dimethylamino)(thio-carbonyl)amino | F | H | H | H | H | H | H |
| I-102 | 2-Me-c-Pr | (Methylsulfonyl)amino | F | H | H | H | H | H | H |
| I-103 | c-Pr | $NH_2$ | H | F | H | H | H | H | H |
| I-104 | c-Pr | MeNH | H | F | H | H | H | H | H |
| I-105 | c-Pr | $Me_2N$ | H | F | H | H | H | H | H |
| I-106 | c-Pr | cyclopentyl-NH | H | F | H | H | H | H | H |
| I-107 | c-Pr | Ph—NH | H | F | H | H | H | H | H |
| I-108 | c-Pr | Ph—(Bn)N | H | F | H | H | H | H | H |
| I-109 | c-Pr | (Pyridin-3-yl)amino | H | F | H | H | H | H | H |
| I-110 | c-Pr | Allylamino | H | F | H | H | H | H | H |
| I-111 | c-Pr | Propargylamino | H | F | H | H | H | H | H |
| I-112 | c-Pr | (Pyrrolidin-1-yl) | H | F | H | H | H | H | H |
| I-113 | c-Pr | $F_3CCH_2NH$ | H | F | H | H | H | H | H |
| I-114 | c-Pr | Acetylamino | H | F | H | H | H | H | H |
| I-115 | c-Pr | Benzoylamino | H | F | H | H | H | H | H |
| I-116 | c-Pr | (Ethoxycarbonyl)amino | H | F | H | H | H | H | H |
| I-117 | c-Pr | (N,N-Dimethyl-amino)carbonyl-amino | H | F | H | H | H | H | H |
| I-118 | c-Pr | (N,N-Dimethylamino)(thio-carbonyl)amino | H | F | H | H | H | H | H |
| I-119 | c-Pr | (Methylsulfonyl)amino | H | F | H | H | H | H | H |
| I-120 | c-Pr | $NH_2$ | H | H | F | H | H | H | H |
| I-121 | c-Pr | MeNH | H | H | F | H | H | H | H |
| I-122 | c-Pr | $Me_2N$ | H | H | F | H | H | H | H |
| I-123 | c-Pr | cyclopentyl-NH | H | H | F | H | H | H | H |
| I-124 | c-Pr | Ph—NH | H | H | F | H | H | H | H |
| I-125 | c-Pr | Ph—(Bn)N | H | H | F | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-126 | c-Pr | (Pyridin-3-yl)amino | H | H | F | H | H | H | H |
| I-127 | c-Pr | Allylamino | H | H | F | H | H | H | H |
| I-128 | c-Pr | Propargylamino | H | H | F | H | H | H | H |
| I-129 | c-Pr | (Pyrrolidin-1-yl) | H | H | F | H | H | H | H |
| I-130 | c-Pr | $F_3CCH_2NH$ | H | H | F | H | H | H | H |
| I-131 | c-Pr | Acetylamino | H | H | F | H | H | H | H |
| I-132 | c-Pr | Benzoylamino | H | H | F | H | H | H | H |
| I-133 | c-Pr | (Ethoxycarbonyl)amino | H | H | F | H | H | H | H |
| I-134 | c-Pr | (N,N-Dimethyl-amino)carbonyl-amino | H | H | F | H | H | H | H |
| I-135 | c-Pr | (N,N-Dimethylamino)(thio-carbonyl)amino | H | H | F | H | H | H | H |
| I-136 | c-Pr | (Methylsulfonyl)amino | H | H | F | H | H | H | H |
| I-137 | c-Pr | $NH_2$ | Cl | H | H | H | H | H | H |
| I-138 | c-Pr | MeNH | Cl | H | H | H | H | H | H |
| I-139 | c-Pr | $Me_2N$ | Cl | H | H | H | H | H | H |
| I-140 | c-Pr | cyclopentyl-NH | Cl | H | H | H | H | H | H |
| I-141 | c-Pr | Ph—NH | Cl | H | H | H | H | H | H |
| I-142 | c-Pr | Ph—(Bn)N | Cl | H | H | H | H | H | H |
| I-143 | c-Pr | (Pyridin-3-yl)amino | Cl | H | H | H | H | H | H |
| I-144 | c-Pr | Allylamino | Cl | H | H | H | H | H | H |
| I-145 | c-Pr | Propargylamino | Cl | H | H | H | H | H | H |
| I-146 | c-Pr | (Piperidin-1-yl) | Cl | H | H | H | H | H | H |
| I-147 | c-Pr | morpholin-4-yl | Cl | H | H | H | H | H | H |
| I-148 | c-Pr | Acetylamino | Cl | H | H | H | H | H | H |
| I-149 | c-Pr | Benzoylamino | Cl | H | H | H | H | H | H |
| I-150 | c-Pr | (Ethoxycarbonyl)amino | Cl | H | H | H | H | H | H |
| I-151 | c-Pr | (N,N-Dimethyl-amino)carbonyl-amino | Cl | H | H | H | H | H | H |
| I-152 | c-Pr | (N,N-Dimethylamino)(thio-carbonyl)amino | Cl | H | H | H | H | H | H |
| I-153 | c-Pr | (Methylsulfonyl)amino | Cl | H | H | H | H | H | H |
| I-154 | 1-Me-c-Pr | $NH_2$ | Cl | H | H | H | H | H | H |
| I-155 | 1-Me-c-Pr | MeNH | Cl | H | H | H | H | H | H |
| I-156 | 1-Me-c-Pr | $Me_2N$ | Cl | H | H | H | H | H | H |
| I-157 | 1-Me-c-Pr | cyclopentyl-NH | Cl | H | H | H | H | H | H |
| I-158 | 1-Me-c-Pr | Ph—NH | Cl | H | H | H | H | H | H |
| I-159 | 1-Me-c-Pr | Ph—(Bn)N | Cl | H | H | H | H | H | H |
| I-160 | 1-Me-c-Pr | (Pyridin-3-yl)amino | Cl | H | H | H | H | H | H |
| I-161 | 1-Me-c-Pr | Allylamino | Cl | H | H | H | H | H | H |
| I-162 | 1-Me-c-Pr | Propargylamino | Cl | H | H | H | H | H | H |
| I-163 | 1-Me-c-Pr | (Pyrrolidin-1-yl) | Cl | H | H | H | H | H | H |
| I-164 | 1-Me-c-Pr | $F_3CCH_2NH$ | Cl | H | H | H | H | H | H |
| I-165 | 1-Me-c-Pr | Acetylamino | Cl | H | H | H | H | H | H |
| I-166 | 1-Me-c-Pr | Benzoylamino | Cl | H | H | H | H | H | H |

TABLE 1-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-167 | 1-Me-c-Pr | (Ethoxycarbonyl)amino | Cl | H | H | H | H | H | H |
| I-168 | 1-Me-c-Pr | (N,N-Dimethyl-amino)carbonyl-amino | Cl | H | H | H | H | H | H |
| I-169 | 1-Me-c-Pr | (N,N-Dimethylamino)(thio-carbonyl)amino | Cl | H | H | H | H | H | H |
| I-170 | 1-Me-c-Pr | (Methylsulfonyl)amino | Cl | H | H | H | H | H | H |
| I-171 | 2-Me-c-Pr | $NH_2$ | Cl | H | H | H | H | H | H |
| I-172 | 2-Me-c-Pr | MeNH | Cl | H | H | H | H | H | H |
| I-173 | 2-Me-c-Pr | $Me_2N$ | Cl | H | H | H | H | H | H |
| I-174 | 2-Me-c-Pr | cyclopentyl-NH | Cl | H | H | H | H | H | H |
| I-175 | 2-Me-c-Pr | Ph—NH | Cl | H | H | H | H | H | H |
| I-176 | 2-Me-c-Pr | Ph—(Bn)N | Cl | H | H | H | H | H | H |
| I-177 | 2-Me-c-Pr | (Pyridin-3-yl)amino | Cl | H | H | H | H | H | H |
| I-178 | 2-Me-c-Pr | Allylamino | Cl | H | H | H | H | H | H |
| I-179 | 2-Me-c-Pr | Propargylamino | Cl | H | H | H | H | H | H |
| I-180 | 2-Me-c-Pr | (Pyrrolidin-1-yl) | Cl | H | H | H | H | H | H |
| I-181 | 2-Me-c-Pr | $F_3CCH_2NH$ | Cl | H | H | H | H | H | H |
| I-182 | 2-Me-c-Pr | Acetylamino | Cl | H | H | H | H | H | H |
| I-183 | 2-Me-c-Pr | Benzoylamino | Cl | H | H | H | H | H | H |
| I-184 | 2-Me-c-Pr | (Ethoxycarbonyl)amino | Cl | H | H | H | H | H | H |
| I-185 | 2-Me-c-Pr | (N,N-Dimethyl-amino)carbonyl-amino | Cl | H | H | H | H | H | H |
| I-186 | 2-Me-c-Pr | (N,N-Dimethylamino)(thio-carbonyl)amino | Cl | H | H | H | H | H | H |
| I-187 | 2-Me-c-Pr | (Methylsulfonyl)amino | Cl | H | H | H | H | H | H |
| I-188 | c-Pr | $NH_2$ | H | Cl | H | H | H | H | H |
| I-189 | c-Pr | MeNH | H | Cl | H | H | H | H | H |
| I-190 | c-Pr | $Me_2N$ | H | Cl | H | H | H | H | H |
| I-191 | c-Pr | cyclopentyl-NH | H | Cl | H | H | H | H | H |
| I-192 | c-Pr | Ph—NH | H | Cl | H | H | H | H | H |
| I-193 | c-Pr | Ph—(Bn)N | H | Cl | H | H | H | H | H |
| I-194 | c-Pr | (Pyridin-3-yl)amino | H | Cl | H | H | H | H | H |
| I-195 | c-Pr | Allylamino | H | Cl | H | H | H | H | H |
| I-196 | c-Pr | Propargylamino | H | Cl | H | H | H | H | H |
| I-197 | c-Pr | (Pyrrolidin-1-yl) | H | Cl | H | H | H | H | H |
| I-198 | c-Pr | $F_3CCH_2NH$ | H | Cl | H | H | H | H | H |
| I-199 | c-Pr | Acetylamino | H | Cl | H | H | H | H | H |
| I-200 | c-Pr | Benzoylamino | H | Cl | H | H | H | H | H |
| I-201 | c-Pr | (Ethoxycarbonyl)amino | H | Cl | H | H | H | H | H |
| I-202 | c-Pr | (N,N-Dimethyl-amino)carbonyl-amino | H | Cl | H | H | H | H | H |
| I-203 | c-Pr | (N,N-Dimethylamino)(thio-carbonyl)amino | H | Cl | H | H | H | H | H |
| I-204 | c-Pr | (Methylsulfonyl)amino | H | Cl | H | H | H | H | H |
| I-205 | c-Pr | $NH_2$ | H | H | Cl | H | H | H | H |
| I-206 | c-Pr | MeNH | H | H | Cl | H | H | H | H |
| I-207 | c-Pr | $Me_2N$ | H | H | Cl | H | H | H | H |
| I-208 | c-Pr | cyclopentyl-NH | H | H | Cl | H | H | H | H |
| I-209 | c-Pr | Ph—NH | H | H | Cl | H | H | H | H |
| I-210 | c-Pr | Ph—(Bn)N | H | H | Cl | H | H | H | H |
| I-211 | c-Pr | (Pyridin-3-yl)amino | H | H | Cl | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-212 | c-Pr | Allylamino | H | H | Cl | H | H | H | H |
| I-213 | c-Pr | Propargylamino | H | H | Cl | H | H | H | H |
| I-214 | c-Pr | (Pyrrolidin-1-yl) | H | H | Cl | H | H | H | H |
| I-215 | c-Pr | F$_3$CCH$_2$NH | H | H | Cl | H | H | H | H |
| I-216 | c-Pr | Acetylamino | H | H | Cl | H | H | H | H |
| I-217 | c-Pr | Benzoylamino | H | H | Cl | H | H | H | H |
| I-218 | c-Pr | (Ethoxycarbonyl)amino | H | H | Cl | H | H | H | H |
| I-219 | c-Pr | (N,N-Dimethyl-amino)carbonyl-amino | H | H | Cl | H | H | H | H |
| I-220 | c-Pr | (N,N-Dimethylamino)(thio-carbonyl)amino | H | H | Cl | H | H | H | H |
| I-221 | c-Pr | (Methylsulfonyl)amino | H | H | Cl | H | H | H | H |
| I-222 | c-Pr | NH$_2$ | Me | H | H | H | H | H | H |
| I-223 | c-Pr | MeNH | Me | H | H | H | H | H | H |
| I-224 | c-Pr | Me$_2$N | Me | H | H | H | H | H | H |
| I-225 | c-Pr | cyclopentyl-NH | Me | H | H | H | H | H | H |
| I-226 | c-Pr | Ph—NH | Me | H | H | H | H | H | H |
| I-227 | c-Pr | Ph—(Bn)N | Me | H | H | H | H | H | H |
| I-228 | c-Pr | (Pyridin-3-yl)amino | Me | H | H | H | H | H | H |
| I-229 | c-Pr | Allylamino | Me | H | H | H | H | H | H |
| I-230 | c-Pr | Propargylamino | Me | H | H | H | H | H | H |
| I-231 | c-Pr | (Pyrrolidin-1-yl) | Me | H | H | H | H | H | H |
| I-232 | c-Pr | F$_3$CCH$_2$NH | Me | H | H | H | H | H | H |
| I-233 | c-Pr | Acetylamino | Me | H | H | H | H | H | H |
| I-234 | c-Pr | Benzoylamino | Me | H | H | H | H | H | H |
| I-235 | c-Pr | (Ethoxycarbonyl)amino | Me | H | H | H | H | H | H |
| I-236 | c-Pr | (N,N-Dimethyl-amino)carbonyl-amino | Me | H | H | H | H | H | H |
| I-237 | c-Pr | (N,N-Dimethylamino)(thio-carbonyl)amino | Me | H | H | H | H | H | H |
| I-238 | c-Pr | (Methylsulfonyl)amino | Me | H | H | H | H | H | H |
| I-239 | 1-Me-c-Pr | NH$_2$ | Me | H | H | H | H | H | H |
| I-240 | 1-Me-c-Pr | MeNH | Me | H | H | H | H | H | H |
| I-241 | 1-Me-c-Pr | Me$_2$N | Me | H | H | H | H | H | H |
| I-242 | 1-Me-c-Pr | cyclopentyl-NH | Me | H | H | H | H | H | H |
| I-243 | 1-Me-c-Pr | Ph—NH | Me | H | H | H | H | H | H |
| I-244 | 1-Me-c-Pr | Ph—(Bn)N | Me | H | H | H | H | H | H |
| I-245 | 1-Me-c-Pr | (Pyridin-3-yl)amino | Me | H | H | H | H | H | H |
| I-246 | 1-Me-c-Pr | Allylamino | Me | H | H | H | H | H | H |
| I-247 | 1-Me-c-Pr | Propargylamino | Me | H | H | H | H | H | H |
| I-248 | 1-Me-c-Pr | (Pyrrolidin-1-yl) | Me | H | H | H | H | H | H |
| I-249 | 1-Me-c-Pr | F$_3$CCH$_2$NH | Me | H | H | H | H | H | H |
| I-250 | 1-Me-c-Pr | Acetylamino | Me | H | H | H | H | H | H |
| I-251 | 1-Me-c-Pr | Benzoylamino | Me | H | H | H | H | H | H |
| I-252 | 1-Me-c-Pr | (Ethoxycarbonyl)amino | Me | H | H | H | H | H | H |
| I-253 | 1-Me-c-Pr | (N,N-Dimethyl-amino)carbonyl-amino | Me | H | H | H | H | H | H |
| I-254 | 1-Me-c-Pr | (N,N-Dimethylamino)(thio-carbonyl)amino | Me | H | H | H | H | H | H |
| I-255 | 1-Me-c-Pr | (Methylsulfonyl)amino | Me | H | H | H | H | H | H |
| I-256 | 2-Me-c-Pr | NH$_2$ | Me | H | H | H | H | H | H |
| I-257 | 2-Me-c-Pr | MeNH | Me | H | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-258 | 2-Me-c-Pr | Me₂N | Me | H | H | H | H | H | H |
| I-259 | 2-Me-c-Pr | cyclopentyl-NH | Me | H | H | H | H | H | H |
| I-260 | 2-Me-c-Pr | Ph—NH | Me | H | H | H | H | H | H |
| I-261 | 2-Me-c-Pr | Ph—(Bn)N | Me | H | H | H | H | H | H |
| I-262 | 2-Me-c-Pr | (Pyridin-3-yl)amino | Me | H | H | H | H | H | H |
| I-263 | 2-Me-c-Pr | Allylamino | Me | H | H | H | H | H | H |
| I-264 | 2-Me-c-Pr | Propargylamino | Me | H | H | H | H | H | H |
| I-265 | 2-Me-c-Pr | (Pyrrolidin-1-yl) | Me | H | H | H | H | H | H |
| I-266 | 2-Me-c-Pr | F₃CCH₂NH | Me | H | H | H | H | H | H |
| I-267 | 2-Me-c-Pr | Acetylamino | Me | H | H | H | H | H | H |
| I-268 | 2-Me-c-Pr | Benzoylamino | Me | H | H | H | H | H | H |
| I-269 | 2-Me-c-Pr | (Ethoxycarbonyl)amino | Me | H | H | H | H | H | H |
| I-270 | 2-Me-c-Pr | (N,N-Dimethyl-amino)carbonyl-amino | Me | H | H | H | H | H | H |
| I-271 | 2-Me-c-Pr | (N,N-Dimethylamino)(thio-carbonyl)amino | Me | H | H | H | H | H | H |
| I-272 | 2-Me-c-Pr | (Methylsulfonyl)amino | Me | H | H | H | H | H | H |
| I-273 | c-Pr | NH₂ | H | Me | H | H | H | H | H |
| I-274 | c-Pr | MeNH | H | Me | H | H | H | H | H |
| I-275 | c-Pr | Me₂N | H | Me | H | H | H | H | H |
| I-276 | c-Pr | cyclopentyl-NH | H | Me | H | H | H | H | H |
| I-277 | c-Pr | Ph—NH | H | Me | H | H | H | H | H |
| I-278 | c-Pr | Ph—(Bn)N | H | Me | H | H | H | H | H |
| I-279 | c-Pr | (Pyridin-3-yl)amino | H | Me | H | H | H | H | H |
| I-280 | c-Pr | Allylamino | H | Me | H | H | H | H | H |
| I-281 | c-Pr | Propargylamino | H | Me | H | H | H | H | H |
| I-282 | c-Pr | (Pyrrolidin-1-yl) | H | Me | H | H | H | H | H |
| I-283 | c-Pr | F₃CCH₂NH | H | Me | H | H | H | H | H |
| I-284 | c-Pr | Acetylamino | H | Me | H | H | H | H | H |
| I-285 | c-Pr | Benzoylamino | H | Me | H | H | H | H | H |
| I-286 | c-Pr | (Ethoxycarbonyl)amino | H | Me | H | H | H | H | H |
| I-287 | c-Pr | (N,N-Dimethyl-amino)carbonyl-amino | H | Me | H | H | H | H | H |
| I-288 | c-Pr | (N,N-Dimethylamino)(thio-carbonyl)amino | H | Me | H | H | H | H | H |
| I-289 | c-Pr | (Methylsulfonyl)amino | H | Me | H | H | H | H | H |
| I-290 | c-Pr | NH₂ | H | H | Me | H | H | H | H |
| I-291 | c-Pr | MeNH | H | H | Me | H | H | H | H |
| I-292 | c-Pr | Me₂N | H | H | Me | H | H | H | H |
| I-293 | c-Pr | cyclopentyl-NH | H | H | Me | H | H | H | H |
| I-294 | c-Pr | Ph—NH | H | H | Me | H | H | H | H |
| I-295 | c-Pr | Ph—(Bn)N | H | H | Me | H | H | H | H |
| I-296 | c-Pr | (Pyridin-3-yl)amino | H | H | Me | H | H | H | H |
| I-297 | c-Pr | Allylamino | H | H | Me | H | H | H | H |
| I-298 | c-Pr | Propargylamino | H | H | Me | H | H | H | H |
| I-299 | c-Pr | (Pyrrolidin-1-yl) | H | H | Me | H | H | H | H |
| I-300 | c-Pr | F₃CCH₂NH | H | H | Me | H | H | H | H |
| I-301 | c-Pr | Acetylamino | H | H | Me | H | H | H | H |
| I-302 | c-Pr | Benzoylamino | H | H | Me | H | H | H | H |
| I-303 | c-Pr | (Ethoxycarbonyl)amino | H | H | Me | H | H | H | H |
| I-304 | c-Pr | (N,N-Dimethyl-amino)carbonyl-amino | H | H | Me | H | H | H | H |

TABLE 1-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-305 | c-Pr | (N,N-Dimethylamino)(thiocarbonyl)amino | H | H | Me | H | H | H | H |
| I-306 | c-Pr | (Methylsulfonyl)amino | H | H | Me | H | H | H | H |
| I-307 | c-Pr | $NH_2$ | $CF_3$ | H | H | H | H | H | H |
| I-308 | c-Pr | MeNH | $CF_3$ | H | H | H | H | H | H |
| I-309 | c-Pr | $Me_2N$ | $CF_3$ | H | H | H | H | H | H |
| I-310 | c-Pr | cyclopentyl-NH | $CF_3$ | H | H | H | H | H | H |
| I-311 | c-Pr | Ph—NH | $CF_3$ | H | H | H | H | H | H |
| I-312 | c-Pr | Ph—(Bn)N | $CF_3$ | H | H | H | H | H | H |
| I-313 | c-Pr | (Pyridin-3-yl)amino | $CF_3$ | H | H | H | H | H | H |
| I-314 | c-Pr | Allylamino | $CF_3$ | H | H | H | H | H | H |
| I-315 | c-Pr | Propargylamino | $CF_3$ | H | H | H | H | H | H |
| I-316 | c-Pr | (Pyrrolidin-1-yl) | $CF_3$ | H | H | H | H | H | H |
| I-317 | c-Pr | $F_3CCH_2NH$ | $CF_3$ | H | H | H | H | H | H |
| I-318 | c-Pr | Acetylamino | $CF_3$ | H | H | H | H | H | H |
| I-319 | c-Pr | Benzoylamino | $CF_3$ | H | H | H | H | H | H |
| I-320 | c-Pr | (Ethoxycarbonyl)amino | $CF_3$ | H | H | H | H | H | H |
| I-321 | c-Pr | (N,N-Dimethylamino)carbonylamino | $CF_3$ | H | H | H | H | H | H |
| I-322 | c-Pr | (N,N-Dimethylamino)(thiocarbonyl)amino | $CF_3$ | H | H | H | H | H | H |
| I-323 | c-Pr | (Methylsulfonyl)amino | $CF_3$ | H | H | H | H | H | H |
| I-324 | 1-Me-c-Pr | $NH_2$ | $CF_3$ | H | H | H | H | H | H |
| I-325 | 1-Me-c-Pr | MeNH | $CF_3$ | H | H | H | H | H | H |
| I-326 | 1-Me-c-Pr | $Me_2N$ | $CF_3$ | H | H | H | H | H | H |
| I-327 | 1-Me-c-Pr | cyclopentyl-NH | $CF_3$ | H | H | H | H | H | H |
| I-328 | 1-Me-c-Pr | Ph—NH | $CF_3$ | H | H | H | H | H | H |
| I-329 | 1-Me-c-Pr | Ph—(Bn)N | $CF_3$ | H | H | H | H | H | H |
| I-330 | 1-Me-c-Pr | (Pyridin-3-yl)amino | $CF_3$ | H | H | H | H | H | H |
| I-331 | 1-Me-c-Pr | Allylamino | $CF_3$ | H | H | H | H | H | H |
| I-332 | 1-Me-c-Pr | Propargylamino | $CF_3$ | H | H | H | H | H | H |
| I-333 | 1-Me-c-Pr | (Pyrrolidin-1-yl) | $CF_3$ | H | H | H | H | H | H |
| I-334 | 1-Me-c-Pr | $F_3CCH_2NH$ | $CF_3$ | H | H | H | H | H | H |
| I-335 | 1-Me-c-Pr | Acetylamino | $CF_3$ | H | H | H | H | H | H |
| I-336 | 1-Me-c-Pr | Benzoylamino | $CF_3$ | H | H | H | H | H | H |
| I-337 | 1-Me-c-Pr | (Ethoxycarbonyl)amino | $CF_3$ | H | H | H | H | H | H |
| I-338 | 1-Me-c-Pr | (N,N-Dimethylamino)carbonylamino | $CF_3$ | H | H | H | H | H | H |
| I-339 | 1-Me-c-Pr | (N,N-Dimethylamino)(thiocarbonyl)amino | $CF_3$ | H | H | H | H | H | H |
| I-340 | 1-Me-c-Pr | (Methylsulfonyl)amino | $CF_3$ | H | H | H | H | H | H |
| I-341 | 2-Me-c-Pr | $NH_2$ | $CF_3$ | H | H | H | H | H | H |
| I-342 | 2-Me-c-Pr | MeNH | $CF_3$ | H | H | H | H | H | H |
| I-343 | 2-Me-c-Pr | $Me_2N$ | $CF_3$ | H | H | H | H | H | H |
| I-344 | 2-Me-c-Pr | cyclopentyl-NH | $CF_3$ | H | H | H | H | H | H |
| I-345 | 2-Me-c-Pr | Ph—NH | $CF_3$ | H | H | H | H | H | H |
| I-346 | 2-Me-c-Pr | Ph—(Bn)N | $CF_3$ | H | H | H | H | H | H |
| I-347 | 2-Me-c-Pr | (Pyridin-3-yl)amino | $CF_3$ | H | H | H | H | H | H |
| I-348 | 2-Me-c-Pr | Allylamino | $CF_3$ | H | H | H | H | H | H |
| I-349 | 2-Me-c-Pr | Propargylamino | $CF_3$ | H | H | H | H | H | H |
| I-350 | 2-Me-c-Pr | (Pyrrolidin-1-yl) | $CF_3$ | H | H | H | H | H | H |
| I-351 | 2-Me-c-Pr | $F_3CCH_2NH$ | $CF_3$ | H | H | H | H | H | H |
| I-352 | 2-Me-c-Pr | Acetylamino | $CF_3$ | H | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-353 | 2-Me-c-Pr | Benzoylamino | CF₃ | H | H | H | H | H | H |
| I-354 | 2-Me-c-Pr | (Ethoxycarbonyl)amino | CF₃ | H | H | H | H | H | H |
| I-355 | 2-Me-c-Pr | (N,N-Dimethyl-amino)carbonyl-amino | CF₃ | H | H | H | H | H | H |
| I-356 | 2-Me-c-Pr | (N,N-Dimethylamino)(thio-carbonyl)amino | CF₃ | H | H | H | H | H | H |
| I-357 | 2-Me-c-Pr | (Methylsulfonyl)amino | CF₃ | H | H | H | H | H | H |
| I-358 | c-Pr | NH₂ | H | CF₃ | H | H | H | H | H |
| I-359 | c-Pr | MeNH | H | CF₃ | H | H | H | H | H |
| I-360 | c-Pr | Me₂N | H | CF₃ | H | H | H | H | H |
| I-361 | c-Pr | cyclopentyl-NH | H | CF₃ | H | H | H | H | H |
| I-362 | c-Pr | Ph—NH | H | CF₃ | H | H | H | H | H |
| I-363 | c-Pr | Ph—(Bn)N | H | CF₃ | H | H | H | H | H |
| I-364 | c-Pr | (Pyridin-3-yl)amino | H | CF₃ | H | H | H | H | H |
| I-365 | c-Pr | Allylamino | H | CF₃ | H | H | H | H | H |
| I-366 | c-Pr | Propargylamino | H | CF₃ | H | H | H | H | H |
| I-367 | c-Pr | (Pyrrolidin-1-yl) | H | CF₃ | H | H | H | H | H |
| I-368 | c-Pr | F₃CCH₂NH | H | CF₃ | H | H | H | H | H |
| I-369 | c-Pr | Acetylamino | H | CF₃ | H | H | H | H | H |
| I-370 | c-Pr | Benzoylamino | H | CF₃ | H | H | H | H | H |
| I-371 | c-Pr | (Ethoxycarbonyl)amino | H | CF₃ | H | H | H | H | H |
| I-372 | c-Pr | (N,N-Dimethyl-amino)carbonyl-amino | H | CF₃ | H | H | H | H | H |
| I-373 | c-Pr | (N,N-Dimethylamino)(thio-carbonyl)amino | H | CF₃ | H | H | H | H | H |
| I-374 | c-Pr | (Methylsulfonyl)amino | H | CF₃ | H | H | H | H | H |
| I-375 | c-Pr | NH₂ | H | H | CF₃ | H | H | H | H |
| I-376 | c-Pr | MeNH | H | H | CF₃ | H | H | H | H |
| I-377 | c-Pr | Me₂N | H | H | CF₃ | H | H | H | H |
| I-378 | c-Pr | cyclopentyl-NH | H | H | CF₃ | H | H | H | H |
| I-379 | c-Pr | Ph—NH | H | H | CF₃ | H | H | H | H |
| I-380 | c-Pr | Ph—(Bn)N | H | H | CF₃ | H | H | H | H |
| I-381 | c-Pr | (Pyridin-3-yl)amino | H | H | CF₃ | H | H | H | H |
| I-382 | c-Pr | Allylamino | H | H | CF₃ | H | H | H | H |
| I-383 | c-Pr | Propargylamino | H | H | CF₃ | H | H | H | H |
| I-384 | c-Pr | (Pyrrolidin-1-yl) | H | H | CF₃ | H | H | H | H |
| I-385 | c-Pr | F₃CCH₂NH | H | H | CF₃ | H | H | H | H |
| I-386 | c-Pr | Acetylamino | H | H | CF₃ | H | H | H | H |
| I-387 | c-Pr | Benzoylamino | H | H | CF₃ | H | H | H | H |
| I-388 | c-Pr | (Ethoxycarbonyl)amino | H | H | CF₃ | H | H | H | H |
| I-389 | c-Pr | (N,N-Dimethyl-amino)carbonyl-amino | H | H | CF₃ | H | H | H | H |
| I-390 | c-Pr | (N,N-Dimethylamino)(thio-carbonyl)amino | H | H | CF₃ | H | H | H | H |
| I-391 | c-Pr | (Methylsulfonyl)amino | H | H | CF₃ | H | H | H | H |
| I-392 | c-Pr | NH₂ | MeO | H | H | H | H | H | H |
| I-393 | c-Pr | MeNH | MeO | H | H | H | H | H | H |
| I-394 | c-Pr | Me₂N | MeO | H | H | H | H | H | H |
| I-395 | c-Pr | cyclopentyl-NH | MeO | H | H | H | H | H | H |
| I-396 | c-Pr | Ph—NH | MeO | H | H | H | H | H | H |
| I-397 | c-Pr | Ph—(Bn)N | MeO | H | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-398 | c-Pr | (Pyridin-3-yl)amino | MeO | H | H | H | H | H | H |
| I-399 | c-Pr | Allylamino | MeO | H | H | H | H | H | H |
| I-400 | c-Pr | Propargylamino | MeO | H | H | H | H | H | H |
| I-401 | c-Pr | (Pyrrolidin-1-yl) | MeO | H | H | H | H | H | H |
| I-402 | c-Pr | $F_3CCH_2NH$ | MeO | H | H | H | H | H | H |
| I-403 | c-Pr | Acetylamino | MeO | H | H | H | H | H | H |
| I-404 | c-Pr | Benzoylamino | MeO | H | H | H | H | H | H |
| I-405 | c-Pr | (Ethoxycarbonyl)amino | MeO | H | H | H | H | H | H |
| I-406 | c-Pr | (N,N-Dimethyl-amino)carbonyl-amino | MeO | H | H | H | H | H | H |
| I-407 | c-Pr | (N,N-Dimethylamino)(thio-carbonyl)amino | MeO | H | H | H | H | H | H |
| I-408 | c-Pr | (Methylsulfonyl)amino | MeO | H | H | H | H | H | H |
| I-409 | 1-Me-c-Pr | $NH_2$ | MeO | H | H | H | H | H | H |
| I-410 | 1-Me-c-Pr | MeNH | MeO | H | H | H | H | H | H |
| I-411 | 1-Me-c-Pr | $Me_2N$ | MeO | H | H | H | H | H | H |
| I-412 | 1-Me-c-Pr | cyclopentyl-NH | MeO | H | H | H | H | H | H |
| I-413 | 1-Me-c-Pr | Ph—NH | MeO | H | H | H | H | H | H |
| I-414 | 1-Me-c-Pr | Ph—(Bn)N | MeO | H | H | H | H | H | H |
| I-415 | 1-Me-c-Pr | (Pyridin-3-yl)amino | MeO | H | H | H | H | H | H |
| I-416 | 1-Me-c-Pr | Allylamino | MeO | H | H | H | H | H | H |
| I-417 | 1-Me-c-Pr | Propargylamino | MeO | H | H | H | H | H | H |
| I-418 | 1-Me-c-Pr | (Pyrrolidin-1-yl) | MeO | H | H | H | H | H | H |
| I-419 | 1-Me-c-Pr | $F_3CCH_2NH$ | MeO | H | H | H | H | H | H |
| I-420 | 1-Me-c-Pr | Acetylamino | MeO | H | H | H | H | H | H |
| I-421 | 1-Me-c-Pr | Benzoylamino | MeO | H | H | H | H | H | H |
| I-422 | 1-Me-c-Pr | (Ethoxycarbonyl)amino | MeO | H | H | H | H | H | H |
| I-423 | 1-Me-c-Pr | (N,N-Dimethyl-amino)carbonyl-amino | MeO | H | H | H | H | H | H |
| I-424 | 1-Me-c-Pr | (N,N-Dimethylamino)(thio-carbonyl)amino | MeO | H | H | H | H | H | H |
| I-425 | 1-Me-c-Pr | (Methylsulfonyl)amino | MeO | H | H | H | H | H | H |
| I-426 | c-Pr | $NH_2$ | H | MeO | H | H | H | H | H |
| I-427 | c-Pr | MeNH | H | MeO | H | H | H | H | H |
| I-428 | c-Pr | $Me_2N$ | H | MeO | H | H | H | H | H |
| I-429 | c-Pr | cyclopentyl-NH | H | MeO | H | H | H | H | H |
| I-430 | c-Pr | Ph—NH | H | MeO | H | H | H | H | H |
| I-431 | c-Pr | Ph—(Bn)N | H | MeO | H | H | H | H | H |
| I-432 | c-Pr | (Pyridin-3-yl)amino | H | MeO | H | H | H | H | H |
| I-433 | c-Pr | Allylamino | H | MeO | H | H | H | H | H |
| I-434 | c-Pr | Propargylamino | H | MeO | H | H | H | H | H |
| I-435 | c-Pr | (Pyrrolidin-1-yl) | H | MeO | H | H | H | H | H |
| I-436 | c-Pr | $F_3CCH_2NH$ | H | MeO | H | H | H | H | H |
| I-437 | c-Pr | Acetylamino | H | MeO | H | H | H | H | H |
| I-438 | c-Pr | Benzoylamino | H | MeO | H | H | H | H | H |
| I-439 | c-Pr | (Ethoxycarbonyl)amino | H | MeO | H | H | H | H | H |
| I-440 | c-Pr | (N,N-Dimethyl-amino)carbonyl-amino | H | MeO | H | H | H | H | H |
| I-441 | c-Pr | (N,N-Dimethylamino)(thio-carbonyl)amino | H | MeO | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-442 | c-Pr | (Methylsulfonyl)amino | H | MeO | H | H | H | H | H |
| I-443 | c-Pr | NH$_2$ | H | H | MeO | H | H | H | H |
| I-444 | c-Pr | MeNH | H | H | MeO | H | H | H | H |
| I-445 | c-Pr | Me$_2$N | H | H | MeO | H | H | H | H |
| I-446 | c-Pr | cyclopentyl-NH | H | H | MeO | H | H | H | H |
| I-447 | c-Pr | Ph—NH | H | H | MeO | H | H | H | H |
| I-448 | c-Pr | Ph—(Bn)N | H | H | MeO | H | H | H | H |
| I-449 | c-Pr | (Pyridin-3-yl)amino | H | H | MeO | H | H | H | H |
| I-450 | c-Pr | Allylamino | H | H | MeO | H | H | H | H |
| I-451 | c-Pr | Propargylamino | H | H | MeO | H | H | H | H |
| I-452 | c-Pr | (Pyrrolidin-1-yl) | H | H | MeO | H | H | H | H |
| I-453 | c-Pr | F$_3$CCH$_2$NH | H | H | MeO | H | H | H | H |
| I-454 | c-Pr | Acetylamino | H | H | MeO | H | H | H | H |
| I-455 | c-Pr | Benzoylamino | H | H | MeO | H | H | H | H |
| I-456 | c-Pr | (Ethoxycarbonyl)amino | H | H | MeO | H | H | H | H |
| I-457 | c-Pr | (N,N-Dimethyl-amino)carbonyl-amino | H | H | MeO | H | H | H | H |
| I-458 | c-Pr | (N,N-Dimethylamino)(thio-carbonyl)amino | H | H | MeO | H | H | H | H |
| I-459 | c-Pr | (Methylsulfonyl)amino | H | H | MeO | H | H | H | H |
| I-460 | c-Pr | NH$_2$ | F | F | H | H | H | H | H |
| I-461 | c-Pr | MeNH | F | F | H | H | H | H | H |
| I-462 | c-Pr | Me$_2$N | F | F | H | H | H | H | H |
| I-463 | c-Pr | cyclopentyl-NH | F | F | H | H | H | H | H |
| I-464 | c-Pr | Ph—NH | F | F | H | H | H | H | H |
| I-465 | c-Pr | Ph—(Bn)N | F | F | H | H | H | H | H |
| I-466 | c-Pr | (Pyridin-3-yl)amino | F | F | H | H | H | H | H |
| I-467 | c-Pr | Allylamino | F | F | H | H | H | H | H |
| I-468 | c-Pr | Propargylamino | F | F | H | H | H | H | H |
| I-469 | c-Pr | (Pyrrolidin-1-yl) | F | F | H | H | H | H | H |
| I-470 | c-Pr | F$_3$CCH$_2$NH | F | F | H | H | H | H | H |
| I-471 | c-Pr | Acetylamino | F | F | H | H | H | H | H |
| I-472 | c-Pr | Benzoylamino | F | F | H | H | H | H | H |
| I-473 | c-Pr | (Ethoxycarbonyl)amino | F | F | H | H | H | H | H |
| I-474 | c-Pr | (N,N-Dimethyl-amino)carbonyl-amino | F | F | H | H | H | H | H |
| I-475 | c-Pr | (N,N-Dimethylamino)(thio-carbonyl)amino | F | F | H | H | H | H | H |
| I-476 | c-Pr | (Methylsulfonyl)amino | F | F | H | H | H | H | H |
| I-477 | c-Pr | NH$_2$ | F | H | F | H | H | H | H |
| I-478 | c-Pr | MeNH | F | H | F | H | H | H | H |
| I-479 | c-Pr | Me$_2$N | F | H | F | H | H | H | H |
| I-480 | c-Pr | cyclopentyl-NH | F | H | F | H | H | H | H |
| I-481 | c-Pr | Ph—NH | F | H | F | H | H | H | H |
| I-482 | c-Pr | Ph—(Bn)N | F | H | F | H | H | H | H |
| I-483 | c-Pr | (Pyridin-3-yl)amino | F | H | F | H | H | H | H |
| I-484 | c-Pr | Allylamino | F | H | F | H | H | H | H |
| I-485 | c-Pr | Propargylamino | F | H | F | H | H | H | H |
| I-486 | c-Pr | (Pyrrolidin-1-yl) | F | H | F | H | H | H | H |
| I-487 | c-Pr | F$_3$CCH$_2$NH | F | H | F | H | H | H | H |
| I-488 | c-Pr | Acetylamino | F | H | F | H | H | H | H |
| I-489 | c-Pr | Benzoylamino | F | H | F | H | H | H | H |

TABLE 1-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-490 | c-Pr | (Ethoxycarbonyl)amino | F | H | F | H | H | H | H |
| I-491 | c-Pr | (N,N-Dimethyl-amino)carbonyl-amino | F | H | F | H | H | H | H |
| I-492 | c-Pr | (N,N-Dimethylamino)(thio-carbonyl)amino | F | H | F | H | H | H | H |
| I-493 | c-Pr | (Methylsulfonyl)amino | F | H | F | H | H | H | H |
| I-494 | c-Pr | $NH_2$ | F | H | H | F | H | H | H |
| I-495 | c-Pr | MeNH | F | H | H | F | H | H | H |
| I-496 | c-Pr | $Me_2N$ | F | H | H | F | H | H | H |
| I-497 | c-Pr | cyclopentyl-NH | F | H | H | F | H | H | H |
| I-498 | c-Pr | Ph—NH | F | H | H | F | H | H | H |
| I-499 | c-Pr | Ph—(Bn)N | F | H | H | F | H | H | H |
| I-500 | c-Pr | (Pyridin-3-yl)amino | F | H | H | F | H | H | H |
| I-501 | c-Pr | Allylamino | F | H | H | F | H | H | H |
| I-502 | c-Pr | Propargylamino | F | H | H | F | H | H | H |
| I-503 | c-Pr | (Pyrrolidin-1-yl) | F | H | H | F | H | H | H |
| I-504 | c-Pr | $F_3CCH_2NH$ | F | H | H | F | H | H | H |
| I-505 | c-Pr | Acetylamino | F | H | H | F | H | H | H |
| I-506 | c-Pr | Benzoylamino | F | H | H | F | H | H | H |
| I-507 | c-Pr | (Ethoxycarbonyl)amino | F | H | H | F | H | H | H |
| I-508 | c-Pr | (N,N-Dimethyl-amino)carbonyl-amino | F | H | H | F | H | H | H |
| I-509 | c-Pr | (N,N-Dimethylamino)(thio-carbonyl)amino | F | H | H | F | H | H | H |
| I-510 | c-Pr | (Methylsulfonyl)amino | F | H | H | F | H | H | H |
| I-511 | c-Pr | $NH_2$ | F | H | H | H | F | H | H |
| I-512 | c-Pr | MeNH | F | H | H | H | F | H | H |
| I-513 | c-Pr | $Me_2N$ | F | H | H | H | F | H | H |
| I-514 | c-Pr | cyclopentyl-NH | F | H | H | H | F | H | H |
| I-515 | c-Pr | Ph—NH | F | H | H | H | F | H | H |
| I-516 | c-Pr | Ph—(Bn)N | F | H | H | H | F | H | H |
| I-517 | c-Pr | (Pyridin-3-yl)amino | F | H | H | H | F | H | H |
| I-518 | c-Pr | Allylamino | F | H | H | H | F | H | H |
| I-519 | c-Pr | Propargylamino | F | H | H | H | F | H | H |
| I-520 | c-Pr | (Pyrrolidin-1-yl) | F | H | H | H | F | H | H |
| I-521 | c-Pr | $F_3CCH_2NH$ | F | H | H | H | F | H | H |
| I-522 | c-Pr | Acetylamino | F | H | H | H | F | H | H |
| I-523 | c-Pr | Benzoylamino | F | H | H | H | F | H | H |
| I-524 | c-Pr | (Ethoxycarbonyl)amino | F | H | H | H | F | H | H |
| I-525 | c-Pr | (N,N-Dimethyl-amino)carbonyl-amino | F | H | H | H | F | H | H |
| I-526 | c-Pr | (N,N-Dimethylamino)(thio-carbonyl)amino | F | H | H | H | F | H | H |
| I-527 | c-Pr | (Methylsulfonyl)amino | F | H | H | H | F | H | H |
| I-528 | c-Pr | $NH_2$ | F | Cl | H | H | H | H | H |
| I-529 | c-Pr | MeNH | F | Cl | H | H | H | H | H |
| I-530 | c-Pr | $Me_2N$ | F | Cl | H | H | H | H | H |
| I-531 | c-Pr | cyclopentyl-NH | F | Cl | H | H | H | H | H |
| I-532 | c-Pr | Ph—NH | F | Cl | H | H | H | H | H |
| I-533 | c-Pr | Ph—(Bn)N | F | Cl | H | H | H | H | H |

TABLE 1-continued

Inventive compounds of the formula (I) in which X represents $C(R^{13})(R^{14})$ $$\text{(I)}$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-534 | c-Pr | (Pyridin-3-yl)amino | F | Cl | H | H | H | H | H |
| I-535 | c-Pr | Allylamino | F | Cl | H | H | H | H | H |
| I-536 | c-Pr | Propargylamino | F | Cl | H | H | H | H | H |
| I-537 | c-Pr | (Pyrrolidin-1-yl) | F | Cl | H | H | H | H | H |
| I-538 | c-Pr | $F_3CCH_2NH$ | F | Cl | H | H | H | H | H |
| I-539 | c-Pr | Acetylamino | F | Cl | H | H | H | H | H |
| I-540 | c-Pr | Benzoylamino | F | Cl | H | H | H | H | H |
| I-541 | c-Pr | (Ethoxycarbonyl)amino | F | Cl | H | H | H | H | H |
| I-542 | c-Pr | (N,N-Dimethyl-amino)carbonyl-amino | F | Cl | H | H | H | H | H |
| I-543 | c-Pr | (N,N-Dimethylamino)(thio-carbonyl)amino | F | Cl | H | H | H | H | H |
| I-544 | c-Pr | (Methylsulfonyl)amino | F | Cl | H | H | H | H | H |
| I-545 | c-Pr | $NH_2$ | F | H | Cl | H | H | H | H |
| I-546 | c-Pr | MeNH | F | H | Cl | H | H | H | H |
| I-547 | c-Pr | $Me_2N$ | F | H | Cl | H | H | H | H |
| I-548 | c-Pr | cyclopentyl-NH | F | H | Cl | H | H | H | H |
| I-549 | c-Pr | Ph—NH | F | H | Cl | H | H | H | H |
| I-550 | c-Pr | Ph—(Bn)N | F | H | Cl | H | H | H | H |
| I-551 | c-Pr | (Pyridin-3-yl)amino | F | H | Cl | H | H | H | H |
| I-552 | c-Pr | Allylamino | F | H | Cl | H | H | H | H |
| I-553 | c-Pr | Propargylamino | F | H | Cl | H | H | H | H |
| I-554 | c-Pr | (Pyrrolidin-1-yl) | F | H | Cl | H | H | H | H |
| I-555 | c-Pr | $F_3CCH_2NH$ | F | H | Cl | H | H | H | H |
| I-556 | c-Pr | Acetylamino | F | H | Cl | H | H | H | H |
| I-557 | c-Pr | Benzoylamino | F | H | Cl | H | H | H | H |
| I-558 | c-Pr | (Ethoxycarbonyl)amino | F | H | Cl | H | H | H | H |
| I-559 | c-Pr | (N,N-Dimethyl-amino)carbonyl-amino | F | H | Cl | H | H | H | H |
| I-560 | c-Pr | (N,N-Dimethylamino)(thio-carbonyl)amino | F | H | Cl | H | H | H | H |
| I-561 | c-Pr | (Methylsulfonyl)amino | F | H | Cl | H | H | H | H |
| I-562 | c-Pr | $NH_2$ | F | H | H | Cl | H | H | H |
| I-563 | c-Pr | MeNH | F | H | H | Cl | H | H | H |
| I-564 | c-Pr | $Me_2N$ | F | H | H | Cl | H | H | H |
| I-565 | c-Pr | cyclopentyl-NH | F | H | H | Cl | H | H | H |
| I-566 | c-Pr | Ph—NH | F | H | H | Cl | H | H | H |
| I-567 | c-Pr | Ph—(Bn)N | F | H | H | Cl | H | H | H |
| I-568 | c-Pr | (Pyridin-3-yl)amino | F | H | H | Cl | H | H | H |
| I-569 | c-Pr | Allylamino | F | H | H | Cl | H | H | H |
| I-570 | c-Pr | Propargylamino | F | H | H | Cl | H | H | H |
| I-571 | c-Pr | (Pyrrolidin-1-yl) | F | H | H | Cl | H | H | H |
| I-572 | c-Pr | $F_3CCH_2NH$ | F | H | H | Cl | H | H | H |
| I-573 | c-Pr | Acetylamino | F | H | H | Cl | H | H | H |
| I-574 | c-Pr | Benzoylamino | F | H | H | Cl | H | H | H |
| I-575 | c-Pr | (Ethoxycarbonyl)amino | F | H | H | Cl | H | H | H |
| I-576 | c-Pr | (N,N-Dimethyl-amino)carbonyl-amino | F | H | H | Cl | H | H | H |
| I-577 | c-Pr | (N,N-Dimethylamino)(thio-carbonyl)amino | F | H | H | Cl | H | H | H |

TABLE 1-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-578 | c-Pr | (Methylsulfonyl)amino | F | H | H | Cl | H | H | H |
| I-579 | c-Pr | NH$_2$ | F | H | H | H | Cl | H | H |
| I-580 | c-Pr | MeNH | F | H | H | H | Cl | H | H |
| I-581 | c-Pr | Me$_2$N | F | H | H | H | Cl | H | H |
| I-582 | c-Pr | cyclopentyl-NH | F | H | H | H | Cl | H | H |
| I-583 | c-Pr | Ph—NH | F | H | H | H | Cl | H | H |
| I-584 | c-Pr | Ph—(Bn)N | F | H | H | H | Cl | H | H |
| I-585 | c-Pr | (Pyridin-3-yl)amino | F | H | H | H | Cl | H | H |
| I-586 | c-Pr | Allylamino | F | H | H | H | Cl | H | H |
| I-587 | c-Pr | Propargylamino | F | H | H | H | Cl | H | H |
| I-588 | c-Pr | (Pyrrolidin-1-yl) | F | H | H | H | Cl | H | H |
| I-589 | c-Pr | F$_3$CCH$_2$NH | F | H | H | H | Cl | H | H |
| I-590 | c-Pr | Acetylamino | F | H | H | H | Cl | H | H |
| I-591 | c-Pr | Benzoylamino | F | H | H | H | Cl | H | H |
| I-592 | c-Pr | (Ethoxycarbonyl)amino | F | H | H | H | Cl | H | H |
| I-593 | c-Pr | (N,N-Dimethyl-amino)carbonyl-amino | F | H | H | H | Cl | H | H |
| I-594 | c-Pr | (N,N-Dimethylamino)(thio-carbonyl)amino | F | H | H | H | Cl | H | H |
| I-595 | c-Pr | (Methylsulfonyl)amino | F | H | H | H | Cl | H | H |
| I-596 | c-Pr | NH$_2$ | F | MeO | H | H | H | H | H |
| I-597 | c-Pr | MeNH | F | MeO | H | H | H | H | H |
| I-598 | c-Pr | Me$_2$N | F | MeO | H | H | H | H | H |
| I-599 | c-Pr | cyclopentyl-NH | F | MeO | H | H | H | H | H |
| I-600 | c-Pr | Ph—NH | F | MeO | H | H | H | H | H |
| I-601 | c-Pr | Ph—(Bn)N | F | MeO | H | H | H | H | H |
| I-602 | c-Pr | (Pyridin-3-yl)amino | F | MeO | H | H | H | H | H |
| I-603 | c-Pr | Allylamino | F | MeO | H | H | H | H | H |
| I-604 | c-Pr | Propargylamino | F | MeO | H | H | H | H | H |
| I-605 | c-Pr | (Pyrrolidin-1-yl) | F | MeO | H | H | H | H | H |
| I-606 | c-Pr | F$_3$CCH$_2$NH | F | MeO | H | H | H | H | H |
| I-607 | c-Pr | Acetylamino | F | MeO | H | H | H | H | H |
| I-608 | c-Pr | Benzoylamino | F | MeO | H | H | H | H | H |
| I-609 | c-Pr | (Ethoxycarbonyl)amino | F | MeO | H | H | H | H | H |
| I-610 | c-Pr | (N,N-Dimethyl-amino)carbonyl-amino | F | MeO | H | H | H | H | H |
| I-611 | c-Pr | (N,N-Dimethylamino)(thio-carbonyl)amino | F | MeO | H | H | H | H | H |
| I-612 | c-Pr | (Methylsulfonyl)amino | F | MeO | H | H | H | H | H |
| I-613 | c-Pr | NH$_2$ | F | H | MeO | H | H | H | H |
| I-614 | c-Pr | MeNH | F | H | MeO | H | H | H | H |
| I-615 | c-Pr | Me$_2$N | F | H | MeO | H | H | H | H |
| I-616 | c-Pr | cyclopentyl-NH | F | H | MeO | H | H | H | H |
| I-617 | c-Pr | Ph—NH | F | H | MeO | H | H | H | H |
| I-618 | c-Pr | Ph—(Bn)N | F | H | MeO | H | H | H | H |
| I-619 | c-Pr | (Pyridin-3-yl)amino | F | H | MeO | H | H | H | H |
| I-620 | c-Pr | Allylamino | F | H | MeO | H | H | H | H |
| I-621 | c-Pr | Propargylamino | F | H | MeO | H | H | H | H |
| I-622 | c-Pr | (Pyrrolidin-1-yl) | F | H | MeO | H | H | H | H |
| I-623 | c-Pr | F$_3$CCH$_2$NH | F | H | MeO | H | H | H | H |
| I-624 | c-Pr | Acetylamino | F | H | MeO | H | H | H | H |
| I-625 | c-Pr | Benzoylamino | F | H | MeO | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-626 | c-Pr | (Ethoxycarbonyl)amino | F | H | MeO | H | H | H | H |
| I-627 | c-Pr | (N,N-Dimethyl-amino)carbonyl-amino | F | H | MeO | H | H | H | H |
| I-628 | c-Pr | (N,N-Dimethylamino)(thio-carbonyl)amino | F | H | MeO | H | H | H | H |
| I-629 | c-Pr | (Methylsulfonyl)amino | F | H | MeO | H | H | H | H |
| I-630 | c-Pr | $NH_2$ | F | H | H | MeO | H | H | H |
| I-631 | c-Pr | MeNH | F | H | H | MeO | H | H | H |
| I-632 | c-Pr | $Me_2N$ | F | H | H | MeO | H | H | H |
| I-633 | c-Pr | cyclopentyl-NH | F | H | H | MeO | H | H | H |
| I-634 | c-Pr | Ph—NH | F | H | H | MeO | H | H | H |
| I-635 | c-Pr | Ph—(Bn)N | F | H | H | MeO | H | H | H |
| I-636 | c-Pr | (Pyridin-3-yl)amino | F | H | H | MeO | H | H | H |
| I-637 | c-Pr | Allylamino | F | H | H | MeO | H | H | H |
| I-638 | c-Pr | Propargylamino | F | H | H | MeO | H | H | H |
| I-639 | c-Pr | (Pyrrolidin-1-yl) | F | H | H | MeO | H | H | H |
| I-640 | c-Pr | $F_3CCH_2NH$ | F | H | H | MeO | H | H | H |
| I-641 | c-Pr | Acetylamino | F | H | H | MeO | H | H | H |
| I-642 | c-Pr | Benzoylamino | F | H | H | MeO | H | H | H |
| I-643 | c-Pr | (Ethoxycarbonyl)amino | F | H | H | MeO | H | H | H |
| I-644 | c-Pr | (N,N-Dimethyl-amino)carbonyl-amino | F | H | H | MeO | H | H | H |
| I-645 | c-Pr | (N,N-Dimethylamino)(thio-carbonyl)amino | F | H | H | MeO | H | H | H |
| I-646 | c-Pr | (Methylsulfonyl)amino | F | H | H | MeO | H | H | H |
| I-647 | c-Pr | $NH_2$ | F | H | H | H | MeO | H | H |
| I-648 | c-Pr | MeNH | F | H | H | H | MeO | H | H |
| I-649 | c-Pr | $Me_2N$ | F | H | H | H | MeO | H | H |
| I-650 | c-Pr | cyclopentyl-NH | F | H | H | H | MeO | H | H |
| I-651 | c-Pr | Ph—NH | F | H | H | H | MeO | H | H |
| I-652 | c-Pr | Ph—(Bn)N | F | H | H | H | MeO | H | H |
| I-653 | c-Pr | (Pyridin-3-yl)amino | F | H | H | H | MeO | H | H |
| I-654 | c-Pr | Allylamino | F | H | H | H | MeO | H | H |
| I-655 | c-Pr | Propargylamino | F | H | H | H | MeO | H | H |
| I-656 | c-Pr | (Pyrrolidin-1-yl) | F | H | H | H | MeO | H | H |
| I-657 | c-Pr | $F_3CCH_2NH$ | F | H | H | H | MeO | H | H |
| I-658 | c-Pr | Acetylamino | F | H | H | H | MeO | H | H |
| I-659 | c-Pr | Benzoylamino | F | H | H | H | MeO | H | H |
| I-660 | c-Pr | (Ethoxycarbonyl)amino | F | H | H | H | MeO | H | H |
| I-661 | c-Pr | (N,N-Dimethyl-amino)carbonyl-amino | F | H | H | H | MeO | H | H |
| I-662 | c-Pr | (N,N-Dimethylamino)(thio-carbonyl)amino | F | H | H | H | MeO | H | H |
| I-663 | c-Pr | (Methylsulfonyl)amino | F | H | H | H | MeO | H | H |
| I-664 | c-Pr | $NH_2$ | Cl | F | H | H | H | H | H |
| I-665 | c-Pr | MeNH | Cl | F | H | H | H | H | H |
| I-666 | c-Pr | $Me_2N$ | Cl | F | H | H | H | H | H |
| I-667 | c-Pr | cyclopentyl-NH | Cl | F | H | H | H | H | H |
| I-668 | c-Pr | Ph—NH | Cl | F | H | H | H | H | H |
| I-669 | c-Pr | Ph—(Bn)N | Cl | F | H | H | H | H | H |
| I-670 | c-Pr | (Pyridin-3-yl)amino | Cl | F | H | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-671 | c-Pr | Allylamino | Cl | F | H | H | H | H | H |
| I-672 | c-Pr | Propargylamino | Cl | F | H | H | H | H | H |
| I-673 | c-Pr | (Pyrrolidin-1-yl) | Cl | F | H | H | H | H | H |
| I-674 | c-Pr | $F_3CCH_2NH$ | Cl | F | H | H | H | H | H |
| I-675 | c-Pr | Acetylamino | Cl | F | H | H | H | H | H |
| I-676 | c-Pr | Benzoylamino | Cl | F | H | H | H | H | H |
| I-677 | c-Pr | (Ethoxycarbonyl)amino | Cl | F | H | H | H | H | H |
| I-678 | c-Pr | (N,N-Dimethyl-amino)carbonyl-amino | Cl | F | H | H | H | H | H |
| I-679 | c-Pr | (N,N-Dimethylamino)(thio-carbonyl)amino | Cl | F | H | H | H | H | H |
| I-680 | c-Pr | (Methylsulfonyl)amino | Cl | F | H | H | H | H | H |
| I-681 | c-Pr | $NH_2$ | Cl | H | F | H | H | H | H |
| I-682 | c-Pr | MeNH | Cl | H | F | H | H | H | H |
| I-683 | c-Pr | $Me_2N$ | Cl | H | F | H | H | H | H |
| I-684 | c-Pr | cyclopentyl-NH | Cl | H | F | H | H | H | H |
| I-685 | c-Pr | Ph—NH | Cl | H | F | H | H | H | H |
| I-686 | c-Pr | Ph—(Bn)N | Cl | H | F | H | H | H | H |
| I-687 | c-Pr | (Pyridin-3-yl)amino | Cl | H | F | H | H | H | H |
| I-688 | c-Pr | Allylamino | Cl | H | F | H | H | H | H |
| I-689 | c-Pr | Propargylamino | Cl | H | F | H | H | H | H |
| I-690 | c-Pr | (Pyrrolidin-1-yl) | Cl | H | F | H | H | H | H |
| I-691 | c-Pr | $F_3CCH_2NH$ | Cl | H | F | H | H | H | H |
| I-692 | c-Pr | Acetylamino | Cl | H | F | H | H | H | H |
| I-693 | c-Pr | Benzoylamino | Cl | H | F | H | H | H | H |
| I-694 | c-Pr | (Ethoxycarbonyl)amino | Cl | H | F | H | H | H | H |
| I-695 | c-Pr | (N,N-Dimethyl-amino)carbonyl-amino | Cl | H | F | H | H | H | H |
| I-696 | c-Pr | (N,N-Dimethylamino)(thio-carbonyl)amino | Cl | H | F | H | H | H | H |
| I-697 | c-Pr | (Methylsulfonyl)amino | Cl | H | F | H | H | H | H |
| I-698 | c-Pr | $NH_2$ | Cl | H | H | F | H | H | H |
| I-699 | c-Pr | MeNH | Cl | H | H | F | H | H | H |
| I-700 | c-Pr | $Me_2N$ | Cl | H | H | F | H | H | H |
| I-701 | c-Pr | cyclopentyl-NH | Cl | H | H | F | H | H | H |
| I-702 | c-Pr | Ph—NH | Cl | H | H | F | H | H | H |
| I-703 | c-Pr | Ph—(Bn)N | Cl | H | H | F | H | H | H |
| I-704 | c-Pr | (Pyridin-3-yl)amino | Cl | H | H | F | H | H | H |
| I-705 | c-Pr | Allylamino | Cl | H | H | F | H | H | H |
| I-706 | c-Pr | Propargylamino | Cl | H | H | F | H | H | H |
| I-707 | c-Pr | (Pyrrolidin-1-yl) | Cl | H | H | F | H | H | H |
| I-708 | c-Pr | $F_3CCH_2NH$ | Cl | H | H | F | H | H | H |
| I-709 | c-Pr | Acetylamino | Cl | H | H | F | H | H | H |
| I-710 | c-Pr | Benzoylamino | Cl | H | H | F | H | H | H |
| I-711 | c-Pr | (Ethoxycarbonyl)amino | Cl | H | H | F | H | H | H |
| I-712 | c-Pr | (N,N-Dimethyl-amino)carbonyl-amino | Cl | H | H | F | H | H | H |
| I-713 | c-Pr | (N,N-Dimethylamino)(thio-carbonyl)amino | Cl | H | H | F | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-714 | c-Pr | (Methylsulfonyl)amino | Cl | H | H | F | H | H | H |
| I-715 | c-Pr | NH$_2$ | Cl | Cl | H | H | H | H | H |
| I-716 | c-Pr | MeNH | Cl | Cl | H | H | H | H | H |
| I-717 | c-Pr | Me$_2$N | Cl | Cl | H | H | H | H | H |
| I-718 | c-Pr | cyclopentyl-NH | Cl | Cl | H | H | H | H | H |
| I-719 | c-Pr | Ph—NH | Cl | Cl | H | H | H | H | H |
| I-720 | c-Pr | Ph—(Bn)N | Cl | Cl | H | H | H | H | H |
| I-721 | c-Pr | (Pyridin-3-yl)amino | Cl | Cl | H | H | H | H | H |
| I-722 | c-Pr | Allylamino | Cl | Cl | H | H | H | H | H |
| I-723 | c-Pr | Propargylamino | Cl | Cl | H | H | H | H | H |
| I-724 | c-Pr | (Pyrrolidin-1-yl) | Cl | Cl | H | H | H | H | H |
| I-725 | c-Pr | F$_3$CCH$_2$NH | Cl | Cl | H | H | H | H | H |
| I-726 | c-Pr | Acetylamino | Cl | Cl | H | H | H | H | H |
| I-727 | c-Pr | Benzoylamino | Cl | Cl | H | H | H | H | H |
| I-728 | c-Pr | (Ethoxycarbonyl)amino | Cl | Cl | H | H | H | H | H |
| I-729 | c-Pr | (N,N-Dimethyl-amino)carbonyl-amino | Cl | Cl | H | H | H | H | H |
| I-730 | c-Pr | (N,N-Dimethylamino)(thio-carbonyl)amino | Cl | Cl | H | H | H | H | H |
| I-731 | c-Pr | (Methylsulfonyl)amino | Cl | Cl | H | H | H | H | H |
| I-732 | c-Pr | NH$_2$ | Cl | H | Cl | H | H | H | H |
| I-733 | c-Pr | MeNH | Cl | H | Cl | H | H | H | H |
| I-734 | c-Pr | Me$_2$N | Cl | H | Cl | H | H | H | H |
| I-735 | c-Pr | cyclopentyl-NH | Cl | H | Cl | H | H | H | H |
| I-736 | c-Pr | Ph—NH | Cl | H | Cl | H | H | H | H |
| I-737 | c-Pr | Ph—(Bn)N | Cl | H | Cl | H | H | H | H |
| I-738 | c-Pr | (Pyridin-3-yl)amino | Cl | H | Cl | H | H | H | H |
| I-739 | c-Pr | Allylamino | Cl | H | Cl | H | H | H | H |
| I-740 | c-Pr | Propargylamino | Cl | H | Cl | H | H | H | H |
| I-741 | c-Pr | (Pyrrolidin-1-yl) | Cl | H | Cl | H | H | H | H |
| I-742 | c-Pr | F$_3$CCH$_2$NH | Cl | H | Cl | H | H | H | H |
| I-743 | c-Pr | Acetylamino | Cl | H | Cl | H | H | H | H |
| I-744 | c-Pr | Benzoylamino | Cl | H | Cl | H | H | H | H |
| I-745 | c-Pr | (Ethoxycarbonyl)amino | Cl | H | Cl | H | H | H | H |
| I-746 | c-Pr | (N,N-Dimethyl-amino)carbonyl-amino | Cl | H | Cl | H | H | H | H |
| I-747 | c-Pr | (N,N-Dimethylamino)(thio-carbonyl)amino | Cl | H | Cl | H | H | H | H |
| I-748 | c-Pr | (Methylsulfonyl)amino | Cl | H | Cl | H | H | H | H |
| I-749 | c-Pr | NH$_2$ | Cl | H | H | Cl | H | H | H |
| I-750 | c-Pr | MeNH | Cl | H | H | Cl | H | H | H |
| I-751 | c-Pr | Me$_2$N | Cl | H | H | Cl | H | H | H |
| I-752 | c-Pr | cyclopentyl-NH | Cl | H | H | Cl | H | H | H |
| I-753 | c-Pr | Ph—NH | Cl | H | H | Cl | H | H | H |
| I-754 | c-Pr | Ph—(Bn)N | Cl | H | H | Cl | H | H | H |
| I-755 | c-Pr | (Pyridin-3-yl)amino | Cl | H | H | Cl | H | H | H |
| I-756 | c-Pr | Allylamino | Cl | H | H | Cl | H | H | H |
| I-757 | c-Pr | Propargylamino | Cl | H | H | Cl | H | H | H |
| I-758 | c-Pr | (Pyrrolidin-1-yl) | Cl | H | H | Cl | H | H | H |
| I-759 | c-Pr | F$_3$CCH$_2$NH | Cl | H | H | Cl | H | H | H |
| I-760 | c-Pr | Acetylamino | Cl | H | H | Cl | H | H | H |

TABLE 1-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-761 | c-Pr | Benzoylamino | Cl | H | H | Cl | H | H | H |
| I-762 | c-Pr | (Ethoxycarbonyl)amino | Cl | H | H | Cl | H | H | H |
| I-763 | c-Pr | (N,N-Dimethyl-amino)carbonyl-amino | Cl | H | H | Cl | H | H | H |
| I-764 | c-Pr | (N,N-Dimethylamino)(thio-carbonyl)amino | Cl | H | H | Cl | H | H | H |
| I-765 | c-Pr | (Methylsulfonyl)amino | Cl | H | H | Cl | H | H | H |
| I-766 | c-Pr | $NH_2$ | Cl | H | H | H | Cl | H | H |
| I-767 | c-Pr | MeNH | Cl | H | H | H | Cl | H | H |
| I-768 | c-Pr | $Me_2N$ | Cl | H | H | H | Cl | H | H |
| I-769 | c-Pr | cyclopentyl-NH | Cl | H | H | H | Cl | H | H |
| I-770 | c-Pr | Ph—NH | Cl | H | H | H | Cl | H | H |
| I-771 | c-Pr | Ph—(Bn)N | Cl | H | H | H | Cl | H | H |
| I-772 | c-Pr | (Pyridin-3-yl)amino | Cl | H | H | H | Cl | H | H |
| I-773 | c-Pr | Allylamino | Cl | H | H | H | Cl | H | H |
| I-774 | c-Pr | Propargylamino | Cl | H | H | H | Cl | H | H |
| I-775 | c-Pr | (Pyrrolidin-1-yl) | Cl | H | H | H | Cl | H | H |
| I-776 | c-Pr | $F_3CCH_2NH$ | Cl | H | H | H | Cl | H | H |
| I-777 | c-Pr | Acetylamino | Cl | H | H | H | Cl | H | H |
| I-778 | c-Pr | Benzoylamino | Cl | H | H | H | Cl | H | H |
| I-779 | c-Pr | (Ethoxycarbonyl)amino | Cl | H | H | H | Cl | H | H |
| I-780 | c-Pr | (N,N-Dimethyl-amino)carbonyl-amino | Cl | H | H | H | Cl | H | H |
| I-781 | c-Pr | (N,N-Dimethylamino)(thio-carbonyl)amino | Cl | H | H | H | Cl | H | H |
| I-782 | c-Pr | (Methylsulfonyl)amino | Cl | H | H | H | Cl | H | H |
| I-783 | c-Pr | $NH_2$ | Cl | Me | H | H | H | H | H |
| I-784 | c-Pr | $Me_2N$ | Cl | Me | H | H | H | H | H |
| I-785 | c-Pr | $Me_2N$ | Cl | Me | H | H | H | H | H |
| I-786 | c-Pr | cyclopentyl-NH | Cl | Me | H | H | H | H | H |
| I-787 | c-Pr | Ph—NH | Cl | Me | H | H | H | H | H |
| I-788 | c-Pr | Ph—(Bn)N | Cl | Me | H | H | H | H | H |
| I-789 | c-Pr | (Pyridin-3-yl)amino | Cl | Me | H | H | H | H | H |
| I-790 | c-Pr | Allylamino | Cl | Me | H | H | H | H | H |
| I-791 | c-Pr | Propargylamino | Cl | Me | H | H | H | H | H |
| I-792 | c-Pr | (Pyrrolidin-1-yl) | Cl | Me | H | H | H | H | H |
| I-793 | c-Pr | $F_3CCH_2NH$ | Cl | Me | H | H | H | H | H |
| I-794 | c-Pr | Acetylamino | Cl | Me | H | H | H | H | H |
| I-795 | c-Pr | Benzoylamino | Cl | Me | H | H | H | H | H |
| I-796 | c-Pr | (Ethoxycarbonyl)amino | Cl | Me | H | H | H | H | H |
| I-797 | c-Pr | (N,N-Dimethyl-amino)carbonyl-amino | Cl | Me | H | H | H | H | H |
| I-798 | c-Pr | (N,N-Dimethylamino)(thio-carbonyl)amino | Cl | Me | H | H | H | H | H |
| I-799 | c-Pr | (Methylsulfonyl)amino | Cl | Me | H | H | H | H | H |
| I-800 | c-Pr | $NH_2$ | Cl | H | Me | H | H | H | H |
| I-801 | c-Pr | $Me_2N$ | Cl | H | Me | H | H | H | H |
| I-802 | c-Pr | $Me_2N$ | Cl | H | Me | H | H | H | H |
| I-803 | c-Pr | cyclopentyl-NH | Cl | H | Me | H | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-804 | c-Pr | Ph—NH | Cl | H | Me | H | H | H | H |
| I-805 | c-Pr | Ph—(Bn)N | Cl | H | Me | H | H | H | H |
| I-806 | c-Pr | (Pyridin-3-yl)amino | Cl | H | Me | H | H | H | H |
| I-807 | c-Pr | Allylamino | Cl | H | Me | H | H | H | H |
| I-808 | c-Pr | Propargylamino | Cl | H | Me | H | H | H | H |
| I-809 | c-Pr | (Pyrrolidin-1-yl) | Cl | H | Me | H | H | H | H |
| I-810 | c-Pr | $F_3CCH_2NH$ | Cl | H | Me | H | H | H | H |
| I-811 | c-Pr | Acetylamino | Cl | H | Me | H | H | H | H |
| I-812 | c-Pr | Benzoylamino | Cl | H | Me | H | H | H | H |
| I-813 | c-Pr | (Ethoxycarbonyl)amino | Cl | H | Me | H | H | H | H |
| I-814 | c-Pr | (N,N-Dimethyl-amino)carbonyl-amino | Cl | H | Me | H | H | H | H |
| I-815 | c-Pr | (N,N-Dimethylamino)(thio-carbonyl)amino | Cl | H | Me | H | H | H | H |
| I-816 | c-Pr | (Methylsulfonyl)amino | Cl | H | Me | H | H | H | H |
| I-817 | c-Pr | $NH_2$ | Cl | H | H | Me | H | H | H |
| I-818 | c-Pr | MeNH | Cl | H | H | Me | H | H | H |
| I-819 | c-Pr | $Me_2N$ | Cl | H | H | Me | H | H | H |
| I-820 | c-Pr | cyclopentyl-NH | Cl | H | H | Me | H | H | H |
| I-821 | c-Pr | Ph—NH | Cl | H | H | Me | H | H | H |
| I-822 | c-Pr | Ph—(Bn)N | Cl | H | H | Me | H | H | H |
| I-823 | c-Pr | (Pyridin-3-yl)amino | Cl | H | H | Me | H | H | H |
| I-824 | c-Pr | Allylamino | Cl | H | H | Me | H | H | H |
| I-825 | c-Pr | Propargylamino | Cl | H | H | Me | H | H | H |
| I-826 | c-Pr | (Pyrrolidin-1-yl) | Cl | H | H | Me | H | H | H |
| I-827 | c-Pr | $F_3CCH_2NH$ | Cl | H | H | Me | H | H | H |
| I-828 | c-Pr | Acetylamino | Cl | H | H | Me | H | H | H |
| I-829 | c-Pr | Benzoylamino | Cl | H | H | Me | H | H | H |
| I-830 | c-Pr | (Ethoxycarbonyl)amino | Cl | H | H | Me | H | H | H |
| I-831 | c-Pr | (N,N-Dimethyl-amino)carbonyl-amino | Cl | H | H | Me | H | H | H |
| I-832 | c-Pr | (N,N-Dimethylamino)(thio-carbonyl)amino | Cl | H | H | Me | H | H | H |
| I-833 | c-Pr | (Methylsulfonyl)amino | Cl | H | H | Me | H | H | H |
| I-834 | c-Pr | $NH_2$ | Cl | H | H | H | Me | H | H |
| I-835 | c-Pr | MeNH | Cl | H | H | H | Me | H | H |
| I-836 | c-Pr | $Me_2N$ | Cl | H | H | H | Me | H | H |
| I-837 | c-Pr | cyclopentyl-NH | Cl | H | H | H | Me | H | H |
| I-838 | c-Pr | Ph—NH | Cl | H | H | H | Me | H | H |
| I-839 | c-Pr | Ph—(Bn)N | Cl | H | H | H | Me | H | H |
| I-840 | c-Pr | (Pyridin-3-yl)amino | Cl | H | H | H | Me | H | H |
| I-841 | c-Pr | Allylamino | Cl | H | H | H | Me | H | H |
| I-842 | c-Pr | Propargylamino | Cl | H | H | H | Me | H | H |
| I-843 | c-Pr | (Pyrrolidin-1-yl) | Cl | H | H | H | Me | H | H |
| I-844 | c-Pr | $F_3CCH_2NH$ | Cl | H | H | H | Me | H | H |
| I-845 | c-Pr | Acetylamino | Cl | H | H | H | Me | H | H |
| I-846 | c-Pr | Benzoylamino | Cl | H | H | H | Me | H | H |
| I-847 | c-Pr | (Ethoxycarbonyl)amino | Cl | H | H | H | Me | H | H |
| I-848 | c-Pr | (N,N-Dimethyl-amino)carbonyl-amino | Cl | H | H | H | Me | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-849 | c-Pr | (N,N-Dimethylamino)(thiocarbonyl)amino | Cl | H | H | H | Me | H | H |
| I-850 | c-Pr | (Methylsulfonyl)amino | Cl | H | H | H | Me | H | H |
| I-851 | c-Pr | NH$_2$ | Cl | MeO | H | H | H | H | H |
| I-852 | c-Pr | MeNH | Cl | MeO | H | H | H | H | H |
| I-853 | c-Pr | Me$_2$N | Cl | MeO | H | H | H | H | H |
| I-854 | c-Pr | cyclopentyl-NH | Cl | MeO | H | H | H | H | H |
| I-855 | c-Pr | Ph—NH | Cl | MeO | H | H | H | H | H |
| I-856 | c-Pr | Ph—(Bn)N | Cl | MeO | H | H | H | H | H |
| I-857 | c-Pr | (Pyridin-3-yl)amino | Cl | MeO | H | H | H | H | H |
| I-858 | c-Pr | Allylamino | Cl | MeO | H | H | H | H | H |
| I-859 | c-Pr | Propargylamino | Cl | MeO | H | H | H | H | H |
| I-860 | c-Pr | (Pyrrolidin-1-yl) | Cl | MeO | H | H | H | H | H |
| I-861 | c-Pr | F$_3$CCH$_2$NH | Cl | MeO | H | H | H | H | H |
| I-862 | c-Pr | Acetylamino | Cl | MeO | H | H | H | H | H |
| I-863 | c-Pr | Benzoylamino | Cl | MeO | H | H | H | H | H |
| I-864 | c-Pr | (Ethoxycarbonyl)amino | Cl | MeO | H | H | H | H | H |
| I-865 | c-Pr | (N,N-Dimethyl-amino)carbonyl-amino | Cl | MeO | H | H | H | H | H |
| I-866 | c-Pr | (N,N-Dimethylamino)(thiocarbonyl)amino | Cl | MeO | H | H | H | H | H |
| I-867 | c-Pr | (Methylsulfonyl)amino | Cl | MeO | H | H | H | H | H |
| I-868 | c-Pr | NH$_2$ | Cl | H | MeO | H | H | H | H |
| I-869 | c-Pr | MeNH | Cl | H | MeO | H | H | H | H |
| I-870 | c-Pr | Me$_2$N | Cl | H | MeO | H | H | H | H |
| I-871 | c-Pr | cyclopentyl-NH | Cl | H | MeO | H | H | H | H |
| I-872 | c-Pr | Ph—NH | Cl | H | MeO | H | H | H | H |
| I-873 | c-Pr | Ph—(Bn)N | Cl | H | MeO | H | H | H | H |
| I-874 | c-Pr | (Pyridin-3-yl)amino | Cl | H | MeO | H | H | H | H |
| I-875 | c-Pr | Allylamino | Cl | H | MeO | H | H | H | H |
| I-876 | c-Pr | Propargylamino | Cl | H | MeO | H | H | H | H |
| I-877 | c-Pr | (Pyrrolidin-1-yl) | Cl | H | MeO | H | H | H | H |
| I-878 | c-Pr | F$_3$CCH$_2$NH | Cl | H | MeO | H | H | H | H |
| I-879 | c-Pr | Acetylamino | Cl | H | H | MeO | H | H | H |
| I-880 | c-Pr | Benzoylamino | Cl | H | H | MeO | H | H | H |
| I-881 | c-Pr | (Ethoxycarbonyl)amino | Cl | H | H | MeO | H | H | H |
| I-882 | c-Pr | (N,N-Dimethyl-amino)carbonyl-amino | Cl | H | H | MeO | H | H | H |
| I-883 | c-Pr | (N,N-Dimethyl-amino)(thio-carbonyl)amino | Cl | H | H | MeO | H | H | H |
| I-884 | c-Pr | (Methylsulfonyl)amino | Cl | H | H | MeO | H | H | H |
| I-885 | c-Pr | NH$_2$ | Cl | H | H | MeO | H | H | H |
| I-886 | c-Pr | MeNH | Cl | H | H | MeO | H | H | H |
| I-887 | c-Pr | Me$_2$N | Cl | H | H | MeO | H | H | H |
| I-888 | c-Pr | cyclopentyl-NH | Cl | H | H | MeO | H | H | H |
| I-889 | c-Pr | Ph—NH | Cl | H | H | MeO | H | H | H |
| I-890 | c-Pr | Ph—(Bn)N | Cl | H | H | MeO | H | H | H |
| I-891 | c-Pr | (Pyridin-3-yl)amino | Cl | H | H | MeO | H | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-892 | c-Pr | Allylamino | Cl | H | H | MeO | H | H | H |
| I-893 | c-Pr | Propargylamino | Cl | H | H | MeO | H | H | H |
| I-894 | c-Pr | (Pyrrolidin-1-yl) | Cl | H | H | MeO | H | H | H |
| I-895 | c-Pr | $F_3CCH_2NH$ | Cl | H | H | MeO | H | H | H |
| I-896 | c-Pr | Acetylamino | Cl | H | H | MeO | H | H | H |
| I-897 | c-Pr | Benzoylamino | Cl | H | H | MeO | H | H | H |
| I-898 | c-Pr | (Ethoxycarbonyl)amino | Cl | H | H | MeO | H | H | H |
| I-899 | c-Pr | (N,N-Dimethyl-amino)carbonyl-amino | Cl | H | H | MeO | H | H | H |
| I-900 | c-Pr | (N,N-Dimethylamino)(thio-carbonyl)amino | Cl | H | H | MeO | H | H | H |
| I-901 | c-Pr | (Methylsulfonyl)amino | Cl | H | H | MeO | H | H | H |
| I-902 | c-Pr | $NH_2$ | Cl | H | H | H | MeO | H | H |
| I-903 | c-Pr | MeNH | Cl | H | H | H | MeO | H | H |
| I-904 | c-Pr | $Me_2N$ | Cl | H | H | H | MeO | H | H |
| I-905 | c-Pr | cyclopentyl-NH | Cl | H | H | H | MeO | H | H |
| I-906 | c-Pr | Ph—NH | Cl | H | H | H | MeO | H | H |
| I-907 | c-Pr | Ph—(Bn)N | Cl | H | H | H | MeO | H | H |
| I-908 | c-Pr | (Pyridin-3-yl)amino | Cl | H | H | H | MeO | H | H |
| I-909 | c-Pr | Allylamino | Cl | H | H | H | MeO | H | H |
| I-910 | c-Pr | Propargylamino | Cl | H | H | H | MeO | H | H |
| I-911 | c-Pr | (Pyrrolidin-l-yl) | Cl | H | H | H | MeO | H | H |
| I-912 | c-Pr | $F_3CCH_2NH$ | Cl | H | H | H | MeO | H | H |
| I-913 | c-Pr | Acetylamino | Cl | H | H | H | MeO | H | H |
| I-914 | c-Pr | Benzoylamino | Cl | H | H | H | MeO | H | H |
| I-915 | c-Pr | (Ethoxycarbonyl)amino | Cl | H | H | H | MeO | H | H |
| I-916 | c-Pr | (N,N-Dimethyl-amino)carbonyl-amino | Cl | H | H | H | MeO | H | H |
| I-917 | c-Pr | (N,N-Dimethylamino)(thio-carbonyl)amino | Cl | H | H | H | MeO | H | H |
| I-918 | c-Pr | (Methylsulfonyl)amino | Cl | H | H | H | MeO | H | H |
| I-919 | c-Pr | $NH_2$ | Me | Me | H | H | H | H | H |
| I-920 | c-Pr | MeNH | Me | Me | H | H | H | H | H |
| I-921 | c-Pr | $Me_2N$ | Me | Me | H | H | H | H | H |
| I-922 | c-Pr | cyclopentyl-NH | Me | Me | H | H | H | H | H |
| I-923 | c-Pr | Ph—NH | Me | Me | H | H | H | H | H |
| I-924 | c-Pr | Ph—(Bn)N | Me | Me | H | H | H | H | H |
| I-925 | c-Pr | (Pyridin-3-yl)amino | Me | Me | H | H | H | H | H |
| I-926 | c-Pr | Allylamino | Me | Me | H | H | H | H | H |
| I-927 | c-Pr | Propargylamino | Me | Me | H | H | H | H | H |
| I-928 | c-Pr | (Pyrrolidin-1-yl) | Me | Me | H | H | H | H | H |
| I-929 | c-Pr | $F_3CCH_2NH$ | Me | Me | H | H | H | H | H |
| I-930 | c-Pr | Acetylamino | Me | Me | H | H | H | H | H |
| I-931 | c-Pr | Benzoylamino | Me | Me | H | H | H | H | H |
| I-932 | c-Pr | (Ethoxycarbonyl)amino | Me | Me | H | H | H | H | H |
| I-933 | c-Pr | (N,N-Dimethyl-amino)carbonyl-amino | Me | Me | H | H | H | H | H |
| I-934 | c-Pr | (N,N-Dimethylamino)(thio-carbonyl)amino | Me | Me | H | H | H | H | H |

TABLE 1-continued

Inventive compounds of the formula (I) in which X represents $C(R^{13})(R^{14})$ $$\text{(I)}$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-935 | c-Pr | (Methylsulfonyl)amino | Me | Me | H | H | H | H | H |
| I-936 | c-Pr | NH$_2$ | Me | H | Me | H | H | H | H |
| I-937 | c-Pr | MeNH | Me | H | Me | H | H | H | H |
| I-938 | c-Pr | Me$_2$N | Me | H | Me | H | H | H | H |
| I-939 | c-Pr | cyclopentyl-NH | Me | H | Me | H | H | H | H |
| I-940 | c-Pr | Ph—NH | Me | H | Me | H | H | H | H |
| I-941 | c-Pr | Ph—(Bn)N | Me | H | Me | H | H | H | H |
| I-942 | c-Pr | (Pyridin-3-yl)amino | Me | H | Me | H | H | H | H |
| I-943 | c-Pr | Allylamino | Me | H | Me | H | H | H | H |
| I-944 | c-Pr | Propargylamino | Me | H | Me | H | H | H | H |
| I-945 | c-Pr | (Pyrrolidin-1-yl) | Me | H | Me | H | H | H | H |
| I-946 | c-Pr | F$_3$CCH$_2$NH | Me | H | Me | H | H | H | H |
| I-947 | c-Pr | Acetylamino | Me | H | Me | H | H | H | H |
| I-948 | c-Pr | Benzoylamino | Me | H | Me | H | H | H | H |
| I-949 | c-Pr | (Ethoxycarbonyl)amino | Me | H | Me | H | H | H | H |
| I-950 | c-Pr | (N,N-Dimethyl-amino)carbonyl-amino | Me | H | Me | H | H | H | H |
| I-951 | c-Pr | (N,N-Dimethylamino)(thio-carbonyl)amino | Me | H | Me | H | H | H | H |
| I-952 | c-Pr | (Methylsulfonyl)amino | Me | H | Me | H | H | H | H |
| I-953 | c-Pr | NH$_2$ | Me | H | H | Me | H | H | H |
| I-954 | c-Pr | MeNH | Me | H | H | Me | H | H | H |
| I-955 | c-Pr | Me$_2$N | Me | H | H | Me | H | H | H |
| I-956 | c-Pr | cyclopentyl-NH | Me | H | H | Me | H | H | H |
| I-957 | c-Pr | Ph—NH | Me | H | H | Me | H | H | H |
| I-958 | c-Pr | Ph—(Bn)N | Me | H | H | Me | H | H | H |
| I-959 | c-Pr | (Pyridin-3-yl)amino | Me | H | H | Me | H | H | H |
| I-960 | c-Pr | Allylamino | Me | H | H | Me | H | H | H |
| I-961 | c-Pr | Propargylamino | Me | H | H | Me | H | H | H |
| I-962 | c-Pr | (Pyrrolidin-1-yl) | Me | H | H | Me | H | H | H |
| I-963 | c-Pr | F$_3$CCH$_2$NH | Me | H | H | Me | H | H | H |
| I-964 | c-Pr | Acetylamino | Me | H | H | Me | H | H | H |
| I-965 | c-Pr | Benzoylamino | Me | H | H | Me | H | H | H |
| I-966 | c-Pr | (Ethoxycarbonyl)amino | Me | H | H | Me | H | H | H |
| I-967 | c-Pr | (N,N-Dimethyl-amino)carbonyl-amino | Me | H | H | Me | H | H | H |
| I-968 | c-Pr | (N,N-Dimethylamino)(thio-carbonyl)amino | Me | H | H | Me | H | H | H |
| I-969 | c-Pr | (Methylsulfonyl)amino | Me | H | H | Me | H | H | H |
| I-970 | c-Pr | NH$_2$ | Me | H | H | H | Me | H | H |
| I-971 | c-Pr | MeNH | Me | H | H | H | Me | H | H |
| I-972 | c-Pr | Me$_2$N | Me | H | H | H | Me | H | H |
| I-973 | c-Pr | cyclopentyl-NH | Me | H | H | H | Me | H | H |
| I-974 | c-Pr | Ph—NH | Me | H | H | H | Me | H | H |
| I-975 | c-Pr | Ph—(Bn)N | Me | H | H | H | Me | H | H |
| I-976 | c-Pr | (Pyridin-3-yl)amino | Me | H | H | H | Me | H | H |
| I-977 | c-Pr | Allylamino | Me | H | H | H | Me | H | H |
| I-978 | c-Pr | Propargylamino | Me | H | H | H | Me | H | H |
| I-979 | c-Pr | (Pyrrolidin-1-yl) | Me | H | H | H | Me | H | H |
| I-980 | c-Pr | F$_3$CCH$_2$NH | Me | H | H | H | Me | H | H |
| I-981 | c-Pr | Acetylamino | Me | H | H | H | Me | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-982 | c-Pr | Benzoylamino | Me | H | H | H | Me | H | H |
| I-983 | c-Pr | (Ethoxycarbonyl)amino | Me | H | H | H | Me | H | H |
| I-984 | c-Pr | (N,N-Dimethyl-amino)carbonyl-amino | Me | H | H | H | Me | H | H |
| I-985 | c-Pr | (N,N-Dimethylamino)(thio-carbonyl)amino | Me | H | H | H | Me | H | H |
| I-986 | c-Pr | (Methylsulfonyl)amino | Me | H | H | H | Me | H | H |
| I-987 | c-Pr | $NH_2$ | $CF_3$ | F | H | H | H | H | H |
| I-988 | c-Pr | MeNH | $CF_3$ | F | H | H | H | H | H |
| I-989 | c-Pr | $Me_2N$ | $CF_3$ | F | H | H | H | H | H |
| I-990 | c-Pr | cyclopentyl-NH | $CF_3$ | F | H | H | H | H | H |
| I-991 | c-Pr | Ph—NH | $CF_3$ | F | H | H | H | H | H |
| I-992 | c-Pr | Ph—(Bn)N | $CF_3$ | F | H | H | H | H | H |
| I-993 | c-Pr | (Pyridin-3-yl)amino | $CF_3$ | F | H | H | H | H | H |
| I-994 | c-Pr | Allylamino | $CF_3$ | F | H | H | H | H | H |
| I-995 | c-Pr | Propargylamino | $CF_3$ | F | H | H | H | H | H |
| I-996 | c-Pr | (Pyrrolidin-1-yl) | $CF_3$ | F | H | H | H | H | H |
| I-997 | c-Pr | $F_3CCH_2NH$ | $CF_3$ | F | H | H | H | H | H |
| I-998 | c-Pr | Acetylamino | $CF_3$ | F | H | H | H | H | H |
| I-999 | c-Pr | Benzoylamino | $CF_3$ | F | H | H | H | H | H |
| I-1000 | c-Pr | (Ethoxycarbonyl)amino | $CF_3$ | F | H | H | H | H | H |
| I-1001 | c-Pr | (N,N-Dimethyl-amino)carbonyl-amino | $CF_3$ | F | H | H | H | H | H |
| I-1002 | c-Pr | (N,N-Dimethylamino)(thio-carbonyl)amino | $CF_3$ | F | H | H | H | H | H |
| I-1003 | c-Pr | (Methylsulfonyl)amino | $CF_3$ | F | H | H | H | H | H |
| I-1004 | c-Pr | $NH_2$ | $CF_3$ | H | F | H | H | H | H |
| I-1005 | c-Pr | MeNH | $CF_3$ | H | F | H | H | H | H |
| I-1006 | c-Pr | $Me_2N$ | $CF_3$ | H | F | H | H | H | H |
| I-1007 | c-Pr | cyclopentyl-NH | $CF_3$ | H | F | H | H | H | H |
| I-1008 | c-Pr | Ph—NH | $CF_3$ | H | F | H | H | H | H |
| I-1009 | c-Pr | Ph—(Bn)N | $CF_3$ | H | F | H | H | H | H |
| I-1010 | c-Pr | (Pyridin-3-yl)amino | $CF_3$ | H | F | H | H | H | H |
| I-1011 | c-Pr | Allylamino | $CF_3$ | H | F | H | H | H | H |
| I-1012 | c-Pr | Propargylamino | $CF_3$ | H | F | H | H | H | H |
| I-1013 | c-Pr | (Pyrrolidin-1-yl) | $CF_3$ | H | F | H | H | H | H |
| I-1014 | c-Pr | $F_3CCH_2NH$ | $CF_3$ | H | F | H | H | H | H |
| I-1015 | c-Pr | Acetylamino | $CF_3$ | H | F | H | H | H | H |
| I-1016 | c-Pr | Benzoylamino | $CF_3$ | H | F | H | H | H | H |
| I-1017 | c-Pr | (Ethoxycarbonyl)amino | $CF_3$ | H | F | H | H | H | H |
| I-1018 | c-Pr | (N,N-Dimethyl-amino)carbonyl-amino | $CF_3$ | H | F | H | H | H | H |
| I-1019 | c-Pr | (N,N-Dimethylamino)(thio-carbonyl)amino | $CF_3$ | H | F | H | H | H | H |
| I-1020 | c-Pr | (Methylsulfonyl)amino | $CF_3$ | H | F | H | H | H | H |
| I-1021 | c-Pr | $NH_2$ | $CF_3$ | H | H | F | H | H | H |
| I-1022 | c-Pr | MeNH | $CF_3$ | H | H | F | H | H | H |
| I-1023 | c-Pr | $Me_2N$ | $CF_3$ | H | H | F | H | H | H |
| I-1024 | c-Pr | cyclopentyl-NH | $CF_3$ | H | H | F | H | H | H |

TABLE 1-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| I-1025 | c-Pr | Ph—NH | CF₃ | H | H | F | H | H | H |
| I-1026 | c-Pr | Ph—(Bn)N | CF₃ | H | H | F | H | H | H |
| I-1027 | c-Pr | (Pyridin-3-yl)amino | CF₃ | H | H | F | H | H | H |
| I-1028 | c-Pr | Allylamino | CF₃ | H | H | F | H | H | H |
| I-1029 | c-Pr | Propargylamino | CF₃ | H | H | F | H | H | H |
| I-1030 | c-Pr | (Pyrrolidin-1-yl) | CF₃ | H | H | F | H | H | H |
| I-1031 | c-Pr | F₃CCH₂NH | CF₃ | H | H | F | H | H | H |
| I-1032 | c-Pr | Acetylamino | CF₃ | H | H | F | H | H | H |
| I-1033 | c-Pr | Benzoylamino | CF₃ | H | H | F | H | H | H |
| I-1034 | c-Pr | (Ethoxycarbonyl)amino | CF₃ | H | H | F | H | H | H |
| I-1035 | c-Pr | (N,N-Dimethyl-amino)carbonyl-amino | CF₃ | H | H | F | H | H | H |
| I-1036 | c-Pr | (N,N-Dimethylamino)(thio-carbonyl)amino | CF₃ | H | H | F | H | H | H |
| I-1037 | c-Pr | (Methylsulfonyl)amino | CF₃ | H | H | F | H | H | H |
| I-1038 | c-Pr | NH₂ | CF₃ | H | H | H | F | H | H |
| I-1039 | c-Pr | MeNH | CF₃ | H | H | H | F | H | H |
| I-1040 | c-Pr | Me₂N | CF₃ | H | H | H | F | H | H |
| I-1041 | c-Pr | cyclopentyl-NH | CF₃ | H | H | H | F | H | H |
| I-1042 | c-Pr | Ph—NH | CF₃ | H | H | H | F | H | H |
| I-1043 | c-Pr | Ph—(Bn)N | CF₃ | H | H | H | F | H | H |
| I-1044 | c-Pr | (Pyridin-3-yl)amino | CF₃ | H | H | H | F | H | H |
| I-1045 | c-Pr | Allylamino | CF₃ | H | H | H | F | H | H |
| I-1046 | c-Pr | Propargylamino | CF₃ | H | H | H | F | H | H |
| I-1047 | c-Pr | (Pyrrolidin-1-yl) | CF₃ | H | H | H | F | H | H |
| I-1048 | c-Pr | F₃CCH₂NH | CF₃ | H | H | H | F | H | H |
| I-1049 | c-Pr | Acetylamino | CF₃ | H | H | H | F | H | H |
| I-1050 | c-Pr | Benzoylamino | CF₃ | H | H | H | F | H | H |
| I-1051 | c-Pr | (Ethoxycarbonyl)amino | CF₃ | H | H | H | F | H | H |
| I-1052 | c-Pr | (N,N-Dimethyl-amino)carbonyl-amino | CF₃ | H | H | H | F | H | H |
| I-1053 | c-Pr | (N,N-Dimethylamino)(thio-carbonyl)amino | CF₃ | H | H | H | F | H | H |
| I-1054 | c-Pr | (Methylsulfonyl)amino | CF₃ | H | H | H | F | H | H |
| I-1055 | c-Pr | NH₂ | CF₃ | Cl | H | H | H | H | H |
| I-1056 | c-Pr | MeNH | CF₃ | Cl | H | H | H | H | H |
| I-1057 | c-Pr | Me₂N | CF₃ | Cl | H | H | H | H | H |
| I-1058 | c-Pr | cyclopentyl-NH | CF₃ | Cl | H | H | H | H | H |
| I-1059 | c-Pr | Ph—NH | CF₃ | Cl | H | H | H | H | H |
| I-1060 | c-Pr | Ph—(Bn)N | CF₃ | Cl | H | H | H | H | H |
| I-1061 | c-Pr | (Pyridin-3-yl)amino | CF₃ | Cl | H | H | H | H | H |
| I-1062 | c-Pr | Allylamino | CF₃ | Cl | H | H | H | H | H |
| I-1063 | c-Pr | Propargylamino | CF₃ | Cl | H | H | H | H | H |
| I-1064 | c-Pr | (Pyrrolidin-1-yl) | CF₃ | Cl | H | H | H | H | H |
| I-1065 | c-Pr | F₃CCH₂NH | CF₃ | Cl | H | H | H | H | H |
| I-1066 | c-Pr | Acetylamino | CF₃ | Cl | H | H | H | H | H |
| I-1067 | c-Pr | Benzoylamino | CF₃ | Cl | H | H | H | H | H |
| I-1068 | c-Pr | (Ethoxycarbonyl)amino | CF₃ | Cl | H | H | H | H | H |
| I-1069 | c-Pr | (N,N-Dimethyl-amino)carbonyl-amino | CF₃ | Cl | H | H | H | H | H |

TABLE 1-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-1070 | c-Pr | (N,N-Dimethylamino)(thiocarbonyl)amino | CF$_3$ | Cl | H | H | H | H | H |
| I-1071 | c-Pr | (Methylsulfonyl)amino | CF$_3$ | Cl | H | H | H | H | H |
| I-1072 | c-Pr | NH$_2$ | CF$_3$ | H | Cl | H | H | H | H |
| I-1073 | c-Pr | MeNH | CF$_3$ | H | Cl | H | H | H | H |
| I-1074 | c-Pr | Me$_2$N | CF$_3$ | H | Cl | H | H | H | H |
| I-1075 | c-Pr | cyclopentyl-NH | CF$_3$ | H | Cl | H | H | H | H |
| I-1076 | c-Pr | Ph—NH | CF$_3$ | H | Cl | H | H | H | H |
| I-1077 | c-Pr | Ph—(Bn)N | CF$_3$ | H | Cl | H | H | H | H |
| I-1078 | c-Pr | (Pyridin-3-yl)amino | CF$_3$ | H | Cl | H | H | H | H |
| I-1079 | c-Pr | Allylamino | CF$_3$ | H | Cl | H | H | H | H |
| I-1080 | c-Pr | Propargylamino | CF$_3$ | H | Cl | H | H | H | H |
| I-1081 | c-Pr | (Pyrrolidin-1-yl) | CF$_3$ | H | Cl | H | H | H | H |
| I-1082 | c-Pr | F$_3$CCH$_2$NH | CF$_3$ | H | Cl | H | H | H | H |
| I-1083 | c-Pr | Acetylamino | CF$_3$ | H | Cl | H | H | H | H |
| I-1084 | c-Pr | Benzoylamino | CF$_3$ | H | Cl | H | H | H | H |
| I-1085 | c-Pr | (Ethoxycarbonyl)amino | CF$_3$ | H | Cl | H | H | H | H |
| I-1086 | c-Pr | (N,N-Dimethylamino)carbonyl-amino | CF$_3$ | H | Cl | H | H | H | H |
| I-1087 | c-Pr | (N,N-Dimethylamino)(thiocarbonyl)amino | CF$_3$ | H | Cl | H | H | H | H |
| I-1088 | c-Pr | (Methylsulfonyl)amino | CF$_3$ | H | Cl | H | H | H | H |
| I-1089 | c-Pr | NH$_2$ | CF$_3$ | H | H | Cl | H | H | H |
| I-1090 | c-Pr | MeNH | CF$_3$ | H | H | Cl | H | H | H |
| I-1091 | c-Pr | Me$_2$N | CF$_3$ | H | H | Cl | H | H | H |
| I-1092 | c-Pr | cyclopentyl-NH | CF$_3$ | H | H | Cl | H | H | H |
| I-1093 | c-Pr | Ph—NH | CF$_3$ | H | H | Cl | H | H | H |
| I-1094 | c-Pr | Ph—(Bn)N | CF$_3$ | H | H | Cl | H | H | H |
| I-1095 | c-Pr | (Pyridin-3-yl)amino | CF$_3$ | H | H | Cl | H | H | H |
| I-1096 | c-Pr | Allylamino | CF$_3$ | H | H | Cl | H | H | H |
| I-1097 | c-Pr | Propargylamino | CF$_3$ | H | H | Cl | H | H | H |
| I-1098 | c-Pr | (Pyrrolidin-1-yl) | CF$_3$ | H | H | Cl | H | H | H |
| I-1099 | c-Pr | F$_3$CCH$_2$NH | CF$_3$ | H | H | Cl | H | H | H |
| I-1100 | c-Pr | Acetylamino | CF$_3$ | H | H | Cl | H | H | H |
| I-1101 | c-Pr | Benzoylamino | CF$_3$ | H | H | Cl | H | H | H |
| I-1102 | c-Pr | (Ethoxycarbonyl)amino | CF$_3$ | H | H | Cl | H | H | H |
| I-1103 | c-Pr | (N,N-Dimethyl-amino)carbonyl-amino | CF$_3$ | H | H | Cl | H | H | H |
| I-1104 | c-Pr | (N,N-Dimethylamino)(thiocarbonyl)amino | CF$_3$ | H | H | Cl | H | H | H |
| I-1105 | c-Pr | (Methylsulfonyl)amino | CF$_3$ | H | H | Cl | H | H | H |
| I-1106 | c-Pr | NH$_2$ | CF$_3$ | H | H | H | Cl | H | H |
| I-1107 | c-Pr | MeNH | CF$_3$ | H | H | H | Cl | H | H |
| I-1108 | c-Pr | Me$_2$N | CF$_3$ | H | H | H | Cl | H | H |
| I-1109 | c-Pr | cyclopentyl-NH | CF$_3$ | H | H | H | Cl | H | H |
| I-1110 | c-Pr | Ph—NH | CF$_3$ | H | H | H | Cl | H | H |
| I-1111 | c-Pr | Ph—(Bn)N | CF$_3$ | H | H | H | Cl | H | H |
| I-1112 | c-Pr | (Pyridin-3-yl)amino | CF$_3$ | H | H | H | Cl | H | H |
| I-1113 | c-Pr | Allylamino | CF$_3$ | H | H | H | Cl | H | H |
| I-1114 | c-Pr | Propargylamino | CF$_3$ | H | H | H | Cl | H | H |
| I-1115 | c-Pr | (Pyrrolidin-1-yl) | CF$_3$ | H | H | H | Cl | H | H |
| I-1116 | c-Pr | F$_3$CCH$_2$NH | CF$_3$ | H | H | H | Cl | H | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1117 | c-Pr | Acetylamino | $CF_3$ | H | H | H | Cl | H | H |
| I-1118 | c-Pr | Benzoylamino | $CF_3$ | H | H | H | Cl | H | H |
| I-1119 | c-Pr | (Ethoxycarbonyl)amino | $CF_3$ | H | H | H | Cl | H | H |
| I-1120 | c-Pr | (N,N-Dimethyl-amino)carbonyl-amino | $CF_3$ | H | H | H | Cl | H | H |
| I-1121 | c-Pr | (N,N-Dimethylamino)(thio-carbonyl)amino | $CF_3$ | H | H | H | Cl | H | H |
| I-1122 | c-Pr | (Methylsulfonyl)amino | $CF_3$ | H | H | H | Cl | H | H |
| I-1123 | c-Pr | $NH_2$ | Cl | F | H | H | Cl | H | H |
| I-1124 | c-Pr | MeNH | Cl | F | H | H | Cl | H | H |
| I-1125 | c-Pr | $Me_2N$ | Cl | F | H | H | Cl | H | H |
| I-1126 | c-Pr | cyclopentyl-NH | Cl | F | H | H | Cl | H | H |
| I-1127 | c-Pr | Ph—NH | Cl | F | H | H | Cl | H | H |
| I-1128 | c-Pr | Ph—(Bn)N | Cl | F | H | H | Cl | H | H |
| I-1129 | c-Pr | (Pyridin-3-yl)amino | Cl | F | H | H | Cl | H | H |
| I-1130 | c-Pr | Allylamino | Cl | F | H | H | Cl | H | H |
| I-1131 | c-Pr | Propargylamino | Cl | F | H | H | Cl | H | H |
| I-1132 | c-Pr | (Pyrrolidin-1-yl) | Cl | F | H | H | Cl | H | H |
| I-1133 | c-Pr | $F_3CCH_2NH$ | Cl | F | H | H | Cl | H | H |
| I-1134 | c-Pr | Acetylamino | Cl | F | H | H | Cl | H | H |
| I-1135 | c-Pr | Benzoylamino | Cl | F | H | H | Cl | H | H |
| I-1136 | c-Pr | (Ethoxycarbonyl)amino | Cl | F | H | H | Cl | H | H |
| I-1137 | c-Pr | (N,N-Dimethyl-amino)carbonyl-amino | Cl | F | H | H | Cl | H | H |
| I-1138 | c-Pr | (N,N-Dimethylamino)(thio-carbonyl)amino | Cl | F | H | H | Cl | H | H |
| I-1139 | c-Pr | (Methylsulfonyl)amino | Cl | F | H | H | Cl | H | H |
| I-1140 | c-Pr | $NH_2$ | Cl | H | F | H | Cl | H | H |
| I-1141 | c-Pr | MeNH | Cl | H | F | H | Cl | H | H |
| I-1142 | c-Pr | $Me_2N$ | Cl | H | F | H | Cl | H | H |
| I-1143 | c-Pr | cyclopentyl-NH | Cl | H | F | H | Cl | H | H |
| I-1144 | c-Pr | Ph—NH | Cl | H | F | H | Cl | H | H |
| I-1145 | c-Pr | Ph—(Bn)N | Cl | H | F | H | Cl | H | H |
| I-1146 | c-Pr | (Pyridin-3-yl)amino | Cl | H | F | H | Cl | H | H |
| I-1147 | c-Pr | Allylamino | Cl | H | F | H | Cl | H | H |
| I-1148 | c-Pr | Propargylamino | Cl | H | F | H | Cl | H | H |
| I-1149 | c-Pr | (Pyrrolidin-1-yl) | Cl | H | F | H | Cl | H | H |
| I-1150 | c-Pr | $F_3CCH_2NH$ | Cl | H | F | H | Cl | H | H |
| I-1151 | c-Pr | Acetylamino | Cl | H | F | H | Cl | H | H |
| I-1152 | c-Pr | Benzoylamino | Cl | H | F | H | Cl | H | H |
| I-1153 | c-Pr | (Ethoxycarbonyl)amino | Cl | H | F | H | Cl | H | H |
| I-1154 | c-Pr | (N,N-Dimethyl-amino)carbonyl-amino | Cl | H | F | H | Cl | H | H |
| I-1155 | c-Pr | (N,N-Dimethylamino)(thio-carbonyl)amino | Cl | H | F | H | Cl | H | H |
| I-1156 | c-Pr | (Methylsulfonyl)amino | Cl | H | F | H | Cl | H | H |
| I-1157 | c-Pr | $NH_2$ | Cl | H | H | H | Cl | H | H |
| I-1158 | c-Pr | MeNH | Cl | H | H | Cl | Cl | H | H |
| I-1159 | c-Pr | $Me_2N$ | Cl | H | H | Cl | Cl | H | H |
| I-1160 | c-Pr | cyclopentyl-NH | Cl | H | H | Cl | Cl | H | H |

TABLE 1-continued

Inventive compounds of the formula (I) in which X represents C(R$^{13}$)(R$^{14}$)

$$\text{(I)}$$

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-1161 | c-Pr | Ph—NH | Cl | H | H | Cl | Cl | H | H |
| I-1162 | c-Pr | Ph—(Bn)N | Cl | H | H | Cl | Cl | H | H |
| I-1163 | c-Pr | (Pyridin-3-yl)amino | Cl | H | H | Cl | Cl | H | H |
| I-1164 | c-Pr | Allylamino | Cl | H | H | Cl | Cl | H | H |
| I-1165 | c-Pr | Propargylamino | Cl | H | H | Cl | Cl | H | H |
| I-1166 | c-Pr | (Pyrrolidin-1-yl) | Cl | H | H | Cl | Cl | H | H |
| I-1167 | c-Pr | F$_3$CCH$_2$NH | Cl | H | H | Cl | Cl | H | H |
| I-1168 | c-Pr | Acetylamino | Cl | H | H | Cl | Cl | H | H |
| I-1169 | c-Pr | Benzoylamino | Cl | H | H | Cl | Cl | H | H |
| I-1170 | c-Pr | (Ethoxycarbonyl)amino | Cl | H | H | Cl | Cl | H | H |
| I-1171 | c-Pr | (N,N-Dimethyl-amino)carbonyl-amino | Cl | H | H | Cl | Cl | H | H |
| I-1172 | c-Pr | (N,N-Dimethylamino)(thio-carbonyl)amino | Cl | H | H | Cl | Cl | H | H |
| I-1173 | c-Pr | (Methylsulfonyl)amino | Cl | H | H | Cl | Cl | H | H |
| I-1174 | c-Pr | NH$_2$ | MeO | H | F | F | H | H | H |
| I-1175 | c-Pr | MeNH | MeO | H | F | F | H | H | H |
| I-1176 | c-Pr | Me$_2$N | MeO | H | F | F | H | H | H |
| I-1177 | c-Pr | cyclopentyl-NH | MeO | H | F | F | H | H | H |
| I-1178 | c-Pr | Ph—NH | MeO | H | F | F | H | H | H |
| I-1179 | c-Pr | Ph—(Bn)N | MeO | H | F | F | H | H | H |
| I-1180 | c-Pr | (Pyridin-3-yl)amino | MeO | H | F | F | H | H | H |
| I-1181 | c-Pr | Allylamino | MeO | H | F | F | H | H | H |
| I-1182 | c-Pr | Propargylamino | MeO | H | F | F | H | H | H |
| I-1183 | c-Pr | (Pyrrolidin-1-yl) | MeO | H | F | F | H | H | H |
| I-1184 | c-Pr | F$_3$CCH$_2$NH | MeO | H | F | F | H | H | H |
| I-1185 | c-Pr | Acetylamino | MeO | H | F | F | H | H | H |
| I-1186 | c-Pr | Benzoylamino | MeO | H | F | F | H | H | H |
| I-1187 | c-Pr | (Ethoxycarbonyl)amino | MeO | H | F | F | H | H | H |
| I-1188 | c-Pr | (N,N-Dimethyl-amino)carbonyl-amino | MeO | H | F | F | H | H | H |
| I-1189 | c-Pr | (N,N-Dimethylamino)(thio-carbonyl)amino | MeO | H | F | F | H | H | H |
| I-1190 | c-Pr | (Methylsulfonyl)amino | MeO | H | F | F | H | H | H |
| I-1191 | c-Pr | NH$_2$ | H | H | H | H | H | Me | H |
| I-1192 | c-Pr | MeNH | H | H | H | H | H | Me | H |
| I-1193 | c-Pr | Me$_2$N | H | H | H | H | H | Me | H |
| I-1194 | c-Pr | cyclopentyl-NH | H | H | H | H | H | Me | H |
| I-1195 | c-Pr | Ph—NH | H | H | H | H | H | Me | H |
| I-1196 | c-Pr | Ph—(Bn)N | H | H | H | H | H | Me | H |
| I-1197 | c-Pr | (Pyridin-3-yl)amino | H | H | H | H | H | Me | H |
| I-1198 | c-Pr | Allylamino | H | H | H | H | H | Me | H |
| I-1199 | c-Pr | Propargylamino | H | H | H | H | H | Me | H |
| I-1200 | c-Pr | (Pyrrolidin-1-yl) | H | H | H | H | H | Me | H |
| I-1201 | c-Pr | F$_3$CCH$_2$NH | H | H | H | H | H | Me | H |
| I-1202 | c-Pr | Acetylamino | H | H | H | H | H | Me | H |
| I-1203 | c-Pr | Benzoylamino | H | H | H | H | H | Me | H |
| I-1204 | c-Pr | (Ethoxycarbonyl)amino | H | H | H | H | H | Me | H |
| I-1205 | c-Pr | (N,N-Dimethyl-amino)carbonyl-amino | H | H | H | H | H | Me | H |

TABLE 1-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-1206 | c-Pr | (N,N-Dimethylamino)(thio-carbonyl)amino | H | H | H | H | H | Me | H |
| I-1207 | c-Pr | (Methylsulfonyl)amino | H | H | H | H | H | Me | H |
| I-1208 | c-Pr | NH$_2$ | H | H | H | H | H | Me | Me |
| I-1209 | c-Pr | MeNH | H | H | H | H | H | Me | Me |
| I-1210 | c-Pr | Me$_2$N | H | H | H | H | H | Me | Me |
| I-1211 | c-Pr | cyclopentyl-NH | H | H | H | H | H | Me | Me |
| I-1212 | c-Pr | Ph—NH | H | H | H | H | H | Me | Me |
| I-1213 | c-Pr | Ph—(Bn)N | H | H | H | H | H | Me | Me |
| I-1214 | c-Pr | (Pyridin-3-yl)amino | H | H | H | H | H | Me | Me |
| I-1215 | c-Pr | Allylamino | H | H | H | H | H | Me | Me |
| I-1216 | c-Pr | Propargylamino | H | H | H | H | H | Me | Me |
| I-1217 | c-Pr | (Pyrrolidin-1-yl) | H | H | H | H | H | Me | Me |
| I-1218 | c-Pr | F$_3$CCH$_2$NH | H | H | H | H | H | Me | Me |
| I-1219 | c-Pr | Acetylamino | H | H | H | H | H | Me | Me |
| I-1220 | c-Pr | Benzoylamino | H | H | H | H | H | Me | Me |
| I-1221 | c-Pr | (Ethoxycarbonyl)amino | H | H | H | H | H | Me | Me |
| I-1222 | c-Pr | (N,N-Dimethyl-amino)carbonyl-amino | H | H | H | H | H | Me | Me |
| I-1223 | c-Pr | (N,N-Dimethylamino)(thio-carbonyl)amino | H | H | H | H | H | Me | Me |
| I-1224 | c-Pr | (Methylsulfonyl)amino | H | H | H | H | H | Me | Me |
| I-1225 | c-Pr | NH$_2$ | H | H | H | H | H | CO$_2$Et | H |
| I-1226 | c-Pr | MeNH | H | H | H | H | H | CO$_2$Et | H |
| I-1227 | c-Pr | Me$_2$N | H | H | H | H | H | CO$_2$Et | H |
| I-1228 | c-Pr | cyclopentyl-NH | H | H | H | H | H | CO$_2$Et | H |
| I-1229 | c-Pr | Ph—NH | H | H | H | H | H | CO$_2$Et | H |
| I-1230 | c-Pr | Ph—(Bn)N | H | H | H | H | H | CO$_2$Et | H |
| I-1231 | c-Pr | (Pyridin-3-yl)amino | H | H | H | H | H | CO$_2$Et | H |
| I-1232 | c-Pr | Allylamino | H | H | H | H | H | CO$_2$Et | H |
| I-1233 | c-Pr | Propargylamino | H | H | H | H | H | CO$_2$Et | H |
| I-1234 | c-Pr | (Pyrrolidin-1-yl) | H | H | H | H | H | CO$_2$Et | H |
| I-1235 | c-Pr | F$_3$CCH$_2$NH | H | H | H | H | H | CO$_2$Et | H |
| I-1236 | c-Pr | Acetylamino | H | H | H | H | H | CO$_2$Et | H |
| I-1237 | c-Pr | Benzoylamino | H | H | H | H | H | CO$_2$Et | H |
| I-1238 | c-Pr | (Ethoxycarbonyl)amino | H | H | H | H | H | CO$_2$Et | H |
| I-1239 | c-Pr | (N,N-Dimethyl-amino)carbonyl-amino | H | H | H | H | H | CO$_2$Et | H |
| I-1240 | c-Pr | (N,N-Dimethylamino)(thio-carbonyl)amino | H | H | H | H | H | CO$_2$Et | H |
| I-1241 | c-Pr | (Methylsulfonyl)amino | H | H | H | H | H | CO$_2$Et | H |
| I-1242 | c-Pr | NH$_2$ | H | H | H | H | H | CN | H |
| I-1243 | c-Pr | MeNH | H | H | H | H | H | CN | H |
| I-1244 | c-Pr | Me$_2$N | H | H | H | H | H | CN | H |
| I-1245 | c-Pr | cyclopentyl-NH | H | H | H | H | H | CN | H |
| I-1246 | c-Pr | Ph—NH | H | H | H | H | H | CN | H |
| I-1247 | c-Pr | Ph—(Bn)N | H | H | H | H | H | CN | H |
| I-1248 | c-Pr | (Pyridin-3-yl)amino | H | H | H | H | H | CN | H |
| I-1249 | c-Pr | Allylamino | H | H | H | H | H | CN | H |
| I-1250 | c-Pr | Propargylamino | H | H | H | H | H | CN | H |
| I-1251 | c-Pr | (Pyrrolidin-1-yl) | H | H | H | H | H | CN | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1252 | c-Pr | F$_3$CCH$_2$NH | H | H | H | H | H | CN | H |
| I-1253 | c-Pr | Acetylamino | H | H | H | H | H | CN | H |
| I-1254 | c-Pr | Benzoylamino | H | H | H | H | H | CN | H |
| I-1255 | c-Pr | (Ethoxycarbonyl)amino | H | H | H | H | H | CN | H |
| I-1256 | c-Pr | (N,N-Dimethyl-amino)carbonyl-amino | H | H | H | H | H | CN | H |
| I-1257 | c-Pr | (N,N-Dimethylamino)(thio-carbonyl)amino | H | H | H | H | H | CN | H |
| I-1258 | c-Pr | (Methylsulfonyl)amino | H | H | H | H | H | CN | H |
| I-1259 | c-Pr | NH$_2$ | F | H | H | H | H | Me | H |
| I-1260 | c-Pr | MeNH | F | H | H | H | H | Me | H |
| I-1261 | c-Pr | Me$_2$N | F | H | H | H | H | Me | H |
| I-1262 | c-Pr | cyclopentyl-NH | F | H | H | H | H | Me | H |
| I-1263 | c-Pr | Ph—NH | F | H | H | H | H | Me | H |
| I-1264 | c-Pr | Ph—(Bn)N | F | H | H | H | H | Me | H |
| I-1265 | c-Pr | (Pyridin-3-yl)amino | F | H | H | H | H | Me | H |
| I-1266 | c-Pr | Allylamino | F | H | H | H | H | Me | H |
| I-1267 | c-Pr | Propargylamino | F | H | H | H | H | Me | H |
| I-1268 | c-Pr | (Pyrrolidin-1-yl) | F | H | H | H | H | Me | H |
| I-1269 | c-Pr | F$_3$CCH$_2$NH | F | H | H | H | H | Me | H |
| I-1270 | c-Pr | Acetylamino | F | H | H | H | H | Me | H |
| I-1271 | c-Pr | Benzoylamino | F | H | H | H | H | Me | H |
| I-1272 | c-Pr | (Ethoxycarbonyl)amino | F | H | H | H | H | Me | H |
| I-1273 | c-Pr | (N,N-Dimethyl-amino)carbonyl-amino | F | H | H | H | H | Me | H |
| I-1274 | c-Pr | (N,N-Dimethylamino)(thio-carbonyl)amino | F | H | H | H | H | Me | H |
| I-1275 | c-Pr | (Methylsulfonyl)amino | F | H | H | H | H | Me | H |
| I-1276 | c-Pr | NH$_2$ | F | H | H | H | H | Me | Me |
| I-1277 | c-Pr | MeNH | F | H | H | H | H | Me | Me |
| I-1278 | c-Pr | Me$_2$N | F | H | H | H | H | Me | Me |
| I-1279 | c-Pr | cyclopentyl-NH | F | H | H | H | H | Me | Me |
| I-1280 | c-Pr | Ph—NH | F | H | H | H | H | Me | Me |
| I-1281 | c-Pr | Ph—(Bn)N | F | H | H | H | H | Me | Me |
| I-1282 | c-Pr | (Pyridin-3-yl)amino | F | H | H | H | H | Me | Me |
| I-1283 | c-Pr | Allylamino | F | H | H | H | H | Me | Me |
| I-1284 | c-Pr | Propargylamino | F | H | H | H | H | Me | Me |
| I-1285 | c-Pr | (Pyrrolidin-1-yl) | F | H | H | H | H | Me | Me |
| I-1286 | c-Pr | F$_3$CCH$_2$NH | F | H | H | H | H | Me | Me |
| I-1287 | c-Pr | Acetylamino | F | H | H | H | H | Me | Me |
| I-1288 | c-Pr | Benzoylamino | F | H | H | H | H | Me | Me |
| I-1289 | c-Pr | (Ethoxycarbonyl)amino | F | H | H | H | H | Me | Me |
| I-1290 | c-Pr | (N,N-Dimethyl-amino)carbonyl-amino | F | H | H | H | H | Me | Me |
| I-1291 | c-Pr | (N,N-Dimethylamino)(thio-carbonyl)amino | F | H | H | H | H | Me | Me |
| I-1292 | c-Pr | (Methylsulfonyl)amino | F | H | H | H | H | Me | Me |
| I-1293 | c-Pr | NH$_2$ | F | H | H | H | H | CO$_2$Et | H |
| I-1294 | c-Pr | MeNH | F | H | H | H | H | CO$_2$Et | H |
| I-1295 | c-Pr | Me$_2$N | F | H | H | H | H | CO$_2$Et | H |

TABLE 1-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-1296 | c-Pr | cyclopentyl-NH | F | H | H | H | H | CO$_2$Et | H |
| I-1297 | c-Pr | Ph—NH | F | H | H | H | H | CO$_2$Et | H |
| I-1298 | c-Pr | Ph—(Bn)N | F | H | H | H | H | CO$_2$Et | H |
| I-1299 | c-Pr | (Pyridin-3-yl)amino | F | H | H | H | H | CO$_2$Et | H |
| I-1300 | c-Pr | Allylamino | F | H | H | H | H | CO$_2$Et | H |
| I-1301 | c-Pr | Propargylamino | F | H | H | H | H | CO$_2$Et | H |
| I-1302 | c-Pr | (Pyrrolidin-1-yl) | F | H | H | H | H | CO$_2$Et | H |
| I-1303 | c-Pr | F$_3$CCH$_2$NH | F | H | H | H | H | CO$_2$Et | H |
| I-1304 | c-Pr | Acetylamino | F | H | H | H | H | CO$_2$Et | H |
| I-1305 | c-Pr | Benzoylamino | F | H | H | H | H | CO$_2$Et | H |
| I-1306 | c-Pr | (Ethoxycarbonyl)amine | F | H | H | H | H | CO$_2$Et | H |
| I-1307 | c-Pr | (N,N-Dimethyl-amino)carbonyl-amino | F | H | H | H | H | CO$_2$Et | H |
| I-1308 | c-Pr | (N,N-Dimethylamino)(thio-carbonyl)amino | F | H | H | H | H | CO$_2$Et | H |
| I-1309 | c-Pr | (Methylsulfonyl)amino | F | H | H | H | H | CO$_2$Et | H |
| I-1310 | c-Pr | NH$_2$ | F | H | H | H | H | CN | H |
| I-1311 | c-Pr | MeNH | F | H | H | H | H | CN | H |
| I-1312 | c-Pr | Me$_2$N | F | H | H | H | H | CN | H |
| I-1313 | c-Pr | cyclopentyl-NH | F | H | H | H | H | CN | H |
| I-1314 | c-Pr | Ph—NH | F | H | H | H | H | CN | H |
| I-1315 | c-Pr | Ph—(Bn)N | F | H | H | H | H | CN | H |
| I-1316 | c-Pr | (Pyridin-3-yl)amino | F | H | H | H | H | CN | H |
| I-1317 | c-Pr | Allylamino | F | H | H | H | H | CN | H |
| I-1318 | c-Pr | Propargylamino | F | H | H | H | H | CN | H |
| I-1319 | c-Pr | (Pyrrolidin-1-yl) | F | H | H | H | H | CN | H |
| I-1320 | c-Pr | F$_3$CCH$_2$NH | F | H | H | H | H | CN | H |
| I-1321 | c-Pr | Acetylamino | F | H | H | H | H | CN | H |
| I-1322 | c-Pr | Benzoylamino | F | H | H | H | H | CN | H |
| I-1323 | c-Pr | (Ethoxycarbonyl)amine | F | H | H | H | H | CN | H |
| I-1324 | c-Pr | (N,N-Dimethyl-amino)carbonyl-amino | F | H | H | H | H | CN | H |
| I-1325 | c-Pr | (N,N-Dimethylamino)(thio-carbonyl)amino | F | H | H | H | H | CN | H |
| I-1326 | c-Pr | (Methylsulfonyl)amino | F | H | H | H | H | CN | H |
| I-1327 | c-Pr | NH$_2$ | F | F | H | H | H | Me | H |
| I-1328 | c-Pr | MeNH | F | F | H | H | H | Me | H |
| I-1329 | c-Pr | Me$_2$N | F | F | H | H | H | Me | H |
| I-1330 | c-Pr | cyclopentyl-NH | F | F | H | H | H | Me | H |
| I-1331 | c-Pr | Ph—NH | F | F | H | H | H | Me | H |
| I-1332 | c-Pr | Ph—(Bn)N | F | F | H | H | H | Me | H |
| I-1333 | c-Pr | (Pyridin-3-yl)amino | F | F | H | H | H | Me | H |
| I-1334 | c-Pr | Allylamino | F | F | H | H | H | Me | H |
| I-1335 | c-Pr | Propargylamino | F | F | H | H | H | Me | H |
| I-1336 | c-Pr | (Pyrrolidin-1-yl) | F | F | H | H | H | Me | H |
| I-1337 | c-Pr | F$_3$CCH$_2$NH | F | F | H | H | H | Me | H |
| I-1338 | c-Pr | Acetylamino | F | F | H | H | H | Me | H |
| I-1339 | c-Pr | Benzoylamino | F | F | H | H | H | Me | H |
| I-1340 | c-Pr | (Ethoxycarbonyl)amine | F | F | H | H | H | Me | H |
| I-1341 | c-Pr | (N,N-Dimethyl-amino)carbonyl-amino | F | F | H | H | H | Me | H |

TABLE 1-continued

Inventive compounds of the formula (I) in which X represents $C(R^{13})(R^{14})$

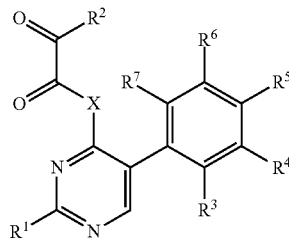

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1342 | c-Pr | (N,N-Dimethylamino)(thio-carbonyl)amino | F | F | H | H | H | Me | H |
| I-1343 | c-Pr | (Methylsulfonyl)amino | F | F | H | H | H | Me | H |
| I-1344 | c-Pr | $NH_2$ | F | F | H | H | H | Me | Me |
| I-1345 | c-Pr | MeNH | F | F | H | H | H | Me | Me |
| I-1346 | c-Pr | $Me_2N$ | F | F | H | H | H | Me | Me |
| I-1347 | c-Pr | cyclopentyl-NH | F | F | H | H | H | Me | Me |
| I-1348 | c-Pr | Ph—NH | F | F | H | H | H | Me | Me |
| I-1349 | c-Pr | Ph—(Bn)N | F | F | H | H | H | Me | Me |
| I-1350 | c-Pr | (Pyridin-3-yl)amino | F | F | H | H | H | Me | Me |
| I-1351 | c-Pr | Allylamino | F | F | H | H | H | Me | Me |
| I-1352 | c-Pr | Propargylamino | F | F | H | H | H | Me | Me |
| I-1353 | c-Pr | (Pyrrolidin-1-yl) | F | F | H | H | H | Me | Me |
| I-1354 | c-Pr | $F_3CCH_2NH$ | F | F | H | H | H | Me | Me |
| I-1355 | c-Pr | Acetylamino | F | F | H | H | H | Me | Me |
| I-1356 | c-Pr | Benzoylamino | F | F | H | H | H | Me | Me |
| I-1357 | c-Pr | (Ethoxycarbonyl)amino | F | F | H | H | H | Me | Me |
| I-1358 | c-Pr | (N,N-Dimethyl-amino)carbonyl-amino | F | F | H | H | H | Me | Me |
| I-1359 | c-Pr | (N,N-Dimethylamino)(thio-carbonyl)amino | F | F | H | H | H | Me | Me |
| I-1360 | c-Pr | (Methylsulfonyl)amino | F | F | H | H | H | Me | Me |
| I-1361 | c-Pr | $NH_2$ | F | F | H | H | H | $CO_2Et$ | H |
| I-1362 | c-Pr | MeNH | F | F | H | H | H | $CO_2Et$ | H |
| I-1363 | c-Pr | $Me_2N$ | F | F | H | H | H | $CO_2Et$ | H |
| I-1364 | c-Pr | cyclopentyl-NH | F | F | H | H | H | $CO_2Et$ | H |
| I-1365 | c-Pr | Ph—NH | F | F | H | H | H | $CO_2Et$ | H |
| I-1366 | c-Pr | Ph—(Bn)N | F | F | H | H | H | $CO_2Et$ | H |
| I-1367 | c-Pr | (Pyridin-3-yl)amino | F | F | H | H | H | $CO_2Et$ | H |
| I-1368 | c-Pr | Allylamino | F | F | H | H | H | $CO_2Et$ | H |
| I-1369 | c-Pr | Propargylamino | F | F | H | H | H | $CO_2Et$ | H |
| I-1370 | c-Pr | (Pyrrolidin-1-yl) | F | F | H | H | H | $CO_2Et$ | H |
| I-1371 | c-Pr | $F_3CCH_2NH$ | F | F | H | H | H | $CO_2Et$ | H |
| I-1372 | c-Pr | Acetylamino | F | F | H | H | H | $CO_2Et$ | H |
| I-1373 | c-Pr | Benzoylamino | F | F | H | H | H | $CO_2Et$ | H |
| I-1374 | c-Pr | (Ethoxycarbonyl)amino | F | F | H | H | H | $CO_2Et$ | H |
| I-1375 | c-Pr | (N,N-Dimethyl-amino)carbonyl-amino | F | F | H | H | H | $CO_2Et$ | H |
| I-1376 | c-Pr | (N,N-Dimethylamino)(thio-carbonyl)amino | F | F | H | H | H | $CO_2Et$ | H |
| I-1377 | c-Pr | (Methylsulfonyl)amino | F | F | H | H | H | $CO_2Et$ | H |
| I-1378 | c-Pr | $NH_2$ | F | F | H | H | H | CN | H |
| I-1379 | c-Pr | MeNH | F | F | H | H | H | CN | H |
| I-1380 | c-Pr | $Me_2N$ | F | F | H | H | H | CN | H |
| I-1381 | c-Pr | cyclopentyl-NH | F | F | H | H | H | CN | H |
| I-1382 | c-Pr | Ph—NH | F | F | H | H | H | CN | H |
| I-1383 | c-Pr | Ph—(Bn)N | F | F | H | H | H | CN | H |
| I-1384 | c-Pr | (Pyridin-3-yl)amino | F | F | H | H | H | CN | H |
| I-1385 | c-Pr | Allylamino | F | F | H | H | H | CN | H |
| I-1386 | c-Pr | Propargylamino | F | F | H | H | H | CN | H |
| I-1387 | c-Pr | (Pyrrolidin-1-yl) | F | F | H | H | H | CN | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1388 | c-Pr | $F_3CCH_2NH$ | F | F | H | H | H | CN | H |
| I-1389 | c-Pr | Acetylamino | F | F | H | H | H | CN | H |
| I-1390 | c-Pr | Benzoylamino | F | F | H | H | H | CN | H |
| I-1391 | c-Pr | (Ethoxycarbonyl)amino | F | F | H | H | H | CN | H |
| I-1392 | c-Pr | (N,N-Dimethyl-amino)carbonyl-amino | F | F | H | H | H | CN | H |
| I-1393 | c-Pr | (N,N-Dimethylamino)(thio-carbonyl)amino | F | F | H | H | H | CN | H |
| I-1394 | c-Pr | (Methylsulfonyl)amino | F | F | H | H | H | CN | H |
| I-1395 | c-Pr | $NH_2$ | F | H | F | H | H | Me | H |
| I-1396 | c-Pr | MeNH | F | H | F | H | H | Me | H |
| I-1397 | c-Pr | $Me_2N$ | F | H | F | H | H | Me | H |
| I-1398 | c-Pr | cyclopentyl-NH | F | H | F | H | H | Me | H |
| I-1399 | c-Pr | Ph—NH | F | H | F | H | H | Me | H |
| I-1400 | c-Pr | Ph—(Bn)N | F | H | F | H | H | Me | H |
| I-1401 | c-Pr | (Pyridin-3-yl)amino | F | H | F | H | H | Me | H |
| I-1402 | c-Pr | Allylamino | F | H | F | H | H | Me | H |
| I-1403 | c-Pr | Propargylamino | F | H | F | H | H | Me | H |
| I-1404 | c-Pr | (Pyrrolidin-1-yl) | F | H | F | H | H | Me | H |
| I-1405 | c-Pr | $F_3CCH_2NH$ | F | H | F | H | H | Me | H |
| I-1406 | c-Pr | Acetylamino | F | H | F | H | H | Me | H |
| I-1407 | c-Pr | Benzoylamino | F | H | F | H | H | Me | H |
| I-1408 | c-Pr | (Ethoxycarbonyl)amino | F | H | F | H | H | Me | H |
| I-1409 | c-Pr | (N,N-Dimethyl-amino)carbonyl-amino | F | H | F | H | H | Me | H |
| I-1410 | c-Pr | (N,N-Dimethylamino)(thio-carbonyl)amino | F | H | F | H | H | Me | H |
| I-1411 | c-Pr | (Methylsulfonyl)amino | F | H | F | H | H | Me | H |
| I-1412 | c-Pr | $NH_2$ | F | H | F | H | H | Me | Me |
| I-1413 | c-Pr | MeNH | F | H | F | H | H | Me | Me |
| I-1414 | c-Pr | $Me_2N$ | F | H | F | H | H | Me | Me |
| I-1415 | c-Pr | cyclopentyl-NH | F | H | F | H | H | Me | Me |
| I-1416 | c-Pr | Ph—NH | F | H | F | H | H | Me | Me |
| I-1417 | c-Pr | Ph—(Bn)N | F | H | F | H | H | Me | Me |
| I-1418 | c-Pr | (Pyridin-3-yl)amino | F | H | F | H | H | Me | Me |
| I-1419 | c-Pr | Allylamino | F | H | F | H | H | Me | Me |
| I-1420 | c-Pr | Propargylamino | F | H | F | H | H | Me | Me |
| I-1421 | c-Pr | (Pyrrolidin-1-yl) | F | H | F | H | H | Me | Me |
| I-1422 | c-Pr | $F_3CCH_2NH$ | F | H | F | H | H | Me | Me |
| I-1423 | c-Pr | Acetylamino | F | H | F | H | H | Me | Me |
| I-1424 | c-Pr | Benzoylamino | F | H | F | H | H | Me | Me |
| I-1425 | c-Pr | (Ethoxycarbonyl)amino | F | H | F | H | H | Me | Me |
| I-1426 | c-Pr | (N,N-Dimethyl-amino)carbonyl-amino | F | H | F | H | H | Me | Me |
| I-1427 | c-Pr | (N,N-Dimethylamino)(thio-carbonyl)amino | F | H | F | H | H | Me | Me |
| I-1428 | c-Pr | (Methylsulfonyl)amino | F | H | F | H | H | Me | Me |
| I-1429 | c-Pr | $NH_2$ | F | H | F | H | H | $CO_2Et$ | H |
| I-1430 | c-Pr | MeNH | F | H | F | H | H | $CO_2Et$ | H |
| I-1431 | c-Pr | $Me_2N$ | F | H | F | H | H | $CO_2Et$ | H |

TABLE 1-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-1432 | c-Pr | cyclopentyl-NH | F | H | F | H | H | CO$_2$Et | H |
| I-1433 | c-Pr | Ph—NH | F | H | F | H | H | CO$_2$Et | H |
| I-1434 | c-Pr | Ph—(Bn)N | F | H | F | H | H | CO$_2$Et | H |
| I-1435 | c-Pr | (Pyridin-3-yl)amino | F | H | F | H | H | CO$_2$Et | H |
| I-1436 | c-Pr | Allylamino | F | H | F | H | H | CO$_2$Et | H |
| I-1437 | c-Pr | Propargylamino | F | H | F | H | H | CO$_2$Et | H |
| I-1438 | c-Pr | (Pyrrolidin-1-yl) | F | H | F | H | H | CO$_2$Et | H |
| I-1439 | c-Pr | F$_3$CCH$_2$NH | F | H | F | H | H | CO$_2$Et | H |
| I-1440 | c-Pr | Acetylamino | F | H | F | H | H | CO$_2$Et | H |
| I-1441 | c-Pr | Benzoylamino | F | H | F | H | H | CO$_2$Et | H |
| I-1442 | c-Pr | (Ethoxycarbonyl)amino | F | H | F | H | H | CO$_2$Et | H |
| I-1443 | c-Pr | (N,N-Dimethyl-amino)carbonyl-amino | F | H | F | H | H | CO$_2$Et | H |
| I-1444 | c-Pr | (N,N-Dimethylamino)(thio-carbonyl)amino | F | H | F | H | H | CO$_2$Et | H |
| I-1445 | c-Pr | (Methylsulfonyl)amino | F | H | F | H | H | CO$_2$Et | H |
| I-1446 | c-Pr | NH$_2$ | F | H | F | H | H | CN | H |
| I-1447 | c-Pr | MeNH | F | H | F | H | H | CN | H |
| I-1448 | c-Pr | Me$_2$N | F | H | F | H | H | CN | H |
| I-1449 | c-Pr | cyclopentyl-NH | F | H | F | H | H | CN | H |
| I-1450 | c-Pr | Ph—NH | F | H | F | H | H | CN | H |
| I-1451 | c-Pr | Ph—(Bn)N | F | H | F | H | H | CN | H |
| I-1452 | c-Pr | (Pyridin-3-yl)amino | F | H | F | H | H | CN | H |
| I-1453 | c-Pr | Allylamino | F | H | F | H | H | CN | H |
| I-1454 | c-Pr | Propargylamino | F | H | F | H | H | CN | H |
| I-1455 | c-Pr | (Pyrrolidin-1-yl) | F | H | F | H | H | CN | H |
| I-1456 | c-Pr | F$_3$CCH$_2$NH | F | H | F | H | H | CN | H |
| I-1457 | c-Pr | Acetylamino | F | H | F | H | H | CN | H |
| I-1458 | c-Pr | Benzoylamino | F | H | F | H | H | CN | H |
| I-1459 | c-Pr | (Ethoxycarbonyl)amino | F | H | F | H | H | CN | H |
| I-1460 | c-Pr | (N,N-Dimethyl-amino)carbonyl-amino | F | H | F | H | H | CN | H |
| I-1461 | c-Pr | (N,N-Dimethylamino)(thio-carbonyl)amino | F | H | F | H | H | CN | H |
| I-1462 | c-Pr | (Methylsulfonyl)amino | F | H | F | H | H | CN | H |
| I-1463 | c-Pr | NH$_2$ | F | H | H | F | H | Me | H |
| I-1464 | c-Pr | MeNH | F | H | H | F | H | Me | H |
| I-1465 | c-Pr | Me$_2$N | F | H | H | F | H | Me | H |
| I-1466 | c-Pr | cyclopentyl-NH | F | H | H | F | H | Me | H |
| I-1467 | c-Pr | Ph—NH | F | H | H | F | H | Me | H |
| I-1468 | c-Pr | Ph—(Bn)N | F | H | H | F | H | Me | H |
| I-1469 | c-Pr | (Pyridin-3-yl)amino | F | H | H | F | H | Me | H |
| I-1470 | c-Pr | Allylamino | F | H | H | F | H | Me | H |
| I-1471 | c-Pr | Propargylamino | F | H | H | F | H | Me | H |
| I-1472 | c-Pr | (Pyrrolidin-1-yl) | F | H | H | F | H | Me | H |
| I-1473 | c-Pr | F$_3$CCH$_2$NH | F | H | H | F | H | Me | H |
| I-1474 | c-Pr | Acetylamino | F | H | H | F | H | Me | H |
| I-1475 | c-Pr | Benzoylamino | F | H | H | F | H | Me | H |
| I-1476 | c-Pr | (Ethoxycarbonyl)amino | F | H | H | F | H | Me | H |
| I-1477 | c-Pr | (N,N-Dimethyl-amino)carbonyl-amino | F | H | H | F | H | Me | H |

TABLE 1-continued

Inventive compounds of the formula (I) in which X represents $C(R^{13})(R^{14})$

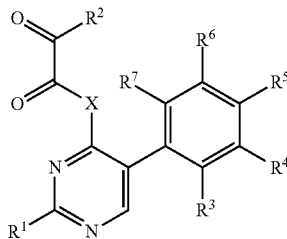

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1478 | c-Pr | (N,N-Dimethylamino)(thiocarbonyl)amino | F | H | H | F | H | Me | H |
| I-1479 | c-Pr | (Methylsulfonyl)amino | F | H | H | F | H | Me | H |
| I-1480 | c-Pr | $NH_2$ | F | H | H | F | H | Me | Me |
| I-1481 | c-Pr | MeNH | F | H | H | F | H | Me | Me |
| I-1482 | c-Pr | $Me_2N$ | F | H | H | F | H | Me | Me |
| I-1483 | c-Pr | cyclopentyl-NH | F | H | H | F | H | Me | Me |
| I-1484 | c-Pr | Ph—NH | F | H | H | F | H | Me | Me |
| I-1485 | c-Pr | Ph—(Bn)N | F | H | H | F | H | Me | Me |
| I-1486 | c-Pr | (Pyridin-3-yl)amino | F | H | H | F | H | Me | Me |
| I-1487 | c-Pr | Allylamino | F | H | H | F | H | Me | Me |
| I-1488 | c-Pr | Propargylamino | F | H | H | F | H | Me | Me |
| I-1489 | c-Pr | (Pyrrolidin-1-yl) | F | H | H | F | H | Me | Me |
| I-1490 | c-Pr | $F_3CCH_2NH$ | F | H | H | F | H | Me | Me |
| I-1491 | c-Pr | Acetylamino | F | H | H | F | H | Me | Me |
| I-1492 | c-Pr | Benzoylamino | F | H | H | F | H | Me | Me |
| I-1493 | c-Pr | (Ethoxycarbonyl)amino | F | H | H | F | H | Me | Me |
| I-1494 | c-Pr | (N,N-Dimethyl-amino)carbonyl-amino | F | H | H | F | H | Me | Me |
| I-1495 | c-Pr | (N,N-Dimethylamino)(thiocarbonyl)amino | F | H | H | F | H | Me | Me |
| I-1496 | c-Pr | (Methylsulfonyl)amino | F | H | H | F | H | Me | Me |
| I-1497 | c-Pr | $NH_2$ | F | H | H | F | H | $CO_2Et$ | H |
| I-1498 | c-Pr | MeNH | F | H | H | F | H | $CO_2Et$ | H |
| I-1499 | c-Pr | $Me_2N$ | F | H | H | F | H | $CO_2Et$ | H |
| I-1500 | c-Pr | cyclopentyl-NH | F | H | H | F | H | $CO_2Et$ | H |
| I-1501 | c-Pr | Ph—NH | F | H | H | F | H | $CO_2Et$ | H |
| I-1502 | c-Pr | Ph—(Bn)N | F | H | H | F | H | $CO_2Et$ | H |
| I-1503 | c-Pr | (Pyridin-3-yl)amino | F | H | H | F | H | $CO_2Et$ | H |
| I-1504 | c-Pr | Allylamino | F | H | H | F | H | $CO_2Et$ | H |
| I-1505 | c-Pr | Propargylamino | F | H | H | F | H | $CO_2Et$ | H |
| I-1506 | c-Pr | (Pyrrolidin-1-yl) | F | H | H | F | H | $CO_2Et$ | H |
| I-1507 | c-Pr | $F_3CCH_2NH$ | F | H | H | F | H | $CO_2Et$ | H |
| I-1508 | c-Pr | Acetylamino | F | H | H | F | H | $CO_2Et$ | H |
| I-1509 | c-Pr | Benzoylamino | F | H | H | F | H | $CO_2Et$ | H |
| I-1510 | c-Pr | (Ethoxycarbonyl)amino | F | H | H | F | H | $CO_2Et$ | H |
| I-1511 | c-Pr | (N,N-Dimethyl-amino)carbonyl-amino | F | H | H | F | H | $CO_2Et$ | H |
| I-1512 | c-Pr | (N,N-Dimethylamino)(thiocarbonyl)amino | F | H | H | F | H | $CO_2Et$ | H |
| I-1513 | c-Pr | (Methylsulfonyl)amino | F | H | H | F | H | $CO_2Et$ | H |
| I-1514 | c-Pr | $NH_2$ | F | H | H | F | H | CN | H |
| I-1515 | c-Pr | MeNH | F | H | H | F | H | CN | H |
| I-1516 | c-Pr | $Me_2N$ | F | H | H | F | H | CN | H |
| I-1517 | c-Pr | cyclopentyl-NH | F | H | H | F | H | CN | H |
| I-1518 | c-Pr | Ph—NH | F | H | H | F | H | CN | H |
| I-1519 | c-Pr | Ph—(Bn)N | F | H | H | F | H | CN | H |
| I-1520 | c-Pr | (Pyridin-3-yl)amino | F | H | H | F | H | CN | H |
| I-1521 | c-Pr | Allylamino | F | H | H | F | H | CN | H |
| I-1522 | c-Pr | Propargylamino | F | H | H | F | H | CN | H |
| I-1523 | c-Pr | (Pyrrolidin-1-yl) | F | H | H | F | H | CN | H |

TABLE 1-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-1524 | c-Pr | F$_3$CCH$_2$NH | F | H | H | F | H | CN | H |
| I-1525 | c-Pr | Acetylamino | F | H | H | F | H | CN | H |
| I-1526 | c-Pr | Benzoylamino | F | H | H | F | H | CN | H |
| I-1527 | c-Pr | (Ethoxycarbonyl)amino | F | H | H | F | H | CN | H |
| I-1528 | c-Pr | (N,N-Dimethyl-amino)carbonyl-amino | F | H | H | F | H | CN | H |
| I-1529 | c-Pr | (N,N-Dimethylamino)(thio-carbonyl)amino | F | H | H | F | H | CN | H |
| I-1530 | c-Pr | (Methylsulfonyl)amino | F | H | H | F | H | CN | H |
| I-1531 | c-Pr | NH$_2$ | F | H | H | H | F | Me | H |
| I-1532 | c-Pr | MeNH | F | H | H | H | F | Me | H |
| I-1533 | c-Pr | Me$_2$N | F | H | H | H | F | Me | H |
| I-1534 | c-Pr | cyclopentyl-NH | F | H | H | H | F | Me | H |
| I-1535 | c-Pr | Ph—NH | F | H | H | H | F | Me | H |
| I-1536 | c-Pr | Ph—(Bn)N | F | H | H | H | F | Me | H |
| I-1537 | c-Pr | (Pyridin-3-yl)amino | F | H | H | H | F | Me | H |
| I-1538 | c-Pr | Allylamino | F | H | H | H | F | Me | H |
| I-1539 | c-Pr | Propargylamino | F | H | H | H | F | Me | H |
| I-1540 | c-Pr | (Pyrrolidin-1-yl) | F | H | H | H | F | Me | H |
| I-1541 | c-Pr | F$_3$CCH$_2$NH | F | H | H | H | F | Me | H |
| I-1542 | c-Pr | Acetylamino | F | H | H | H | F | Me | H |
| I-1543 | c-Pr | Benzoylamino | F | H | H | H | F | Me | H |
| I-1544 | c-Pr | (Ethoxycarbonyl)amino | F | H | H | H | F | Me | H |
| I-1545 | c-Pr | (N,N-Dimethyl-amino)carbonyl-amino | F | H | H | H | F | Me | H |
| I-1546 | c-Pr | (N,N-Dimethylamino)(thio-carbonyl)amino | F | H | H | H | F | Me | H |
| I-1547 | c-Pr | (Methylsulfonyl)amino | F | H | H | H | F | Me | H |
| I-1548 | c-Pr | NH$_2$ | F | H | H | H | F | Me | Me |
| I-1549 | c-Pr | MeNH | F | H | H | H | F | Me | Me |
| I-1550 | c-Pr | Me$_2$N | F | H | H | H | F | Me | Me |
| I-1551 | c-Pr | cyclopentyl-NH | F | H | H | H | F | Me | Me |
| I-1552 | c-Pr | Ph—NH | F | H | H | H | F | Me | Me |
| I-1553 | c-Pr | Ph—(Bn)N | F | H | H | H | F | Me | Me |
| I-1554 | c-Pr | (Pyridin-3-yl)amino | F | H | H | H | F | Me | Me |
| I-1555 | c-Pr | Allylamino | F | H | H | H | F | Me | Me |
| I-1556 | c-Pr | Propargylamino | F | H | H | H | F | Me | Me |
| I-1557 | c-Pr | (Pyrrolidin-1-yl) | F | H | H | H | F | Me | Me |
| I-1558 | c-Pr | F$_3$CCH$_2$NH | F | H | H | H | F | Me | Me |
| I-1559 | c-Pr | Acetylamino | F | H | H | H | F | Me | Me |
| I-1560 | c-Pr | Benzoylamino | F | H | H | H | F | Me | Me |
| I-1561 | c-Pr | (Ethoxycarbonyl)amino | F | H | H | H | F | Me | Me |
| I-1562 | c-Pr | (N,N-Dimethyl-amino)carbonyl-amino | F | H | H | H | F | Me | Me |
| I-1563 | c-Pr | (N,N-Dimethylamino)(thio-carbonyl)amino | F | H | H | H | F | Me | Me |
| I-1564 | c-Pr | (Methylsulfonyl)amino | F | H | H | H | F | Me | Me |
| I-1565 | c-Pr | NH$_2$ | F | H | H | H | F | CO$_2$Et | H |
| I-1566 | c-Pr | MeNH | F | H | H | H | F | CO$_2$Et | H |

TABLE 1-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1567 | c-Pr | Me$_2$N | F | H | H | H | F | CO$_2$Et | H |
| I-1568 | c-Pr | cyclopentyl-NH | F | H | H | H | F | CO$_2$Et | H |
| I-1569 | c-Pr | Ph—NH | F | H | H | H | F | CO$_2$Et | H |
| I-1570 | c-Pr | Ph—(Bn)N | F | H | H | H | F | CO$_2$Et | H |
| I-1571 | c-Pr | (Pyridin-3-yl)amino | F | H | H | H | F | CO$_2$Et | H |
| I-1572 | c-Pr | Allylamino | F | H | H | H | F | CO$_2$Et | H |
| I-1573 | c-Pr | Propargylamino | F | H | H | H | F | CO$_2$Et | H |
| I-1574 | c-Pr | (Pyrrolidin-1-yl) | F | H | H | H | F | CO$_2$Et | H |
| I-1575 | c-Pr | F$_3$CCH$_2$NH | F | H | H | H | F | CO$_2$Et | H |
| I-1576 | c-Pr | Acetylamino | F | H | H | H | F | CO$_2$Et | H |
| I-1577 | c-Pr | Benzoylamino | F | H | H | H | F | CO$_2$Et | H |
| I-1578 | c-Pr | (Ethoxycarbonyl)amino | F | H | H | H | F | CO$_2$Et | H |
| I-1579 | c-Pr | (N,N-Dimethyl-amino)carbonyl-amino | F | H | H | H | F | CO$_2$Et | H |
| I-1580 | c-Pr | (N,N-Dimethylamino)(thio-carbonyl)amino | F | H | H | H | F | CO$_2$Et | H |
| I-1581 | c-Pr | (Methylsulfonyl)amino | F | H | H | H | F | CO$_2$Et | H |
| I-1582 | c-Pr | NH$_2$ | F | H | H | H | F | CN | H |
| I-1583 | c-Pr | MeNH | F | H | H | H | F | CN | H |
| I-1584 | c-Pr | Me$_2$N | F | H | H | H | F | CN | H |
| I-1585 | c-Pr | cyclopentyl-NH | F | H | H | H | F | CN | H |
| I-1586 | c-Pr | Ph—NH | F | H | H | H | F | CN | H |
| I-1587 | c-Pr | Ph—(Bn)N | F | H | H | H | F | CN | H |
| I-1588 | c-Pr | (Pyridin-3-yl)amino | F | H | H | H | F | CN | H |
| I-1589 | c-Pr | Allylamino | F | H | H | H | F | CN | H |
| I-1590 | c-Pr | Propargylamino | F | H | H | H | F | CN | H |
| I-1591 | c-Pr | (Pyrrolidin-1-yl) | F | H | H | H | F | CN | H |
| I-1592 | c-Pr | F$_3$CCH$_2$NH | F | H | H | H | F | CN | H |
| I-1593 | c-Pr | Acetylamino | F | H | H | H | F | CN | H |
| I-1594 | c-Pr | Benzoylamino | F | H | H | H | F | CN | H |
| I-1595 | c-Pr | (Ethoxycarbonyl)amino | F | H | H | H | F | CN | H |
| I-1596 | c-Pr | (N,N-Dimethyl-amino)carbonyl-amino | F | H | H | H | F | CN | H |
| I-1597 | c-Pr | (N,N-Dimethylamino)(thio-carbonyl)amino | F | H | H | H | F | CN | H |
| I-1598 | c-Pr | (Methylsulfonyl)amino | F | H | H | H | F | CN | H |
| I-1599 | c-Pr | NH$_2$ | Cl | F | H | H | H | Me | H |
| I-1600 | c-Pr | MeNH | Cl | F | H | H | H | Me | H |
| I-1601 | c-Pr | Me$_2$N | Cl | F | H | H | H | Me | H |
| I-1602 | c-Pr | cyclopentyl-NH | Cl | F | H | H | H | Me | H |
| I-1603 | c-Pr | Ph—NH | Cl | F | H | H | H | Me | H |
| I-1604 | c-Pr | Ph—(Bn)N | Cl | F | H | H | H | Me | H |
| I-1605 | c-Pr | (Pyridin-3-yl)amino | Cl | F | H | H | H | Me | H |
| I-1606 | c-Pr | Allylamino | Cl | F | H | H | H | Me | H |
| I-1607 | c-Pr | Propargylamino | Cl | F | H | H | H | Me | H |
| I-1608 | c-Pr | (Pyrrolidin-1-yl) | Cl | F | H | H | H | Me | H |
| I-1609 | c-Pr | F$_3$CCH$_2$NH | Cl | F | H | H | H | Me | H |
| I-1610 | c-Pr | Acetylamino | Cl | F | H | H | H | Me | H |
| I-1611 | c-Pr | Benzoylamino | Cl | F | H | H | H | Me | H |
| I-1612 | c-Pr | (Ethoxycarbonyl)amino | Cl | F | H | H | H | Me | H |
| I-1613 | c-Pr | (N,N-Dimethyl-amino)carbonyl-amino | Cl | F | H | H | H | Me | H |

TABLE 1-continued

Inventive compounds of the formula (I) in which X represents $C(R^{13})(R^{14})$

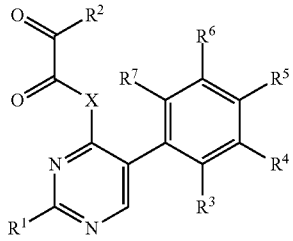

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1614 | c-Pr | (N,N-Dimethylamino)(thiocarbonyl)amino | Cl | F | H | H | H | Me | H |
| I-1615 | c-Pr | (Methylsulfonyl)amino | Cl | F | H | H | H | Me | H |
| I-1616 | c-Pr | $NH_2$ | Cl | F | H | H | H | Me | Me |
| I-1617 | c-Pr | MeNH | Cl | F | H | H | H | Me | Me |
| I-1618 | c-Pr | $Me_2N$ | Cl | F | H | H | H | Me | Me |
| I-1619 | c-Pr | cyclopentyl-NH | Cl | F | H | H | H | Me | Me |
| I-1620 | c-Pr | Ph—NH | Cl | F | H | H | H | Me | Me |
| I-1621 | c-Pr | Ph—(Bn)N | Cl | F | H | H | H | Me | Me |
| I-1622 | c-Pr | (Pyridin-3-yl)amino | Cl | F | H | H | H | Me | Me |
| I-1623 | c-Pr | Allylamino | Cl | F | H | H | H | Me | Me |
| I-1624 | c-Pr | Propargylamino | Cl | F | H | H | H | Me | Me |
| I-1625 | c-Pr | (Pyrrolidin-1-yl) | Cl | F | H | H | H | Me | Me |
| I-1626 | c-Pr | $F_3CCH_2NH$ | Cl | F | H | H | H | Me | Me |
| I-1627 | c-Pr | Acetylamino | Cl | F | H | H | H | Me | Me |
| I-1628 | c-Pr | Benzoylamino | Cl | F | H | H | H | Me | Me |
| I-1629 | c-Pr | (Ethoxycarbonyl)amino | Cl | F | H | H | H | Me | Me |
| I-1630 | c-Pr | (N,N-Dimethyl-amino)carbonyl-amino | Cl | F | H | H | H | Me | Me |
| I-1631 | c-Pr | (N,N-Dimethylamino)(thiocarbonyl)amino | Cl | F | H | H | H | Me | Me |
| I-1632 | c-Pr | (Methylsulfonyl)amino | Cl | F | H | H | H | Me | Me |
| I-1633 | c-Pr | $NH_2$ | Cl | F | H | H | H | $CO_2Et$ | H |
| I-1634 | c-Pr | MeNH | Cl | F | H | H | H | $CO_2Et$ | H |
| I-1635 | c-Pr | $Me_2N$ | Cl | F | H | H | H | $CO_2Et$ | H |
| I-1636 | c-Pr | cyclopentyl-NH | Cl | F | H | H | H | $CO_2Et$ | H |
| I-1637 | c-Pr | Ph—NH | Cl | F | H | H | H | $CO_2Et$ | H |
| I-1638 | c-Pr | Ph—(Bn)N | Cl | F | H | H | H | $CO_2Et$ | H |
| I-1639 | c-Pr | (Pyridin-3-yl)amino | Cl | F | H | H | H | $CO_2Et$ | H |
| I-1640 | c-Pr | Allylamino | Cl | F | H | H | H | $CO_2Et$ | H |
| I-1641 | c-Pr | Propargylamino | Cl | F | H | H | H | $CO_2Et$ | H |
| I-1642 | c-Pr | (Pyrrolidin-1-yl) | Cl | F | H | H | H | $CO_2Et$ | H |
| I-1643 | c-Pr | $F_3CCH_2NH$ | Cl | F | H | H | H | $CO_2Et$ | H |
| I-1644 | c-Pr | Acetylamino | Cl | F | H | H | H | $CO_2Et$ | H |
| I-1645 | c-Pr | Benzoylamino | Cl | F | H | H | H | $CO_2Et$ | H |
| I-1646 | c-Pr | (Ethoxycarbonyl)amino | Cl | F | H | H | H | $CO_2Et$ | H |
| I-1647 | c-Pr | (N,N-Dimethyl-amino)carbonyl-amino | Cl | F | H | H | H | $CO_2Et$ | H |
| I-1648 | c-Pr | (N,N-Dimethylamino)(thiocarbonyl)amino | Cl | F | H | H | H | $CO_2Et$ | H |
| I-1649 | c-Pr | (Methylsulfonyl)amino | Cl | F | H | H | H | $CO_2Et$ | H |
| I-1650 | c-Pr | $NH_2$ | Cl | F | H | H | H | CN | H |
| I-1651 | c-Pr | MeNH | Cl | F | H | H | H | CN | H |
| I-1652 | c-Pr | $Me_2N$ | Cl | F | H | H | H | CN | H |
| I-1653 | c-Pr | cyclopentyl-NH | Cl | F | H | H | H | CN | H |
| I-1654 | c-Pr | Ph—NH | Cl | F | H | H | H | CN | H |
| I-1655 | c-Pr | Ph—(Bn)N | Cl | F | H | H | H | CN | H |
| I-1656 | c-Pr | (Pyridin-3-yl)amino | Cl | F | H | H | H | CN | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1657 | c-Pr | Allylamino | Cl | F | H | H | H | CN | H |
| I-1658 | c-Pr | Propargylamino | Cl | F | H | H | H | CN | H |
| I-1659 | c-Pr | (Pyrrolidin-1-yl) | Cl | F | H | H | H | CN | H |
| I-1660 | c-Pr | $F_3CCH_2NH$ | Cl | F | H | H | H | CN | H |
| I-1661 | c-Pr | Acetylamino | Cl | F | H | H | H | CN | H |
| I-1662 | c-Pr | Benzoylamino | Cl | F | H | H | H | CN | H |
| I-1663 | c-Pr | (Ethoxycarbonyl)amino | Cl | F | H | H | H | CN | H |
| I-1664 | c-Pr | (N,N-Dimethyl-amino)carbonyl-amino | Cl | F | H | H | H | CN | H |
| I-1665 | c-Pr | (N,N-Dimethylamino)(thio-carbonyl)amino | Cl | F | H | H | H | CN | H |
| I-1666 | c-Pr | (Methylsulfonyl)amino | Cl | F | H | H | H | CN | H |
| I-1667 | c-Pr | $NH_2$ | Cl | H | F | H | H | Me | H |
| I-1668 | c-Pr | MeNH | Cl | H | F | H | H | Me | H |
| I-1669 | c-Pr | $Me_2N$ | Cl | H | F | H | H | Me | H |
| I-1670 | c-Pr | cyclopentyl-NH | Cl | H | F | H | H | Me | H |
| I-1671 | c-Pr | Ph—NH | Cl | H | F | H | H | Me | H |
| I-1672 | c-Pr | Ph—(Bn)N | Cl | H | F | H | H | Me | H |
| I-1673 | c-Pr | (Pyridin-3-yl)amino | Cl | H | F | H | H | Me | H |
| I-1674 | c-Pr | Allylamino | Cl | H | F | H | H | Me | H |
| I-1675 | c-Pr | Propargylamino | Cl | H | F | H | H | Me | H |
| I-1676 | c-Pr | (Pyrrolidin-1-yl) | Cl | H | F | H | H | Me | H |
| I-1677 | c-Pr | $F_3CCH_2NH$ | Cl | H | F | H | H | Me | H |
| I-1678 | c-Pr | Acetylamino | Cl | H | F | H | H | Me | H |
| I-1679 | c-Pr | Benzoylamino | Cl | H | F | H | H | Me | H |
| I-1680 | c-Pr | (Ethoxycarbonyl)amino | Cl | H | F | H | H | Me | H |
| I-1681 | c-Pr | (N,N-Dimethyl-amino)carbonyl-amino | Cl | H | F | H | H | Me | H |
| I-1682 | c-Pr | (N,N-Dimethylamino)(thio-carbonyl)amino | Cl | H | F | H | H | Me | H |
| I-1683 | c-Pr | (Methylsulfonyl)amino | Cl | H | F | H | H | Me | H |
| I-1684 | c-Pr | $NH_2$ | Cl | H | F | H | H | Me | Me |
| I-1685 | c-Pr | MeNH | Cl | H | F | H | H | Me | Me |
| I-1686 | c-Pr | $Me_2N$ | Cl | H | F | H | H | Me | Me |
| I-1687 | c-Pr | cyclopentyl-NH | Cl | H | F | H | H | Me | Me |
| I-1688 | c-Pr | Ph—NH | Cl | H | F | H | H | Me | Me |
| I-1689 | c-Pr | Ph—(Bn)N | Cl | H | F | H | H | Me | Me |
| I-1690 | c-Pr | (Pyridin-3-yl)amino | Cl | H | F | H | H | Me | Me |
| I-1691 | c-Pr | Allylamino | Cl | H | F | H | H | Me | Me |
| I-1692 | c-Pr | Propargylamino | Cl | H | F | H | H | Me | Me |
| I-1693 | c-Pr | (Pyrrolidin-1-yl) | Cl | H | F | H | H | Me | Me |
| I-1694 | c-Pr | $F_3CCH_2NH$ | Cl | H | F | H | H | Me | Me |
| I-1695 | c-Pr | Acetylamino | Cl | H | F | H | H | Me | Me |
| I-1696 | c-Pr | Benzoylamino | Cl | H | F | H | H | Me | Me |
| I-1697 | c-Pr | (Ethoxycarbonyl)amino | Cl | H | F | H | H | Me | Me |
| I-1698 | c-Pr | (N,N-Dimethyl-amino)carbonyl-amino | Cl | H | F | H | H | Me | Me |
| I-1699 | c-Pr | (N,N-Dimethylamino)(thio-carbonyl)amino | Cl | H | F | H | H | Me | Me |
| I-1700 | c-Pr | (Methylsulfonyl)amino | Cl | H | F | H | H | Me | Me |
| I-1701 | c-Pr | $NH_2$ | Cl | H | F | H | H | $CO_2Et$ | H |
| I-1702 | c-Pr | MeNH | Cl | H | F | H | H | $CO_2Et$ | H |

TABLE 1-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1703 | c-Pr | Me₂N | Cl | H | F | H | H | CO₂Et | H |
| I-1704 | c-Pr | cyclopentyl-NH | Cl | H | F | H | H | CO₂Et | H |
| I-1705 | c-Pr | Ph—NH | Cl | H | F | H | H | CO₂Et | H |
| I-1706 | c-Pr | Ph—(Bn)N | Cl | H | F | H | H | CO₂Et | H |
| I-1707 | c-Pr | (Pyridin-3-yl)amino | Cl | H | F | H | H | CO₂Et | H |
| I-1708 | c-Pr | Allylamino | Cl | H | F | H | H | CO₂Et | H |
| I-1709 | c-Pr | Propargylamino | Cl | H | F | H | H | CO₂Et | H |
| I-1710 | c-Pr | (Pyrrolidin-1-yl) | Cl | H | F | H | H | CO₂Et | H |
| I-1711 | c-Pr | F₃CCH₂NH | Cl | H | F | H | H | CO₂Et | H |
| I-1712 | c-Pr | Acetylamino | Cl | H | F | H | H | CO₂Et | H |
| I-1713 | c-Pr | Benzoylamino | Cl | H | F | H | H | CO₂Et | H |
| I-1714 | c-Pr | (Ethoxycarbonyl)amino | Cl | H | F | H | H | CO₂Et | H |
| I-1715 | c-Pr | (N,N-Dimethyl-amino)carbonyl-amino | Cl | H | F | H | H | CO₂Et | H |
| I-1716 | c-Pr | (N,N-Dimethylamino)(thio-carbonyl)amino | Cl | H | F | H | H | CO₂Et | H |
| I-1717 | c-Pr | (Methylsulfonyl)amino | Cl | H | F | H | H | CO₂Et | H |
| I-1718 | c-Pr | NH₂ | Cl | H | F | H | H | CN | H |
| I-1719 | c-Pr | MeNH | Cl | H | F | H | H | CN | H |
| I-1720 | c-Pr | Me₂N | Cl | H | F | H | H | CN | H |
| I-1721 | c-Pr | cyclopentyl-NH | Cl | H | F | H | H | CN | H |
| I-1722 | c-Pr | Ph—NH | Cl | H | F | H | H | CN | H |
| I-1723 | c-Pr | Ph—(Bn)N | Cl | H | F | H | H | CN | H |
| I-1724 | c-Pr | (Pyridin-3-yl)amino | Cl | H | F | H | H | CN | H |
| I-1725 | c-Pr | Allylamino | Cl | H | F | H | H | CN | H |
| I-1726 | c-Pr | Propargylamino | Cl | H | F | H | H | CN | H |
| I-1727 | c-Pr | (Pyrrolidin-1-yl) | Cl | H | F | H | H | CN | H |
| I-1728 | c-Pr | F₃CCH₂NH | Cl | H | F | H | H | CN | H |
| I-1729 | c-Pr | Acetylamino | Cl | H | F | H | H | CN | H |
| I-1730 | c-Pr | Benzoylamino | Cl | H | F | H | H | CN | H |
| I-1731 | c-Pr | (Ethoxycarbonyl)amino | Cl | H | F | H | H | CN | H |
| I-1732 | c-Pr | (N,N-Dimethyl-amino)carbonyl-amino | Cl | H | F | H | H | CN | H |
| I-1733 | c-Pr | (N,N-Dimethylamino)(thio-carbonyl)amino | Cl | H | F | H | H | CN | H |
| I-1734 | c-Pr | (Methylsulfonyl)amino | Cl | H | F | H | H | CN | H |
| I-1735 | c-Pr | NH₂ | Cl | H | H | F | H | Me | H |
| I-1736 | c-Pr | MeNH | Cl | H | H | F | H | Me | H |
| I-1737 | c-Pr | Me₂N | Cl | H | H | F | H | Me | H |
| I-1738 | c-Pr | cyclopentyl-NH | Cl | H | H | F | H | Me | H |
| I-1739 | c-Pr | Ph—NH | Cl | H | H | F | H | Me | H |
| I-1740 | c-Pr | Ph—(Bn)N | Cl | H | H | F | H | Me | H |
| I-1741 | c-Pr | (Pyridin-3-yl)amino | Cl | H | H | F | H | Me | H |
| I-1742 | c-Pr | Allylamino | Cl | H | H | F | H | Me | H |
| I-1743 | c-Pr | Propargylamino | Cl | H | H | F | H | Me | H |
| I-1744 | c-Pr | (Pyrrolidin-1-yl) | Cl | H | H | F | H | Me | H |
| I-1745 | c-Pr | F₃CCH₂NH | Cl | H | H | F | H | Me | H |
| I-1746 | c-Pr | Acetylamino | Cl | H | H | F | H | Me | H |
| I-1747 | c-Pr | Benzoylamino | Cl | H | H | F | H | Me | H |
| I-1748 | c-Pr | (Ethoxycarbonyl)amino | Cl | H | H | F | H | Me | H |
| I-1749 | c-Pr | (N,N-Dimethyl-amino)carbonyl-amino | Cl | H | H | F | H | Me | H |

TABLE 1-continued

Inventive compounds of the formula (I) in which X represents $C(R^{13})(R^{14})$

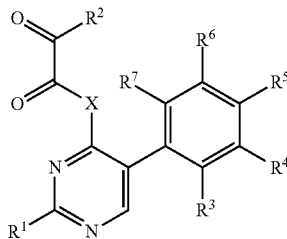

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1750 | c-Pr | (N,N-Dimethylamino)(thio-carbonyl)amino | Cl | H | H | F | H | Me | H |
| I-1751 | c-Pr | (Methylsulfonyl)amino | Cl | H | H | F | H | Me | H |
| I-1752 | c-Pr | $NH_2$ | Cl | H | H | F | H | Me | Me |
| I-1753 | c-Pr | MeNH | Cl | H | H | F | H | Me | Me |
| I-1754 | c-Pr | $Me_2N$ | Cl | H | H | F | H | Me | Me |
| I-1755 | c-Pr | cyclopentyl-NH | Cl | H | H | F | H | Me | Me |
| I-1756 | c-Pr | Ph—NH | Cl | H | H | F | H | Me | Me |
| I-1757 | c-Pr | Ph—(Bn)N | Cl | H | H | F | H | Me | Me |
| I-1758 | c-Pr | (Pyridin-3-yl)amino | Cl | H | H | F | H | Me | Me |
| I-1759 | c-Pr | Allylamino | Cl | H | H | F | H | Me | Me |
| I-1760 | c-Pr | Propargylamino | Cl | H | H | F | H | Me | Me |
| I-1761 | c-Pr | (Pyrrolidin-1-yl) | Cl | H | H | F | H | Me | Me |
| I-1762 | c-Pr | $F_3CCH_2NH$ | Cl | H | H | F | H | Me | Me |
| I-1763 | c-Pr | Acetylamino | Cl | H | H | F | H | Me | Me |
| I-1764 | c-Pr | Benzoylamino | Cl | H | H | F | H | Me | Me |
| I-1765 | c-Pr | (Ethoxycarbonyl)amino | Cl | H | H | F | H | Me | Me |
| I-1766 | c-Pr | (N,N-Dimethyl-amino)carbonyl-amino | Cl | H | H | F | H | Me | Me |
| I-1767 | c-Pr | (N,N-Dimethylamino)(thio-carbonyl)amino | Cl | H | H | F | H | Me | Me |
| I-1768 | c-Pr | (Methylsulfonyl)amino | Cl | H | H | F | H | Me | Me |
| I-1769 | c-Pr | $NH_2$ | Cl | H | H | F | H | $CO_2Et$ | H |
| I-1770 | c-Pr | MeNH | Cl | H | H | F | H | $CO_2Et$ | H |
| I-1771 | c-Pr | $Me_2N$ | Cl | H | H | F | H | $CO_2Et$ | H |
| I-1772 | c-Pr | cyclopentyl-NH | Cl | H | H | F | H | $CO_2Et$ | H |
| I-1773 | c-Pr | Ph—NH | Cl | H | H | F | H | $CO_2Et$ | H |
| I-1774 | c-Pr | Ph—(Bn)N | Cl | H | H | F | H | $CO_2Et$ | H |
| I-1775 | c-Pr | (Pyridin-3-yl)amino | Cl | H | H | F | H | $CO_2Et$ | H |
| I-1776 | c-Pr | Allylamino | Cl | H | H | F | H | $CO_2Et$ | H |
| I-1777 | c-Pr | Propargylamino | Cl | H | H | F | H | $CO_2Et$ | H |
| I-1778 | c-Pr | (Pyrrolidin-1-yl) | Cl | H | H | F | H | $CO_2Et$ | H |
| I-1779 | c-Pr | $F_3CCH_2NH$ | Cl | H | H | F | H | $CO_2Et$ | H |
| I-1780 | c-Pr | Acetylamino | Cl | H | H | F | H | $CO_2Et$ | H |
| I-1781 | c-Pr | Benzoylamino | Cl | H | H | F | H | $CO_2Et$ | H |
| I-1782 | c-Pr | (Ethoxycarbonyl)amino | Cl | H | H | F | H | $CO_2Et$ | H |
| I-1783 | c-Pr | (N,N-Dimethyl-amino)carbonyl-amino | Cl | H | H | F | H | $CO_2Et$ | H |
| I-1784 | c-Pr | (N,N-Dimethylamino)(thio-carbonyl)amino | Cl | H | H | F | H | $CO_2Et$ | H |
| I-1785 | c-Pr | (Methylsulfonyl)amino | Cl | H | H | F | H | $CO_2Et$ | H |
| I-1786 | c-Pr | $NH_2$ | Cl | H | H | F | H | CN | H |
| I-1787 | c-Pr | MeNH | Cl | H | H | F | H | CN | H |
| I-1788 | c-Pr | $Me_2N$ | Cl | H | H | F | H | CN | H |
| I-1789 | c-Pr | cyclopentyl-NH | Cl | H | H | F | H | CN | H |
| I-1790 | c-Pr | Ph—NH | Cl | H | H | F | H | CN | H |
| I-1791 | c-Pr | Ph—(Bn)N | Cl | H | H | F | H | CN | H |
| I-1792 | c-Pr | (Pyridin-3-yl)amino | Cl | H | H | F | H | CN | H |
| I-1793 | c-Pr | Allylamino | Cl | H | H | F | H | CN | H |
| I-1794 | c-Pr | Propargylamino | Cl | H | H | F | H | CN | H |
| I-1795 | c-Pr | (Pyrrolidin-1-yl) | Cl | H | H | F | H | CN | H |
| I-1796 | c-Pr | $F_3CCH_2NH$ | Cl | H | H | F | H | CN | H |
| I-1797 | c-Pr | Acetylamino | Cl | H | H | F | H | CN | H |

TABLE 1-continued

Inventive compounds of the formula (I) in which X represents $C(R^{13})(R^{14})$

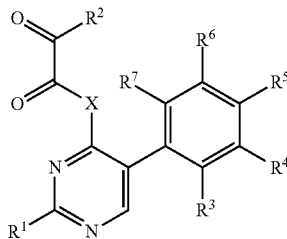

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1798 | c-Pr | Benzoylamino | Cl | H | H | F | H | CN | H |
| I-1799 | c-Pr | (Ethoxycarbonyl)amino | Cl | H | H | F | H | CN | H |
| I-1800 | c-Pr | (N,N-Dimethyl-amino)carbonyl-amino | Cl | H | H | F | H | CN | H |
| I-1801 | c-Pr | (N,N-Dimethylamino)(thio-carbonyl)amino | Cl | H | H | F | H | CN | H |
| I-1802 | c-Pr | (Methylsulfonyl)amino | Cl | H | H | F | H | CN | H |
| I-1803 | c-Pr | $NH_2$ | Cl | H | H | H | F | Me | H |
| I-1804 | c-Pr | MeNH | Cl | H | H | H | F | Me | H |
| I-1805 | c-Pr | $Me_2N$ | Cl | H | H | H | F | Me | H |
| I-1806 | c-Pr | cyclopentyl-NH | Cl | H | H | H | F | Me | H |
| I-1807 | c-Pr | Ph—NH | Cl | H | H | H | F | Me | H |
| I-1808 | c-Pr | Ph—(Bn)N | Cl | H | H | H | F | Me | H |
| I-1809 | c-Pr | (Pyridin-3-yl)amino | Cl | H | H | H | F | Me | H |
| I-1810 | c-Pr | Allylamino | Cl | H | H | H | F | Me | H |
| I-1811 | c-Pr | Propargylamino | Cl | H | H | H | F | Me | H |
| I-1812 | c-Pr | (Pyrrolidin-1-yl) | Cl | H | H | H | F | Me | H |
| I-1813 | c-Pr | $F_3CCH_2NH$ | Cl | H | H | H | F | Me | H |
| I-1814 | c-Pr | Acetylamino | Cl | H | H | H | F | Me | H |
| I-1815 | c-Pr | Benzoylamino | Cl | H | H | H | F | Me | H |
| I-1816 | c-Pr | (Ethoxycarbonyl)amino | Cl | H | H | H | F | Me | H |
| I-1817 | c-Pr | (N,N-Dimethyl-amino)carbonyl-amino | Cl | H | H | H | F | Me | H |
| I-1818 | c-Pr | (N,N-Dimethylamino)(thio-carbonyl)amino | Cl | H | H | H | F | Me | H |
| I-1819 | c-Pr | (Methylsulfonyl)amino | Cl | H | H | H | F | Me | H |
| I-1820 | c-Pr | $NH_2$ | Cl | H | H | H | F | Me | Me |
| I-1821 | c-Pr | MeNH | Cl | H | H | H | F | Me | Me |
| I-1822 | c-Pr | $Me_2N$ | Cl | H | H | H | F | Me | Me |
| I-1823 | c-Pr | cyclopentyl-NH | Cl | H | H | H | F | Me | Me |
| I-1824 | c-Pr | Ph—NH | Cl | H | H | H | F | Me | Me |
| I-1825 | c-Pr | Ph—(Bn)N | Cl | H | H | H | F | Me | Me |
| I-1826 | c-Pr | (Pyridin-3-yl)amino | Cl | H | H | H | F | Me | Me |
| I-1827 | c-Pr | Allylamino | Cl | H | H | H | F | Me | Me |
| I-1828 | c-Pr | Propargylamino | Cl | H | H | H | F | Me | Me |
| I-1829 | c-Pr | (Pyrrolidin-1-yl) | Cl | H | H | H | F | Me | Me |
| I-1830 | c-Pr | $F_3CCH_2NH$ | Cl | H | H | H | F | Me | Me |
| I-1831 | c-Pr | Acetylamino | Cl | H | H | H | F | Me | Me |
| I-1832 | c-Pr | Benzoylamino | Cl | H | H | H | F | Me | Me |
| I-1833 | c-Pr | (Ethoxycarbonyl)amino | Cl | H | H | H | F | Me | Me |
| I-1834 | c-Pr | (N,N-Dimethyl-amino)carbonyl-amino | Cl | H | H | H | F | Me | Me |
| I-1835 | c-Pr | (N,N-Dimethylamino)(thio carbonyl)amino | Cl | H | H | H | F | Me | Me |
| I-1836 | c-Pr | (Methylsulfonyl)amino | Cl | H | H | H | F | Me | Me |
| I-1837 | c-Pr | $NH_2$ | Cl | H | H | H | F | $CO_2Et$ | H |
| I-1838 | c-Pr | MeNH | Cl | H | H | H | F | $CO_2Et$ | H |
| I-1839 | c-Pr | $Me_2N$ | Cl | H | H | H | F | $CO_2Et$ | H |
| I-1840 | c-Pr | cyclopentyl-NH | Cl | H | H | H | F | $CO_2Et$ | H |
| I-1841 | c-Pr | Ph—NH | Cl | H | H | H | F | $CO_2Et$ | H |
| I-1842 | c-Pr | Ph—(Bn)N | Cl | H | H | H | F | $CO_2Et$ | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1843 | c-Pr | (Pyridin-3-yl)amino | Cl | H | H | H | F | CO$_2$Et | H |
| I-1844 | c-Pr | Allylamino | Cl | H | H | H | F | CO$_2$Et | H |
| I-1845 | c-Pr | Propargylamino | Cl | H | H | H | F | CO$_2$Et | H |
| I-1846 | c-Pr | (Pyrrolidin-1-yl) | Cl | H | H | H | F | CO$_2$Et | H |
| I-1847 | c-Pr | F$_3$CCH$_2$NH | Cl | H | H | H | F | CO$_2$Et | H |
| I-1848 | c-Pr | Acetylamino | Cl | H | H | H | F | CO$_2$Et | H |
| I-1849 | c-Pr | Benzoylamino | Cl | H | H | H | F | CO$_2$Et | H |
| I-1850 | c-Pr | (Ethoxycarbonyl)amino | Cl | H | H | H | F | CO$_2$Et | H |
| I-1851 | c-Pr | (N,N-Dimethyl-amino)carbonyl-amino | Cl | H | H | H | F | CO$_2$Et | H |
| I-1852 | c-Pr | (N,N-Dimethylamino)(thio-carbonyl)amino | Cl | H | H | H | F | CO$_2$Et | H |
| I-1853 | c-Pr | (Methylsulfonyl)amino | Cl | H | H | H | F | CO$_2$Et | H |
| I-1854 | c-Pr | NH$_2$ | Cl | H | H | H | F | CN | H |
| I-1855 | c-Pr | MeNH | Cl | H | H | H | F | CN | H |
| I-1856 | c-Pr | Me$_2$N | Cl | H | H | H | F | CN | H |
| I-1857 | c-Pr | cyclopentyl-NH | Cl | H | H | H | F | CN | H |
| I-1858 | c-Pr | Ph—NH | Cl | H | H | H | F | CN | H |
| I-1859 | c-Pr | Ph—(Bn)N | Cl | H | H | H | F | CN | H |
| I-1860 | c-Pr | (Pyridin-3-yl)amino | Cl | H | H | H | F | CN | H |
| I-1861 | c-Pr | Allylamino | Cl | H | H | H | F | CN | H |
| I-1862 | c-Pr | Propargylamino | Cl | H | H | H | F | CN | H |
| I-1863 | c-Pr | (Pyrrolidin-1-yl) | Cl | H | H | H | F | CN | H |
| I-1864 | c-Pr | F$_3$CCH$_2$NH | Cl | H | H | H | F | CN | H |
| I-1865 | c-Pr | Acetylamino | Cl | H | H | H | F | CN | H |
| I-1866 | c-Pr | Benzoylamino | Cl | H | H | H | F | CN | H |
| I-1867 | c-Pr | (Ethoxycarbonyl)amino | Cl | H | H | H | F | CN | H |
| I-1868 | c-Pr | (N,N-Dimethyl-amino)carbonyl-amino | Cl | H | H | H | F | CN | H |
| I-1869 | c-Pr | (N,N-Dimethylamino)(thio-carbonyl)amino | Cl | H | H | H | F | CN | H |
| I-1870 | c-Pr | (Methylsulfonyl)amino | Cl | H | H | H | F | CN | H |
| I-1871 | c-Pr | NH$_2$ | Cl | Cl | H | H | H | Me | H |
| I-1872 | c-Pr | MeNH | Cl | Cl | H | H | H | Me | H |
| I-1873 | c-Pr | Me$_2$N | Cl | Cl | H | H | H | Me | H |
| I-1874 | c-Pr | cyclopentyl-NH | Cl | Cl | H | H | H | Me | H |
| I-1875 | c-Pr | Ph—NH | Cl | Cl | H | H | H | Me | H |
| I-1876 | c-Pr | Ph—(Bn)N | Cl | Cl | H | H | H | Me | H |
| I-1877 | c-Pr | (Pyridin-3-yl)amino | Cl | Cl | H | H | H | Me | H |
| I-1878 | c-Pr | Allylamino | Cl | Cl | H | H | H | Me | H |
| I-1879 | c-Pr | Propargylamino | Cl | Cl | H | H | H | Me | H |
| I-1880 | c-Pr | (Pyrrolidin-1-yl) | Cl | Cl | H | H | H | Me | H |
| I-1881 | c-Pr | F$_3$CCH$_2$NH | Cl | Cl | H | H | H | Me | H |
| I-1882 | c-Pr | Acetylamino | Cl | Cl | H | H | H | Me | H |
| I-1883 | c-Pr | Benzoylamino | Cl | Cl | H | H | H | Me | H |
| I-1884 | c-Pr | (Ethoxycarbonyl)amino | Cl | Cl | H | H | H | Me | H |
| I-1885 | c-Pr | (N,N-Dimethyl-amino)carbonyl-amino | Cl | Cl | H | H | H | Me | H |
| I-1886 | c-Pr | (N,N-Dimethylamino)(thio-carbonyl)amino | Cl | Cl | H | H | H | Me | H |

TABLE 1-continued

Inventive compounds of the formula (I) in which X represents $C(R^{13})(R^{14})$ $$(I)$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1887 | c-Pr | (Methylsulfonyl)amino | Cl | Cl | H | H | H | Me | H |
| I-1888 | c-Pr | NH$_2$ | Cl | Cl | H | H | H | Me | Me |
| I-1889 | c-Pr | MeNH | Cl | Cl | H | H | H | Me | Me |
| I-1890 | c-Pr | Me$_2$N | Cl | Cl | H | H | H | Me | Me |
| I-1891 | c-Pr | cyclopentyl-NH | Cl | Cl | H | H | H | Me | Me |
| I-1892 | c-Pr | Ph—NH | Cl | Cl | H | H | H | Me | Me |
| I-1893 | c-Pr | Ph—(Bn)N | Cl | Cl | H | H | H | Me | Me |
| I-1894 | c-Pr | (Pyridin-3-yl)amino | Cl | Cl | H | H | H | Me | Me |
| I-1895 | c-Pr | Allylamino | Cl | Cl | H | H | H | Me | Me |
| I-1896 | c-Pr | Propargylamino | Cl | Cl | H | H | H | Me | Me |
| I-1897 | c-Pr | (Pyrrolidin-1-yl) | Cl | Cl | H | H | H | Me | Me |
| I-1898 | c-Pr | F$_3$CCH$_2$NH | Cl | Cl | H | H | H | Me | Me |
| I-1899 | c-Pr | Acetylamino | Cl | Cl | H | H | H | Me | Me |
| I-1900 | c-Pr | Benzoylamino | Cl | Cl | H | H | H | Me | Me |
| I-1901 | c-Pr | (Ethoxycarbonyl)amino | Cl | Cl | H | H | H | Me | Me |
| I-1902 | c-Pr | (N,N-Dimethyl-amino)carbonyl-amino | Cl | Cl | H | H | H | Me | Me |
| I-1903 | c-Pr | (N,N-Dimethylamino)(thio-carbonyl)amino | Cl | Cl | H | H | H | Me | Me |
| I-1904 | c-Pr | (Methylsulfonyl)amino | Cl | Cl | H | H | H | Me | Me |
| I-1905 | c-Pr | NH$_2$ | Cl | Cl | H | H | H | CO$_2$Et | H |
| I-1906 | c-Pr | MeNH | Cl | Cl | H | H | H | CO$_2$Et | H |
| I-1907 | c-Pr | Me$_2$N | Cl | Cl | H | H | H | CO$_2$Et | H |
| I-1908 | c-Pr | cyclopentyl-NH | Cl | Cl | H | H | H | CO$_2$Et | H |
| I-1909 | c-Pr | Ph—NH | Cl | Cl | H | H | H | CO$_2$Et | H |
| I-1910 | c-Pr | Ph—(Bn)N | Cl | Cl | H | H | H | CO$_2$Et | H |
| I-1911 | c-Pr | (Pyridin-3-yl)amino | Cl | Cl | H | H | H | CO$_2$Et | H |
| I-1912 | c-Pr | Allylamino | Cl | Cl | H | H | H | CO$_2$Et | H |
| I-1913 | c-Pr | Propargylamino | Cl | Cl | H | H | H | CO$_2$Et | H |
| I-1914 | c-Pr | (Pyrrolidin-1-yl) | Cl | Cl | H | H | H | CO$_2$Et | H |
| I-1915 | c-Pr | F$_3$CCH$_2$NH | Cl | Cl | H | H | H | CO$_2$Et | H |
| I-1916 | c-Pr | Acetylamino | Cl | Cl | H | H | H | CO$_2$Et | H |
| I-1917 | c-Pr | Benzoylamino | Cl | Cl | H | H | H | CO$_2$Et | H |
| I-1918 | c-Pr | (Ethoxycarbonyl)amino | Cl | Cl | H | H | H | CO$_2$Et | H |
| I-1919 | c-Pr | (N,N-Dimethyl-amino)carbonyl-amino | Cl | Cl | H | H | H | CO$_2$Et | H |
| I-1920 | c-Pr | (N,N-Dimethylamino)(thio-carbonyl)amino | Cl | Cl | H | H | H | CO$_2$Et | H |
| I-1921 | c-Pr | (Methylsulfonyl)amino | Cl | Cl | H | H | H | CO$_2$Et | H |
| I-1922 | c-Pr | NH$_2$ | Cl | Cl | H | H | H | CN | H |
| I-1923 | c-Pr | MeNH | Cl | Cl | H | H | H | CN | H |
| I-1924 | c-Pr | Me$_2$N | Cl | Cl | H | H | H | CN | H |
| I-1925 | c-Pr | cyclopentyl-NH | Cl | Cl | H | H | H | CN | H |
| I-1926 | c-Pr | Ph—NH | Cl | Cl | H | H | H | CN | H |
| I-1927 | c-Pr | Ph—(Bn)N | Cl | Cl | H | H | H | CN | H |
| I-1928 | c-Pr | (Pyridin-3-yl)amino | Cl | Cl | H | H | H | CN | H |
| I-1929 | c-Pr | Allylamino | Cl | Cl | H | H | H | CN | H |
| I-1930 | c-Pr | Propargylamino | Cl | Cl | H | H | H | CN | H |
| I-1931 | c-Pr | (Pyrrolidin-1-yl) | Cl | Cl | H | H | H | CN | H |
| I-1932 | c-Pr | F$_3$CCH$_2$NH | Cl | Cl | H | H | H | CN | H |
| I-1933 | c-Pr | Acetylamino | Cl | Cl | H | H | H | CN | H |
| I-1934 | c-Pr | Benzoylamino | Cl | Cl | H | H | H | CN | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1935 | c-Pr | (Ethoxycarbonyl)amino | Cl | Cl | H | H | H | CN | H |
| I-1936 | c-Pr | (N,N-Dimethyl-amino)carbonyl-amino | Cl | Cl | H | H | H | CN | H |
| I-1937 | c-Pr | (N,N-Dimethylamino)(thio-carbonyl)amino | Cl | Cl | H | H | H | CN | H |
| I-1938 | c-Pr | (Methylsulfonyl)amino | Cl | Cl | H | H | H | CN | H |
| I-1939 | c-Pr | $NH_2$ | Cl | H | Cl | H | H | Me | H |
| I-1940 | c-Pr | MeNH | Cl | H | Cl | H | H | Me | H |
| I-1941 | c-Pr | $Me_2N$ | Cl | H | Cl | H | H | Me | H |
| I-1942 | c-Pr | cyclopentyl-NH | Cl | H | Cl | H | H | Me | H |
| I-1943 | c-Pr | Ph—NH | Cl | H | Cl | H | H | Me | H |
| I-1944 | c-Pr | Ph—(Bn)N | Cl | H | Cl | H | H | Me | H |
| I-1945 | c-Pr | (Pyridin-3-yl)amino | Cl | H | Cl | H | H | Me | H |
| I-1946 | c-Pr | Allylamino | Cl | H | Cl | H | H | Me | H |
| I-1947 | c-Pr | Propargylamino | Cl | H | Cl | H | H | Me | H |
| I-1948 | c-Pr | (Pyrrolidin-1-yl) | Cl | H | Cl | H | H | Me | H |
| I-1949 | c-Pr | $F_3CCH_2NH$ | Cl | H | Cl | H | H | Me | H |
| I-1950 | c-Pr | Acetylamino | Cl | H | Cl | H | H | Me | H |
| I-1951 | c-Pr | Benzoylamino | Cl | H | Cl | H | H | Me | H |
| I-1952 | c-Pr | (Ethoxycarbonyl)amino | Cl | H | Cl | H | H | Me | H |
| I-1953 | c-Pr | (N,N-Dimethyl-amino)carbonyl-amino | Cl | H | Cl | H | H | Me | H |
| I-1954 | c-Pr | (N,N-Dimethylamino)(thio-carbonyl)amino | Cl | H | Cl | H | H | Me | H |
| I-1955 | c-Pr | (Methylsulfonyl)amino | Cl | H | Cl | H | H | Me | H |
| I-1956 | c-Pr | $NH_2$ | Cl | H | Cl | H | H | Me | Me |
| I-1957 | c-Pr | MeNH | Cl | H | Cl | H | H | Me | Me |
| I-1958 | c-Pr | $Me_2N$ | Cl | H | Cl | H | H | Me | Me |
| I-1959 | c-Pr | cyclopentyl-NH | Cl | H | Cl | H | H | Me | Me |
| I-1960 | c-Pr | Ph—NH | Cl | H | Cl | H | H | Me | Me |
| I-1961 | c-Pr | Ph—(Bn)N | Cl | H | Cl | H | H | Me | Me |
| I-1962 | c-Pr | (Pyridin-3-yl)amino | Cl | H | Cl | H | H | Me | Me |
| I-1963 | c-Pr | Allylamino | Cl | H | Cl | H | H | Me | Me |
| I-1964 | c-Pr | Propargylamino | Cl | H | Cl | H | H | Me | Me |
| I-1965 | c-Pr | (Pyrrolidin-1-yl) | Cl | H | Cl | H | H | Me | Me |
| I-1966 | c-Pr | $F_3CCH_2NH$ | Cl | H | Cl | H | H | Me | Me |
| I-1967 | c-Pr | Acetylamino | Cl | H | Cl | H | H | Me | Me |
| I-1968 | c-Pr | Benzoylamino | Cl | H | Cl | H | H | Me | Me |
| I-1969 | c-Pr | (Ethoxycarbonyl)amino | Cl | H | Cl | H | H | Me | Me |
| I-1970 | c-Pr | (N,N-Dimethyl-amino)carbonyl-amino | Cl | H | Cl | H | H | Me | Me |
| I-1971 | c-Pr | (N,N-Dimethylamino)(thio-carbonyl)amino | Cl | H | Cl | H | H | Me | Me |
| I-1972 | c-Pr | (Methylsulfonyl)amino | Cl | H | Cl | H | H | Me | Me |
| I-1973 | c-Pr | $NH_2$ | Cl | H | Cl | H | H | $CO_2Et$ | H |
| I-1974 | c-Pr | MeNH | Cl | H | Cl | H | H | $CO_2Et$ | H |
| I-1975 | c-Pr | $Me_2N$ | Cl | H | Cl | H | H | $CO_2Et$ | H |
| I-1976 | c-Pr | cyclopentyl-NH | Cl | H | Cl | H | H | $CO_2Et$ | H |
| I-1977 | c-Pr | Ph—NH | Cl | H | Cl | H | H | $CO_2Et$ | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-1978 | c-Pr | Ph—(Bn)N | Cl | H | Cl | H | H | CO$_2$Et | H |
| I-1979 | c-Pr | (Pyridin-3-yl)amino | Cl | H | Cl | H | H | CO$_2$Et | H |
| I-1980 | c-Pr | Allylamino | Cl | H | Cl | H | H | CO$_2$Et | H |
| I-1981 | c-Pr | Propargylamino | Cl | H | Cl | H | H | CO$_2$Et | H |
| I-1982 | c-Pr | (Pyrrolidin-1-yl) | Cl | H | Cl | H | H | CO$_2$Et | H |
| I-1983 | c-Pr | F$_3$CCH$_2$NH | Cl | H | Cl | H | H | CO$_2$Et | H |
| I-1984 | c-Pr | Acetylamino | Cl | H | Cl | H | H | CO$_2$Et | H |
| I-1985 | c-Pr | Benzoylamino | Cl | H | Cl | H | H | CO$_2$Et | H |
| I-1986 | c-Pr | (Ethoxycarbonyl)amino | Cl | H | Cl | H | H | CO$_2$Et | H |
| I-1987 | c-Pr | (N,N-Dimethyl-amino)carbonyl-amino | Cl | H | Cl | H | H | CO$_2$Et | H |
| I-1988 | c-Pr | (N,N-Dimethylamino)(thio-carbonyl)amino | Cl | H | Cl | H | H | CO$_2$Et | H |
| I-1989 | c-Pr | (Methylsulfonyl)amino | Cl | H | Cl | H | H | CO$_2$Et | H |
| I-1990 | c-Pr | NH$_2$ | Cl | H | Cl | H | H | CN | H |
| I-1991 | c-Pr | MeNH | Cl | H | Cl | H | H | CN | H |
| I-1992 | c-Pr | Me$_2$N | Cl | H | Cl | H | H | CN | H |
| I-1993 | c-Pr | cyclopentyl-NH | Cl | H | Cl | H | H | CN | H |
| I-1994 | c-Pr | Ph—NH | Cl | H | Cl | H | H | CN | H |
| I-1995 | c-Pr | Ph—(Bn)N | Cl | H | Cl | H | H | CN | H |
| I-1996 | c-Pr | (Pyridin-3-yl)amino | Cl | H | Cl | H | H | CN | H |
| I-1997 | c-Pr | Allylamino | Cl | H | Cl | H | H | CN | H |
| I-1998 | c-Pr | Propargylamino | Cl | H | Cl | H | H | CN | H |
| I-1999 | c-Pr | (Pyrrolidin-1-yl) | Cl | H | Cl | H | H | CN | H |
| I-2000 | c-Pr | F$_3$CCH$_2$NH | Cl | H | Cl | H | H | CN | H |
| I-2001 | c-Pr | Acetylamino | Cl | H | Cl | H | H | CN | H |
| I-2002 | c-Pr | Benzoylamino | Cl | H | Cl | H | H | CN | H |
| I-2003 | c-Pr | (Ethoxycarbonyl)amino | Cl | H | Cl | H | H | CN | H |
| I-2004 | c-Pr | (N,N-Dimethyl-amino)carbonyl-amino | Cl | H | Cl | H | H | CN | H |
| I-2005 | c-Pr | (N,N-Dimethylamino)(thio-carbonyl)amino | Cl | H | Cl | H | H | CN | H |
| I-2006 | c-Pr | (Methylsulfonyl)amino | Cl | H | Cl | H | H | CN | H |
| I-2007 | c-Pr | NH$_2$ | Cl | H | H | Cl | H | Me | H |
| I-2008 | c-Pr | MeNH | Cl | H | H | Cl | H | Me | H |
| I-2009 | c-Pr | Me$_2$N | Cl | H | H | Cl | H | Me | H |
| I-2010 | c-Pr | cyclopentyl-NH | Cl | H | H | Cl | H | Me | H |
| I-2011 | c-Pr | Ph—NH | Cl | H | H | Cl | H | Me | H |
| I-2012 | c-Pr | Ph—(Bn)N | Cl | H | H | Cl | H | Me | H |
| I-2013 | c-Pr | (Pyridin-3-yl)amino | Cl | H | H | Cl | H | Me | H |
| I-2014 | c-Pr | Allylamino | Cl | H | H | Cl | H | Me | H |
| I-2015 | c-Pr | Propargylamino | Cl | H | H | Cl | H | Me | H |
| I-2016 | c-Pr | (Pyrrolidin-1-yl) | Cl | H | H | Cl | H | Me | H |
| I-2017 | c-Pr | F$_3$CCH$_2$NH | Cl | H | H | Cl | H | Me | H |
| I-2018 | c-Pr | Acetylamino | Cl | H | H | Cl | H | Me | H |
| I-2019 | c-Pr | Benzoylamino | Cl | H | H | Cl | H | Me | H |
| I-2020 | c-Pr | (Ethoxycarbonyl)amino | Cl | H | H | Cl | H | Me | H |
| I-2021 | c-Pr | (N,N-Dimethyl-amino)carbonyl-amino | Cl | H | H | Cl | H | Me | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-2022 | c-Pr | (N,N-Dimethylamino)(thiocarbonyl)amino | Cl | H | H | Cl | H | Me | H |
| I-2023 | c-Pr | (Methylsulfonyl)amino | Cl | H | H | Cl | H | Me | H |
| I-2024 | c-Pr | $NH_2$ | Cl | H | H | Cl | H | Me | Me |
| I-2025 | c-Pr | MeNH | Cl | H | H | Cl | H | Me | Me |
| I-2026 | c-Pr | $Me_2N$ | Cl | H | H | Cl | H | Me | Me |
| I-2027 | c-Pr | cyclopentyl-NH | Cl | H | H | Cl | H | Me | Me |
| I-2028 | c-Pr | Ph—NH | Cl | H | H | Cl | H | Me | Me |
| I-2029 | c-Pr | Ph—(Bn)N | Cl | H | H | Cl | H | Me | Me |
| I-2030 | c-Pr | (Pyridin-3-yl)amino | Cl | H | H | Cl | H | Me | Me |
| I-2031 | c-Pr | Allylamino | Cl | H | H | Cl | H | Me | Me |
| I-2032 | c-Pr | Propargylamino | Cl | H | H | Cl | H | Me | Me |
| I-2033 | c-Pr | (Pyrrolidin-1-yl) | Cl | H | H | Cl | H | Me | Me |
| I-2034 | c-Pr | $F_3CCH_2NH$ | Cl | H | H | Cl | H | Me | Me |
| I-2035 | c-Pr | Acetylamino | Cl | H | H | Cl | H | Me | Me |
| I-2036 | c-Pr | Benzoylamino | Cl | H | H | Cl | H | Me | Me |
| I-2037 | c-Pr | (Ethoxycarbonyl)amino | Cl | H | H | Cl | H | Me | Me |
| I-2038 | c-Pr | (N,N-Dimethyl-amino)carbonyl-amino | Cl | H | H | Cl | H | Me | Me |
| I-2039 | c-Pr | (N,N-Dimethylamino)(thiocarbonyl)amino | Cl | H | H | Cl | H | Me | Me |
| I-2040 | c-Pr | (Methylsulfonyl)amino | Cl | H | H | Cl | H | Me | Me |
| I-2041 | c-Pr | $NH_2$ | Cl | H | H | Cl | H | $CO_2Et$ | H |
| I-2042 | c-Pr | MeNH | Cl | H | H | Cl | H | $CO_2Et$ | H |
| I-2043 | c-Pr | $Me_2N$ | Cl | H | H | Cl | H | $CO_2Et$ | H |
| I-2044 | c-Pr | cyclopentyl-NH | Cl | H | H | Cl | H | $CO_2Et$ | H |
| I-2045 | c-Pr | Ph—NH | Cl | H | H | Cl | H | $CO_2Et$ | H |
| I-2046 | c-Pr | Ph—(Bn)N | Cl | H | H | Cl | H | $CO_2Et$ | H |
| I-2047 | c-Pr | (Pyridin-3-yl)amino | Cl | H | H | Cl | H | $CO_2Et$ | H |
| I-2048 | c-Pr | Allylamino | Cl | H | H | Cl | H | $CO_2Et$ | H |
| I-2049 | c-Pr | Propargylamino | Cl | H | H | Cl | H | $CO_2Et$ | H |
| I-2050 | c-Pr | (Pyrrolidin-1-yl) | Cl | H | H | Cl | H | $CO_2Et$ | H |
| I-2051 | c-Pr | $F_3CCH_2NH$ | Cl | H | H | Cl | H | $CO_2Et$ | H |
| I-2052 | c-Pr | Acetylamino | Cl | H | H | Cl | H | $CO_2Et$ | H |
| I-2053 | c-Pr | Benzoylamino | Cl | H | H | Cl | H | $CO_2Et$ | H |
| I-2054 | c-Pr | (Ethoxycarbonyl)amino | Cl | H | H | Cl | H | $CO_2Et$ | H |
| I-2055 | c-Pr | (N,N-Dimethyl-amino)carbonyl-amino | Cl | H | H | Cl | H | $CO_2Et$ | H |
| I-2056 | c-Pr | (N,N-Dimethylamino)(thiocarbonyl)amino | Cl | H | H | Cl | H | $CO_2Et$ | H |
| I-2057 | c-Pr | (Methylsulfonyl)amino | Cl | H | H | Cl | H | $CO_2Et$ | H |
| I-2058 | c-Pr | $NH_2$ | Cl | H | H | Cl | H | CN | H |
| I-2059 | c-Pr | MeNH | Cl | H | H | Cl | H | CN | H |
| I-2060 | c-Pr | $Me_2N$ | Cl | H | H | Cl | H | CN | H |
| I-2061 | c-Pr | cyclopentyl-NH | Cl | H | H | Cl | H | CN | H |
| I-2062 | c-Pr | Ph—NH | Cl | H | H | Cl | H | CN | H |
| I-2063 | c-Pr | Ph—(Bn)N | Cl | H | H | Cl | H | CN | H |
| I-2064 | c-Pr | (Pyridin-3-yl)amino | Cl | H | H | Cl | H | CN | H |
| I-2065 | c-Pr | Allylamino | Cl | H | H | Cl | H | CN | H |
| I-2066 | c-Pr | Propargylamino | Cl | H | H | Cl | H | CN | H |
| I-2067 | c-Pr | (Pyrrolidin-1-yl) | Cl | H | H | Cl | H | CN | H |

TABLE 1-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| I-2068 | c-Pr | F$_3$CCH$_2$NH | Cl | H | H | Cl | H | CN | H |
| I-2069 | c-Pr | Acetylamino | Cl | H | H | Cl | H | CN | H |
| I-2070 | c-Pr | Benzoylamino | Cl | H | H | Cl | H | CN | H |
| I-2071 | c-Pr | (Ethoxycarbonyl)amino | Cl | H | H | Cl | H | CN | H |
| I-2072 | c-Pr | (N,N-Dimethyl-amino)carbonyl-amino | Cl | H | H | Cl | H | CN | H |
| I-2073 | c-Pr | (N,N-Dimethylamino)(thio-carbonyl)amino | Cl | H | H | Cl | H | CN | H |
| I-2074 | c-Pr | (Methylsulfonyl)amino | Cl | H | H | Cl | H | CN | H |
| I-2075 | c-Pr | NH$_2$ | Cl | H | H | H | Cl | Me | H |
| I-2076 | c-Pr | MeNH | Cl | H | H | H | Cl | Me | H |
| I-2077 | c-Pr | Me$_2$N | Cl | H | H | H | Cl | Me | H |
| I-2078 | c-Pr | cyclopentyl-NH | Cl | H | H | H | Cl | Me | H |
| I-2079 | c-Pr | Ph—NH | Cl | H | H | H | Cl | Me | H |
| I-2080 | c-Pr | Ph—(Bn)N | Cl | H | H | H | Cl | Me | H |
| I-2081 | c-Pr | (Pyridin-3-yl)amino | Cl | H | H | H | Cl | Me | H |
| I-2082 | c-Pr | Allylamino | Cl | H | H | H | Cl | Me | H |
| I-2083 | c-Pr | Propargylamino | Cl | H | H | H | Cl | Me | H |
| I-2084 | c-Pr | (Pyrrolidin-1-yl) | Cl | H | H | H | Cl | Me | H |
| I-2085 | c-Pr | F$_3$CCH$_2$NH | Cl | H | H | H | Cl | Me | H |
| I-2086 | c-Pr | Acetylamino | Cl | H | H | H | Cl | Me | H |
| I-2087 | c-Pr | Benzoylamino | Cl | H | H | H | Cl | Me | H |
| I-2088 | c-Pr | (Ethoxycarbonyl)amino | Cl | H | H | H | Cl | Me | H |
| I-2089 | c-Pr | (N,N-Dimethyl-amino)carbonyl-amino | Cl | H | H | H | Cl | Me | H |
| I-2090 | c-Pr | (N,N-Dimethylamino)(thio-carbonyl)amino | Cl | H | H | H | Cl | Me | H |
| I-2091 | c-Pr | (Methylsulfonyl)amino | Cl | H | H | H | Cl | Me | H |
| I-2092 | c-Pr | NH$_2$ | Cl | H | H | H | Cl | Me | Me |
| I-2093 | c-Pr | MeNH | Cl | H | H | H | Cl | Me | Me |
| I-2094 | c-Pr | Me$_2$N | Cl | H | H | H | Cl | Me | Me |
| I-2095 | c-Pr | cyclopentyl-NH | Cl | H | H | H | Cl | Me | Me |
| I-2096 | c-Pr | Ph—NH | Cl | H | H | H | Cl | Me | Me |
| I-2097 | c-Pr | Ph—(Bn)N | Cl | H | H | H | Cl | Me | Me |
| I-2098 | c-Pr | (Pyridin-3-yl)amino | Cl | H | H | H | Cl | Me | Me |
| I-2099 | c-Pr | Allylamino | Cl | H | H | H | Cl | Me | Me |
| I-2100 | c-Pr | Propargylamino | Cl | H | H | H | Cl | Me | Me |
| I-2101 | c-Pr | (Pyrrolidin-1-yl) | Cl | H | H | H | Cl | Me | Me |
| I-2102 | c-Pr | F$_3$CCH$_2$NH | Cl | H | H | H | Cl | Me | Me |
| I-2103 | c-Pr | Acetylamino | Cl | H | H | H | Cl | Me | Me |
| I-2104 | c-Pr | Benzoylamino | Cl | H | H | H | Cl | Me | Me |
| I-2105 | c-Pr | (Ethoxycarbonyl)amino | Cl | H | H | H | Cl | Me | Me |
| I-2106 | c-Pr | (N,N-Dimethyl-amino)carbonyl-amino | Cl | H | H | H | Cl | Me | Me |
| I-2107 | c-Pr | (N,N-Dimethylamino)(thio-carbonyl)amino | Cl | H | H | H | Cl | Me | Me |
| I-2108 | c-Pr | (Methylsulfonyl)amino | Cl | H | H | H | Cl | Me | Me |
| I-2109 | c-Pr | NH$_2$ | Cl | H | H | H | Cl | CO$_2$Et | H |
| I-2110 | c-Pr | MeNH | Cl | H | H | H | Cl | CO$_2$Et | H |

TABLE 1-continued

Inventive compounds of the formula (I) in which X represents $C(R^{13})(R^{14})$

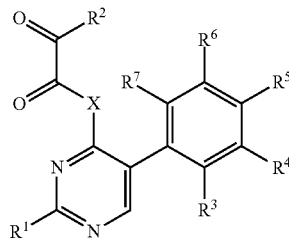

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-2111 | c-Pr | Me$_2$N | Cl | H | H | H | Cl | CO$_2$Et | H |
| I-2112 | c-Pr | cyclopentyl-NH | Cl | H | H | H | Cl | CO$_2$Et | H |
| I-2113 | c-Pr | Ph—NH | Cl | H | H | H | Cl | CO$_2$Et | H |
| I-2114 | c-Pr | Ph—(Bn)N | Cl | H | H | H | Cl | CO$_2$Et | H |
| I-2115 | c-Pr | (Pyridin-3-yl)amino | Cl | H | H | H | Cl | CO$_2$Et | H |
| I-2116 | c-Pr | Allylamino | Cl | H | H | H | Cl | CO$_2$Et | H |
| I-2117 | c-Pr | Propargylamino | Cl | H | H | H | Cl | CO$_2$Et | H |
| I-2118 | c-Pr | (Pyrrolidin-1-yl) | Cl | H | H | H | Cl | CO$_2$Et | H |
| I-2119 | c-Pr | F$_3$CCH$_2$NH | Cl | H | H | H | Cl | CO$_2$Et | H |
| I-2120 | c-Pr | Acetylamino | Cl | H | H | H | Cl | CO$_2$Et | H |
| I-2121 | c-Pr | Benzoylamino | Cl | H | H | H | Cl | CO$_2$Et | H |
| I-2122 | c-Pr | (Ethoxycarbonyl)amino | Cl | H | H | H | Cl | CO$_2$Et | H |
| I-2123 | c-Pr | (N,N-Dimethyl-amino)carbonyl-amino | Cl | H | H | H | Cl | CO$_2$Et | H |
| I-2124 | c-Pr | (N,N-Dimethylamino)(thio-carbonyl)amino | Cl | H | H | H | Cl | CO$_2$Et | H |
| I-2125 | c-Pr | (Methylsulfonyl)amino | Cl | H | H | H | Cl | CO$_2$Et | H |
| I-2126 | c-Pr | NH$_2$ | Cl | H | H | H | Cl | CN | H |
| I-2127 | c-Pr | MeNH | Cl | H | H | H | Cl | CN | H |
| I-2128 | c-Pr | Me$_2$N | Cl | H | H | H | Cl | CN | H |
| I-2129 | c-Pr | cyclopentyl-NH | Cl | H | H | H | Cl | CN | H |
| I-2130 | c-Pr | Ph—NH | Cl | H | H | H | Cl | CN | H |
| I-2131 | c-Pr | Ph—(Bn)N | Cl | H | H | H | Cl | CN | H |
| I-2132 | c-Pr | (Pyridin-3-yl)amino | Cl | H | H | H | Cl | CN | H |
| I-2133 | c-Pr | Allylamino | Cl | H | H | H | Cl | CN | H |
| I-2134 | c-Pr | Propargylamino | Cl | H | H | H | Cl | CN | H |
| I-2135 | c-Pr | (Pyrrolidin-1-yl) | Cl | H | H | H | Cl | CN | H |
| I-2136 | c-Pr | F$_3$CCH$_2$NH | Cl | H | H | H | Cl | CN | H |
| I-2137 | c-Pr | Acetylamino | Cl | H | H | H | Cl | CN | H |
| I-2138 | c-Pr | Benzoylamino | Cl | H | H | H | Cl | CN | H |
| I-2139 | c-Pr | (Ethoxycarbonyl)amino | Cl | H | H | H | Cl | CN | H |
| I-2140 | c-Pr | (N,N-Dimethyl-amino)carbonyl-amino | Cl | H | H | H | Cl | CN | H |
| I-2141 | c-Pr | (N,N-Dimethylamino)(thio-carbonyl)amino | Cl | H | H | H | Cl | CN | H |
| I-2142 | c-Pr | (Methylsulfonyl)amino | Cl | H | H | H | Cl | CN | H |
| I-2143 | c-Pr | NH$_2$ | Me | H | H | H | H | Me | H |
| I-2144 | c-Pr | MeNH | Me | H | H | H | H | Me | H |
| I-2145 | c-Pr | Me$_2$N | Me | H | H | H | H | Me | H |
| I-2146 | c-Pr | cyclopentyl-NH | Me | H | H | H | H | Me | H |
| I-2147 | c-Pr | Ph—NH | Me | H | H | H | H | Me | H |
| I-2148 | c-Pr | Ph—(Bn)N | Me | H | H | H | H | Me | H |
| I-2149 | c-Pr | (Pyridin-3-yl)amino | Me | H | H | H | H | Me | H |
| I-2150 | c-Pr | Allylamino | Me | H | H | H | H | Me | H |
| I-2151 | c-Pr | Propargylamino | Me | H | H | H | H | Me | H |
| I-2152 | c-Pr | (Pyrrolidin-1-yl) | Me | H | H | H | H | Me | H |
| I-2153 | c-Pr | F$_3$CCH$_2$NH | Me | H | H | H | H | Me | H |
| I-2154 | c-Pr | Acetylamino | Me | H | H | H | H | Me | H |
| I-2155 | c-Pr | Benzoylamino | Me | H | H | H | H | Me | H |
| I-2156 | c-Pr | (Ethoxycarbonyl)amino | Me | H | H | H | H | Me | H |
| I-2157 | c-Pr | (N,N-Dimethyl-amino)carbonyl-amino | Me | H | H | H | H | Me | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
| --- | --- | --- | --- | --- | --- | --- | --- | --- | --- |
| I-2158 | c-Pr | (N,N-Dimethylamino)(thiocarbonyl)amino | Me | H | H | H | H | Me | H |
| I-2159 | c-Pr | (Methylsulfonyl)amino | Me | H | H | H | H | Me | H |
| I-2160 | c-Pr | $NH_2$ | Me | H | H | H | H | Me | Me |
| I-2161 | c-Pr | MeNH | Me | H | H | H | H | Me | Me |
| I-2162 | c-Pr | $Me_2N$ | Me | H | H | H | H | Me | Me |
| I-2163 | c-Pr | cyclopentyl-NH | Me | H | H | H | H | Me | Me |
| I-2164 | c-Pr | Ph—NH | Me | H | H | H | H | Me | Me |
| I-2165 | c-Pr | Ph—(Bn)N | Me | H | H | H | H | Me | Me |
| I-2166 | c-Pr | (Pyridin-3-yl)amino | Me | H | H | H | H | Me | Me |
| I-2167 | c-Pr | Allylamino | Me | H | H | H | H | Me | Me |
| I-2168 | c-Pr | Propargylamino | Me | H | H | H | H | Me | Me |
| I-2169 | c-Pr | (Pyrrolidin-1-yl) | Me | H | H | H | H | Me | Me |
| I-2170 | c-Pr | $F_3CCH_2NH$ | Me | H | H | H | H | Me | Me |
| I-2171 | c-Pr | Acetylamino | Me | H | H | H | H | Me | Me |
| I-2172 | c-Pr | Benzoylamino | Me | H | H | H | H | Me | Me |
| I-2173 | c-Pr | (Ethoxycarbonyl)amino | Me | H | H | H | H | Me | Me |
| I-2174 | c-Pr | (N,N-Dimethylamino)carbonylamino | Me | H | H | H | H | Me | Me |
| I-2175 | c-Pr | (N,N-Dimethylamino)(thiocarbonyl)amino | Me | H | H | H | H | Me | Me |
| I-2176 | c-Pr | (Methylsulfonyl)amino | Me | H | H | H | H | Me | Me |
| I-2177 | c-Pr | $NH_2$ | Me | H | H | H | H | Me | H |
| I-2178 | c-Pr | MeNH | Me | H | H | H | H | $CO_2Et$ | H |
| I-2179 | c-Pr | $Me_2N$ | Me | H | H | H | H | $CO_2Et$ | H |
| I-2180 | c-Pr | cyclopentyl-NH | Me | H | H | H | H | $CO_2Et$ | H |
| I-2181 | c-Pr | Ph—NH | Me | H | H | H | H | $CO_2Et$ | H |
| I-2182 | c-Pr | Ph—(Bn)N | Me | H | H | H | H | $CO_2Et$ | H |
| I-2183 | c-Pr | (Pyridin-3-yl)amino | Me | H | H | H | H | $CO_2Et$ | H |
| I-2184 | c-Pr | Allylamino | Me | H | H | H | H | $CO_2Et$ | H |
| I-2185 | c-Pr | Propargylamino | Me | H | H | H | H | $CO_2Et$ | H |
| I-2186 | c-Pr | (Pyrrolidin-1-yl) | Me | H | H | H | H | $CO_2Et$ | H |
| I-2187 | c-Pr | $F_3CCH_2NH$ | Me | H | H | H | H | $CO_2Et$ | H |
| I-2188 | c-Pr | Acetylamino | Me | H | H | H | H | $CO_2Et$ | H |
| I-2189 | c-Pr | Benzoylamino | Me | H | H | H | H | $CO_2Et$ | H |
| I-2190 | c-Pr | (Ethoxycarbonyl)amino | Me | H | H | H | H | $CO_2Et$ | H |
| I-2191 | c-Pr | (N,N-Dimethylamino)carbonylamino | Me | H | H | H | H | $CO_2Et$ | H |
| I-2192 | c-Pr | (N,N-Dimethylamino)(thiocarbonyl)amino | Me | H | H | H | H | $CO_2Et$ | H |
| I-2193 | c-Pr | (Methylsulfonyl)amino | Me | H | H | H | H | $CO_2Et$ | H |
| I-2194 | c-Pr | $NH_2$ | Me | H | H | H | H | CN | H |
| I-2195 | c-Pr | MeNH | Me | H | H | H | H | CN | H |
| I-2196 | c-Pr | $Me_2N$ | Me | H | H | H | H | CN | H |
| I-2197 | c-Pr | cyclopentyl-NH | Me | H | H | H | H | CN | H |
| I-2198 | c-Pr | Ph—NH | Me | H | H | H | H | CN | H |
| I-2199 | c-Pr | Ph—(Bn)N | Me | H | H | H | H | CN | H |
| I-2200 | c-Pr | (Pyridin-3-yl)amino | Me | H | H | H | H | CN | H |
| I-2201 | c-Pr | Allylamino | Me | H | H | H | H | CN | H |
| I-2202 | c-Pr | Propargylamino | Me | H | H | H | H | CN | H |
| I-2203 | c-Pr | (Pyrrolidin-1-yl) | Me | H | H | H | H | CN | H |

TABLE 1-continued

Inventive compounds of the formula (I) in which X represents $C(R^{13})(R^{14})$

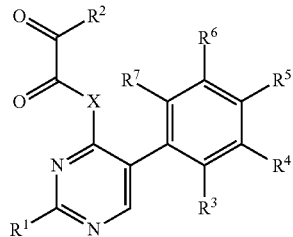

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-2204 | c-Pr | $F_3CCH_2NH$ | Me | H | H | H | H | CN | H |
| I-2205 | c-Pr | Acetylamino | Me | H | H | H | H | CN | H |
| I-2206 | c-Pr | Benzoylamino | Me | H | H | H | H | CN | H |
| I-2207 | c-Pr | (Ethoxycarbonyl)amino | Me | H | H | H | H | CN | H |
| I-2208 | c-Pr | (N,N-Dimethyl-amino)carbonyl-amino | Me | H | H | H | H | CN | H |
| I-2209 | c-Pr | (N,N-Dimethylamino)(thio-carbonyl)amino | Me | H | H | H | H | CN | H |
| I-2210 | c-Pr | (Methylsulfonyl)amino | Me | H | H | H | H | CN | H |
| I-2211 | c-Pr | $NH_2$ | $CF_3$ | H | H | H | H | Me | H |
| I-2212 | c-Pr | MeNH | $CF_3$ | H | H | H | H | Me | H |
| I-2213 | c-Pr | $Me_2N$ | $CF_3$ | H | H | H | H | Me | H |
| I-2214 | c-Pr | cyclopentyl-NH | $CF_3$ | H | H | H | H | Me | H |
| I-2215 | c-Pr | Ph—NH | $CF_3$ | H | H | H | H | Me | H |
| I-2216 | c-Pr | Ph—(Bn)N | $CF_3$ | H | H | H | H | Me | H |
| I-2217 | c-Pr | (Pyridin-3-yl)amino | $CF_3$ | H | H | H | H | Me | H |
| I-2218 | c-Pr | Allylamino | $CF_3$ | H | H | H | H | Me | H |
| I-2219 | c-Pr | Propargylamino | $CF_3$ | H | H | H | H | Me | H |
| I-2220 | c-Pr | (Pyrrolidin-1-yl) | $CF_3$ | H | H | H | H | Me | H |
| I-2221 | c-Pr | $F_3CCH_2NH$ | $CF_3$ | H | H | H | H | Me | H |
| I-2222 | c-Pr | Acetylamino | $CF_3$ | H | H | H | H | Me | H |
| I-2223 | c-Pr | Benzoylamino | $CF_3$ | H | H | H | H | Me | H |
| I-2224 | c-Pr | (Ethoxycarbonyl)amino | $CF_3$ | H | H | H | H | Me | H |
| I-2225 | c-Pr | (N,N-Dimethyl-amino)carbonyl-amino | $CF_3$ | H | H | H | H | Me | H |
| I-2226 | c-Pr | (N,N-Dimethylamino)(thio-carbonyl)amino | $CF_3$ | H | H | H | H | Me | H |
| I-2227 | c-Pr | (Methylsulfonyl)amino | $CF_3$ | H | H | H | H | Me | H |
| I-2228 | c-Pr | $NH_2$ | $CF_3$ | H | H | H | H | Me | Me |
| I-2229 | c-Pr | MeNH | $CF_3$ | H | H | H | H | Me | Me |
| I-2230 | c-Pr | $Me_2N$ | $CF_3$ | H | H | H | H | Me | Me |
| I-2231 | c-Pr | cyclopentyl-NH | $CF_3$ | H | H | H | H | Me | Me |
| I-2232 | c-Pr | Ph—NH | $CF_3$ | H | H | H | H | Me | Me |
| I-2233 | c-Pr | Ph—(Bn)N | $CF_3$ | H | H | H | H | Me | Me |
| I-2234 | c-Pr | (Pyridin-3-yl)amino | $CF_3$ | H | H | H | H | Me | Me |
| I-2235 | c-Pr | Allylamino | $CF_3$ | H | H | H | H | Me | Me |
| I-2236 | c-Pr | Propargylamino | $CF_3$ | H | H | H | H | Me | Me |
| I-2237 | c-Pr | (Pyrrolidin-1-yl) | $CF_3$ | H | H | H | H | Me | Me |
| I-2238 | c-Pr | $F_3CCH_2NH$ | $CF_3$ | H | H | H | H | Me | Me |
| I-2239 | c-Pr | Acetylamino | $CF_3$ | H | H | H | H | Me | Me |
| I-2240 | c-Pr | Benzoylamino | $CF_3$ | H | H | H | H | Me | Me |
| I-2241 | c-Pr | (Ethoxycarbonyl)amino | $CF_3$ | H | H | H | H | Me | Me |
| I-2242 | c-Pr | (N,N-Dimethyl-amino)carbonyl-amino | $CF_3$ | H | H | H | H | Me | Me |
| I-2243 | c-Pr | (N,N-Dimethylamino)(thio-carbonyl)amino | $CF_3$ | H | H | H | H | Me | Me |
| I-2244 | c-Pr | (Methylsulfonyl)amino | $CF_3$ | H | H | H | H | Me | Me |
| I-2245 | c-Pr | $NH_2$ | $CF_3$ | H | H | H | H | $CO_2Et$ | H |
| I-2246 | c-Pr | MeNH | $CF_3$ | H | H | H | H | $CO_2Et$ | H |
| I-2247 | c-Pr | $Me_2N$ | $CF_3$ | H | H | H | H | $CO_2Et$ | H |

TABLE 1-continued

Inventive compounds of the formula (I) in which X represents $C(R^{13})(R^{14})$ $$(I)$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-2248 | c-Pr | cyclopentyl-NH | $CF_3$ | H | H | H | H | $CO_2Et$ | H |
| I-2249 | c-Pr | Ph—NH | $CF_3$ | H | H | H | H | $CO_2Et$ | H |
| I-2250 | c-Pr | Ph—(Bn)N | $CF_3$ | H | H | H | H | $CO_2Et$ | H |
| I-2251 | c-Pr | (Pyridin-3-yl)amino | $CF_3$ | H | H | H | H | $CO_2Et$ | H |
| I-2252 | c-Pr | Allylamino | $CF_3$ | H | H | H | H | $CO_2Et$ | H |
| I-2253 | c-Pr | Propargylamino | $CF_3$ | H | H | H | H | $CO_2Et$ | H |
| I-2254 | c-Pr | (Pyrrolidin-1-yl) | $CF_3$ | H | H | H | H | $CO_2Et$ | H |
| I-2255 | c-Pr | $F_3CCH_2NH$ | $CF_3$ | H | H | H | H | $CO_2Et$ | H |
| I-2256 | c-Pr | Acetylamino | $CF_3$ | H | H | H | H | $CO_2Et$ | H |
| I-2257 | c-Pr | Benzoylamino | $CF_3$ | H | H | H | H | $CO_2Et$ | H |
| I-2258 | c-Pr | (Ethoxycarbonyl)amino | $CF_3$ | H | H | H | H | $CO_2Et$ | H |
| I-2259 | c-Pr | (N,N-Dimethyl-amino)carbonyl-amino | $CF_3$ | H | H | H | H | $CO_2Et$ | H |
| I-2260 | c-Pr | (N,N-Dimethylamino)(thio-carbonyl)amino | $CF_3$ | H | H | H | H | $CO_2Et$ | H |
| I-2261 | c-Pr | (Methylsulfonyl)amino | $CF_3$ | H | H | H | H | $CO_2Et$ | H |
| I-2262 | c-Pr | $NH_2$ | $CF_3$ | H | H | H | H | CN | H |
| I-2263 | c-Pr | MeNH | $CF_3$ | H | H | H | H | CN | H |
| I-2264 | c-Pr | $Me_2N$ | $CF_3$ | H | H | H | H | CN | H |
| I-2265 | c-Pr | cyclopentyl-NH | $CF_3$ | H | H | H | H | CN | H |
| I-2266 | c-Pr | Ph—NH | $CF_3$ | H | H | H | H | CN | H |
| I-2267 | c-Pr | Ph—(Bn)N | $CF_3$ | H | H | H | H | CN | H |
| I-2268 | c-Pr | (Pyridin-3-yl)amino | $CF_3$ | H | H | H | H | CN | H |
| I-2269 | c-Pr | Allylamino | $CF_3$ | H | H | H | H | CN | H |
| I-2270 | c-Pr | Propargylamino | $CF_3$ | H | H | H | H | CN | H |
| I-2271 | c-Pr | (Pyrrolidin-1-yl) | $CF_3$ | H | H | H | H | CN | H |
| I-2272 | c-Pr | $F_3CCH_2NH$ | $CF_3$ | H | H | H | H | CN | H |
| I-2273 | c-Pr | Acetylamino | $CF_3$ | H | H | H | H | CN | H |
| I-2274 | c-Pr | Benzoylamino | $CF_3$ | H | H | H | H | CN | H |
| I-2275 | c-Pr | (Ethoxycarbonyl)amino | $CF_3$ | H | H | H | H | CN | H |
| I-2276 | c-Pr | (N,N-Dimethyl-amino)carbonyl-amino | $CF_3$ | H | H | H | H | CN | H |
| I-2277 | c-Pr | (N,N-Dimethylamino)(thio-carbonyl)amino | $CF_3$ | H | H | H | H | CN | H |
| I-2278 | c-Pr | (Methylsulfonyl)amino | $CF_3$ | H | H | H | H | CN | H |
| I-2279 | c-Pr | $NH_2$ | MeO | H | H | H | H | Me | H |
| I-2280 | c-Pr | MeNH | MeO | H | H | H | H | Me | H |
| I-2281 | c-Pr | $Me_2N$ | MeO | H | H | H | H | Me | H |
| I-2282 | c-Pr | cyclopentyl-NH | MeO | H | H | H | H | Me | H |
| I-2283 | c-Pr | Ph—NH | MeO | H | H | H | H | Me | H |
| I-2284 | c-Pr | Ph—(Bn)N | MeO | H | H | H | H | Me | H |
| I-2285 | c-Pr | (Pyridin-3-yl)amino | MeO | H | H | H | H | Me | H |
| I-2286 | c-Pr | Allylamino | MeO | H | H | H | H | Me | H |
| I-2287 | c-Pr | Propargylamino | MeO | H | H | H | H | Me | H |
| I-2288 | c-Pr | (Pyrrolidin-1-yl) | MeO | H | H | H | H | Me | H |
| I-2289 | c-Pr | $F_3CCH_2NH$ | MeO | H | H | H | H | Me | H |
| I-2290 | c-Pr | Acetylamino | MeO | H | H | H | H | Me | H |
| I-2291 | c-Pr | Benzoylamino | MeO | H | H | H | H | Me | H |
| I-2292 | c-Pr | (Ethoxycarbonyl)amino | MeO | H | H | H | H | Me | H |
| I-2293 | c-Pr | (N,N-Dimethyl-amino)carbonyl-amino | MeO | H | H | H | H | Me | H |

TABLE 1-continued

Inventive compounds of the formula (I) in which X represents $C(R^{13})(R^{14})$

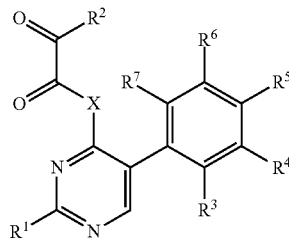

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-2294 | c-Pr | (N,N-Dimethylamino)(thio-carbonyl)amino | MeO | H | H | H | H | Me | H |
| I-2295 | c-Pr | (Methylsulfonyl)amino | MeO | H | H | H | H | Me | H |
| I-2296 | c-Pr | $NH_2$ | MeO | H | H | H | H | Me | Me |
| I-2297 | c-Pr | MeNH | MeO | H | H | H | H | Me | Me |
| I-2298 | c-Pr | $Me_2N$ | MeO | H | H | H | H | Me | Me |
| I-2299 | c-Pr | cyclopentyl-NH | MeO | H | H | H | H | Me | Me |
| I-2300 | c-Pr | Ph—NH | MeO | H | H | H | H | Me | Me |
| I-2301 | c-Pr | Ph—(Bn)N | MeO | H | H | H | H | Me | Me |
| I-2302 | c-Pr | (Pyridin-3-yl)amino | MeO | H | H | H | H | Me | Me |
| I-2303 | c-Pr | Allylamino | MeO | H | H | H | H | Me | Me |
| I-2304 | c-Pr | Propargylamino | MeO | H | H | H | H | Me | Me |
| I-2305 | c-Pr | (Pyrrolidin-1-yl) | MeO | H | H | H | H | Me | Me |
| I-2306 | c-Pr | $F_3CCH_2NH$ | MeO | H | H | H | H | Me | Me |
| I-2307 | c-Pr | Acetylamino | MeO | H | H | H | H | Me | Me |
| I-2308 | c-Pr | Benzoylamino | MeO | H | H | H | H | Me | Me |
| I-2309 | c-Pr | (Ethoxycarbonyl)amino | MeO | H | H | H | H | Me | Me |
| I-2310 | c-Pr | (N,N-Dimethyl-amino)carbonyl-amino | MeO | H | H | H | H | Me | Me |
| I-2311 | c-Pr | (N,N-Dimethylamino)(thio-carbonyl)amino | MeO | H | H | H | H | Me | Me |
| I-2312 | c-Pr | (Methylsulfonyl)amino | MeO | H | H | H | H | Me | Me |
| I-2313 | c-Pr | $NH_2$ | MeO | H | H | H | H | Me | H |
| I-2314 | c-Pr | MeNH | MeO | H | H | H | H | $CO_2Et$ | H |
| I-2315 | c-Pr | $Me_2N$ | MeO | H | H | H | H | $CO_2Et$ | H |
| I-2316 | c-Pr | cyclopentyl-NH | MeO | H | H | H | H | $CO_2Et$ | H |
| I-2317 | c-Pr | Ph—NH | MeO | H | H | H | H | $CO_2Et$ | H |
| I-2318 | c-Pr | Ph—(Bn)N | MeO | H | H | H | H | $CO_2Et$ | H |
| I-2319 | c-Pr | (Pyridin-3-yl)amino | MeO | H | H | H | H | $CO_2Et$ | H |
| I-2320 | c-Pr | Allylamino | MeO | H | H | H | H | $CO_2Et$ | H |
| I-2321 | c-Pr | Propargylamino | MeO | H | H | H | H | $CO_2Et$ | H |
| I-2322 | c-Pr | (Pyrrolidin-1-yl) | MeO | H | H | H | H | $CO_2Et$ | H |
| I-2323 | c-Pr | $F_3CCH_2NH$ | MeO | H | H | H | H | $CO_2Et$ | H |
| I-2324 | c-Pr | Acetylamino | MeO | H | H | H | H | CN | H |
| I-2325 | c-Pr | Benzoylamino | MeO | H | H | H | H | CN | H |
| I-2326 | c-Pr | (Ethoxycarbonyl)amino | MeO | H | H | H | H | CN | H |
| I-2327 | c-Pr | (N,N-Dimethyl-amino)carbonyl-amino | MeO | H | H | H | H | CN | H |
| I-2328 | c-Pr | (N,N-Dimethylamino)(thio-carbonyl)amino | MeO | H | H | H | H | CN | H |
| I-2329 | c-Pr | (Methylsulfonyl)amino | MeO | H | H | H | H | CN | H |
| I-2330 | c-Pr | $NH_2$ | MeO | H | H | H | H | CN | H |
| I-2331 | c-Pr | MeNH | MeO | H | H | H | H | CN | H |
| I-2332 | c-Pr | $Me_2N$ | MeO | H | H | H | H | CN | H |
| I-2333 | c-Pr | cyclopentyl-NH | MeO | H | H | H | H | CN | H |
| I-2334 | c-Pr | Ph—NH | MeO | H | H | H | H | CN | H |
| I-2335 | c-Pr | Ph—(Bn)N | MeO | H | H | H | H | CN | H |
| I-2336 | c-Pr | (Pyridin-3-yl)amino | MeO | H | H | H | H | CN | H |
| I-2337 | c-Pr | Allylamino | MeO | H | H | H | H | CN | H |
| I-2338 | c-Pr | Propargylamino | MeO | H | H | H | H | CN | H |
| I-2339 | c-Pr | (Pyrrolidin-1-yl) | MeO | H | H | H | H | CN | H |

TABLE 1-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| I-2340 | c-Pr | F₃CCH₂NH | MeO | H | H | H | H | CN | H |
| I-2341 | c-Pr | Acetylamino | MeO | H | H | H | H | CN | H |
| I-2342 | c-Pr | Benzoylamino | MeO | H | H | H | H | CN | H |
| I-2343 | c-Pr | (Ethoxycarbonyl)amino | MeO | H | H | H | H | CN | H |
| I-2344 | c-Pr | (N,N-Dimethyl-amino)carbonyl-amino | MeO | H | H | H | H | CN | H |
| I-2345 | c-Pr | (N,N-Dimethylamino)(thio-carbonyl)amino | MeO | H | H | H | H | CN | H |
| I-2346 | c-Pr | (Methylsulfonyl)amino | MeO | H | H | H | H | CN | H |

TABLE 2

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-001 | c-Pr | HO | H | H | H | H | H | H | |
| II-002 | c-Pr | MeO | H | H | H | H | H | H | |
| II-003 | c-Pr | EtO | H | H | H | H | H | H | |
| II-004 | c-Pr | n-PrO | H | H | H | H | H | H | |
| II-005 | c-Pr | i-PrO | H | H | H | H | H | H | |
| II-006 | c-Pr | n-BuO | H | H | H | H | H | H | |
| II-007 | c-Pr | i-BuO | H | H | H | H | H | H | |
| II-008 | c-Pr | PhCH₂O | H | H | H | H | H | H | |
| II-009 | c-Pr | CH₂=CHCH₂O | H | H | H | H | H | H | |
| II-010 | c-Pr | HC≡CCH₂O | H | H | H | H | H | H | |
| II-011 | c-Pr | F₃CCH₂O | H | H | H | H | H | H | |
| II-012 | c-Pr | H₃COCH₂CH₂O | H | H | H | H | H | H | |
| II-013 | 1-Me-c-Pr | HO | H | H | H | H | H | H | |
| II-014 | 1-Me-c-Pr | MeO | H | H | H | H | H | H | |
| II-015 | 1-Me-c-Pr | EtO | H | H | H | H | H | H | |
| II-016 | 1-Me-c-Pr | n-PrO | H | H | H | H | H | H | |
| II-017 | 1-Me-c-Pr | i-PrO | H | H | H | H | H | H | |
| II-018 | 1-Me-c-Pr | n-BuO | H | H | H | H | H | H | |
| II-019 | 1-Me-c-Pr | i-BuO | H | H | H | H | H | H | |
| II-020 | 1-Me-c-Pr | PhCH₂O | H | H | H | H | H | H | |
| II-021 | 1-Me-c-Pr | CH₂=CHCH₂O | H | H | H | H | H | H | |
| II-022 | 1-Me-c-Pr | HC≡CCH₂O | H | H | H | H | H | H | |
| II-023 | 1-Me-c-Pr | F₃CCH₂O | H | H | H | H | H | H | |
| II-024 | 1-Me-c-Pr | H₃COCH₂CH₂O | H | H | H | H | H | H | |
| II-025 | 2-Me-c-Pr | HO | H | H | H | H | H | H | |
| II-026 | 2-Me-c-Pr | MeO | H | H | H | H | H | H | |
| II-027 | 2-Me-c-Pr | EtO | H | H | H | H | H | H | |
| II-028 | 2-Me-c-Pr | n-PrO | H | H | H | H | H | H | |

TABLE 2-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-029 | 2-Me-c-Pr | i-PrO | H | H | H | H | H | H | H |
| II-030 | 2-Me-c-Pr | n-BuO | H | H | H | H | H | H | H |
| II-031 | 2-Me-c-Pr | i-BuO | H | H | H | H | H | H | H |
| II-032 | 2-Me-c-Pr | PhCH$_2$O | H | H | H | H | H | H | H |
| II-033 | 2-Me-c-Pr | CH$_2$=CHCH$_2$O | H | H | H | H | H | H | H |
| II-034 | 2-Me-c-Pr | HC≡CCH$_2$O | H | H | H | H | H | H | H |
| II-035 | 2-Me-c-Pr | F$_3$CCH$_2$O | H | H | H | H | H | H | H |
| II-036 | 2-Me-c-Pr | H$_3$COCH$_2$CH$_2$O | H | H | H | H | H | H | H |
| II-037 | c-Pr | HO | F | H | H | H | H | H | H |
| II-038 | c-Pr | MeO | F | H | H | H | H | H | H |
| II-039 | c-Pr | EtO | F | H | H | H | H | H | H |
| II-040 | c-Pr | n-PrO | F | H | H | H | H | H | H |
| II-041 | c-Pr | i-PrO | F | H | H | H | H | H | H |
| II-042 | c-Pr | n-BuO | F | H | H | H | H | H | H |
| II-043 | c-Pr | i-BuO | F | H | H | H | H | H | H |
| II-044 | c-Pr | PhCH$_2$O | F | H | H | H | H | H | H |
| II-045 | c-Pr | CH$_2$=CHCH$_2$O | F | H | H | H | H | H | H |
| II-046 | c-Pr | HC≡CCH$_2$O | F | H | H | H | H | H | H |
| II-047 | c-Pr | F$_3$CCH$_2$O | F | H | H | H | H | H | H |
| II-048 | c-Pr | H$_3$COCH$_2$CH$_2$O | F | H | H | H | H | H | H |
| II-049 | 1-Me-c-Pr | HO | F | H | H | H | H | H | H |
| II-050 | 1-Me-c-Pr | MeO | F | H | H | H | H | H | H |
| II-051 | 1-Me-c-Pr | EtO | F | H | H | H | H | H | H |
| II-052 | 1-Me-c-Pr | n-PrO | F | H | H | H | H | H | H |
| II-053 | 1-Me-c-Pr | i-PrO | F | H | H | H | H | H | H |
| II-054 | 1-Me-c-Pr | n-BuO | F | H | H | H | H | H | H |
| II-055 | 1-Me-c-Pr | i-BuO | F | H | H | H | H | H | H |
| II-056 | 1-Me-c-Pr | PhCH$_2$O | F | H | H | H | H | H | H |
| II-057 | 1-Me-c-Pr | CH$_2$=CHCH$_2$O | F | H | H | H | H | H | H |
| II-058 | 1-Me-c-Pr | HC≡CCH$_2$O | F | H | H | H | H | H | H |
| II-059 | 1-Me-c-Pr | F$_3$CCH$_2$O | F | H | H | H | H | H | H |
| II-060 | 1-Me-c-Pr | H$_3$COCH$_2$CH$_2$O | F | H | H | H | H | H | H |
| II-061 | 2-Me-c-Pr | HO | F | H | H | H | H | H | H |
| II-062 | 2-Me-c-Pr | MeO | F | H | H | H | H | H | H |
| II-063 | 2-Me-c-Pr | EtO | F | H | H | H | H | H | H |
| II-064 | 2-Me-c-Pr | n-PrO | F | H | H | H | H | H | H |
| II-065 | 2-Me-c-Pr | i-PrO | F | H | H | H | H | H | H |
| II-066 | 2-Me-c-Pr | n-BuO | F | H | H | H | H | H | H |
| II-067 | 2-Me-c-Pr | i-BuO | F | H | H | H | H | H | H |
| II-068 | 2-Me-c-Pr | PhCH$_2$O | F | H | H | H | H | H | H |
| II-069 | 2-Me-c-Pr | CH$_2$=CHCH$_2$O | F | H | H | H | H | H | H |
| II-070 | 2-Me-c-Pr | HC≡CCH$_2$O | F | H | H | H | H | H | H |
| II-071 | 2-Me-c-Pr | F$_3$CCH$_2$O | F | H | H | H | H | H | H |
| II-072 | 2-Me-c-Pr | H$_3$COCH$_2$CH$_2$O | F | H | H | H | H | H | H |
| II-073 | c-Pr | HO | H | F | H | H | H | H | H |
| II-074 | c-Pr | MeO | H | F | H | H | H | H | H |
| II-075 | c-Pr | EtO | H | F | H | H | H | H | H |
| II-076 | c-Pr | n-PrO | H | F | H | H | H | H | H |
| II-077 | c-Pr | i-PrO | H | F | H | H | H | H | H |
| II-078 | c-Pr | n-BuO | H | F | H | H | H | H | H |
| II-079 | c-Pr | i-BuO | H | F | H | H | H | H | H |
| II-080 | c-Pr | PhCH$_2$O | H | F | H | H | H | H | H |
| II-081 | c-Pr | CH$_2$=CHCH$_2$O | H | F | H | H | H | H | H |
| II-082 | c-Pr | HC≡CCH$_2$O | H | F | H | H | H | H | H |
| II-083 | c-Pr | F$_3$CCH$_2$O | H | F | H | H | H | H | H |
| II-084 | c-Pr | H$_3$COCH$_2$CH$_2$O | H | F | H | H | H | H | H |
| II-085 | c-Pr | HO | H | H | F | H | H | H | H |
| II-086 | c-Pr | MeO | H | H | F | H | H | H | H |
| II-087 | c-Pr | EtO | H | H | F | H | H | H | H |
| II-088 | c-Pr | n-PrO | H | H | F | H | H | H | H |
| II-089 | c-Pr | i-PrO | H | H | F | H | H | H | H |
| II-090 | c-Pr | n-BuO | H | H | F | H | H | H | H |
| II-091 | c-Pr | i-BuO | H | H | F | H | H | H | H |

TABLE 2-continued

Inventive compounds of the formula (I) in which X represents $C(R^{13})(R^{14})$ $$\text{(I)}$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-092 | c-Pr | PhCH$_2$O | H | H | F | H | H | H | H |
| II-093 | c-Pr | CH$_2$=CHCH$_2$O | H | H | F | H | H | H | H |
| II-094 | c-Pr | HC≡CCH$_2$O | H | H | F | H | H | H | H |
| II-095 | c-Pr | F$_3$CCH$_2$O | H | H | F | H | H | H | H |
| II-096 | c-Pr | H$_3$COCH$_2$CH$_2$O | H | H | F | H | H | H | H |
| II-097 | c-Pr | HO | Cl | H | H | H | H | H | H |
| II-098 | c-Pr | MeO | Cl | H | H | H | H | H | H |
| II-099 | c-Pr | EtO | Cl | H | H | H | H | H | H |
| II-100 | c-Pr | n-PrO | Cl | H | H | H | H | H | H |
| II-101 | c-Pr | i-PrO | Cl | H | H | H | H | H | H |
| II-102 | c-Pr | n-BuO | Cl | H | H | H | H | H | H |
| II-103 | c-Pr | i-BuO | Cl | H | H | H | H | H | H |
| II-104 | c-Pr | PhCH$_2$O | Cl | H | H | H | H | H | H |
| II-105 | c-Pr | CH$_2$=CHCH$_2$O | Cl | H | H | H | H | H | H |
| II-106 | c-Pr | HC≡CCH$_2$O | Cl | H | H | H | H | H | H |
| II-107 | c-Pr | F$_3$CCH$_2$O | Cl | H | H | H | H | H | H |
| II-108 | c-Pr | H$_3$COCH$_2$CH$_2$O | Cl | H | H | H | H | H | H |
| II-109 | 1-Me-c-Pr | HO | Cl | H | H | H | H | H | H |
| II-110 | 1-Me-c-Pr | MeO | Cl | H | H | H | H | H | H |
| II-111 | 1-Me-c-Pr | EtO | Cl | H | H | H | H | H | H |
| II-112 | 1-Me-c-Pr | n-PrO | Cl | H | H | H | H | H | H |
| II-113 | 1-Me-c-Pr | i-PrO | Cl | H | H | H | H | H | H |
| II-114 | 1-Me-c-Pr | n-BuO | Cl | H | H | H | H | H | H |
| II-115 | 1-Me-c-Pr | i-BuO | Cl | H | H | H | H | H | H |
| II-116 | 1-Me-c-Pr | PhCH$_2$O | Cl | H | H | H | H | H | H |
| II-117 | 1-Me-c-Pr | CH$_2$=CHCH$_2$O | Cl | H | H | H | H | H | H |
| II-118 | 1-Me-c-Pr | HC≡CCH$_2$O | Cl | H | H | H | H | H | H |
| II-119 | 1-Me-c-Pr | F$_3$CCH$_2$O | Cl | H | H | H | H | H | H |
| II-120 | 1-Me-c-Pr | H$_3$COCH$_2$CH$_2$O | Cl | H | H | H | H | H | H |
| II-121 | 2-Me-c-Pr | HO | Cl | H | H | H | H | H | H |
| II-122 | 2-Me-c-Pr | MeO | Cl | H | H | H | H | H | H |
| II-123 | 2-Me-c-Pr | EtO | Cl | H | H | H | H | H | H |
| II-124 | 2-Me-c-Pr | n-PrO | Cl | H | H | H | H | H | H |
| II-125 | 2-Me-c-Pr | i-PrO | Cl | H | H | H | H | H | H |
| II-126 | 2-Me-c-Pr | n-BuO | Cl | H | H | H | H | H | H |
| II-127 | 2-Me-c-Pr | i-BuO | Cl | H | H | H | H | H | H |
| II-128 | 2-Me-c-Pr | PhCH$_2$O | Cl | H | H | H | H | H | H |
| II-129 | 2-Me-c-Pr | CH$_2$=CHCH$_2$O | Cl | H | H | H | H | H | H |
| II-130 | 2-Me-c-Pr | HC≡CCH$_2$O | Cl | H | H | H | H | H | H |
| II-131 | 2-Me-c-Pr | F$_3$CCH$_2$O | Cl | H | H | H | H | H | H |
| II-132 | 2-Me-c-Pr | H$_3$COCH$_2$CH$_2$O | Cl | H | H | H | H | H | H |
| II-133 | c-Pr | HO | H | Cl | H | H | H | H | H |
| II-134 | c-Pr | MeO | H | Cl | H | H | H | H | H |
| II-135 | c-Pr | EtO | H | Cl | H | H | H | H | H |
| II-136 | c-Pr | n-PrO | H | Cl | H | H | H | H | H |
| II-137 | c-Pr | i-PrO | H | Cl | H | H | H | H | H |
| II-138 | c-Pr | n-BuO | H | Cl | H | H | H | H | H |
| II-139 | c-Pr | i-BuO | H | Cl | H | H | H | H | H |
| II-140 | c-Pr | PhCH$_2$O | H | Cl | H | H | H | H | H |
| II-141 | c-Pr | CH$_2$=CHCH$_2$O | H | Cl | H | H | H | H | H |
| II-142 | c-Pr | HC≡CCH$_2$O | H | Cl | H | H | H | H | H |
| II-143 | c-Pr | F$_3$CCH$_2$O | H | Cl | H | H | H | H | H |
| II-144 | c-Pr | H$_3$COCH$_2$CH$_2$O | H | Cl | H | H | H | H | H |
| II-145 | c-Pr | HO | H | H | Cl | H | H | H | H |
| II-146 | c-Pr | MeO | H | H | Cl | H | H | H | H |
| II-147 | c-Pr | EtO | H | H | Cl | H | H | H | H |
| II-148 | c-Pr | n-PrO | H | H | Cl | H | H | H | H |
| II-149 | c-Pr | i-PrO | H | H | Cl | H | H | H | H |
| II-150 | c-Pr | n-BuO | H | H | Cl | H | H | H | H |
| II-151 | c-Pr | i-BuO | H | H | Cl | H | H | H | H |
| II-152 | c-Pr | PhCH$_2$O | H | H | Cl | H | H | H | H |
| II-153 | c-Pr | CH$_2$=CHCH$_2$O | H | H | Cl | H | H | H | H |
| II-154 | c-Pr | HC≡CCH$_2$O | H | H | Cl | H | H | H | H |

TABLE 2-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-155 | c-Pr | $F_3CCH_2O$ | H | H | Cl | H | H | H | H |
| II-156 | c-Pr | $H_3COCH_2CH_2O$ | H | H | Cl | H | H | H | H |
| II-157 | c-Pr | HO | Me | H | H | H | H | H | H |
| II-158 | c-Pr | MeO | Me | H | H | H | H | H | H |
| II-159 | c-Pr | EtO | Me | H | H | H | H | H | H |
| II-160 | c-Pr | n-PrO | Me | H | H | H | H | H | H |
| II-161 | c-Pr | i-PrO | Me | H | H | H | H | H | H |
| II-162 | c-Pr | n-BuO | Me | H | H | H | H | H | H |
| II-163 | c-Pr | i-BuO | Me | H | H | H | H | H | H |
| II-164 | c-Pr | $PhCH_2O$ | Me | H | H | H | H | H | H |
| II-165 | c-Pr | $CH_2=CHCH_2O$ | Me | H | H | H | H | H | H |
| II-166 | c-Pr | $HC\equiv CCH_2O$ | Me | H | H | H | H | H | H |
| II-167 | c-Pr | $F_3CCH_2O$ | Me | H | H | H | H | H | H |
| II-168 | c-Pr | $H_3COCH_2CH_2O$ | Me | H | H | H | H | H | H |
| II-169 | 1-Me-c-Pr | HO | Me | H | H | H | H | H | H |
| II-170 | 1-Me-c-Pr | MeO | Me | H | H | H | H | H | H |
| II-171 | 1-Me-c-Pr | EtO | Me | H | H | H | H | H | H |
| II-172 | 1-Me-c-Pr | n-PrO | Me | H | H | H | H | H | H |
| II-173 | 1-Me-c-Pr | i-PrO | Me | H | H | H | H | H | H |
| II-174 | 1-Me-c-Pr | n-BuO | Me | H | H | H | H | H | H |
| II-175 | 1-Me-c-Pr | i-BuO | Me | H | H | H | H | H | H |
| II-176 | 1-Me-c-Pr | $PhCH_2O$ | Me | H | H | H | H | H | H |
| II-177 | 1-Me-c-Pr | $CH_2=CHCH_2O$ | Me | H | H | H | H | H | H |
| II-178 | 1-Me-c-Pr | $HC\equiv CCH_2O$ | Me | H | H | H | H | H | H |
| II-179 | 1-Me-c-Pr | $F_3CCH_2O$ | Me | H | H | H | H | H | H |
| II-180 | 1-Me-c-Pr | $H_3COCH_2CH_2O$ | Me | H | H | H | H | H | H |
| II-181 | 2-Me-c-Pr | HO | Me | H | H | H | H | H | H |
| II-182 | 2-Me-c-Pr | MeO | Me | H | H | H | H | H | H |
| II-183 | 2-Me-c-Pr | EtO | Me | H | H | H | H | H | H |
| II-184 | 2-Me-c-Pr | n-PrO | Me | H | H | H | H | H | H |
| II-185 | 2-Me-c-Pr | i-PrO | Me | H | H | H | H | H | H |
| II-186 | 2-Me-c-Pr | n-BuO | Me | H | H | H | H | H | H |
| II-187 | 2-Me-c-Pr | i-BuO | Me | H | H | H | H | H | H |
| II-188 | 2-Me-c-Pr | $PhCH_2O$ | Me | H | H | H | H | H | H |
| II-189 | 2-Me-c-Pr | $CH_2=CHCH_2O$ | Me | H | H | H | H | H | H |
| II-190 | 2-Me-c-Pr | $HC\equiv CCH_2O$ | Me | H | H | H | H | H | H |
| II-191 | 2-Me-c-Pr | $F_3CCH_2O$ | Me | H | H | H | H | H | H |
| II-192 | 2-Me-c-Pr | $H_3COCH_2CH_2O$ | Me | H | H | H | H | H | H |
| II-193 | c-Pr | HO | H | Me | H | H | H | H | H |
| II-194 | c-Pr | MeO | H | Me | H | H | H | H | H |
| II-195 | c-Pr | EtO | H | Me | H | H | H | H | H |
| II-196 | c-Pr | n-PrO | H | Me | H | H | H | H | H |
| II-197 | c-Pr | i-PrO | H | Me | H | H | H | H | H |
| II-198 | c-Pr | n-BuO | H | Me | H | H | H | H | H |
| II-199 | c-Pr | i-BuO | H | Me | H | H | H | H | H |
| II-200 | c-Pr | $PhCH_2O$ | H | Me | H | H | H | H | H |
| II-201 | c-Pr | $CH_2=CHCH_2O$ | H | Me | H | H | H | H | H |
| II-202 | c-Pr | $HC\equiv CCH_2O$ | H | Me | H | H | H | H | H |
| II-203 | c-Pr | $F_3CCH_2O$ | H | Me | H | H | H | H | H |
| II-204 | c-Pr | $H_3COCH_2CH_2O$ | H | Me | H | H | H | H | H |
| II-205 | c-Pr | HO | H | H | Me | H | H | H | H |
| II-206 | c-Pr | MeO | H | H | Me | H | H | H | H |
| II-207 | c-Pr | EtO | H | H | Me | H | H | H | H |
| II-208 | c-Pr | n-PrO | H | H | Me | H | H | H | H |
| II-209 | c-Pr | i-PrO | H | H | Me | H | H | H | H |
| II-210 | c-Pr | n-BuO | H | H | Me | H | H | H | H |
| II-211 | c-Pr | i-BuO | H | H | Me | H | H | H | H |
| II-212 | c-Pr | $PhCH_2O$ | H | H | Me | H | H | H | H |
| II-213 | c-Pr | $CH_2=CHCH_2O$ | H | H | Me | H | H | H | H |
| II-214 | c-Pr | $HC\equiv CCH_2O$ | H | H | Me | H | H | H | H |
| II-215 | c-Pr | $F_3CCH_2O$ | H | H | Me | H | H | H | H |
| II-216 | c-Pr | $H_3COCH_2CH_2O$ | H | H | Me | H | H | H | H |
| II-217 | c-Pr | HO | $CF_3$ | H | H | H | H | H | H |

TABLE 2-continued

Inventive compounds of the formula (I) in which X represents $C(R^{13})(R^{14})$

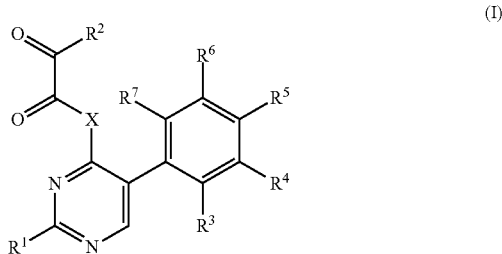

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-218 | c-Pr | MeO | $CF_3$ | H | H | H | H | H | H |
| II-219 | c-Pr | EtO | $CF_3$ | H | H | H | H | H | H |
| II-220 | c-Pr | n-PrO | $CF_3$ | H | H | H | H | H | H |
| II-221 | c-Pr | i-PrO | $CF_3$ | H | H | H | H | H | H |
| II-222 | c-Pr | n-BuO | $CF_3$ | H | H | H | H | H | H |
| II-223 | c-Pr | i-BuO | $CF_3$ | H | H | H | H | H | H |
| II-224 | c-Pr | $PhCH_2O$ | $CF_3$ | H | H | H | H | H | H |
| II-225 | c-Pr | $CH_2$=$CHCH_2O$ | $CF_3$ | H | H | H | H | H | H |
| II-226 | c-Pr | HC≡$CCH_2O$ | $CF_3$ | H | H | H | H | H | H |
| II-227 | c-Pr | $F_3CCH_2O$ | $CF_3$ | H | H | H | H | H | H |
| II-228 | c-Pr | $H_3COCH_2CH_2O$ | $CF_3$ | H | H | H | H | H | H |
| II-229 | 1-Me-c-Pr | HO | $CF_3$ | H | H | H | H | H | H |
| II-230 | 1-Me-c-Pr | MeO | $CF_3$ | H | H | H | H | H | H |
| II-231 | 1-Me-c-Pr | EtO | $CF_3$ | H | H | H | H | H | H |
| II-232 | 1-Me-c-Pr | n-PrO | $CF_3$ | H | H | H | H | H | H |
| II-233 | 1-Me-c-Pr | i-PrO | $CF_3$ | H | H | H | H | H | H |
| II-234 | 1-Me-c-Pr | n-BuO | $CF_3$ | H | H | H | H | H | H |
| II-235 | 1-Me-c-Pr | i-BuO | $CF_3$ | H | H | H | H | H | H |
| II-236 | 1-Me-c-Pr | $PhCH_2O$ | $CF_3$ | H | H | H | H | H | H |
| II-237 | 1-Me-c-Pr | $CH_2$=$CHCH_2O$ | $CF_3$ | H | H | H | H | H | H |
| II-238 | 1-Me-c-Pr | HC≡$CCH_2O$ | $CF_3$ | H | H | H | H | H | H |
| II-239 | 1-Me-c-Pr | $F_3CCH_2$ | $CF_3$ | H | H | H | H | H | H |
| II-240 | 1-Me-c-Pr | $H_3COCH_2CH_2O$ | $CF_3$ | H | H | H | H | H | H |
| II-241 | 2-Me-c-Pr | HO | $CF_3$ | H | H | H | H | H | H |
| II-242 | 2-Me-c-Pr | MeO | $CF_3$ | H | H | H | H | H | H |
| II-243 | 2-Me-c-Pr | EtO | $CF_3$ | H | H | H | H | H | H |
| II-244 | 2-Me-c-Pr | n-PrO | $CF_3$ | H | H | H | H | H | H |
| II-245 | 2-Me-c-Pr | i-PrO | $CF_3$ | H | H | H | H | H | H |
| II-246 | 2-Me-c-Pr | n-BuO | $CF_3$ | H | H | H | H | H | H |
| II-247 | 2-Me-c-Pr | i-BuO | $CF_3$ | H | H | H | H | H | H |
| II-248 | 2-Me-c-Pr | $PhCH_2O$ | $CF_3$ | H | H | H | H | H | H |
| II-249 | 2-Me-c-Pr | $CH_2$=$CHCH_2O$ | $CF_3$ | H | H | H | H | H | H |
| II-250 | 2-Me-c-Pr | HC≡$CCH_2O$ | $CF_3$ | H | H | H | H | H | H |
| II-251 | 2-Me-c-Pr | $F_3CCH_2O$ | $CF_3$ | H | H | H | H | H | H |
| II-252 | 2-Me-c-Pr | $H_3COCH_2CH_2O$ | $CF_3$ | H | H | H | H | H | H |
| II-253 | c-Pr | HO | H | $CF_3$ | H | H | H | H | H |
| II-254 | c-Pr | MeO | H | $CF_3$ | H | H | H | H | H |
| II-255 | c-Pr | EtO | H | $CF_3$ | H | H | H | H | H |
| II-256 | c-Pr | n-PrO | H | $CF_3$ | H | H | H | H | H |
| II-257 | c-Pr | i-PrO | H | $CF_3$ | H | H | H | H | H |
| II-258 | c-Pr | n-BuO | H | $CF_3$ | H | H | H | H | H |
| II-259 | c-Pr | i-BuO | H | $CF_3$ | H | H | H | H | H |
| II-260 | c-Pr | $PhCH_2O$ | H | $CF_3$ | H | H | H | H | H |
| II-261 | c-Pr | $CH_2$=$CHCH_2O$ | H | $CF_3$ | H | H | H | H | H |
| II-262 | c-Pr | HC≡$CCH_2O$ | H | $CF_3$ | H | H | H | H | H |
| II-263 | c-Pr | $F_3CCH_2O$ | H | $CF_3$ | H | H | H | H | H |
| II-264 | c-Pr | $H_3COCH_2CH_2O$ | H | $CF_3$ | H | H | H | H | H |
| II-265 | c-Pr | HO | H | H | $CF_3$ | H | H | H | H |
| II-266 | c-Pr | MeO | H | H | $CF_3$ | H | H | H | H |
| II-267 | c-Pr | EtO | H | H | $CF_3$ | H | H | H | H |
| II-268 | c-Pr | n-PrO | H | H | $CF_3$ | H | H | H | H |
| II-269 | c-Pr | i-PrO | H | H | $CF_3$ | H | H | H | H |
| II-270 | c-Pr | n-BuO | H | H | $CF_3$ | H | H | H | H |
| II-271 | c-Pr | i-BuO | H | H | $CF_3$ | H | H | H | H |
| II-272 | c-Pr | $PhCH_2O$ | H | H | $CF_3$ | H | H | H | H |
| II-273 | c-Pr | $CH_2$=$CHCH_2O$ | H | H | $CF_3$ | H | H | H | H |
| II-274 | c-Pr | HC≡$CCH_2O$ | H | H | $CF_3$ | H | H | H | H |
| II-275 | c-Pr | $F_3CCH_2O$ | H | H | $CF_3$ | H | H | H | H |
| II-276 | c-Pr | $H_3COCH_2CH_2O$ | H | H | $CF_3$ | H | H | H | H |
| II-277 | c-Pr | HO | MeO | H | H | H | H | H | H |
| II-278 | c-Pr | MeO | MeO | H | H | H | H | H | H |
| II-279 | c-Pr | EtO | MeO | H | H | H | H | H | H |
| II-280 | c-Pr | n-PrO | MeO | H | H | H | H | H | H |

TABLE 2-continued

Inventive compounds of the formula (I) in which X represents $C(R^{13})(R^{14})$

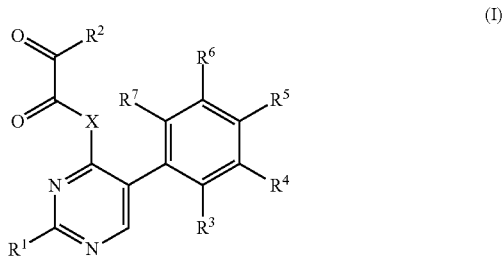

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-281 | c-Pr | i-PrO | MeO | H | H | H | H | H | H |
| II-282 | c-Pr | n-BuO | MeO | H | H | H | H | H | H |
| II-283 | c-Pr | i-BuO | MeO | H | H | H | H | H | H |
| II-284 | c-Pr | PhCH$_2$O | MeO | H | H | H | H | H | H |
| II-285 | c-Pr | CH$_2$=CHCH$_2$O | MeO | H | H | H | H | H | H |
| II-286 | c-Pr | HC≡CCH$_2$O | MeO | H | H | H | H | H | H |
| II-287 | c-Pr | F$_3$CCH$_2$O | MeO | H | H | H | H | H | H |
| II-288 | c-Pr | H$_3$COCH$_2$CH$_2$O | MeO | H | H | H | H | H | H |
| II-289 | 1-Me-c-Pr | HO | MeO | H | H | H | H | H | H |
| II-290 | 1-Me-c-Pr | MeO | MeO | H | H | H | H | H | H |
| II-291 | 1-Me-c-Pr | EtO | MeO | H | H | H | H | H | H |
| II-292 | 1-Me-c-Pr | n-PrO | MeO | H | H | H | H | H | H |
| II-293 | 1-Me-c-Pr | i-PrO | MeO | H | H | H | H | H | H |
| II-294 | 1-Me-c-Pr | n-BuO | MeO | H | H | H | H | H | H |
| II-295 | 1-Me-c-Pr | i-BuO | MeO | H | H | H | H | H | H |
| II-296 | 1-Me-c-Pr | PhCH$_2$O | MeO | H | H | H | H | H | H |
| II-297 | 1-Me-c-Pr | CH$_2$=CHCH$_2$O | MeO | H | H | H | H | H | H |
| II-298 | 1-Me-c-Pr | HC≡CCH$_2$O | MeO | H | H | H | H | H | H |
| II-299 | 1-Me-c-Pr | F$_3$CCH$_2$O | MeO | H | H | H | H | H | H |
| II-300 | 1-Me-c-Pr | H$_3$COCH$_2$CH$_2$O | MeO | H | H | H | H | H | H |
| II-301 | c-Pr | HO | H | MeO | H | H | H | H | H |
| II-302 | c-Pr | MeO | H | MeO | H | H | H | H | H |
| II-303 | c-Pr | EtO | H | MeO | H | H | H | H | H |
| II-304 | c-Pr | n-PrO | H | MeO | H | H | H | H | H |
| II-305 | c-Pr | i-PrO | H | MeO | H | H | H | H | H |
| II-306 | c-Pr | n-BuO | H | MeO | H | H | H | H | H |
| II-307 | c-Pr | i-BuO | H | MeO | H | H | H | H | H |
| II-308 | c-Pr | PhCH$_2$O | H | MeO | H | H | H | H | H |
| II-309 | c-Pr | CH$_2$=CHCH$_2$O | H | MeO | H | H | H | H | H |
| II-310 | c-Pr | HC≡CCH$_2$O | H | MeO | H | H | H | H | H |
| II-311 | c-Pr | F$_3$CCH$_2$O | H | MeO | H | H | H | H | H |
| II-312 | c-Pr | H$_3$COCH$_2$CH$_2$O | H | MeO | H | H | H | H | H |
| II-313 | c-Pr | HO | H | H | MeO | H | H | H | H |
| II-314 | c-Pr | MeO | H | H | MeO | H | H | H | H |
| II-315 | c-Pr | EtO | H | H | MeO | H | H | H | H |
| II-316 | c-Pr | n-PrO | H | H | MeO | H | H | H | H |
| II-317 | c-Pr | i-PrO | H | H | MeO | H | H | H | H |
| II-318 | c-Pr | n-BuO | H | H | MeO | H | H | H | H |
| II-319 | c-Pr | i-BuO | H | H | MeO | H | H | H | H |
| II-320 | c-Pr | PhCH$_2$O | H | H | MeO | H | H | H | H |
| II-321 | c-Pr | CH$_2$=CHCH$_2$O | H | H | MeO | H | H | H | H |
| II-322 | c-Pr | HC≡CCH$_2$O | H | H | MeO | H | H | H | H |
| II-323 | c-Pr | F$_3$CCH$_2$O | H | H | MeO | H | H | H | H |
| II-324 | c-Pr | H$_3$COCH$_2$CH$_2$O | H | H | MeO | H | H | H | H |
| II-325 | c-Pr | HO | F | F | H | H | H | H | H |
| II-326 | c-Pr | MeO | F | F | H | H | H | H | H |
| II-327 | c-Pr | EtO | F | F | H | H | H | H | H |
| II-328 | c-Pr | n-PrO | F | F | H | H | H | H | H |
| II-329 | c-Pr | i-PrO | F | F | H | H | H | H | H |
| II-330 | c-Pr | n-BuO | F | F | H | H | H | H | H |
| II-331 | c-Pr | i-BuO | F | F | H | H | H | H | H |
| II-332 | c-Pr | PhCH$_2$O | F | F | H | H | H | H | H |
| II-333 | c-Pr | CH$_2$=CHCH$_2$O | F | F | H | H | H | H | H |
| II-334 | c-Pr | HC≡CCH$_2$O | F | F | H | H | H | H | H |
| II-335 | c-Pr | F$_3$CCH$_2$O | F | F | H | H | H | H | H |
| II-336 | c-Pr | H$_3$COCH$_2$CH$_2$O | F | F | H | H | H | H | H |
| II-337 | c-Pr | HO | F | H | F | H | H | H | H |
| II-338 | c-Pr | MeO | F | H | F | H | H | H | H |
| II-339 | c-Pr | EtO | F | H | F | H | H | H | H |
| II-340 | c-Pr | n-PrO | F | H | F | H | H | H | H |
| II-341 | c-Pr | i-PrO | F | H | F | H | H | H | H |
| II-342 | c-Pr | n-BuO | F | H | F | H | H | H | H |
| II-343 | c-Pr | i-BuO | F | H | F | H | H | H | H |

TABLE 2-continued

Inventive compounds of the formula (I) in which X represents $C(R^{13})(R^{14})$

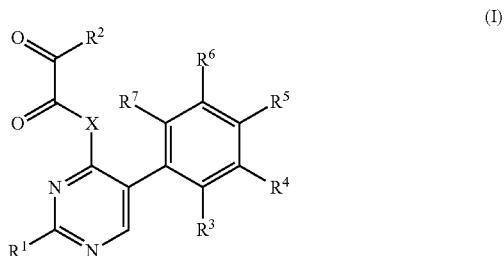

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-344 | c-Pr | PhCH$_2$O | F | H | F | H | H | H | H |
| II-345 | c-Pr | CH$_2$=CHCH$_2$O | F | H | F | H | H | H | H |
| II-346 | c-Pr | HC≡CCH$_2$O | F | H | F | H | H | H | H |
| II-347 | c-Pr | F$_3$CCH$_2$O | F | H | F | H | H | H | H |
| II-348 | c-Pr | H$_3$COCH$_2$CH$_2$O | F | H | F | H | H | H | H |
| II-349 | c-Pr | HO | F | H | H | F | H | H | H |
| II-350 | c-Pr | MeO | F | H | H | F | H | H | H |
| II-351 | c-Pr | EtO | F | H | H | F | H | H | H |
| II-352 | c-Pr | n-PrO | F | H | H | F | H | H | H |
| II-353 | c-Pr | i-PrO | F | H | H | F | H | H | H |
| II-354 | c-Pr | n-BuO | F | H | H | F | H | H | H |
| II-355 | c-Pr | i-BuO | F | H | H | F | H | H | H |
| II-356 | c-Pr | PhCH$_2$O | F | H | H | F | H | H | H |
| II-357 | c-Pr | CH$_2$=CHCH$_2$O | F | H | H | F | H | H | H |
| II-358 | c-Pr | HC≡CCH$_2$O | F | H | H | F | H | H | H |
| II-359 | c-Pr | F$_3$CCH$_2$O | F | H | H | F | H | H | H |
| II-360 | c-Pr | H$_3$COCH$_2$CH$_2$O | F | H | H | F | H | H | H |
| II-361 | c-Pr | HO | F | H | H | H | F | H | H |
| II-362 | c-Pr | MeO | F | H | H | H | F | H | H |
| II-363 | c-Pr | EtO | F | H | H | H | F | H | H |
| II-364 | c-Pr | n-PrO | F | H | H | H | F | H | H |
| II-365 | c-Pr | i-PrO | F | H | H | H | F | H | H |
| II-366 | c-Pr | n-BuO | F | H | H | H | F | H | H |
| II-367 | c-Pr | i-BuO | F | H | H | H | F | H | H |
| II-368 | c-Pr | PhCH$_2$O | F | H | H | H | F | H | H |
| II-369 | c-Pr | CH$_2$=CHCH$_2$O | F | H | H | H | F | H | H |
| II-370 | c-Pr | HC≡CCH$_2$O | F | H | H | H | F | H | H |
| II-371 | c-Pr | F$_3$CCH$_2$O | F | H | H | H | F | H | H |
| II-372 | c-Pr | H$_3$COCH$_2$CH$_2$O | F | H | H | H | F | H | H |
| II-373 | c-Pr | HO | F | Cl | H | H | H | H | H |
| II-374 | c-Pr | MeO | F | Cl | H | H | H | H | H |
| II-375 | c-Pr | EtO | F | Cl | H | H | H | H | H |
| II-376 | c-Pr | n-PrO | F | Cl | H | H | H | H | H |
| II-377 | c-Pr | i-PrO | F | Cl | H | H | H | H | H |
| II-378 | c-Pr | n-BuO | F | Cl | H | H | H | H | H |
| II-379 | c-Pr | i-BuO | F | Cl | H | H | H | H | H |
| II-380 | c-Pr | PhCH$_2$O | F | Cl | H | H | H | H | H |
| II-381 | c-Pr | CH$_2$=CHCH$_2$O | F | Cl | H | H | H | H | H |
| II-382 | c-Pr | HC≡CCH$_2$O | F | Cl | H | H | H | H | H |
| II-383 | c-Pr | F$_3$CCH$_2$O | F | Cl | H | H | H | H | H |
| II-384 | c-Pr | H$_3$COCH$_2$CH$_2$O | F | Cl | H | H | H | H | H |
| II-385 | c-Pr | HO | F | H | Cl | H | H | H | H |
| II-386 | c-Pr | MeO | F | H | Cl | H | H | H | H |
| II-387 | c-Pr | EtO | F | H | Cl | H | H | H | H |
| II-388 | c-Pr | n-PrO | F | H | Cl | H | H | H | H |
| II-389 | c-Pr | i-PrO | F | H | Cl | H | H | H | H |
| II-390 | c-Pr | n-BuO | F | H | Cl | H | H | H | H |
| II-391 | c-Pr | i-BuO | F | H | Cl | H | H | H | H |
| II-392 | c-Pr | PhCH$_2$O | F | H | Cl | H | H | H | H |
| II-393 | c-Pr | CH$_2$=CHCH$_2$O | F | H | Cl | H | H | H | H |
| II-394 | c-Pr | HC≡CCH$_2$O | F | H | Cl | H | H | H | H |
| II-395 | c-Pr | F$_3$CCH$_2$O | F | H | Cl | H | H | H | H |
| II-396 | c-Pr | H$_3$COCH$_2$CH$_2$O | F | H | Cl | H | H | H | H |
| II-397 | c-Pr | HO | F | H | H | Cl | H | H | H |
| II-398 | c-Pr | MeO | F | H | H | Cl | H | H | H |
| II-399 | c-Pr | EtO | F | H | H | Cl | H | H | H |
| II-400 | c-Pr | n-PrO | F | H | H | Cl | H | H | H |
| II-401 | c-Pr | i-PrO | F | H | H | Cl | H | H | H |
| II-402 | c-Pr | n-BuO | F | H | H | Cl | H | H | H |
| II-403 | c-Pr | i-BuO | F | H | H | Cl | H | H | H |
| II-404 | c-Pr | PhCH$_2$O | F | H | H | Cl | H | H | H |
| II-405 | c-Pr | CH$_2$=CHCH$_2$O | F | H | H | Cl | H | H | H |
| II-406 | c-Pr | HC≡CCH$_2$O | F | H | H | Cl | H | H | H |

TABLE 2-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-407 | c-Pr | $F_3CCH_2O$ | F | H | H | Cl | H | H | H |
| II-408 | c-Pr | $H_3COCH_2CH_2O$ | F | H | H | Cl | H | H | H |
| II-409 | c-Pr | HO | F | H | H | H | Cl | H | H |
| II-410 | c-Pr | MeO | F | H | H | H | Cl | H | H |
| II-411 | c-Pr | EtO | F | H | H | H | Cl | H | H |
| II-412 | c-Pr | n-PrO | F | H | H | H | Cl | H | H |
| II-413 | c-Pr | i-PrO | F | H | H | H | Cl | H | H |
| II-414 | c-Pr | n-BuO | F | H | H | H | Cl | H | H |
| II-415 | c-Pr | i-BuO | F | H | H | H | Cl | H | H |
| II-416 | c-Pr | $PhCH_2O$ | F | H | H | H | Cl | H | H |
| II-417 | c-Pr | $CH_2=CHCH_2O$ | F | H | H | H | Cl | H | H |
| II-418 | c-Pr | $HC\equiv CCH_2O$ | F | H | H | H | Cl | H | H |
| II-419 | c-Pr | $F_3CCH_2O$ | F | H | H | H | Cl | H | H |
| II-420 | c-Pr | $H_3COCH_2CH_2O$ | F | H | H | H | Cl | H | H |
| II-421 | c-Pr | HO | F | MeO | H | H | H | H | H |
| II-422 | c-Pr | MeO | F | MeO | H | H | H | H | H |
| II-423 | c-Pr | EtO | F | MeO | H | H | H | H | H |
| II-424 | c-Pr | n-PrO | F | MeO | H | H | H | H | H |
| II-425 | c-Pr | i-PrO | F | MeO | H | H | H | H | H |
| II-426 | c-Pr | n-BuO | F | MeO | H | H | H | H | H |
| II-427 | c-Pr | i-BuO | F | MeO | H | H | H | H | H |
| II-428 | c-Pr | $PhCH_2O$ | F | MeO | H | H | H | H | H |
| II-429 | c-Pr | $CH_2=CHCH_2O$ | F | MeO | H | H | H | H | H |
| II-430 | c-Pr | $HC\equiv CCH_2O$ | F | MeO | H | H | H | H | H |
| II-431 | c-Pr | $F_3CCH_2O$ | F | MeO | H | H | H | H | H |
| II-432 | c-Pr | $H_3COCH_2CH_2O$ | F | MeO | H | H | H | H | H |
| II-433 | c-Pr | HO | F | H | MeO | H | H | H | H |
| II-434 | c-Pr | MeO | F | H | MeO | H | H | H | H |
| II-435 | c-Pr | EtO | F | H | MeO | H | H | H | H |
| II-436 | c-Pr | n-PrO | F | H | MeO | H | H | H | H |
| II-437 | c-Pr | i-PrO | F | H | MeO | H | H | H | H |
| II-438 | c-Pr | n-BuO | F | H | MeO | H | H | H | H |
| II-439 | c-Pr | i-BuO | F | H | MeO | H | H | H | H |
| II-440 | c-Pr | $PhCH_2O$ | F | H | MeO | H | H | H | H |
| II-441 | c-Pr | $CH_2=CHCH_2O$ | F | H | MeO | H | H | H | H |
| II-442 | c-Pr | $HC\equiv CCH_2O$ | F | H | MeO | H | H | H | H |
| II-443 | c-Pr | $F_3CCH_2O$ | F | H | MeO | H | H | H | H |
| II-444 | c-Pr | $H_3COCH_2CH_2O$ | F | H | MeO | H | H | H | H |
| II-445 | c-Pr | HO | F | H | H | MeO | H | H | H |
| II-446 | c-Pr | MeO | F | H | H | MeO | H | H | H |
| II-447 | c-Pr | EtO | F | H | H | MeO | H | H | H |
| II-448 | c-Pr | n-PrO | F | H | H | MeO | H | H | H |
| II-449 | c-Pr | i-PrO | F | H | H | MeO | H | H | H |
| II-450 | c-Pr | n-BuO | F | H | H | MeO | H | H | H |
| II-451 | c-Pr | i-BuO | F | H | H | MeO | H | H | H |
| II-452 | c-Pr | $PhCH_2O$ | F | H | H | MeO | H | H | H |
| II-453 | c-Pr | $CH_2=CHCH_2O$ | F | H | H | MeO | H | H | H |
| II-454 | c-Pr | $HC\equiv CCH_2O$ | F | H | H | MeO | H | H | H |
| II-455 | c-Pr | $F_3CCH_2O$ | F | H | H | MeO | H | H | H |
| II-456 | c-Pr | $H_3COCH_2CH_2O$ | F | H | H | MeO | H | H | H |
| II-457 | c-Pr | HO | F | H | H | H | MeO | H | H |
| II-458 | c-Pr | MeO | F | H | H | H | MeO | H | H |
| II-459 | c-Pr | EtO | F | H | H | H | MeO | H | H |
| II-460 | c-Pr | n-PrO | F | H | H | H | MeO | H | H |
| II-461 | c-Pr | i-PrO | F | H | H | H | MeO | H | H |
| II-462 | c-Pr | n-BuO | F | H | H | H | MeO | H | H |
| II-463 | c-Pr | i-BuO | F | H | H | H | MeO | H | H |
| II-464 | c-Pr | $PhCH_2O$ | F | H | H | H | MeO | H | H |
| II-465 | c-Pr | $CH_2=CHCH_2O$ | F | H | H | H | MeO | H | H |
| II-466 | c-Pr | $HC\equiv CCH_2O$ | F | H | H | H | MeO | H | H |
| II-467 | c-Pr | $F_3CCH_2O$ | F | H | H | H | MeO | H | H |
| II-468 | c-Pr | $H_3COCH_2CH_2O$ | F | H | H | H | MeO | H | H |
| II-469 | c-Pr | HO | Cl | F | H | H | H | H | H |

TABLE 2-continued

Inventive compounds of the formula (I) in which X represents $C(R^{13})(R^{14})$

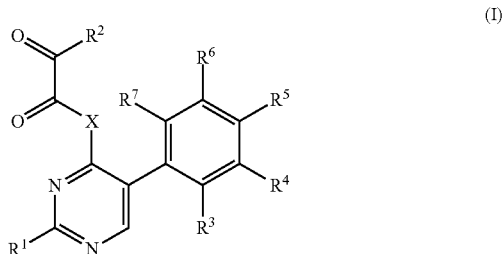

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-470 | c-Pr | MeO | Cl | F | H | H | H | H | H |
| II-471 | c-Pr | EtO | Cl | F | H | H | H | H | H |
| II-472 | c-Pr | n-PrO | Cl | F | H | H | H | H | H |
| II-473 | c-Pr | i-PrO | Cl | F | H | H | H | H | H |
| II-474 | c-Pr | n-BuO | Cl | F | H | H | H | H | H |
| II-475 | c-Pr | i-BuO | Cl | F | H | H | H | H | H |
| II-476 | c-Pr | PhCH$_2$O | Cl | F | H | H | H | H | H |
| II-477 | c-Pr | CH$_2$=CHCH$_2$O | Cl | F | H | H | H | H | H |
| II-478 | c-Pr | HC≡CCH$_2$O | Cl | F | H | H | H | H | H |
| II-479 | c-Pr | F$_3$CCH$_2$O | Cl | F | H | H | H | H | H |
| II-480 | c-Pr | H$_3$COCH$_2$CH$_2$O | Cl | F | H | H | H | H | H |
| II-481 | c-Pr | HO | Cl | H | F | H | H | H | H |
| II-482 | c-Pr | MeO | Cl | H | F | H | H | H | H |
| II-483 | c-Pr | EtO | Cl | H | F | H | H | H | H |
| II-484 | c-Pr | n-PrO | Cl | H | F | H | H | H | H |
| II-485 | c-Pr | i-PrO | Cl | H | F | H | H | H | H |
| II-486 | c-Pr | n-BuO | Cl | H | F | H | H | H | H |
| II-487 | c-Pr | i-BuO | Cl | H | F | H | H | H | H |
| II-488 | c-Pr | PhCH$_2$O | Cl | H | F | H | H | H | H |
| II-489 | c-Pr | CH$_2$=CHCH$_2$O | Cl | H | F | H | H | H | H |
| II-490 | c-Pr | HC≡CCH$_2$O | Cl | H | F | H | H | H | H |
| II-491 | c-Pr | F$_3$CCH$_2$O | Cl | H | F | H | H | H | H |
| II-492 | c-Pr | H3COCH$_2$CH$_2$O | Cl | H | F | H | H | H | H |
| II-493 | c-Pr | HO | Cl | H | H | F | H | H | H |
| II-494 | c-Pr | MeO | Cl | H | H | F | H | H | H |
| II-495 | c-Pr | EtO | Cl | H | H | F | H | H | H |
| II-496 | c-Pr | n-PrO | Cl | H | H | F | H | H | H |
| II-497 | c-Pr | i-PrO | Cl | H | H | F | H | H | H |
| II-498 | c-Pr | n-BuO | Cl | H | H | F | H | H | H |
| II-499 | c-Pr | i-BuO | Cl | H | H | F | H | H | H |
| II-500 | c-Pr | PhCH$_2$O | Cl | H | H | F | H | H | H |
| II-501 | c-Pr | CH$_2$=CHCH$_2$O | Cl | H | H | F | H | H | H |
| II-502 | c-Pr | HC≡CCH$_2$O | Cl | H | H | F | H | H | H |
| II-503 | c-Pr | F$_3$CCH$_2$O | Cl | H | H | F | H | H | H |
| II-504 | c-Pr | H$_3$COCH$_2$CH$_2$O | Cl | H | H | F | H | H | H |
| II-505 | c-Pr | HO | Cl | Cl | H | H | H | H | H |
| II-506 | c-Pr | MeO | Cl | Cl | H | H | H | H | H |
| II-507 | c-Pr | EtO | Cl | Cl | H | H | H | H | H |
| II-508 | c-Pr | n-PrO | Cl | Cl | H | H | H | H | H |
| II-509 | c-Pr | i-PrO | Cl | Cl | H | H | H | H | H |
| II-510 | c-Pr | n-BuO | Cl | Cl | H | H | H | H | H |
| II-511 | c-Pr | i-BuO | Cl | Cl | H | H | H | H | H |
| II-512 | c-Pr | PhCH$_2$O | Cl | Cl | H | H | H | H | H |
| II-513 | c-Pr | CH$_2$=CHCH$_2$O | Cl | Cl | H | H | H | H | H |
| II-514 | c-Pr | HC≡CCH$_2$O | Cl | Cl | H | H | H | H | H |
| II-515 | c-Pr | F$_3$CCH$_2$O | Cl | Cl | H | H | H | H | H |
| II-516 | c-Pr | H$_3$COCH$_2$CH$_2$O | Cl | Cl | H | H | H | H | H |
| II-517 | c-Pr | HO | Cl | H | Cl | H | H | H | H |
| II-518 | c-Pr | MeO | Cl | H | Cl | H | H | H | H |
| II-519 | c-Pr | EtO | Cl | H | Cl | H | H | H | H |
| II-520 | c-Pr | n-PrO | Cl | H | Cl | H | H | H | H |
| II-521 | c-Pr | i-PrO | Cl | H | Cl | H | H | H | H |
| II-522 | c-Pr | n-BuO | Cl | H | Cl | H | H | H | H |
| II-523 | c-Pr | i-BuO | Cl | H | Cl | H | H | H | H |
| II-524 | c-Pr | PhCH$_2$O | Cl | H | Cl | H | H | H | H |
| II-525 | c-Pr | CH$_2$=CHCH$_2$O | Cl | H | Cl | H | H | H | H |
| II-526 | c-Pr | HC≡CCH$_2$O | Cl | H | Cl | H | H | H | H |
| II-527 | c-Pr | F$_3$CCH$_2$O | Cl | H | Cl | H | H | H | H |
| II-528 | c-Pr | H$_3$COCH$_2$CH$_2$O | Cl | H | Cl | H | H | H | H |
| II-529 | c-Pr | HO | Cl | H | H | Cl | H | H | H |
| II-530 | c-Pr | MeO | Cl | H | H | Cl | H | H | H |
| II-531 | c-Pr | EtO | Cl | H | H | Cl | H | H | H |
| II-532 | c-Pr | n-PrO | Cl | H | H | Cl | H | H | H |

TABLE 2-continued

Inventive compounds of the formula (I) in which X represents $C(R^{13})(R^{14})$

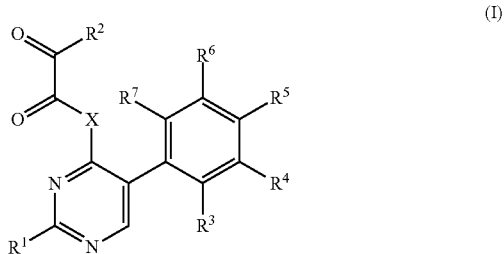

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-533 | c-Pr | i-PrO | Cl | H | H | Cl | H | H | H |
| II-534 | c-Pr | n-BuO | Cl | H | H | Cl | H | H | H |
| II-535 | c-Pr | i-BuO | Cl | H | H | Cl | H | H | H |
| II-536 | c-Pr | PhCH$_2$O | Cl | H | H | Cl | H | H | H |
| II-537 | c-Pr | CH$_2$=CHCH$_2$O | Cl | H | H | Cl | H | H | H |
| II-538 | c-Pr | HC≡CCH$_2$O | Cl | H | H | Cl | H | H | H |
| II-539 | c-Pr | F$_3$CCH$_2$O | Cl | H | H | Cl | H | H | H |
| II-540 | c-Pr | H$_3$COCH$_2$CH$_2$O | Cl | H | H | Cl | H | H | H |
| II-541 | c-Pr | HO | Cl | H | H | H | Cl | H | H |
| II-542 | c-Pr | MeO | Cl | H | H | H | Cl | H | H |
| II-543 | c-Pr | EtO | Cl | H | H | H | Cl | H | H |
| II-544 | c-Pr | n-PrO | Cl | H | H | H | Cl | H | H |
| II-545 | c-Pr | i-PrO | Cl | H | H | H | Cl | H | H |
| II-546 | c-Pr | n-BuO | Cl | H | H | H | Cl | H | H |
| II-547 | c-Pr | i-BuO | Cl | H | H | H | Cl | H | H |
| II-548 | c-Pr | PhCH$_2$O | Cl | H | H | H | Cl | H | H |
| II-549 | c-Pr | CH$_2$=CHCH$_2$O | Cl | H | H | H | Cl | H | H |
| II-550 | c-Pr | HC≡CCH$_2$O | Cl | H | H | H | Cl | H | H |
| II-551 | c-Pr | F$_3$CCH$_2$O | Cl | H | H | H | Cl | H | H |
| II-552 | c-Pr | H$_3$COCH$_2$CH$_2$O | Cl | H | H | H | Cl | H | H |
| II-553 | c-Pr | HO | Cl | Me | H | H | H | H | H |
| II-554 | c-Pr | MeO | Cl | Me | H | H | H | H | H |
| II-555 | c-Pr | EtO | Cl | Me | H | H | H | H | H |
| II-556 | c-Pr | n-PrO | Cl | Me | H | H | H | H | H |
| II-557 | c-Pr | i-PrO | Cl | Me | H | H | H | H | H |
| II-558 | c-Pr | n-BuO | Cl | Me | H | H | H | H | H |
| II-559 | c-Pr | i-BuO | Cl | Me | H | H | H | H | H |
| II-560 | c-Pr | PhCH$_2$O | Cl | Me | H | H | H | H | H |
| II-561 | c-Pr | CH$_2$=CHCH$_2$O | Cl | Me | H | H | H | H | H |
| II-562 | c-Pr | HC≡CCH$_2$O | Cl | Me | H | H | H | H | H |
| II-563 | c-Pr | F$_3$CCH$_2$O | Cl | Me | H | H | H | H | H |
| II-564 | c-Pr | H$_3$COCH$_2$CH$_2$O | Cl | Me | H | H | H | H | H |
| II-565 | c-Pr | HO | Cl | H | Me | H | H | H | H |
| II-566 | c-Pr | MeO | Cl | H | Me | H | H | H | H |
| II-567 | c-Pr | EtO | Cl | H | Me | H | H | H | H |
| II-568 | c-Pr | n-PrO | Cl | H | Me | H | H | H | H |
| II-569 | c-Pr | i-PrO | Cl | H | Me | H | H | H | H |
| II-570 | c-Pr | n-BuO | Cl | H | Me | H | H | H | H |
| II-571 | c-Pr | i-BuO | Cl | H | Me | H | H | H | H |
| II-572 | c-Pr | PhCH$_2$O | Cl | H | Me | H | H | H | H |
| II-573 | c-Pr | CH$_2$=CHCH$_2$O | Cl | H | Me | H | H | H | H |
| II-574 | c-Pr | HC≡CCH$_2$O | Cl | H | Me | H | H | H | H |
| II-575 | c-Pr | F$_3$CCH$_2$O | Cl | H | Me | H | H | H | H |
| II-576 | c-Pr | H$_3$COCH$_2$CH$_2$O | Cl | H | Me | H | H | H | H |
| II-577 | c-Pr | HO | Cl | H | H | Me | H | H | H |
| II-578 | c-Pr | MeO | Cl | H | H | Me | H | H | H |
| II-579 | c-Pr | EtO | Cl | H | H | Me | H | H | H |
| II-580 | c-Pr | n-PrO | Cl | H | H | Me | H | H | H |
| II-581 | c-Pr | i-PrO | Cl | H | H | Me | H | H | H |
| II-582 | c-Pr | n-BuO | Cl | H | H | Me | H | H | H |
| II-583 | c-Pr | i-BuO | Cl | H | H | Me | H | H | H |
| II-584 | c-Pr | PhCH$_2$O | Cl | H | H | Me | H | H | H |
| II-585 | c-Pr | CH$_2$=CHCH$_2$O | Cl | H | H | Me | H | H | H |
| II-586 | c-Pr | HC≡CCH$_2$O | Cl | H | H | Me | H | H | H |
| II-587 | c-Pr | F$_3$CCH$_2$O | Cl | H | H | Me | H | H | H |
| II-588 | c-Pr | H$_3$COCH$_2$CH$_2$O | Cl | H | H | Me | H | H | H |
| II-589 | c-Pr | HO | Cl | H | H | H | Me | H | H |
| II-590 | c-Pr | MeO | Cl | H | H | H | Me | H | H |
| II-591 | c-Pr | EtO | Cl | H | H | H | Me | H | H |
| II-592 | c-Pr | n-PrO | Cl | H | H | H | Me | H | H |
| II-593 | c-Pr | i-PrO | Cl | H | H | H | Me | H | H |
| II-594 | c-Pr | n-BuO | Cl | H | H | H | Me | H | H |
| II-595 | c-Pr | i-BuO | Cl | H | H | H | Me | H | H |

TABLE 2-continued

Inventive compounds of the formula (I) in which X represents $C(R^{13})(R^{14})$

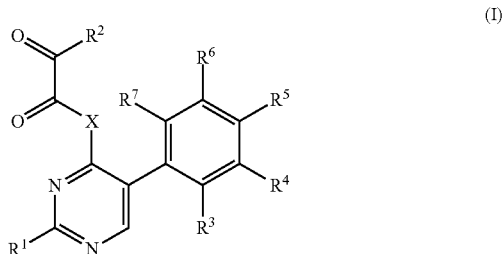

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-596 | c-Pr | PhCH$_2$O | Cl | H | H | H | Me | H | H |
| II-597 | c-Pr | CH$_2$=CHCH$_2$O | Cl | H | H | H | Me | H | H |
| II-598 | c-Pr | HC≡CCH$_2$O | Cl | H | H | H | Me | H | H |
| II-599 | c-Pr | F$_3$CCH$_2$O | Cl | H | H | H | Me | H | H |
| II-600 | c-Pr | H$_3$COCH$_2$CH$_2$O | Cl | H | H | H | Me | H | H |
| II-601 | c-Pr | HO | Cl | MeO | H | H | H | H | H |
| II-602 | c-Pr | MeO | Cl | MeO | H | H | H | H | H |
| II-603 | c-Pr | EtO | Cl | MeO | H | H | H | H | H |
| II-604 | c-Pr | n-PrO | Cl | MeO | H | H | H | H | H |
| II-605 | c-Pr | i-PrO | Cl | MeO | H | H | H | H | H |
| II-606 | c-Pr | n-BuO | Cl | MeO | H | H | H | H | H |
| II-607 | c-Pr | i-BuO | Cl | MeO | H | H | H | H | H |
| II-608 | c-Pr | PhCH$_2$O | Cl | MeO | H | H | H | H | H |
| II-609 | c-Pr | CH$_2$=CHCH$_2$O | Cl | MeO | H | H | H | H | H |
| II-610 | c-Pr | HC≡CCH$_2$O | Cl | MeO | H | H | H | H | H |
| II-611 | c-Pr | F$_3$CCH$_2$O | Cl | MeO | H | H | H | H | H |
| II-612 | c-Pr | H$_3$COCH$_2$CH$_2$O | Cl | MeO | H | H | H | H | H |
| II-613 | c-Pr | HO | Cl | H | MeO | H | H | H | H |
| II-614 | c-Pr | MeO | Cl | H | MeO | H | H | H | H |
| II-615 | c-Pr | EtO | Cl | H | MeO | H | H | H | H |
| II-616 | c-Pr | n-PrO | Cl | H | MeO | H | H | H | H |
| II-617 | c-Pr | i-PrO | Cl | H | MeO | H | H | H | H |
| II-618 | c-Pr | n-BuO | Cl | H | MeO | H | H | H | H |
| II-619 | c-Pr | i-BuO | Cl | H | MeO | H | H | H | H |
| II-620 | c-Pr | PhCH$_2$O | Cl | H | MeO | H | H | H | H |
| II-621 | c-Pr | CH$_2$=CHCH$_2$O | Cl | H | MeO | H | H | H | H |
| II-622 | c-Pr | HC≡CCH$_2$O | Cl | H | MeO | H | H | H | H |
| II-623 | c-Pr | F$_3$CCH$_2$O | Cl | H | MeO | H | H | H | H |
| II-624 | c-Pr | H$_3$COCH$_2$CH$_2$O | Cl | H | H | MeO | H | H | H |
| II-625 | c-Pr | HO | Cl | H | H | MeO | H | H | H |
| II-626 | c-Pr | MeO | Cl | H | H | MeO | H | H | H |
| II-627 | c-Pr | EtO | Cl | H | H | MeO | H | H | H |
| II-628 | c-Pr | n-PrO | Cl | H | H | MeO | H | H | H |
| II-629 | c-Pr | i-PrO | Cl | H | H | MeO | H | H | H |
| II-630 | c-Pr | n-BuO | Cl | H | H | MeO | H | H | H |
| II-631 | c-Pr | i-BuO | Cl | H | H | MeO | H | H | H |
| II-632 | c-Pr | PhCH$_2$O | Cl | H | H | MeO | H | H | H |
| II-633 | c-Pr | CH$_2$=CHCH$_2$O | Cl | H | H | MeO | H | H | H |
| II-634 | c-Pr | HC≡CCH$_2$O | Cl | H | H | MeO | H | H | H |
| II-635 | c-Pr | F$_3$CCH$_2$O | Cl | H | H | MeO | H | H | H |
| II-636 | c-Pr | H$_3$COCH$_2$CH$_2$O | Cl | H | H | MeO | H | H | H |
| II-637 | c-Pr | HO | Cl | H | H | H | MeO | H | H |
| II-638 | c-Pr | MeO | Cl | H | H | H | MeO | H | H |
| II-639 | c-Pr | EtO | Cl | H | H | H | MeO | H | H |
| II-640 | c-Pr | n-PrO | Cl | H | H | H | MeO | H | H |
| II-641 | c-Pr | i-PrO | Cl | H | H | H | MeO | H | H |
| II-642 | c-Pr | n-BuO | Cl | H | H | H | MeO | H | H |
| II-643 | c-Pr | i-BuO | Cl | H | H | H | MeO | H | H |
| II-644 | c-Pr | PhCH$_2$O | Cl | H | H | H | MeO | H | H |
| II-645 | c-Pr | CH$_2$=CHCH$_2$O | Cl | H | H | H | MeO | H | H |
| II-646 | c-Pr | HC≡CCH$_2$O | Cl | H | H | H | MeO | H | H |
| II-647 | c-Pr | F$_3$CCH$_2$O | Cl | H | H | H | MeO | H | H |
| II-648 | c-Pr | H$_3$COCH$_2$CH$_2$O | Cl | H | H | H | MeO | H | H |
| II-649 | c-Pr | HO | Me | Me | H | H | H | H | H |
| II-650 | c-Pr | MeO | Me | Me | H | H | H | H | H |
| II-651 | c-Pr | EtO | Me | Me | H | H | H | H | H |
| II-652 | c-Pr | n-PrO | Me | Me | H | H | H | H | H |
| II-653 | c-Pr | i-PrO | Me | Me | H | H | H | H | H |
| II-654 | c-Pr | n-BuO | Me | Me | H | H | H | H | H |
| II-655 | c-Pr | i-BuO | Me | Me | H | H | H | H | H |
| II-656 | c-Pr | PhCH$_2$O | Me | Me | H | H | H | H | H |
| II-657 | c-Pr | CH$_2$=CHCH$_2$O | Me | Me | H | H | H | H | H |
| II-658 | c-Pr | HC≡CCH$_2$O | Me | Me | H | H | H | H | H |

TABLE 2-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-659 | c-Pr | F₃CCH₂O | Me | Me | H | H | H | H | H |
| II-660 | c-Pr | H₃COCH₂CH₂O | Me | Me | H | H | H | H | H |
| II-661 | c-Pr | HO | Me | H | Me | H | H | H | H |
| II-662 | c-Pr | MeO | Me | H | Me | H | H | H | H |
| II-663 | c-Pr | EtO | Me | H | Me | H | H | H | H |
| II-664 | c-Pr | n-PrO | Me | H | Me | H | H | H | H |
| II-665 | c-Pr | i-PrO | Me | H | Me | H | H | H | H |
| II-666 | c-Pr | n-BuO | Me | H | Me | H | H | H | H |
| II-667 | c-Pr | i-BuO | Me | H | Me | H | H | H | H |
| II-668 | c-Pr | PhCH₂O | Me | H | Me | H | H | H | H |
| II-669 | c-Pr | CH₂=CHCH₂O | Me | H | Me | H | H | H | H |
| II-670 | c-Pr | HC≡CCH₂O | Me | H | Me | H | H | H | H |
| II-671 | c-Pr | F₃CCH₂O | Me | H | Me | H | H | H | H |
| II-672 | c-Pr | H₃COCH₂CH₂O | Me | H | Me | H | H | H | H |
| II-673 | c-Pr | HO | Me | H | H | Me | H | H | H |
| II-674 | c-Pr | MeO | Me | H | H | Me | H | H | H |
| II-675 | c-Pr | EtO | Me | H | H | Me | H | H | H |
| II-676 | c-Pr | n-PrO | Me | H | H | Me | H | H | H |
| II-677 | c-Pr | i-PrO | Me | H | H | Me | H | H | H |
| II-678 | c-Pr | n-BuO | Me | H | H | Me | H | H | H |
| II-679 | c-Pr | i-BuO | Me | H | H | Me | H | H | H |
| II-680 | c-Pr | PhCH₂O | Me | H | H | Me | H | H | H |
| II-681 | c-Pr | CH₂=CHCH₂O | Me | H | H | Me | H | H | H |
| II-682 | c-Pr | HC≡CCH₂O | Me | H | H | Me | H | H | H |
| II-683 | c-Pr | F₃CCH₂O | Me | H | H | Me | H | H | H |
| II-684 | c-Pr | H₃COCH₂CH₂O | Me | H | H | Me | H | H | H |
| II-685 | c-Pr | HO | Me | H | H | H | Me | H | H |
| II-686 | c-Pr | MeO | Me | H | H | H | Me | H | H |
| II-687 | c-Pr | EtO | Me | H | H | H | Me | H | H |
| II-688 | c-Pr | n-PrO | Me | H | H | H | Me | H | H |
| II-689 | c-Pr | i-PrO | Me | H | H | H | Me | H | H |
| II-690 | c-Pr | n-BuO | Me | H | H | H | Me | H | H |
| II-691 | c-Pr | i-BuO | Me | H | H | H | Me | H | H |
| II-692 | c-Pr | PhCH₂O | Me | H | H | H | Me | H | H |
| II-693 | c-Pr | CH₂=CHCH₂O | Me | H | H | H | Me | H | H |
| II-694 | c-Pr | HC≡CCH₂O | Me | H | H | H | Me | H | H |
| II-695 | c-Pr | F₃CCH₂O | Me | H | H | H | Me | H | H |
| II-696 | c-Pr | H₃COCH₂CH₂O | Me | H | H | H | Me | H | H |
| II-697 | c-Pr | HO | CF₃ | F | H | H | H | H | H |
| II-698 | c-Pr | MeO | CF₃ | F | H | H | H | H | H |
| II-699 | c-Pr | EtO | CF₃ | F | H | H | H | H | H |
| II-700 | c-Pr | n-PrO | CF₃ | F | H | H | H | H | H |
| II-701 | c-Pr | i-PrO | CF₃ | F | H | H | H | H | H |
| II-702 | c-Pr | n-BuO | CF₃ | F | H | H | H | H | H |
| II-703 | c-Pr | i-BuO | CF₃ | F | H | H | H | H | H |
| II-704 | c-Pr | PhCH₂O | CF₃ | F | H | H | H | H | H |
| II-705 | c-Pr | CH₂=CHCH₂O | CF₃ | F | H | H | H | H | H |
| II-706 | c-Pr | HC≡CCH₂O | CF₃ | F | H | H | H | H | H |
| II-707 | c-Pr | F₃CCH₂O | CF₃ | F | H | H | H | H | H |
| II-708 | c-Pr | H₃COCH₂CH₂O | CF₃ | F | H | H | H | H | H |
| II-709 | c-Pr | HO | CF₃ | H | F | H | H | H | H |
| II-710 | c-Pr | MeO | CF₃ | H | F | H | H | H | H |
| II-711 | c-Pr | EtO | CF₃ | H | F | H | H | H | H |
| II-712 | c-Pr | n-PrO | CF₃ | H | F | H | H | H | H |
| II-713 | c-Pr | i-PrO | CF₃ | H | F | H | H | H | H |
| II-714 | c-Pr | n-BuO | CF₃ | H | F | H | H | H | H |
| II-715 | c-Pr | i-BuO | CF₃ | H | F | H | H | H | H |
| II-716 | c-Pr | PhCH₂O | CF₃ | H | F | H | H | H | H |
| II-717 | c-Pr | CH₂=CHCH₂O | CF₃ | H | F | H | H | H | H |
| II-718 | c-Pr | HC≡CCH₂O | CF₃ | H | F | H | H | H | H |
| II-719 | c-Pr | F₃CCH₂O | CF₃ | H | F | H | H | H | H |
| II-720 | c-Pr | H₃COCH₂CH₂O | CF₃ | H | F | H | H | H | H |
| II-721 | c-Pr | HO | CF₃ | H | H | F | H | H | H |

TABLE 2-continued

Inventive compounds of the formula (I) in which X represents $C(R^{13})(R^{14})$ $$(I)$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-722 | c-Pr | MeO | $CF_3$ | H | H | F | H | H | H |
| II-723 | c-Pr | EtO | $CF_3$ | H | H | F | H | H | H |
| II-724 | c-Pr | n-PrO | $CF_3$ | H | H | F | H | H | H |
| II-725 | c-Pr | i-PrO | $CF_3$ | H | H | F | H | H | H |
| II-726 | c-Pr | n-BuO | $CF_3$ | H | H | F | H | H | H |
| II-727 | c-Pr | i-BuO | $CF_3$ | H | H | F | H | H | H |
| II-728 | c-Pr | $PhCH_2O$ | $CF_3$ | H | H | F | H | H | H |
| II-729 | c-Pr | $CH_2=CHCH_2O$ | $CF_3$ | H | H | F | H | H | H |
| II-730 | c-Pr | $HC\equiv CCH_2O$ | $CF_3$ | H | H | F | H | H | H |
| II-731 | c-Pr | $F_3CCH_2O$ | $CF_3$ | H | H | F | H | H | H |
| II-732 | c-Pr | $H_3COCH_2CH_2O$ | $CF_3$ | H | H | F | H | H | H |
| II-733 | c-Pr | HO | $CF_3$ | H | H | H | F | H | H |
| II-734 | c-Pr | MeO | $CF_3$ | H | H | H | F | H | H |
| II-735 | c-Pr | EtO | $CF_3$ | H | H | H | F | H | H |
| II-736 | c-Pr | n-PrO | $CF_3$ | H | H | H | F | H | H |
| II-737 | c-Pr | i-PrO | $CF_3$ | H | H | H | F | H | H |
| II-738 | c-Pr | n-BuO | $CF_3$ | H | H | H | F | H | H |
| II-739 | c-Pr | i-BuO | $CF_3$ | H | H | H | F | H | H |
| II-740 | c-Pr | $PhCH_2O$ | $CF_3$ | H | H | H | F | H | H |
| II-741 | c-Pr | $CH_2=CHCH_2O$ | $CF_3$ | H | H | H | F | H | H |
| II-742 | c-Pr | $HC\equiv CCH_2O$ | $CF_3$ | H | H | H | F | H | H |
| II-743 | c-Pr | $F_3CCH_2O$ | $CF_3$ | H | H | H | F | H | H |
| II-744 | c-Pr | $H_3COCH_2CH_2O$ | $CF_3$ | H | H | H | F | H | H |
| II-745 | c-Pr | HO | $CF_3$ | Cl | H | H | H | H | H |
| II-746 | c-Pr | MeO | $CF_3$ | Cl | H | H | H | H | H |
| II-747 | c-Pr | EtO | $CF_3$ | Cl | H | H | H | H | H |
| II-748 | c-Pr | n-PrO | $CF_3$ | Cl | H | H | H | H | H |
| II-749 | c-Pr | i-PrO | $CF_3$ | Cl | H | H | H | H | H |
| II-750 | c-Pr | n-BuO | $CF_3$ | Cl | H | H | H | H | H |
| II-751 | c-Pr | i-BuO | $CF_3$ | Cl | H | H | H | H | H |
| II-752 | c-Pr | $PhCH_2O$ | $CF_3$ | Cl | H | H | H | H | H |
| II-753 | c-Pr | $CH_2=CHCH_2O$ | $CF_3$ | Cl | H | H | H | H | H |
| II-754 | c-Pr | $HC\equiv CCH_2O$ | $CF_3$ | Cl | H | H | H | H | H |
| II-755 | c-Pr | $F_3CCH_2O$ | $CF_3$ | Cl | H | H | H | H | H |
| II-756 | c-Pr | $H_3COCH_2CH_2O$ | $CF_3$ | Cl | H | H | H | H | H |
| II-757 | c-Pr | HO | $CF_3$ | H | Cl | H | H | H | H |
| II-758 | c-Pr | MeO | $CF_3$ | H | Cl | H | H | H | H |
| II-759 | c-Pr | EtO | $CF_3$ | H | Cl | H | H | H | H |
| II-760 | c-Pr | n-PrO | $CF_3$ | H | Cl | H | H | H | H |
| II-761 | c-Pr | i-PrO | $CF_3$ | H | Cl | H | H | H | H |
| II-762 | c-Pr | n-BuO | $CF_3$ | H | Cl | H | H | H | H |
| II-763 | c-Pr | i-BuO | $CF_3$ | H | Cl | H | H | H | H |
| II-764 | c-Pr | $PhCH_2O$ | $CF_3$ | H | Cl | H | H | H | H |
| II-765 | c-Pr | $CH_2=CHCH_2O$ | $CF_3$ | H | Cl | H | H | H | H |
| II-766 | c-Pr | $HC\equiv CCH_2O$ | $CF_3$ | H | Cl | H | H | H | H |
| II-767 | c-Pr | $F_3CCH_2O$ | $CF_3$ | H | Cl | H | H | H | H |
| II-768 | c-Pr | $H_3COCH_2CH_2O$ | $CF_3$ | H | Cl | H | H | H | H |
| II-769 | c-Pr | HO | $CF_3$ | H | H | Cl | H | H | H |
| II-770 | c-Pr | MeO | $CF_3$ | H | H | Cl | H | H | H |
| II-771 | c-Pr | EtO | $CF_3$ | H | H | Cl | H | H | H |
| II-772 | c-Pr | n-PrO | $CF_3$ | H | H | Cl | H | H | H |
| II-773 | c-Pr | i-PrO | $CF_3$ | H | H | Cl | H | H | H |
| II-774 | c-Pr | n-BuO | $CF_3$ | H | H | Cl | H | H | H |
| II-775 | c-Pr | i-BuO | $CF_3$ | H | H | Cl | H | H | H |
| II-776 | c-Pr | $PhCH_2O$ | $CF_3$ | H | H | Cl | H | H | H |
| II-777 | c-Pr | $CH_2=CHCH_2O$ | $CF_3$ | H | H | Cl | H | H | H |
| II-778 | c-Pr | $HC\equiv CCH_2O$ | $CF_3$ | H | H | Cl | H | H | H |
| II-779 | c-Pr | $F_3CCH_2O$ | $CF_3$ | H | H | Cl | H | H | H |
| II-780 | c-Pr | $H_3COCH_2CH_2O$ | $CF_3$ | H | H | Cl | H | H | H |
| II-781 | c-Pr | HO | $CF_3$ | H | H | H | Cl | H | H |
| II-782 | c-Pr | MeO | $CF_3$ | H | H | H | Cl | H | H |
| II-783 | c-Pr | EtO | $CF_3$ | H | H | H | Cl | H | H |
| II-784 | c-Pr | n-PrO | $CF_3$ | H | H | H | Cl | H | H |

TABLE 2-continued

Inventive compounds of the formula (I) in which X represents $C(R^{13})(R^{14})$

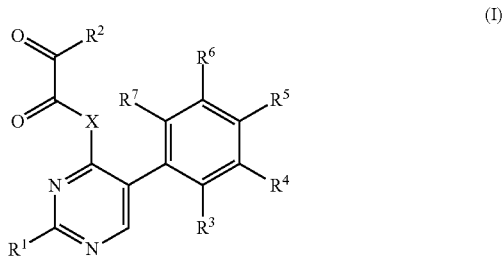

| No. | $R^1$ | $R^2$ | $R^3$ | $R^4$ | $R^5$ | $R^6$ | $R^7$ | $R^{13}$ | $R^{14}$ |
| --- | --- | --- | --- | --- | --- | --- | --- | --- | --- |
| II-785 | c-Pr | i-PrO | $CF_3$ | H | H | H | Cl | H | H |
| II-786 | c-Pr | n-BuO | $CF_3$ | H | H | H | Cl | H | H |
| II-787 | c-Pr | i-BuO | $CF_3$ | H | H | H | Cl | H | H |
| II-788 | c-Pr | $PhCH_2O$ | $CF_3$ | H | H | H | Cl | H | H |
| II-789 | c-Pr | $CH_2\!=\!CHCH_2O$ | $CF_3$ | H | H | H | Cl | H | H |
| II-790 | c-Pr | $HC\!\equiv\!CCH_2O$ | $CF_3$ | H | H | H | Cl | H | H |
| II-791 | c-Pr | $F_3CCH_2O$ | $CF_3$ | H | H | H | Cl | H | H |
| II-792 | c-Pr | $H_3COCH_2CH_2O$ | $CF_3$ | H | H | H | Cl | H | H |
| II-793 | c-Pr | HO | Cl | F | H | H | Cl | H | H |
| II-794 | c-Pr | MeO | Cl | F | H | H | Cl | H | H |
| II-795 | c-Pr | EtO | Cl | F | H | H | Cl | H | H |
| II-796 | c-Pr | n-PrO | Cl | F | H | H | Cl | H | H |
| II-797 | c-Pr | i-PrO | Cl | F | H | H | Cl | H | H |
| II-798 | c-Pr | n-BuO | Cl | F | H | H | Cl | H | H |
| II-799 | c-Pr | i-BuO | Cl | F | H | H | Cl | H | H |
| II-800 | c-Pr | $PhCH_2O$ | Cl | F | H | H | Cl | H | H |
| II-801 | c-Pr | $CH_2\!=\!CHCH_2O$ | Cl | F | H | H | Cl | H | H |
| II-802 | c-Pr | $HC\!\equiv\!CCH_2O$ | Cl | F | H | H | Cl | H | H |
| II-803 | c-Pr | $F_3CCH_2O$ | Cl | F | H | H | Cl | H | H |
| II-804 | c-Pr | $H_3COCH_2CH_2O$ | Cl | F | H | H | Cl | H | H |
| II-805 | c-Pr | HO | Cl | H | F | H | Cl | H | H |
| II-806 | c-Pr | MeO | Cl | H | F | H | Cl | H | H |
| II-807 | c-Pr | EtO | Cl | H | F | H | Cl | H | H |
| II-808 | c-Pr | n-PrO | Cl | H | F | H | Cl | H | H |
| II-809 | c-Pr | i-PrO | Cl | H | F | H | Cl | H | H |
| II-810 | c-Pr | n-BuO | Cl | H | F | H | Cl | H | H |
| II-811 | c-Pr | i-BuO | Cl | H | F | H | Cl | H | H |
| II-812 | c-Pr | $PhCH_2O$ | Cl | H | F | H | Cl | H | H |
| II-813 | c-Pr | $CH_2\!=\!CHCH_2O$ | Cl | H | F | H | Cl | H | H |
| II-814 | c-Pr | $HC\!\equiv\!CCH_2O$ | Cl | H | F | H | Cl | H | H |
| II-815 | c-Pr | $F_3CCH_2O$ | Cl | H | F | H | Cl | H | H |
| II-816 | c-Pr | $H_3COCH_2CH_2O$ | Cl | H | F | H | Cl | H | H |
| II-817 | c-Pr | HO | Cl | H | H | Cl | Cl | H | H |
| II-818 | c-Pr | MeO | Cl | H | H | Cl | Cl | H | H |
| II-819 | c-Pr | EtO | Cl | H | H | Cl | Cl | H | H |
| II-820 | c-Pr | n-PrO | Cl | H | H | Cl | Cl | H | H |
| II-821 | c-Pr | i-PrO | Cl | H | H | Cl | Cl | H | H |
| II-822 | c-Pr | n-BuO | Cl | H | H | Cl | Cl | H | H |
| II-823 | c-Pr | i-BuO | Cl | H | H | Cl | Cl | H | H |
| II-824 | c-Pr | $PhCH_2O$ | Cl | H | H | Cl | Cl | H | H |
| II-825 | c-Pr | $CH_2\!=\!CHCH_2O$ | Cl | H | H | Cl | Cl | H | H |
| II-826 | c-Pr | $HC\!\equiv\!CCH_2O$ | Cl | H | H | Cl | Cl | H | H |
| II-827 | c-Pr | $F_3CCH_2O$ | Cl | H | H | Cl | Cl | H | H |
| II-828 | c-Pr | $H_3COCH_2CH_2O$ | Cl | H | H | Cl | Cl | H | H |
| II-829 | c-Pr | HO | MeO | H | F | F | H | H | H |
| II-830 | c-Pr | MeO | MeO | H | F | F | H | H | H |
| II-831 | c-Pr | EtO | MeO | H | F | F | H | H | H |
| II-832 | c-Pr | n-PrO | MeO | H | F | F | H | H | H |
| II-833 | c-Pr | i-PrO | MeO | H | F | F | H | H | H |
| II-834 | c-Pr | n-BuO | MeO | H | F | F | H | H | H |
| II-835 | c-Pr | i-BuO | MeO | H | F | F | H | H | H |
| II-836 | c-Pr | $PhCH_2O$ | MeO | H | F | F | H | H | H |
| II-837 | c-Pr | $CH_2\!=\!CHCH_2O$ | MeO | H | F | F | H | H | H |
| II-838 | c-Pr | $HC\!\equiv\!CCH_2O$ | MeO | H | F | F | H | H | H |
| II-839 | c-Pr | $F_3CCH_2O$ | MeO | H | F | F | H | H | H |
| II-840 | c-Pr | $H_3COCH_2CH_2O$ | MeO | H | F | F | H | H | H |
| II-841 | c-Pr | HO | H | H | H | H | H | Me | H |
| II-842 | c-Pr | MeO | H | H | H | H | H | Me | H |
| II-843 | c-Pr | EtO | H | H | H | H | H | Me | H |
| II-844 | c-Pr | n-PrO | H | H | H | H | H | Me | H |
| II-845 | c-Pr | i-PrO | H | H | H | H | H | Me | H |
| II-846 | c-Pr | n-BuO | H | H | H | H | H | Me | H |
| II-847 | c-Pr | i-BuO | H | H | H | H | H | Me | H |

TABLE 2-continued

Inventive compounds of the formula (I) in which X represents $C(R^{13})(R^{14})$

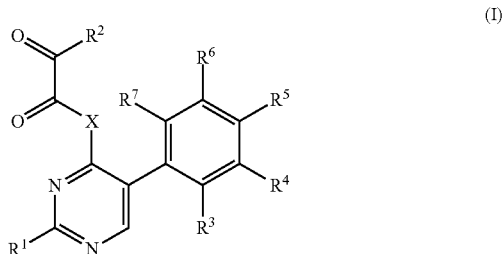

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-848 | c-Pr | PhCH$_2$O | H | H | H | H | H | Me | H |
| II-849 | c-Pr | CH$_2$=CHCH$_2$O | H | H | H | H | H | Me | H |
| II-850 | c-Pr | HC≡CCH$_2$O | H | H | H | H | H | Me | H |
| II-851 | c-Pr | F$_3$CCH$_2$O | H | H | H | H | H | Me | H |
| II-852 | c-Pr | H$_3$COCH$_2$CH$_2$O | H | H | H | H | H | Me | H |
| II-853 | c-Pr | HO | H | H | H | H | H | Me | Me |
| II-854 | c-Pr | MeO | H | H | H | H | H | Me | Me |
| II-855 | c-Pr | EtO | H | H | H | H | H | Me | Me |
| II-856 | c-Pr | n-PrO | H | H | H | H | H | Me | Me |
| II-857 | c-Pr | i-PrO | H | H | H | H | H | Me | Me |
| II-858 | c-Pr | n-BuO | H | H | H | H | H | Me | Me |
| II-859 | c-Pr | i-BuO | H | H | H | H | H | Me | Me |
| II-860 | c-Pr | PhCH$_2$O | H | H | H | H | H | Me | Me |
| II-861 | c-Pr | CH$_2$=CHCH$_2$O | H | H | H | H | H | Me | Me |
| II-862 | c-Pr | HC≡CCH$_2$O | H | H | H | H | H | Me | Me |
| II-863 | c-Pr | F$_3$CCH$_2$O | H | H | H | H | H | Me | Me |
| II-864 | c-Pr | H$_3$COCH$_2$CH$_2$O | H | H | H | H | H | Me | Me |
| II-865 | c-Pr | HO | H | H | H | H | H | CO$_2$Et | H |
| II-866 | c-Pr | MeO | H | H | H | H | H | CO$_2$Et | H |
| II-867 | c-Pr | EtO | H | H | H | H | H | CO$_2$Et | H |
| II-868 | c-Pr | n-PrO | H | H | H | H | H | CO$_2$Et | H |
| II-869 | c-Pr | i-PrO | H | H | H | H | H | CO$_2$Et | H |
| II-870 | c-Pr | n-BuO | H | H | H | H | H | CO$_2$Et | H |
| II-871 | c-Pr | i-BuO | H | H | H | H | H | CO$_2$Et | H |
| II-872 | c-Pr | PhCH$_2$O | H | H | H | H | H | CO$_2$Et | H |
| II-873 | c-Pr | CH$_2$=CHCH$_2$O | H | H | H | H | H | CO$_2$Et | H |
| II-874 | c-Pr | HC≡CCH$_2$O | H | H | H | H | H | CO$_2$Et | H |
| II-875 | c-Pr | F$_3$CCH$_2$O | H | H | H | H | H | CO$_2$Et | H |
| II-876 | c-Pr | H$_3$COCH$_2$CH$_2$O | H | H | H | H | H | CO$_2$Et | H |
| II-877 | c-Pr | HO | H | H | H | H | H | CN | H |
| II-878 | c-Pr | MeO | H | H | H | H | H | CN | H |
| II-879 | c-Pr | EtO | H | H | H | H | H | CN | H |
| II-880 | c-Pr | n-PrO | H | H | H | H | H | CN | H |
| II-881 | c-Pr | i-PrO | H | H | H | H | H | CN | H |
| II-882 | c-Pr | n-BuO | H | H | H | H | H | CN | H |
| II-883 | c-Pr | i-BuO | H | H | H | H | H | CN | H |
| II-884 | c-Pr | PhCH$_2$O | H | H | H | H | H | CN | H |
| II-885 | c-Pr | CH$_2$=CHCH$_2$O | H | H | H | H | H | CN | H |
| II-886 | c-Pr | HC≡CCH$_2$O | H | H | H | H | H | CN | H |
| II-887 | c-Pr | F$_3$CCH$_2$O | H | H | H | H | H | CN | H |
| II-888 | c-Pr | H$_3$COCH$_2$CH$_2$O | H | H | H | H | H | CN | H |
| II-889 | c-Pr | HO | F | H | H | H | H | Me | H |
| II-890 | c-Pr | MeO | F | H | H | H | H | Me | H |
| II-891 | c-Pr | EtO | F | H | H | H | H | Me | H |
| II-892 | c-Pr | n-PrO | F | H | H | H | H | Me | H |
| II-893 | c-Pr | i-PrO | F | H | H | H | H | Me | H |
| II-894 | c-Pr | n-BuO | F | H | H | H | H | Me | H |
| II-895 | c-Pr | i-BuO | F | H | H | H | H | Me | H |
| II-896 | c-Pr | PhCH$_2$O | F | H | H | H | H | Me | H |
| II-897 | c-Pr | CH$_2$=CHCH$_2$O | F | H | H | H | H | Me | H |
| II-898 | c-Pr | HC≡CCH$_2$O | F | H | H | H | H | Me | H |
| II-899 | c-Pr | F$_3$CCH$_2$O | F | H | H | H | H | Me | H |
| II-900 | c-Pr | H$_3$COCH$_2$CH$_2$O | F | H | H | H | H | Me | H |
| II-901 | c-Pr | HO | F | H | H | H | H | Me | Me |
| II-902 | c-Pr | MeO | F | H | H | H | H | Me | Me |
| II-903 | c-Pr | EtO | F | H | H | H | H | Me | Me |
| II-904 | c-Pr | n-PrO | F | H | H | H | H | Me | Me |
| II-905 | c-Pr | i-PrO | F | H | H | H | H | Me | Me |
| II-906 | c-Pr | n-BuO | F | H | H | H | H | Me | Me |
| II-907 | c-Pr | i-BuO | F | H | H | H | H | Me | Me |
| II-908 | c-Pr | PhCH$_2$ | F | H | H | H | H | Me | Me |
| II-909 | c-Pr | CH$_2$=CHCH$_2$O | F | H | H | H | H | Me | Me |
| II-910 | c-Pr | HC≡CCH$_2$O | F | H | H | H | H | Me | Me |

TABLE 2-continued

Inventive compounds of the formula (I) in which X represents $C(R^{13})(R^{14})$

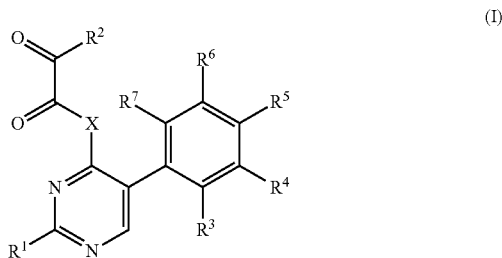

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-911 | c-Pr | F$_3$CCH$_2$O | F | H | H | H | H | Me | Me |
| II-912 | c-Pr | H$_3$COCH$_2$CH$_2$O | F | H | H | H | H | Me | Me |
| II-913 | c-Pr | HO | F | H | H | H | H | CO$_2$Et | H |
| II-914 | c-Pr | MeO | F | H | H | H | H | CO$_2$Et | H |
| II-915 | c-Pr | EtO | F | H | H | H | H | CO$_2$Et | H |
| II-916 | c-Pr | n-PrO | F | H | H | H | H | CO$_2$Et | H |
| II-917 | c-Pr | i-PrO | F | H | H | H | H | CO$_2$Et | H |
| II-918 | c-Pr | n-BuO | F | H | H | H | H | CO$_2$Et | H |
| II-919 | c-Pr | i-BuO | F | H | H | H | H | CO$_2$Et | H |
| II-920 | c-Pr | PhCH$_2$O | F | H | H | H | H | CO$_2$Et | H |
| II-921 | c-Pr | CH$_2$=CHCH$_2$O | F | H | H | H | H | CO$_2$Et | H |
| II-922 | c-Pr | HC≡CCH$_2$O | F | H | H | H | H | CO$_2$Et | H |
| II-923 | c-Pr | F$_3$CCH$_2$O | F | H | H | H | H | CO$_2$Et | H |
| II-924 | c-Pr | H$_3$COCH$_2$CH$_2$O | F | H | H | H | H | CO$_2$Et | H |
| II-925 | c-Pr | HO | F | H | H | H | H | CN | H |
| II-926 | c-Pr | MeO | F | H | H | H | H | CN | H |
| II-927 | c-Pr | EtO | F | H | H | H | H | CN | H |
| II-928 | c-Pr | n-PrO | F | H | H | H | H | CN | H |
| II-929 | c-Pr | i-PrO | F | H | H | H | H | CN | H |
| II-930 | c-Pr | n-BuO | F | H | H | H | H | CN | H |
| II-931 | c-Pr | i-BuO | F | H | H | H | H | CN | H |
| II-932 | c-Pr | PhCH$_2$O | F | H | H | H | H | CN | H |
| II-933 | c-Pr | CH$_2$=CHCH$_2$O | F | H | H | H | H | CN | H |
| II-934 | c-Pr | HC≡CCH$_2$O | F | H | H | H | H | CN | H |
| II-935 | c-Pr | F$_3$CCH$_2$O | F | H | H | H | H | CN | H |
| II-936 | c-Pr | H$_3$COCH$_2$CH$_2$O | F | H | H | H | H | CN | H |
| II-937 | c-Pr | HO | F | F | H | H | H | Me | H |
| II-938 | c-Pr | MeO | F | F | H | H | H | Me | H |
| II-939 | c-Pr | EtO | F | F | H | H | H | Me | H |
| II-940 | c-Pr | n-PrO | F | F | H | H | H | Me | H |
| II-941 | c-Pr | i-PrO | F | F | H | H | H | Me | H |
| II-942 | c-Pr | n-BuO | F | F | H | H | H | Me | H |
| II-943 | c-Pr | i-BuO | F | F | H | H | H | Me | H |
| II-944 | c-Pr | PhCH$_2$O | F | F | H | H | H | Me | H |
| II-945 | c-Pr | CH$_2$=CHCH$_2$O | F | F | H | H | H | Me | H |
| II-946 | c-Pr | HC≡CCH$_2$O | F | F | H | H | H | Me | H |
| II-947 | c-Pr | F$_3$CCH$_2$O | F | F | H | H | H | Me | H |
| II-948 | c-Pr | H$_3$COCH$_2$CH$_2$O | F | F | H | H | H | Me | H |
| II-949 | c-Pr | HO | F | F | H | H | H | Me | Me |
| II-950 | c-Pr | MeO | F | F | H | H | H | Me | Me |
| II-951 | c-Pr | EtO | F | F | H | H | H | Me | Me |
| II-952 | c-Pr | n-PrO | F | F | H | H | H | Me | Me |
| II-953 | c-Pr | i-PrO | F | F | H | H | H | Me | Me |
| II-954 | c-Pr | n-BuO | F | F | H | H | H | Me | Me |
| II-955 | c-Pr | i-BuO | F | F | H | H | H | Me | Me |
| II-956 | c-Pr | PhCH$_2$O | F | F | H | H | H | Me | Me |
| II-957 | c-Pr | CH$_2$=CHCH$_2$O | F | F | H | H | H | Me | Me |
| II-958 | c-Pr | HC≡CCH$_2$O | F | F | H | H | H | Me | Me |
| II-959 | c-Pr | F$_3$CCH$_2$O | F | F | H | H | H | Me | Me |
| II-960 | c-Pr | H$_3$COCH$_2$CH$_2$O | F | F | H | H | H | Me | Me |
| II-961 | c-Pr | HO | F | F | H | H | H | CO$_2$Et | H |
| II-962 | c-Pr | MeO | F | F | H | H | H | CO$_2$Et | H |
| II-963 | c-Pr | EtO | F | F | H | H | H | CO$_2$Et | H |
| II-964 | c-Pr | n-PrO | F | F | H | H | H | CO$_2$Et | H |
| II-965 | c-Pr | i-PrO | F | F | H | H | H | CO$_2$Et | H |
| II-966 | c-Pr | n-BuO | F | F | H | H | H | CO$_2$Et | H |
| II-967 | c-Pr | i-BuO | F | F | H | H | H | CO$_2$Et | H |
| II-968 | c-Pr | PhCH$_2$O | F | F | H | H | H | CO$_2$Et | H |
| II-969 | c-Pr | CH$_2$=CHCH$_2$O | F | F | H | H | H | CO$_2$Et | H |
| II-970 | c-Pr | HC≡CCH$_2$O | F | F | H | H | H | CO$_2$Et | H |
| II-971 | c-Pr | F$_3$CCH$_2$O | F | F | H | H | H | CO$_2$Et | H |
| II-972 | c-Pr | H$_3$COCH$_2$CH$_2$O | F | F | H | H | H | CO$_2$Et | H |
| II-973 | c-Pr | HO | F | F | H | H | H | CN | H |

TABLE 2-continued

Inventive compounds of the formula (I) in which X represents $C(R^{13})(R^{14})$ $$(I)$$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-974 | c-Pr | MeO | F | F | H | H | H | CN | H |
| II-975 | c-Pr | EtO | F | F | H | H | H | CN | H |
| II-976 | c-Pr | n-PrO | F | F | H | H | H | CN | H |
| II-977 | c-Pr | i-PrO | F | F | H | H | H | CN | H |
| II-978 | c-Pr | n-BuO | F | F | H | H | H | CN | H |
| II-979 | c-Pr | i-BuO | F | F | H | H | H | CN | H |
| II-980 | c-Pr | PhCH$_2$O | F | F | H | H | H | CN | H |
| II-981 | c-Pr | CH$_2$=CHCH$_2$O | F | F | H | H | H | CN | H |
| II-982 | c-Pr | HC≡CCH$_2$O | F | F | H | H | H | CN | H |
| II-983 | c-Pr | F$_3$CCH$_2$O | F | F | H | H | H | CN | H |
| II-984 | c-Pr | H$_3$COCH$_2$CH$_2$O | F | F | H | H | H | CN | H |
| II-985 | c-Pr | HO | F | H | F | H | H | Me | H |
| II-986 | c-Pr | MeO | F | H | F | H | H | Me | H |
| II-987 | c-Pr | EtO | F | H | F | H | H | Me | H |
| II-988 | c-Pr | n-PrO | F | H | F | H | H | Me | H |
| II-989 | c-Pr | i-PrO | F | H | F | H | H | Me | H |
| II-990 | c-Pr | n-BuO | F | H | F | H | H | Me | H |
| II-991 | c-Pr | i-BuO | F | H | F | H | H | Me | H |
| II-992 | c-Pr | PhCH$_2$O | F | H | F | H | H | Me | H |
| II-993 | c-Pr | CH$_2$=CHCH$_2$O | F | H | F | H | H | Me | H |
| II-994 | c-Pr | HC≡CCH$_2$O | F | H | F | H | H | Me | H |
| II-995 | c-Pr | F$_3$CCH$_2$O | F | H | F | H | H | Me | H |
| II-996 | c-Pr | H$_3$COCH$_2$CH$_2$O | F | H | F | H | H | Me | H |
| II-997 | c-Pr | HO | F | H | F | H | H | Me | Me |
| II-998 | c-Pr | MeO | F | H | F | H | H | Me | Me |
| II-999 | c-Pr | EtO | F | H | F | H | H | Me | Me |
| II-1000 | c-Pr | n-PrO | F | H | F | H | H | Me | Me |
| II-1001 | c-Pr | i-PrO | F | H | F | H | H | Me | Me |
| II-1002 | c-Pr | n-BuO | F | H | F | H | H | Me | Me |
| II-1003 | c-Pr | i-BuO | F | H | F | H | H | Me | Me |
| II-1004 | c-Pr | PhCH$_2$O | F | H | F | H | H | Me | Me |
| II-1005 | c-Pr | CH$_2$=CHCH$_2$O | F | H | F | H | H | Me | Me |
| II-1006 | c-Pr | HC≡CCH$_2$O | F | H | F | H | H | Me | Me |
| II-1007 | c-Pr | F$_3$CCH$_2$O | F | H | F | H | H | Me | Me |
| II-1008 | c-Pr | H$_3$COCH$_2$CH$_2$O | F | H | F | H | H | Me | Me |
| II-1009 | c-Pr | HO | F | H | F | H | H | CO$_2$Et | H |
| II-1010 | c-Pr | MeO | F | H | F | H | H | CO$_2$Et | H |
| II-1011 | c-Pr | EtO | F | H | F | H | H | CO$_2$Et | H |
| II-1012 | c-Pr | n-PrO | F | H | F | H | H | CO$_2$Et | H |
| II-1013 | c-Pr | i-PrO | F | H | F | H | H | CO$_2$Et | H |
| II-1014 | c-Pr | n-BuO | F | H | F | H | H | CO$_2$Et | H |
| II-1015 | c-Pr | i-BuO | F | H | F | H | H | CO$_2$Et | H |
| II-1016 | c-Pr | PhCH$_2$O | F | H | F | H | H | CO$_2$Et | H |
| II-1017 | c-Pr | CH$_2$=CHCH$_2$O | F | H | F | H | H | CO$_2$Et | H |
| II-1018 | c-Pr | HC≡CCH$_2$O | F | H | F | H | H | CO$_2$Et | H |
| II-1019 | c-Pr | F$_3$CCH$_2$O | F | H | F | H | H | CO$_2$Et | H |
| II-1020 | c-Pr | H$_3$COCH$_2$CH$_2$O | F | H | F | H | H | CO$_2$Et | H |
| II-1021 | c-Pr | HO | F | H | F | H | H | CN | H |
| II-1022 | c-Pr | MeO | F | H | F | H | H | CN | H |
| II-1023 | c-Pr | EtO | F | H | F | H | H | CN | H |
| II-1024 | c-Pr | n-PrO | F | H | F | H | H | CN | H |
| II-1025 | c-Pr | i-PrO | F | H | F | H | H | CN | H |
| II-1026 | c-Pr | n-BuO | F | H | F | H | H | CN | H |
| II-1027 | c-Pr | i-BuO | F | H | F | H | H | CN | H |
| II-1028 | c-Pr | PhCH$_2$O | F | H | F | H | H | CN | H |
| II-1029 | c-Pr | CH$_2$=CHCH$_2$O | F | H | F | H | H | CN | H |
| II-1030 | c-Pr | HC≡CCH$_2$O | F | H | F | H | H | CN | H |
| II-1031 | c-Pr | F$_3$CCH$_2$O | F | H | F | H | H | CN | H |
| II-1032 | c-Pr | H$_3$COCH$_2$CH$_2$O | F | H | F | H | H | CN | H |
| II-1033 | c-Pr | HO | F | H | H | F | H | Me | H |
| II-1034 | c-Pr | MeO | F | H | H | F | H | Me | H |
| II-1035 | c-Pr | EtO | F | H | H | F | H | Me | H |
| II-1036 | c-Pr | n-PrO | F | H | H | F | H | Me | H |

TABLE 2-continued

Inventive compounds of the formula (I) in which X represents $C(R^{13})(R^{14})$

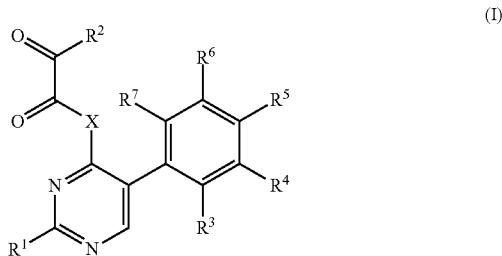

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1037 | c-Pr | i-PrO | F | H | H | F | H | Me | H |
| II-1038 | c-Pr | n-BuO | F | H | H | F | H | Me | H |
| II-1039 | c-Pr | i-BuO | F | H | H | F | H | Me | H |
| II-1040 | c-Pr | PhCH$_2$O | F | H | H | F | H | Me | H |
| II-1041 | c-Pr | CH$_2$=CHCH$_2$O | F | H | H | F | H | Me | H |
| II-1042 | c-Pr | HC≡CCH$_2$O | F | H | H | F | H | Me | H |
| II-1043 | c-Pr | F$_3$CCH$_2$O | F | H | H | F | H | Me | H |
| II-1044 | c-Pr | H$_3$COCH$_2$CH$_2$O | F | H | H | F | H | Me | H |
| II-1045 | c-Pr | HO | F | H | H | F | H | Me | Me |
| II-1046 | c-Pr | MeO | F | H | H | F | H | Me | Me |
| II-1047 | c-Pr | EtO | F | H | H | F | H | Me | Me |
| II-1048 | c-Pr | n-PrO | F | H | H | F | H | Me | Me |
| II-1049 | c-Pr | i-PrO | F | H | H | F | H | Me | Me |
| II-1050 | c-Pr | n-BuO | F | H | H | F | H | Me | Me |
| II-1051 | c-Pr | i-BuO | F | H | H | F | H | Me | Me |
| II-1052 | c-Pr | PhCH$_2$O | F | H | H | F | H | Me | Me |
| II-1053 | c-Pr | CH$_2$=CHCH$_2$O | F | H | H | F | H | Me | Me |
| II-1054 | c-Pr | HC≡CCH$_2$O | F | H | H | F | H | Me | Me |
| II-1055 | c-Pr | F$_3$CCH$_2$O | F | H | H | F | H | Me | Me |
| II-1056 | c-Pr | H$_3$COCH$_2$CH$_2$O | F | H | H | F | H | Me | Me |
| II-1057 | c-Pr | HO | F | H | H | F | H | CO$_2$Et | H |
| II-1058 | c-Pr | MeO | F | H | H | F | H | CO$_2$Et | H |
| II-1059 | c-Pr | EtO | F | H | H | F | H | CO$_2$Et | H |
| II-1060 | c-Pr | n-PrO | F | H | H | F | H | CO$_2$Et | H |
| II-1061 | c-Pr | i-PrO | F | H | H | F | H | CO$_2$Et | H |
| II-1062 | c-Pr | n-BuO | F | H | H | F | H | CO$_2$Et | H |
| II-1063 | c-Pr | i-BuO | F | H | H | F | H | CO$_2$Et | H |
| II-1064 | c-Pr | PhCH$_2$O | F | H | H | F | H | CO$_2$Et | H |
| II-1065 | c-Pr | CH$_2$=CHCH$_2$O | F | H | H | F | H | CO$_2$Et | H |
| II-1066 | c-Pr | HC≡CCH$_2$O | F | H | H | F | H | CO$_2$Et | H |
| II-1067 | c-Pr | F$_3$CCH$_2$O | F | H | H | F | H | CO$_2$Et | H |
| II-1068 | c-Pr | H$_3$COCH$_2$CH$_2$O | F | H | H | F | H | CO$_2$Et | H |
| II-1069 | c-Pr | HO | F | H | H | F | H | CN | H |
| II-1070 | c-Pr | MeO | F | H | H | F | H | CN | H |
| II-1071 | c-Pr | EtO | F | H | H | F | H | CN | H |
| II-1072 | c-Pr | n-PrO | F | H | H | F | H | CN | H |
| II-1073 | c-Pr | i-PrO | F | H | H | F | H | CN | H |
| II-1074 | c-Pr | n-BuO | F | H | H | F | H | CN | H |
| II-1075 | c-Pr | i-BuO | F | H | H | F | H | CN | H |
| II-1076 | c-Pr | PhCH$_2$O | F | H | H | F | H | CN | H |
| II-1077 | c-Pr | CH$_2$=CHCH$_2$O | F | H | H | F | H | CN | H |
| II-1078 | c-Pr | HC≡CCH$_2$O | F | H | H | F | H | CN | H |
| II-1079 | c-Pr | F$_3$CCH$_2$O | F | H | H | F | H | CN | H |
| II-1080 | c-Pr | H$_3$COCH$_2$CH$_2$O | F | H | H | F | H | CN | H |
| II-1081 | c-Pr | HO | F | H | H | H | F | Me | H |
| II-1082 | c-Pr | MeO | F | H | H | H | F | Me | H |
| II-1083 | c-Pr | EtO | F | H | H | H | F | Me | H |
| II-1084 | c-Pr | n-PrO | F | H | H | H | F | Me | H |
| II-1085 | c-Pr | i-PrO | F | H | H | H | F | Me | H |
| II-1086 | c-Pr | n-BuO | F | H | H | H | F | Me | H |
| II-1087 | c-Pr | i-BuO | F | H | H | H | F | Me | H |
| II-1088 | c-Pr | PhCH$_2$O | F | H | H | H | F | Me | H |
| II-1089 | c-Pr | CH$_2$=CHCH$_2$O | F | H | H | H | F | Me | H |
| II-1090 | c-Pr | HC≡CCH$_2$O | F | H | H | H | F | Me | H |
| II-1091 | c-Pr | F$_3$CCH$_2$O | F | H | H | H | F | Me | H |
| II-1092 | c-Pr | H$_3$COCH$_2$CH$_2$O | F | H | H | H | F | Me | H |
| II-1093 | c-Pr | HO | F | H | H | H | F | Me | Me |
| II-1094 | c-Pr | MeO | F | H | H | H | F | Me | Me |
| II-1095 | c-Pr | EtO | F | H | H | H | F | Me | Me |
| II-1096 | c-Pr | n-PrO | F | H | H | H | F | Me | Me |
| II-1097 | c-Pr | i-PrO | F | H | H | H | F | Me | Me |
| II-1098 | c-Pr | n-BuO | F | H | H | H | F | Me | Me |
| II-1099 | c-Pr | i-BuO | F | H | H | H | F | Me | Me |

TABLE 2-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
| --- | --- | --- | --- | --- | --- | --- | --- | --- | --- |
| II-1100 | c-Pr | PhCH$_2$O | F | H | H | H | F | Me | Me |
| II-1101 | c-Pr | CH$_2$=CHCH$_2$O | F | H | H | H | F | Me | Me |
| II-1102 | c-Pr | HC≡CCH$_2$O | F | H | H | H | F | Me | Me |
| II-1103 | c-Pr | F$_3$CCH$_2$O | F | H | H | H | F | Me | Me |
| II-1104 | c-Pr | H$_3$COCH$_2$CH$_2$O | F | H | H | H | F | Me | Me |
| II-1105 | c-Pr | HO | F | H | H | H | F | CO$_2$Et | H |
| II-1106 | c-Pr | MeO | F | H | H | H | F | CO$_2$Et | H |
| II-1107 | c-Pr | EtO | F | H | H | H | F | CO$_2$Et | H |
| II-1108 | c-Pr | n-PrO | F | H | H | H | F | CO$_2$Et | H |
| II-1109 | c-Pr | i-PrO | F | H | H | H | F | CO$_2$Et | H |
| II-1110 | c-Pr | n-BuO | F | H | H | H | F | CO$_2$Et | H |
| II-1111 | c-Pr | i-BuO | F | H | H | H | F | CO$_2$Et | H |
| II-1112 | c-Pr | PhCH$_2$O | F | H | H | H | F | CO$_2$Et | H |
| II-1113 | c-Pr | CH$_2$=CHCH$_2$O | F | H | H | H | F | CO$_2$Et | H |
| II-1114 | c-Pr | HC≡CCH$_2$O | F | H | H | H | F | CO$_2$Et | H |
| II-1115 | c-Pr | F$_3$CCH$_2$O | F | H | H | H | F | CO$_2$Et | H |
| II-1116 | c-Pr | H$_3$COCH$_2$CH$_2$O | F | H | H | H | F | CO$_2$Et | H |
| II-1117 | c-Pr | HO | F | H | H | H | F | CN | H |
| II-1118 | c-Pr | MeO | F | H | H | H | F | CN | H |
| II-1119 | c-Pr | EtO | F | H | H | H | F | CN | H |
| II-1120 | c-Pr | n-PrO | F | H | H | H | F | CN | H |
| II-1121 | c-Pr | i-PrO | F | H | H | H | F | CN | H |
| II-1122 | c-Pr | n-BuO | F | H | H | H | F | CN | H |
| II-1123 | c-Pr | i-BuO | F | H | H | H | F | CN | H |
| II-1124 | c-Pr | PhCH$_2$O | F | H | H | H | F | CN | H |
| II-1125 | c-Pr | CH$_2$=CHCH$_2$O | F | H | H | H | F | CN | H |
| II-1126 | c-Pr | HC≡CCH$_2$O | F | H | H | H | F | CN | H |
| II-1127 | c-Pr | F$_3$CCH$_2$O | F | H | H | H | F | CN | H |
| II-1128 | c-Pr | H$_3$COCH$_2$CH$_2$O | F | H | H | H | F | CN | H |
| II-1129 | c-Pr | HO | Cl | F | H | H | H | Me | H |
| II-1130 | c-Pr | MeO | Cl | F | H | H | H | Me | H |
| II-1131 | c-Pr | EtO | Cl | F | H | H | H | Me | H |
| II-1132 | c-Pr | n-PrO | Cl | F | H | H | H | Me | H |
| II-1133 | c-Pr | i-PrO | Cl | F | H | H | H | Me | H |
| II-1134 | c-Pr | n-BuO | Cl | F | H | H | H | Me | H |
| II-1135 | c-Pr | i-BuO | Cl | F | H | H | H | Me | H |
| II-1136 | c-Pr | PhCH$_2$O | Cl | F | H | H | H | Me | H |
| II-1137 | c-Pr | CH$_2$=CHCH$_2$O | Cl | F | H | H | H | Me | H |
| II-1138 | c-Pr | HC≡CCH$_2$O | Cl | F | H | H | H | Me | H |
| II-1139 | c-Pr | F$_3$CCH$_2$O | Cl | F | H | H | H | Me | H |
| II-1140 | c-Pr | H$_3$COCH$_2$CH$_2$O | Cl | F | H | H | H | Me | H |
| II-1141 | c-Pr | HO | Cl | F | H | H | H | Me | Me |
| II-1142 | c-Pr | MeO | Cl | F | H | H | H | Me | Me |
| II-1143 | c-Pr | EtO | Cl | F | H | H | H | Me | Me |
| II-1144 | c-Pr | n-PrO | Cl | F | H | H | H | Me | Me |
| II-1145 | c-Pr | i-PrO | Cl | F | H | H | H | Me | Me |
| II-1146 | c-Pr | n-BuO | Cl | F | H | H | H | Me | Me |
| II-1147 | c-Pr | i-BuO | Cl | F | H | H | H | Me | Me |
| II-1148 | c-Pr | PhCH$_2$O | Cl | F | H | H | H | Me | Me |
| II-1149 | c-Pr | CH$_2$=CHCH$_2$O | Cl | F | H | H | H | Me | Me |
| II-1150 | c-Pr | HC≡CCH$_2$O | Cl | F | H | H | H | Me | Me |
| II-1151 | c-Pr | F$_3$CCH$_2$O | Cl | F | H | H | H | Me | Me |
| II-1152 | c-Pr | H$_3$COCH$_2$CH$_2$O | Cl | F | H | H | H | Me | Me |
| II-1153 | c-Pr | HO | Cl | F | H | H | H | CO$_2$Et | H |
| II-1154 | c-Pr | MeO | Cl | F | H | H | H | CO$_2$Et | H |
| II-1155 | c-Pr | EtO | Cl | F | H | H | H | CO$_2$Et | H |
| II-1156 | c-Pr | n-PrO | Cl | F | H | H | H | CO$_2$Et | H |
| II-1157 | c-Pr | i-PrO | Cl | F | H | H | H | CO$_2$Et | H |
| II-1158 | c-Pr | n-BuO | Cl | F | H | H | H | CO$_2$Et | H |
| II-1159 | c-Pr | i-BuO | Cl | F | H | H | H | CO$_2$Et | H |
| II-1160 | c-Pr | PhCH$_2$O | Cl | F | H | H | H | CO$_2$Et | H |
| II-1161 | c-Pr | CH$_2$=CHCH$_2$O | Cl | F | H | H | H | CO$_2$Et | H |
| II-1162 | c-Pr | HC≡CCH$_2$O | Cl | F | H | H | H | CO$_2$Et | H |

TABLE 2-continued

Inventive compounds of the formula (I) in which X represents $C(R^{13})(R^{14})$

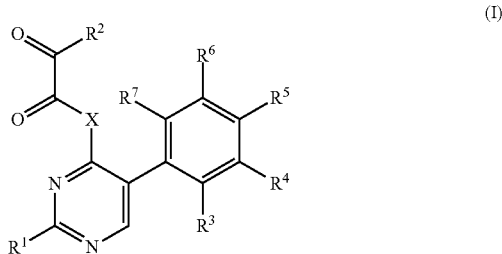

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1163 | c-Pr | $F_3CCH_2O$ | Cl | F | H | H | H | $CO_2Et$ | H |
| II-1164 | c-Pr | $H_3COCH_2CH_2O$ | Cl | F | H | H | H | $CO_2Et$ | H |
| II-1165 | c-Pr | HO | Cl | F | H | H | H | CN | H |
| II-1166 | c-Pr | MeO | Cl | F | H | H | H | CN | H |
| II-1167 | c-Pr | EtO | Cl | F | H | H | H | CN | H |
| II-1168 | c-Pr | n-PrO | Cl | F | H | H | H | CN | H |
| II-1169 | c-Pr | i-PrO | Cl | F | H | H | H | CN | H |
| II-1170 | c-Pr | n-BuO | Cl | F | H | H | H | CN | H |
| II-1171 | c-Pr | i-BuO | Cl | F | H | H | H | CN | H |
| II-1172 | c-Pr | $PhCH_2O$ | Cl | F | H | H | H | CN | H |
| II-1173 | c-Pr | $CH_2\!=\!CHCH_2O$ | Cl | F | H | H | H | CN | H |
| II-1174 | c-Pr | $HC\!\equiv\!CCH_2O$ | Cl | F | H | H | H | CN | H |
| II-1175 | c-Pr | $F_3CCH_2O$ | Cl | F | H | H | H | CN | H |
| II-1176 | c-Pr | $H_3COCH_2CH_2O$ | Cl | F | H | H | H | CN | H |
| II-1177 | c-Pr | HO | Cl | H | F | H | H | Me | H |
| II-1178 | c-Pr | MeO | Cl | H | F | H | H | Me | H |
| II-1179 | c-Pr | EtO | Cl | H | F | H | H | Me | H |
| II-1180 | c-Pr | n-PrO | Cl | H | F | H | H | Me | H |
| II-1181 | c-Pr | i-PrO | Cl | H | F | H | H | Me | H |
| II-1182 | c-Pr | n-BuO | Cl | H | F | H | H | Me | H |
| II-1183 | c-Pr | i-BuO | Cl | H | F | H | H | Me | H |
| II-1184 | c-Pr | $PhCH_2O$ | Cl | H | F | H | H | Me | H |
| II-1185 | c-Pr | $CH_2\!=\!CHCH_2O$ | Cl | H | F | H | H | Me | H |
| II-1186 | c-Pr | $HC\!\equiv\!CCH_2O$ | Cl | H | F | H | H | Me | H |
| II-1187 | c-Pr | $F_3CCH_2O$ | Cl | H | F | H | H | Me | H |
| II-1188 | c-Pr | $H_3COCH_2CH_2O$ | Cl | H | F | H | H | Me | H |
| II-1189 | c-Pr | HO | Cl | H | F | H | H | Me | Me |
| II-1190 | c-Pr | MeO | Cl | H | F | H | H | Me | Me |
| II-1191 | c-Pr | EtO | Cl | H | F | H | H | Me | Me |
| II-1192 | c-Pr | n-PrO | Cl | H | F | H | H | Me | Me |
| II-1193 | c-Pr | i-PrO | Cl | H | F | H | H | Me | Me |
| II-1194 | c-Pr | n-BuO | Cl | H | F | H | H | Me | Me |
| II-1195 | c-Pr | i-BuO | Cl | H | F | H | H | Me | Me |
| II-1196 | c-Pr | $PhCH_2O$ | Cl | H | F | H | H | Me | Me |
| II-1197 | c-Pr | $CH_2\!=\!CHCH_2O$ | Cl | H | F | H | H | Me | Me |
| II-1198 | c-Pr | $HC\!\equiv\!CCH_2O$ | Cl | H | F | H | H | Me | Me |
| II-1199 | c-Pr | $F_3CCH_2O$ | Cl | H | F | H | H | Me | Me |
| II-1200 | c-Pr | $H_3COCH_2CH_2O$ | Cl | H | F | H | H | Me | Me |
| II-1201 | c-Pr | HO | Cl | H | F | H | H | $CO_2Et$ | H |
| II-1202 | c-Pr | MeO | Cl | H | F | H | H | $CO_2Et$ | H |
| II-1203 | c-Pr | EtO | Cl | H | F | H | H | $CO_2Et$ | H |
| II-1204 | c-Pr | n-PrO | Cl | H | F | H | H | $CO_2Et$ | H |
| II-1205 | c-Pr | i-PrO | Cl | H | F | H | H | $CO_2Et$ | H |
| II-1206 | c-Pr | n-BuO | Cl | H | F | H | H | $CO_2Et$ | H |
| II-1207 | c-Pr | i-BuO | Cl | H | F | H | H | $CO_2Et$ | H |
| II-1208 | c-Pr | $PhCH_2O$ | Cl | H | F | H | H | $CO_2Et$ | H |
| II-1209 | c-Pr | $CH_2\!=\!CHCH_2O$ | Cl | H | F | H | H | $CO_2Et$ | H |
| II-1210 | c-Pr | $HC\!\equiv\!CCH_2O$ | Cl | H | F | H | H | $CO_2Et$ | H |
| II-1211 | c-Pr | $F_3CCH_2O$ | Cl | H | F | H | H | $CO_2Et$ | H |
| II-1212 | c-Pr | $H_3COCH_2CH_2O$ | Cl | H | F | H | H | $CO_2Et$ | H |
| II-1213 | c-Pr | HO | Cl | H | F | H | H | CN | H |
| II-1214 | c-Pr | MeO | Cl | H | F | H | H | CN | H |
| II-1215 | c-Pr | EtO | Cl | H | F | H | H | CN | H |
| II-1216 | c-Pr | n-PrO | Cl | H | F | H | H | CN | H |
| II-1217 | c-Pr | i-PrO | Cl | H | F | H | H | CN | H |
| II-1218 | c-Pr | n-BuO | Cl | H | F | H | H | CN | H |
| II-1219 | c-Pr | i-BuO | Cl | H | F | H | H | CN | H |
| II-1220 | c-Pr | $PhCH_2O$ | Cl | H | F | H | H | CN | H |
| II-1221 | c-Pr | $CH_2\!=\!CHCH_2O$ | Cl | H | F | H | H | CN | H |
| II-1222 | c-Pr | $HC\!\equiv\!CCH_2O$ | Cl | H | F | H | H | CN | H |
| II-1223 | c-Pr | $F_3CCH_2O$ | Cl | H | F | H | H | CN | H |
| II-1224 | c-Pr | $H_3COCH_2CH_2O$ | Cl | H | F | H | H | CN | H |
| II-1225 | c-Pr | HO | Cl | H | H | F | H | Me | H |

TABLE 2-continued

Inventive compounds of the formula (I) in which X represents $C(R^{13})(R^{14})$

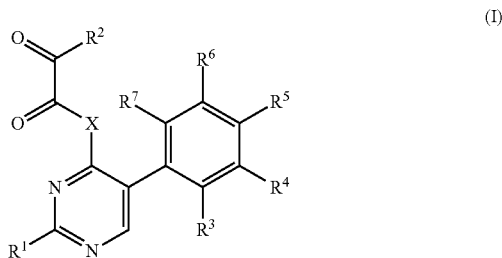

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1226 | c-Pr | MeO | Cl | H | H | F | H | Me | H |
| II-1227 | c-Pr | EtO | Cl | H | H | F | H | Me | H |
| II-1228 | c-Pr | n-PrO | Cl | H | H | F | H | Me | H |
| II-1229 | c-Pr | i-PrO | Cl | H | H | F | H | Me | H |
| II-1230 | c-Pr | n-BuO | Cl | H | H | F | H | Me | H |
| II-1231 | c-Pr | i-BuO | Cl | H | H | F | H | Me | H |
| II-1232 | c-Pr | PhCH$_2$O | Cl | H | H | F | H | Me | H |
| II-1233 | c-Pr | CH$_2$=CHCH$_2$O | Cl | H | H | F | H | Me | H |
| II-1234 | c-Pr | HC≡CCH$_2$O | Cl | H | H | F | H | Me | H |
| II-1235 | c-Pr | F$_3$CCH$_2$O | Cl | H | H | F | H | Me | H |
| II-1236 | c-Pr | H$_3$COCH$_2$CH$_2$O | Cl | H | H | F | H | Me | H |
| II-1237 | c-Pr | HO | Cl | H | H | F | H | Me | Me |
| II-1238 | c-Pr | MeO | Cl | H | H | F | H | Me | Me |
| II-1239 | c-Pr | EtO | Cl | H | H | F | H | Me | Me |
| II-1240 | c-Pr | n-PrO | Cl | H | H | F | H | Me | Me |
| II-1241 | c-Pr | i-PrO | Cl | H | H | F | H | Me | Me |
| II-1242 | c-Pr | n-BuO | Cl | H | H | F | H | Me | Me |
| II-1243 | c-Pr | i-BuO | Cl | H | H | F | H | Me | Me |
| II-1244 | c-Pr | PhCH$_2$O | Cl | H | H | F | H | Me | Me |
| II-1245 | c-Pr | CH$_2$=CHCH$_2$O | Cl | H | H | F | H | Me | Me |
| II-1246 | c-Pr | HC≡CCH$_2$O | Cl | H | H | F | H | Me | Me |
| II-1247 | c-Pr | F$_3$CCH$_2$O | Cl | H | H | F | H | Me | Me |
| II-1248 | c-Pr | H$_3$COCH$_2$CH$_2$O | Cl | H | H | F | H | Me | Me |
| II-1249 | c-Pr | HO | Cl | H | H | F | H | CO$_2$Et | H |
| II-1250 | c-Pr | MeO | Cl | H | H | F | H | CO$_2$Et | H |
| II-1251 | c-Pr | EtO | Cl | H | H | F | H | CO$_2$Et | H |
| II-1252 | c-Pr | n-PrO | Cl | H | H | F | H | CO$_2$Et | H |
| II-1253 | c-Pr | i-PrO | Cl | H | H | F | H | CO$_2$Et | H |
| II-1254 | c-Pr | n-BuO | Cl | H | H | F | H | CO$_2$Et | H |
| II-1255 | c-Pr | i-BuO | Cl | H | H | F | H | CO$_2$Et | H |
| II-1256 | c-Pr | PhCH$_2$O | Cl | H | H | F | H | CO$_2$Et | H |
| II-1257 | c-Pr | CH$_2$=CHCH$_2$O | Cl | H | H | F | H | CO$_2$Et | H |
| II-1258 | c-Pr | HC≡CCH$_2$O | Cl | H | H | F | H | CO$_2$Et | H |
| II-1259 | c-Pr | F$_3$CCH$_2$O | Cl | H | H | F | H | CO$_2$Et | H |
| II-1260 | c-Pr | H$_3$COCH$_2$CH$_2$O | Cl | H | H | F | H | CO$_2$Et | H |
| II-1261 | c-Pr | HO | Cl | H | H | F | H | CN | H |
| II-1262 | c-Pr | MeO | Cl | H | H | F | H | CN | H |
| II-1263 | c-Pr | EtO | Cl | H | H | F | H | CN | H |
| II-1264 | c-Pr | n-PrO | Cl | H | H | F | H | CN | H |
| II-1265 | c-Pr | i-PrO | Cl | H | H | F | H | CN | H |
| II-1266 | c-Pr | n-BuO | Cl | H | H | F | H | CN | H |
| II-1267 | c-Pr | i-BuO | Cl | H | H | F | H | CN | H |
| II-1268 | c-Pr | PhCH$_2$O | Cl | H | H | F | H | CN | H |
| II-1269 | c-Pr | CH$_2$=CHCH$_2$O | Cl | H | H | F | H | CN | H |
| II-1270 | c-Pr | HC≡CCH$_2$O | Cl | H | H | F | H | CN | H |
| II-1271 | c-Pr | F$_3$CCH$_2$O | Cl | H | H | F | H | CN | H |
| II-1272 | c-Pr | H$_3$COCH$_2$CH$_2$O | Cl | H | H | F | H | CN | H |
| II-1273 | c-Pr | HO | Cl | H | H | H | F | Me | H |
| II-1274 | c-Pr | MeO | Cl | H | H | H | F | Me | H |
| II-1275 | c-Pr | EtO | Cl | H | H | H | F | Me | H |
| II-1276 | c-Pr | n-PrO | Cl | H | H | H | F | Me | H |
| II-1277 | c-Pr | i-PrO | Cl | H | H | H | F | Me | H |
| II-1278 | c-Pr | n-BuO | Cl | H | H | H | F | Me | H |
| II-1279 | c-Pr | i-BuO | Cl | H | H | H | F | Me | H |
| II-1280 | c-Pr | PhCH$_2$O | Cl | H | H | H | F | Me | H |
| II-1281 | c-Pr | CH$_2$=CHCH$_2$O | Cl | H | H | H | F | Me | H |
| II-1282 | c-Pr | HC≡CCH$_2$O | Cl | H | H | H | F | Me | H |
| II-1283 | c-Pr | F$_3$CCH$_2$O | Cl | H | H | H | F | Me | H |
| II-1284 | c-Pr | H$_3$COCH$_2$CH$_2$O | Cl | H | H | H | F | Me | H |
| II-1285 | c-Pr | HO | Cl | H | H | H | F | Me | Me |
| II-1286 | c-Pr | MeO | Cl | H | H | H | F | Me | Me |
| II-1287 | c-Pr | EtO | Cl | H | H | H | F | Me | Me |
| II-1288 | c-Pr | n-PrO | Cl | H | H | H | F | Me | Me |

TABLE 2-continued

Inventive compounds of the formula (I) in which X represents $C(R^{13})(R^{14})$

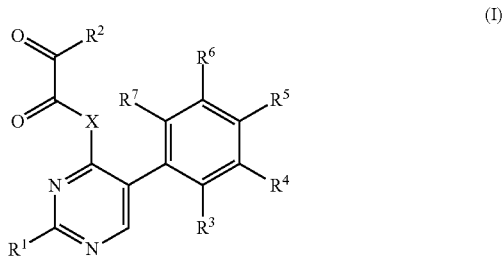

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1289 | c-Pr | i-PrO | Cl | H | H | H | F | Me | Me |
| II-1290 | c-Pr | n-BuO | Cl | H | H | H | F | Me | Me |
| II-1291 | c-Pr | i-BuO | Cl | H | H | H | F | Me | Me |
| II-1292 | c-Pr | PhCH$_2$O | Cl | H | H | H | F | Me | Me |
| II-1293 | c-Pr | CH$_2$=CHCH$_2$O | Cl | H | H | H | F | Me | Me |
| II-1294 | c-Pr | HC≡CCH$_2$O | Cl | H | H | H | F | Me | Me |
| II-1295 | c-Pr | F$_3$CCH$_2$O | Cl | H | H | H | F | Me | Me |
| II-1296 | c-Pr | H$_3$COCH$_2$CH$_2$O | Cl | H | H | H | F | Me | Me |
| II-1297 | c-Pr | HO | Cl | H | H | H | F | CO$_2$Et | H |
| II-1298 | c-Pr | MeO | Cl | H | H | H | F | CO$_2$Et | H |
| II-1299 | c-Pr | EtO | Cl | H | H | H | F | CO$_2$Et | H |
| II-1300 | c-Pr | n-PrO | Cl | H | H | H | F | CO$_2$Et | H |
| II-1301 | c-Pr | i-PrO | Cl | H | H | H | F | CO$_2$Et | H |
| II-1302 | c-Pr | n-BuO | Cl | H | H | H | F | CO$_2$Et | H |
| II-1303 | c-Pr | i-BuO | Cl | H | H | H | F | CO$_2$Et | H |
| II-1304 | c-Pr | PhCH$_2$O | Cl | H | H | H | F | CO$_2$Et | H |
| II-1305 | c-Pr | CH$_2$=CHCH$_2$O | Cl | H | H | H | F | CO$_2$Et | H |
| II-1306 | c-Pr | HC≡CCH$_2$O | Cl | H | H | H | F | CO$_2$Et | H |
| II-1307 | c-Pr | F$_3$CCH$_2$O | Cl | H | H | H | F | CO$_2$Et | H |
| II-1308 | c-Pr | H$_3$COCH$_2$CH$_2$O | Cl | H | H | H | F | CO$_2$Et | H |
| II-1309 | c-Pr | HO | Cl | H | H | H | F | CN | H |
| II-1310 | c-Pr | MeO | Cl | H | H | H | F | CN | H |
| II-1311 | c-Pr | EtO | Cl | H | H | H | F | CN | H |
| II-1312 | c-Pr | n-PrO | Cl | H | H | H | F | CN | H |
| II-1313 | c-Pr | i-PrO | Cl | H | H | H | F | CN | H |
| II-1314 | c-Pr | n-BuO | Cl | H | H | H | F | CN | H |
| II-1315 | c-Pr | i-BuO | Cl | H | H | H | F | CN | H |
| II-1316 | c-Pr | PhCH$_2$O | Cl | H | H | H | F | CN | H |
| II-1317 | c-Pr | CH$_2$=CHCH$_2$O | Cl | H | H | H | F | CN | H |
| II-1318 | c-Pr | HC≡CCH$_2$O | Cl | H | H | H | F | CN | H |
| II-1319 | c-Pr | F$_3$CCH$_2$O | Cl | H | H | H | F | CN | H |
| II-1320 | c-Pr | H$_3$COCH$_2$CH$_2$O | Cl | H | H | H | F | CN | H |
| II-1321 | c-Pr | HO | Cl | Cl | H | H | H | Me | H |
| II-1322 | c-Pr | MeO | Cl | Cl | H | H | H | Me | H |
| II-1323 | c-Pr | EtO | Cl | Cl | H | H | H | Me | H |
| II-1324 | c-Pr | n-PrO | Cl | Cl | H | H | H | Me | H |
| II-1325 | c-Pr | i-PrO | Cl | Cl | H | H | H | Me | H |
| II-1326 | c-Pr | n-BuO | Cl | Cl | H | H | H | Me | H |
| II-1327 | c-Pr | i-BuO | Cl | Cl | H | H | H | Me | H |
| II-1328 | c-Pr | PhCH$_2$O | Cl | Cl | H | H | H | Me | H |
| II-1329 | c-Pr | CH$_2$=CHCH$_2$O | Cl | Cl | H | H | H | Me | H |
| II-1330 | c-Pr | HC≡CCH$_2$O | Cl | Cl | H | H | H | Me | H |
| II-1331 | c-Pr | F$_3$CCH$_2$O | Cl | Cl | H | H | H | Me | H |
| II-1332 | c-Pr | H$_3$COCH$_2$CH$_2$O | Cl | Cl | H | H | H | Me | H |
| II-1333 | c-Pr | HO | Cl | Cl | H | H | H | Me | Me |
| II-1334 | c-Pr | MeO | Cl | Cl | H | H | H | Me | Me |
| II-1335 | c-Pr | EtO | Cl | Cl | H | H | H | Me | Me |
| II-1336 | c-Pr | n-PrO | Cl | Cl | H | H | H | Me | Me |
| II-1337 | c-Pr | i-PrO | Cl | Cl | H | H | H | Me | Me |
| II-1338 | c-Pr | n-BuO | Cl | Cl | H | H | H | Me | Me |
| II-1339 | c-Pr | i-BuO | Cl | Cl | H | H | H | Me | Me |
| II-1340 | c-Pr | PhCH$_2$O | Cl | Cl | H | H | H | Me | Me |
| II-1341 | c-Pr | CH$_2$=CHCH$_2$O | Cl | Cl | H | H | H | Me | Me |
| II-1342 | c-Pr | HC≡CCH$_2$O | Cl | Cl | H | H | H | Me | Me |
| II-1343 | c-Pr | F$_3$CCH$_2$O | Cl | Cl | H | H | H | Me | Me |
| II-1344 | c-Pr | H$_3$COCH$_2$CH$_2$O | Cl | Cl | H | H | H | Me | Me |
| II-1345 | c-Pr | HO | Cl | Cl | H | H | H | CO$_2$Et | H |
| II-1346 | c-Pr | MeO | Cl | Cl | H | H | H | CO$_2$Et | H |
| II-1347 | c-Pr | EtO | Cl | Cl | H | H | H | CO$_2$Et | H |
| II-1348 | c-Pr | n-PrO | Cl | Cl | H | H | H | CO$_2$Et | H |
| II-1349 | c-Pr | i-PrO | Cl | Cl | H | H | H | CO$_2$Et | H |
| II-1350 | c-Pr | n-BuO | Cl | Cl | H | H | H | CO$_2$Et | H |
| II-1351 | c-Pr | i-BuO | Cl | Cl | H | H | H | CO$_2$Et | H |

TABLE 2-continued

Inventive compounds of the formula (I) in which X represents $C(R^{13})(R^{14})$

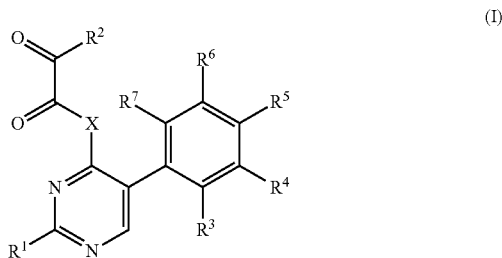

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1352 | c-Pr | PhCH$_2$O | Cl | Cl | H | H | H | CO$_2$Et | H |
| II-1353 | c-Pr | CH$_2$=CHCH$_2$O | Cl | Cl | H | H | H | CO$_2$Et | H |
| II-1354 | c-Pr | HC≡CCH$_2$O | Cl | Cl | H | H | H | CO$_2$Et | H |
| II-1355 | c-Pr | F$_3$CCH$_2$O | Cl | Cl | H | H | H | CO$_2$Et | H |
| II-1356 | c-Pr | H$_3$COCH$_2$CH$_2$O | Cl | Cl | H | H | H | CO$_2$Et | H |
| II-1357 | c-Pr | HO | Cl | Cl | H | H | H | CN | H |
| II-1358 | c-Pr | MeO | Cl | Cl | H | H | H | CN | H |
| II-1359 | c-Pr | EtO | Cl | Cl | H | H | H | CN | H |
| II-1360 | c-Pr | n-PrO | Cl | Cl | H | H | H | CN | H |
| II-1361 | c-Pr | i-PrO | Cl | Cl | H | H | H | CN | H |
| II-1362 | c-Pr | n-BuO | Cl | Cl | H | H | H | CN | H |
| II-1363 | c-Pr | i-BuO | Cl | Cl | H | H | H | CN | H |
| II-1364 | c-Pr | PhCH$_2$O | Cl | Cl | H | H | H | CN | H |
| II-1365 | c-Pr | CH$_2$=CHCH$_2$O | Cl | Cl | H | H | H | CN | H |
| II-1366 | c-Pr | HC≡CCH$_2$O | Cl | Cl | H | H | H | CN | H |
| II-1367 | c-Pr | F$_3$CCH$_2$O | Cl | Cl | H | H | H | CN | H |
| II-1368 | c-Pr | H$_3$COCH$_2$CH$_2$O | Cl | Cl | H | H | H | CN | H |
| II-1369 | c-Pr | HO | Cl | H | Cl | H | H | Me | H |
| II-1370 | c-Pr | MeO | Cl | H | Cl | H | H | Me | H |
| II-1371 | c-Pr | EtO | Cl | H | Cl | H | H | Me | H |
| II-1372 | c-Pr | n-PrO | Cl | H | Cl | H | H | Me | H |
| II-1373 | c-Pr | i-PrO | Cl | H | Cl | H | H | Me | H |
| II-1374 | c-Pr | n-BuO | Cl | H | Cl | H | H | Me | H |
| II-1375 | c-Pr | i-BuO | Cl | H | Cl | H | H | Me | H |
| II-1376 | c-Pr | PhCH$_2$O | Cl | H | Cl | H | H | Me | H |
| II-1377 | c-Pr | CH$_2$=CHCH$_2$O | Cl | H | Cl | H | H | Me | H |
| II-1378 | c-Pr | HC≡CCH$_2$O | Cl | H | Cl | H | H | Me | H |
| II-1379 | c-Pr | F$_3$CCH$_2$O | Cl | H | Cl | H | H | Me | H |
| II-1380 | c-Pr | H$_3$COCH$_2$CH$_2$O | Cl | H | Cl | H | H | Me | H |
| II-1381 | c-Pr | HO | Cl | H | Cl | H | H | Me | Me |
| II-1382 | c-Pr | MeO | Cl | H | Cl | H | H | Me | Me |
| II-1383 | c-Pr | EtO | Cl | H | Cl | H | H | Me | Me |
| II-1384 | c-Pr | n-PrO | Cl | H | Cl | H | H | Me | Me |
| II-1385 | c-Pr | i-PrO | Cl | H | Cl | H | H | Me | Me |
| II-1386 | c-Pr | n-BuO | Cl | H | Cl | H | H | Me | Me |
| II-1387 | c-Pr | i-BuO | Cl | H | Cl | H | H | Me | Me |
| II-1388 | c-Pr | PhCH$_2$O | Cl | H | Cl | H | H | Me | Me |
| II-1389 | c-Pr | CH$_2$=CHCH$_2$O | Cl | H | Cl | H | H | Me | Me |
| II-1390 | c-Pr | HC≡CCH$_2$O | Cl | H | Cl | H | H | Me | Me |
| II-1391 | c-Pr | F$_3$CCH$_2$O | Cl | H | Cl | H | H | Me | Me |
| II-1392 | c-Pr | H$_3$COCH$_2$CH$_2$O | Cl | H | Cl | H | H | Me | Me |
| II-1393 | c-Pr | HO | Cl | H | Cl | H | H | CO$_2$Et | H |
| II-1394 | c-Pr | MeO | Cl | H | Cl | H | H | CO$_2$Et | H |
| II-1395 | c-Pr | EtO | Cl | H | Cl | H | H | CO$_2$Et | H |
| II-1396 | c-Pr | n-PrO | Cl | H | Cl | H | H | CO$_2$Et | H |
| II-1397 | c-Pr | i-PrO | Cl | H | Cl | H | H | CO$_2$Et | H |
| II-1398 | c-Pr | n-BuO | Cl | H | Cl | H | H | CO$_2$Et | H |
| II-1399 | c-Pr | i-BuO | Cl | H | Cl | H | H | CO$_2$Et | H |
| II-1400 | c-Pr | PhCH$_2$O | Cl | H | Cl | H | H | CO$_2$Et | H |
| II-1401 | c-Pr | CH$_2$=CHCH$_2$O | Cl | H | Cl | H | H | CO$_2$Et | H |
| II-1402 | c-Pr | HC≡CCH$_2$O | Cl | H | Cl | H | H | CO$_2$Et | H |
| II-1403 | c-Pr | F$_3$CCH$_2$O | Cl | H | Cl | H | H | CO$_2$Et | H |
| II-1404 | c-Pr | H$_3$COCH$_2$CH$_2$O | Cl | H | Cl | H | H | CO$_2$Et | H |
| II-1405 | c-Pr | HO | Cl | H | Cl | H | H | CN | H |
| II-1406 | c-Pr | MeO | Cl | H | Cl | H | H | CN | H |
| II-1407 | c-Pr | EtO | Cl | H | Cl | H | H | CN | H |
| II-1408 | c-Pr | n-PrO | Cl | H | Cl | H | H | CN | H |
| II-1409 | c-Pr | i-PrO | Cl | H | Cl | H | H | CN | H |
| II-1410 | c-Pr | n-BuO | Cl | H | Cl | H | H | CN | H |
| II-1411 | c-Pr | i-BuO | Cl | H | Cl | H | H | CN | H |
| II-1412 | c-Pr | PhCH$_2$ | Cl | H | Cl | H | H | CN | H |
| II-1413 | c-Pr | CH$_2$=CHCH$_2$O | Cl | H | Cl | H | H | CN | H |
| II-1414 | c-Pr | HC≡CCH$_2$O | Cl | H | Cl | H | H | CN | H |

TABLE 2-continued

Inventive compounds of the formula (I) in which X represents $C(R^{13})(R^{14})$

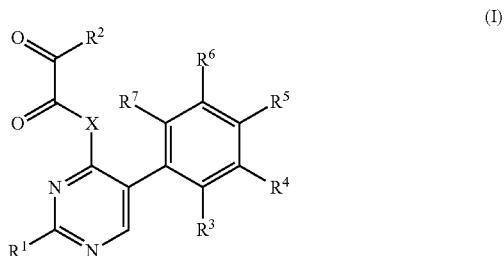

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1415 | c-Pr | F$_3$CCH$_2$O | Cl | H | Cl | H | H | CN | H |
| II-1416 | c-Pr | H$_3$COCH$_2$CH$_2$O | Cl | H | Cl | H | H | CN | H |
| II-1417 | c-Pr | HO | Cl | H | H | Cl | H | Me | H |
| II-1418 | c-Pr | MeO | Cl | H | H | Cl | H | Me | H |
| II-1419 | c-Pr | EtO | Cl | H | H | Cl | H | Me | H |
| II-1420 | c-Pr | n-PrO | Cl | H | H | Cl | H | Me | H |
| II-1421 | c-Pr | i-PrO | Cl | H | H | Cl | H | Me | H |
| II-1422 | c-Pr | n-BuO | Cl | H | H | Cl | H | Me | H |
| II-1423 | c-Pr | i-BuO | Cl | H | H | Cl | H | Me | H |
| II-1424 | c-Pr | PhCH$_2$O | Cl | H | H | Cl | H | Me | H |
| II-1425 | c-Pr | CH$_2$=CHCH$_2$O | Cl | H | H | Cl | H | Me | H |
| II-1426 | c-Pr | HC≡CCH$_2$O | Cl | H | H | Cl | H | Me | H |
| II-1427 | c-Pr | F$_3$CCH$_2$O | Cl | H | H | Cl | H | Me | H |
| II-1428 | c-Pr | H$_3$COCH$_2$CH$_2$O | Cl | H | H | Cl | H | Me | H |
| II-1429 | c-Pr | HO | Cl | H | H | Cl | H | Me | Me |
| II-1430 | c-Pr | MeO | Cl | H | H | Cl | H | Me | Me |
| II-1431 | c-Pr | EtO | Cl | H | H | Cl | H | Me | Me |
| II-1432 | c-Pr | n-PrO | Cl | H | H | Cl | H | Me | Me |
| II-1433 | c-Pr | i-PrO0 | Cl | H | H | Cl | H | Me | Me |
| II-1434 | c-Pr | n-BuO | Cl | H | H | Cl | H | Me | Me |
| II-1435 | c-Pr | i-BuO | Cl | H | H | Cl | H | Me | Me |
| II-1436 | c-Pr | PhCH$_2$O | Cl | H | H | Cl | H | Me | Me |
| II-1437 | c-Pr | CH$_2$=CHCH$_2$O | Cl | H | H | Cl | H | Me | Me |
| II-1438 | c-Pr | HC≡CCH$_2$O | Cl | H | H | Cl | H | Me | Me |
| II-1439 | c-Pr | F$_3$CCH$_2$O | Cl | H | H | Cl | H | Me | Me |
| II-1440 | c-Pr | H$_3$COCH$_2$CH$_2$O | Cl | H | H | Cl | H | Me | Me |
| II-1441 | c-Pr | HO | Cl | H | H | Cl | H | CO$_2$Et | H |
| II-1442 | c-Pr | MeO | Cl | H | H | Cl | H | CO$_2$Et | H |
| II-1443 | c-Pr | EtO | Cl | H | H | Cl | H | CO$_2$Et | H |
| II-1444 | c-Pr | n-PrO | Cl | H | H | Cl | H | CO$_2$Et | H |
| II-1445 | c-Pr | i-PrO | Cl | H | H | Cl | H | CO$_2$Et | H |
| II-1446 | c-Pr | n-BuO | Cl | H | H | Cl | H | CO$_2$Et | H |
| II-1447 | c-Pr | i-BuO | Cl | H | H | Cl | H | CO$_2$Et | H |
| II-1448 | c-Pr | PhCH$_2$O | Cl | H | H | Cl | H | CO$_2$Et | H |
| II-1449 | c-Pr | CH$_2$=CHCH$_2$O | Cl | H | H | Cl | H | CO$_2$Et | H |
| II-1450 | c-Pr | HC≡CCH$_2$O | Cl | H | H | Cl | H | CO$_2$Et | H |
| II-1451 | c-Pr | F$_3$CCH$_2$O | Cl | H | H | Cl | H | CO$_2$Et | H |
| II-1452 | c-Pr | H$_3$COCH$_2$CH$_2$O | Cl | H | H | Cl | H | CO$_2$Et | H |
| II-1453 | c-Pr | HO | Cl | H | H | Cl | H | CN | H |
| II-1454 | c-Pr | MeO | Cl | H | H | Cl | H | CN | H |
| II-1455 | c-Pr | EtO | Cl | H | H | Cl | H | CN | H |
| II-1456 | c-Pr | n-PrO | Cl | H | H | Cl | H | CN | H |
| II-1457 | c-Pr | i-PrO | Cl | H | H | Cl | H | CN | H |
| II-1458 | c-Pr | n-BuO | Cl | H | H | Cl | H | CN | H |
| II-1459 | c-Pr | i-BuO | Cl | H | H | Cl | H | CN | H |
| II-1460 | c-Pr | PhCH$_2$O | Cl | H | H | Cl | H | CN | H |
| II-1461 | c-Pr | CH$_2$=CHCH$_2$O | Cl | H | H | Cl | H | CN | H |
| II-1462 | c-Pr | HC≡CCH$_2$O | Cl | H | H | Cl | H | CN | H |
| II-1463 | c-Pr | F$_3$CCH$_2$O | Cl | H | H | Cl | H | CN | H |
| II-1464 | c-Pr | H$_3$COCH$_2$CH$_2$O | Cl | H | H | Cl | H | CN | H |
| II-1465 | c-Pr | HO | Cl | H | H | H | Cl | Me | H |
| II-1466 | c-Pr | MeO | Cl | H | H | H | Cl | Me | H |
| II-1467 | c-Pr | EtO | Cl | H | H | H | Cl | Me | H |
| II-1468 | c-Pr | n-PrO | Cl | H | H | H | Cl | Me | H |
| II-1469 | c-Pr | i-PrO | Cl | H | H | H | Cl | Me | H |
| II-1470 | c-Pr | n-BuO | Cl | H | H | H | Cl | Me | H |
| II-1471 | c-Pr | i-BuO | Cl | H | H | H | Cl | Me | H |
| II-1472 | c-Pr | PhCH$_2$O | Cl | H | H | H | Cl | Me | H |
| II-1473 | c-Pr | CH$_2$=CHCH$_2$O | Cl | H | H | H | Cl | Me | H |
| II-1474 | c-Pr | HC≡CCH$_2$O | Cl | H | H | H | Cl | Me | H |
| II-1475 | c-Pr | F$_3$CCH$_2$O | Cl | H | H | H | Cl | Me | H |
| II-1476 | c-Pr | H$_3$COCH$_2$CH$_2$O | Cl | H | H | H | Cl | Me | H |
| II-1477 | c-Pr | HO | Cl | H | H | H | Cl | Me | Me |

TABLE 2-continued

Inventive compounds of the formula (I) in which X represents C(R$^{13}$) (R$^{14}$)

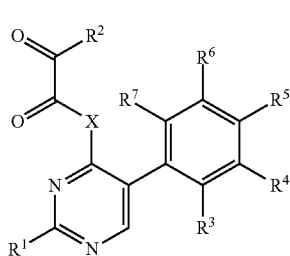

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| II-1478 | c-Pr | MeO | Cl | H | H | H | Cl | Me | Me |
| II-1479 | c-Pr | EtO | Cl | H | H | H | Cl | Me | Me |
| II-1480 | c-Pr | n-PrO | Cl | H | H | H | Cl | Me | Me |
| II-1481 | c-Pr | i-PrO | Cl | H | H | H | Cl | Me | Me |
| II-1482 | c-Pr | n-BuO | Cl | H | H | H | Cl | Me | Me |
| II-1483 | c-Pr | i-BuO | Cl | H | H | H | Cl | Me | Me |
| II-1484 | c-Pr | PhCH$_2$O | Cl | H | H | H | Cl | Me | Me |
| II-1485 | c-Pr | CH$_2$=CHCH$_2$O | Cl | H | H | H | Cl | Me | Me |
| II-1486 | c-Pr | HC≡CCH$_2$O | Cl | H | H | H | Cl | Me | Me |
| II-1487 | c-Pr | F$_3$CCH$_2$O | Cl | H | H | H | Cl | Me | Me |
| II-1488 | c-Pr | H$_3$COCH$_2$CH$_2$O | Cl | H | H | H | Cl | Me | Me |
| II-1489 | c-Pr | HO | Cl | H | H | H | Cl | CO$_2$Et | H |
| II-1490 | c-Pr | MeO | Cl | H | H | H | Cl | CO$_2$Et | H |
| II-1491 | c-Pr | EtO | Cl | H | H | H | Cl | CO$_2$Et | H |
| II-1492 | c-Pr | n-PrO | Cl | H | H | H | Cl | CO$_2$Et | H |
| II-1493 | c-Pr | i-PrO | Cl | H | H | H | Cl | CO$_2$Et | H |
| II-1494 | c-Pr | n-BuO | Cl | H | H | H | Cl | CO$_2$Et | H |
| II-1495 | c-Pr | i-BuO | Cl | H | H | H | Cl | CO$_2$Et | H |
| II-1496 | c-Pr | PhCH$_2$O | Cl | H | H | H | Cl | CO$_2$Et | H |
| II-1497 | c-Pr | CH$_2$=CHCH$_2$O | Cl | H | H | H | Cl | CO$_2$Et | H |
| II-1498 | c-Pr | HC≡CCH$_2$O | Cl | H | H | H | Cl | CO$_2$Et | H |
| II-1499 | c-Pr | F$_3$CCH$_2$O | Cl | H | H | H | Cl | CO$_2$Et | H |
| II-1500 | c-Pr | H$_3$COCH$_2$CH$_2$O | Cl | H | H | H | Cl | CO$_2$Et | H |
| II-1501 | c-Pr | HO | Cl | H | H | H | Cl | CN | H |
| II-1502 | c-Pr | MeO | Cl | H | H | H | Cl | CN | H |
| II-1503 | c-Pr | EtO | Cl | H | H | H | Cl | CN | H |
| II-1504 | c-Pr | n-PrO | Cl | H | H | H | Cl | CN | H |
| II-1505 | c-Pr | i-PrO | Cl | H | H | H | Cl | CN | H |
| II-1506 | c-Pr | n-BuO | Cl | H | H | H | Cl | CN | H |
| II-1507 | c-Pr | i-BuO | Cl | H | H | H | Cl | CN | H |
| II-1508 | c-Pr | PhCH$_2$O | Cl | H | H | H | Cl | CN | H |
| II-1509 | c-Pr | CH$_2$=CHCH$_2$O | Cl | H | H | H | Cl | CN | H |
| II-1510 | c-Pr | HC≡CCH$_2$O | Cl | H | H | H | Cl | CN | H |
| II-1511 | c-Pr | F$_3$CCH$_2$O | Cl | H | H | H | Cl | CN | H |
| II-1512 | c-Pr | H$_3$COCH$_2$CH$_2$O | Cl | H | H | H | Cl | CN | H |
| II-1513 | c-Pr | HO | Me | H | H | H | H | Me | H |
| II-1514 | c-Pr | MeO | Me | H | H | H | H | Me | H |
| II-1515 | c-Pr | EtO | Me | H | H | H | H | Me | H |
| II-1516 | c-Pr | n-PrO | Me | H | H | H | H | Me | H |
| II-1517 | c-Pr | i-PrO | Me | H | H | H | H | Me | H |
| II-1518 | c-Pr | n-BuO | Me | H | H | H | H | Me | H |
| II-1519 | c-Pr | i-BuO | Me | H | H | H | H | Me | H |
| II-1520 | c-Pr | PhCH$_2$O | Me | H | H | H | H | Me | H |
| II-1521 | c-Pr | CH$_2$=CHCH$_2$O | Me | H | H | H | H | Me | H |
| II-1522 | c-Pr | HC≡CCH$_2$O | Me | H | H | H | H | Me | H |
| II-1523 | c-Pr | F$_3$CCH$_2$O | Me | H | H | H | H | Me | H |
| II-1524 | c-Pr | H$_3$COCH$_2$CH$_2$O | Me | H | H | H | H | Me | H |
| II-1525 | c-Pr | HO | Me | H | H | H | H | Me | Me |
| II-1526 | c-Pr | MeO | Me | H | H | H | H | Me | Me |
| II-1527 | c-Pr | EtO | Me | H | H | H | H | Me | Me |
| II-1528 | c-Pr | n-PrO | Me | H | H | H | H | Me | Me |
| II-1529 | c-Pr | i-PrO | Me | H | H | H | H | Me | Me |
| II-1530 | c-Pr | n-BuO | Me | H | H | H | H | Me | Me |
| II-1531 | c-Pr | i-BuO | Me | H | H | H | H | Me | Me |
| II-1532 | c-Pr | PhCH$_2$O | Me | H | H | H | H | Me | Me |
| II-1533 | c-Pr | CH$_2$=CHCH$_2$O | Me | H | H | H | H | Me | Me |
| II-1534 | c-Pr | HC≡CCH$_2$O | Me | H | H | H | H | Me | Me |
| II-1535 | c-Pr | F$_3$CCH$_2$O | Me | H | H | H | H | Me | Me |
| II-1536 | c-Pr | H$_3$COCH$_2$CH$_2$O | Me | H | H | H | H | Me | Me |
| II-1537 | c-Pr | HO | Me | H | H | H | H | Me | H |
| II-1538 | c-Pr | MeO | Me | H | H | H | H | CO$_2$Et | H |
| II-1539 | c-Pr | EtO | Me | H | H | H | H | CO$_2$Et | H |
| II-1540 | c-Pr | n-PrO | Me | H | H | H | H | CO$_2$Et | H |

TABLE 2-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| II-1541 | c-Pr | i-PrO | Me | H | H | H | H | CO$_2$Et | H |
| II-1542 | c-Pr | n-BuO | Me | H | H | H | H | CO$_2$Et | H |
| II-1543 | c-Pr | i-BuO | Me | H | H | H | H | CO$_2$Et | H |
| II-1544 | c-Pr | PhCH$_2$O | Me | H | H | H | H | CO$_2$Et | H |
| II-1545 | c-Pr | CH$_2$=CHCH$_2$O | Me | H | H | H | H | CO$_2$Et | H |
| II-1546 | c-Pr | HC≡CCH$_2$O | Me | H | H | H | H | CO$_2$Et | H |
| II-1547 | c-Pr | F$_3$CCH$_2$O | Me | H | H | H | H | CO$_2$Et | H |
| II-1548 | c-Pr | H$_3$COCH$_2$CH$_2$O | Me | H | H | H | H | CO$_2$Et | H |
| II-1549 | c-Pr | HO | Me | H | H | H | H | CN | H |
| II-1550 | c-Pr | MeO | Me | H | H | H | H | CN | H |
| II-1551 | c-Pr | EtO | Me | H | H | H | H | CN | H |
| II-1552 | c-Pr | n-PrO | Me | H | H | H | H | CN | H |
| II-1553 | c-Pr | i-PrO | Me | H | H | H | H | CN | H |
| II-1554 | c-Pr | n-BuO | Me | H | H | H | H | CN | H |
| II-1555 | c-Pr | i-BuO | Me | H | H | H | H | CN | H |
| II-1556 | c-Pr | PhCH$_2$O | Me | H | H | H | H | CN | H |
| II-1557 | c-Pr | CH$_2$=CHCH$_2$O | Me | H | H | H | H | CN | H |
| II-1558 | c-Pr | HC≡CCH$_2$O | Me | H | H | H | H | CN | H |
| II-1559 | c-Pr | F$_3$CCH$_2$O | Me | H | H | H | H | CN | H |
| II-1560 | c-Pr | H$_3$COCH$_2$CH$_2$O | Me | H | H | H | H | CN | H |
| II-1561 | c-Pr | HO | CF$_3$ | H | H | H | H | Me | H |
| II-1562 | c-Pr | MeO | CF$_3$ | H | H | H | H | Me | H |
| II-1563 | c-Pr | EtO | CF$_3$ | H | H | H | H | Me | H |
| II-1564 | c-Pr | n-PrO | CF$_3$ | H | H | H | H | Me | H |
| II-1565 | c-Pr | i-PrO | CF$_3$ | H | H | H | H | Me | H |
| II-1566 | c-Pr | n-BuO | CF$_3$ | H | H | H | H | Me | H |
| II-1567 | c-Pr | i-BuO | CF$_3$ | H | H | H | H | Me | H |
| II-1568 | c-Pr | PhCH$_2$O | CF$_3$ | H | H | H | H | Me | H |
| II-1569 | c-Pr | CH$_2$=CHCH$_2$O | CF$_3$ | H | H | H | H | Me | H |
| II-1570 | c-Pr | HC≡CCH$_2$O | CF$_3$ | H | H | H | H | Me | H |
| II-1571 | c-Pr | F$_3$CCH$_2$O | CF$_3$ | H | H | H | H | Me | H |
| II-1572 | c-Pr | H$_3$COCH$_2$CH$_2$O | CF$_3$ | H | H | H | H | Me | H |
| II-1573 | c-Pr | HO | CF$_3$ | H | H | H | H | Me | Me |
| II-1574 | c-Pr | MeO | CF$_3$ | H | H | H | H | Me | Me |
| II-1575 | c-Pr | EtO | CF$_3$ | H | H | H | H | Me | Me |
| II-1576 | c-Pr | n-PrO | CF$_3$ | H | H | H | H | Me | Me |
| II-1577 | c-Pr | i-PrO | CF$_3$ | H | H | H | H | Me | Me |
| II-1578 | c-Pr | n-BuO | CF$_3$ | H | H | H | H | Me | Me |
| II-1579 | c-Pr | i-BuO | CF$_3$ | H | H | H | H | Me | Me |
| II-1580 | c-Pr | PhCH$_2$O | CF$_3$ | H | H | H | H | Me | Me |
| II-1581 | c-Pr | CH$_2$=CHCH$_2$O | CF$_3$ | H | H | H | H | Me | Me |
| II-1582 | c-Pr | HC≡CCH$_2$O | CF$_3$ | H | H | H | H | Me | Me |
| II-1583 | c-Pr | F$_3$CCH$_2$O | CF$_3$ | H | H | H | H | Me | Me |
| II-1584 | c-Pr | H$_3$COCH$_2$CH$_2$O | CF$_3$ | H | H | H | H | Me | Me |
| II-1585 | c-Pr | HO | CF$_3$ | H | H | H | H | CO$_2$Et | H |
| II-1586 | c-Pr | MeO | CF$_3$ | H | H | H | H | CO$_2$Et | H |
| II-1587 | c-Pr | EtO | CF$_3$ | H | H | H | H | CO$_2$Et | H |
| II-1588 | c-Pr | n-PrO | CF$_3$ | H | H | H | H | CO$_2$Et | H |
| II-1589 | c-Pr | i-PrO | CF$_3$ | H | H | H | H | CO$_2$Et | H |
| II-1590 | c-Pr | n-BuO | CF$_3$ | H | H | H | H | CO$_2$Et | H |
| II-1591 | c-Pr | i-BuO | CF$_3$ | H | H | H | H | CO$_2$Et | H |
| II-1592 | c-Pr | PhCH$_2$O | CF$_3$ | H | H | H | H | CO$_2$Et | H |
| II-1593 | c-Pr | CH$_2$=CHCH$_2$O | CF$_3$ | H | H | H | H | CO$_2$Et | H |
| II-1594 | c-Pr | HC≡CCH$_2$O | CF$_3$ | H | H | H | H | CO$_2$Et | H |
| II-1595 | c-Pr | F$_3$CCH$_2$O | CF$_3$ | H | H | H | H | CO$_2$Et | H |
| II-1596 | c-Pr | H$_3$COCH$_2$CH$_2$O | CF$_3$ | H | H | H | H | CO$_2$Et | H |
| II-1597 | c-Pr | HO | CF$_3$ | H | H | H | H | CN | H |
| II-1598 | c-Pr | MeO | CF$_3$ | H | H | H | H | CN | H |
| II-1599 | c-Pr | EtO | CF$_3$ | H | H | H | H | CN | H |
| II-1600 | c-Pr | n-PrO | CF$_3$ | H | H | H | H | CN | H |
| II-1601 | c-Pr | i-PrO | CF$_3$ | H | H | H | H | CN | H |
| II-1602 | c-Pr | n-BuO | CF$_3$ | H | H | H | H | CN | H |
| II-1603 | c-Pr | i-BuO | CF$_3$ | H | H | H | H | CN | H |

TABLE 2-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| II-1604 | c-Pr | PhCH$_2$O | CF$_3$ | H | H | H | H | CN | H |
| II-1605 | c-Pr | CH$_2$=CHCH$_2$O | CF$_3$ | H | H | H | H | CN | H |
| II-1606 | c-Pr | HC≡CCH$_2$O | CF$_3$ | H | H | H | H | CN | H |
| II-1607 | c-Pr | F$_3$CCH$_2$O | CF$_3$ | H | H | H | H | CN | H |
| II-1608 | c-Pr | H$_3$COCH$_2$CH$_2$O | CF$_3$ | H | H | H | H | CN | H |
| II-1609 | c-Pr | HO | MeO | H | H | H | H | Me | H |
| II-1610 | c-Pr | MeO | MeO | H | H | H | H | Me | H |
| II-1611 | c-Pr | EtO | MeO | H | H | H | H | Me | H |
| II-1612 | c-Pr | n-PrO | MeO | H | H | H | H | Me | H |
| II-1613 | c-Pr | i-PrO | MeO | H | H | H | H | Me | H |
| II-1614 | c-Pr | n-BuO | MeO | H | H | H | H | Me | H |
| II-1615 | c-Pr | i-BuO | MeO | H | H | H | H | Me | H |
| II-1616 | c-Pr | PhCH$_2$O | MeO | H | H | H | H | Me | H |
| II-1617 | c-Pr | CH$_2$=CHCH$_2$O | MeO | H | H | H | H | Me | H |
| II-1618 | c-Pr | HC≡CCH$_2$O | MeO | H | H | H | H | Me | H |
| II-1619 | c-Pr | F$_3$CCH$_2$O | MeO | H | H | H | H | Me | H |
| II-1620 | c-Pr | H$_3$COCH$_2$CH$_2$O | MeO | H | H | H | H | Me | H |
| II-1621 | c-Pr | HO | MeO | H | H | H | H | Me | Me |
| II-1622 | c-Pr | MeO | MeO | H | H | H | H | Me | Me |
| II-1623 | c-Pr | EtO | MeO | H | H | H | H | Me | Me |
| II-1624 | c-Pr | n-PrO | MeO | H | H | H | H | Me | Me |
| II-1625 | c-Pr | i-PrO | MeO | H | H | H | H | Me | Me |
| II-1626 | c-Pr | n-BuO | MeO | H | H | H | H | Me | Me |
| II-1627 | c-Pr | i-BuO | MeO | H | H | H | H | Me | Me |
| II-1628 | c-Pr | PhCH$_2$O | MeO | H | H | H | H | Me | Me |
| II-1629 | c-Pr | CH$_2$=CHCH$_2$O | MeO | H | H | H | H | Me | Me |
| II-1630 | c-Pr | HC≡CCH$_2$O | MeO | H | H | H | H | Me | Me |
| II-1631 | c-Pr | F$_3$CCH$_2$O | MeO | H | H | H | H | Me | Me |
| II-1632 | c-Pr | H$_3$COCH$_2$CH$_2$O | MeO | H | H | H | H | Me | Me |
| II-1633 | c-Pr | HO | MeO | H | H | H | H | Me | H |
| II-1634 | c-Pr | MeO | MeO | H | H | H | H | CO$_2$Et | H |
| II-1635 | c-Pr | EtO | MeO | H | H | H | H | CO$_2$Et | H |
| II-1636 | c-Pr | n-PrO | MeO | H | H | H | H | CO$_2$Et | H |
| II-1637 | c-Pr | i-PrO | MeO | H | H | H | H | CO$_2$Et | H |
| II-1638 | c-Pr | n-BuO | MeO | H | H | H | H | CO$_2$Et | H |
| II-1639 | c-Pr | i-BuO | MeO | H | H | H | H | CO$_2$Et | H |
| II-1640 | c-Pr | PhCH$_2$O | MeO | H | H | H | H | CO$_2$Et | H |
| II-1641 | c-Pr | CH$_2$=CHCH$_2$O | MeO | H | H | H | H | CO$_2$Et | H |
| II-1642 | c-Pr | HC≡CCH$_2$O | MeO | H | H | H | H | CO$_2$Et | H |
| II-1643 | c-Pr | F$_3$CCH$_2$O | MeO | H | H | H | H | CO$_2$Et | H |
| II-1644 | c-Pr | H$_3$COCH$_2$CH$_2$O | MeO | H | H | H | H | CO$_2$Et | H |
| II-1645 | c-Pr | HO | MeO | H | H | H | H | CN | H |
| II-1646 | c-Pr | MeO | MeO | H | H | H | H | CN | H |
| II-1647 | c-Pr | EtO | MeO | H | H | H | H | CN | H |
| II-1648 | c-Pr | n-PrO | MeO | H | H | H | H | CN | H |
| II-1649 | c-Pr | i-PrO | MeO | H | H | H | H | CN | H |
| II-1650 | c-Pr | n-BuO | MeO | H | H | H | H | CN | H |
| II-1651 | c-Pr | i-BuO | MeO | H | H | H | H | CN | H |
| II-1652 | c-Pr | PhCH$_2$O | MeO | H | H | H | H | CN | H |
| II-1653 | c-Pr | CH$_2$=CHCH$_2$O | MeO | H | H | H | H | CN | H |
| II-1654 | c-Pr | HC≡CCH$_2$O | MeO | H | H | H | H | CN | H |
| II-1655 | c-Pr | F$_3$CCH$_2$O | MeO | H | H | H | H | CN | H |
| II-1656 | c-Pr | H$_3$COCH$_2$CH$_2$O | MeO | H | H | H | H | CN | H |

TABLE 3

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-001 | c-Pr | HO—NH | H | H | H | H | H | H | H |
| III-002 | c-Pr | HO—N(Me) | H | H | H | H | H | H | H |
| III-003 | c-Pr | MeO—NH | H | H | H | H | H | H | H |
| III-004 | c-Pr | MeO—N(Me) | H | H | H | H | H | H | H |
| III-005 | c-Pr | AllylO—NH | H | H | H | H | H | H | H |
| III-006 | c-Pr | HO—N(iPr) | H | H | H | H | H | H | H |
| III-007 | c-Pr | HOCH$_2$CH$_2$O—NH | H | H | H | H | H | H | H |
| III-008 | c-Pr | (isoxazolidinyl) | H | H | H | H | H | H | H |
| III-009 | c-Pr | (1,2-oxazinan-2-yl) | H | H | H | H | H | H | H |
| III-010 | c-Pr | (tetrahydropyran-2-yl)O—NH | H | H | H | H | H | H | H |
| III-011 | c-Pr | PhO—NH | H | H | H | H | H | H | H |
| III-012 | c-Pr | BnO—NH | H | H | H | H | H | H | H |
| III-013 | 1-Me-c-Pr | HO—NH | H | H | H | H | H | H | H |
| III-014 | 1-Me-c-Pr | HO—N(Me) | H | H | H | H | H | H | H |
| III-015 | 1-Me-c-Pr | MeO—NH | H | H | H | H | H | H | H |
| III-016 | 1-Me-c-Pr | MeO—N(Me) | H | H | H | H | H | H | H |
| III-017 | 1-Me-c-Pr | AllylO—NH | H | H | H | H | H | H | H |
| III-018 | 1-Me-c-Pr | HO—N(iPr) | H | H | H | H | H | H | H |
| III-019 | 1-Me-c-Pr | HOCH$_2$CH$_2$O—NH | H | H | H | H | H | H | H |
| III-020 | 1-Me-c-Pr | (isoxazolidinyl) | H | H | H | H | H | H | H |
| III-021 | 1-Me-c-Pr | (1,2-oxazinan-2-yl) | H | H | H | H | H | H | H |
| III-022 | 1-Me-c-Pr | (tetrahydropyran-2-yl)O—NH | H | H | H | H | H | H | H |
| III-023 | 1-Me-c-Pr | PhO—NH | H | H | H | H | H | H | H |
| III-024 | 1-Me-c-Pr | BnO—NH | H | H | H | H | H | H | H |
| III-025 | 2-Me-c-Pr | HO—NH | H | H | H | H | H | H | H |
| III-026 | 2-Me-c-Pr | HO—N(Me) | H | H | H | H | H | H | H |
| III-027 | 2-Me-c-Pr | MeO—NH | H | H | H | H | H | H | H |
| III-028 | 2-Me-c-Pr | MeO—N(Me) | H | H | H | H | H | H | H |
| III-029 | 2-Me-c-Pr | AllylO—NH | H | H | H | H | H | H | H |
| III-030 | 2-Me-c-Pr | HO—N(iPr) | H | H | H | H | H | H | H |
| III-031 | 2-Me-c-Pr | HOCH$_2$CH$_2$O—NH | H | H | H | H | H | H | H |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-032 | 2-Me-c-Pr | isoxazolidine | H | H | H | H | H | H | H |
| III-033 | 2-Me-c-Pr | 1,2-oxazinane | H | H | H | H | H | H | H |
| III-034 | 2-Me-c-Pr | tetrahydropyran-2-yl-O-NH | H | H | H | H | H | H | H |
| III-035 | 2-Me-c-Pr | PhO—NH | H | H | H | H | H | H | H |
| III-036 | 2-Me-c-Pr | BnO—NH | H | H | H | H | H | H | H |
| III-037 | c-Pr | HO—NH | F | H | H | H | H | H | H |
| III-038 | c-Pr | HO—N(Me) | F | H | H | H | H | H | H |
| III-039 | c-Pr | MeO—NH | F | H | H | H | H | H | H |
| III-040 | c-Pr | MeO—N(Me) | F | H | H | H | H | H | H |
| III-041 | c-Pr | AllylO—NH | F | H | H | H | H | H | H |
| III-042 | c-Pr | HO—N(iPr) | F | H | H | H | H | H | H |
| III-043 | c-Pr | HOCH$_2$CH$_2$O—NH | F | H | H | H | H | H | H |
| III-044 | c-Pr | isoxazolidine | F | H | H | H | H | H | H |
| III-045 | c-Pr | 1,2-oxazinane | F | H | H | H | H | H | H |
| III-046 | c-Pr | tetrahydropyran-2-yl-O-NH | F | H | H | H | H | H | H |
| III-047 | c-Pr | PhO—NH | F | H | H | H | H | H | H |
| III-048 | c-Pr | BnO—NH | F | H | H | H | H | H | H |
| III-049 | 1-Me-c-Pr | HO—NH | F | H | H | H | H | H | H |
| III-050 | 1-Me-c-Pr | HO—N(Me) | F | H | H | H | H | H | H |
| III-051 | 1-Me-c-Pr | MeO—NH | F | H | H | H | H | H | H |
| III-052 | 1-Me-c-Pr | MeO—N(Me) | F | H | H | H | H | H | H |
| III-053 | 1-Me-c-Pr | AllylO—NH | F | H | H | H | H | H | H |
| III-054 | 1-Me-c-Pr | HO—N(iPr) | F | H | H | H | H | H | H |
| III-055 | 1-Me-c-Pr | HOCH$_2$CH$_2$O—NH | F | H | H | H | H | H | H |
| III-056 | 1-Me-c-Pr | isoxazolidine | F | H | H | H | H | H | H |
| III-057 | 1-Me-c-Pr | 1,2-oxazinane | F | H | H | H | H | H | H |

TABLE 3-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-058 | 1-Me-c-Pr | tetrahydropyranyl-O-NH | F | H | H | H | H | H | H |
| III-059 | 1-Me-c-Pr | PhO—NH | F | H | H | H | H | H | H |
| III-060 | 1-Me-c-Pr | BnO—NH | F | H | H | H | H | H | H |
| III-061 | 2-Me-c-Pr | HO—NH | F | H | H | H | H | H | H |
| III-062 | 2-Me-c-Pr | HO—N(Me) | F | H | H | H | H | H | H |
| III-063 | 2-Me-c-Pr | MeO—NH | F | H | H | H | H | H | H |
| III-064 | 2-Me-c-Pr | MeO—N(Me) | F | H | H | H | H | H | H |
| III-065 | 2-Me-c-Pr | AllylO—NH | F | H | H | H | H | H | H |
| III-066 | 2-Me-c-Pr | HO—N(iPr) | F | H | H | H | H | H | H |
| III-067 | 2-Me-c-Pr | HOCH$_2$CH$_2$O—NH | F | H | H | H | H | H | H |
| III-068 | 2-Me-c-Pr | isoxazolidinyl | F | H | H | H | H | H | H |
| III-069 | 2-Me-c-Pr | 1,2-oxazinanyl | F | H | H | H | H | H | H |
| III-070 | 2-Me-c-Pr | tetrahydropyranyl-O-NH | F | H | H | H | H | H | H |
| III-071 | 2-Me-c-Pr | PhO—NH | F | H | H | H | H | H | H |
| III-072 | 2-Me-c-Pr | BnO—NH | F | H | H | H | H | H | H |
| III-073 | c-Pr | HO—NH | H | F | H | H | H | H | H |
| III-074 | c-Pr | HO—N(Me) | H | F | H | H | H | H | H |
| III-075 | c-Pr | MeO—NH | H | F | H | H | H | H | H |
| III-076 | c-Pr | MeO—N(Me) | H | F | H | H | H | H | H |
| III-077 | c-Pr | AllylO—NH | H | F | H | H | H | H | H |
| III-078 | c-Pr | HO—N(iPr) | H | F | H | H | H | H | H |
| III-079 | c-Pr | HOCH$_2$CH$_2$O—NH | H | F | H | H | H | H | H |
| III-080 | c-Pr | isoxazolidinyl | H | F | H | H | H | H | H |
| III-081 | c-Pr | 1,2-oxazinanyl | H | F | H | H | H | H | H |
| III-082 | c-Pr | tetrahydropyranyl-O-NH | H | F | H | H | H | H | H |
| III-083 | c-Pr | PhO—NH | H | F | H | H | H | H | H |
| III-084 | c-Pr | BnO—NH | H | F | F | H | H | H | H |
| III-085 | c-Pr | HO—NH | H | H | F | H | H | H | H |
| III-086 | c-Pr | HO—N(Me) | H | H | F | H | H | H | H |
| III-087 | c-Pr | MeO—NH | H | H | F | H | H | H | H |
| III-088 | c-Pr | MeO—N(Me) | H | H | F | H | H | H | H |

TABLE 3-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-089 | c-Pr | AllylO—NH | H | H | F | H | H | H | H |
| III-090 | c-Pr | HO—N(iPr) | H | H | F | H | H | H | H |
| III-091 | c-Pr | HOCH$_2$CH$_2$O—NH | H | H | F | H | H | H | H |
| III-092 | c-Pr | (isoxazolidine) | H | H | F | H | H | H | H |
| III-093 | c-Pr | (1,2-oxazinane) | H | H | F | H | H | H | H |
| III-094 | c-Pr | (THP-O-NH) | H | H | F | H | H | H | H |
| III-095 | c-Pr | PhO—NH | H | H | F | H | H | H | H |
| III-096 | c-Pr | BnO—NH | H | H | F | H | H | H | H |
| III-097 | c-Pr | HO—NH | Cl | H | H | H | H | H | H |
| III-098 | c-Pr | HO—N(Me) | Cl | H | H | H | H | H | H |
| III-099 | c-Pr | MeO—NH | Cl | H | H | H | H | H | H |
| III-100 | c-Pr | MeO—N(Me) | Cl | H | H | H | H | H | H |
| III-101 | c-Pr | AllylO—NH | Cl | H | H | H | H | H | H |
| III-102 | c-Pr | HO—N(iPr) | Cl | H | H | H | H | H | H |
| III-103 | c-Pr | HOCH$_2$CH$_2$O—NH | Cl | H | H | H | H | H | H |
| III-104 | c-Pr | (isoxazolidine) | Cl | H | H | H | H | H | H |
| III-105 | c-Pr | (1,2-oxazinane) | Cl | H | H | H | H | H | H |
| III-106 | c-Pr | (THP-O-NH) | Cl | H | H | H | H | H | H |
| III-107 | c-Pr | PhO—NH | Cl | H | H | H | H | H | H |
| III-108 | c-Pr | BnO—NH | Cl | H | H | H | H | H | H |
| III-109 | 1-Me-c-Pr | HO—NH | Cl | H | H | H | H | H | H |
| III-110 | 1-Me-c-Pr | HO—N(Me) | Cl | H | H | H | H | H | H |
| III-111 | 1-Me-c-Pr | MeO—NH | Cl | H | H | H | H | H | H |
| III-112 | 1-Me-c-Pr | MeO—N(Me) | Cl | H | H | H | H | H | H |
| III-113 | 1-Me-c-Pr | AllylO—NH | Cl | H | H | H | H | H | H |
| III-114 | 1-Me-c-Pr | HO—N(iPr) | Cl | H | H | H | H | H | H |
| III-115 | 1-Me-c-Pr | HOCH$_2$CH$_2$O—NH | Cl | H | H | H | H | H | H |
| III-116 | 1-Me-c-Pr | (isoxazolidine) | Cl | H | H | H | H | H | H |

TABLE 3-continued

Inventive compounds of the formula (I) in which X represents C(R$^{13}$) (R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-117 | 1-Me-c-Pr | (1,2-oxazinan-2-yl) | Cl | H | H | H | H | H | H |
| III-118 | 1-Me-c-Pr | (tetrahydropyran-2-yl)-O-NH | Cl | H | H | H | H | H | H |
| III-119 | 1-Me-c-Pr | PhO—NH | Cl | H | H | H | H | H | H |
| III-120 | 1-Me-c-Pr | BnO—NH | Cl | H | H | H | H | H | H |
| III-121 | 2-Me-c-Pr | HO—NH | Cl | H | H | H | H | H | H |
| III-122 | 2-Me-c-Pr | HO—N(Me) | Cl | H | H | H | H | H | H |
| III-123 | 2-Me-c-Pr | MeO—NH | Cl | H | H | H | H | H | H |
| III-124 | 2-Me-c-Pr | MeO—N(Me) | Cl | H | H | H | H | H | H |
| III-125 | 2-Me-c-Pr | AllylO—NH | Cl | H | H | H | H | H | H |
| III-126 | 2-Me-c-Pr | HO—N(iPr) | Cl | H | H | H | H | H | H |
| III-127 | 2-Me-c-Pr | HOCH$_2$CH$_2$O—NH | Cl | H | H | H | H | H | H |
| III-128 | 2-Me-c-Pr | (isoxazolidin-2-yl) | Cl | H | H | H | H | H | H |
| III-129 | 2-Me-c-Pr | (1,2-oxazinan-2-yl) | Cl | H | H | H | H | H | H |
| III-130 | 2-Me-c-Pr | (tetrahydropyran-2-yl)-O-NH | Cl | H | H | H | H | H | H |
| III-131 | 2-Me-c-Pr | PhO—NH | Cl | H | H | H | H | H | H |
| III-132 | 2-Me-c-Pr | BnO—NH | Cl | H | H | H | H | H | H |
| III-133 | c-Pr | HO—NH | H | Cl | H | H | H | H | H |
| III-134 | c-Pr | HO—N(Me) | H | Cl | H | H | H | H | H |
| III-135 | c-Pr | MeO—NH | H | Cl | H | H | H | H | H |
| III-136 | c-Pr | MeO—N(Me) | H | Cl | H | H | H | H | H |
| III-137 | c-Pr | AllylO—NH | H | Cl | H | H | H | H | H |
| III-138 | c-Pr | HO—N(iPr) | H | Cl | H | H | H | H | H |
| III-139 | c-Pr | HOCH$_2$CH$_2$O—NH | H | Cl | H | H | H | H | H |
| III-140 | c-Pr | (isoxazolidin-2-yl) | H | Cl | H | H | H | H | H |
| III-141 | c-Pr | (1,2-oxazinan-2-yl) | H | Cl | H | H | H | H | H |
| III-142 | c-Pr | (tetrahydropyran-2-yl)-O-NH | H | Cl | H | H | H | H | H |

TABLE 3-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-143 | c-Pr | PhO—NH | H | Cl | H | H | H | H | H |
| III-144 | c-Pr | BnO—NH | H | Cl | H | H | H | H | H |
| III-145 | c-Pr | HO—NH | H | H | Cl | H | H | H | H |
| III-146 | c-Pr | HO—N(Me) | H | H | Cl | H | H | H | H |
| III-147 | c-Pr | MeO—NH | H | H | Cl | H | H | H | H |
| III-148 | c-Pr | MeO—N(Me) | H | H | Cl | H | H | H | H |
| III-149 | c-Pr | AllylO—NH | H | H | Cl | H | H | H | H |
| III-150 | c-Pr | HO—N(iPr) | H | H | Cl | H | H | H | H |
| III-151 | c-Pr | HOCH$_2$CH$_2$O—NH | H | H | Cl | H | H | H | H |
| III-152 | c-Pr | isoxazolidine | H | H | Cl | H | H | H | H |
| III-153 | c-Pr | 1,2-oxazinane | H | H | CL | H | H | H | H |
| III-154 | c-Pr | THP-O-NH | H | H | CL | H | H | H | H |
| III-155 | c-Pr | PhO—NH | H | H | Cl | H | H | H | H |
| III-156 | c-Pr | BnO—NH | H | H | Cl | H | H | H | H |
| III-157 | c-Pr | HO—NH | Me | H | H | H | H | H | H |
| III-158 | c-Pr | HO—N(Me) | Me | H | H | H | H | H | H |
| III-159 | c-Pr | MeO—NH | Me | H | H | H | H | H | H |
| III-160 | c-Pr | MeO—N(Me) | Me | H | H | H | H | H | H |
| III-161 | c-Pr | AllylO—NH | Me | H | H | H | H | H | H |
| III-162 | c-Pr | HO—N(iPr) | Me | H | H | H | H | H | H |
| III-163 | c-Pr | HOCH$_2$CH$_2$O—NH | Me | H | H | H | H | H | H |
| III-164 | c-Pr | isoxazolidine | Me | H | H | H | H | H | H |
| III-165 | c-Pr | 1,2-oxazinane | Me | H | H | H | H | H | H |
| III-166 | c-Pr | THP-O-NH | Me | H | H | H | H | H | H |
| III-167 | c-Pr | PhO—NH | Me | H | H | H | H | H | H |
| III-168 | c-Pr | BnO—NH | Me | H | H | H | H | H | H |
| III-169 | 1-Me-c-Pr | HO—NH | Me | H | H | H | H | H | H |
| III-170 | 1-Me-c-Pr | HO—N(Me) | Me | H | H | H | H | H | H |
| III-171 | 1-Me-c-Pr | MeO—NH | Me | H | H | H | H | H | H |
| III-172 | 1-Me-c-Pr | MeO—N(Me) | Me | H | H | H | H | H | H |
| III-173 | 1-Me-c-Pr | AllylO—NH | Me | H | H | H | H | H | H |
| III-174 | 1-Me-c-Pr | HO—N(iPr) | Me | H | H | H | H | H | H |
| III-175 | 1-Me-c-Pr | HOCH$_2$CH$_2$O—NH | Me | H | H | H | H | H | H |

TABLE 3-continued

Inventive compounds of the formula (I) in which X represents C(R$^{13}$)(R$^{14}$)

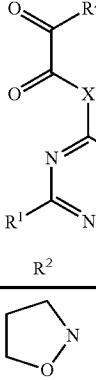
(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-176 | 1-Me-c-Pr |  | Me | H | H | H | H | H | H |
| III-177 | 1-Me-c-Pr | 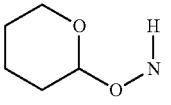 | Me | H | H | H | H | H | H |
| III-178 | 1-Me-c-Pr |  | Me | H | H | H | H | H | H |
| III-179 | 1-Me-c-Pr | PhO—NH | Me | H | H | H | H | H | H |
| III-180 | 1-Me-c-Pr | BnO—NH | Me | H | H | H | H | H | H |
| III-181 | 2-Me-c-Pr | HO—NH | Me | H | H | H | H | H | H |
| III-182 | 2-Me-c-Pr | HO-N(Me) | Me | H | H | H | H | H | H |
| III-183 | 2-Me-c-Pr | MeO—NH | Me | H | H | H | H | H | H |
| III-184 | 2-Me-c-Pr | MeO—N(Me) | Me | H | H | H | H | H | H |
| III-185 | 2-Me-c-Pr | AllylO—NH | Me | H | H | H | H | H | H |
| III-186 | 2-Me-c-Pr | HO—N(iPr) | Me | H | H | H | H | H | H |
| III-187 | 2-Me-c-Pr | HOCH$_2$CH$_2$O—NH | Me | H | H | H | H | H | H |
| III-188 | 2-Me-c-Pr |  | Me | H | H | H | H | H | H |
| III-189 | 2-Me-c-Pr | 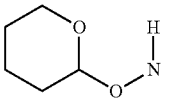 | Me | H | H | H | H | H | H |
| III-190 | 2-Me-c-Pr |  | Me | H | H | H | H | H | H |
| III-191 | 2-Me-c-Pr | PhO—NH | Me | H | H | H | H | H | H |
| III-192 | 2-Me-c-Pr | BnO—NH | Me | H | H | H | H | H | H |
| III-193 | c-Pr | HO—NH | H | Me | H | H | H | H | H |
| III-194 | c-Pr | HO—N(Me) | H | Me | H | H | H | H | H |
| III-195 | c-Pr | MeO—NH | H | Me | H | H | H | H | H |
| III-196 | c-Pr | MeO—N(Me) | H | Me | H | H | H | H | H |
| III-197 | c-Pr | AllylO—NH | H | Me | H | H | H | H | H |
| III-198 | c-Pr | HO—N(iPr) | H | Me | H | H | H | H | H |
| III-199 | c-Pr | HOCH$_2$CH$_2$O—NH | H | Me | H | H | H | H | H |
| III-200 | c-Pr |  | H | Me | H | H | H | H | H |
| III-201 | c-Pr |  | H | Me | H | H | H | H | H |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-202 | c-Pr | (tetrahydropyran-2-yl-O-NH) | H | Me | H | H | H | H | H |
| III-203 | c-Pr | PhO—NH | H | Me | H | H | H | H | H |
| III-204 | c-Pr | BnO—NH | H | Me | H | H | H | H | H |
| III-205 | c-Pr | HO—NH | H | H | Me | H | H | H | H |
| III-206 | c-Pr | HO—N(Me) | H | H | Me | H | H | H | H |
| III-207 | c-Pr | MeO—NH | H | H | Me | H | H | H | H |
| III-208 | c-Pr | MeO—N(Me) | H | H | Me | H | H | H | H |
| III-209 | c-Pr | AllylO—NH | H | H | Me | H | H | H | H |
| III-210 | c-Pr | HO—N(iPr) | H | H | Me | H | H | H | H |
| III-211 | c-Pr | $HOCH_2CH_2O$—NH | H | H | Me | H | H | H | H |
| III-212 | c-Pr | (isoxazolidin-2-yl) | H | H | Me | H | H | H | H |
| III-213 | c-Pr | (1,2-oxazinan-2-yl) | H | H | Me | H | H | H | H |
| III-214 | c-Pr | (tetrahydropyran-2-yl-O-NH) | H | H | Me | H | H | H | H |
| III-215 | c-Pr | PhO—NH | H | H | Me | H | H | H | H |
| III-216 | c-Pr | BnO—NH | H | H | Me | H | H | H | H |
| III-217 | c-Pr | HO—NH | $CF_3$ | H | H | H | H | H | H |
| III-218 | c-Pr | HO—N(Me) | $CF_3$ | H | H | H | H | H | H |
| III-219 | c-Pr | MeO—NH | $CF_3$ | H | H | H | H | H | H |
| III-220 | c-Pr | MeO—N(Me) | $CF_3$ | H | H | H | H | H | H |
| III-221 | c-Pr | AllylO—NH | $CF_3$ | H | H | H | H | H | H |
| III-222 | c-Pr | HO—N(iPr) | $CF_3$ | H | H | H | H | H | H |
| III-223 | c-Pr | $HOCH_2CH_2O$—NH | $CF_3$ | H | H | H | H | H | H |
| III-224 | c-Pr | (isoxazolidin-2-yl) | $CF_3$ | H | H | H | H | H | H |
| III-225 | c-Pr | (1,2-oxazinan-2-yl) | $CF_3$ | H | H | H | H | H | H |
| III-226 | c-Pr | (tetrahydropyran-2-yl-O-NH) | $CF_3$ | H | H | H | H | H | H |
| III-227 | c-Pr | PhO—NH | $CF_3$ | H | H | H | H | H | H |
| III-228 | c-Pr | BnO—NH | $CF_3$ | H | H | H | H | H | H |
| III-229 | 1-Me-c-Pr | HO—NH | $CF_3$ | H | H | H | H | H | H |
| III-230 | 1-Me-c-Pr | HO—N(Me) | $CF_3$ | H | H | H | H | H | H |
| III-231 | 1-Me-c-Pr | MeO—NH | $CF_3$ | H | H | H | H | H | H |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-232 | 1-Me-c-Pr | MeO—N(Me) | $CF_3$ | H | H | H | H | H | H |
| III-233 | 1-Me-c-Pr | AllylO—NH | $CF_3$ | H | H | H | H | H | H |
| III-234 | 1-Me-c-Pr | HO—N(iPr) | $CF_3$ | H | H | H | H | H | H |
| III-235 | 1-Me-c-Pr | $HOCH_2CH_2O$—NH | $CF_3$ | H | H | H | H | H | H |
| III-236 | 1-Me-c-Pr | isoxazolidinyl | $CF_3$ | H | H | H | H | H | H |
| III-237 | 1-Me-c-Pr | 1,2-oxazinanyl | $CF_3$ | H | H | H | H | H | H |
| III-238 | 1-Me-c-Pr | (tetrahydropyran-2-yl)oxy-NH | $CF_3$ | H | H | H | H | H | H |
| III-239 | 1-Me-c-Pr | PhO—NH | $CF_3$ | H | H | H | H | H | H |
| III-240 | 1-Me-c-Pr | BnO—NH | $CF_3$ | H | H | H | H | H | H |
| III-241 | 2-Me-c-Pr | HO—NH | $CF_3$ | H | H | H | H | H | H |
| III-242 | 2-Me-c-Pr | HO—N(Me) | $CF_3$ | H | H | H | H | H | H |
| III-243 | 2-Me-c-Pr | MeO—NH | $CF_3$ | H | H | H | H | H | H |
| III-244 | 2-Me-c-Pr | MeO—N(Me) | $CF_3$ | H | H | H | H | H | H |
| III-245 | 2-Me-c-Pr | AllylO—NH | $CF_3$ | H | H | H | H | H | H |
| III-246 | 2-Me-c-Pr | HO—N(iPr) | $CF_3$ | H | H | H | H | H | H |
| III-247 | 2-Me-c-Pr | $HOCH_2CH_2O$-NH | $CF_3$ | H | H | H | H | H | H |
| III-248 | 2-Me-c-Pr | isoxazolidinyl | $CF_3$ | H | H | H | H | H | H |
| III-249 | 2-Me-c-Pr | 1,2-oxazinanyl | $CF_3$ | H | H | H | H | H | H |
| III-250 | 2-Me-c-Pr | (tetrahydropyran-2-yl)oxy-NH | $CF_3$ | H | H | H | H | H | H |
| III-251 | 2-Me-c-Pr | PhO—NH | $CF_3$ | H | H | H | H | H | H |
| III-252 | 2-Me-c-Pr | BnO—NH | $CF_3$ | H | H | H | H | H | H |
| III-253 | c-Pr | HO—NH | H | $CF_3$ | H | H | H | H | H |
| III-254 | c-Pr | HO—N(Me) | H | $CF_3$ | H | H | H | H | H |
| III-255 | c-Pr | MeO—NH | H | $CF_3$ | H | H | H | H | H |
| III-256 | c-Pr | MeO—N(Me) | H | $CF_3$ | H | H | H | H | H |
| III-257 | c-Pr | AllylO—NH | H | $CF_3$ | H | H | H | H | H |
| III-258 | c-Pr | HO—N(iPr) | H | $CF_3$ | H | H | H | H | H |
| III-259 | c-Pr | $HOCH_2CH_2O$—NH | H | $CF_3$ | H | H | H | H | H |
| III-260 | c-Pr | isoxazolidinyl | H | $CF_3$ | H | H | H | H | H |

TABLE 3-continued

Inventive compounds of the formula (I) in which X represents C(R$^{13}$)(R$^{14}$)

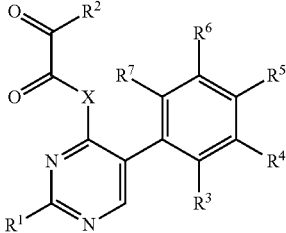

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-261 | c-Pr | 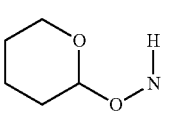 | H | CF$_3$ | H | H | H | H | H |
| III-262 | c-Pr |  | H | CF$_3$ | H | H | H | H | H |
| III-263 | c-Pr | PhO—NH | H | CF$_3$ | H | H | H | H | H |
| III-264 | c-Pr | BnO—NH | H | CF$_3$ | H | H | H | H | H |
| III-265 | c-Pr | HO—NH | H | H | CF$_3$ | H | H | H | H |
| III-266 | c-Pr | HO—N(Me) | H | H | CF$_3$ | H | H | H | H |
| III-267 | c-Pr | MeO—NH | H | H | CF$_3$ | H | H | H | H |
| III-268 | c-Pr | MeO—N(Me) | H | H | CF$_3$ | H | H | H | H |
| III-269 | c-Pr | AllylO—NH | H | H | CF$_3$ | H | H | H | H |
| III-270 | c-Pr | HO—N(iPr) | H | H | CF$_3$ | H | H | H | H |
| III-271 | c-Pr | HOCH$_2$CH$_2$O—NH | H | H | CF$_3$ | H | H | H | H |
| III-272 | c-Pr | 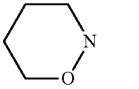 | H | H | CF$_3$ | H | H | H | H |
| III-273 | c-Pr | 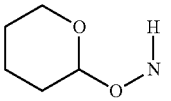 | H | H | CF$_3$ | H | H | H | H |
| III-274 | c-Pr |  | H | H | CF$_3$ | H | H | H | H |
| III-275 | c-Pr | PhO—NH | H | H | CF$_3$ | H | H | H | H |
| III-276 | c-Pr | BnO—NH | H | H | CF$_3$ | H | H | H | H |
| III-277 | c-Pr | HO—NH | MeO | H | H | H | H | H | H |
| III-278 | c-Pr | HO—N(Me) | MeO | H | H | H | H | H | H |
| III-279 | c-Pr | MeO—NH | MeO | H | H | H | H | H | H |
| III-280 | c-Pr | MeO—N(Me) | MeO | H | H | H | H | H | H |
| III-281 | c-Pr | AllylO—NH | MeO | H | H | H | H | H | H |
| III-282 | c-Pr | HO—N(iPr) | MeO | H | H | H | H | H | H |
| III-283 | c-Pr | HOCH$_2$CH$_2$O—NH | MeO | H | H | H | H | H | H |
| III-284 | c-Pr | 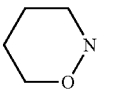 | MeO | H | H | H | H | H | H |
| III-285 | c-Pr | 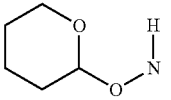 | MeO | H | H | H | H | H | H |
| III-286 | c-Pr |  | MeO | H | H | H | H | H | H |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-287 | c-Pr | PhO—NH | MeO | H | H | H | H | H | H |
| III-288 | c-Pr | BnO—NH | MeO | H | H | H | H | H | H |
| III-289 | 1-Me-c-Pr | HO—NH | MeO | H | H | H | H | H | H |
| III-290 | 1-Me-c-Pr | HO—N(Me) | MeO | H | H | H | H | H | H |
| III-291 | 1-Me-c-Pr | MeO—NH | MeO | H | H | H | H | H | H |
| III-292 | 1-Me-c-Pr | MeO—N(Me) | MeO | H | H | H | H | H | H |
| III-293 | 1-Me-c-Pr | AllylO—NH | MeO | H | H | H | H | H | H |
| III-294 | 1-Me-c-Pr | HO—N(iPr) | MeO | H | H | H | H | H | H |
| III-295 | 1-Me-c-Pr | HOCH$_2$CH$_2$O—NH | MeO | H | H | H | H | H | H |
| III-296 | 1-Me-c-Pr | (isoxazolidine) | MeO | H | H | H | H | H | H |
| III-297 | 1-Me-c-Pr | (1,2-oxazinane) | MeO | H | H | H | H | H | H |
| III-298 | 1-Me-c-Pr | (tetrahydropyranyloxy-NH) | MeO | H | H | H | H | H | H |
| III-299 | 1-Me-c-Pr | PhO—NH | MeO | H | H | H | H | H | H |
| III-300 | 1-Me-c-Pr | BnO—NH | MeO | H | H | H | H | H | H |
| III-301 | c-Pr | HO—NH | H | MeO | H | H | H | H | H |
| III-302 | c-Pr | HO—N(Me) | H | MeO | H | H | H | H | H |
| III-303 | c-Pr | MeO—NH | H | MeO | H | H | H | H | H |
| III-304 | c-Pr | MeO—N(Me) | H | MeO | H | H | H | H | H |
| III-305 | c-Pr | AllylO—NH | H | MeO | H | H | H | H | H |
| III-306 | c-Pr | HO—N(iPr) | H | MeO | H | H | H | H | H |
| III-307 | c-Pr | HOCH$_2$CH$_2$O—NH | H | MeO | H | H | H | H | H |
| III-308 | c-Pr | (isoxazolidine) | H | MeO | H | H | H | H | H |
| III-309 | c-Pr | (1,2-oxazinane) | H | MeO | H | H | H | H | H |
| III-310 | c-Pr | (tetrahydropyranyloxy-NH) | H | MeO | H | H | H | H | H |
| III-311 | c-Pr | PhO—NH | H | MeO | H | H | H | H | H |
| III-312 | c-Pr | BnO—NH | H | MeO | H | H | H | H | H |
| III-313 | c-Pr | HO—NH | H | H | MeO | H | H | H | H |
| III-314 | c-Pr | HO—N(Me) | H | H | MeO | H | H | H | H |
| III-315 | c-Pr | MeO—NH | H | H | MeO | H | H | H | H |
| III-316 | c-Pr | MeO—N(Me) | H | H | MeO | H | H | H | H |
| III-317 | c-Pr | AllylO—NH | H | H | MeO | H | H | H | H |
| III-318 | c-Pr | HO—N(iPr) | H | H | MeO | H | H | H | H |
| III-319 | c-Pr | HOCH$_2$CH$_2$O—NH | H | H | MeO | H | H | H | H |

TABLE 3-continued

Inventive compounds of the formula (I) in which X represents C(R¹³)(R¹⁴)

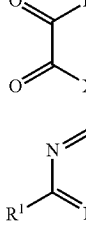

(I)

| No. | R¹ | R² | R³ | R⁴ | R⁵ | R⁶ | R⁷ | R¹³ | R¹⁴ |
|---|---|---|---|---|---|---|---|---|---|
| III-320 | c-Pr |  | H | H | MeO | H | H | H | H |
| III-321 | c-Pr | 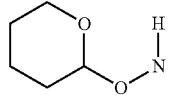 | H | H | MeO | H | H | H | H |
| III-322 | c-Pr |  | H | H | MeO | H | H | H | H |
| III-323 | c-Pr | PhO—NH | H | H | MeO | H | H | H | H |
| III-324 | c-Pr | BnO—NH | H | H | MeO | H | H | H | H |
| III-325 | c-Pr | HO—NH | F | F | H | H | H | H | H |
| III-326 | c-Pr | HO—N(Me) | F | F | H | H | H | H | H |
| III-327 | c-Pr | MeO—NH | F | F | H | H | H | H | H |
| III-328 | c-Pr | MeO—N(Me) | F | F | H | H | H | H | H |
| III-329 | c-Pr | AllylO—NH | F | F | H | H | H | H | H |
| III-330 | c-Pr | HO—N(iPr) | F | F | H | H | H | H | H |
| III-331 | c-Pr | HOCH₂CH₂O—NH | F | F | H | H | H | H | H |
| III-332 | c-Pr |  | F | F | H | H | H | H | H |
| III-333 | c-Pr | 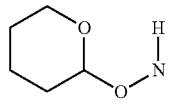 | F | F | H | H | H | H | H |
| III-334 | c-Pr |  | F | F | H | H | H | H | H |
| III-335 | c-Pr | PhO—NH | F | F | H | H | H | H | H |
| III-336 | c-Pr | BnO—NH | F | F | H | H | H | H | H |
| III-337 | c-Pr | HO—NH | F | H | F | H | H | H | H |
| III-338 | c-Pr | HO—N(Me) | F | H | F | H | H | H | H |
| III-339 | c-Pr | MeO—NH | F | H | F | H | H | H | H |
| III-340 | c-Pr | MeO—N(Me) | F | H | F | H | H | H | H |
| III-341 | c-Pr | AllylO—NH | F | H | F | H | H | H | H |
| III-342 | c-Pr | HO—N(iPr) | F | H | F | H | H | H | H |
| III-343 | c-Pr | HOCH₂CH₂O—NH | F | H | F | H | H | H | H |
| III-344 | c-Pr |  | F | H | F | H | H | H | H |
| III-345 | c-Pr |  | F | H | F | H | H | H | H |

TABLE 3-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-346 | c-Pr | (tetrahydropyran-2-yl)-O-NH | F | H | F | H | H | H | H |
| III-347 | c-Pr | PhO—NH | F | H | F | H | H | H | H |
| III-348 | c-Pr | BnO—NH | F | H | F | H | H | H | H |
| III-349 | c-Pr | HO—NH | F | H | H | F | H | H | H |
| III-350 | c-Pr | HO—N(Me) | F | H | H | F | H | H | H |
| III-351 | c-Pr | MeO—NH | F | H | H | F | H | H | H |
| III-352 | c-Pr | MeO—N(Me) | F | H | H | F | H | H | H |
| III-353 | c-Pr | AllylO—NH | F | H | H | F | H | H | H |
| III-354 | c-Pr | HO—N(iPr) | F | H | H | F | H | H | H |
| III-355 | c-Pr | HOCH$_2$CH$_2$O—NH | F | H | H | F | H | H | H |
| III-356 | c-Pr | isoxazolidine | F | H | H | F | H | H | H |
| III-357 | c-Pr | 1,2-oxazinane | F | H | H | F | H | H | H |
| III-358 | c-Pr | (tetrahydropyran-2-yl)-O-NH | F | H | H | F | H | H | H |
| III-359 | c-Pr | PhO—NH | F | H | H | F | H | H | H |
| III-360 | c-Pr | BnO—NH | F | H | H | F | H | H | H |
| III-361 | c-Pr | HO—NH | F | H | H | H | F | H | H |
| III-362 | c-Pr | HO—N(Me) | F | H | H | H | F | H | H |
| III-363 | c-Pr | MeO—NH | F | H | H | H | F | H | H |
| III-364 | c-Pr | MeO—N(Me) | F | H | H | H | F | H | H |
| III-365 | c-Pr | AllylO—NH | F | H | H | H | F | H | H |
| III-366 | c-Pr | HO—N(iPr) | F | H | H | H | F | H | H |
| III-367 | c-Pr | HOCH$_2$CH$_2$O—NH | F | H | H | H | F | H | H |
| III-368 | c-Pr | isoxazolidine | F | H | H | H | F | H | H |
| III-369 | c-Pr | 1,2-oxazinane | F | H | H | H | F | H | H |
| III-370 | c-Pr | (tetrahydropyran-2-yl)-O-NH | F | H | H | H | F | H | H |
| III-371 | c-Pr | PhO—NH | F | H | H | H | F | H | H |
| III-372 | c-Pr | BnO—NH | F | H | H | H | F | H | H |
| III-373 | c-Pr | HO—NH | F | Cl | H | H | H | H | H |
| III-374 | c-Pr | HO—N(Me) | F | Cl | H | H | H | H | H |
| III-375 | c-Pr | MeO—NH | F | Cl | H | H | H | H | H |

TABLE 3-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-376 | c-Pr | MeO—N(Me) | F | Cl | H | H | H | H | H |
| III-377 | c-Pr | AllylO—NH | F | Cl | H | H | H | H | H |
| III-378 | c-Pr | HO—N(iPr) | F | Cl | H | H | H | H | H |
| III-379 | c-Pr | HOCH$_2$CH$_2$O—NH | F | Cl | H | H | H | H | H |
| III-380 | c-Pr | isoxazolidinyl | F | Cl | H | H | H | H | H |
| III-381 | c-Pr | 1,2-oxazinanyl | F | Cl | H | H | H | H | H |
| III-382 | c-Pr | THP-O-NH | F | Cl | H | H | H | H | H |
| III-383 | c-Pr | PhO—NH | F | Cl | H | H | H | H | H |
| III-384 | c-Pr | BnO—NH | F | Cl | H | H | H | H | H |
| III-385 | c-Pr | HO—NH | F | H | Cl | H | H | H | H |
| III-386 | c-Pr | HO—N(Me) | F | H | Cl | H | H | H | H |
| III-387 | c-Pr | MeO—NH | F | H | Cl | H | H | H | H |
| III-388 | c-Pr | MeO—N(Me) | F | H | Cl | H | H | H | H |
| III-389 | c-Pr | AllylO—NH | F | H | Cl | H | H | H | H |
| III-390 | c-Pr | HO—N(iPr) | F | H | Cl | H | H | H | H |
| III-391 | c-Pr | HOCH$_2$CH$_2$O—NH | F | H | Cl | H | H | H | H |
| III-392 | c-Pr | isoxazolidinyl | F | H | Cl | H | H | H | H |
| III-393 | c-Pr | 1,2-oxazinanyl | F | H | Cl | H | H | H | H |
| III-394 | c-Pr | THP-O-NH | F | H | Cl | H | H | H | H |
| III-395 | c-Pr | PhO—NH | F | H | Cl | H | H | H | H |
| III-396 | c-Pr | BnO—NH | F | H | Cl | H | H | H | H |
| III-397 | c-Pr | HO—NH | F | H | H | Cl | H | H | H |
| III-398 | c-Pr | HO—N(Me) | F | H | H | Cl | H | H | H |
| III-399 | c-Pr | MeO—NH | F | H | H | Cl | H | H | H |
| III-400 | c-Pr | MeO—N(Me) | F | H | H | Cl | H | H | H |
| III-401 | c-Pr | AllylO—NH | F | H | H | Cl | H | H | H |
| III-402 | c-Pr | HO—N(iPr) | F | H | H | Cl | H | H | H |
| III-403 | c-Pr | HOCH$_2$CH$_2$O—NH | F | H | H | Cl | H | H | H |
| III-404 | c-Pr | isoxazolidinyl | F | H | H | Cl | H | H | H |

TABLE 3-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-405 | c-Pr | 1,2-oxazinane | F | H | H | Cl | H | H | H |
| III-406 | c-Pr | (tetrahydropyran-2-yl)oxy-NH | F | H | H | Cl | H | H | H |
| III-407 | c-Pr | PhO—NH | F | H | H | Cl | H | H | H |
| III-408 | c-Pr | BnO—NH | F | H | H | Cl | H | H | H |
| III-409 | c-Pr | HO—NH | F | H | H | H | Cl | H | H |
| III-410 | c-Pr | HO—N(Me) | F | H | H | H | Cl | H | H |
| III-411 | c-Pr | MeO—NH | F | H | H | H | Cl | H | H |
| III-412 | c-Pr | MeO—N(Me) | F | H | H | H | Cl | H | H |
| III-413 | c-Pr | AllylO—NH | F | H | H | H | Cl | H | H |
| III-414 | c-Pr | HO—N(iPr) | F | H | H | H | Cl | H | H |
| III-415 | c-Pr | HOCH$_2$CH$_2$O—NH | F | H | H | H | Cl | H | H |
| III-416 | c-Pr | isoxazolidine | F | H | H | H | Cl | H | H |
| III-417 | c-Pr | 1,2-oxazinane | F | H | H | H | Cl | H | H |
| III-418 | c-Pr | (tetrahydropyran-2-yl)oxy-NH | F | H | H | H | Cl | H | H |
| III-419 | c-Pr | PhO—NH | F | H | H | H | Cl | H | H |
| III-420 | c-Pr | BnO—NH | F | H | H | H | Cl | H | H |
| III-421 | c-Pr | HO—NH | F | MeO | H | H | H | H | H |
| III-422 | c-Pr | HO—N(Me) | F | MeO | H | H | H | H | H |
| III-423 | c-Pr | MeO—NH | F | MeO | H | H | H | H | H |
| III-424 | c-Pr | MeO—N(Me) | F | MeO | H | H | H | H | H |
| III-425 | c-Pr | AllylO—NH | F | MeO | H | H | H | H | H |
| III-426 | c-Pr | HO—N(iPr) | F | MeO | H | H | H | H | H |
| III-427 | c-Pr | HOCH$_2$CH$_2$O—NH | F | MeO | H | H | H | H | H |
| III-428 | c-Pr | isoxazolidine | F | MeO | H | H | H | H | H |
| III-429 | c-Pr | 1,2-oxazinane | F | MeO | H | H | H | H | H |
| III-430 | c-Pr | (tetrahydropyran-2-yl)oxy-NH | F | MeO | H | H | H | H | H |

TABLE 3-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-431 | c-Pr | PhO—NH | F | MeO | H | H | H | H | H |
| III-432 | c-Pr | BnO—NH | F | MeO | H | H | H | H | H |
| III-433 | c-Pr | HO—NH | F | H | MeO | H | H | H | H |
| III-434 | c-Pr | HO—N(Me) | F | H | MeO | H | H | H | H |
| III-435 | c-Pr | MeO—NH | F | H | MeO | H | H | H | H |
| III-436 | c-Pr | MeO—N(Me) | F | H | MeO | H | H | H | H |
| III-437 | c-Pr | AllylO—NH | F | H | MeO | H | H | H | H |
| III-438 | c-Pr | HO—N(iPr) | F | H | MeO | H | H | H | H |
| III-439 | c-Pr | HOCH$_2$CH$_2$O—NH | F | H | MeO | H | H | H | H |
| III-440 | c-Pr | isoxazolidinyl | F | H | MeO | H | H | H | H |
| III-441 | c-Pr | 1,2-oxazinanyl | F | H | MeO | H | H | H | H |
| III-442 | c-Pr | tetrahydropyran-2-yl-O-NH | F | H | MeO | H | H | H | H |
| III-443 | c-Pr | PhO—NH | F | H | MeO | H | H | H | H |
| III-444 | c-Pr | BnO—NH | F | H | MeO | H | H | H | H |
| III-445 | c-Pr | HO—NH | F | H | H | MeO | H | H | H |
| III-446 | c-Pr | HO—N(Me) | F | H | H | MeO | H | H | H |
| III-447 | c-Pr | MeO—NH | F | H | H | MeO | H | H | H |
| III-448 | c-Pr | MeO—N(Me) | F | H | H | MeO | H | H | H |
| III-449 | c-Pr | AllylO—NH | F | H | H | MeO | H | H | H |
| III-450 | c-Pr | HO—N(iPr) | F | H | H | MeO | H | H | H |
| III-451 | c-Pr | HOCH$_2$CH$_2$O—NH | F | H | H | MeO | H | H | H |
| III-452 | c-Pr | isoxazolidinyl | F | H | H | MeO | H | H | H |
| III-453 | c-Pr | 1,2-oxazinanyl | F | H | H | MeO | H | H | H |
| III-454 | c-Pr | tetrahydropyran-2-yl-O-NH | F | H | H | MeO | H | H | H |
| III-455 | c-Pr | PhO—NH | F | H | H | MeO | H | H | H |
| III-456 | c-Pr | BnO—NH | F | H | H | MeO | H | H | H |
| III-457 | c-Pr | HO—NH | F | H | H | H | MeO | H | H |
| III-458 | c-Pr | HO—N(Me) | F | H | H | H | MeO | H | H |
| III-459 | c-Pr | MeO—NH | F | H | H | H | MeO | H | H |
| III-460 | c-Pr | MeO—N(Me) | F | H | H | H | MeO | H | H |
| III-461 | c-Pr | AllylO—NH | F | H | H | H | MeO | H | H |
| III-462 | c-Pr | HO—N(iPr) | F | H | H | H | MeO | H | H |
| III-463 | c-Pr | HOCH$_2$CH$_2$O—NH | F | H | H | H | MeO | H | H |

TABLE 3-continued

Inventive compounds of the formula (I) in which X represents C(R¹³)(R¹⁴)

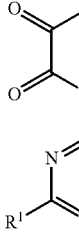

| No. | R¹ | R² | R³ | R⁴ | R⁵ | R⁶ | R⁷ | R¹³ | R¹⁴ |
|---|---|---|---|---|---|---|---|---|---|
| III-464 | c-Pr |  | F | H | H | H | MeO | H | H |
| III-465 | c-Pr | 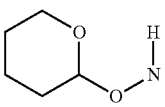 | F | H | H | H | MeO | H | H |
| III-466 | c-Pr |  | F | H | H | H | MeO | H | H |
| III-467 | c-Pr | PhO—NH | F | H | H | H | MeO | H | H |
| III-468 | c-Pr | BnO—NH | F | H | H | H | MeO | H | H |
| III-469 | c-Pr | HO—NH | Cl | F | H | H | H | H | H |
| III-470 | c-Pr | HO—N(Me) | Cl | F | H | H | H | H | H |
| III-471 | c-Pr | MeO—NH | Cl | F | H | H | H | H | H |
| III-472 | c-Pr | MeO—N(Me) | Cl | F | H | H | H | H | H |
| III-473 | c-Pr | AllylO—NH | Cl | F | H | H | H | H | H |
| III-474 | c-Pr | HO—N(iPr) | Cl | F | H | H | H | H | H |
| III-475 | c-Pr | HOCH₂CH₂O—NH | Cl | F | H | H | H | H | H |
| III-476 | c-Pr |  | Cl | F | H | H | H | H | H |
| III-477 | c-Pr | 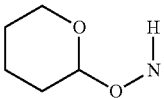 | Cl | F | H | H | H | H | H |
| III-478 | c-Pr |  | Cl | F | H | H | H | H | H |
| III-479 | c-Pr | PhO—NH | Cl | F | H | H | H | H | H |
| III-480 | c-Pr | BnO—NH | Cl | F | H | H | H | H | H |
| III-481 | c-Pr | HO—NH | Cl | H | F | H | H | H | H |
| III-482 | c-Pr | HO—N(Me) | Cl | H | F | H | H | H | H |
| III-483 | c-Pr | MeO—NH | Cl | H | F | H | H | H | H |
| III-484 | c-Pr | MeO—N(Me) | Cl | H | F | H | H | H | H |
| III-485 | c-Pr | AllylO—NH | Cl | H | F | H | H | H | H |
| III-486 | c-Pr | HO—N(iPr) | Cl | H | F | H | H | H | H |
| III-487 | c-Pr | HOCH₂CH₂O—NH | Cl | H | F | H | H | H | H |
| III-488 | c-Pr |  | Cl | H | F | H | H | H | H |
| III-489 | c-Pr |  | Cl | H | F | H | H | H | H |

TABLE 3-continued

Inventive compounds of the formula (I) in which X represents C(R¹³)(R¹⁴)

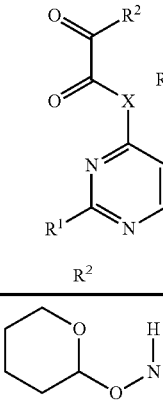

| No. | R¹ | R² | R³ | R⁴ | R⁵ | R⁶ | R⁷ | R¹³ | R¹⁴ |
|---|---|---|---|---|---|---|---|---|---|
| III-490 | c-Pr | 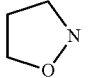 | CL | H | F | H | H | H | H |
| III-491 | c-Pr | PhO—NH | Cl | H | F | H | H | H | H |
| III-492 | c-Pr | BnO—NH | Cl | H | F | H | H | H | H |
| III-493 | c-Pr | HO—NH | Cl | H | H | F | H | H | H |
| III-494 | c-Pr | HO—N(Me) | Cl | H | H | F | H | H | H |
| III-495 | c-Pr | MeO—NH | Cl | H | H | F | H | H | H |
| III-496 | c-Pr | MeO—N(Me) | Cl | H | H | F | H | H | H |
| III-497 | c-Pr | AllylO—NH | Cl | H | H | F | H | H | H |
| III-498 | c-Pr | HO—N(iPr) | Cl | H | H | F | H | H | H |
| III-499 | c-Pr | HOCH₂CH₂O—NH | Cl | H | H | F | H | H | H |
| III-500 | c-Pr | 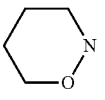 | Cl | H | H | F | H | H | H |
| III-501 | c-Pr | 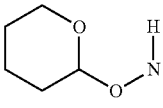 | CL | H | H | F | H | H | H |
| III-502 | c-Pr | 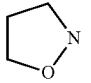 | CL | H | H | F | H | H | H |
| III-503 | c-Pr | PhO—NH | Cl | H | H | F | H | H | H |
| III-504 | c-Pr | BnO—NH | Cl | H | H | F | H | H | H |
| III-505 | c-Pr | HO—NH | Cl | Cl | H | H | H | H | H |
| III-506 | c-Pr | HO—N(Me) | Cl | Cl | H | H | H | H | H |
| III-507 | c-Pr | MeO—NH | Cl | Cl | H | H | H | H | H |
| III-508 | c-Pr | MeO—N(Me) | Cl | Cl | H | H | H | H | H |
| III-509 | c-Pr | AllylO—NH | Cl | Cl | H | H | H | H | H |
| III-510 | c-Pr | HO—N(iPr) | Cl | Cl | H | H | H | H | H |
| III-511 | c-Pr | HOCH₂CH₂O—NH | Cl | Cl | H | H | H | H | H |
| III-512 | c-Pr | 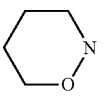 | Cl | Cl | H | H | H | H | H |
| III-513 | c-Pr | 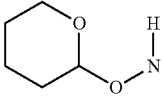 | Cl | Cl | H | H | H | H | H |
| III-514 | c-Pr |  | Cl | Cl | H | H | H | H | H |
| III-515 | c-Pr | PhO—NH | Cl | Cl | H | H | H | H | H |
| III-516 | c-Pr | BnO—NH | Cl | Cl | H | H | H | H | H |
| III-517 | c-Pr | HO—NH | Cl | H | Cl | H | H | H | H |
| III-518 | c-Pr | HO—N(Me) | Cl | H | Cl | H | H | H | H |
| III-519 | c-Pr | MeO—NH | Cl | H | Cl | H | H | H | H |

TABLE 3-continued

Inventive compounds of the formula (I) in which X represents C($R^{13}$) ($R^{14}$)

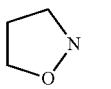

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-520 | c-Pr | MeO—N(Me) | Cl | H | Cl | H | H | H | H |
| III-521 | c-Pr | AllylO—NH | Cl | H | Cl | H | H | H | H |
| III-522 | c-Pr | HO—N(iPr) | Cl | H | Cl | H | H | H | H |
| III-523 | c-Pr | HOCH$_2$CH$_2$O—NH | Cl | H | Cl | H | H | H | H |
| III-524 | c-Pr | 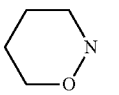 | Cl | H | Cl | H | H | H | H |
| III-525 | c-Pr | 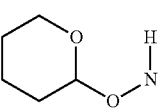 | CL | H | CL | H | H | H | H |
| III-526 | c-Pr | 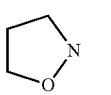 | CL | H | CL | H | H | H | H |
| III-527 | c-Pr | PhO—NH | Cl | H | Cl | H | H | H | H |
| III-528 | c-Pr | BnO—NH | Cl | H | Cl | H | H | H | H |
| III-529 | c-Pr | HO—NH | Cl | H | H | Cl | H | H | H |
| III-530 | c-Pr | HO—N(Me) | Cl | H | H | Cl | H | H | H |
| III-531 | c-Pr | MeO—NH | Cl | H | H | Cl | H | H | H |
| III-532 | c-Pr | MeO—N(Me) | Cl | H | H | Cl | H | H | H |
| III-533 | c-Pr | AllylO—NH | Cl | H | H | Cl | H | H | H |
| III-534 | c-Pr | HO—N(iPr) | Cl | H | H | Cl | H | H | H |
| III-535 | c-Pr | HOCH$_2$CH$_2$O—NH | Cl | H | H | Cl | H | H | H |
| III-536 | c-Pr | 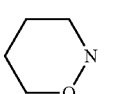 | Cl | H | H | Cl | H | H | H |
| III-537 | c-Pr | 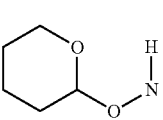 | Cl | H | H | Cl | H | H | H |
| III-538 | c-Pr | 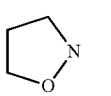 | Cl | H | H | Cl | H | H | H |
| III-539 | c-Pr | PhO—NH | Cl | H | H | Cl | H | H | H |
| III-540 | c-Pr | BnO—NH | Cl | H | H | Cl | H | H | H |
| III-541 | c-Pr | HO—NH | Cl | H | H | H | Cl | H | H |
| III-542 | c-Pr | HO—N(Me) | Cl | H | H | H | Cl | H | H |
| III-543 | c-Pr | MeO—NH | Cl | H | H | H | Cl | H | H |
| III-544 | c-Pr | MeO—N(Me) | Cl | H | H | H | Cl | H | H |
| III-545 | c-Pr | AllylO—NH | Cl | H | H | H | Cl | H | H |
| III-546 | c-Pr | HO—N(iPr) | Cl | H | H | H | Cl | H | H |
| III-547 | c-Pr | HOCH$_2$CH$_2$O—NH | Cl | H | H | H | Cl | H | H |
| III-548 | c-Pr | | Cl | H | H | H | Cl | H | H |

TABLE 3-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-549 | c-Pr | (1,2-oxazinane) | Cl | H | H | H | Cl | H | H |
| III-550 | c-Pr | (tetrahydropyran-2-yl-O-NH) | Cl | H | H | H | Cl | H | H |
| III-551 | c-Pr | PhO—NH | Cl | H | H | H | Cl | H | H |
| III-552 | c-Pr | BnO—NH | Cl | H | H | H | Cl | H | H |
| III-553 | c-Pr | HO—NH | Cl | Me | H | H | H | H | H |
| III-554 | c-Pr | HO—N(Me) | Cl | Me | H | H | H | H | H |
| III-555 | c-Pr | MeO—NH | Cl | Me | H | H | H | H | H |
| III-556 | c-Pr | MeO—N(Me) | Cl | Me | H | H | H | H | H |
| III-557 | c-Pr | AllylO—NH | Cl | Me | H | H | H | H | H |
| III-558 | c-Pr | HO—N(iPr) | Cl | Me | H | H | H | H | H |
| III-559 | c-Pr | HOCH$_2$CH$_2$O—NH | Cl | Me | H | H | H | H | H |
| III-560 | c-Pr | (isoxazolidine) | Cl | Me | H | H | H | H | H |
| III-561 | c-Pr | (1,2-oxazinane) | Cl | Me | H | H | H | H | H |
| III-562 | c-Pr | (tetrahydropyran-2-yl-O-NH) | Cl | Me | H | H | H | H | H |
| III-563 | c-Pr | PhO—NH | Cl | Me | H | H | H | H | H |
| III-564 | c-Pr | BnO—NH | Cl | Me | H | H | H | H | H |
| III-565 | c-Pr | HO—NH | Cl | H | Me | H | H | H | H |
| III-566 | c-Pr | HO—N(Me) | Cl | H | Me | H | H | H | H |
| III-567 | c-Pr | MeO—NH | Cl | H | Me | H | H | H | H |
| III-568 | c-Pr | MeO—N(Me) | Cl | H | Me | H | H | H | H |
| III-569 | c-Pr | AllylO—NH | Cl | H | Me | H | H | H | H |
| III-570 | c-Pr | HO—N(iPr) | Cl | H | Me | H | H | H | H |
| III-571 | c-Pr | HOCH$_2$CH$_2$O—NH | Cl | H | Me | H | H | H | H |
| III-572 | c-Pr | (isoxazolidine) | Cl | H | Me | H | H | H | H |
| III-573 | c-Pr | (1,2-oxazinane) | Cl | H | Me | H | H | H | H |
| III-574 | c-Pr | (tetrahydropyran-2-yl-O-NH) | Cl | H | Me | H | H | H | H |

TABLE 3-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-575 | c-Pr | PhO—NH | Cl | H | Me | H | H | H | H |
| III-576 | c-Pr | BnO—NH | Cl | H | Me | H | H | H | H |
| III-577 | c-Pr | HO—NH | Cl | H | H | Me | H | H | H |
| III-578 | c-Pr | HO—N(Me) | Cl | H | H | Me | H | H | H |
| III-579 | c-Pr | MeO—NH | Cl | H | H | Me | H | H | H |
| III-580 | c-Pr | MeO—N(Me) | Cl | H | H | Me | H | H | H |
| III-581 | c-Pr | AllylO—NH | Cl | H | H | Me | H | H | H |
| III-582 | c-Pr | HO—N(iPr) | Cl | H | H | Me | H | H | H |
| III-583 | c-Pr | HOCH$_2$CH$_2$O—NH | Cl | H | H | Me | H | H | H |
| III-584 | c-Pr | isoxazolidin-2-yl | Cl | H | H | Me | H | H | H |
| III-585 | c-Pr | 1,2-oxazinan-2-yl | Cl | H | H | Me | H | H | H |
| III-586 | c-Pr | (tetrahydropyran-2-yl)oxy-NH | Cl | H | H | Me | H | H | H |
| III-587 | c-Pr | PhO—NH | Cl | H | H | Me | H | H | H |
| III-588 | c-Pr | BnO—NH | Cl | H | H | Me | H | H | H |
| III-589 | c-Pr | HO—NH | Cl | H | H | H | Me | H | H |
| III-590 | c-Pr | HO—N(Me) | Cl | H | H | H | Me | H | H |
| III-591 | c-Pr | MeO—NH | Cl | H | H | H | Me | H | H |
| III-592 | c-Pr | MeO—N(Me) | Cl | H | H | H | Me | H | H |
| III-593 | c-Pr | AllylO—NH | Cl | H | H | H | Me | H | H |
| III-594 | c-Pr | HO—N(iPr) | Cl | H | H | H | Me | H | H |
| III-595 | c-Pr | HOCH$_2$CH$_2$O—NH | Cl | H | H | H | Me | H | H |
| III-596 | c-Pr | isoxazolidin-2-yl | Cl | H | H | H | Me | H | H |
| III-597 | c-Pr | 1,2-oxazinan-2-yl | Cl | H | H | H | Me | H | H |
| III-598 | c-Pr | (tetrahydropyran-2-yl)oxy-NH | Cl | H | H | H | Me | H | H |
| III-599 | c-Pr | PhO—NH | Cl | H | H | H | Me | H | H |
| III-600 | c-Pr | BnO—NH | Cl | H | H | H | Me | H | H |
| III-601 | c-Pr | HO—NH | Cl | MeO | H | H | H | H | H |
| III-602 | c-Pr | HO—N(Me) | Cl | MeO | H | H | H | H | H |
| III-603 | c-Pr | MeO—NH | Cl | MeO | H | H | H | H | H |
| III-604 | c-Pr | MeO—N(Me) | Cl | MeO | H | H | H | H | H |
| III-605 | c-Pr | AllylO—NH | Cl | MeO | H | H | H | H | H |
| III-606 | c-Pr | HO—N(iPr) | Cl | MeO | H | H | H | H | H |
| III-607 | c-Pr | HOCH$_2$CH$_2$O—NH | Cl | MeO | H | H | H | H | H |

TABLE 3-continued

Inventive compounds of the formula (I) in which X represents C(R¹³)(R¹⁴)

| No. | R¹ | R² | R³ | R⁴ | R⁵ | R⁶ | R⁷ | R¹³ | R¹⁴ |
|---|---|---|---|---|---|---|---|---|---|
| III-608 | c-Pr | isoxazolidinyl | Cl | MeO | H | H | H | H | H |
| III-609 | c-Pr | 1,2-oxazinanyl | Cl | MeO | H | H | H | H | H |
| III-610 | c-Pr | (tetrahydropyran-2-yl)O—NH | Cl | MeO | H | H | H | H | H |
| III-611 | c-Pr | PhO—NH | Cl | MeO | H | H | H | H | H |
| III-612 | c-Pr | BnO—NH | Cl | MeO | H | H | H | H | H |
| III-613 | c-Pr | HO—NH | Cl | H | MeO | H | H | H | H |
| III-614 | c-Pr | HO—N(Me) | Cl | H | MeO | H | H | H | H |
| III-615 | c-Pr | MeO—NH | Cl | H | MeO | H | H | H | H |
| III-616 | c-Pr | MeO—N(Me) | Cl | H | MeO | H | H | H | H |
| III-617 | c-Pr | AllylO—NH | Cl | H | MeO | H | H | H | H |
| III-618 | c-Pr | HO—N(iPr) | Cl | H | MeO | H | H | H | H |
| III-619 | c-Pr | HOCH₂CH₂O—NH | Cl | H | MeO | H | H | H | H |
| III-620 | c-Pr | isoxazolidinyl | Cl | H | MeO | H | H | H | H |
| III-621 | c-Pr | 1,2-oxazinanyl | Cl | H | MeO | H | H | H | H |
| III-622 | c-Pr | (tetrahydropyran-2-yl)O—NH | Cl | H | MeO | H | H | H | H |
| III-623 | c-Pr | PhO—NH | Cl | H | MeO | H | H | H | H |
| III-624 | c-Pr | BnO—NH | Cl | H | H | MeO | H | H | H |
| III-625 | c-Pr | HO—NH | Cl | H | H | MeO | H | H | H |
| III-626 | c-Pr | HO—N(Me) | Cl | H | H | MeO | H | H | H |
| III-627 | c-Pr | MeO—NH | Cl | H | H | MeO | H | H | H |
| III-628 | c-Pr | MeO—N(Me) | Cl | H | H | MeO | H | H | H |
| III-629 | c-Pr | AllylO—NH | Cl | H | H | MeO | H | H | H |
| III-630 | c-Pr | HO—N(iPr) | Cl | H | H | MeO | H | H | H |
| III-631 | c-Pr | HOCH₂CH₂O—NH | Cl | H | H | MeO | H | H | H |
| III-632 | c-Pr | isoxazolidinyl | Cl | H | H | MeO | H | H | H |
| III-633 | c-Pr | 1,2-oxazinanyl | Cl | H | H | MeO | H | H | H |

TABLE 3-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-634 | c-Pr | (tetrahydropyran-2-yl)O—NH | Cl | H | H | MeO | H | H | H |
| III-635 | c-Pr | PhO—NH | Cl | H | H | MeO | H | H | H |
| III-636 | c-Pr | BnO—NH | Cl | H | H | MeO | H | H | H |
| III-637 | c-Pr | HO—NH | Cl | H | H | H | MeO | H | H |
| III-638 | c-Pr | HO—N(Me) | Cl | H | H | H | MeO | H | H |
| III-639 | c-Pr | MeO—NH | Cl | H | H | H | MeO | H | H |
| III-640 | c-Pr | MeO—N(Me) | Cl | H | H | H | MeO | H | H |
| III-641 | c-Pr | AllylO—NH | Cl | H | H | H | MeO | H | H |
| III-642 | c-Pr | HO—N(iPr) | Cl | H | H | H | MeO | H | H |
| III-643 | c-Pr | HOCH$_2$CH$_2$O—NH | Cl | H | H | H | MeO | H | H |
| III-644 | c-Pr | isoxazolidinyl | Cl | H | H | H | MeO | H | H |
| III-645 | c-Pr | 1,2-oxazinanyl | Cl | H | H | H | MeO | H | H |
| III-646 | c-Pr | (tetrahydropyran-2-yl)O—NH | Cl | H | H | H | MeO | H | H |
| III-647 | c-Pr | PhO—NH | Cl | H | H | H | MeO | H | H |
| III-648 | c-Pr | BnO—NH | Cl | H | H | H | MeO | H | H |
| III-649 | c-Pr | HO—NH | Me | Me | H | H | H | H | H |
| III-650 | c-Pr | HO—N(Me) | Me | Me | H | H | H | H | H |
| III-651 | c-Pr | MeO—NH | Me | Me | H | H | H | H | H |
| III-652 | c-Pr | MeO—N(Me) | Me | Me | H | H | H | H | H |
| III-653 | c-Pr | AllylO—NH | Me | Me | H | H | H | H | H |
| III-654 | c-Pr | HO—N(iPr) | Me | Me | H | H | H | H | H |
| III-655 | c-Pr | HOCH$_2$CH$_2$O—NH | Me | Me | H | H | H | H | H |
| III-656 | c-Pr | isoxazolidinyl | Me | Me | H | H | H | H | H |
| III-657 | c-Pr | 1,2-oxazinanyl | Me | Me | H | H | H | H | H |
| III-658 | c-Pr | (tetrahydropyran-2-yl)O—NH | Me | Me | H | H | H | H | H |
| III-659 | c-Pr | PhO—NH | Me | Me | H | H | H | H | H |
| III-660 | c-Pr | BnO—NH | Me | Me | H | H | H | H | H |
| III-661 | c-Pr | HO—NH | Me | H | Me | H | H | H | H |
| III-662 | c-Pr | HO—N(Me) | Me | H | Me | H | H | H | H |
| III-663 | c-Pr | MeO—NH | Me | H | Me | H | H | H | H |

TABLE 3-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| III-664 | c-Pr | MeO—N(Me) | Me | H | Me | H | H | H | H |
| III-665 | c-Pr | AllylO—NH | Me | H | Me | H | H | H | H |
| III-666 | c-Pr | HO—N(iPr) | Me | H | Me | H | H | H | H |
| III-667 | c-Pr | HOCH₂CH₂O—NH | Me | H | Me | H | H | H | H |
| III-668 | c-Pr | (isoxazolidine) | Me | H | Me | H | H | H | H |
| III-669 | c-Pr | (1,2-oxazinane) | Me | H | Me | H | H | H | H |
| III-670 | c-Pr | (THP-O-NH) | Me | H | Me | H | H | H | H |
| III-671 | c-Pr | PhO—NH | Me | H | Me | H | H | H | H |
| III-672 | c-Pr | BnO—NH | Me | H | Me | H | H | H | H |
| III-673 | c-Pr | HO—NH | Me | H | H | Me | H | H | H |
| III-674 | c-Pr | HO—N(Me) | Me | H | H | Me | H | H | H |
| III-675 | c-Pr | MeO—NH | Me | H | H | Me | H | H | H |
| III-676 | c-Pr | MeO—N(Me) | Me | H | H | Me | H | H | H |
| III-677 | c-Pr | AllylO—NH | Me | H | H | Me | H | H | H |
| III-678 | c-Pr | HO—N(iPr) | Me | H | H | Me | H | H | H |
| III-679 | c-Pr | HOCH₂CH₂O—NH | Me | H | H | Me | H | H | H |
| III-680 | c-Pr | (isoxazolidine) | Me | H | H | Me | H | H | H |
| III-681 | c-Pr | (1,2-oxazinane) | Me | H | H | Me | H | H | H |
| III-682 | c-Pr | (THP-O-NH) | Me | H | H | Me | H | H | H |
| III-683 | c-Pr | PhO—NH | Me | H | H | Me | H | H | H |
| III-684 | c-Pr | BnO—NH | Me | H | H | Me | H | H | H |
| III-685 | c-Pr | HO—NH | Me | H | H | H | Me | H | H |
| III-686 | c-Pr | HO—N(Me) | Me | H | H | H | Me | H | H |
| III-687 | c-Pr | MeO—NH | Me | H | H | H | Me | H | H |
| III-688 | c-Pr | MeO—N(Me) | Me | H | H | H | Me | H | H |
| III-689 | c-Pr | AllylO—NH | Me | H | H | H | Me | H | H |
| III-690 | c-Pr | HO—N(iPr) | Me | H | H | H | Me | H | H |
| III-691 | c-Pr | HOCH₂CH₂O—NH | Me | H | H | H | Me | H | H |
| III-692 | c-Pr | (isoxazolidine) | Me | H | H | H | Me | H | H |

TABLE 3-continued

Inventive compounds of the formula (I) in which X represents C(R¹³)(R¹⁴)

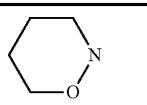
(I)

| No. | R¹ | R² | R³ | R⁴ | R⁵ | R⁶ | R⁷ | R¹³ | R¹⁴ |
|---|---|---|---|---|---|---|---|---|---|
| III-693 | c-Pr | 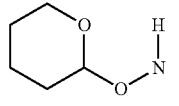 | Me | H | H | H | Me | H | H |
| III-694 | c-Pr | 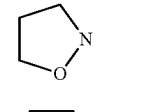 | Me | H | H | H | Me | H | H |
| III-695 | c-Pr | PhO—NH | Me | H | H | H | Me | H | H |
| III-696 | c-Pr | BnO—NH | Me | H | H | H | Me | H | H |
| III-697 | c-Pr | HO—NH | $CF_3$ | F | H | H | H | H | H |
| III-698 | c-Pr | HO—N(Me) | $CF_3$ | F | H | H | H | H | H |
| III-699 | c-Pr | MeO—NH | $CF_3$ | F | H | H | H | H | H |
| III-700 | c-Pr | MeO—N(Me) | $CF_3$ | F | H | H | H | H | H |
| III-701 | c-Pr | AllylO—NH | $CF_3$ | F | H | H | H | H | H |
| III-702 | c-Pr | HO—N(iPr) | $CF_3$ | F | H | H | H | H | H |
| III-703 | c-Pr | $HOCH_2CH_2O$—NH | $CF_3$ | F | H | H | H | H | H |
| III-704 | c-Pr | 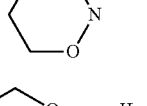 | $CF_3$ | F | H | H | H | H | H |
| III-705 | c-Pr | 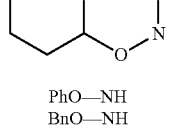 | $CF_3$ | F | H | H | H | H | H |
| III-706 | c-Pr | 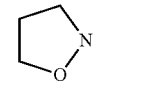 | $CF_3$ | F | H | H | H | H | H |
| III-707 | c-Pr | PhO—NH | $CF_3$ | F | H | H | H | H | H |
| III-708 | c-Pr | BnO—NH | $CF_3$ | F | H | H | H | H | H |
| III-709 | c-Pr | HO—NH | $CF_3$ | H | F | H | H | H | H |
| III-710 | c-Pr | HO—N(Me) | $CF_3$ | H | F | H | H | H | H |
| III-711 | c-Pr | MeO—NH | $CF_3$ | H | F | H | H | H | H |
| III-712 | c-Pr | MeO—N(Me) | $CF_3$ | H | F | H | H | H | H |
| III-713 | c-Pr | AllylO—NH | $CF_3$ | H | F | H | H | H | H |
| III-714 | c-Pr | HO—N(iPr) | $CF_3$ | H | F | H | H | H | H |
| III-715 | c-Pr | $HOCH_2CH_2O$—NH | $CF_3$ | H | F | H | H | H | H |
| III-716 | c-Pr | 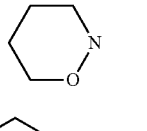 | $CF_3$ | H | F | H | H | H | H |
| III-717 | c-Pr | 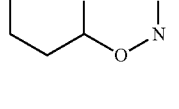 | $CF_3$ | H | F | H | H | H | H |
| III-718 | c-Pr |  | $CF_3$ | H | F | H | H | H | H |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-719 | c-Pr | PhO—NH | $CF_3$ | H | F | H | H | H | H |
| III-720 | c-Pr | BnO—NH | $CF_3$ | H | F | H | H | H | H |
| III-721 | c-Pr | HO—NH | $CF_3$ | H | H | F | H | H | H |
| III-722 | c-Pr | HO—N(Me) | $CF_3$ | H | H | F | H | H | H |
| III-723 | c-Pr | MeO—NH | $CF_3$ | H | H | F | H | H | H |
| III-724 | c-Pr | MeO—N(Me) | $CF_3$ | H | H | F | H | H | H |
| III-725 | c-Pr | AllylO—NH | $CF_3$ | H | H | F | H | H | H |
| III-726 | c-Pr | HO—N(iPr) | $CF_3$ | H | H | F | H | H | H |
| III-727 | c-Pr | $HOCH_2CH_2O$—NH | $CF_3$ | H | H | F | H | H | H |
| III-728 | c-Pr | isoxazolidine | $CF_3$ | H | H | F | H | H | H |
| III-729 | c-Pr | 1,2-oxazinane | $CF_3$ | H | H | F | H | H | H |
| III-730 | c-Pr | THP-O-NH | $CF_3$ | H | H | F | H | H | H |
| III-731 | c-Pr | PhO—NH | $CF_3$ | H | H | F | H | H | H |
| III-732 | c-Pr | BnO—NH | $CF_3$ | H | H | F | H | H | H |
| III-733 | c-Pr | HO—NH | $CF_3$ | H | H | H | F | H | H |
| III-734 | c-Pr | HO—N(Me) | $CF_3$ | H | H | H | F | H | H |
| III-735 | c-Pr | MeO—NH | $CF_3$ | H | H | H | F | H | H |
| III-736 | c-Pr | MeO—N(Me) | $CF_3$ | H | H | H | F | H | H |
| III-737 | c-Pr | AllylO—NH | $CF_3$ | H | H | H | F | H | H |
| III-738 | c-Pr | HO—N(iPr) | $CF_3$ | H | H | H | F | H | H |
| III-739 | c-Pr | $HOCH_2CH_2O$—NH | $CF_3$ | H | H | H | F | H | H |
| III-740 | c-Pr | isoxazolidine | $CF_3$ | H | H | H | F | H | H |
| III-741 | c-Pr | 1,2-oxazinane | $CF_3$ | H | H | H | F | H | H |
| III-742 | c-Pr | THP-O-NH | $CF_3$ | H | H | H | F | H | H |
| III-743 | c-Pr | PhO—NH | $CF_3$ | H | H | H | F | H | H |
| III-744 | c-Pr | BnO—NH | $CF_3$ | H | H | H | F | H | H |
| III-745 | c-Pr | HO—NH | $CF_3$ | Cl | H | H | H | H | H |
| III-746 | c-Pr | HO—N(Me) | $CF_3$ | Cl | H | H | H | H | H |
| III-747 | c-Pr | MeO—NH | $CF_3$ | Cl | H | H | H | H | H |
| III-748 | c-Pr | MeO—N(Me) | $CF_3$ | Cl | H | H | H | H | H |
| III-749 | c-Pr | AllylO—NH | $CF_3$ | Cl | H | H | H | H | H |
| III-750 | c-Pr | HO—N(iPr) | $CF_3$ | Cl | H | H | H | H | H |
| III-751 | c-Pr | $HOCH_2CH_2O$—NH | $CF_3$ | Cl | H | H | H | H | H |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-752 | c-Pr | isoxazolidine | $CF_3$ | Cl | H | H | H | H | H |
| III-753 | c-Pr | 1,2-oxazinane | $CF_3$ | Cl | H | H | H | H | H |
| III-754 | c-Pr | (tetrahydropyran-2-yl)oxy-NH | $CF_3$ | Cl | H | H | H | H | H |
| III-755 | c-Pr | PhO—NH | $CF_3$ | Cl | H | H | H | H | H |
| III-756 | c-Pr | BnO—NH | $CF_3$ | Cl | H | H | H | H | H |
| III-757 | c-Pr | HO—NH | $CF_3$ | H | Cl | H | H | H | H |
| III-758 | c-Pr | HO—N(Me) | $CF_3$ | H | Cl | H | H | H | H |
| III-759 | c-Pr | MeO—NH | $CF_3$ | H | Cl | H | H | H | H |
| III-760 | c-Pr | MeO—N(Me) | $CF_3$ | H | Cl | H | H | H | H |
| III-761 | c-Pr | AllylO—NH | $CF_3$ | H | Cl | H | H | H | H |
| III-762 | c-Pr | HO—N(iPr) | $CF_3$ | H | Cl | H | H | H | H |
| III-763 | c-Pr | $HOCH_2CH_2O$—NH | $CF_3$ | H | Cl | H | H | H | H |
| III-764 | c-Pr | isoxazolidine | $CF_3$ | H | Cl | H | H | H | H |
| III-765 | c-Pr | 1,2-oxazinane | $CF_3$ | H | Cl | H | H | H | H |
| III-766 | c-Pr | (tetrahydropyran-2-yl)oxy-NH | $CF_3$ | H | Cl | H | H | H | H |
| III-767 | c-Pr | PhO—NH | $CF_3$ | H | Cl | H | H | H | H |
| III-768 | c-Pr | BnO—NH | $CF_3$ | H | Cl | H | H | H | H |
| III-769 | c-Pr | HO—NH | $CF_3$ | H | H | Cl | H | H | H |
| III-770 | c-Pr | HO—N(Me) | $CF_3$ | H | H | Cl | H | H | H |
| III-771 | c-Pr | MeO—NH | $CF_3$ | H | H | Cl | H | H | H |
| III-772 | c-Pr | MeO—N(Me) | $CF_3$ | H | H | Cl | H | H | H |
| III-773 | c-Pr | AllylO—NH | $CF_3$ | H | H | Cl | H | H | H |
| III-774 | c-Pr | HO—N(iPr) | $CF_3$ | H | H | Cl | H | H | H |
| III-775 | c-Pr | $HOCH_2CH_2O$—NH | $CF_3$ | H | H | Cl | H | H | H |
| III-776 | c-Pr | isoxazolidine | $CF_3$ | H | H | Cl | H | H | H |
| III-777 | c-Pr | 1,2-oxazinane | $CF_3$ | H | H | Cl | H | H | H |

TABLE 3-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-778 | c-Pr | tetrahydropyran-2-yl-O-NH | CF$_3$ | H | H | Cl | H | H | H |
| III-779 | c-Pr | PhO—NH | CF$_3$ | H | H | Cl | H | H | H |
| III-780 | c-Pr | BnO—NH | CF$_3$ | H | H | Cl | H | H | H |
| III-781 | c-Pr | HO—NH | CF$_3$ | H | H | H | Cl | H | H |
| III-782 | c-Pr | HO—N(Me) | CF$_3$ | H | H | H | Cl | H | H |
| III-783 | c-Pr | MeO—NH | CF$_3$ | H | H | H | Cl | H | H |
| III-784 | c-Pr | MeO—N(Me) | CF$_3$ | H | H | H | Cl | H | H |
| III-785 | c-Pr | AllylO—NH | CF$_3$ | H | H | H | Cl | H | H |
| III-786 | c-Pr | HO—N(iPr) | CF$_3$ | H | H | H | Cl | H | H |
| III-787 | c-Pr | HOCH$_2$CH$_2$O—NH | CF$_3$ | H | H | H | Cl | H | H |
| III-788 | c-Pr | isoxazolidinyl | CF$_3$ | H | H | H | Cl | H | H |
| III-789 | c-Pr | 1,2-oxazinanyl | CF$_3$ | H | H | H | Cl | H | H |
| III-790 | c-Pr | tetrahydropyran-2-yl-O-NH | CF$_3$ | H | H | H | Cl | H | H |
| III-791 | c-Pr | PhO—NH | CF$_3$ | H | H | H | Cl | H | H |
| III-792 | c-Pr | BnO—NH | CF$_3$ | H | H | H | Cl | H | H |
| III-793 | c-Pr | HO—NH | Cl | F | H | H | Cl | H | H |
| III-794 | c-Pr | HO—N(Me) | Cl | F | H | H | Cl | H | H |
| III-795 | c-Pr | MeO—NH | Cl | F | H | H | Cl | H | H |
| III-796 | c-Pr | MeO—N(Me) | Cl | F | H | H | Cl | H | H |
| III-797 | c-Pr | AllylO—NH | Cl | F | H | H | Cl | H | H |
| III-798 | c-Pr | HO—N(iPr) | Cl | F | H | H | Cl | H | H |
| III-799 | c-Pr | HOCH$_2$CH$_2$O—NH | Cl | F | H | H | Cl | H | H |
| III-800 | c-Pr | isoxazolidinyl | Cl | F | H | H | Cl | H | H |
| III-801 | c-Pr | 1,2-oxazinanyl | Cl | F | H | H | Cl | H | H |
| III-802 | c-Pr | tetrahydropyran-2-yl-O-NH | Cl | F | H | H | Cl | H | H |
| III-803 | c-Pr | PhO—NH | Cl | F | H | H | Cl | H | H |
| III-804 | c-Pr | BnO—NH | Cl | F | H | H | Cl | H | H |
| III-805 | c-Pr | HO—NH | Cl | H | F | H | Cl | H | H |
| III-806 | c-Pr | HO—N(Me) | Cl | H | F | H | Cl | H | H |
| III-807 | c-Pr | MeO—NH | Cl | H | F | H | Cl | H | H |

TABLE 3-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-808 | c-Pr | MeO—N(Me) | Cl | H | F | H | Cl | H | H |
| III-809 | c-Pr | AllylO—NH | Cl | H | F | H | Cl | H | H |
| III-810 | c-Pr | HO—N(iPr) | Cl | H | F | H | Cl | H | H |
| III-811 | c-Pr | HOCH$_2$CH$_2$O—NH | Cl | H | F | H | Cl | H | H |
| III-812 | c-Pr | isoxazolidine | Cl | H | F | H | Cl | H | H |
| III-813 | c-Pr | 1,2-oxazinane | Cl | H | F | H | Cl | H | H |
| III-814 | c-Pr | THP-O-NH | Cl | H | F | H | Cl | H | H |
| III-815 | c-Pr | PhO—NH | Cl | H | F | H | Cl | H | H |
| III-816 | c-Pr | BnO—NH | Cl | H | F | H | Cl | H | H |
| III-817 | c-Pr | HO—NH | Cl | H | H | H | Cl | H | H |
| III-818 | c-Pr | HO—N(Me) | Cl | H | H | Cl | Cl | H | H |
| III-819 | c-Pr | MeO—NH | Cl | H | H | Cl | Cl | H | H |
| III-820 | c-Pr | MeO—N(Me) | Cl | H | H | Cl | Cl | H | H |
| III-821 | c-Pr | AllylO—NH | Cl | H | H | Cl | Cl | H | H |
| III-822 | c-Pr | HO—N(iPr) | Cl | H | H | Cl | Cl | H | H |
| III-823 | c-Pr | HOCH$_2$CH$_2$O—NH | Cl | H | H | Cl | Cl | H | H |
| III-824 | c-Pr | isoxazolidine | Cl | H | H | Cl | Cl | H | H |
| III-825 | c-Pr | 1,2-oxazinane | Cl | H | H | Cl | Cl | H | H |
| III-826 | c-Pr | THP-O-NH | Cl | H | H | Cl | Cl | H | H |
| III-827 | c-Pr | PhO—NH | Cl | H | H | Cl | Cl | H | H |
| III-828 | c-Pr | BnO—NH | Cl | H | H | Cl | Cl | H | H |
| III-829 | c-Pr | HO—NH | MeO | H | F | F | H | H | H |
| III-830 | c-Pr | HO—N(Me) | MeO | H | F | F | H | H | H |
| III-831 | c-Pr | MeO—NH | MeO | H | F | F | H | H | H |
| III-832 | c-Pr | MeO—N(Me) | MeO | H | F | F | H | H | H |
| III-833 | c-Pr | AllylO—NH | MeO | H | F | F | H | H | H |
| III-834 | c-Pr | HO—N(iPr) | MeO | H | F | F | H | H | H |
| III-835 | c-Pr | HOCH$_2$CH$_2$O—NH | MeO | H | F | F | H | H | H |
| III-836 | c-Pr | isoxazolidine | MeO | H | F | F | H | H | H |

TABLE 3-continued

Inventive compounds of the formula (I) in which X represents C(R¹³)(R¹⁴)

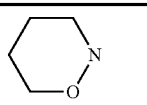

| No. | R¹ | R² | R³ | R⁴ | R⁵ | R⁶ | R⁷ | R¹³ | R¹⁴ |
|---|---|---|---|---|---|---|---|---|---|
| III-837 | c-Pr | 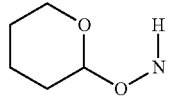 | MeO | H | F | F | H | H | H |
| III-838 | c-Pr | 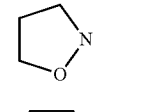 | MeO | H | F | F | H | H | H |
| III-839 | c-Pr | PhO—NH | MeO | H | F | F | H | H | H |
| III-840 | c-Pr | BnO—NH | MeO | H | F | F | H | H | H |
| III-841 | c-Pr | HO—NH | H | H | H | H | H | Me | H |
| III-842 | c-Pr | HO—N(Me) | H | H | H | H | H | Me | H |
| III-843 | c-Pr | MeO—NH | H | H | H | H | H | Me | H |
| III-844 | c-Pr | MeO—N(Me) | H | H | H | H | H | Me | H |
| III-845 | c-Pr | AllylO—NH | H | H | H | H | H | Me | H |
| III-846 | c-Pr | HO—N(iPr) | H | H | H | H | H | Me | H |
| III-847 | c-Pr | HOCH₂CH₂O—NH | H | H | H | H | H | Me | H |
| III-848 | c-Pr | 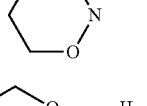 | H | H | H | H | H | Me | H |
| III-849 | c-Pr | 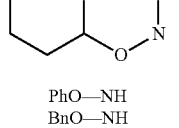 | H | H | H | H | H | Me | H |
| III-850 | c-Pr | 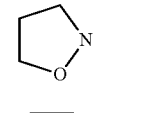 | H | H | H | H | H | Me | H |
| III-851 | c-Pr | PhO—NH | H | H | H | H | H | Me | H |
| III-852 | c-Pr | BnO—NH | H | H | H | H | H | Me | H |
| III-853 | c-Pr | HO—NH | H | H | H | H | H | Me | Me |
| III-854 | c-Pr | HO—N(Me) | H | H | H | H | H | Me | Me |
| III-855 | c-Pr | MeO—NH | H | H | H | H | H | Me | Me |
| III-856 | c-Pr | MeO—N(Me) | H | H | H | H | H | Me | Me |
| III-857 | c-Pr | AllylO—NH | H | H | H | H | H | Me | Me |
| III-858 | c-Pr | HO—N(iPr) | H | H | H | H | H | Me | Me |
| III-859 | c-Pr | HOCH₂CH₂O—NH | H | H | H | H | H | Me | Me |
| III-860 | c-Pr | 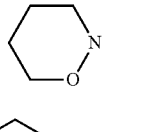 | H | H | H | H | H | Me | Me |
| III-861 | c-Pr | 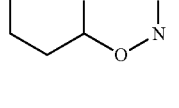 | H | H | H | H | H | Me | Me |
| III-862 | c-Pr |  | H | H | H | H | H | Me | Me |

TABLE 3-continued

Inventive compounds of the formula (I) in which X represents $C(R^{13})(R^{14})$ (I)

[Structure: pyrimidine with R¹ at 2-position, substituted phenyl (R³-R⁷) at 5-position, and N(X)-C(=O)-C(=O)-R² at 4-position]

| No. | R¹ | R² | R³ | R⁴ | R⁵ | R⁶ | R⁷ | R¹³ | R¹⁴ |
|---|---|---|---|---|---|---|---|---|---|
| III-863 | c-Pr | PhO—NH | H | H | H | H | H | Me | Me |
| III-864 | c-Pr | BnO—NH | H | H | H | H | H | Me | Me |
| III-865 | c-Pr | HO—NH | H | H | H | H | H | CO₂Et | H |
| III-866 | c-Pr | HO—N(Me) | H | H | H | H | H | CO₂Et | H |
| III-867 | c-Pr | MeO—NH | H | H | H | H | H | CO₂Et | H |
| III-868 | c-Pr | MeO—N(Me) | H | H | H | H | H | CO₂Et | H |
| III-869 | c-Pr | AllylO—NH | H | H | H | H | H | CO₂Et | H |
| III-870 | c-Pr | HO—N(iPr) | H | H | H | H | H | CO₂Et | H |
| III-871 | c-Pr | HOCH₂CH₂O—NH | H | H | H | H | H | CO₂Et | H |
| III-872 | c-Pr | isoxazolidinyl | H | H | H | H | H | CO₂Et | H |
| III-873 | c-Pr | 1,2-oxazinan-2-yl | H | H | H | H | H | CO₂Et | H |
| III-874 | c-Pr | (tetrahydropyran-2-yl)oxy—NH | H | H | H | H | H | CO₂Et | H |
| III-875 | c-Pr | PhO—NH | H | H | H | H | H | CO₂Et | H |
| III-876 | c-Pr | BnO—NH | H | H | H | H | H | CO₂Et | H |
| III-877 | c-Pr | HO—NH | H | H | H | H | H | CN | H |
| III-878 | c-Pr | HO—N(Me) | H | H | H | H | H | CN | H |
| III-879 | c-Pr | MeO—NH | H | H | H | H | H | CN | H |
| III-880 | c-Pr | MeO—N(Me) | H | H | H | H | H | CN | H |
| III-881 | c-Pr | AllylO—NH | H | H | H | H | H | CN | H |
| III-882 | c-Pr | HO—N(iPr) | H | H | H | H | H | CN | H |
| III-883 | c-Pr | HOCH₂CH₂O—NH | H | H | H | H | H | CN | H |
| III-884 | c-Pr | isoxazolidinyl | H | H | H | H | H | CN | H |
| III-885 | c-Pr | 1,2-oxazinan-2-yl | H | H | H | H | H | CN | H |
| III-886 | c-Pr | (tetrahydropyran-2-yl)oxy—NH | H | H | H | H | H | CN | H |
| III-887 | c-Pr | PhO—NH | H | H | H | H | H | CN | H |
| III-888 | c-Pr | BnO—NH | H | H | H | H | H | CN | H |
| III-889 | c-Pr | HO—NH | F | H | H | H | H | Me | H |
| III-890 | c-Pr | HO—N(Me) | F | H | H | H | H | Me | H |
| III-891 | c-Pr | MeO—NH | F | H | H | H | H | Me | H |
| III-892 | c-Pr | MeO—N(Me) | F | H | H | H | H | Me | H |
| III-893 | c-Pr | AllylO—NH | F | H | H | H | H | Me | H |
| III-894 | c-Pr | HO—N(iPr) | F | H | H | H | H | Me | H |
| III-895 | c-Pr | HOCH₂CH₂O—NH | F | H | H | H | H | Me | H |

TABLE 3-continued

Inventive compounds of the formula (I) in which X represents $C(R^{13})(R^{14})$

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-896 | c-Pr |  | F | H | H | H | H | Me | H |
| III-897 | c-Pr | 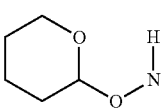 | F | H | H | H | H | Me | H |
| III-898 | c-Pr |  | F | H | H | H | H | Me | H |
| III-899 | c-Pr | PhO—NH | F | H | H | H | H | Me | H |
| III-900 | c-Pr | BnO—NH | F | H | H | H | H | Me | H |
| III-901 | c-Pr | HO—NH | F | H | H | H | H | Me | Me |
| III-902 | c-Pr | HO—N(Me) | F | H | H | H | H | Me | Me |
| III-903 | c-Pr | MeO—NH | F | H | H | H | H | Me | Me |
| III-904 | c-Pr | MeO—N(Me) | F | H | H | H | H | Me | Me |
| III-905 | c-Pr | AllylO—NH | F | H | H | H | H | Me | Me |
| III-906 | c-Pr | HO—N(iPr) | F | H | H | H | H | Me | Me |
| III-907 | c-Pr | HOCH$_2$CH$_2$O—NH | F | H | H | H | H | Me | Me |
| III-908 | c-Pr |  | F | H | H | H | H | Me | Me |
| III-909 | c-Pr | 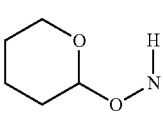 | F | H | H | H | H | Me | Me |
| III-910 | c-Pr |  | F | H | H | H | H | Me | Me |
| III-911 | c-Pr | PhO—NH | F | H | H | H | H | Me | Me |
| III-912 | c-Pr | BnO—NH | F | H | H | H | H | Me | Me |
| III-913 | c-Pr | HO—NH | F | H | H | H | H | CO$_2$Et | H |
| III-914 | c-Pr | HO—N(Me) | F | H | H | H | H | CO$_2$Et | H |
| III-915 | c-Pr | MeO—NH | F | H | H | H | H | CO$_2$Et | H |
| III-916 | c-Pr | MeO—N(Me) | F | H | H | H | H | CO$_2$Et | H |
| III-917 | c-Pr | AllylO—NH | F | H | H | H | H | CO$_2$Et | H |
| III-918 | c-Pr | HO—N(iPr) | F | H | H | H | H | CO$_2$Et | H |
| III-919 | c-Pr | HOCH$_2$CH$_2$O—NH | F | H | H | H | H | CO$_2$Et | H |
| III-920 | c-Pr |  | F | H | H | H | H | CO$_2$Et | H |
| III-921 | c-Pr |  | F | H | H | H | H | CO$_2$Et | H |

TABLE 3-continued

Inventive compounds of the formula (I) in which X represents C(R^13)(R^14)

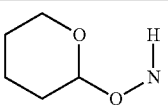

(I)

| No. | R¹ | R² | R³ | R⁴ | R⁵ | R⁶ | R⁷ | R¹³ | R¹⁴ |
|---|---|---|---|---|---|---|---|---|---|
| III-922 | c-Pr | 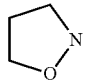 | F | H | H | H | H | CO₂Et | H |
| III-923 | c-Pr | PhO—NH | F | H | H | H | H | CO₂Et | H |
| III-924 | c-Pr | BnO—NH | F | H | H | H | H | CO₂Et | H |
| III-925 | c-Pr | HO—NH | F | H | H | H | H | CN | H |
| III-926 | c-Pr | HO—N(Me) | F | H | H | H | H | CN | H |
| III-927 | c-Pr | MeO—NH | F | H | H | H | H | CN | H |
| III-928 | c-Pr | MeO—N(Me) | F | H | H | H | H | CN | H |
| III-929 | c-Pr | AllylO—NH | F | H | H | H | H | CN | H |
| III-930 | c-Pr | HO—N(iPr) | F | H | H | H | H | CN | H |
| III-931 | c-Pr | HOCH₂CH₂O—NH | F | H | H | H | H | CN | H |
| III-932 | c-Pr | 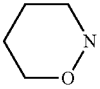 | F | H | H | H | H | CN | H |
| III-933 | c-Pr | 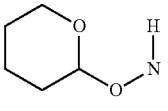 | F | H | H | H | H | CN | H |
| III-934 | c-Pr | 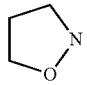 | F | H | H | H | H | CN | H |
| III-935 | c-Pr | PhO—NH | F | H | H | H | H | CN | H |
| III-936 | c-Pr | BnO—NH | F | H | H | H | H | CN | H |
| III-937 | c-Pr | HO—NH | F | F | H | H | H | Me | H |
| III-938 | c-Pr | HO—N(Me) | F | F | H | H | H | Me | H |
| III-939 | c-Pr | MeO—NH | F | F | H | H | H | Me | H |
| III-940 | c-Pr | MeO—N(Me) | F | F | H | H | H | Me | H |
| III-941 | c-Pr | AllylO—NH | F | F | H | H | H | Me | H |
| III-942 | c-Pr | HO—N(iPr) | F | F | H | H | H | Me | H |
| III-943 | c-Pr | HOCH₂CH₂O—NH | F | F | H | H | H | Me | H |
| III-944 | c-Pr |  | F | F | H | H | H | Me | H |
| III-945 | c-Pr | 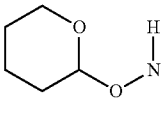 | F | F | H | H | H | Me | H |
| III-946 | c-Pr |  | F | F | H | H | H | Me | H |
| III-947 | c-Pr | PhO—NH | F | F | H | H | H | Me | H |
| III-948 | c-Pr | BnO—NH | F | F | H | H | H | Me | H |
| III-949 | c-Pr | HO—NH | F | F | H | H | H | Me | Me |
| III-950 | c-Pr | HO—N(Me) | F | F | H | H | H | Me | Me |
| III-951 | c-Pr | MeO—NH | F | F | H | H | H | Me | Me |

TABLE 3-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-952 | c-Pr | MeO—N(Me) | F | F | H | H | H | Me | Me |
| III-953 | c-Pr | AllylO—NH | F | F | H | H | H | Me | Me |
| III-954 | c-Pr | HO—N(iPr) | F | F | H | H | H | Me | Me |
| III-955 | c-Pr | HOCH$_2$CH$_2$O—NH | F | F | H | H | H | Me | Me |
| III-956 | c-Pr | (isoxazolidine) | F | F | H | H | H | Me | Me |
| III-957 | c-Pr | (1,2-oxazinane) | F | F | H | H | H | Me | Me |
| III-958 | c-Pr | (THP-O-NH) | F | F | H | H | H | Me | Me |
| III-959 | c-Pr | PhO—NH | F | F | H | H | H | Me | Me |
| III-960 | c-Pr | BnO—NH | F | F | H | H | H | Me | Me |
| III-961 | c-Pr | HO—NH | F | F | H | H | H | CO$_2$Et | H |
| III-962 | c-Pr | HO—N(Me) | F | F | H | H | H | CO$_2$Et | H |
| III-963 | c-Pr | MeO—NH | F | F | H | H | H | CO$_2$Et | H |
| III-964 | c-Pr | MeO—N(Me) | F | F | H | H | H | CO$_2$Et | H |
| III-965 | c-Pr | AllylO—NH | F | F | H | H | H | CO$_2$Et | H |
| III-966 | c-Pr | HO—N(iPr) | F | F | H | H | H | CO$_2$Et | H |
| III-967 | c-Pr | HOCH$_2$CH$_2$O—NH | F | F | H | H | H | CO$_2$Et | H |
| III-968 | c-Pr | (isoxazolidine) | F | F | H | H | H | CO$_2$Et | H |
| III-969 | c-Pr | (1,2-oxazinane) | F | F | H | H | H | CO$_2$Et | H |
| III-970 | c-Pr | (THP-O-NH) | F | F | H | H | H | CO$_2$Et | H |
| III-971 | c-Pr | PhO—NH | F | F | H | H | H | CO$_2$Et | H |
| III-972 | c-Pr | BnO—NH | F | F | H | H | H | CO$_2$Et | H |
| III-973 | c-Pr | HO—NH | F | F | H | H | H | CN | H |
| III-974 | c-Pr | HO—N(Me) | F | F | H | H | H | CN | H |
| III-975 | c-Pr | MeO—NH | F | F | H | H | H | CN | H |
| III-976 | c-Pr | MeO—N(Me) | F | F | H | H | H | CN | H |
| III-977 | c-Pr | AllylO—NH | F | F | H | H | H | CN | H |
| III-978 | c-Pr | HO—N(iPr) | F | F | H | H | H | CN | H |
| III-979 | c-Pr | HOCH$_2$CH$_2$O—NH | F | F | H | H | H | CN | H |
| III-980 | c-Pr | (isoxazolidine) | F | F | H | H | H | CN | H |

TABLE 3-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-981 | c-Pr | (1,2-oxazinane) | F | F | H | H | H | CN | H |
| III-982 | c-Pr | (tetrahydropyran-2-yl-O-NH) | F | F | H | H | H | CN | H |
| III-983 | c-Pr | PhO—NH | F | F | H | H | H | CN | H |
| III-984 | c-Pr | BnO—NH | F | F | H | H | H | CN | H |
| III-985 | c-Pr | HO—NH | F | H | F | H | H | Me | H |
| III-986 | c-Pr | HO—N(Me) | F | H | F | H | H | Me | H |
| III-987 | c-Pr | MeO—NH | F | H | F | H | H | Me | H |
| III-988 | c-Pr | MeO—N(Me) | F | H | F | H | H | Me | H |
| III-989 | c-Pr | AllylO—NH | F | H | F | H | H | Me | H |
| III-990 | c-Pr | HO—N(iPr) | F | H | F | H | H | Me | H |
| III-991 | c-Pr | $HOCH_2CH_2O$—NH | F | H | F | H | H | Me | H |
| III-992 | c-Pr | (isoxazolidine) | F | H | F | H | H | Me | H |
| III-993 | c-Pr | (1,2-oxazinane) | F | H | F | H | H | Me | H |
| III-994 | c-Pr | (tetrahydropyran-2-yl-O-NH) | F | H | F | H | H | Me | H |
| III-995 | c-Pr | PhO—NH | F | H | F | H | H | Me | H |
| III-996 | c-Pr | BnO—NH | F | H | F | H | H | Me | H |
| III-997 | c-Pr | HO—NH | F | H | F | H | H | Me | Me |
| III-998 | c-Pr | HO—N(Me) | F | H | F | H | H | Me | Me |
| III-999 | c-Pr | MeO—NH | F | H | F | H | H | Me | Me |
| III-1000 | c-Pr | MeO—N(Me) | F | H | F | H | H | Me | Me |
| III-1001 | c-Pr | AllylO—NH | F | H | F | H | H | Me | Me |
| III-1002 | c-Pr | HO—N(iPr) | F | H | F | H | H | Me | Me |
| III-1003 | c-Pr | $HOCH_2CH_2O$—NH | F | H | F | H | H | Me | Me |
| III-1004 | c-Pr | (isoxazolidine) | F | H | F | H | H | Me | Me |
| III-1005 | c-Pr | (1,2-oxazinane) | F | H | F | H | H | Me | Me |
| III-1006 | c-Pr | (tetrahydropyran-2-yl-O-NH) | F | H | F | H | H | Me | Me |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-1007 | c-Pr | PhO—NH | F | H | F | H | H | Me | Me |
| III-1008 | c-Pr | BnO—NH | F | H | F | H | H | Me | Me |
| III-1009 | c-Pr | HO—NH | F | H | F | H | H | $CO_2Et$ | H |
| III-1010 | c-Pr | HO—N(Me) | F | H | F | H | H | $CO_2Et$ | H |
| III-1011 | c-Pr | MeO—NH | F | H | F | H | H | $CO_2Et$ | H |
| III-1012 | c-Pr | MeO—N(Me) | F | H | F | H | H | $CO_2Et$ | H |
| III-1013 | c-Pr | AllylO—NH | F | H | F | H | H | $CO_2Et$ | H |
| III-1014 | c-Pr | HO—N(iPr) | F | H | F | H | H | $CO_2Et$ | H |
| III-1015 | c-Pr | $HOCH_2CH_2O$—NH | F | H | F | H | H | $CO_2Et$ | H |
| III-1016 | c-Pr | (isoxazolidine) | F | H | F | H | H | $CO_2Et$ | H |
| III-1017 | c-Pr | (1,2-oxazinane) | F | H | F | H | H | $CO_2Et$ | H |
| III-1018 | c-Pr | (tetrahydropyranyl-O-NH) | F | H | F | H | H | $CO_2Et$ | H |
| III-1019 | c-Pr | PhO—NH | F | H | F | H | H | $CO_2Et$ | H |
| III-1020 | c-Pr | BnO—NH | F | H | F | H | H | $CO_2Et$ | H |
| III-1021 | c-Pr | HO—NH | F | H | F | H | H | CN | H |
| III-1022 | c-Pr | HO—N(Me) | F | H | F | H | H | CN | H |
| III-1023 | c-Pr | MeO—NH | F | H | F | H | H | CN | H |
| III-1024 | c-Pr | MeO—N(Me) | F | H | F | H | H | CN | H |
| III-1025 | c-Pr | AllylO—NH | F | H | F | H | H | CN | H |
| III-1026 | c-Pr | HO—N(iPr) | F | H | F | H | H | CN | H |
| III-1027 | c-Pr | $HOCH_2CH_2O$—NH | F | H | F | H | H | CN | H |
| III-1028 | c-Pr | (isoxazolidine) | F | H | F | H | H | CN | H |
| III-1029 | c-Pr | (1,2-oxazinane) | F | H | F | H | H | CN | H |
| III-1030 | c-Pr | (tetrahydropyranyl-O-NH) | F | H | F | H | H | CN | H |
| III-1031 | c-Pr | PhO—NH | F | H | F | H | H | CN | H |
| III-1032 | c-Pr | BnO—NH | F | H | F | H | H | CN | H |
| III-1033 | c-Pr | HO—NH | F | H | H | F | H | Me | H |
| III-1034 | c-Pr | HO—N(Me) | F | H | H | F | H | Me | H |
| III-1035 | c-Pr | MeO—NH | F | H | H | F | H | Me | H |
| III-1036 | c-Pr | MeO—N(Me) | F | H | H | F | H | Me | H |
| III-1037 | c-Pr | AllylO—NH | F | H | H | F | H | Me | H |
| III-1038 | c-Pr | HO—N(iPr) | F | H | H | F | H | Me | H |
| III-1039 | c-Pr | $HOCH_2CH_2O$—NH | F | H | H | F | H | Me | H |

TABLE 3-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| III-1040 | c-Pr | isoxazolidine (5-membered N-O ring) | F | H | H | F | H | Me | H |
| III-1041 | c-Pr | 1,2-oxazinane (6-membered N-O ring) | F | H | H | F | H | Me | H |
| III-1042 | c-Pr | tetrahydropyran-2-yl-O-NH | F | H | H | F | H | Me | H |
| III-1043 | c-Pr | PhO—NH | F | H | H | F | H | Me | H |
| III-1044 | c-Pr | BnO—NH | F | H | H | F | H | Me | H |
| III-1045 | c-Pr | HO—NH | F | H | H | F | H | Me | Me |
| III-1046 | c-Pr | HO—N(Me) | F | H | H | F | H | Me | Me |
| III-1047 | c-Pr | MeO—NH | F | H | H | F | H | Me | Me |
| III-1048 | c-Pr | MeO—N(Me) | F | H | H | F | H | Me | Me |
| III-1049 | c-Pr | AllylO—NH | F | H | H | F | H | Me | Me |
| III-1050 | c-Pr | HO—N(iPr) | F | H | H | F | H | Me | Me |
| III-1051 | c-Pr | HOCH$_2$CH$_2$O—NH | F | H | H | F | H | Me | Me |
| III-1052 | c-Pr | isoxazolidine (5-membered N-O ring) | F | H | H | F | H | Me | Me |
| III-1053 | c-Pr | 1,2-oxazinane (6-membered N-O ring) | F | H | H | F | H | Me | Me |
| III-1054 | c-Pr | tetrahydropyran-2-yl-O-NH | F | H | H | F | H | Me | Me |
| III-1055 | c-Pr | PhO—NH | F | H | H | F | H | Me | Me |
| III-1056 | c-Pr | BnO—NH | F | H | H | F | H | Me | Me |
| III-1057 | c-Pr | HO—NH | F | H | H | F | H | CO$_2$Et | H |
| III-1058 | c-Pr | HO—N(Me) | F | H | H | F | H | CO$_2$Et | H |
| III-1059 | c-Pr | MeO—NH | F | H | H | F | H | CO$_2$Et | H |
| III-1060 | c-Pr | MeO—N(Me) | F | H | H | F | H | CO$_2$Et | H |
| III-1061 | c-Pr | AllylO—NH | F | H | H | F | H | CO$_2$Et | H |
| III-1062 | c-Pr | HO—N(iPr) | F | H | H | F | H | CO$_2$Et | H |
| III-1063 | c-Pr | HOCH$_2$CH$_2$O—NH | F | H | H | F | H | CO$_2$Et | H |
| III-1064 | c-Pr | isoxazolidine (5-membered N-O ring) | F | H | H | F | H | CO$_2$Et | H |
| III-1065 | c-Pr | 1,2-oxazinane (6-membered N-O ring) | F | H | H | F | H | CO$_2$Et | H |

TABLE 3-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1066 | c-Pr | (tetrahydropyran-2-yl)-O-NH- | F | H | H | F | H | CO$_2$Et | H |
| III-1067 | c-Pr | PhO—NH | F | H | H | F | H | CO$_2$Et | H |
| III-1068 | c-Pr | BnO—NH | F | H | H | F | H | CO$_2$Et | H |
| III-1069 | c-Pr | HO—NH | F | H | H | F | H | CN | H |
| III-1070 | c-Pr | HO—N(Me) | F | H | H | F | H | CN | H |
| III-1071 | c-Pr | MeO—NH | F | H | H | F | H | CN | H |
| III-1072 | c-Pr | MeO—N(Me) | F | H | H | F | H | CN | H |
| III-1073 | c-Pr | AllylO—NH | F | H | H | F | H | CN | H |
| III-1074 | c-Pr | HO—N(iPr) | F | H | H | F | H | CN | H |
| III-1075 | c-Pr | HOCH$_2$CH$_2$O—NH | F | H | H | F | H | CN | H |
| III-1076 | c-Pr | isoxazolidin-2-yl | F | H | H | F | H | CN | H |
| III-1077 | c-Pr | 1,2-oxazinan-2-yl | F | H | H | F | H | CN | H |
| III-1078 | c-Pr | (tetrahydropyran-2-yl)-O-NH- | F | H | H | F | H | CN | H |
| III-1079 | c-Pr | PhO—NH | F | H | H | F | H | CN | H |
| III-1080 | c-Pr | BnO—NH | F | H | H | F | H | CN | H |
| III-1081 | c-Pr | HO—NH | F | H | H | H | F | Me | H |
| III-1082 | c-Pr | HO—N(Me) | F | H | H | H | F | Me | H |
| III-1083 | c-Pr | MeO—NH | F | H | H | H | F | Me | H |
| III-1084 | c-Pr | MeO—N(Me) | F | H | H | H | F | Me | H |
| III-1085 | c-Pr | AllylO—NH | F | H | H | H | F | Me | H |
| III-1086 | c-Pr | HO—N(iPr) | F | H | H | H | F | Me | H |
| III-1087 | c-Pr | HOCH$_2$CH$_2$O—NH | F | H | H | H | F | Me | H |
| III-1088 | c-Pr | isoxazolidin-2-yl | F | H | H | H | F | Me | H |
| III-1089 | c-Pr | 1,2-oxazinan-2-yl | F | H | H | H | F | Me | H |
| III-1090 | c-Pr | (tetrahydropyran-2-yl)-O-NH- | F | H | H | H | F | Me | H |
| III-1091 | c-Pr | PhO—NH | F | H | H | H | F | Me | H |
| III-1092 | c-Pr | BnO—NH | F | H | H | H | F | Me | H |
| III-1093 | c-Pr | HO—NH | F | H | H | H | F | Me | Me |
| III-1094 | c-Pr | HO—N(Me) | F | H | H | H | F | Me | Me |
| III-1095 | c-Pr | MeO—NH | F | H | H | H | F | Me | Me |

TABLE 3-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1096 | c-Pr | MeO—N(Me) | F | H | H | H | F | Me | Me |
| III-1097 | c-Pr | AllylO—NH | F | H | H | H | F | Me | Me |
| III-1098 | c-Pr | HO—N(iPr) | F | H | H | H | F | Me | Me |
| III-1099 | c-Pr | HOCH$_2$CH$_2$O—NH | F | H | H | H | F | Me | Me |
| III-1100 | c-Pr | (isoxazolidine) | F | H | H | H | F | Me | Me |
| III-1101 | c-Pr | (1,2-oxazinane) | F | H | H | H | F | Me | Me |
| III-1102 | c-Pr | (THP-O-NH) | F | H | H | H | F | Me | Me |
| III-1103 | c-Pr | PhO—NH | F | H | H | H | F | Me | Me |
| III-1104 | c-Pr | BnO—NH | F | H | H | H | F | Me | Me |
| III-1105 | c-Pr | HO—NH | F | H | H | H | F | CO$_2$Et | H |
| III-1106 | c-Pr | HO—N(Me) | F | H | H | H | F | CO$_2$Et | H |
| III-1107 | c-Pr | MeO—NH | F | H | H | H | F | CO$_2$Et | H |
| III-1108 | c-Pr | MeO—N(Me) | F | H | H | H | F | CO$_2$Et | H |
| III-1109 | c-Pr | AllylO—NH | F | H | H | H | F | CO$_2$Et | H |
| III-1110 | c-Pr | HO—N(iPr) | F | H | H | H | F | CO$_2$Et | H |
| III-1111 | c-Pr | HOCH$_2$CH$_2$O—NH | F | H | H | H | F | CO$_2$Et | H |
| III-1112 | c-Pr | (isoxazolidine) | F | H | H | H | F | CO$_2$Et | H |
| III-1113 | c-Pr | (1,2-oxazinane) | F | H | H | H | F | CO$_2$Et | H |
| III-1114 | c-Pr | (THP-O-NH) | F | H | H | H | F | CO$_2$Et | H |
| III-1115 | c-Pr | PhO—NH | F | H | H | H | F | CO$_2$Et | H |
| III-1116 | c-Pr | BnO—NH | F | H | H | H | F | CO$_2$Et | H |
| III-1117 | c-Pr | HO—NH | F | H | H | H | F | CN | H |
| III-1118 | c-Pr | HO—N(Me) | F | H | H | H | F | CN | H |
| III-1119 | c-Pr | MeO—NH | F | H | H | H | F | CN | H |
| III-1120 | c-Pr | MeO—N(Me) | F | H | H | H | F | CN | H |
| III-1121 | c-Pr | AllylO—NH | F | H | H | H | F | CN | H |
| III-1122 | c-Pr | HO—N(iPr) | F | H | H | H | F | CN | H |
| III-1123 | c-Pr | HOCH$_2$CH$_2$O—NH | F | H | H | H | F | CN | H |
| III-1124 | c-Pr | (isoxazolidine) | F | H | H | H | F | CN | H |

TABLE 3-continued

Inventive compounds of the formula (I) in which X represents C(R$^{13}$) (R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1125 | c-Pr | (1,2-oxazinane) | F | H | H | H | F | CN | H |
| III-1126 | c-Pr | (tetrahydropyranyl-O-NH) | F | H | H | H | F | CN | H |
| III-1127 | c-Pr | PhO—NH | F | H | H | H | F | CN | H |
| III-1128 | c-Pr | BnO—NH | F | H | H | H | F | CN | H |
| III-1129 | c-Pr | HO—NH | Cl | F | H | H | H | Me | H |
| III-1130 | c-Pr | HO—N(Me) | Cl | F | H | H | H | Me | H |
| III-1131 | c-Pr | MeO—NH | Cl | F | H | H | H | Me | H |
| III-1132 | c-Pr | MeO—N(Me) | Cl | F | H | H | H | Me | H |
| III-1133 | c-Pr | AllylO—NH | Cl | F | H | H | H | Me | H |
| III-1134 | c-Pr | HO—N(iPr) | Cl | F | H | H | H | Me | H |
| III-1135 | c-Pr | HOCH$_2$CH$_2$O—NH | Cl | F | H | H | H | Me | H |
| III-1136 | c-Pr | (isoxazolidine) | Cl | F | H | H | H | Me | H |
| III-1137 | c-Pr | (1,2-oxazinane) | Cl | F | H | H | H | Me | H |
| III-1138 | c-Pr | (tetrahydropyranyl-O-NH) | Cl | F | H | H | H | Me | H |
| III-1139 | c-Pr | PhO—NH | Cl | F | H | H | H | Me | H |
| III-1140 | c-Pr | BnO—NH | Cl | F | H | H | H | Me | H |
| III-1141 | c-Pr | HO—NH | Cl | F | H | H | H | Me | Me |
| III-1142 | c-Pr | HO—N(Me) | Cl | F | H | H | H | Me | Me |
| III-1143 | c-Pr | MeO—NH | Cl | F | H | H | H | Me | Me |
| III-1144 | c-Pr | MeO—N(Me) | Cl | F | H | H | H | Me | Me |
| III-1145 | c-Pr | AllylO—NH | Cl | F | H | H | H | Me | Me |
| III-1146 | c-Pr | HO—N(iPr) | Cl | F | H | H | H | Me | Me |
| III-1147 | c-Pr | HOCH$_2$CH$_2$O—NH | Cl | F | H | H | H | Me | Me |
| III-1148 | c-Pr | (isoxazolidine) | Cl | F | H | H | H | Me | Me |
| III-1149 | c-Pr | (1,2-oxazinane) | Cl | F | H | H | H | Me | Me |
| III-1150 | c-Pr | (tetrahydropyranyl-O-NH) | Cl | F | H | H | H | Me | Me |

TABLE 3-continued

Inventive compounds of the formula (I) in which X represents C(R$^{13}$) (R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1151 | c-Pr | PhO—NH | Cl | F | H | H | H | Me | Me |
| III-1152 | c-Pr | BnO—NH | Cl | F | H | H | H | Me | Me |
| III-1153 | c-Pr | HO—NH | Cl | F | H | H | H | CO$_2$Et | H |
| III-1154 | c-Pr | HO—N(Me) | Cl | F | H | H | H | CO$_2$Et | H |
| III-1155 | c-Pr | MeO—NH | Cl | F | H | H | H | CO$_2$Et | H |
| III-1156 | c-Pr | MeO—N(Me) | Cl | F | H | H | H | CO$_2$Et | H |
| III-1157 | c-Pr | AllylO—NH | Cl | F | H | H | H | CO$_2$Et | H |
| III-1158 | c-Pr | HO—N(iPr) | Cl | F | H | H | H | CO$_2$Et | H |
| III-1159 | c-Pr | HOCH$_2$CH$_2$O—NH | Cl | F | H | H | H | CO$_2$Et | H |
| III-1160 | c-Pr | isoxazolidin-2-yl | Cl | F | H | H | H | CO$_2$Et | H |
| III-1161 | c-Pr | 1,2-oxazinan-2-yl | Cl | F | H | H | H | CO$_2$Et | H |
| III-1162 | c-Pr | (tetrahydropyran-2-yl)O—NH | Cl | F | H | H | H | CO$_2$Et | H |
| III-1163 | c-Pr | PhO—NH | Cl | F | H | H | H | CO$_2$Et | H |
| III-1164 | c-Pr | BnO—NH | Cl | F | H | H | H | CO$_2$Et | H |
| III-1165 | c-Pr | HO—NH | Cl | F | H | H | H | CN | H |
| III-1166 | c-Pr | HO—N(Me) | Cl | F | H | H | H | CN | H |
| III-1167 | c-Pr | MeO—NH | Cl | F | H | H | H | CN | H |
| III-1168 | c-Pr | MeO—N(Me) | Cl | F | H | H | H | CN | H |
| III-1169 | c-Pr | AllylO—NH | Cl | F | H | H | H | CN | H |
| III-1170 | c-Pr | HO—N(iPr) | Cl | F | H | H | H | CN | H |
| III-1171 | c-Pr | HOCH$_2$CH$_2$O—NH | Cl | F | H | H | H | CN | H |
| III-1172 | c-Pr | isoxazolidin-2-yl | Cl | F | H | H | H | CN | H |
| III-1173 | c-Pr | 1,2-oxazinan-2-yl | Cl | F | H | H | H | CN | H |
| III-1174 | c-Pr | (tetrahydropyran-2-yl)O—NH | Cl | F | H | H | H | CN | H |
| III-1175 | c-Pr | PhO—NH | Cl | F | H | H | H | CN | H |
| III-1176 | c-Pr | BnO—NH | Cl | F | H | H | H | CN | H |
| III-1177 | c-Pr | HO—NH | Cl | H | F | H | H | Me | H |
| III-1178 | c-Pr | HO—N(Me) | Cl | H | F | H | H | Me | H |
| III-1179 | c-Pr | MeO—NH | Cl | H | F | H | H | Me | H |
| III-1180 | c-Pr | MeO—N(Me) | Cl | H | F | H | H | Me | H |
| III-1181 | c-Pr | AllylO—NH | Cl | H | F | H | H | Me | H |
| III-1182 | c-Pr | HO—N(iPr) | Cl | H | F | H | H | Me | H |
| III-1183 | c-Pr | HOCH$_2$CH$_2$O—NH | Cl | H | F | H | H | Me | H |

TABLE 3-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| III-1184 | c-Pr | isoxazolidine (5-membered N-O ring) | Cl | H | F | H | H | Me | H |
| III-1185 | c-Pr | 1,2-oxazinane (6-membered N-O ring) | Cl | H | F | H | H | Me | H |
| III-1186 | c-Pr | tetrahydropyran-2-yl-O-NH- | Cl | H | F | H | H | Me | H |
| III-1187 | c-Pr | PhO—NH | Cl | H | F | H | H | Me | H |
| III-1188 | c-Pr | BnO—NH | Cl | H | F | H | H | Me | H |
| III-1189 | c-Pr | HO—NH | Cl | H | F | H | H | Me | Me |
| III-1190 | c-Pr | HO—N(Me) | Cl | H | F | H | H | Me | Me |
| III-1191 | c-Pr | MeO—NH | Cl | H | F | H | H | Me | Me |
| III-1192 | c-Pr | MeO—N(Me) | Cl | H | F | H | H | Me | Me |
| III-1193 | c-Pr | AllylO—NH | Cl | H | F | H | H | Me | Me |
| III-1194 | c-Pr | HO—N(iPr) | Cl | H | F | H | H | Me | Me |
| III-1195 | c-Pr | HOCH₂CH₂O—NH | Cl | H | F | H | H | Me | Me |
| III-1196 | c-Pr | isoxazolidine (5-membered N-O ring) | Cl | H | F | H | H | Me | Me |
| III-1197 | c-Pr | 1,2-oxazinane (6-membered N-O ring) | Cl | H | F | H | H | Me | Me |
| III-1198 | c-Pr | tetrahydropyran-2-yl-O-NH- | Cl | H | F | H | H | Me | Me |
| III-1199 | c-Pr | PhO—NH | Cl | H | F | H | H | Me | Me |
| III-1200 | c-Pr | BnO—NH | Cl | H | F | H | H | Me | Me |
| III-1201 | c-Pr | HO—NH | Cl | H | F | H | H | CO₂Et | H |
| III-1202 | c-Pr | HO—N(Me) | Cl | H | F | H | H | CO₂Et | H |
| III-1203 | c-Pr | MeO—NH | Cl | H | F | H | H | CO₂Et | H |
| III-1204 | c-Pr | MeO—N(Me) | Cl | H | F | H | H | CO₂Et | H |
| III-1205 | c-Pr | AllylO—NH | Cl | H | F | H | H | CO₂Et | H |
| III-1206 | c-Pr | HO—N(iPr) | Cl | H | F | H | H | CO₂Et | H |
| III-1207 | c-Pr | HOCH₂CH₂O—NH | Cl | H | F | H | H | CO₂Et | H |
| III-1208 | c-Pr | isoxazolidine (5-membered N-O ring) | Cl | H | F | H | H | CO₂Et | H |
| III-1209 | c-Pr | 1,2-oxazinane (6-membered N-O ring) | Cl | H | F | H | H | CO₂Et | H |

TABLE 3-continued

Inventive compounds of the formula (I) in which X represents $C(R^{13})(R^{14})$

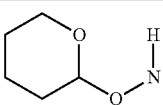

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-1210 | c-Pr |  | Cl | H | F | H | H | CO$_2$Et | H |
| III-1211 | c-Pr | PhO—NH | Cl | H | F | H | H | CO$_2$Et | H |
| III-1212 | c-Pr | BnO—NH | Cl | H | F | H | H | CO$_2$Et | H |
| III-1213 | c-Pr | HO—NH | Cl | H | F | H | H | CN | H |
| III-1214 | c-Pr | HO—N(Me) | Cl | H | F | H | H | CN | H |
| III-1215 | c-Pr | MeO—NH | Cl | H | F | H | H | CN | H |
| III-1216 | c-Pr | MeO—N(Me) | Cl | H | F | H | H | CN | H |
| III-1217 | c-Pr | AllylO—NH | Cl | H | F | H | H | CN | H |
| III-1218 | c-Pr | HO—N(iPr) | Cl | H | F | H | H | CN | H |
| III-1219 | c-Pr | HOCH$_2$CH$_2$O—NH | Cl | H | F | H | H | CN | H |
| III-1220 | c-Pr |  | Cl | H | F | H | H | CN | H |
| III-1221 | c-Pr | 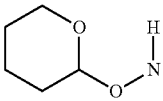 | Cl | H | F | H | H | CN | H |
| III-1222 | c-Pr |  | Cl | H | F | H | H | CN | H |
| III-1223 | c-Pr | PhO—NH | Cl | H | F | H | H | CN | H |
| III-1224 | c-Pr | BnO—NH | Cl | H | F | H | H | CN | H |
| III-1225 | c-Pr | HO—NH | Cl | H | H | F | H | Me | H |
| III-1226 | c-Pr | HO—N(Me) | Cl | H | H | F | H | Me | H |
| III-1227 | c-Pr | MeO—NH | Cl | H | H | F | H | Me | H |
| III-1228 | c-Pr | MeO—N(Me) | Cl | H | H | F | H | Me | H |
| III-1229 | c-Pr | AllylO—NH | Cl | H | H | F | H | Me | H |
| III-1230 | c-Pr | HO—N(iPr) | Cl | H | H | F | H | Me | H |
| III-1231 | c-Pr | HOCH$_2$CH$_2$O—NH | Cl | H | H | F | H | Me | H |
| III-1232 | c-Pr |  | Cl | H | H | F | H | Me | H |
| III-1233 | c-Pr | 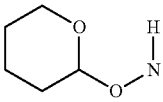 | Cl | H | H | F | H | Me | H |
| III-1234 | c-Pr |  | Cl | H | H | F | H | Me | H |
| III-1235 | c-Pr | PhO—NH | Cl | H | H | F | H | Me | H |
| III-1236 | c-Pr | BnO—NH | Cl | H | H | F | H | Me | H |
| III-1237 | c-Pr | HO—NH | Cl | H | H | F | H | Me | Me |
| III-1238 | c-Pr | HO—N(Me) | Cl | H | H | F | H | Me | Me |
| III-1239 | c-Pr | MeO—NH | Cl | H | H | F | H | Me | Me |

TABLE 3-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-1240 | c-Pr | MeO—N(Me) | Cl | H | H | F | H | Me | Me |
| III-1241 | c-Pr | AllylO—NH | Cl | H | H | F | H | Me | Me |
| III-1242 | c-Pr | HO—N(iPr) | Cl | H | H | F | H | Me | Me |
| III-1243 | c-Pr | HOCH$_2$CH$_2$O—NH | Cl | H | H | F | H | Me | Me |
| III-1244 | c-Pr | isoxazolidinyl | Cl | H | H | F | H | Me | Me |
| III-1245 | c-Pr | 1,2-oxazinanyl | Cl | H | H | F | H | Me | Me |
| III-1246 | c-Pr | THP-O-NH | Cl | H | H | F | H | Me | Me |
| III-1247 | c-Pr | PhO—NH | Cl | H | H | F | H | Me | Me |
| III-1248 | c-Pr | BnO—NH | Cl | H | H | F | H | Me | Me |
| III-1249 | c-Pr | HO—NH | Cl | H | H | F | H | CO$_2$Et | H |
| III-1250 | c-Pr | HO—N(Me) | Cl | H | H | F | H | CO$_2$Et | H |
| III-1251 | c-Pr | MeO—NH | Cl | H | H | F | H | CO$_2$Et | H |
| III-1252 | c-Pr | MeO—N(Me) | Cl | H | H | F | H | CO$_2$Et | H |
| III-1253 | c-Pr | AllylO—NH | Cl | H | H | F | H | CO$_2$Et | H |
| III-1254 | c-Pr | HO—N(iPr) | Cl | H | H | F | H | CO$_2$Et | H |
| III-1255 | c-Pr | HOCH$_2$CH$_2$O—NH | Cl | H | H | F | H | CO$_2$Et | H |
| III-1256 | c-Pr | isoxazolidinyl | Cl | H | H | F | H | CO$_2$Et | H |
| III-1257 | c-Pr | 1,2-oxazinanyl | Cl | H | H | F | H | CO$_2$Et | H |
| III-1258 | c-Pr | THP-O-NH | Cl | H | H | F | H | CO$_2$Et | H |
| III-1259 | c-Pr | PhO—NH | Cl | H | H | F | H | CO$_2$Et | H |
| III-1260 | c-Pr | BnO—NH | Cl | H | H | F | H | CO$_2$Et | H |
| III-1261 | c-Pr | HO—NH | Cl | H | H | F | H | CN | H |
| III-1262 | c-Pr | HO—N(Me) | Cl | H | H | F | H | CN | H |
| III-1263 | c-Pr | MeO—NH | Cl | H | H | F | H | CN | H |
| III-1264 | c-Pr | MeO—N(Me) | Cl | H | H | F | H | CN | H |
| III-1265 | c-Pr | AllylO—NH | Cl | H | H | F | H | CN | H |
| III-1266 | c-Pr | HO—N(iPr) | Cl | H | H | F | H | CN | H |
| III-1267 | c-Pr | HOCH$_2$CH$_2$O—NH | Cl | H | H | F | H | CN | H |
| III-1268 | c-Pr | isoxazolidinyl | Cl | H | H | F | H | CN | H |

TABLE 3-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1269 | c-Pr | (1,2-oxazinane) | Cl | H | H | F | H | CN | H |
| III-1270 | c-Pr | (tetrahydropyran-2-yl-O-NH) | Cl | H | H | F | H | CN | H |
| III-1271 | c-Pr | PhO—NH | Cl | H | H | F | H | CN | H |
| III-1272 | c-Pr | BnO—NH | Cl | H | H | F | H | CN | H |
| III-1273 | c-Pr | HO—NH | Cl | H | H | H | F | Me | H |
| III-1274 | c-Pr | HO—N(Me) | Cl | H | H | H | F | Me | H |
| III-1275 | c-Pr | MeO—NH | Cl | H | H | H | F | Me | H |
| III-1276 | c-Pr | MeO—N(Me) | Cl | H | H | H | F | Me | H |
| III-1277 | c-Pr | AllylO—NH | Cl | H | H | H | F | Me | H |
| III-1278 | c-Pr | HO—N(iPr) | Cl | H | H | H | F | Me | H |
| III-1279 | c-Pr | HOCH$_2$CH$_2$O—NH | Cl | H | H | H | F | Me | H |
| III-1280 | c-Pr | (isoxazolidine) | Cl | H | H | H | F | Me | H |
| III-1281 | c-Pr | (1,2-oxazinane) | Cl | H | H | H | F | Me | H |
| III-1282 | c-Pr | (tetrahydropyran-2-yl-O-NH) | Cl | H | H | H | F | Me | H |
| III-1283 | c-Pr | PhO—NH | Cl | H | H | H | F | Me | H |
| III-1284 | c-Pr | BnO—NH | Cl | H | H | H | F | Me | H |
| III-1285 | c-Pr | HO—NH | Cl | H | H | H | F | Me | Me |
| III-1286 | c-Pr | HO—N(Me) | Cl | H | H | H | F | Me | Me |
| III-1287 | c-Pr | MeO—NH | Cl | H | H | H | F | Me | Me |
| III-1288 | c-Pr | MeO—N(Me) | Cl | H | H | H | F | Me | Me |
| III-1289 | c-Pr | AllylO—NH | Cl | H | H | H | F | Me | Me |
| III-1290 | c-Pr | HO—N(iPr) | Cl | H | H | H | F | Me | Me |
| III-1291 | c-Pr | HOCH$_2$CH$_2$O—NH | Cl | H | H | H | F | Me | Me |
| III-1292 | c-Pr | (isoxazolidine) | Cl | H | H | H | F | Me | Me |
| III-1293 | c-Pr | (1,2-oxazinane) | Cl | H | H | H | F | Me | Me |
| III-1294 | c-Pr | (tetrahydropyran-2-yl-O-NH) | Cl | H | H | H | F | Me | Me |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-1295 | c-Pr | PhO—NH | Cl | H | H | H | F | Me | Me |
| III-1296 | c-Pr | BnO—NH | Cl | H | H | H | F | Me | Me |
| III-1297 | c-Pr | HO—NH | Cl | H | H | H | F | $CO_2Et$ | H |
| III-1298 | c-Pr | HO—N(Me) | Cl | H | H | H | F | $CO_2Et$ | H |
| III-1299 | c-Pr | MeO—NH | Cl | H | H | H | F | $CO_2Et$ | H |
| III-1300 | c-Pr | MeO—N(Me) | Cl | H | H | H | F | $CO_2Et$ | H |
| III-1301 | c-Pr | AllylO—NH | Cl | H | H | H | F | $CO_2Et$ | H |
| III-1302 | c-Pr | HO—N(iPr) | Cl | H | H | H | F | $CO_2Et$ | H |
| III-1303 | c-Pr | $HOCH_2CH_2O$—NH | Cl | H | H | H | F | $CO_2Et$ | H |
| III-1304 | c-Pr | isoxazolidine | Cl | H | H | H | F | $CO_2Et$ | H |
| III-1305 | c-Pr | 1,2-oxazinane | Cl | H | H | H | F | $CO_2Et$ | H |
| III-1306 | c-Pr | tetrahydropyranyl-O-NH | Cl | H | H | H | F | $CO_2Et$ | H |
| III-1307 | c-Pr | PhO—NH | Cl | H | H | H | F | $CO_2Et$ | H |
| III-1308 | c-Pr | BnO—NH | Cl | H | H | H | F | $CO_2Et$ | H |
| III-1309 | c-Pr | HO—NH | Cl | H | H | H | F | CN | H |
| III-1310 | c-Pr | HO—N(Me) | Cl | H | H | H | F | CN | H |
| III-1311 | c-Pr | MeO—NH | Cl | H | H | H | F | CN | H |
| III-1312 | c-Pr | MeO—N(Me) | Cl | H | H | H | F | CN | H |
| III-1313 | c-Pr | AllylO—NH | Cl | H | H | H | F | CN | H |
| III-1314 | c-Pr | HO—N(iPr) | Cl | H | H | H | F | CN | H |
| III-1315 | c-Pr | $HOCH_2CH_2O$—NH | Cl | H | H | H | F | CN | H |
| III-1316 | c-Pr | isoxazolidine | Cl | H | H | H | F | CN | H |
| III-1317 | c-Pr | 1,2-oxazinane | Cl | H | H | H | F | CN | H |
| III-1318 | c-Pr | tetrahydropyranyl-O-NH | Cl | H | H | H | F | CN | H |
| III-1319 | c-Pr | PhO—NH | Cl | H | H | H | F | CN | H |
| III-1320 | c-Pr | BnO—NH | Cl | H | H | H | F | CN | H |
| III-1321 | c-Pr | HO—NH | Cl | Cl | H | H | H | Me | H |
| III-1322 | c-Pr | HO—N(Me) | Cl | Cl | H | H | H | Me | H |
| III-1323 | c-Pr | MeO—NH | Cl | Cl | H | H | H | Me | H |
| III-1324 | c-Pr | MeO—N(Me) | Cl | Cl | H | H | H | Me | H |
| III-1325 | c-Pr | AllylO—NH | Cl | Cl | H | H | H | Me | H |
| III-1326 | c-Pr | HO—N(iPr) | Cl | Cl | H | H | H | Me | H |
| III-1327 | c-Pr | $HOCH_2CH_2O$—NH | Cl | Cl | H | H | H | Me | H |

TABLE 3-continued

Inventive compounds of the formula (I) in which X represents C(R$^{13}$) (R$^{14}$)

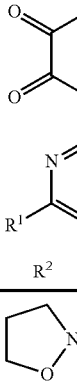

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1328 | c-Pr | 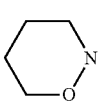 | Cl | Cl | H | H | H | Me | H |
| III-1329 | c-Pr | 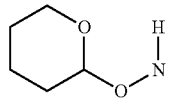 | Cl | Cl | H | H | H | Me | H |
| III-1330 | c-Pr |  | Cl | Cl | H | H | H | Me | H |
| III-1331 | c-Pr | PhO—NH | Cl | Cl | H | H | H | Me | H |
| III-1332 | c-Pr | BnO—NH | Cl | Cl | H | H | H | Me | H |
| III-1333 | c-Pr | HO—NH | Cl | Cl | H | H | H | Me | Me |
| III-1334 | c-Pr | HO—N(Me) | Cl | Cl | H | H | H | Me | Me |
| III-1335 | c-Pr | MeO—NH | Cl | Cl | H | H | H | Me | Me |
| III-1336 | c-Pr | MeO—N(Me) | Cl | Cl | H | H | H | Me | Me |
| III-1337 | c-Pr | AllylO—NH | Cl | Cl | H | H | H | Me | Me |
| III-1338 | c-Pr | HO—N(iPr) | Cl | Cl | H | H | H | Me | Me |
| III-1339 | c-Pr | HOCH$_2$CH$_2$O—NH | Cl | Cl | H | H | H | Me | Me |
| III-1340 | c-Pr | 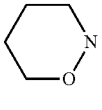 | Cl | Cl | H | H | H | Me | Me |
| III-1341 | c-Pr | 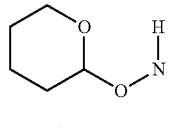 | Cl | Cl | H | H | H | Me | Me |
| III-1342 | c-Pr |  | Cl | Cl | H | H | H | Me | Me |
| III-1343 | c-Pr | PhO—NH | Cl | Cl | H | H | H | Me | Me |
| III-1344 | c-Pr | BnO—NH | Cl | Cl | H | H | H | Me | Me |
| III-1345 | c-Pr | HO—NH | Cl | Cl | H | H | H | CO$_2$Et | H |
| III-1346 | c-Pr | HO—N(Me) | Cl | Cl | H | H | H | CO$_2$Et | H |
| III-1347 | c-Pr | MeO—NH | Cl | Cl | H | H | H | CO$_2$Et | H |
| III-1348 | c-Pr | MeO—N(Me) | Cl | Cl | H | H | H | CO$_2$Et | H |
| III-1349 | c-Pr | AllylO—NH | Cl | Cl | H | H | H | CO$_2$Et | H |
| III-1350 | c-Pr | HO—N(iPr) | Cl | Cl | H | H | H | CO$_2$Et | H |
| III-1351 | c-Pr | HOCH$_2$CH$_2$O—NH | Cl | Cl | H | H | H | CO$_2$Et | H |
| III-1352 | c-Pr | 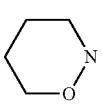 | Cl | Cl | H | H | H | CO$_2$Et | H |
| III-1353 | c-Pr |  | Cl | Cl | H | H | H | CO$_2$Et | H |

TABLE 3-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1354 | c-Pr | (tetrahydropyran-2-yl)-O-NH- | Cl | Cl | H | H | H | CO$_2$Et | H |
| III-1355 | c-Pr | PhO—NH | Cl | Cl | H | H | H | CO$_2$Et | H |
| III-1356 | c-Pr | BnO—NH | Cl | Cl | H | H | H | CO$_2$Et | H |
| III-1357 | c-Pr | HO—NH | Cl | Cl | H | H | H | CN | H |
| III-1358 | c-Pr | HO—N(Me) | Cl | Cl | H | H | H | CN | H |
| III-1359 | c-Pr | MeO—NH | Cl | Cl | H | H | H | CN | H |
| III-1360 | c-Pr | MeO—N(Me) | Cl | Cl | H | H | H | CN | H |
| III-1361 | c-Pr | AllylO—NH | Cl | Cl | H | H | H | CN | H |
| III-1362 | c-Pr | HO—N(iPr) | Cl | Cl | H | H | H | CN | H |
| III-1363 | c-Pr | HOCH$_2$CH$_2$O—NH | Cl | Cl | H | H | H | CN | H |
| III-1364 | c-Pr | isoxazolidin-2-yl | Cl | Cl | H | H | H | CN | H |
| III-1365 | c-Pr | 1,2-oxazinan-2-yl | Cl | Cl | H | H | H | CN | H |
| III-1366 | c-Pr | (tetrahydropyran-2-yl)-O-NH- | Cl | Cl | H | H | H | CN | H |
| III-1367 | c-Pr | PhO—NH | Cl | Cl | H | H | H | CN | H |
| III-1368 | c-Pr | BnO—NH | Cl | Cl | H | H | H | CN | H |
| III-1369 | c-Pr | HO—NH | Cl | H | Cl | H | H | Me | H |
| III-1370 | c-Pr | HO—N(Me) | Cl | H | Cl | H | H | Me | H |
| III-1371 | c-Pr | MeO—NH | Cl | H | Cl | H | H | Me | H |
| III-1372 | c-Pr | MeO—N(Me) | Cl | H | Cl | H | H | Me | H |
| III-1373 | c-Pr | AllylO—NH | Cl | H | Cl | H | H | Me | H |
| III-1374 | c-Pr | HO—N(iPr) | Cl | H | Cl | H | H | Me | H |
| III-1375 | c-Pr | HOCH$_2$CH$_2$O—NH | Cl | H | Cl | H | H | Me | H |
| III-1376 | c-Pr | isoxazolidin-2-yl | Cl | H | Cl | H | H | Me | H |
| III-1377 | c-Pr | 1,2-oxazinan-2-yl | Cl | H | Cl | H | H | Me | H |
| III-1378 | c-Pr | (tetrahydropyran-2-yl)-O-NH- | Cl | H | Cl | H | H | Me | H |
| III-1379 | c-Pr | PhO—NH | Cl | H | Cl | H | H | Me | H |
| III-1380 | c-Pr | BnO—NH | Cl | H | Cl | H | H | Me | H |
| III-1381 | c-Pr | HO—NH | Cl | H | Cl | H | H | Me | Me |
| III-1382 | c-Pr | HO—N(Me) | Cl | H | Cl | H | H | Me | Me |
| III-1383 | c-Pr | MeO—NH | Cl | H | Cl | H | H | Me | Me |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-1384 | c-Pr | MeO—N(Me) | Cl | H | Cl | H | H | Me | Me |
| III-1385 | c-Pr | AllylO—NH | Cl | H | Cl | H | H | Me | Me |
| III-1386 | c-Pr | HO—N(iPr) | Cl | H | Cl | H | H | Me | Me |
| III-1387 | c-Pr | HOCH$_2$CH$_2$O—NH | Cl | H | Cl | H | H | Me | Me |
| III-1388 | c-Pr | isoxazolidinyl | Cl | H | Cl | H | H | Me | Me |
| III-1389 | c-Pr | 1,2-oxazinanyl | Cl | H | Cl | H | H | Me | Me |
| III-1390 | c-Pr | THP-O-NH | Cl | H | Cl | H | H | Me | Me |
| III-1391 | c-Pr | PhO—NH | Cl | H | Cl | H | H | Me | Me |
| III-1392 | c-Pr | BnO—NH | Cl | H | Cl | H | H | Me | Me |
| III-1393 | c-Pr | HO—NH | Cl | H | Cl | H | H | CO$_2$Et | H |
| III-1394 | c-Pr | HO—N(Me) | Cl | H | Cl | H | H | CO$_2$Et | H |
| III-1395 | c-Pr | MeO—NH | Cl | H | Cl | H | H | CO$_2$Et | H |
| III-1396 | c-Pr | MeO—N(Me) | Cl | H | Cl | H | H | CO$_2$Et | H |
| III-1397 | c-Pr | AllylO—NH | Cl | H | Cl | H | H | CO$_2$Et | H |
| III-1398 | c-Pr | HO—N(iPr) | Cl | H | Cl | H | H | CO$_2$Et | H |
| III-1399 | c-Pr | HOCH$_2$CH$_2$O—NH | Cl | H | Cl | H | H | CO$_2$Et | H |
| III-1400 | c-Pr | isoxazolidinyl | Cl | H | Cl | H | H | CO$_2$Et | H |
| III-1401 | c-Pr | 1,2-oxazinanyl | Cl | H | Cl | H | H | CO$_2$Et | H |
| III-1402 | c-Pr | THP-O-NH | Cl | H | Cl | H | H | CO$_2$Et | H |
| III-1403 | c-Pr | PhO—NH | Cl | H | Cl | H | H | CO$_2$Et | H |
| III-1404 | c-Pr | BnO—NH | Cl | H | Cl | H | H | CO$_2$Et | H |
| III-1405 | c-Pr | HO—NH | Cl | H | Cl | H | H | CN | H |
| III-1406 | c-Pr | HO—N(Me) | Cl | H | Cl | H | H | CN | H |
| III-1407 | c-Pr | MeO—NH | Cl | H | Cl | H | H | CN | H |
| III-1408 | c-Pr | MeO—N(Me) | Cl | H | Cl | H | H | CN | H |
| III-1409 | c-Pr | AllylO—NH | Cl | H | Cl | H | H | CN | H |
| III-1410 | c-Pr | HO—N(iPr) | Cl | H | Cl | H | H | CN | H |
| III-1411 | c-Pr | HOCH$_2$CH$_2$O—NH | Cl | H | Cl | H | H | CN | H |
| III-1412 | c-Pr | isoxazolidinyl | Cl | H | Cl | H | H | CN | H |

TABLE 3-continued

Inventive compounds of the formula (I) in which X represents C(R¹³)(R¹⁴)

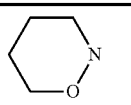

(I)

| No. | R¹ | R² | R³ | R⁴ | R⁵ | R⁶ | R⁷ | R¹³ | R¹⁴ |
|---|---|---|---|---|---|---|---|---|---|
| III-1413 | c-Pr | 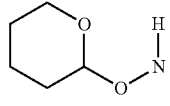 | Cl | H | Cl | H | H | CN | H |
| III-1414 | c-Pr | 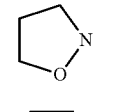 | Cl | H | Cl | H | H | CN | H |
| III-1415 | c-Pr | PhO—NH | Cl | H | Cl | H | H | CN | H |
| III-1416 | c-Pr | BnO—NH | Cl | H | Cl | H | H | CN | H |
| III-1417 | c-Pr | HO—NH | Cl | H | H | Cl | H | Me | H |
| III-1418 | c-Pr | HO—N(Me) | Cl | H | H | Cl | H | Me | H |
| III-1419 | c-Pr | MeO—NH | Cl | H | H | Cl | H | Me | H |
| III-1420 | c-Pr | MeO—N(Me) | Cl | H | H | Cl | H | Me | H |
| III-1421 | c-Pr | AllylO—NH | Cl | H | H | Cl | H | Me | H |
| III-1422 | c-Pr | HO—N(iPr) | Cl | H | H | Cl | H | Me | H |
| III-1423 | c-Pr | HOCH₂CH₂O—NH | Cl | H | H | Cl | H | Me | H |
| III-1424 | c-Pr | 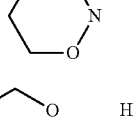 | Cl | H | H | Cl | H | Me | H |
| III-1425 | c-Pr | 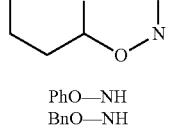 | Cl | H | H | Cl | H | Me | H |
| III-1426 | c-Pr | 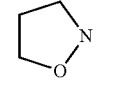 | Cl | H | H | Cl | H | Me | H |
| III-1427 | c-Pr | PhO—NH | Cl | H | H | Cl | H | Me | H |
| III-1428 | c-Pr | BnO—NH | Cl | H | H | Cl | H | Me | H |
| III-1429 | c-Pr | HO—NH | Cl | H | H | Cl | H | Me | Me |
| III-1430 | c-Pr | HO—N(Me) | Cl | H | H | Cl | H | Me | Me |
| III-1431 | c-Pr | MeO—NH | Cl | H | H | Cl | H | Me | Me |
| III-1432 | c-Pr | MeO—N(Me) | Cl | H | H | Cl | H | Me | Me |
| III-1433 | c-Pr | AllylO—NH | Cl | H | H | Cl | H | Me | Me |
| III-1434 | c-Pr | HO—N(iPr) | Cl | H | H | Cl | H | Me | Me |
| III-1435 | c-Pr | HOCH₂CH₂O—NH | Cl | H | H | Cl | H | Me | Me |
| III-1436 | c-Pr | 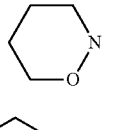 | Cl | H | H | Cl | H | Me | Me |
| III-1437 | c-Pr | 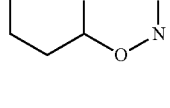 | Cl | H | H | Cl | H | Me | Me |
| III-1438 | c-Pr |  | Cl | H | H | Cl | H | Me | Me |

TABLE 3-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| III-1439 | c-Pr | PhO—NH | Cl | H | H | Cl | H | Me | Me |
| III-1440 | c-Pr | BnO—NH | Cl | H | H | Cl | H | Me | Me |
| III-1441 | c-Pr | HO—NH | Cl | H | H | Cl | H | $CO_2Et$ | H |
| III-1442 | c-Pr | HO—N(Me) | Cl | H | H | Cl | H | $CO_2Et$ | H |
| III-1443 | c-Pr | MeO—NH | Cl | H | H | Cl | H | $CO_2Et$ | H |
| III-1444 | c-Pr | MeO—N(Me) | Cl | H | H | Cl | H | $CO_2Et$ | H |
| III-1445 | c-Pr | AllylO—NH | Cl | H | H | Cl | H | $CO_2Et$ | H |
| III-1446 | c-Pr | HO—N(iPr) | Cl | H | H | Cl | H | $CO_2Et$ | H |
| III-1447 | c-Pr | $HOCH_2CH_2O$—NH | Cl | H | H | Cl | H | $CO_2Et$ | H |
| III-1448 | c-Pr | isoxazolidinyl | Cl | H | H | Cl | H | $CO_2Et$ | H |
| III-1449 | c-Pr | 1,2-oxazinanyl | Cl | H | H | Cl | H | $CO_2Et$ | H |
| III-1450 | c-Pr | THP-O-NH | Cl | H | H | Cl | H | $CO_2Et$ | H |
| III-1451 | c-Pr | PhO—NH | Cl | H | H | Cl | H | $CO_2Et$ | H |
| III-1452 | c-Pr | BnO—NH | Cl | H | H | Cl | H | $CO_2Et$ | H |
| III-1453 | c-Pr | HO—NH | Cl | H | H | Cl | H | CN | H |
| III-1454 | c-Pr | HO—N(Me) | Cl | H | H | Cl | H | CN | H |
| III-1455 | c-Pr | MeO—NH | Cl | H | H | Cl | H | CN | H |
| III-1456 | c-Pr | MeO—N(Me) | Cl | H | H | Cl | H | CN | H |
| III-1457 | c-Pr | AllylO—NH | Cl | H | H | Cl | H | CN | H |
| III-1458 | c-Pr | HO—N(iPr) | Cl | H | H | Cl | H | CN | H |
| III-1459 | c-Pr | $HOCH_2CH_2O$—NH | Cl | H | H | Cl | H | CN | H |
| III-1460 | c-Pr | isoxazolidinyl | Cl | H | H | Cl | H | CN | H |
| III-1461 | c-Pr | 1,2-oxazinanyl | Cl | H | H | Cl | H | CN | H |
| III-1462 | c-Pr | THP-O-NH | Cl | H | H | Cl | H | CN | H |
| III-1463 | c-Pr | PhO—NH | Cl | H | H | Cl | H | CN | H |
| III-1464 | c-Pr | BnO—NH | Cl | H | H | Cl | H | CN | H |
| III-1465 | c-Pr | HO—NH | Cl | H | H | H | Cl | Me | H |
| III-1466 | c-Pr | HO—N(Me) | Cl | H | H | H | Cl | Me | H |
| III-1467 | c-Pr | MeO—NH | Cl | H | H | H | Cl | Me | H |
| III-1468 | c-Pr | MeO—N(Me) | Cl | H | H | H | Cl | Me | H |
| III-1469 | c-Pr | AllylO—NH | Cl | H | H | H | Cl | Me | H |
| III-1470 | c-Pr | HO—N(iPr) | Cl | H | H | H | Cl | Me | H |
| III-1471 | c-Pr | $HOCH_2CH_2O$—NH | Cl | H | H | H | Cl | Me | H |

TABLE 3-continued

Inventive compounds of the formula (I) in which X represents C(R¹³)(R¹⁴)

(Structural formula (I) showing pyrimidine with R¹, substituted phenyl ring with R³-R⁷, and X-linked dicarbonyl group with R²)

| No. | R¹ | R² | R³ | R⁴ | R⁵ | R⁶ | R⁷ | R¹³ | R¹⁴ |
|---|---|---|---|---|---|---|---|---|---|
| III-1472 | c-Pr | isoxazolidine (5-membered N-O ring) | Cl | H | H | H | Cl | Me | H |
| III-1473 | c-Pr | 1,2-oxazinane (6-membered N-O ring) | Cl | H | H | H | Cl | Me | H |
| III-1474 | c-Pr | tetrahydropyran-2-yl-O-NH | Cl | H | H | H | Cl | Me | H |
| III-1475 | c-Pr | PhO—NH | Cl | H | H | H | Cl | Me | H |
| III-1476 | c-Pr | BnO—NH | Cl | H | H | H | Cl | Me | H |
| III-1477 | c-Pr | HO—NH | Cl | H | H | H | Cl | Me | Me |
| III-1478 | c-Pr | HO—N(Me) | Cl | H | H | H | Cl | Me | Me |
| III-1479 | c-Pr | MeO—NH | Cl | H | H | H | Cl | Me | Me |
| III-1480 | c-Pr | MeO—N(Me) | Cl | H | H | H | Cl | Me | Me |
| III-1481 | c-Pr | AllylO—NH | Cl | H | H | H | Cl | Me | Me |
| III-1482 | c-Pr | HO—N(iPr) | Cl | H | H | H | Cl | Me | Me |
| III-1483 | c-Pr | HOCH₂CH₂O—NH | Cl | H | H | H | Cl | Me | Me |
| III-1484 | c-Pr | isoxazolidine (5-membered N-O ring) | Cl | H | H | H | Cl | Me | Me |
| III-1485 | c-Pr | 1,2-oxazinane (6-membered N-O ring) | Cl | H | H | H | Cl | Me | Me |
| III-1486 | c-Pr | tetrahydropyran-2-yl-O-NH | Cl | H | H | H | Cl | Me | Me |
| III-1487 | c-Pr | PhO—NH | Cl | H | H | H | Cl | Me | Me |
| III-1488 | c-Pr | BnO—NH | Cl | H | H | H | Cl | Me | Me |
| III-1489 | c-Pr | HO—NH | Cl | H | H | H | Cl | CO₂Et | H |
| III-1490 | c-Pr | HO—N(Me) | Cl | H | H | H | Cl | CO₂Et | H |
| III-1491 | c-Pr | MeO—NH | Cl | H | H | H | Cl | CO₂Et | H |
| III-1492 | c-Pr | MeO—N(Me) | Cl | H | H | H | Cl | CO₂Et | H |
| III-1493 | c-Pr | AllylO—NH | Cl | H | H | H | Cl | CO₂Et | H |
| III-1494 | c-Pr | HO—N(iPr) | Cl | H | H | H | Cl | CO₂Et | H |
| III-1495 | c-Pr | HOCH₂CH₂O—NH | Cl | H | H | H | Cl | CO₂Et | H |
| III-1496 | c-Pr | isoxazolidine (5-membered N-O ring) | Cl | H | H | H | Cl | CO₂Et | H |
| III-1497 | c-Pr | 1,2-oxazinane (6-membered N-O ring) | Cl | H | H | H | Cl | CO₂Et | H |

TABLE 3-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| III-1498 | c-Pr | (tetrahydropyran-2-yl)-O-NH | Cl | H | H | H | Cl | CO₂Et | H |
| III-1499 | c-Pr | PhO—NH | Cl | H | H | H | Cl | CO₂Et | H |
| III-1500 | c-Pr | BnO—NH | Cl | H | H | H | Cl | CO₂Et | H |
| III-1501 | c-Pr | HO—NH | Cl | H | H | H | Cl | CN | H |
| III-1502 | c-Pr | HO—N(Me) | Cl | H | H | H | Cl | CN | H |
| III-1503 | c-Pr | MeO—NH | Cl | H | H | H | Cl | CN | H |
| III-1504 | c-Pr | MeO—N(Me) | Cl | H | H | H | Cl | CN | H |
| III-1505 | c-Pr | AllylO—NH | Cl | H | H | H | Cl | CN | H |
| III-1506 | c-Pr | HO—N(iPr) | Cl | H | H | H | Cl | CN | H |
| III-1507 | c-Pr | HOCH₂CH₂O—NH | Cl | H | H | H | Cl | CN | H |
| III-1508 | c-Pr | isoxazolidin-2-yl | Cl | H | H | H | Cl | CN | H |
| III-1509 | c-Pr | 1,2-oxazinan-2-yl | Cl | H | H | H | Cl | CN | H |
| III-1510 | c-Pr | (tetrahydropyran-2-yl)-O-NH | Cl | H | H | H | Cl | CN | H |
| III-1511 | c-Pr | PhO—NH | Cl | H | H | H | Cl | CN | H |
| III-1512 | c-Pr | BnO—NH | Cl | H | H | H | Cl | CN | H |
| III-1513 | c-Pr | HO—NH | Me | H | H | H | H | Me | H |
| III-1514 | c-Pr | HO—N(Me) | Me | H | H | H | H | Me | H |
| III-1515 | c-Pr | MeO—NH | Me | H | H | H | H | Me | H |
| III-1516 | c-Pr | MeO—N(Me) | Me | H | H | H | H | Me | H |
| III-1517 | c-Pr | AllylO—NH | Me | H | H | H | H | Me | H |
| III-1518 | c-Pr | HO—N(iPr) | Me | H | H | H | H | Me | H |
| III-1519 | c-Pr | HOCH₂CH₂O—NH | Me | H | H | H | H | Me | H |
| III-1520 | c-Pr | isoxazolidin-2-yl | Me | H | H | H | H | Me | H |
| III-1521 | c-Pr | 1,2-oxazinan-2-yl | Me | H | H | H | H | Me | H |
| III-1522 | c-Pr | (tetrahydropyran-2-yl)-O-NH | Me | H | H | H | H | Me | H |
| III-1523 | c-Pr | PhO—NH | Me | H | H | H | H | Me | H |
| III-1524 | c-Pr | BnO—NH | Me | H | H | H | H | Me | H |
| III-1525 | c-Pr | HO—NH | Me | H | H | H | H | Me | Me |
| III-1526 | c-Pr | HO—N(Me) | Me | H | H | H | H | Me | Me |
| III-1527 | c-Pr | MeO—NH | Me | H | H | H | H | Me | Me |

TABLE 3-continued

Inventive compounds of the formula (I) in which X represents C(R$^{13}$) (R$^{14}$)

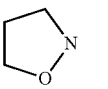

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1528 | c-Pr | MeO—N(Me) | Me | H | H | H | H | Me | Me |
| III-1529 | c-Pr | AllylO—NH | Me | H | H | H | H | Me | Me |
| III-1530 | c-Pr | HO—N(iPr) | Me | H | H | H | H | Me | Me |
| III-1531 | c-Pr | HOCH$_2$CH$_2$O—NH | Me | H | H | H | H | Me | Me |
| III-1532 | c-Pr | 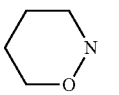 | Me | H | H | H | H | Me | Me |
| III-1533 | c-Pr | 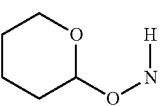 | Me | H | H | H | H | Me | Me |
| III-1534 | c-Pr | 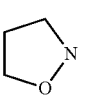 | Me | H | H | H | H | Me | Me |
| III-1535 | c-Pr | PhO—NH | Me | H | H | H | H | Me | Me |
| III-1536 | c-Pr | BnO—NH | Me | H | H | H | H | Me | Me |
| III-1537 | c-Pr | HO—NH | Me | H | H | H | H | Me | H |
| III-1538 | c-Pr | HO—N(Me) | Me | H | H | H | H | CO$_2$Et | H |
| III-1539 | c-Pr | MeO—NH | Me | H | H | H | H | CO$_2$Et | H |
| III-1540 | c-Pr | MeO—N(Me) | Me | H | H | H | H | CO$_2$Et | H |
| III-1541 | c-Pr | AllylO—NH | Me | H | H | H | H | CO$_2$Et | H |
| III-1542 | c-Pr | HO—N(iPr) | Me | H | H | H | H | CO$_2$Et | H |
| III-1543 | c-Pr | HOCH$_2$CH$_2$O—NH | Me | H | H | H | H | CO$_2$Et | H |
| III-1544 | c-Pr | 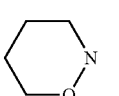 | Me | H | H | H | H | CO$_2$Et | H |
| III-1545 | c-Pr | 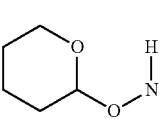 | Me | H | H | H | H | CO$_2$Et | H |
| III-1546 | c-Pr | 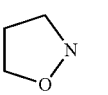 | Me | H | H | H | H | CO$_2$Et | H |
| III-1547 | c-Pr | PhO—NH | Me | H | H | H | H | CO$_2$Et | H |
| III-1548 | c-Pr | BnO—NH | Me | H | H | H | H | CO$_2$Et | H |
| III-1549 | c-Pr | HO—NH | Me | H | H | H | H | CN | H |
| III-1550 | c-Pr | HO—N(Me) | Me | H | H | H | H | CN | H |
| III-1551 | c-Pr | MeO—NH | Me | H | H | H | H | CN | H |
| III-1552 | c-Pr | MeO—N(Me) | Me | H | H | H | H | CN | H |
| III-1553 | c-Pr | AllylO—NH | Me | H | H | H | H | CN | H |
| III-1554 | c-Pr | HO—N(iPr) | Me | H | H | H | H | CN | H |
| III-1555 | c-Pr | HOCH$_2$CH$_2$O—NH | Me | H | H | H | H | CN | H |
| III-1556 | c-Pr |  | Me | H | H | H | H | CN | H |

TABLE 3-continued

Inventive compounds of the formula (I) in which X represents C(R$^{13}$) (R$^{14}$)

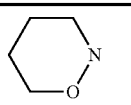

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1557 | c-Pr | 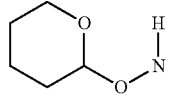 | Me | H | H | H | H | CN | H |
| III-1558 | c-Pr | 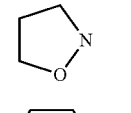 | Me | H | H | H | H | CN | H |
| III-1559 | c-Pr | PhO—NH | Me | H | H | H | H | CN | H |
| III-1560 | c-Pr | BnO—NH | Me | H | H | H | H | CN | H |
| III-1561 | c-Pr | HO—NH | CF$_3$ | H | H | H | H | Me | H |
| III-1562 | c-Pr | HO—N(Me) | CF$_3$ | H | H | H | H | Me | H |
| III-1563 | c-Pr | MeO—NH | CF$_3$ | H | H | H | H | Me | H |
| III-1564 | c-Pr | MeO—N(Me) | CF$_3$ | H | H | H | H | Me | H |
| III-1565 | c-Pr | AllylO—NH | CF$_3$ | H | H | H | H | Me | H |
| III-1566 | c-Pr | HO—N(iPr) | CF$_3$ | H | H | H | H | Me | H |
| III-1567 | c-Pr | HOCH$_2$CH$_2$O—NH | CF$_3$ | H | H | H | H | Me | H |
| III-1568 | c-Pr | 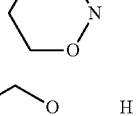 | CF$_3$ | H | H | H | H | Me | H |
| III-1569 | c-Pr | 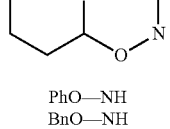 | CF$_3$ | H | H | H | H | Me | H |
| III-1570 | c-Pr | 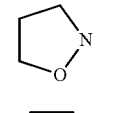 | CF$_3$ | H | H | H | H | Me | H |
| III-1571 | c-Pr | PhO—NH | CF$_3$ | H | H | H | H | Me | H |
| III-1572 | c-Pr | BnO—NH | CF$_3$ | H | H | H | H | Me | H |
| III-1573 | c-Pr | HO—NH | CF$_3$ | H | H | H | H | Me | Me |
| III-1574 | c-Pr | HO—N(Me) | CF$_3$ | H | H | H | H | Me | Me |
| III-1575 | c-Pr | MeO—NH | CF$_3$ | H | H | H | H | Me | Me |
| III-1576 | c-Pr | MeO—N(Me) | CF$_3$ | H | H | H | H | Me | Me |
| III-1577 | c-Pr | AllylO—NH | CF$_3$ | H | H | H | H | Me | Me |
| III-1578 | c-Pr | HO—N(iPr) | CF$_3$ | H | H | H | H | Me | Me |
| III-1579 | c-Pr | HOCH$_2$CH$_2$O—NH | CF$_3$ | H | H | H | H | Me | Me |
| III-1580 | c-Pr | 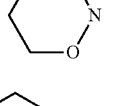 | CF$_3$ | H | H | H | H | Me | Me |
| III-1581 | c-Pr | 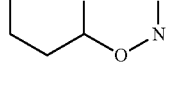 | CF$_3$ | H | H | H | H | Me | Me |
| III-1582 | c-Pr |  | CF$_3$ | H | H | H | H | Me | Me |

TABLE 3-continued

Inventive compounds of the formula (I) in which X represents C(R¹³)(R¹⁴)

| No. | R¹ | R² | R³ | R⁴ | R⁵ | R⁶ | R⁷ | R¹³ | R¹⁴ |
|---|---|---|---|---|---|---|---|---|---|
| III-1583 | c-Pr | PhO—NH | CF$_3$ | H | H | H | H | Me | Me |
| III-1584 | c-Pr | BnO—NH | CF$_3$ | H | H | H | H | Me | Me |
| III-1585 | c-Pr | HO—NH | CF$_3$ | H | H | H | H | CO$_2$Et | H |
| III-1586 | c-Pr | HO—N(Me) | CF$_3$ | H | H | H | H | CO$_2$Et | H |
| III-1587 | c-Pr | MeO—NH | CF$_3$ | H | H | H | H | CO$_2$Et | H |
| III-1588 | c-Pr | MeO—N(Me) | CF$_3$ | H | H | H | H | CO$_2$Et | H |
| III-1589 | c-Pr | AllylO—NH | CF$_3$ | H | H | H | H | CO$_2$Et | H |
| III-1590 | c-Pr | HO—N(iPr) | CF$_3$ | H | H | H | H | CO$_2$Et | H |
| III-1591 | c-Pr | HOCH$_2$CH$_2$O—NH | CF$_3$ | H | H | H | H | CO$_2$Et | H |
| III-1592 | c-Pr | isoxazolidinyl | CF$_3$ | H | H | H | H | CO$_2$Et | H |
| III-1593 | c-Pr | 1,2-oxazinanyl | CF$_3$ | H | H | H | H | CO$_2$Et | H |
| III-1594 | c-Pr | THP-O-NH | CF$_3$ | H | H | H | H | CO$_2$Et | H |
| III-1595 | c-Pr | PhO—NH | CF$_3$ | H | H | H | H | CO$_2$Et | H |
| III-1596 | c-Pr | BnO—NH | CF$_3$ | H | H | H | H | CO$_2$Et | H |
| III-1597 | c-Pr | HO—NH | CF$_3$ | H | H | H | H | CN | H |
| III-1598 | c-Pr | HO—N(Me) | CF$_3$ | H | H | H | H | CN | H |
| III-1599 | c-Pr | MeO—NH | CF$_3$ | H | H | H | H | CN | H |
| III-1600 | c-Pr | MeO—N(Me) | CF$_3$ | H | H | H | H | CN | H |
| III-1601 | c-Pr | AllylO—NH | CF$_3$ | H | H | H | H | CN | H |
| III-1602 | c-Pr | HO—N(iPr) | CF$_3$ | H | H | H | H | CN | H |
| III-1603 | c-Pr | HOCH$_2$CH$_2$O—NH | CF$_3$ | H | H | H | H | CN | H |
| III-1604 | c-Pr | isoxazolidinyl | CF$_3$ | H | H | H | H | CN | H |
| III-1605 | c-Pr | 1,2-oxazinanyl | CF$_3$ | H | H | H | H | CN | H |
| III-1606 | c-Pr | THP-O-NH | CF$_3$ | H | H | H | H | CN | H |
| III-1607 | c-Pr | PhO—NH | CF$_3$ | H | H | H | H | CN | H |
| III-1608 | c-Pr | BnO—NH | CF$_3$ | H | H | H | H | CN | H |
| III-1609 | c-Pr | HO—NH | MeO | H | H | H | H | Me | H |
| III-1610 | c-Pr | HO—N(Me) | MeO | H | H | H | H | Me | H |
| III-1611 | c-Pr | MeO—NH | MeO | H | H | H | H | Me | H |
| III-1612 | c-Pr | MeO—N(Me) | MeO | H | H | H | H | Me | H |
| III-1613 | c-Pr | AllylO—NH | MeO | H | H | H | H | Me | H |
| III-1614 | c-Pr | HO—N(iPr) | MeO | H | H | H | H | Me | H |
| III-1615 | c-Pr | HOCH$_2$CH$_2$O—NH | MeO | H | H | H | H | Me | H |

TABLE 3-continued

Inventive compounds of the formula (I) in which X represents C(R¹³)(R¹⁴)

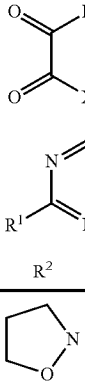

(I)

| No. | R¹ | R² | R³ | R⁴ | R⁵ | R⁶ | R⁷ | R¹³ | R¹⁴ |
|---|---|---|---|---|---|---|---|---|---|
| III-1616 | c-Pr |  | MeO | H | H | H | H | Me | H |
| III-1617 | c-Pr | 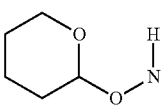 | MeO | H | H | H | H | Me | H |
| III-1618 | c-Pr |  | MeO | H | H | H | H | Me | H |
| III-1619 | c-Pr | PhO—NH | MeO | H | H | H | H | Me | H |
| III-1620 | c-Pr | BnO—NH | MeO | H | H | H | H | Me | H |
| III-1621 | c-Pr | HO—NH | MeO | H | H | H | H | Me | Me |
| III-1622 | c-Pr | HO—N(Me) | MeO | H | H | H | H | Me | Me |
| III-1623 | c-Pr | MeO—NH | MeO | H | H | H | H | Me | Me |
| III-1624 | c-Pr | MeO—N(Me) | MeO | H | H | H | H | Me | Me |
| III-1625 | c-Pr | AllylO—NH | MeO | H | H | H | H | Me | Me |
| III-1626 | c-Pr | HO—N(iPr) | MeO | H | H | H | H | Me | Me |
| III-1627 | c-Pr | HOCH₂CH₂O—NH | MeO | H | H | H | H | Me | Me |
| III-1628 | c-Pr |  | MeO | H | H | H | H | Me | Me |
| III-1629 | c-Pr | 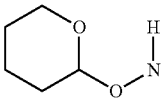 | MeO | H | H | H | H | Me | Me |
| III-1630 | c-Pr |  | MeO | H | H | H | H | Me | Me |
| III-1631 | c-Pr | PhO—NH | MeO | H | H | H | H | Me | Me |
| III-1632 | c-Pr | BnO—NH | MeO | H | H | H | H | Me | Me |
| III-1633 | c-Pr | HO—NH | MeO | H | H | H | H | Me | H |
| III-1634 | c-Pr | HO—N(Me) | MeO | H | H | H | H | CO₂Et | H |
| III-1635 | c-Pr | MeO—NH | MeO | H | H | H | H | CO₂Et | H |
| III-1636 | c-Pr | MeO—N(Me) | MeO | H | H | H | H | CO₂Et | H |
| III-1637 | c-Pr | AllylO—NH | MeO | H | H | H | H | CO₂Et | H |
| III-1638 | c-Pr | HO—N(iPr) | MeO | H | H | H | H | CO₂Et | H |
| III-1639 | c-Pr | HOCH₂CH₂O—NH | MeO | H | H | H | H | CO₂Et | H |
| III-1640 | c-Pr |  | MeO | H | H | H | H | CO₂Et | H |
| III-1641 | c-Pr |  | MeO | H | H | H | H | CO₂Et | H |

TABLE 3-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| III-1642 | c-Pr | (tetrahydropyran-2-yl)oxy—NH | MeO | H | H | H | H | CO$_2$Et | H |
| III-1643 | c-Pr | PhO—NH | MeO | H | H | H | H | CO$_2$Et | H |
| III-1644 | c-Pr | BnO—NH | MeO | H | H | H | H | CO$_2$Et | H |
| III-1645 | c-Pr | HO—NH | MeO | H | H | H | H | CN | H |
| III-1646 | c-Pr | HO—N(Me) | MeO | H | H | H | H | CN | H |
| III-1647 | c-Pr | MeO—NH | MeO | H | H | H | H | CN | H |
| III-1648 | c-Pr | MeO—N(Me) | MeO | H | H | H | H | CN | H |
| III-1649 | c-Pr | AllylO—NH | MeO | H | H | H | H | CN | H |
| III-1650 | c-Pr | HO—N(iPr) | MeO | H | H | H | H | CN | H |
| III-1651 | c-Pr | HOCH$_2$CH$_2$O—NH | MeO | H | H | H | H | CN | H |
| III-1652 | c-Pr | isoxazolidine | MeO | H | H | H | H | CN | H |
| III-1653 | c-Pr | 1,2-oxazinane | MeO | H | H | H | H | CN | H |
| III-1654 | c-Pr | (tetrahydropyran-2-yl)oxy—NH | MeO | H | H | H | H | CN | H |
| III-1655 | c-Pr | PhO—NH | MeO | H | H | H | H | CN | H |
| III-1656 | c-Pr | BnO—NH | MeO | H | H | H | H | CN | H |

TABLE 4

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-001 | c-Pr | H$_2$NNH | H | H | H | H | H | H | H |
| IV-002 | c-Pr | MeNHNH | H | H | H | H | H | H | H |
| IV-003 | c-Pr | H$_2$NN(Me) | H | H | H | H | H | H | H |
| IV-004 | c-Pr | Me$_2$NNH | H | H | H | H | H | H | H |
| IV-005 | c-Pr | MeNN(Me) | H | H | H | H | H | H | H |

TABLE 4-continued

Inventive compounds of the formula (I) in which X represents C(R¹³)(R¹⁴)

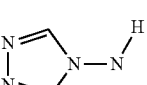

(I)

| No. | R¹ | R² | R³ | R⁴ | R⁵ | R⁶ | R⁷ | R¹³ | R¹⁴ |
|---|---|---|---|---|---|---|---|---|---|
| IV-006 | c-Pr | PhNHNH | H | H | H | H | H | H | H |
| IV-007 | c-Pr | (2-Pyridinyl)NHNH | H | H | H | H | H | H | H |
| IV-008 | c-Pr | 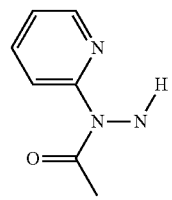 | H | H | H | H | H | H | H |
| IV-009 | c-Pr | Me(C=O)NHNH | H | H | H | H | H | H | H |
| IV-010 | c-Pr | (Me)(Ac)NNH | H | H | H | H | H | H | H |
| IV-011 | c-Pr | Me(SO₂)NHNH | H | H | H | H | H | H | H |
| IV-012 | c-Pr | MeOC(=O)NHNH | H | H | H | H | H | H | H |
| IV-013 | c-Pr | 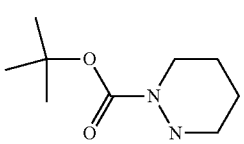 | H | H | H | H | H | H | H |
| IV-014 | c-Pr | 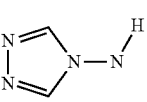 | H | H | H | H | H | H | H |
| IV-015 | c-Pr | Me₂NC(=O)NHNH | H | H | H | H | H | H | H |
| IV-016 | c-Pr | Me2C=NNH | H | H | H | H | H | H | H |
| IV-017 | 1-Me-c-Pr | H₂NNH | H | H | H | H | H | H | H |
| IV-018 | 1-Me-c-Pr | (Me)HNNH | H | H | H | H | H | H | H |
| IV-019 | 1-Me-c-Pr | H₂NN(Me) | H | H | H | H | H | H | H |
| IV-020 | 1-Me-c-Pr | Me₂NNH | H | H | H | H | H | H | H |
| IV-021 | 1-Me-c-Pr | Me₂NN(Me) | H | H | H | H | H | H | H |
| IV-022 | 1-Me-c-Pr | PhNHNH | H | H | H | H | H | H | H |
| IV-023 | 1-Me-c-Pr | (2-Pyridinyl)NHNH | H | H | H | H | H | H | H |
| IV-024 | 1-Me-c-Pr | 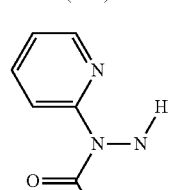 | H | H | H | H | H | H | H |
| IV-025 | 1-Me-c-Pr | Me(C=O)NHNH | H | H | H | H | H | H | H |
| IV-026 | 1-Me-c-Pr | (Me)(Ac)NNH | H | H | H | H | H | H | H |
| IV-027 | 1-Me-c-Pr | Me(SO₂)NHNH | H | H | H | H | H | H | H |
| IV-028 | 1-Me-c-Pr | MeOC(=O)NHNH | H | H | H | H | H | H | H |
| IV-029 | 1-Me-c-Pr | | H | H | H | H | H | H | H |

TABLE 4-continued

Inventive compounds of the formula (I) in which X represents C(R$^{13}$) (R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-030 | 1-Me-c-Pr | *tert-butyl hexahydropyridazine-1-carboxylate group* | H | H | H | H | H | H | H |
| IV-031 | 1-Me-c-Pr | Me$_2$NC(=O)NHNH | H | H | H | H | H | H | H |
| IV-032 | 1-Me-c-Pr | Me$_2$C=NNH | H | H | H | H | H | H | H |
| IV-033 | 2-Me-c-Pr | H2NNH | H | H | H | H | H | H | H |
| IV-034 | 2-Me-c-Pr | MeNHNH | H | H | H | H | H | H | H |
| IV-035 | 2-Me-c-Pr | H$_2$NN(Me) | H | H | H | H | H | H | H |
| IV-036 | 2-Me-c-Pr | Me$_2$NNH | H | H | H | H | H | H | H |
| IV-037 | 2-Me-c-Pr | Me$_2$NN(Me) | H | H | H | H | H | H | H |
| IV-038 | 2-Me-c-Pr | PhNHNH | H | H | H | H | H | H | H |
| IV-039 | 2-Me-c-Pr | (2-Pyridinyl)NHNH | H | H | H | H | H | H | H |
| IV-040 | 2-Me-c-Pr | *1,2,4-triazol-1-yl-NH group* | H | H | H | H | H | H | H |
| IV-041 | 2-Me-c-Pr | Me(C=O)NHNH | H | H | H | H | H | H | H |
| IV-042 | 2-Me-c-Pr | (Me)(Ac)NN | H | H | H | H | H | H | H |
| IV-043 | 2-Me-c-Pr | Me(SO$_2$)NHN | H | H | H | H | H | H | H |
| IV-044 | 2-Me-c-Pr | MeOC(=O)NHNH | H | H | H | H | H | H | H |
| IV-045 | 2-Me-c-Pr | *N-acetyl-N-(2-pyridinyl)hydrazinyl group* | H | H | H | H | H | H | H |
| IV-046 | 2-Me-c-Pr | *tert-butyl hexahydropyridazine-1-carboxylate group* | H | H | H | H | H | H | H |
| IV-047 | 2-Me-c-Pr | Me$_2$NC(=O)NHNH | H | H | H | H | H | H | H |
| IV-048 | 2-Me-c-Pr | Me2C=NNH | H | H | H | H | H | H | H |
| IV-049 | c-Pr | H$_2$NNH | F | H | H | H | H | H | H |
| IV-050 | c-Pr | MeNHNH | F | H | H | H | H | H | H |
| IV-051 | c-Pr | H$_2$NN(Me) | F | H | H | H | H | H | H |
| IV-052 | c-Pr | Me$_2$NNH | F | H | H | H | H | H | H |
| IV-053 | c-Pr | Me$_2$NN(Me) | F | H | H | H | H | H | H |
| IV-054 | c-Pr | PhNHNH | F | H | H | H | H | H | H |
| IV-055 | c-Pr | (2-Pyridinyl)NHNH | F | H | H | H | H | H | H |
| IV-056 | c-Pr | *1,2,4-triazol-1-yl-NH group* | F | H | H | H | H | H | H |
| IV-057 | c-Pr | Me(C=))NHNH | F | H | H | H | H | H | H |
| IV-058 | c-Pr | (Me)(Ac)NNH | F | H | H | H | H | H | H |
| IV-059 | c-Pr | Me(SO$_2$)NHNH | F | H | H | H | H | H | H |
| IV-060 | c-Pr | MeOC(=O)NHNH | F | H | H | H | H | H | H |

TABLE 4-continued

Inventive compounds of the formula (I) in which X represents C(R$^{13}$)(R$^{14}$)

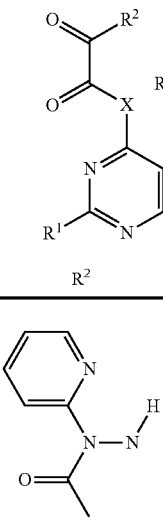

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-061 | c-Pr | 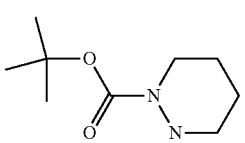 | F | H | H | H | H | H | H |
| IV-062 | c-Pr | 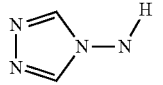 | F | H | H | H | H | H | H |
| IV-063 | c-Pr | Me$_2$NC(=O)NHNH | F | H | H | H | H | H | H |
| IV-064 | c-Pr | Me2C=NNH | F | H | H | H | H | H | H |
| IV-065 | 1-Me-c-Pr | H$_2$NNH | F | H | H | H | H | H | H |
| IV-066 | 1-Me-c-Pr | MeNHNH | F | H | H | H | H | H | H |
| IV-067 | 1-Me-c-Pr | H$_2$NN(Me) | F | H | H | H | H | H | H |
| IV-068 | 1-Me-c-Pr | Me$_2$NNH | F | H | H | H | H | H | H |
| IV-069 | 1-Me-c-Pr | Me$_2$NN(Me) | F | H | H | H | H | H | H |
| IV-070 | 1-Me-c-Pr | PhNHNH | F | H | H | H | H | H | H |
| IV-071 | 1-Me-c-Pr | (2-Pyridinyl)NHNH | F | H | H | H | H | H | H |
| IV-072 | 1-Me-c-Pr 1 | 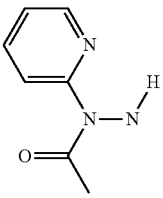 | F | H | H | H | H | H | H |
| IV-073 | 1-Me-c-Pr | Me(C=O)NHNH | F | H | H | H | H | H | H |
| IV-074 | 1-Me-c-Pr | (Me)(Ac)NNH | F | H | H | H | H | H | H |
| IV-075 | 1-Me-c-Pr | Me(SO$_2$)NHNH | F | H | H | H | H | H | H |
| IV-076 | 1-Me-c-Pr | MeOC(=O)NHNH | F | H | H | H | H | H | H |
| IV-077 | 1-Me-c-Pr | 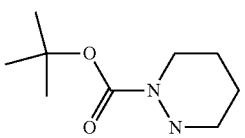 | F | H | H | H | H | H | H |
| IV-078 | 1-Me-c-Pr | | F | H | H | H | H | H | H |
| IV-079 | 1-Me-c-Pr | Me$_2$NC(=O)NHNH | F | H | H | H | H | H | H |
| IV-080 | 1-Me-c-Pr | Me2C=NNH | F | H | H | H | H | H | H |
| IV-081 | 2-Me-c-Pr | H$_2$NNH | F | H | H | H | H | H | H |
| IV-082 | 2-Me-c-Pr | MeNHNH | F | H | H | H | H | H | H |
| IV-083 | 2-Me-c-Pr | H$_2$NN(Me) | F | H | H | H | H | H | H |
| IV-084 | 2-Me-c-Pr | Me$_2$NNH | F | H | H | H | H | H | H |
| IV-085 | 2-Me-c-Pr | Me$_2$NN(Me) | F | H | H | H | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-086 | 2-Me-c-Pr | PhNHNH | F | H | H | H | H | H | H |
| IV-087 | 2-Me-c-Pr | (2-Pyridinyl)NHNH | F | H | H | H | H | H | H |
| IV-088 | 2-Me-c-Pr | [1,2,4-triazol-4-yl-NH] | F | H | H | H | H | H | H |
| IV-089 | 2-Me-c-Pr | Me(C=O)NHNH | F | H | H | H | H | H | H |
| IV-090 | 2-Me-c-Pr | (Me)(Ac)NNH | F | H | H | H | H | H | H |
| IV-091 | 2-Me-c-Pr | Me(SO$_2$)NHNH | F | H | H | H | H | H | H |
| IV-092 | 2-Me-c-Pr | MeOC(C=O)NHNH | F | H | H | H | H | H | H |
| IV-093 | 2-Me-c-Pr | [N-(2-pyridinyl)-N-acetyl-NH] | H | H | H | H | H | H | |
| IV-094 | 2-Me-c-Pr | [Boc-piperidazine] | F | H | H | H | H | H | H |
| IV-095 | 2-Me-c-Pr | Me$_2$NC(C=O)NHNH | F | H | H | H | H | H | H |
| IV-096 | 2-Me-c-Pr | Me2C=NNH | F | H | H | H | H | H | H |
| IV-097 | c-Pr | H$_2$NNH | H | F | H | H | H | H | H |
| IV-098 | c-Pr | MeNHNH | H | F | H | H | H | H | H |
| IV-099 | c-Pr | H$_2$NN(Me) | H | F | H | H | H | H | H |
| IV-100 | c-Pr | Me$_2$NNH | H | F | H | H | H | H | H |
| IV-101 | c-Pr | Me$_2$NN(Me) | H | F | H | H | H | H | H |
| IV-102 | c-Pr | PhNHNH | H | F | H | H | H | H | H |
| IV-103 | c-Pr | (2-Pyridinyl)NHNH | F | H | H | H | H | H | H |
| IV-104 | c-Pr | [1,2,4-triazol-4-yl-NH] | H | F | H | H | H | H | H |
| IV-105 | c-Pr | Me(C=O)NHNH | H | F | H | H | H | H | H |
| IV-106 | c-Pr | (Me)(Ac)NNH | H | F | H | H | H | H | H |
| IV-107 | c-Pr | Me(SO$_2$)NHNH | H | F | H | H | H | H | H |
| IV-108 | c-Pr | MeOC(C=O)NHNH | H | F | F | H | H | H | H |
| IV-109 | c-Pr | [N-(2-pyridinyl)-N-acetyl-NH] | H | F | F | H | H | H | H |

TABLE 4-continued

Inventive compounds of the formula (I) in which X represents C(R¹³)(R¹⁴)

$$(I)$$

| No. | R¹ | R² | R³ | R⁴ | R⁵ | R⁶ | R⁷ | R¹³ | R¹⁴ |
|---|---|---|---|---|---|---|---|---|---|
| IV-110 | c-Pr | tert-butyl piperidazine-1-carboxylate | H | F | F | H | H | H | H |
| IV-111 | c-Pr | Me₂NC(=O)NHNH | H | F | F | H | H | H | H |
| IV-112 | c-Pr | Me2C=NNH | H | F | F | H | H | H | H |
| IV-113 | c-Pr | H₂NNH | H | H | F | H | H | H | H |
| IV-114 | c-Pr | MeNHNH | H | H | F | H | H | H | H |
| IV-115 | c-Pr | H₂NN(Me) | H | H | F | H | H | H | H |
| IV-116 | c-Pr | Me₂NNH | H | H | F | H | H | H | H |
| IV-117 | c-Pr | Me2NN(Me) | H | H | F | H | H | H | H |
| IV-118 | c-Pr | PhNHNH | H | H | F | H | H | H | H |
| IV-119 | c-Pr | (2-Pyridinyl)NHNH | H | H | F | H | H | H | H |
| IV-120 | c-Pr | 1,2,4-triazol-1-yl-NH | H | H | F | H | H | H | H |
| IV-121 | c-Pr | Me (C=O)NHNH | H | H | F | H | H | H | H |
| IV-122 | c-Pr | (Me)(Ac)NNH | H | H | F | H | H | H | H |
| IV-123 | c-Pr | Me(SO₂)NHNH | H | H | F | H | H | H | H |
| IV-124 | c-Pr | MeOC(=O)NHNH | H | H | F | H | H | H | H |
| IV-125 | c-Pr | N-(2-pyridinyl)-N-acetyl-hydrazinyl | H | H | F | H | H | H | H |
| IV-126 | c-Pr | tert-butyl piperidazine-1-carboxylate | H | H | F | H | H | H | H |
| IV-127 | c-Pr | Me₂NC(=O)NHNH | H | H | F | H | H | H | H |
| IV-128 | c-Pr | Me2C=NNH | H | H | F | H | H | H | H |
| IV-129 | c-Pr | H₂NNH | Cl | H | H | H | H | H | H |
| IV-130 | c-Pr | MeNHNH | Cl | H | H | H | H | H | H |
| IV-131 | c-Pr | H₂NN(Me) | Cl | H | H | H | H | H | H |
| IV-132 | c-Pr | Me₂NNH | Cl | H | H | H | H | H | H |
| IV-133 | c-Pr | Me₂NN(Me) | Cl | H | H | H | H | H | H |
| IV-134 | c-Pr | PhNHNH | Cl | H | H | H | H | H | H |
| IV-135 | c-Pr | (2-Pyridinyl)NHNH | Cl | H | H | H | H | H | H |
| IV-136 | c-Pr | 1,2,4-triazol-1-yl-NH | Cl | H | H | H | H | H | H |
| IV-137 | c-Pr | tBu(C=O)(Me)NHN | Cl | H | H | H | H | H | H |
| IV-138 | c-Pr | (Me)(Ac)NNH | Cl | H | H | H | H | H | H |
| IV-139 | c-Pr | Me (SO₂)NHNH | Cl | H | H | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-140 | c-Pr | *methanesulfonyl-N(Me)-NH* | Cl | H | H | H | H | H | H |
| IV-141 | c-Pr | *N-(2-pyridinyl)-N-acetyl-hydrazinyl* | Cl | H | H | H | H | H | H |
| IV-142 | c-Pr | *tert-butyl hexahydropyridazine-1-carboxylate* | Cl | H | H | H | H | H | H |
| IV-143 | c-Pr | Me$_2$NC(=O)NHNH | Cl | H | H | H | H | H | H |
| IV-144 | c-Pr | Me2C=NNH | Cl | H | H | H | H | H | H |
| IV-145 | 1-Me-c-Pr | H$_2$NNH | Cl | H | H | H | H | H | H |
| IV-146 | 1-Me-c-Pr | MeNHNH | Cl | H | H | H | H | H | H |
| IV-147 | 1-Me-c-Pr | H$_2$NN(Me) | Cl | H | H | H | H | H | H |
| IV-148 | 1-Me-c-Pr | Me$_2$NNH | Cl | H | H | H | H | H | H |
| IV-149 | 1-Me-c-Pr | Me$_2$NN(Me) | Cl | H | H | H | H | H | H |
| IV-150 | 1-Me-c-Pr | PhNHNH | Cl | H | H | H | H | H | H |
| IV-151 | 1-Me-c-Pr | (2-Pyridinyl)NHNH | Cl | H | H | H | H | H | H |
| IV-152 | 1-Me-c-Pr | *1,2,4-triazol-1-yl-NH* | Cl | H | H | H | H | H | H |
| IV-153 | 1-Me-c-Pr | Me(C=O)NHNH | Cl | H | H | H | H | H | H |
| IV-154 | 1-Me-c-Pr | (Me)(Ac)NNH | Cl | H | H | H | H | H | H |
| IV-155 | 1-Me-c-Pr | Me(SO$_2$)NHNH | Cl | H | H | H | H | H | H |
| IV-156 | 1-Me-c-Pr | MeOC(=O)NHNH | Cl | H | H | H | H | H | H |
| IV-157 | 1-Me-c-Pr | *N-(2-pyridinyl)-N-acetyl-hydrazinyl* | Cl | H | H | H | H | H | H |
| IV-158 | 1-Me-c-Pr | *tert-butyl hexahydropyridazine-1-carboxylate* | Cl | H | H | H | H | H | H |

TABLE 4-continued

Inventive compounds of the formula (I) in which X represents C(R$^{13}$)(R$^{14}$)

[Structure of formula (I): pyrimidine with R$^1$ at 2-position, substituent at 4-position with X linked to C(=O)C(=O)R$^2$, and phenyl group at 5-position bearing R$^3$–R$^7$]

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-159 | 1-Me-c-Pr | Me$_2$NC(=O)NHNH | Cl | H | H | H | H | H | H |
| IV-160 | 1-Me-c-Pr | Me2C=NNH | Cl | H | H | H | H | H | H |
| IV-161 | 2-Me-c-Pr | H$_2$NNH | Cl | H | H | H | H | H | H |
| IV-162 | 2-Me-c-Pr | MeNHNH | Cl | H | H | H | H | H | H |
| IV-163 | 2-Me-c-Pr | H$_2$NN(Me) | Cl | H | H | H | H | H | H |
| IV-164 | 2-Me-c-Pr | Me$_2$NNH | Cl | H | H | H | H | H | H |
| IV-165 | 2-Me-c-Pr | Me$_2$NN(Me) | Cl | H | H | H | H | H | H |
| IV-166 | 2-Me-c-Pr | PhNHNH | Cl | H | H | H | H | H | H |
| IV-167 | 2-Me-c-Pr | (2-Pyridinyl)NHNH | Cl | H | H | H | H | H | H |
| IV-168 | 2-Me-c-Pr | [1,2,4-triazol-1-yl-NH] | Cl | H | H | H | H | H | H |
| IV-169 | 2-Me-c-Pr | Me(C=O)NHNH | Cl | H | H | H | H | H | H |
| IV-170 | 2-Me-c-Pr | (Me)(Ac)NNH | Cl | H | H | H | H | H | H |
| IV-171 | 2-Me-c-Pr | Me(SO$_2$)NHNH | Cl | H | H | H | H | H | H |
| IV-172 | 2-Me-c-Pr | MeOC(=O)NHNH | Cl | H | H | H | H | H | H |
| IV-173 | 2-Me-c-Pr | [N-(pyridin-2-yl)-N-acetyl-hydrazinyl] | Cl | H | H | H | H | H | H |
| IV-174 | 2-Me-c-Pr | [1-(tert-butoxycarbonyl)hexahydropyridazin-2-yl] | Cl | H | H | H | H | H | H |
| IV-175 | 2-Me-c-Pr | Me$_2$NC(=O)NHNH | Cl | H | H | H | H | H | H |
| IV-176 | 2-Me-c-Pr | Me2C=NNH | Cl | H | H | H | H | H | H |
| IV-177 | c-Pr | H$_2$NNH | H | Cl | H | H | H | H | H |
| IV-178 | c-Pr | MeNHNH | H | Cl | H | H | H | H | H |
| IV-179 | c-Pr | H$_2$NN(Me) | H | Cl | H | H | H | H | H |
| IV-180 | c-Pr | Me$_2$NNH | H | Cl | H | H | H | H | H |
| IV-181 | c-Pr | Me$_2$NN(Me) | H | Cl | H | H | H | H | H |
| IV-182 | c-Pr | PhNHNH | H | Cl | H | H | H | H | H |
| IV-183 | c-Pr | (2-Pyridinyl)NHNH | H | Cl | H | H | H | H | H |
| IV-184 | c-Pr | [1,2,4-triazol-1-yl-NH] | H | Cl | H | H | H | H | H |
| IV-185 | c-Pr | Me(C=O)NHNH | H | Cl | H | H | H | H | H |
| IV-186 | c-Pr | (Me)(Ac)NNH | H | Cl | H | H | H | H | H |
| IV-187 | c-Pr | Me(SO$_2$)NHNH | H | Cl | H | H | H | H | H |
| IV-188 | c-Pr | MeOC(=O)NHNH | H | Cl | H | H | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-189 | c-Pr | [2-pyridinyl-N(Ac)-NH-] | H | Cl | H | H | H | H | H |
| IV-190 | c-Pr | [tert-butyl hexahydropyridazine-1-carboxylate] | H | Cl | H | H | H | H | H |
| IV-191 | c-Pr | Me$_2$NC(=O)NHNH | H | Cl | H | H | H | H | H |
| IV-192 | c-Pr | Me2C=NNH | H | Cl | H | H | H | H | H |
| IV-193 | c-Pr | H$_2$NNH | H | H | Cl | H | H | H | H |
| IV-194 | c-Pr | MeNHNH | H | H | Cl | H | H | H | H |
| IV-195 | c-Pr | H$_2$NN(Me) | H | H | Cl | H | H | H | H |
| IV-196 | c-Pr | Me$_2$NNH | H | H | Cl | H | H | H | H |
| IV-197 | c-Pr | Me$_2$NN(Me) | H | H | Cl | H | H | H | H |
| IV-198 | c-Pr | PhNHNH | H | H | Cl | H | H | H | H |
| IV-199 | c-Pr | (2-Pyridinyl)NHNH | H | H | Cl | H | H | H | H |
| IV-200 | c-Pr | [1,2,4-triazol-1-yl-NH-] | H | H | Cl | H | H | H | H |
| IV-201 | c-Pr | Me(C=O)NHNH | H | H | Cl | H | H | H | H |
| IV-202 | c-Pr | (Me)(Ac)NNH | H | H | Cl | H | H | H | H |
| IV-203 | c-Pr | Me(SO$_2$)NHNH | H | H | Cl | H | H | H | H |
| IV-204 | c-Pr | MeOC(=O)NHNH | H | H | Cl | H | H | H | H |
| IV-205 | c-Pr | [2-pyridinyl-N(Ac)-NH-] | H | H | Cl | H | H | H | H |
| IV-206 | c-Pr | [tert-butyl hexahydropyridazine-1-carboxylate] | H | H | Cl | H | H | H | H |
| IV-207 | c-Pr | Me$_2$NC(=O)NHNH | H | H | Cl | H | H | H | H |
| IV-208 | c-Pr | Me2C=NNH | H | H | Cl | H | H | H | H |
| IV-209 | c-Pr | H$_2$NNH | Me | H | H | H | H | H | H |
| IV-210 | c-Pr | MeNHNH | Me | H | H | H | H | H | H |
| IV-211 | c-Pr | H$_2$NN(Me) | Me | H | H | H | H | H | H |
| IV-212 | c-Pr | Me$_2$NNH | Me | H | H | H | H | H | H |
| IV-213 | c-Pr | Me$_2$NN(Me) | Me | H | H | H | H | H | H |

TABLE 4-continued

Inventive compounds of the formula (I) in which X represents C(R¹³)(R¹⁴)

| No. | R¹ | R² | R³ | R⁴ | R⁵ | R⁶ | R⁷ | R¹³ | R¹⁴ |
|---|---|---|---|---|---|---|---|---|---|
| IV-214 | c-Pr | PhNHNH | Me | H | H | H | H | H | H |
| IV-215 | c-Pr | (2-Pyridinyl)NHNH | Me | H | H | H | H | H | H |
| IV-216 | c-Pr | [1,2,4-triazol-4-yl-NH] | Me | H | H | H | H | H | H |
| IV-217 | c-Pr | Me(C=O)NHNH | Me | H | H | H | H | H | H |
| IV-218 | c-Pr | (Me)(Ac)NNH | Me | H | H | H | H | H | H |
| IV-219 | c-Pr | Me(SO₂)NHNH | Me | H | H | H | H | H | H |
| IV-220 | c-Pr | MeOC(=O)NHNH | Me | H | H | H | H | H | H |
| IV-221 | c-Pr | [N-(2-pyridinyl)-N-acetyl-hydrazino] | Me | H | H | H | H | H | H |
| IV-222 | c-Pr | [tert-butoxycarbonyl-hexahydropyridazin-1-yl] | Me | H | H | H | H | H | H |
| IV-223 | c-Pr | Me₂NC(=O)NHNH | Me | H | H | H | H | H | H |
| IV-224 | c-Pr | Me2C=NNH | Me | H | H | H | H | H | H |
| IV-225 | 1-Me-c-Pr | H₂NNH | Me | H | H | H | H | H | H |
| IV-226 | 1-Me-c-Pr | MeNHNH | Me | H | H | H | H | H | H |
| IV-227 | 1-Me-c-Pr | H₂NN(Me) | Me | H | H | H | H | H | H |
| IV-228 | 1-Me-c-Pr | Me₂NNH | Me | H | H | H | H | H | H |
| IV-229 | 1-Me-c-Pr | Me₂NN(Me) | Me | H | H | H | H | H | H |
| IV-230 | 1-Me-c-Pr | PhNHNH | Me | H | H | H | H | H | H |
| IV-231 | 1-Me-c-Pr | (2-Pyridinyl)NHNH | Me | H | H | H | H | H | H |
| IV-232 | 1-Me-c-Pr | [1,2,4-triazol-4-yl-NH] | Me | H | H | H | H | H | H |
| IV-233 | 1-Me-c-Pr | Me(C=O)NHNH | Me | H | H | H | H | H | H |
| IV-234 | 1-Me-c-Pr | (Me)(Ac)NNH | Me | H | H | H | H | H | H |
| IV-235 | 1-Me-c-Pr | Me(SO₂)NHNH | Me | H | H | H | H | H | H |
| IV-236 | 1-Me-c-Pr | MeOC(=O)NHNH | Me | H | H | H | H | H | H |
| IV-237 | 1-Me-c-Pr | [N-(2-pyridinyl)-N-acetyl-hydrazino] | Me | H | H | H | H | H | H |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-238 | 1-Me-c-Pr | *tert-butyl piperidin-1-yl carboxylate group* | Me | H | H | H | H | H | H |
| IV-239 | 1-Me-c-Pr | Me₂NC(=O)NHNH | Me | H | H | H | H | H | H |
| IV-240 | 1-Me-c-Pr | Me2C=NNH | Me | H | H | H | H | H | H |
| IV-241 | 2-Me-c-Pr | H₂NNH | Me | H | H | H | H | H | H |
| IV-242 | 2-Me-c-Pr | MeNHNH | Me | H | H | H | H | H | H |
| IV-243 | 2-Me-c-Pr | H₂NN(Me) | Me | H | H | H | H | H | H |
| IV-244 | 2-Me-c-Pr | Me₂NNH | Me | H | H | H | H | H | H |
| IV-245 | 2-Me-c-Pr | Me₂NN(Me) | Me | H | H | H | H | H | H |
| IV-246 | 2-Me-c-Pr | PhNHNH | Me | H | H | H | H | H | H |
| IV-247 | 2-Me-c-Pr | (2-Pyridinyl)NHNH | Me | H | H | H | H | H | H |
| IV-248 | 2-Me-c-Pr | *1,2,4-triazol-4-yl-NH* | Me | H | H | H | H | H | H |
| IV-249 | 2-Me-c-Pr | Me(C=O)NHNH | Me | H | H | H | H | H | H |
| IV-250 | 2-Me-c-Pr | (Me)(Ac)NNH | Me | H | H | H | H | H | H |
| IV-251 | 2-Me-c-Pr | Me(SO₂)NHNH | Me | H | H | H | H | H | H |
| IV-252 | 2-Me-c-Pr | MeOC(=O)NHNH | Me | H | H | H | H | H | H |
| IV-253 | 2-Me-c-Pr | *N-acetyl-N-(pyridin-2-yl)hydrazinyl group* | Me | H | H | H | H | H | H |
| IV-254 | 2-Me-c-Pr | *tert-butyl piperidin-1-yl carboxylate group* | Me | H | H | H | H | H | H |
| IV-255 | 2-Me-c-Pr | Me₂NC(=O)NHNH | Me | H | H | H | H | H | H |
| IV-256 | 2-Me-c-Pr | Me2C=NNH | Me | H | H | H | H | H | H |
| IV-257 | c-Pr | H₂NNH | H | Me | H | H | H | H | H |
| IV-258 | c-Pr | MeNHNH | H | Me | H | H | H | H | H |
| IV-259 | c-Pr | H₂NN(Me) | H | Me | H | H | H | H | H |
| IV-260 | c-Pr | Me₂NNH | H | Me | H | H | H | H | H |
| IV-261 | c-Pr | Me₂NN(Me) | H | Me | H | H | H | H | H |
| IV-262 | c-Pr | PhNHNH | H | Me | H | H | H | H | H |
| IV-263 | c-Pr | (2-Pyridinyl)NHNH | H | Me | H | H | H | H | H |
| IV-264 | c-Pr | *1,2,4-triazol-4-yl-NH* | H | Me | H | H | H | H | H |
| IV-265 | c-Pr | Me(C=O)NHNH | H | Me | H | H | H | H | H |
| IV-266 | c-Pr | (Me)(Ac)NNH | H | Me | H | H | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-267 | c-Pr | Me(SO$_2$)NHNH | H | Me | H | H | H | H | H |
| IV-268 | c-Pr | MeOC(=O)NHNH | H | Me | H | H | H | H | H |
| IV-269 | c-Pr | (N-(2-pyridinyl)-N-acetyl-hydrazino) | H | Me | H | H | H | H | H |
| IV-270 | c-Pr | (tert-butyl hexahydropyridazine-1-carboxylate) | H | Me | H | H | H | H | H |
| IV-271 | c-Pr | Me$_2$NC(=O)NHNH | H | Me | H | H | H | H | H |
| IV-272 | c-Pr | Me$_2$C=NNH | H | Me | H | H | H | H | H |
| IV-273 | c-Pr | H$_2$NNH | H | H | Me | H | H | H | H |
| IV-274 | c-Pr | MeNHNH | H | H | Me | H | H | H | H |
| IV-275 | c-Pr | H$_2$NN(Me) | H | H | Me | H | H | H | H |
| IV-276 | c-Pr | Me$_2$NNH | H | H | Me | H | H | H | H |
| IV-277 | c-Pr | Me$_2$NN(Me) | H | H | Me | H | H | H | H |
| IV-278 | c-Pr | PhNHNH | H | H | Me | H | H | H | H |
| IV-279 | c-Pr | (2-Pyridinyl)NHNH | H | H | Me | H | H | H | H |
| IV-280 | c-Pr | (1,2,4-triazol-1-yl)NH | H | H | Me | H | H | H | H |
| IV-281 | c-Pr | Me(C=O)NHNH | H | H | Me | H | H | H | H |
| IV-282 | c-Pr | (Me)(Ac)NNH | H | H | Me | H | H | H | H |
| IV-283 | c-Pr | Me(SO$_2$)NHNH | H | H | Me | H | H | H | H |
| IV-284 | c-Pr | MeOC(=O)NHNH | H | H | Me | H | H | H | H |
| IV-285 | c-Pr | (N-(2-pyridinyl)-N-acetyl-hydrazino) | H | H | Me | H | H | H | H |
| IV-286 | c-Pr | (tert-butyl hexahydropyridazine-1-carboxylate) | H | H | Me | H | H | H | H |
| IV-287 | c-Pr | Me$_2$NC(=O)NHNH | H | H | Me | H | H | H | H |
| IV-288 | c-Pr | Me$_2$C=NNH | H | H | Me | H | H | H | H |
| IV-289 | c-Pr | H$_2$NNH | CF$_3$ | H | H | H | H | H | H |
| IV-290 | c-Pr | MeNHNH | CF$_3$ | H | H | H | H | H | H |

TABLE 4-continued

Inventive compounds of the formula (I) in which X represents C(R¹³)(R¹⁴)

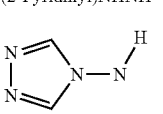

(I)

| No. | R¹ | R² | R³ | R⁴ | R⁵ | R⁶ | R⁷ | R¹³ | R¹⁴ |
|---|---|---|---|---|---|---|---|---|---|
| IV-291 | c-Pr | H₂NN(Me) | CF₃ | H | H | H | H | H | H |
| IV-292 | c-Pr | Me₂NNH | CF₃ | H | H | H | H | H | H |
| IV-293 | c-Pr | Me₂NN(Me) | CF₃ | H | H | H | H | H | H |
| IV-294 | c-Pr | PhNHNH | CF₃ | H | H | H | H | H | H |
| IV-295 | c-Pr | (2-Pyridinyl)NHNH | CF₃ | H | H | H | H | H | H |
| IV-296 | c-Pr | 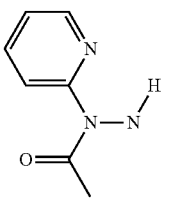 | CF₃ | H | H | H | H | H | H |
| IV-297 | c-Pr | Me(C=O)NHNH | CF₃ | H | H | H | H | H | H |
| IV-298 | c-Pr | (Me)(Ac)NNH | CF₃ | H | H | H | H | H | H |
| IV-299 | c-Pr | Me(SO₂)NHNH | CF₃ | H | H | H | H | H | H |
| IV-300 | c-Pr | MeOC(=O)NHNH | CF₃ | H | H | H | H | H | H |
| IV-301 | c-Pr | 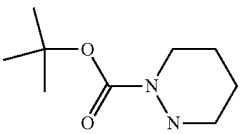 | CF₃ | H | H | H | H | H | H |
| IV-302 | c-Pr | 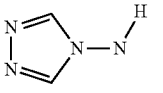 | CF₃ | H | H | H | H | H | H |
| IV-303 | c-Pr | Me₂NC(=O)NHNH | CF₃ | H | H | H | H | H | H |
| IV-304 | c-Pr | Me2C=NNH | CF₃ | H | H | H | H | H | H |
| IV-305 | 1-Me-c-Pr | H₂NNH | CF₃ | H | H | H | H | H | H |
| IV-306 | 1-Me-c-Pr | MeNHNH | CF₃ | H | H | H | H | H | H |
| IV-307 | 1-Me-c-Pr | H₂NN(Me) | CF₃ | H | H | H | H | H | H |
| IV-308 | 1-Me-c-Pr | Me₂NNH | CF₃ | H | H | H | H | H | H |
| IV-309 | 1-Me-c-Pr | Me₂NN(Me) | CF₃ | H | H | H | H | H | H |
| IV-310 | 1-Me-c-Pr | PhNHNH | CF₃ | H | H | H | H | H | H |
| IV-311 | 1-Me-c-Pr | (2-Pyridinyl)NHNH | CF₃ | H | H | H | H | H | H |
| IV-312 | 1-Me-c-Pr | 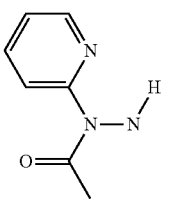 | CF₃ | H | H | H | H | H | H |
| IV-313 | 1-Me-c-Pr | Me(C=O)NHNH | CF₃ | H | H | H | H | H | H |
| IV-314 | 1-Me-c-Pr | (Me)(Ac)NNH | CF₃ | H | H | H | H | H | H |
| IV-315 | 1-Me-c-Pr | Me(SO₂)NHNH | CF₃ | H | H | H | H | H | H |
| IV-316 | 1-Me-c-Pr | MeOC(=O)NHNH | CF₃ | H | H | H | H | H | H |
| IV-317 | 1-Me-c-Pr | | CF₃ | H | H | H | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-318 | 1-Me-c-Pr | tert-butyl hexahydropyridazine-1-carboxylate | CF$_3$ | H | H | H | H | H | H |
| IV-319 | 1-Me-c-Pr | Me$_2$NC(=O)NHNH | CF$_3$ | H | H | H | H | H | H |
| IV-320 | 1-Me-c-Pr | Me2C=NNH | CF$_3$ | H | H | H | H | H | H |
| IV-321 | 2-Me-c-Pr | H$_2$NNH | CF$_3$ | H | H | H | H | H | H |
| IV-322 | 2-Me-c-Pr | MeNHNH | CF$_3$ | H | H | H | H | H | H |
| IV-323 | 2-Me-c-Pr | H$_2$NN(Me) | CF$_3$ | H | H | H | H | H | H |
| IV-324 | 2-Me-c-Pr | Me$_2$NNH | CF$_3$ | H | H | H | H | H | H |
| IV-325 | 2-Me-c-Pr | Me$_2$NN(Me) | CF$_3$ | H | H | H | H | H | H |
| IV-326 | 2-Me-c-Pr | PhNHNH | CF$_3$ | H | H | H | H | H | H |
| IV-327 | 2-Me-c-Pr | (2-Pyridinyl)NHNH | CF$_3$ | H | H | H | H | H | H |
| IV-328 | 2-Me-c-Pr | 1,2,4-triazol-1-yl-NH | CF$_3$ | H | H | H | H | H | H |
| IV-329 | 2-Me-c-Pr | Me(C=O)NHNH | CF$_3$ | H | H | H | H | H | H |
| IV-330 | 2-Me-c-Pr | (Me)(Ac)NNH | CF$_3$ | H | H | H | H | H | H |
| IV-331 | 2-Me-c-Pr | Me(SO$_2$)NHNH | CF$_3$ | H | H | H | H | H | H |
| IV-332 | 2-Me-c-Pr | MeOC(=O)NHNH | CF$_3$ | H | H | H | H | H | H |
| IV-333 | 2-Me-c-Pr | N-acetyl-N-(2-pyridinyl)hydrazino | CF$_3$ | H | H | H | H | H | H |
| IV-334 | 2-Me-c-Pr | tert-butyl hexahydropyridazine-1-carboxylate | CF$_3$ | H | H | H | H | H | H |
| IV-335 | 2-Me-c-Pr | Me$_2$NC(=O)NHNH | CF$_3$ | H | H | H | H | H | H |
| IV-336 | 2-Me-c-Pr | Me2C=NNH | CF$_3$ | H | H | H | H | H | H |
| IV-337 | c-Pr | H$_2$NNH | H | CF$_3$ | H | H | H | H | H |
| IV-338 | c-Pr | MeNHNH | H | CF$_3$ | H | H | H | H | H |
| IV-339 | c-Pr | H$_2$NN(Me) | H | CF$_3$ | H | H | H | H | H |
| IV-340 | c-Pr | Me$_2$NNH | H | CF$_3$ | H | H | H | H | H |
| IV-341 | c-Pr | Me$_2$NN(Me) | H | CF$_3$ | H | H | H | H | H |
| IV-342 | c-Pr | PhNHNH | H | CF$_3$ | H | H | H | H | H |
| IV-343 | c-Pr | (2-Pyridinyl)NHNH | H | CF$_3$ | H | H | H | H | H |
| IV-344 | c-Pr | 1,2,4-triazol-1-yl-NH | H | CF$_3$ | H | H | H | H | H |
| IV-345 | c-Pr | Me(C=O)NHNH | H | CF$_3$ | H | H | H | H | H |
| IV-346 | c-Pr | (Me)(Ac)NNH | H | CF$_3$ | H | H | H | H | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-347 | c-Pr | Me(SO$_2$)NHNH | H | CF$_3$ | H | H | H | H | H |
| IV-348 | c-Pr | MeOC(=O)NHNH | H | CF$_3$ | H | H | H | H | H |
| IV-349 | c-Pr | (N-(2-pyridinyl)-N-acetyl)NH | H | CF$_3$ | H | H | H | H | H |
| IV-350 | c-Pr | (tert-butoxycarbonyl-hexahydropyridazin-1-yl) | H | CF$_3$ | H | H | H | H | H |
| IV-351 | c-Pr | Me$_2$NC(=O)NHNH | H | CF$_3$ | H | H | H | H | H |
| IV-352 | c-Pr | Me$_2$C=NNH | H | CF$_3$ | H | H | H | H | H |
| IV-353 | c-Pr | H$_2$NNH | H | H | CF$_3$ | H | H | H | H |
| IV-354 | c-Pr | MeNHNH | H | H | CF$_3$ | H | H | H | H |
| IV-355 | c-Pr | H$_2$NN(Me) | H | H | CF$_3$ | H | H | H | H |
| IV-356 | c-Pr | Me$_2$NNH | H | H | CF$_3$ | H | H | H | H |
| IV-357 | c-Pr | Me$_2$NN(Me) | H | H | CF$_3$ | H | H | H | H |
| IV-358 | c-Pr | PhNHNH | H | H | CF$_3$ | H | H | H | H |
| IV-359 | c-Pr | (2-Pyridinyl)NHNH | H | H | CF$_3$ | H | H | H | H |
| IV-360 | c-Pr | (1,2,4-triazol-1-yl)NH | H | H | CF$_3$ | H | H | H | H |
| IV-361 | c-Pr | Me(C=O)NHNH | H | H | CF$_3$ | H | H | H | H |
| IV-362 | c-Pr | (Me)(Ac)NNH | H | H | CF$_3$ | H | H | H | H |
| IV-363 | c-Pr | Me(SO$_2$)NHNH | H | H | CF$_3$ | H | H | H | H |
| IV-364 | c-Pr | MeOC(=O)NHNH | H | H | CF$_3$ | H | H | H | H |
| IV-365 | c-Pr | (N-(2-pyridinyl)-N-acetyl)NH | H | H | CF$_3$ | H | H | H | H |
| IV-366 | c-Pr | (tert-butoxycarbonyl-hexahydropyridazin-1-yl) | H | H | CF$_3$ | H | H | H | H |
| IV-367 | c-Pr | Me$_2$NC(=O)NHNH | H | H | CF$_3$ | H | H | H | H |
| IV-368 | c-Pr | Me2C=NNH | H | H | CF$_3$ | H | H | H | H |
| IV-369 | c-Pr | H$_2$NNH | MeO | H | H | H | H | H | H |
| IV-370 | c-Pr | MeNHNH | MeO | H | H | H | H | H | H |

TABLE 4-continued

Inventive compounds of the formula (I) in which X represents C(R¹³)(R¹⁴)

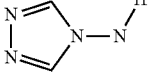

| No. | R¹ | R² | R³ | R⁴ | R⁵ | R⁶ | R⁷ | R¹³ | R¹⁴ |
|---|---|---|---|---|---|---|---|---|---|
| IV-371 | c-Pr | H₂NN(Me) | MeO | H | H | H | H | H | H |
| IV-372 | c-Pr | Me₂NNH | MeO | H | H | H | H | H | H |
| IV-373 | c-Pr | Me₂NN(Me) | MeO | H | H | H | H | H | H |
| IV-374 | c-Pr | PhNHNH | MeO | H | H | H | H | H | H |
| IV-375 | c-Pr | (2-Pyridinyl)NHNH | MeO | H | H | H | H | H | H |
| IV-376 | c-Pr | 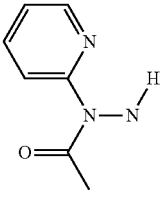 | MeO | H | H | H | H | H | H |
| IV-377 | c-Pr | Me(C=O)NHNH | MeO | H | H | H | H | H | H |
| IV-378 | c-Pr | (Me)(Ac)NNH | MeO | H | H | H | H | H | H |
| IV-379 | c-Pr | Me(SO₂)NHNH | MeO | H | H | H | H | H | H |
| IV-380 | c-Pr | MeOC(=O)NHNH | MeO | H | H | H | H | H | H |
| IV-381 | c-Pr | 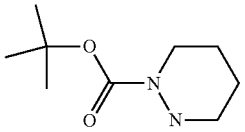 | MeO | H | H | H | H | H | H |
| IV-382 | c-Pr | 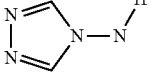 | MeO | H | H | H | H | H | H |
| IV-383 | c-Pr | Me₂NC(=O)NHNH | MeO | H | H | H | H | H | H |
| IV-384 | c-Pr | Me₂ME2C=NNH C=NNH | MeO | H | H | H | H | H | H |
| IV-385 | 1-Me-c-Pr | H₂NNH | MeO | H | H | H | H | H | H |
| IV-386 | 1-Me-c-Pr | MeNHNH | MeO | H | H | H | H | H | H |
| IV-387 | 1-Me-c-Pr | H₂NN(Me) | MeO | H | H | H | H | H | H |
| IV-388 | 1-Me-c-Pr | Me₂NNH | MeO | H | H | H | H | H | H |
| IV-389 | 1-Me-c-Pr | Me₂NN(Me) | MeO | H | H | H | H | H | H |
| IV-390 | 1-Me-c-Pr | PhNHNH | MeO | H | H | H | H | H | H |
| IV-391 | 1-Me-c-Pr | (2-Pyridinyl)NHNH | MeO | H | H | H | H | H | H |
| IV-392 | 1-Me-c-Pr | 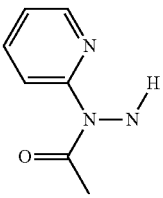 | MeO | H | H | H | H | H | H |
| IV-393 | 1-Me-c-Pr | Me(C=O)NHNH | MeO | H | H | H | H | H | H |
| IV-394 | 1-Me-c-Pr | (Me)(Ac)NNH | MeO | H | H | H | H | H | H |
| IV-395 | 1-Me-c-Pr | Me(SO₂)NHNH | MeO | H | H | H | H | H | H |
| IV-396 | 1-Me-c-Pr | MeOC(=O)NHNH | MeO | H | H | H | H | H | H |
| IV-397 | 1-Me-c-Pr | | MeO | H | H | H | H | H | H |

TABLE 4-continued

Inventive compounds of the formula (I) in which X represents C(R$^{13}$)(R$^{14}$)

(I)

[Structure: pyrimidine with R$^1$ at 2-position, connected at 4-position to a phenyl ring bearing R$^3$, R$^4$, R$^5$, R$^6$, R$^7$; the 4-position also bears X linked to two C(=O) groups, one of which bears R$^2$]

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-398 | 1-Me-c-Pr | tert-butyl N-piperidazine-1-carboxylate group | MeO | H | H | H | H | H | H |
| IV-399 | 1-Me-c-Pr | Me$_2$NC(=O)NHNH | MeO | H | H | H | H | H | H |
| IV-400 | 1-Me-c-Pr | Me$_2$C=NNHMe2 C=NNH | MeO | H | H | H | H | H | H |
| IV-401 | c-Pr | H$_2$NNH | H | MeO | H | H | H | H | H |
| IV-402 | c-Pr | MeNHNH | H | MeO | H | H | H | H | H |
| IV-403 | c-Pr | H$_2$NN(Me) | H | MeO | H | H | H | H | H |
| IV-404 | c-Pr | Me$_2$NNH | H | MeO | H | H | H | H | H |
| IV-405 | c-Pr | Me$_2$NN(Me) | H | MeO | H | H | H | H | H |
| IV-406 | c-Pr | PhNHNH | H | MeO | H | H | H | H | H |
| IV-407 | c-Pr | (2-Pyridinyl)NHNH | H | MeO | H | H | H | H | H |
| IV-408 | c-Pr | 1,2,4-triazol-1-yl-NH | H | MeO | H | H | H | H | H |
| IV-409 | c-Pr | Me(C=O)NHNH | H | MeO | H | H | H | H | H |
| IV-410 | c-Pr | (Me)(Ac)NNH | H | MeO | H | H | H | H | H |
| IV-411 | c-Pr | Me(SO$_2$)NHNH | H | MeO | H | H | H | H | H |
| IV-412 | c-Pr | MeOC(=O)NHNH | H | MeO | H | H | H | H | H |
| IV-413 | c-Pr | N-(2-pyridinyl)-N-acetylhydrazinyl group | H | MeO | H | H | H | H | H |
| IV-414 | c-Pr | tert-butyl N-piperidazine-1-carboxylate group | H | MeO | H | H | H | H | H |
| IV-415 | c-Pr | Me$_2$NC(=O)NHNH | H | MeO | H | H | H | H | H |
| IV-416 | c-Pr | Me$_2$NC=NNH | H | MeO | H | H | H | H | H |
| IV-417 | c-Pr | H$_2$NNH | H | H | MeO | H | H | H | H |
| IV-418 | c-Pr | MeNHNH | H | H | MeO | H | H | H | H |
| IV-419 | c-Pr | H$_2$NN(Me) | H | H | MeO | H | H | H | H |
| IV-420 | c-Pr | Me$_2$NNH | H | H | MeO | H | H | H | H |
| IV-421 | c-Pr | Me$_2$NN(Me) | H | H | MeO | H | H | H | H |
| IV-422 | c-Pr | PhNHNH | H | H | MeO | H | H | H | H |
| IV-423 | c-Pr | (2-Pyridinyl)NHNH | H | H | MeO | H | H | H | H |
| IV-424 | c-Pr | 1,2,4-triazol-1-yl-NH | H | H | MeO | H | H | H | H |
| IV-425 | c-Pr | Me(C=O)NHNH | H | H | MeO | H | H | H | H |
| IV-426 | c-Pr | (Me)(Ac)NNH | H | H | MeO | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-427 | c-Pr | Me(SO$_2$)NHNH | H | H | MeO | H | H | H | H |
| IV-428 | c-Pr | MeOC(=O)NHNH | H | H | MeO | H | H | H | H |
| IV-429 | c-Pr | (2-pyridinyl-N(C(=O)Me)-NH) | H | H | MeO | H | H | H | H |
| IV-430 | c-Pr | (tBuO-C(=O)-piperidazinyl) | H | H | MeO | H | H | H | H |
| IV-431 | c-Pr | Me$_2$NC(=O)NHNH | H | H | MeO | H | H | H | H |
| IV-432 | c-Pr | Me2C=NNH | H | H | MeO | H | H | H | H |
| IV-433 | c-Pr | H$_2$NNH | F | F | H | H | H | H | H |
| IV-434 | c-Pr | MeNHNH | F | F | H | H | H | H | H |
| IV-435 | c-Pr | H2NN(Me) | F | F | H | H | H | H | H |
| IV-436 | c-Pr | Me2NNH | F | F | H | H | H | H | H |
| IV-437 | c-Pr | Me2NN(Me) | F | F | H | H | H | H | H |
| IV-438 | c-Pr | PhNHNH | F | F | H | H | H | H | H |
| IV-439 | c-Pr | (2-Pyridinyl)NHNH | F | F | H | H | H | H | H |
| IV-440 | c-Pr | (1,2,4-triazolyl-NH) | F | F | H | H | H | H | H |
| IV-441 | c-Pr | Me(C=O)NHNH | F | F | H | H | H | H | H |
| IV-442 | c-Pr | (Me)(Ac)NNH | F | F | H | H | H | H | H |
| IV-443 | c-Pr | Me(SO$_2$)NHNH | F | F | H | H | H | H | H |
| IV-444 | c-Pr | MeOC(=O)NHNH | F | F | H | H | H | H | H |
| IV-445 | c-Pr | (2-pyridinyl-N(C(=O)Me)-NH) | F | F | H | H | H | H | H |
| IV-446 | c-Pr | (tBuO-C(=O)-piperidazinyl) | F | F | H | H | H | H | H |
| IV-447 | c-Pr | Me$_2$NC(=O)NHNH | F | F | H | H | H | H | H |
| IV-448 | c-Pr | Me2C=NNH | F | F | H | H | H | H | H |
| IV-449 | c-Pr | H$_2$NNH | F | H | F | H | H | H | H |
| IV-450 | c-Pr | MeNHNH | F | H | F | H | H | H | H |
| IV-451 | c-Pr | H$_2$NN(Me) | F | H | F | H | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-452 | c-Pr | Me$_2$NNH | F | H | F | H | H | H | H |
| IV-453 | c-Pr | Me$_2$NN(Me) | F | H | F | H | H | H | H |
| IV-454 | c-Pr | PhNHNH | F | H | F | H | H | H | H |
| IV-455 | c-Pr | (2-Pyridinyl)NHNH | F | H | F | H | H | H | H |
| IV-456 | c-Pr | [triazolyl-NH] | F | H | F | H | H | H | H |
| IV-457 | c-Pr | Me(C=O)NHNH | F | H | F | H | H | H | H |
| IV-458 | c-Pr | (Me)(Ac)NNH | F | H | F | H | H | H | H |
| IV-459 | c-Pr | Me(SO$_2$)NHNH | F | H | F | H | H | H | H |
| IV-460 | c-Pr | MeOC(=O)NHNH | F | H | F | H | H | H | H |
| IV-461 | c-Pr | [pyridinyl-N(Ac)-NH] | F | H | F | H | H | H | H |
| IV-462 | c-Pr | [Boc-piperidazine] | F | H | F | H | H | H | H |
| IV-463 | c-Pr | Me$_2$NC(=O)NHNH | F | H | F | H | H | H | H |
| IV-464 | c-Pr | Me$_2$NC=NNH | F | H | F | H | H | H | H |
| IV-465 | c-Pr | H$_2$NNH | F | H | H | F | H | H | H |
| IV-466 | c-Pr | MeNHNH | F | H | H | F | H | H | H |
| IV-467 | c-Pr | H2NN(Me) | F | H | H | F | H | H | H |
| IV-468 | c-Pr | Me2NNH | F | H | H | F | H | H | H |
| IV-469 | c-Pr | Me2NN(Me) | F | H | H | F | H | H | H |
| IV-470 | c-Pr | PhNHNH | F | H | H | F | H | H | H |
| IV-471 | c-Pr | (2-Pyridinyl)NHNH | F | H | H | F | H | H | H |
| IV-472 | c-Pr | [triazolyl-NH] | F | H | H | F | H | H | H |
| IV-473 | c-Pr | Me(C=O)NHNH | F | H | H | F | H | H | H |
| IV-474 | c-Pr | (Me)(Ac)NNH | F | H | H | F | H | H | H |
| IV-475 | c-Pr | Me(SO$_2$)NHNH | F | H | H | F | H | H | H |
| IV-476 | c-Pr | MeOC(=O)NHNH | F | H | H | F | H | H | H |
| IV-477 | c-Pr | [pyridinyl-N(Ac)-NH] | F | H | H | F | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-478 | c-Pr | tert-butyl piperidine-1-carboxylate (N-N) | F | H | H | F | H | H | H |
| IV-479 | c-Pr | Me$_2$NC(=O)NHNH | F | H | H | F | H | H | H |
| IV-480 | c-Pr | Me2C=NNH | F | H | H | F | H | H | H |
| IV-481 | c-Pr | H$_2$NNH | F | H | H | H | F | H | H |
| IV-482 | c-Pr | MeNHNH | F | H | H | H | F | H | H |
| IV-483 | c-Pr | H$_2$NN(Me) | F | H | H | H | F | H | H |
| IV-484 | c-Pr | Me$_2$NNH | F | H | H | H | F | H | H |
| IV-485 | c-Pr | Me$_2$NN(Me) | F | H | H | H | F | H | H |
| IV-486 | c-Pr | PhNHNH | F | H | H | H | F | H | H |
| IV-487 | c-Pr | (2-Pyridinyl)NHNH | F | H | H | H | F | H | H |
| IV-488 | c-Pr | 1,2,4-triazol-1-yl-NH | F | H | H | H | F | H | H |
| IV-489 | c-Pr | Me(C=O)NHNH | F | H | H | H | F | H | H |
| IV-490 | c-Pr | (Me)(Ac)NNH | F | H | H | H | F | H | H |
| IV-491 | c-Pr | Me(SO$_2$)NHNH | F | H | H | H | F | H | H |
| IV-492 | c-Pr | MeOC(=O)NHNH | F | H | H | H | F | H | H |
| IV-493 | c-Pr | N-acetyl-N-(2-pyridinyl)hydrazine | F | H | H | H | F | H | H |
| IV-494 | c-Pr | tert-butyl piperidine-1-carboxylate (N-N) | F | H | H | H | F | H | H |
| IV-495 | c-Pr | Me$_2$NC(=O)NHNH | F | H | H | H | F | H | H |
| IV-496 | c-Pr | Me2C=NNH | F | H | H | H | F | H | H |
| IV-497 | c-Pr | H$_2$NNH | F | Cl | H | H | H | H | H |
| IV-498 | c-Pr | MeNHNH | F | Cl | H | H | H | H | H |
| IV-499 | c-Pr | H$_2$NN(Me) | F | Cl | H | H | H | H | H |
| IV-500 | c-Pr | Me$_2$NNH | F | Cl | H | H | H | H | H |
| IV-501 | c-Pr | Me$_2$NN(Me) | F | Cl | H | H | H | H | H |
| IV-502 | c-Pr | PhNHNH | F | Cl | H | H | H | H | H |
| IV-503 | c-Pr | (2-Pyridinyl)NHNH | F | Cl | H | H | H | H | H |
| IV-504 | c-Pr | 1,2,4-triazol-1-yl-NH | F | Cl | H | H | H | H | H |
| IV-505 | c-Pr | Me(C=O)NHNH | F | Cl | H | H | H | H | H |
| IV-506 | c-Pr | (Me)(Ac)NNH | F | Cl | H | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-507 | c-Pr | Me(SO$_2$)NHNH | F | Cl | H | H | H | H | H |
| IV-508 | c-Pr | MeOC(=O)NHNH | F | Cl | H | H | H | H | H |
| IV-509 | c-Pr | (N-acetyl-N-(2-pyridinyl)hydrazinyl) | F | Cl | H | H | H | H | H |
| IV-510 | c-Pr | (tert-butoxycarbonyl hexahydropyridazinyl) | F | Cl | H | H | H | H | H |
| IV-511 | c-Pr | Me$_2$NC(=O)NHNH | F | Cl | H | H | H | H | H |
| IV-512 | c-Pr | Me2C=NNH | F | Cl | H | H | H | H | H |
| IV-513 | c-Pr | H$_2$NNH | F | H | Cl | H | H | H | H |
| IV-514 | c-Pr | MeNHNH | F | H | Cl | H | H | H | H |
| IV-515 | c-Pr | H$_2$NN(Me) | F | H | Cl | H | H | H | H |
| IV-516 | c-Pr | Me$_2$NNH | F | H | Cl | H | H | H | H |
| IV-517 | c-Pr | Me$_2$NN(Me) | F | H | Cl | H | H | H | H |
| IV-518 | c-Pr | PhNHNH | F | H | Cl | H | H | H | H |
| IV-519 | c-Pr | (2-Pyridinyl)NHNH | F | H | Cl | H | H | H | H |
| IV-520 | c-Pr | (1,2,4-triazol-1-yl)NH | F | H | Cl | H | H | H | H |
| IV-521 | c-Pr | Me(C=O)NHNH | F | H | Cl | H | H | H | H |
| IV-522 | c-Pr | (Me)(Ac)NNH | F | H | Cl | H | H | H | H |
| IV-523 | c-Pr | Me(SO$_2$)NHNH | F | H | Cl | H | H | H | H |
| IV-524 | c-Pr | MeOC(=O)NHNH | F | H | Cl | H | H | H | H |
| IV-525 | c-Pr | (N-acetyl-N-(2-pyridinyl)hydrazinyl) | F | H | Cl | H | H | H | H |
| IV-526 | c-Pr | (tert-butoxycarbonyl hexahydropyridazinyl) | F | H | Cl | H | H | H | H |
| IV-527 | c-Pr | Me$_2$NC(=O)NHNH | F | H | Cl | H | H | H | H |
| IV-528 | c-Pr | Me2C=NNH | F | H | Cl | H | H | H | H |
| IV-529 | c-Pr | H$_2$NNH | F | H | H | Cl | H | H | H |
| IV-530 | c-Pr | MeNHNH | F | H | H | Cl | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-531 | c-Pr | H$_2$NN(Me) | F | H | H | Cl | H | H | H |
| IV-532 | c-Pr | Me$_2$NNH | F | H | H | Cl | H | H | H |
| IV-533 | c-Pr | Me$_2$NN(Me) | F | H | H | Cl | H | H | H |
| IV-534 | c-Pr | PhNHNH | F | H | H | Cl | H | H | H |
| IV-535 | c-Pr | (2-Pyridinyl)NHNH | F | H | H | Cl | H | H | H |
| IV-536 | c-Pr | (1,2,4-triazol-1-yl)NH | F | H | H | Cl | H | H | H |
| IV-537 | c-Pr | Me(C=O)NHNH | F | H | H | Cl | H | H | H |
| IV-538 | c-Pr | (Me)(Ac)NNH | F | H | H | Cl | H | H | H |
| IV-539 | c-Pr | Me(SO$_2$)NHNH | F | H | H | Cl | H | H | H |
| IV-540 | c-Pr | MeOC(=O)NHNH | F | H | H | Cl | H | H | H |
| IV-541 | c-Pr | N-(2-pyridinyl)-N-acetylhydrazino | F | H | H | Cl | H | H | H |
| IV-542 | c-Pr | tert-butyl tetrahydropyridazine-1-carboxylate | F | H | H | Cl | H | H | H |
| IV-543 | c-Pr | Me$_2$NC(=O)NHNH | F | H | H | Cl | H | H | H |
| IV-544 | c-Pr | Me2C=NNH | F | H | H | Cl | H | H | H |
| IV-545 | c-Pr | H$_2$NNH | F | H | H | H | Cl | H | H |
| IV-546 | c-Pr | MeNHNH | F | H | H | H | Cl | H | H |
| IV-547 | c-Pr | H$_2$NN(Me) | F | H | H | H | Cl | H | H |
| IV-548 | c-Pr | Me$_2$NNH | F | H | H | H | Cl | H | H |
| IV-549 | c-Pr | Me$_2$NN(Me) | F | H | H | H | Cl | H | H |
| IV-550 | c-Pr | PhNHNH | F | H | H | H | Cl | H | H |
| IV-551 | c-Pr | (2-Pyridinyl)NHNH | F | H | H | H | Cl | H | H |
| IV-552 | c-Pr | (1,2,4-triazol-1-yl)NH | F | H | H | H | Cl | H | H |
| IV-553 | c-Pr | Me(C=O)NHNH | F | H | H | H | Cl | H | H |
| IV-554 | c-Pr | (Me)(Ac)NNH | F | H | H | H | Cl | H | H |
| IV-555 | c-Pr | Me(SO$_2$)NHNH | F | H | H | H | Cl | H | H |
| IV-556 | c-Pr | MeOC(=O)NHNH | F | H | H | H | Cl | H | H |
| IV-557 | c-Pr | N-(2-pyridinyl)-N-acetylhydrazino | F | H | H | H | Cl | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-558 | c-Pr | *tert-butyl piperidine-1-carboxylate* | F | H | H | H | Cl | H | H |
| IV-559 | c-Pr | Me$_2$NC(=O)NHNH | F | H | H | H | Cl | H | H |
| IV-560 | c-Pr | Me2C=NNH | F | H | H | H | Cl | H | H |
| IV-561 | c-Pr | H$_2$NNH | F | MeO | H | H | H | H | H |
| IV-562 | c-Pr | MeNHNH | F | MeO | H | H | H | H | H |
| IV-563 | c-Pr | H$_2$NN(Me) | F | MeO | H | H | H | H | H |
| IV-564 | c-Pr | Me$_2$NNH | F | MeO | H | H | H | H | H |
| IV-565 | c-Pr | Me$_2$NN(Me) | F | MeO | H | H | H | H | H |
| IV-566 | c-Pr | PhNHNH | F | MeO | H | H | H | H | H |
| IV-567 | c-Pr | (2-Pyridinyl)NHNH | F | MeO | H | H | H | H | H |
| IV-568 | c-Pr | *triazolyl-NH* | F | MeO | H | H | H | H | H |
| IV-569 | c-Pr | Me(C=O)NHNH | F | MeO | H | H | H | H | H |
| IV-570 | c-Pr | (Me)(Ac)NNH | F | MeO | H | H | H | H | H |
| IV-571 | c-Pr | Me(SO$_2$)NHNH | F | MeO | H | H | H | H | H |
| IV-572 | c-Pr | MeOC(=O)NHNH | F | MeO | H | H | H | H | H |
| IV-573 | c-Pr | *2-pyridinyl-N(Ac)-NH* | F | MeO | H | H | H | H | H |
| IV-574 | c-Pr | *tert-butyl piperidine-1-carboxylate* | F | MeO | H | H | H | H | H |
| IV-575 | c-Pr | Me$_2$NC(=O)NHNH | F | MeO | H | H | H | H | H |
| IV-576 | c-Pr | Me2C=NNH | F | MeO | H | H | H | H | H |
| IV-577 | c-Pr | H$_2$NNH | F | H | MeO | H | H | H | H |
| IV-578 | c-Pr | MeNHNH | F | H | MeO | H | H | H | H |
| IV-579 | c-Pr | H$_2$NN(Me) | F | H | MeO | H | H | H | H |
| IV-580 | c-Pr | Me$_2$NNH | F | H | MeO | H | H | H | H |
| IV-581 | c-Pr | Me$_2$NN(Me) | F | H | MeO | H | H | H | H |
| IV-582 | c-Pr | PhNHNH | F | H | MeO | H | H | H | H |
| IV-583 | c-Pr | (2-Pyridinyl)NHNH | F | H | MeO | H | H | H | H |
| IV-584 | c-Pr | *triazolyl-NH* | F | H | MeO | H | H | H | H |
| IV-585 | c-Pr | Me(C=O)NHNH | F | H | MeO | H | H | H | H |
| IV-586 | c-Pr | (Me)(Ac)NNH | F | H | MeO | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-587 | c-Pr | Me(SO$_2$)NHNH | F | H | MeO | H | H | H | H |
| IV-588 | c-Pr | MeOC(=O)NHNH | F | H | MeO | H | H | H | H |
| IV-589 | c-Pr | [2-pyridinyl-N(C(=O)Me)-NH] | F | H | MeO | H | H | H | H |
| IV-590 | c-Pr | [tBuO-C(=O)-piperidazinyl] | F | H | MeO | H | H | H | H |
| IV-591 | c-Pr | Me$_2$NC(=O)NHNH | F | H | MeO | H | H | H | H |
| IV-592 | c-Pr | Me2C=NNH | F | H | MeO | H | H | H | H |
| IV-593 | c-Pr | H$_2$NNH | F | H | H | MeO | H | H | H |
| IV-594 | c-Pr | MeNHNH | F | H | H | MeO | H | H | H |
| IV-595 | c-Pr | H$_2$NN(Me) | F | H | H | MeO | H | H | H |
| IV-596 | c-Pr | Me$_2$NNH | F | H | H | MeO | H | H | H |
| IV-597 | c-Pr | Me$_2$NN(Me) | F | H | H | MeO | H | H | H |
| IV-598 | c-Pr | PhNHNH | F | H | H | MeO | H | H | H |
| IV-599 | c-Pr | (2-Pyridinyl)NHNH | F | H | H | MeO | H | H | H |
| IV-600 | c-Pr | [1,2,4-triazolyl-NH] | F | H | H | MeO | H | H | H |
| IV-601 | c-Pr | Me(C=O)NHNH | F | H | H | MeO | H | H | H |
| IV-602 | c-Pr | (Me)(Ac)NNH | F | H | H | MeO | H | H | H |
| IV-603 | c-Pr | Me(SO$_2$)NHNH | F | H | H | MeO | H | H | H |
| IV-604 | c-Pr | MeOC(=O)NHNH | F | H | H | MeO | H | H | H |
| IV-605 | c-Pr | [2-pyridinyl-N(C(=O)Me)-NH] | F | H | H | MeO | H | H | H |
| IV-606 | c-Pr | [tBuO-C(=O)-piperidazinyl] | F | H | H | MeO | H | H | H |
| IV-607 | c-Pr | Me$_2$NC(=O)NHNH | F | H | H | MeO | H | H | H |
| IV-608 | c-Pr | Me2C=NNH | F | H | H | MeO | H | H | H |
| IV-609 | c-Pr | H$_2$NNH | F | H | H | H | MeO | H | H |
| IV-610 | c-Pr | MeNHNH | F | H | H | H | MeO | H | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-611 | c-Pr | H₂NN(Me) | F | H | H | H | MeO | H | H |
| IV-612 | c-Pr | Me₂NNH | F | H | H | H | MeO | H | H |
| IV-613 | c-Pr | Me₂NN(Me) | F | H | H | H | MeO | H | H |
| IV-614 | c-Pr | PhNHNH | F | H | H | H | MeO | H | H |
| IV-615 | c-Pr | (2-Pyridinyl)NHNH | F | H | H | H | MeO | H | H |
| IV-616 | c-Pr | (1,2,4-triazol-1-yl)NH | F | H | H | H | MeO | H | H |
| IV-617 | c-Pr | Me(C═O)NHNH | F | H | H | H | MeO | H | H |
| IV-618 | c-Pr | (Me)(Ac)NNH | F | H | H | H | MeO | H | H |
| IV-619 | c-Pr | Me(SO₂)NHNH | F | H | H | H | MeO | H | H |
| IV-620 | c-Pr | MeOC(═O)NHNH | F | H | H | H | MeO | H | H |
| IV-621 | c-Pr | N-(2-pyridinyl)-N-acetylhydrazino | F | H | H | H | MeO | H | H |
| IV-622 | c-Pr | tert-butyl piperidazine-1-carboxylate | F | H | H | H | MeO | H | H |
| IV-623 | c-Pr | Me₂NC(═O)NHNH | F | H | H | H | MeO | H | H |
| IV-624 | c-Pr | Me2C═NNH | F | H | H | H | MeO | H | H |
| IV-625 | c-Pr | H₂NNH | Cl | F | H | H | H | H | H |
| IV-626 | c-Pr | MeNHNH | Cl | F | H | H | H | H | H |
| IV-627 | c-Pr | H₂NN(Me) | Cl | F | H | H | H | H | H |
| IV-628 | c-Pr | Me₂NNH | Cl | F | H | H | H | H | H |
| IV-629 | c-Pr | Me₂NN(Me) | Cl | F | H | H | H | H | H |
| IV-630 | c-Pr | PhNHNH | Cl | F | H | H | H | H | H |
| IV-631 | c-Pr | (2-Pyridinyl)NHNH | Cl | F | H | H | H | H | H |
| IV-632 | c-Pr | (1,2,4-triazol-1-yl)NH | Cl | F | H | H | H | H | H |
| IV-633 | c-Pr | Me(C═O)NHNH | Cl | F | H | H | H | H | H |
| IV-634 | c-Pr | (Me)(Ac)NNH | Cl | F | H | H | H | H | H |
| IV-635 | c-Pr | Me(SO₂)NHNH | Cl | F | H | H | H | H | H |
| IV-636 | c-Pr | MeOC(═O)NHNH | Cl | F | H | H | H | H | H |
| IV-637 | c-Pr | N-(2-pyridinyl)-N-acetylhydrazino | Cl | F | H | H | H | H | H |

TABLE 4-continued

Inventive compounds of the formula (I) in which X represents C(R$^{13}$)(R$^{14}$)

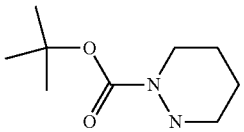

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-638 | c-Pr | 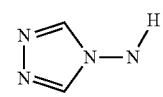 | Cl | F | H | H | H | H | H |
| IV-639 | c-Pr | Me$_2$NC(=O)NHNH | Cl | F | H | H | H | H | H |
| IV-640 | c-Pr | Me2C=NNH | Cl | F | H | H | H | H | H |
| IV-641 | c-Pr | H$_2$NNH | Cl | H | F | H | H | H | H |
| IV-642 | c-Pr | MeNHNH | Cl | H | F | H | H | H | H |
| IV-643 | c-Pr | H$_2$NN(Me) | Cl | H | F | H | H | H | H |
| IV-644 | c-Pr | Me$_2$NNH | Cl | H | F | H | H | H | H |
| IV-645 | c-Pr | Me$_2$NN(Me) | Cl | H | F | H | H | H | H |
| IV-646 | c-Pr | PhNHNH | Cl | H | F | H | H | H | H |
| IV-647 | c-Pr | (2-Pyridinyl)NHNH | Cl | H | F | H | H | H | H |
| IV-648 | c-Pr | 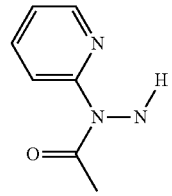 | Cl | H | F | H | H | H | H |
| IV-649 | c-Pr | Me(C=O)NHNH | Cl | H | F | H | H | H | H |
| IV-650 | c-Pr | (Me)(Ac)NNH | Cl | H | F | H | H | H | H |
| IV-651 | c-Pr | Me(SO$_2$)NHNH | Cl | H | F | H | H | H | H |
| IV-652 | c-Pr | MeOC(=O)NHNH | Cl | H | F | H | H | H | H |
| IV-653 | c-Pr | 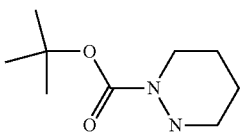 | Cl | H | F | H | H | H | H |
| IV-654 | c-Pr | 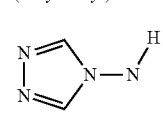 | Cl | H | F | H | H | H | H |
| IV-655 | c-Pr | Me$_2$NC(=O)NHNH | Cl | H | F | H | H | H | H |
| IV-656 | c-Pr | Me2C=NNH | Cl | H | F | H | H | H | H |
| IV-657 | c-Pr | H$_2$NNH | Cl | H | H | F | H | H | H |
| IV-658 | c-Pr | MeNHNH | Cl | H | H | F | H | H | H |
| IV-659 | c-Pr | H$_2$NN(Me) | Cl | H | H | F | H | H | H |
| IV-660 | c-Pr | Me$_2$NNH | Cl | H | H | F | H | H | H |
| IV-661 | c-Pr | Me$_2$NN(Me) | Cl | H | H | F | H | H | H |
| IV-662 | c-Pr | PhNHNH | Cl | H | H | F | H | H | H |
| IV-663 | c-Pr | (2-Pyridinyl)NHNH | Cl | H | H | F | H | H | H |
| IV-664 | c-Pr |  | Cl | H | H | F | H | H | H |
| IV-665 | c-Pr | Me(C=O)NHNH | Cl | H | H | F | H | H | H |
| IV-666 | c-Pr | (Me)(Ac)NNH | Cl | H | H | F | H | H | H |

TABLE 4-continued

Inventive compounds of the formula (I) in which X represents C(R¹³)(R¹⁴)

| No. | R¹ | R² | R³ | R⁴ | R⁵ | R⁶ | R⁷ | R¹³ | R¹⁴ |
|---|---|---|---|---|---|---|---|---|---|
| IV-667 | c-Pr | Me(SO₂)NHNH | Cl | H | H | F | H | H | H |
| IV-668 | c-Pr | MeOC(=O)NHNH | Cl | H | H | F | H | H | H |
| IV-669 | c-Pr | (2-pyridinyl)N(Ac)NH | Cl | H | H | F | H | H | H |
| IV-670 | c-Pr | (1-tert-butoxycarbonyl-hexahydropyridazin-2-yl) | Cl | H | H | F | H | H | H |
| IV-671 | c-Pr | Me₂NC(=O)NHNH | Cl | H | H | F | H | H | H |
| IV-672 | c-Pr | Me2C=NNH | Cl | H | H | F | H | H | H |
| IV-673 | c-Pr | H₂NNH | Cl | Cl | H | H | H | H | H |
| IV-674 | c-Pr | MeNHNH | Cl | Cl | H | H | H | H | H |
| IV-675 | c-Pr | H₂NN(Me) | Cl | Cl | H | H | H | H | H |
| IV-676 | c-Pr | Me₂NNH | Cl | Cl | H | H | H | H | H |
| IV-677 | c-Pr | Me₂NN(Me) | Cl | Cl | H | H | H | H | H |
| IV-678 | c-Pr | PhNHNH | Cl | Cl | H | H | H | H | H |
| IV-679 | c-Pr | (2-Pyridinyl)NHNH | Cl | Cl | H | H | H | H | H |
| IV-680 | c-Pr | (1,2,4-triazol-1-yl)NH | Cl | Cl | H | H | H | H | H |
| IV-681 | c-Pr | Me(C=O)NHNH | Cl | Cl | H | H | H | H | H |
| IV-682 | c-Pr | (Me)(Ac)NNH | Cl | Cl | H | H | H | H | H |
| IV-683 | c-Pr | Me(SO₂)NHNH | Cl | Cl | H | H | H | H | H |
| IV-684 | c-Pr | MeOC(=O)NHNH | Cl | Cl | H | H | H | H | H |
| IV-685 | c-Pr | (2-pyridinyl)N(Ac)NH | Cl | Cl | H | H | H | H | H |
| IV-686 | c-Pr | (1-tert-butoxycarbonyl-hexahydropyridazin-2-yl) | Cl | Cl | H | H | H | H | H |
| IV-687 | c-Pr | Me₂NC(=O)NHNH | Cl | Cl | H | H | H | H | H |
| IV-688 | c-Pr | Me2C=NNH | Cl | Cl | H | H | H | H | H |
| IV-689 | c-Pr | H₂NNH | Cl | H | Cl | H | H | H | H |
| IV-690 | c-Pr | MeNHNH | Cl | H | Cl | H | H | H | H |
| IV-691 | c-Pr | H₂NN(Me) | Cl | H | Cl | H | H | H | H |

TABLE 4-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| IV-692 | c-Pr | Me₂NNH | Cl | H | Cl | H | H | H | H |
| IV-693 | c-Pr | Me₂NN(Me) | Cl | H | Cl | H | H | H | H |
| IV-694 | c-Pr | PhNHNH | Cl | H | Cl | H | H | H | H |
| IV-695 | c-Pr | (2-Pyridinyl)NHNH | Cl | H | Cl | H | H | H | H |
| IV-696 | c-Pr | [triazolyl-NH] | Cl | H | Cl | H | H | H | H |
| IV-697 | c-Pr | Me(C=O)NHNH | Cl | H | Cl | H | H | H | H |
| IV-698 | c-Pr | (Me)(Ac)NNH | Cl | H | Cl | H | H | H | H |
| IV-699 | c-Pr | Me(SO₂)NHNH | Cl | H | Cl | H | H | H | H |
| IV-700 | c-Pr | MeOC(=O)NHNH | Cl | H | Cl | H | H | H | H |
| IV-701 | c-Pr | [2-pyridinyl-N(Ac)-NH] | Cl | H | Cl | H | H | H | H |
| IV-702 | c-Pr | [Boc-hexahydropyridazin-1-yl] | Cl | H | Cl | H | H | H | H |
| IV-703 | c-Pr | Me₂NC(=O)NHNH | Cl | H | Cl | H | H | H | H |
| IV-704 | c-Pr | Me2C=NNH | Cl | H | Cl | H | H | H | H |
| IV-705 | c-Pr | H₂NNH | Cl | H | H | Cl | H | H | H |
| IV-706 | c-Pr | MeNHNH | Cl | H | H | Cl | H | H | H |
| IV-707 | c-Pr | H₂NN(Me) | Cl | H | H | Cl | H | H | H |
| IV-708 | c-Pr | Me₂NNH | Cl | H | H | Cl | H | H | H |
| IV-709 | c-Pr | Me₂NN(Me) | Cl | H | H | Cl | H | H | H |
| IV-710 | c-Pr | PhNHNH | Cl | H | H | Cl | H | H | H |
| IV-711 | c-Pr | (2-Pyridinyl)NHNH | Cl | H | H | Cl | H | H | H |
| IV-712 | c-Pr | [triazolyl-NH] | Cl | H | H | Cl | H | H | H |
| IV-713 | c-Pr | Me(C=O)NHNH | Cl | H | H | Cl | H | H | H |
| IV-714 | c-Pr | (Me)(Ac)NNH | Cl | H | H | Cl | H | H | H |
| IV-715 | c-Pr | Me(SO₂)NHNH | Cl | H | H | Cl | H | H | H |
| IV-716 | c-Pr | MeOC(=O)NHNH | Cl | H | H | Cl | H | H | H |
| IV-717 | c-Pr | [2-pyridinyl-N(Ac)-NH] | Cl | H | H | Cl | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-718 | c-Pr | *tert-butyl piperidine-1-carboxylate hydrazide* | Cl | H | H | Cl | H | H | H |
| IV-719 | c-Pr | Me$_2$NC(=O)NHNH | Cl | H | H | Cl | H | H | H |
| IV-720 | c-Pr | Me2C=NNH | Cl | H | H | Cl | H | H | H |
| IV-721 | c-Pr | H$_2$NNH | Cl | H | H | H | Cl | H | H |
| IV-722 | c-Pr | MeNHNH | Cl | H | H | H | Cl | H | H |
| IV-723 | c-Pr | H$_2$NN(Me) | Cl | H | H | H | Cl | H | H |
| IV-724 | c-Pr | Me$_2$NNH | Cl | H | H | H | Cl | H | H |
| IV-725 | c-Pr | Me$_2$NN(Me) | Cl | H | H | H | Cl | H | H |
| IV-726 | c-Pr | PhNHNH | Cl | H | H | H | Cl | H | H |
| IV-727 | c-Pr | (2-Pyridinyl)NHNH | Cl | H | H | H | Cl | H | H |
| IV-728 | c-Pr | *1,2,4-triazol-4-yl-NH* | Cl | H | H | H | Cl | H | H |
| IV-729 | c-Pr | Me(C=O)NHNH | Cl | H | H | H | Cl | H | H |
| IV-730 | c-Pr | (Me)(Ac)NNH | Cl | H | H | H | Cl | H | H |
| IV-731 | c-Pr | Me(SO$_2$)NHNH | Cl | H | H | H | Cl | H | H |
| IV-732 | c-Pr | MeOC(=O)NHNH | Cl | H | H | H | Cl | H | H |
| IV-733 | c-Pr | *N-(pyridin-2-yl)-N-acetylhydrazide* | Cl | H | H | H | Cl | H | H |
| IV-734 | c-Pr | *tert-butyl piperidine-1-carboxylate hydrazide* | Cl | H | H | H | Cl | H | H |
| IV-735 | c-Pr | Me$_2$NC(=O)NHNH | Cl | H | H | H | Cl | H | H |
| IV-736 | c-Pr | Me2C=NNH | Cl | H | H | H | Cl | H | H |
| IV-737 | c-Pr | H$_2$NNH | Cl | Me | H | H | H | H | H |
| IV-738 | c-Pr | MeNHNH | Cl | Me | H | H | H | H | H |
| IV-739 | c-Pr | H$_2$NN(Me) | Cl | Me | H | H | H | H | H |
| IV-740 | c-Pr | Me$_2$NNH | Cl | Me | H | H | H | H | H |
| IV-741 | c-Pr | Me$_2$NN(Me) | Cl | Me | H | H | H | H | H |
| IV-742 | c-Pr | PhNHNH | Cl | Me | H | H | H | H | H |
| IV-743 | c-Pr | (2-Pyridinyl)NHNH | Cl | Me | H | H | H | H | H |
| IV-744 | c-Pr | *1,2,4-triazol-4-yl-NH* | Cl | Me | H | H | H | H | H |
| IV-745 | c-Pr | Me(C=O)NHNH | Cl | Me | H | H | H | H | H |
| IV-746 | c-Pr | (Me)(Ac)NNH | Cl | Me | H | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-747 | c-Pr | Me(SO$_2$)NHNH | Cl | Me | H | H | H | H | H |
| IV-748 | c-Pr | MeOC(=O)NHNH | Cl | Me | H | H | H | H | H |
| IV-749 | c-Pr | (2-pyridinyl-N(Ac)-NH) | Cl | Me | H | H | H | H | H |
| IV-750 | c-Pr | (Boc-piperidazine) | Cl | Me | H | H | H | H | H |
| IV-751 | c-Pr | Me$_2$NC(=O)NHNH | Cl | Me | H | H | H | H | H |
| IV-752 | c-Pr | Me2C=NNH | Cl | Me | H | H | H | H | H |
| IV-753 | c-Pr | H$_2$NNH | Cl | H | Me | H | H | H | H |
| IV-754 | c-Pr | MeNHNH | Cl | H | Me | H | H | H | H |
| IV-755 | c-Pr | H$_2$NN(Me) | Cl | H | Me | H | H | H | H |
| IV-756 | c-Pr | Me$_2$NNH | Cl | H | Me | H | H | H | H |
| IV-757 | c-Pr | Me$_2$NN(Me) | Cl | H | Me | H | H | H | H |
| IV-758 | c-Pr | PhNHNH | Cl | H | Me | H | H | H | H |
| IV-759 | c-Pr | (2-Pyridinyl)NHNH | Cl | H | Me | H | H | H | H |
| IV-760 | c-Pr | (1,2,4-triazolyl-NH) | Cl | H | Me | H | H | H | H |
| IV-761 | c-Pr | Me(C=O)NHNH | Cl | H | Me | H | H | H | H |
| IV-762 | c-Pr | (Me)(Ac)NNH | Cl | H | Me | H | H | H | H |
| IV-763 | c-Pr | Me(SO$_2$)NHNH | Cl | H | Me | H | H | H | H |
| IV-764 | c-Pr | MeOC(=O)NHNH | Cl | H | Me | H | H | H | H |
| IV-765 | c-Pr | (2-pyridinyl-N(Ac)-NH) | Cl | H | Me | H | H | H | H |
| IV-766 | c-Pr | (Boc-piperidazine) | Cl | H | Me | H | H | H | H |
| IV-767 | c-Pr | Me$_2$NC(=O)NHNH | Cl | H | Me | H | H | H | H |
| IV-768 | c-Pr | Me2C=NNH | Cl | H | Me | H | H | H | H |
| IV-769 | c-Pr | H$_2$NNH | Cl | H | H | Me | H | H | H |
| IV-770 | c-Pr | MeNHNH | Cl | H | H | Me | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-771 | c-Pr | H$_2$NN(Me) | Cl | H | H | Me | H | H | H |
| IV-772 | c-Pr | Me$_2$NNH | Cl | H | H | Me | H | H | H |
| IV-773 | c-Pr | Me$_2$NN(Me) | Cl | H | H | Me | H | H | H |
| IV-774 | c-Pr | PhNHNH | Cl | H | H | Me | H | H | H |
| IV-775 | c-Pr | (2-Pyridinyl)NHNH | Cl | H | H | Me | H | H | H |
| IV-776 | c-Pr | [1,2,4-triazol-1-yl-NH] | Cl | H | H | Me | H | H | H |
| IV-777 | c-Pr | Me(C=O)NHNH | Cl | H | H | Me | H | H | H |
| IV-778 | c-Pr | (Me)(Ac)NNH | Cl | H | H | Me | H | H | H |
| IV-779 | c-Pr | Me(SO$_2$)NHNH | Cl | H | H | Me | H | H | H |
| IV-780 | c-Pr | MeOC(=O)NHNH | Cl | H | H | Me | H | H | H |
| IV-781 | c-Pr | [N-(2-pyridinyl)-N-acetyl-hydrazinyl] | Cl | H | H | Me | H | H | H |
| IV-782 | c-Pr | [tert-butoxycarbonyl-hexahydropyridazinyl] | Cl | H | H | Me | H | H | H |
| IV-783 | c-Pr | Me$_2$NC(=O)NHNH | Cl | H | H | Me | H | H | H |
| IV-784 | c-Pr | Me2C=NNH | Cl | H | H | Me | H | H | H |
| IV-785 | c-Pr | H$_2$NNH | Cl | H | H | H | Me | H | H |
| IV-786 | c-Pr | MeNHNH | Cl | H | H | H | Me | H | H |
| IV-787 | c-Pr | H$_2$NN(Me) | Cl | H | H | H | Me | H | H |
| IV-788 | c-Pr | Me$_2$NNH | Cl | H | H | H | Me | H | H |
| IV-789 | c-Pr | Me$_2$NN(Me) | Cl | H | H | H | Me | H | H |
| IV-790 | c-Pr | PhNHNH | Cl | H | H | H | Me | H | H |
| IV-791 | c-Pr | (2-Pyridinyl)NHNH | Cl | H | H | H | Me | H | H |
| IV-792 | c-Pr | [1,2,4-triazol-1-yl-NH] | Cl | H | H | H | Me | H | H |
| IV-793 | c-Pr | Me(C=O)NHNH | Cl | H | H | H | Me | H | H |
| IV-794 | c-Pr | (Me)(Ac)NNH | Cl | H | H | H | Me | H | H |
| IV-795 | c-Pr | Me(SO$_2$)NHNH | Cl | H | H | H | Me | H | H |
| IV-796 | c-Pr | MeOC(=O)NHNH | Cl | H | H | H | Me | H | H |
| IV-797 | c-Pr | [N-(2-pyridinyl)-N-acetyl-hydrazinyl] | Cl | Cl | H | H | Me | H | H |

TABLE 4-continued

Inventive compounds of the formula (I) in which X represents C(R¹³)(R¹⁴)

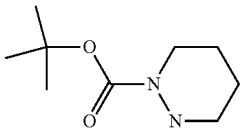

(I)

| No. | R¹ | R² | R³ | R⁴ | R⁵ | R⁶ | R⁷ | R¹³ | R¹⁴ |
|---|---|---|---|---|---|---|---|---|---|
| IV-798 | c-Pr | 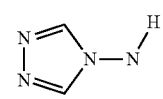 | Cl | Cl | H | H | Me | H | H |
| IV-799 | c-Pr | Me₂NC(=O)NHNH | Cl | H | H | H | Me | H | H |
| IV-800 | c-Pr | Me2C=NNH | Cl | H | H | H | Me | H | H |
| IV-801 | c-Pr | H₂NNH | Cl | MeO | H | H | H | H | H |
| IV-802 | c-Pr | MeNHNH | Cl | MeO | H | H | H | H | H |
| IV-803 | c-Pr | H₂NN(Me) | Cl | MeO | H | H | H | H | H |
| IV-804 | c-Pr | Me₂NNH | Cl | MeO | H | H | H | H | H |
| IV-805 | c-Pr | Me₂NN(Me) | Cl | MeO | H | H | H | H | H |
| IV-806 | c-Pr | PhNHNH | Cl | MeO | H | H | H | H | H |
| IV-807 | c-Pr | (2-Pyridinyl)NHNH | Cl | MeO | H | H | H | H | H |
| IV-808 | c-Pr | 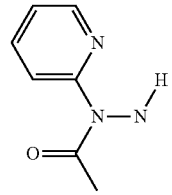 | Cl | MeO | H | H | H | H | H |
| IV-809 | c-Pr | Me(C=O)NHNH | Cl | MeO | H | H | H | H | H |
| IV-810 | c-Pr | (Me)(Ac)NNH | Cl | MeO | H | H | H | H | H |
| IV-811 | c-Pr | Me(SO₂)NHNH | Cl | MeO | H | H | H | H | H |
| IV-812 | c-Pr | MeOC(=O)NHNH | Cl | MeO | H | H | H | H | H |
| IV-813 | c-Pr | 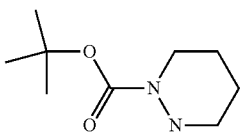 | Cl | MeO | H | H | H | H | H |
| IV-814 | c-Pr | 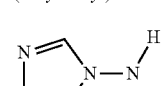 | Cl | MeO | H | H | H | H | H |
| IV-815 | c-Pr | Me₂NC(=O)NHNH | Cl | MeO | H | H | H | H | H |
| IV-816 | c-Pr | Me2C=NNH | Cl | MeO | H | H | H | H | H |
| IV-817 | c-Pr | H₂NNH | Cl | H | MeO | H | H | H | H |
| IV-818 | c-Pr | MeNHNH | Cl | H | MeO | H | H | H | H |
| IV-819 | c-Pr | H₂NN(Me) | Cl | H | MeO | H | H | H | H |
| IV-820 | c-Pr | Me₂NNH | Cl | H | MeO | H | H | H | H |
| IV-821 | c-Pr | Me₂NN(Me) | Cl | H | MeO | H | H | H | H |
| IV-822 | c-Pr | PhNHNH | Cl | H | MeO | H | H | H | H |
| IV-823 | c-Pr | (2-Pyridinyl)NHNH | Cl | H | MeO | H | H | H | H |
| IV-824 | c-Pr | 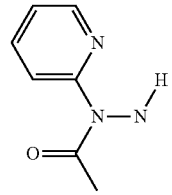 | Cl | H | MeO | H | H | H | H |
| IV-825 | c-Pr | Me(C=O)NHNH | Cl | H | MeO | H | H | H | H |
| IV-826 | c-Pr | (Me)(Ac)NNH | Cl | H | MeO | H | H | H | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-827 | c-Pr | Me(SO$_2$)NHNH | Cl | H | MeO | H | H | H | H |
| IV-828 | c-Pr | MeOC(=O)NHNH | Cl | H | H | MeO | H | H | H |
| IV-829 | c-Pr | [2-pyridinyl-N(Ac)NH] | Cl | H | H | MeO | H | H | H |
| IV-830 | c-Pr | [Boc-hexahydropyridazinyl] | Cl | H | H | MeO | H | H | H |
| IV-831 | c-Pr | Me$_2$NC(=O)NHNH | Cl | H | H | MeO | H | H | H |
| IV-832 | c-Pr | Me2C=NNH | Cl | H | H | MeO | H | H | H |
| IV-833 | c-Pr | H$_2$NNH | Cl | H | H | MeO | H | H | H |
| IV-834 | c-Pr | MeNHNH | Cl | H | H | MeO | H | H | H |
| IV-835 | c-Pr | H$_2$NN(Me) | Cl | H | H | MeO | H | H | H |
| IV-836 | c-Pr | Me$_2$NNH | Cl | H | H | MeO | H | H | H |
| IV-837 | c-Pr | Me$_2$NN(Me) | H | H | H | MeO | H | H | H |
| IV-838 | c-Pr | PhNHNH | Cl | H | H | MeO | H | H | H |
| IV-839 | c-Pr | (2-Pyridinyl)NHNH | Cl | H | H | MeO | H | H | H |
| IV-840 | c-Pr | [1,2,4-triazol-1-yl-NH] | Cl | H | H | MeO | H | H | H |
| IV-841 | c-Pr | Me(C=O)NHNH | Cl | H | H | MeO | H | H | H |
| IV-842 | c-Pr | (Me)(Ac)NNH | H | H | H | MeO | H | H | H |
| IV-843 | c-Pr | Me(SO$_2$)NHNH | H | H | H | MeO | H | H | H |
| IV-844 | c-Pr | MeOC(=O)NHNH | Cl | H | H | MeO | H | H | H |
| IV-845 | c-Pr | [2-pyridinyl-N(Ac)NH] | Cl | H | H | MeO | H | H | H |
| IV-846 | c-Pr | [Boc-hexahydropyridazinyl] | Cl | H | H | MeO | H | H | H |
| IV-847 | c-Pr | Me$_2$NC(=O)NHNH | Cl | H | H | MeO | H | H | H |
| IV-848 | c-Pr | Me2C=NNH | Cl | H | H | MeO | H | H | H |
| IV-849 | c-Pr | H$_2$NNH | Cl | H | H | H | MeO | H | H |
| IV-850 | c-Pr | MeNHNH | Cl | H | H | H | MeO | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-851 | c-Pr | H$_2$NN(Me) | Cl | H | H | H | MeO | H | H |
| IV-852 | c-Pr | Me$_2$NNH | Cl | H | H | H | MeO | H | H |
| IV-853 | c-Pr | Me$_2$NN(Me) | Cl | H | H | H | MeO | H | H |
| IV-854 | c-Pr | PhNHNH | Cl | H | H | H | MeO | H | H |
| IV-855 | c-Pr | (2-Pyridinyl)NHNH | Cl | H | H | H | MeO | H | H |
| IV-856 | c-Pr | [1,2,4-triazol-1-yl-NH] | Cl | H | H | H | MeO | H | H |
| IV-857 | c-Pr | Me(C=O)NHNH | Cl | H | H | H | MeO | H | H |
| IV-858 | c-Pr | (Me)(Ac)NNH | Cl | H | H | H | MeO | H | H |
| IV-859 | c-Pr | Me(SO$_2$)NHNH | Cl | H | H | H | MeO | H | H |
| IV-860 | c-Pr | MeOC(=O)NHNH | Cl | H | H | H | MeO | H | H |
| IV-861 | c-Pr | [2-pyridinyl-N(Ac)-NH] | Cl | H | H | H | MeO | H | H |
| IV-862 | c-Pr | [tert-butoxycarbonyl-hexahydropyridazin-1-yl] | Cl | H | H | H | MeO | H | H |
| IV-863 | c-Pr | Me$_2$NC(=O)NHNH | Cl | H | H | H | MeO | H | H |
| IV-864 | c-Pr | Me2C=NNH | Cl | H | H | H | MeO | H | H |
| IV-865 | c-Pr | H$_2$NNH | Me | Me | H | H | H | H | H |
| IV-866 | c-Pr | MeNHNH | Me | Me | H | H | H | H | H |
| IV-867 | c-Pr | H$_2$NN(Me) | Me | Me | H | H | H | H | H |
| IV-868 | c-Pr | Me$_2$NNH | Me | Me | H | H | H | H | H |
| IV-869 | c-Pr | Me$_2$NN(Me) | Me | Me | H | H | H | H | H |
| IV-870 | c-Pr | PhNHNH | Me | Me | H | H | H | H | H |
| IV-871 | c-Pr | (2-Pyridinyl)NHNH | Me | Me | H | H | H | H | H |
| IV-872 | c-Pr | [1,2,4-triazol-1-yl-NH] | Me | Me | H | H | H | H | H |
| IV-873 | c-Pr | Me(C=O)NHNH | Me | Me | H | H | H | H | H |
| IV-874 | c-Pr | (Me)(Ac)NNH | Me | Me | H | H | H | H | H |
| IV-875 | c-Pr | Me(SO$_2$)NHNH | Me | Me | H | H | H | H | H |
| IV-876 | c-Pr | MeOC(=O)NHNH | Me | Me | H | H | H | H | H |
| IV-877 | c-Pr | [2-pyridinyl-N(Ac)-NH] | Me | Me | H | H | H | H | H |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-878 | c-Pr | tert-butyl tetrahydropyridazine-1-carboxylate | Me | Me | H | H | H | H | H |
| IV-879 | c-Pr | Me$_2$NC(=O)NHNH | Me | Me | H | H | H | H | H |
| IV-880 | c-Pr | Me2C=NNH | Me | Me | H | H | H | H | H |
| IV-881 | c-Pr | H$_2$NNH | Me | H | Me | H | H | H | H |
| IV-882 | c-Pr | MeNHNH | Me | H | Me | H | H | H | H |
| IV-883 | c-Pr | H$_2$NN(Me) | Me | H | Me | H | H | H | H |
| IV-884 | c-Pr | Me$_2$NNH | Me | H | Me | H | H | H | H |
| IV-885 | c-Pr | Me$_2$NN(Me) | Me | H | Me | H | H | H | H |
| IV-886 | c-Pr | PhNHNH | Me | H | Me | H | H | H | H |
| IV-887 | c-Pr | (2-Pyridinyl)NHNH | Me | H | Me | H | H | H | H |
| IV-888 | c-Pr | 1,2,4-triazol-1-yl-NH | Me | H | Me | H | H | H | H |
| IV-889 | c-Pr | Me(C=O)NHNH | Me | H | Me | H | H | H | H |
| IV-890 | c-Pr | (Me)(Ac)NNH | H | H | Me | H | H | H | H |
| IV-891 | c-Pr | Me(SO$_2$)NHNH | H | H | Me | H | H | H | H |
| IV-892 | c-Pr | MeOC(=O)NHNH | Me | H | Me | H | H | H | H |
| IV-893 | c-Pr | N-(2-pyridinyl)-N-acetyl-hydrazino | Me | H | Me | H | H | H | H |
| IV-894 | c-Pr | tert-butyl tetrahydropyridazine-1-carboxylate | Me | H | Me | H | H | H | H |
| IV-895 | c-Pr | Me$_2$NC(=O)NHNH | Me | H | Me | H | H | H | H |
| IV-896 | c-Pr | Me2C=NNH | Me | H | Me | H | H | H | H |
| IV-897 | c-Pr | H$_2$NNH | Me | H | H | Me | H | H | H |
| IV-898 | c-Pr | MeNHNH | Me | H | H | Me | H | H | H |
| IV-899 | c-Pr | H$_2$NN(Me) | Me | H | H | Me | H | H | H |
| IV-900 | c-Pr | Me$_2$NNH | Me | H | H | Me | H | H | H |
| IV-901 | c-Pr | Me$_2$NN(Me) | Me | H | H | Me | H | H | H |
| IV-902 | c-Pr | PhNHNH | Me | H | H | Me | H | H | H |
| IV-903 | c-Pr | (2-Pyridinyl)NHNH | Me | H | H | Me | H | H | H |
| IV-904 | c-Pr | 1,2,4-triazol-1-yl-NH | Me | H | H | Me | H | H | H |
| IV-905 | c-Pr | Me(C=O)NHNH | Me | H | H | Me | H | H | H |
| IV-906 | c-Pr | (Me)(Ac)NNH | Me | H | H | Me | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-907 | c-Pr | Me(SO$_2$)NHNH | Me | H | H | Me | H | H | H |
| IV-908 | c-Pr | MeOC(=O)NHNH | Me | H | H | Me | H | H | H |
| IV-909 | c-Pr | [2-pyridinyl-N(Ac)NH] | Me | H | H | Me | H | H | H |
| IV-910 | c-Pr | [t-BuO-C(=O)-piperidazine] | Me | H | H | Me | H | H | H |
| IV-911 | c-Pr | Me$_2$NC(=O)NHNH | Me | H | H | Me | H | H | H |
| IV-912 | c-Pr | Me2C=NNH | Me | H | H | Me | H | H | H |
| IV-913 | c-Pr | H$_2$NNH | Me | H | H | H | Me | H | H |
| IV-914 | c-Pr | MeNHNH | Me | H | H | H | Me | H | H |
| IV-915 | c-Pr | H$_2$NN(Me) | Me | H | H | H | Me | H | H |
| IV-916 | c-Pr | Me$_2$NNH | Me | H | H | H | Me | H | H |
| IV-917 | c-Pr | Me$_2$NN(Me) | Me | H | H | H | Me | H | H |
| IV-918 | c-Pr | PhNHNH | Me | H | H | H | Me | H | H |
| IV-919 | c-Pr | (2-Pyridinyl)NHNH | Me | H | H | H | Me | H | H |
| IV-920 | c-Pr | [1,2,4-triazolyl-NH] | Me | H | H | H | Me | H | H |
| IV-921 | c-Pr | Me(C=O)NHNH | Me | H | H | H | Me | H | H |
| IV-922 | c-Pr | (Me)(Ac)NNH | Me | H | H | H | Me | H | H |
| IV-923 | c-Pr | Me(SO$_2$)NHNH | Me | H | H | H | Me | H | H |
| IV-924 | c-Pr | MeOC(=O)NHNH | Me | H | H | H | Me | H | H |
| IV-925 | c-Pr | [2-pyridinyl-N(Ac)NH] | Me | H | H | H | Me | H | H |
| IV-926 | c-Pr | [t-BuO-C(=O)-piperidazine] | Me | H | H | H | Me | H | H |
| IV-927 | c-Pr | Me$_2$NC(=O)NHNH | Me | H | H | H | Me | H | H |
| IV-928 | c-Pr | Me2C=NNH | Me | H | H | H | Me | H | H |
| IV-929 | c-Pr | H$_2$NNH | CF$_3$ | F | H | H | H | H | H |
| IV-930 | c-Pr | MeNHNH | CF$_3$ | F | H | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-931 | c-Pr | H$_2$NN(Me) | CF$_3$ | F | H | H | H | H | H |
| IV-932 | c-Pr | Me$_2$NNH | CF$_3$ | F | H | H | H | H | H |
| IV-933 | c-Pr | Me$_2$NN(Me) | CF$_3$ | F | H | H | H | H | H |
| IV-934 | c-Pr | PhNHNH | CF$_3$ | F | H | H | H | H | H |
| IV-935 | c-Pr | (2-Pyridinyl)NHNH | CF$_3$ | F | H | H | H | H | H |
| IV-936 | c-Pr | [triazolyl-NH] | CF$_3$ | F | H | H | H | H | H |
| IV-937 | c-Pr | Me(C=O)NHNH | CF$_3$ | F | H | H | H | H | H |
| IV-938 | c-Pr | (Me)(Ac)NNH | CF$_3$ | F | H | H | H | H | H |
| IV-939 | c-Pr | Me(SO$_2$)NHNH | CF$_3$ | F | H | H | H | H | H |
| IV-940 | c-Pr | MeOC(=O)NHNH | CF$_3$ | F | H | H | H | H | H |
| IV-941 | c-Pr | [2-pyridinyl-N(Ac)-NH] | CF$_3$ | F | H | H | H | H | H |
| IV-942 | c-Pr | [Boc-piperidazinyl] | CF$_3$ | F | H | H | H | H | H |
| IV-943 | c-Pr | Me$_2$NC(=O)NHNH | CF$_3$ | F | H | H | H | H | H |
| IV-944 | c-Pr | Me2C=NNH | CF$_3$ | F | H | H | H | H | H |
| IV-945 | c-Pr | H$_2$NNH | CF$_3$ | H | F | H | H | H | H |
| IV-946 | c-Pr | MeNHNH | CF$_3$ | H | F | H | H | H | H |
| IV-947 | c-Pr | H$_2$NN(Me) | CF$_3$ | H | F | H | H | H | H |
| IV-948 | c-Pr | Me$_2$NNH | CF$_3$ | H | F | H | H | H | H |
| IV-949 | c-Pr | Me$_2$NN(Me) | CF$_3$ | H | F | H | H | H | H |
| IV-950 | c-Pr | PhNHNH | CF$_3$ | H | F | H | H | H | H |
| IV-951 | c-Pr | (2-Pyridinyl)NHNH | CF$_3$ | H | F | H | H | H | H |
| IV-952 | c-Pr | [triazolyl-NH] | CF$_3$ | H | F | H | H | H | H |
| IV-953 | c-Pr | Me(C=O)NHNH | CF$_3$ | H | F | H | H | H | H |
| IV-954 | c-Pr | (Me)(Ac)NNH | CF$_3$ | H | F | H | H | H | H |
| IV-955 | c-Pr | Me(SO$_2$)NHNH | CF$_3$ | H | F | H | H | H | H |
| IV-956 | c-Pr | MeOC(=O)NHNH | CF$_3$ | H | F | H | H | H | H |
| IV-957 | c-Pr | [2-pyridinyl-N(Ac)-NH] | CF$_3$ | H | F | H | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-958 | c-Pr | tert-butyl piperidazine carboxylate | CF$_3$ | H | F | H | H | H | H |
| IV-959 | c-Pr | Me$_2$NC(=O)NHNH | CF$_3$ | H | F | H | H | H | H |
| IV-960 | c-Pr | Me2C=NNH | CF$_3$ | H | F | H | H | H | H |
| IV-961 | c-Pr | H$_2$NNH | CF$_3$ | H | H | F | H | H | H |
| IV-962 | c-Pr | MeNHNH | CF$_3$ | H | H | F | H | H | H |
| IV-963 | c-Pr | H$_2$NN(Me) | CF$_3$ | H | H | F | H | H | H |
| IV-964 | c-Pr | Me$_2$NNH | CF$_3$ | H | H | F | H | H | H |
| IV-965 | c-Pr | Me$_2$NN(Me) | CF$_3$ | H | H | F | H | H | H |
| IV-966 | c-Pr | PhNHNH | CF$_3$ | H | H | F | H | H | H |
| IV-967 | c-Pr | (2-Pyridinyl)NHNH | CF$_3$ | H | H | F | H | H | H |
| IV-968 | c-Pr | triazolyl-NH | CF$_3$ | H | H | F | H | H | H |
| IV-969 | c-Pr | Me(C=O)NHNH | CF$_3$ | H | H | F | H | H | H |
| IV-970 | c-Pr | (Me)(Ac)NNH | CF$_3$ | H | H | F | H | H | H |
| IV-971 | c-Pr | Me(SO$_2$)NHNH | CF$_3$ | H | H | F | H | H | H |
| IV-972 | c-Pr | MeOC(=O)NHNH | CF$_3$ | H | H | F | H | H | H |
| IV-973 | c-Pr | N-acetyl-N-(2-pyridinyl)hydrazine | CF$_3$ | H | H | F | H | H | H |
| IV-974 | c-Pr | tert-butyl piperidazine carboxylate | CF$_3$ | H | H | F | H | H | H |
| IV-975 | c-Pr | Me$_2$NC(=O)NHNH | CF$_3$ | H | H | F | H | H | H |
| IV-976 | c-Pr | Me2C=NNH | CF$_3$ | H | H | F | H | H | H |
| IV-977 | c-Pr | H$_2$NNH | CF$_3$ | H | H | H | F | H | H |
| IV-978 | c-Pr | MeNHNH | CF$_3$ | H | H | H | F | H | H |
| IV-979 | c-Pr | H$_2$NN(Me) | CF$_3$ | H | H | H | F | H | H |
| IV-980 | c-Pr | Me$_2$NNH | CF$_3$ | H | H | H | F | H | H |
| IV-981 | c-Pr | Me$_2$NN(Me) | CF$_3$ | H | H | H | F | H | H |
| IV-982 | c-Pr | PhNHNH | CF$_3$ | H | H | H | F | H | H |
| IV-983 | c-Pr | (2-Pyridinyl)NHNH | CF$_3$ | H | H | H | F | H | H |
| IV-984 | c-Pr | triazolyl-NH | CF$_3$ | H | H | H | F | H | H |
| IV-985 | c-Pr | Me(C=O)NHNH | CF$_3$ | H | H | H | F | H | H |
| IV-986 | c-Pr | (Me)(Ac)NNH | CF$_3$ | H | H | H | F | H | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-987 | c-Pr | Me(SO$_2$)NHNH | CF$_3$ | H | H | H | F | H | H |
| IV-988 | c-Pr | MeOC(=O)NHNH | CF$_3$ | H | H | H | F | H | H |
| IV-989 | c-Pr | (2-pyridinyl-N(Ac)NH) | CF$_3$ | H | H | H | F | H | H |
| IV-990 | c-Pr | (tBuOC(=O)-piperidazinyl) | CF$_3$ | H | H | H | F | H | H |
| IV-991 | c-Pr | Me$_2$NC(=O)NHNH | CF$_3$ | H | H | H | F | H | H |
| IV-992 | c-Pr | Me2C=NNH | CF$_3$ | H | H | H | F | H | H |
| IV-993 | c-Pr | H$_2$NNH | CF$_3$ | Cl | H | H | H | H | H |
| IV-994 | c-Pr | MeNHNH | CF$_3$ | Cl | H | H | H | H | H |
| IV-995 | c-Pr | H$_2$NN(Me) | CF$_3$ | Cl | H | H | H | H | H |
| IV-996 | c-Pr | Me$_2$NNH | CF$_3$ | Cl | H | H | H | H | H |
| IV-997 | c-Pr | Me$_2$NN(Me) | CF$_3$ | Cl | H | H | H | H | H |
| IV-998 | c-Pr | PhNHNH | CF$_3$ | Cl | H | H | H | H | H |
| IV-999 | c-Pr | (2-Pyridinyl)NHNH | CF$_3$ | Cl | H | H | H | H | H |
| IV-1000 | c-Pr | (1,2,4-triazol-1-yl-NH) | CF$_3$ | Cl | H | H | H | H | H |
| IV-1001 | c-Pr | Me(C=O)NHNH | CF$_3$ | Cl | H | H | H | H | H |
| IV-1002 | c-Pr | (Me)(Ac)NNH | CF$_3$ | Cl | H | H | H | H | H |
| IV-1003 | c-Pr | Me(SO$_2$)NHNH | CF$_3$ | Cl | H | H | H | H | H |
| IV-1004 | c-Pr | MeOC(=O)NHNH | CF$_3$ | Cl | H | H | H | H | H |
| IV-1005 | c-Pr | (2-pyridinyl-N(Ac)NH) | CF$_3$ | Cl | H | H | H | H | H |
| IV-1006 | c-Pr | (2-pyridinyl-N(Ac)NH) | CF$_3$ | Cl | H | H | H | H | H |
| IV-1007 | c-Pr | Me$_2$NC(=O)NHNH | CF$_3$ | Cl | H | H | H | H | H |
| IV-1008 | c-Pr | Me2C=NNH | CF$_3$ | Cl | H | H | H | H | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1009 | c-Pr | H$_2$NNH | CF$_3$ | H | Cl | H | H | H | H |
| IV-1010 | c-Pr | MeNHNH | CF$_3$ | H | Cl | H | H | H | H |
| IV-1011 | c-Pr | H$_2$NN(Me) | CF$_3$ | H | Cl | H | H | H | H |
| IV-1012 | c-Pr | Me$_2$NNH | CF$_3$ | H | Cl | H | H | H | H |
| IV-1013 | c-Pr | Me$_2$NN(Me) | CF$_3$ | H | Cl | H | H | H | H |
| IV-1014 | c-Pr | PhNHNH | CF$_3$ | H | Cl | H | H | H | H |
| IV-1015 | c-Pr | (2-Pyridinyl)NHNH | CF$_3$ | H | Cl | H | H | H | H |
| IV-1016 | c-Pr | (1,2,4-triazolyl)N—NH | CF$_3$ | H | Cl | H | H | H | H |
| IV-1017 | c-Pr | Me(C=O)NHNH | CF$_3$ | H | Cl | H | H | H | H |
| IV-1018 | c-Pr | (Me)(Ac)NNH | CF$_3$ | H | Cl | H | H | H | H |
| IV-1019 | c-Pr | Me(SO$_2$)NHNH | CF$_3$ | H | Cl | H | H | H | H |
| IV-1020 | c-Pr | MeOC(=O)NHNH | CF$_3$ | H | Cl | H | H | H | H |
| IV-1021 | c-Pr | (2-pyridinyl)N(Ac)NH | CF$_3$ | H | Cl | H | H | H | H |
| IV-1022 | c-Pr | tBuO-C(=O)-piperidazinyl | CF$_3$ | H | Cl | H | H | H | H |
| IV-1023 | c-Pr | Me$_2$NC(=O)NHNH | CF$_3$ | H | Cl | H | H | H | H |
| IV-1024 | c-Pr | Me2C=NNH | CF$_3$ | H | Cl | H | H | H | H |
| IV-1025 | c-Pr | H$_2$NNH | CF$_3$ | H | H | Cl | H | H | H |
| IV-1026 | c-Pr | MeNHNH | CF$_3$ | H | H | Cl | H | H | H |
| IV-1027 | c-Pr | H$_2$NN(Me) | CF$_3$ | H | H | Cl | H | H | H |
| IV-1028 | c-Pr | Me$_2$NNH | CF$_3$ | H | H | Cl | H | H | H |
| IV-1029 | c-Pr | Me$_2$NN(Me) | CF$_3$ | H | H | Cl | H | H | H |
| IV-1030 | c-Pr | PhNHNH | CF$_3$ | H | H | Cl | H | H | H |
| IV-1031 | c-Pr | (2-Pyridinyl)NHNH | CF$_3$ | H | H | Cl | H | H | H |
| IV-1032 | c-Pr | (1,2,4-triazolyl)N—NH | CF$_3$ | H | H | Cl | H | H | H |
| IV-1033 | c-Pr | Me(C=O)NHNH | CF$_3$ | H | H | Cl | H | H | H |
| IV-1034 | c-Pr | (Me)(Ac)NNH | CF$_3$ | H | H | Cl | H | H | H |
| IV-1035 | c-Pr | Me(SO$_2$)NHNH | CF$_3$ | H | H | Cl | H | H | H |
| IV-1036 | c-Pr | MeOC(=O)NHNH | CF$_3$ | H | H | Cl | H | H | H |

TABLE 4-continued

Inventive compounds of the formula (I) in which X represents C(R¹³)(R¹⁴)

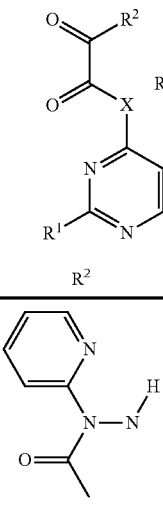
(I)

| No. | R¹ | R² | R³ | R⁴ | R⁵ | R⁶ | R⁷ | R¹³ | R¹⁴ |
|---|---|---|---|---|---|---|---|---|---|
| IV-1037 | c-Pr | 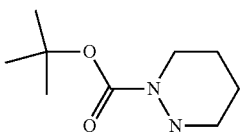 | CF$_3$ | H | H | Cl | H | H | H |
| IV-1038 | c-Pr | 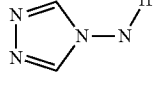 | CF$_3$ | H | H | Cl | H | H | H |
| IV-1039 | c-Pr | Me$_2$NC(=O)NHNH | CF$_3$ | H | H | Cl | H | H | H |
| IV-1040 | c-Pr | Me2C=NNH | CF$_3$ | H | H | Cl | H | H | H |
| IV-1041 | c-Pr | H$_2$NNH | CF$_3$ | H | H | H | Cl | H | H |
| IV-1042 | c-Pr | MeNHNH | CF$_3$ | H | H | H | Cl | H | H |
| IV-1043 | c-Pr | H$_2$NN(Me) | CF$_3$ | H | H | H | Cl | H | H |
| IV-1044 | c-Pr | Me$_2$NNH | CF$_3$ | H | H | H | Cl | H | H |
| IV-1045 | c-Pr | Me$_2$NN(Me) | CF$_3$ | H | H | H | Cl | H | H |
| IV-1046 | c-Pr | PhNHNH | CF$_3$ | H | H | H | Cl | H | H |
| IV-1047 | c-Pr | (2-Pyridinyl)NHNH | CF$_3$ | H | H | H | Cl | H | H |
| IV-1048 | c-Pr | 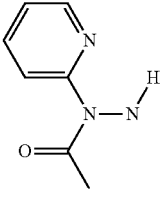 | CF$_3$ | H | H | H | Cl | H | H |
| IV-1049 | c-Pr | Me(C=O)NHNH | CF$_3$ | H | H | H | Cl | H | H |
| IV-1050 | c-Pr | (Me)(Ac)NNH | CF$_3$ | H | H | H | Cl | H | H |
| IV-1051 | c-Pr | Me(SO$_2$)NHNH | CF$_3$ | H | H | H | Cl | H | H |
| IV-1052 | c-Pr | MeOC(=O)NHNH | CF$_3$ | H | H | H | Cl | H | H |
| IV-1053 | c-Pr | 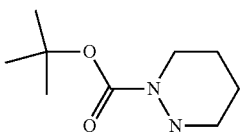 | CF$_3$ | H | H | H | Cl | H | H |
| IV-1054 | c-Pr | 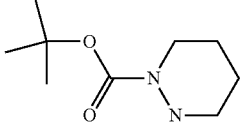 | CF$_3$ | H | H | H | Cl | H | H |
| IV-1055 | c-Pr | Me$_2$NC(=O)NHNH | CF$_3$ | H | H | H | Cl | H | H |
| IV-1056 | c-Pr | Me2C=NNH | CF$_3$ | H | H | H | Cl | H | H |
| IV-1057 | c-Pr | H$_2$NNH | Cl | F | H | H | Cl | H | H |
| IV-1058 | c-Pr | MeNHNH | Cl | F | H | H | Cl | H | H |
| IV-1059 | c-Pr | H$_2$NN(Me) | Cl | F | H | H | Cl | H | H |
| IV-1060 | c-Pr | Me$_2$NNH | Cl | F | H | H | Cl | H | H |
| IV-1061 | c-Pr | Me$_2$NN(Me) | Cl | F | H | H | Cl | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1062 | c-Pr | PhNHNH | Cl | F | H | H | Cl | H | H |
| IV-1063 | c-Pr | (2-Pyridinyl)NHNH | Cl | F | H | H | Cl | H | H |
| IV-1064 | c-Pr | 1,2,4-triazol-4-yl-NH | Cl | F | H | H | Cl | H | H |
| IV-1065 | c-Pr | Me(C=O)NHNH | Cl | F | H | H | Cl | H | H |
| IV-1066 | c-Pr | (Me)(Ac)NNH | Cl | F | H | H | Cl | H | H |
| IV-1067 | c-Pr | Me(SO$_2$)NHNH | Cl | F | H | H | Cl | H | H |
| IV-1068 | c-Pr | MeOC(=O)NHNH | Cl | F | H | H | Cl | H | H |
| IV-1069 | c-Pr | 2-pyridinyl-N(Ac)-NH | Cl | F | H | H | Cl | H | H |
| IV-1070 | c-Pr | N-Boc-hexahydropyridazin-1-yl | Cl | F | H | H | Cl | H | H |
| IV-1071 | c-Pr | Me$_2$NC(=O)NHNH | Cl | F | H | H | Cl | H | H |
| IV-1072 | c-Pr | Me2C=NNH | Cl | F | H | H | Cl | H | H |
| IV-1073 | c-Pr | H$_2$NNH | Cl | H | F | H | Cl | H | H |
| IV-1074 | c-Pr | MeNHNH | Cl | H | F | H | Cl | H | H |
| IV-1075 | c-Pr | H$_2$NN(Me) | Cl | H | F | H | Cl | H | H |
| IV-1076 | c-Pr | Me$_2$NNH | Cl | H | F | H | Cl | H | H |
| IV-1077 | c-Pr | Me$_2$NN(Me) | Cl | H | F | H | Cl | H | H |
| IV-1078 | c-Pr | PhNHNH | Cl | H | F | H | Cl | H | H |
| IV-1079 | c-Pr | (2-Pyridinyl)NHNH | Cl | H | F | H | Cl | H | H |
| IV-1080 | c-Pr | 1,2,4-triazol-4-yl-NH | Cl | H | F | H | Cl | H | H |
| IV-1081 | c-Pr | Me(C=O)NHNH | Cl | H | F | H | Cl | H | H |
| IV-1082 | c-Pr | (Me)(Ac)NNH | Cl | H | F | H | Cl | H | H |
| IV-1083 | c-Pr | Me(SO$_2$)NHNH | Cl | H | F | H | Cl | H | H |
| IV-1084 | c-Pr | MeOC(=O)NHNH | Cl | H | F | H | Cl | H | H |
| IV-1085 | c-Pr | 2-pyridinyl-N(Ac)-NH | Cl | H | F | H | Cl | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1086 | c-Pr | *tert-butyl hexahydropyridazine-1-carboxylate* | Cl | H | F | H | Cl | H | H |
| IV-1087 | c-Pr | Me$_2$NC(=O)NHNH | Cl | H | F | H | Cl | H | H |
| IV-1088 | c-Pr | Me2C=NNH | Cl | H | F | H | Cl | H | H |
| IV-1089 | c-Pr | H$_2$NNH | Cl | H | H | H | Cl | H | H |
| IV-1090 | c-Pr | MeNHNH | Cl | H | H | Cl | Cl | H | H |
| IV-1091 | c-Pr | H$_2$NN(Me) | Cl | H | H | Cl | Cl | H | H |
| IV-1092 | c-Pr | Me$_2$NNH | Cl | H | H | Cl | Cl | H | H |
| IV-1093 | c-Pr | Me$_2$NN(Me) | Cl | H | H | Cl | Cl | H | H |
| IV-1094 | c-Pr | PhNHNH | Cl | H | H | Cl | Cl | H | H |
| IV-1095 | c-Pr | (2-Pyridinyl)NHNH | Cl | H | H | Cl | Cl | H | H |
| IV-1096 | c-Pr | *1,2,4-triazol-1-yl-NH* | Cl | H | H | Cl | Cl | H | H |
| IV-1097 | c-Pr | Me(C=O)NHNH | Cl | H | H | Cl | Cl | H | H |
| IV-1098 | c-Pr | (Me)(Ac)NNH | Cl | H | H | Cl | Cl | H | H |
| IV-1099 | c-Pr | Me(SO$_2$)NHNH | Cl | H | H | Cl | Cl | H | H |
| IV-1100 | c-Pr | MeOC(=O)NHNH | Cl | H | H | Cl | Cl | H | H |
| IV-1101 | c-Pr | *N-acetyl-N-(2-pyridinyl)hydrazine* | Cl | H | H | Cl | Cl | H | H |
| IV-1102 | c-Pr | *tert-butyl hexahydropyridazine-1-carboxylate* | Cl | H | H | Cl | Cl | H | H |
| IV-1103 | c-Pr | Me$_2$NC(=O)NHNH | Cl | H | H | Cl | Cl | H | H |
| IV-1104 | c-Pr | Me2C=NNH | Cl | H | H | Cl | Cl | H | H |
| IV-1105 | c-Pr | H$_2$NNH | MeO | H | F | F | H | H | H |
| IV-1106 | c-Pr | MeNHNH | MeO | H | F | F | H | H | H |
| IV-1107 | c-Pr | H$_2$NN(Me) | MeO | H | F | F | H | H | H |
| IV-1108 | c-Pr | Me$_2$NNH | MeO | H | F | F | H | H | H |
| IV-1109 | c-Pr | Me$_2$NN(Me) | MeO | H | F | F | H | H | H |
| IV-1110 | c-Pr | PhNHNH | MeO | H | F | F | H | H | H |
| IV-1111 | c-Pr | (2-Pyridinyl)NHNH | MeO | H | F | F | H | H | H |
| IV-1112 | c-Pr | *1,2,4-triazol-1-yl-NH* | MeO | H | F | F | H | H | H |
| IV-1113 | c-Pr | Me(C=O)NHNH | MeO | H | F | F | H | H | H |
| IV-1114 | c-Pr | (Me)(Ac)NNH | MeO | H | F | F | H | H | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1115 | c-Pr | Me(SO$_2$)NHNH | MeO | H | F | F | H | H | H |
| IV-1116 | c-Pr | MeOC(=O)NHNH | MeO | H | F | F | H | H | H |
| IV-1117 | c-Pr | [2-pyridinyl-N(C(=O)Me)NH] | MeO | H | F | F | H | H | H |
| IV-1118 | c-Pr | [N-Boc-hexahydropyridazin-1-yl] | MeO | H | F | F | H | H | H |
| IV-1119 | c-Pr | Me$_2$NC(=O)NHNH | MeO | H | F | F | H | H | H |
| IV-1120 | c-Pr | Me2C=NNH | MeO | H | F | F | H | H | H |
| IV-1121 | c-Pr | H$_2$NNH | H | H | H | H | H | Me | H |
| IV-1122 | c-Pr | MeNHNH | H | H | H | H | H | Me | H |
| IV-1123 | c-Pr | H$_2$NN(Me) | H | H | H | H | H | Me | H |
| IV-1124 | c-Pr | Me$_2$NNH | H | H | H | H | H | Me | H |
| IV-1125 | c-Pr | Me$_2$NN(Me) | H | H | H | H | H | Me | H |
| IV-1126 | c-Pr | PhNHNH | H | H | H | H | H | Me | H |
| IV-1127 | c-Pr | (2-Pyridinyl)NHNH | H | H | H | H | H | Me | H |
| IV-1128 | c-Pr | [1,2,4-triazol-1-yl-NH] | H | H | H | H | H | Me | H |
| IV-1129 | c-Pr | Me(C=O)NHNH | H | H | H | H | H | Me | H |
| IV-1130 | c-Pr | (Me)(Ac)NNH | H | H | H | H | H | Me | H |
| IV-1131 | c-Pr | Me(SO$_2$)NHNH | H | H | H | H | H | Me | H |
| IV-1132 | c-Pr | MeOC(=O)NHNH | H | H | H | H | H | Me | H |
| IV-1133 | c-Pr | [2-pyridinyl-N(C(=O)Me)NH] | H | H | H | H | H | Me | H |
| IV-1134 | c-Pr | [N-Boc-hexahydropyridazin-1-yl] | H | H | H | H | H | Me | H |
| IV-1135 | c-Pr | Me$_2$NC(=O)NHNH | H | H | H | H | H | Me | H |
| IV-1136 | c-Pr | Me2C=NNH | H | H | H | H | H | Me | H |
| IV-1137 | c-Pr | H$_2$NNH | H | H | H | H | H | Me | Me |
| IV-1138 | c-Pr | MeNHNH | H | H | H | H | H | Me | Me |
| IV-1139 | c-Pr | H$_2$NN(Me) | H | H | H | H | H | Me | Me |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1140 | c-Pr | Me$_2$NNH | H | H | H | H | H | Me | Me |
| IV-1141 | c-Pr | Me$_2$NN(Me) | H | H | H | H | H | Me | Me |
| IV-1142 | c-Pr | PhNHNH | H | H | H | H | H | Me | Me |
| IV-1143 | c-Pr | (2-Pyridinyl)NHNH | H | H | H | H | H | Me | Me |
| IV-1144 | c-Pr | 1,2,4-triazol-1-yl-NH | H | H | H | H | H | Me | Me |
| IV-1145 | c-Pr | Me(C=O)NHNH | H | H | H | H | H | Me | Me |
| IV-1146 | c-Pr | (Me)(Ac)NNH | H | H | H | H | H | Me | Me |
| IV-1147 | c-Pr | Me(SO$_2$)NHNH | H | H | H | H | H | Me | Me |
| IV-1148 | c-Pr | MeOC(=O)NHNH | H | H | H | H | H | Me | Me |
| IV-1149 | c-Pr | N-(2-pyridinyl)-N-acetyl-hydrazino | H | H | H | H | H | Me | Me |
| IV-1150 | c-Pr | 1-(tert-butoxycarbonyl)hexahydropyridazin-1-yl | H | H | H | H | H | Me | Me |
| IV-1151 | c-Pr | Me$_2$NC(=O)NHNH | H | H | H | H | H | Me | Me |
| IV-1152 | c-Pr | Me2C=NNH | H | H | H | H | H | Me | Me |
| IV-1153 | c-Pr | H$_2$NNH | H | H | H | H | H | CO$_2$Et | H |
| IV-1154 | c-Pr | MeNHNH | H | H | H | H | H | CO$_2$Et | H |
| IV-1155 | c-Pr | H$_2$NN(Me) | H | H | H | H | H | CO$_2$Et | H |
| IV-1156 | c-Pr | Me$_2$NNH | H | H | H | H | H | CO$_2$Et | H |
| IV-1157 | c-Pr | Me$_2$NN(Me) | H | H | H | H | H | CO$_2$Et | H |
| IV-1158 | c-Pr | PhNHNH | H | H | H | H | H | CO$_2$Et | H |
| IV-1159 | c-Pr | (2-Pyridinyl)NHNH | H | H | H | H | H | CO$_2$Et | H |
| IV-1160 | c-Pr | 1,2,4-triazol-1-yl-NH | H | H | H | H | H | CO$_2$Et | H |
| IV-1161 | c-Pr | Me(C=O)NHNH | H | H | H | H | H | CO$_2$Et | H |
| IV-1162 | c-Pr | (Me)(Ac)NNH | H | H | H | H | H | CO$_2$Et | H |
| IV-1163 | c-Pr | Me(SO$_2$)NHNH | H | H | H | H | H | CO$_2$Et | H |
| IV-1164 | c-Pr | MeOC(=O)NHNH | H | H | H | H | H | CO$_2$Et | H |
| IV-1165 | c-Pr | N-(2-pyridinyl)-N-acetyl-hydrazino | H | H | H | H | H | CO$_2$Et | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1166 | c-Pr | tert-butyl hexahydropyridazine-1-carboxylate | H | H | H | H | H | CO$_2$Et | H |
| IV-1167 | c-Pr | Me$_2$NC(=O)NHNH | H | H | H | H | H | CO$_2$Et | H |
| IV-1168 | c-Pr | Me2C=NNH | H | H | H | H | H | CO$_2$Et | H |
| IV-1169 | c-Pr | H$_2$NNH | H | H | H | H | H | CN | H |
| IV-1170 | c-Pr | MeNHNH | H | H | H | H | H | CN | H |
| IV-1171 | c-Pr | H$_2$NN(Me) | H | H | H | H | H | CN | H |
| IV-1172 | c-Pr | Me$_2$NNH | H | H | H | H | H | CN | H |
| IV-1173 | c-Pr | Me$_2$NN(Me) | H | H | H | H | H | CN | H |
| IV-1174 | c-Pr | PhNHNH | H | H | H | H | H | CN | H |
| IV-1175 | c-Pr | (2-Pyridinyl)NHNH | H | H | H | H | H | CN | H |
| IV-1176 | c-Pr | 1,2,4-triazol-1-yl-NH | H | H | H | H | H | CN | H |
| IV-1177 | c-Pr | Me(C=O)NHNH | H | H | H | H | H | CN | H |
| IV-1178 | c-Pr | (Me)(Ac)NNH | H | H | H | H | H | CN | H |
| IV-1179 | c-Pr | Me(SO$_2$)NHNH | H | H | H | H | H | CN | H |
| IV-1180 | c-Pr | MeOC(=O)NHNH | H | H | H | H | H | CN | H |
| IV-1181 | c-Pr | N-acetyl-N-(pyridin-2-yl)hydrazinyl | H | H | H | H | H | CN | H |
| IV-1182 | c-Pr | tert-butyl hexahydropyridazine-1-carboxylate | H | H | H | H | H | CN | H |
| IV-1183 | c-Pr | Me$_2$NC(=O)NHNH | H | H | H | H | H | CN | H |
| IV-1184 | c-Pr | Me2C=NNH | H | H | H | H | H | CN | H |
| IV-1185 | c-Pr | H$_2$NNH | F | H | H | H | H | Me | H |
| IV-1186 | c-Pr | MeNHNH | F | H | H | H | H | Me | H |
| IV-1187 | c-Pr | H$_2$NN(Me) | F | H | H | H | H | Me | H |
| IV-1188 | c-Pr | Me$_2$NNH | F | H | H | H | H | Me | H |
| IV-1189 | c-Pr | Me$_2$NN(Me) | F | H | H | H | H | Me | H |
| IV-1190 | c-Pr | PhNHNH | F | H | H | H | H | Me | H |
| IV-1191 | c-Pr | (2-Pyridinyl)NHNH | F | H | H | H | H | Me | H |
| IV-1192 | c-Pr | 1,2,4-triazol-1-yl-NH | F | H | H | H | H | Me | H |
| IV-1193 | c-Pr | Me(C=O)NHNH | F | H | H | H | H | Me | H |
| IV-1194 | c-Pr | (Me)(Ac)NNH | F | H | H | H | H | Me | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1195 | c-Pr | Me(SO$_2$)NHNH | F | H | H | H | H | Me | H |
| IV-1196 | c-Pr | MeOC(=O)NHNH | F | H | H | H | H | Me | H |
| IV-1197 | c-Pr | (2-pyridinyl-N(Ac)NH) | F | H | H | H | H | Me | H |
| IV-1198 | c-Pr | (tBuOC(=O)-piperidazinyl) | F | H | H | H | H | Me | H |
| IV-1199 | c-Pr | Me$_2$NC(=O)NHNH | F | H | H | H | H | Me | H |
| IV-1200 | c-Pr | Me2C=NNH | F | H | H | H | H | Me | H |
| IV-1201 | c-Pr | H$_2$NNH | F | H | H | H | H | Me | Me |
| IV-1202 | c-Pr | MeNHNH | F | H | H | H | H | Me | Me |
| IV-1203 | c-Pr | H$_2$NN(Me) | F | H | H | H | H | Me | Me |
| IV-1204 | c-Pr | Me$_2$NNH | F | H | H | H | H | Me | Me |
| IV-1205 | c-Pr | Me$_2$NN(Me) | F | H | H | H | H | Me | Me |
| IV-1206 | c-Pr | PhNHNH | F | H | H | H | H | Me | Me |
| IV-1207 | c-Pr | (2-Pyridinyl)NHNH | F | H | H | H | H | Me | Me |
| IV-1208 | c-Pr | (1,2,4-triazolyl-NH) | F | H | H | H | H | Me | Me |
| IV-1209 | c-Pr | Me(C=O)NHNH | H | H | H | H | H | Me | Me |
| IV-1210 | c-Pr | (Me)(Ac)NNH | F | H | H | H | H | Me | Me |
| IV-1211 | c-Pr | Me(SO$_2$)NHNH | H | H | H | H | H | Me | Me |
| IV-1212 | c-Pr | MeOC(=O)NHNH | H | H | H | H | H | Me | Me |
| IV-1213 | c-Pr | (2-pyridinyl-N(Ac)NH) | H | H | H | H | H | Me | Me |
| IV-1214 | c-Pr | (tBuOC(=O)-piperidazinyl) | F | H | H | H | H | Me | Me |
| IV-1215 | c-Pr | Me$_2$NC(=O)NHNH | F | H | H | H | H | Me | Me |
| IV-1216 | c-Pr | Me2C=NNH | F | H | H | H | H | Me | Me |
| IV-1217 | c-Pr | H$_2$NNH | F | H | H | H | H | CO$_2$Et | H |
| IV-1218 | c-Pr | MeNHNH | F | H | H | H | H | CO$_2$Et | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1219 | c-Pr | H$_2$NN(Me) | F | H | H | H | H | CO$_2$Et | H |
| IV-1220 | c-Pr | Me$_2$NNH | F | H | H | H | H | CO$_2$Et | H |
| IV-1221 | c-Pr | Me$_2$NN(Me) | F | H | H | H | H | CO$_2$Et | H |
| IV-1222 | c-Pr | PhNHNH | F | H | H | H | H | CO$_2$Et | H |
| IV-1223 | c-Pr | (2-Pyridinyl)NHNH | F | H | H | H | H | CO$_2$Et | H |
| IV-1224 | c-Pr | (triazolyl-NH) | F | H | H | H | H | CO$_2$Et | H |
| IV-1225 | c-Pr | Me(C=O)NHNH | F | H | H | H | H | CO$_2$Et | H |
| IV-1226 | c-Pr | (Me)(Ac)NNH | F | H | H | H | H | CO$_2$Et | H |
| IV-1227 | c-Pr | Me(SO$_2$)NHNH | F | H | H | H | H | CO$_2$Et | H |
| IV-1228 | c-Pr | MeOC(=O)NHNH | F | H | H | H | H | CO$_2$Et | H |
| IV-1229 | c-Pr | (2-pyridinyl-N(Ac)-NH) | F | H | H | H | H | CO$_2$Et | H |
| IV-1230 | c-Pr | (Boc-piperidazinyl) | F | H | H | H | H | CO$_2$Et | H |
| IV-1231 | c-Pr | Me$_2$NC(=O)NHNH | F | H | H | H | H | CO$_2$Et | H |
| IV-1232 | c-Pr | Me2C=NNH | F | H | H | H | H | CO$_2$Et | H |
| IV-1233 | c-Pr | H$_2$NNH | F | H | H | H | H | CN | H |
| IV-1234 | c-Pr | MeNHNH | F | H | H | H | H | CN | H |
| IV-1235 | c-Pr | H$_2$NN(Me) | F | H | H | H | H | CN | H |
| IV-1236 | c-Pr | Me$_2$NNH | F | H | H | H | H | CN | H |
| IV-1237 | c-Pr | Me$_2$NN(Me) | F | H | H | H | H | CN | H |
| IV-1238 | c-Pr | PhNHNH | F | H | H | H | H | CN | H |
| IV-1239 | c-Pr | (2-Pyridinyl)NHNH | F | H | H | H | H | CN | H |
| IV-1240 | c-Pr | (triazolyl-NH) | F | H | H | H | H | CN | H |
| IV-1241 | c-Pr | Me(C=O)NHNH | F | H | H | H | H | CN | H |
| IV-1242 | c-Pr | (Me)(Ac)NNH | F | H | H | H | H | CN | H |
| IV-1243 | c-Pr | Me(SO$_2$)NHNH | F | H | H | H | H | CN | H |
| IV-1244 | c-Pr | MeOC(=O)NHNH | F | H | H | H | H | CN | H |
| IV-1245 | c-Pr | (2-pyridinyl-N(Ac)-NH) | F | H | H | H | H | CN | H |

TABLE 4-continued

Inventive compounds of the formula (I) in which X represents C(R$^{13}$)(R$^{14}$)

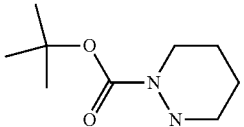

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1246 | c-Pr | 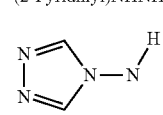 | F | H | H | H | H | CN | H |
| IV-1247 | c-Pr | Me$_2$NC(=O)NHNH | F | H | H | H | H | CN | H |
| IV-1248 | c-Pr | Me2C=NNH | F | H | H | H | H | CN | H |
| IV-1249 | c-Pr | H$_2$NNH | F | F | H | H | H | Me | H |
| IV-1250 | c-Pr | MeNHNH | F | F | H | H | H | Me | H |
| IV-1251 | c-Pr | H$_2$NN(Me) | F | F | H | H | H | Me | H |
| IV-1252 | c-Pr | Me$_2$NNH | F | F | H | H | H | Me | H |
| IV-1253 | c-Pr | Me$_2$NN(Me) | F | F | H | H | H | Me | H |
| IV-1254 | c-Pr | PhNHNH | F | F | H | H | H | Me | H |
| IV-1255 | c-Pr | (2-Pyridinyl)NHNH | F | F | H | H | H | Me | H |
| IV-1256 | c-Pr | 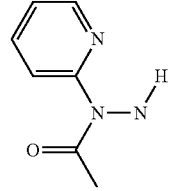 | F | F | H | H | H | Me | H |
| IV-1257 | c-Pr | Me(C=O)NHNH | F | F | H | H | H | Me | H |
| IV-1258 | c-Pr | (Me)(Ac)NNH | F | F | H | H | H | Me | H |
| IV-1259 | c-Pr | Me(SO$_2$)NHNH | F | F | H | H | H | Me | H |
| IV-1260 | c-Pr | MeOC(=O)NHNH | F | F | H | H | H | Me | H |
| IV-1261 | c-Pr | 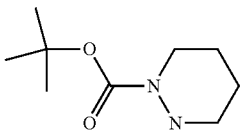 | F | F | H | H | H | Me | H |
| IV-1262 | c-Pr | 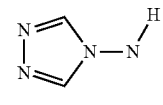 | F | F | H | H | H | Me | H |
| IV-1263 | c-Pr | Me$_2$NC(=O)NHNH | F | F | H | H | H | Me | H |
| IV-1264 | c-Pr | Me2C=NNH | F | F | H | H | H | Me | H |
| IV-1265 | c-Pr | H$_2$NNH | F | F | H | H | H | Me | Me |
| IV-1266 | c-Pr | MeNHNH | F | F | H | H | H | Me | Me |
| IV-1267 | c-Pr | H$_2$NN(Me) | F | F | H | H | H | Me | Me |
| IV-1268 | c-Pr | Me$_2$NNH | F | F | H | H | H | Me | Me |
| IV-1269 | c-Pr | Me$_2$NN(Me) | F | F | H | H | H | Me | Me |
| IV-1270 | c-Pr | PhNHNH | F | F | H | H | H | Me | Me |
| IV-1271 | c-Pr | (2-Pyridinyl)NHNH | F | F | H | H | H | Me | Me |
| IV-1272 | c-Pr | 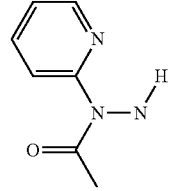 | F | F | H | H | H | Me | Me |
| IV-1273 | c-Pr | Me(C=O)NHNH | F | F | H | H | H | Me | Me |
| IV-1274 | c-Pr | (Me)(Ac)NNH | F | F | H | H | H | Me | Me |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1275 | c-Pr | Me(SO$_2$)NHNH | F | F | H | H | H | Me | Me |
| IV-1276 | c-Pr | MeOC(=O)NHNH | F | F | H | H | H | Me | Me |
| IV-1277 | c-Pr | (2-pyridinyl-N(C(=O)Me)-NH) | F | F | H | H | H | Me | Me |
| IV-1278 | c-Pr | (tBuO-C(=O)-piperidazinyl) | F | F | H | H | H | Me | Me |
| IV-1279 | c-Pr | Me$_2$NC(=O)NHNH | F | F | H | H | H | Me | Me |
| IV-1280 | c-Pr | Me2C=NNH | F | F | H | H | H | Me | Me |
| IV-1281 | c-Pr | H$_2$NNH | F | F | H | H | H | CO$_2$Et | H |
| IV-1282 | c-Pr | MeNHNH | F | F | H | H | H | CO$_2$Et | H |
| IV-1283 | c-Pr | H$_2$NN(Me) | F | F | H | H | H | CO$_2$Et | H |
| IV-1284 | c-Pr | Me$_2$NNH | F | F | H | H | H | CO$_2$Et | H |
| IV-1285 | c-Pr | Me$_2$NN(Me) | F | F | H | H | H | CO$_2$Et | H |
| IV-1286 | c-Pr | PhNHNH | F | F | H | H | H | CO$_2$Et | H |
| IV-1287 | c-Pr | (2-Pyridinyl)NHNH | F | F | H | H | H | CO$_2$Et | H |
| IV-1288 | c-Pr | (1,2,4-triazol-1-yl)NH | F | F | H | H | H | CO$_2$Et | H |
| IV-1289 | c-Pr | Me(C=O)NHNH | F | F | H | H | H | CO$_2$Et | H |
| IV-1290 | c-Pr | (Me)(Ac)NNH | F | F | H | H | H | CO$_2$Et | H |
| IV-1291 | c-Pr | Me(SO$_2$)NHNH | F | F | H | H | H | CO$_2$Et | H |
| IV-1292 | c-Pr | MeOC(=O)NHNH | F | F | H | H | H | CO$_2$Et | H |
| IV-1293 | c-Pr | (2-pyridinyl-N(C(=O)Me)-NH) | F | F | H | H | H | CO$_2$Et | H |
| IV-1294 | c-Pr | (tBuO-C(=O)-piperidazinyl) | F | F | H | H | H | CO$_2$Et | H |
| IV-1295 | c-Pr | Me$_2$NC(=O)NHNH | F | F | H | H | H | CO$_2$Et | H |
| IV-1296 | c-Pr | Me2C=NNH | F | F | H | H | H | CO$_2$Et | H |
| IV-1297 | c-Pr | H$_2$NNH | F | F | H | H | H | CN | H |
| IV-1298 | c-Pr | MeNHNH | F | F | H | H | H | CN | H |
| IV-1299 | c-Pr | H$_2$NN(Me) | F | F | H | H | H | CN | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1300 | c-Pr | Me$_2$NNH | F | F | H | H | H | CN | H |
| IV-1301 | c-Pr | Me$_2$NN(Me) | F | F | H | H | H | CN | H |
| IV-1302 | c-Pr | PhNHNH | F | F | H | H | H | CN | H |
| IV-1303 | c-Pr | (2-Pyridinyl)NHNH | F | F | H | H | H | CN | H |
| IV-1304 | c-Pr | (triazolyl-NH) | F | F | H | H | H | CN | H |
| IV-1305 | c-Pr | Me(C=O)NHNH | F | F | H | H | H | CN | H |
| IV-1306 | c-Pr | (Me)(Ac)NNH | F | F | H | H | H | CN | H |
| IV-1307 | c-Pr | Me(SO$_2$)NHNH | F | F | H | H | H | CN | H |
| IV-1308 | c-Pr | MeOC(=O)NHNH | F | F | H | H | H | CN | H |
| IV-1309 | c-Pr | (2-pyridinyl-N(Ac)-NH) | F | F | H | H | H | CN | H |
| IV-1310 | c-Pr | (Boc-pyridazinyl) | F | F | H | H | H | CN | H |
| IV-1311 | c-Pr | Me$_2$NC(=O)NHNH | F | F | H | H | H | CN | H |
| IV-1312 | c-Pr | Me2C=NNH | F | F | H | H | H | CN | H |
| IV-1313 | c-Pr | H$_2$NNH | F | H | F | H | H | Me | H |
| IV-1314 | c-Pr | MeNHNH | F | H | F | H | H | Me | H |
| IV-1315 | c-Pr | H$_2$NN(Me) | F | H | F | H | H | Me | H |
| IV-1316 | c-Pr | Me$_2$NNH | F | H | F | H | H | Me | H |
| IV-1317 | c-Pr | Me$_2$NN(Me) | F | H | F | H | H | Me | H |
| IV-1318 | c-Pr | PhNHNH | F | H | F | H | H | Me | H |
| IV-1319 | c-Pr | (2-Pyridinyl)NHNH | F | H | F | H | H | Me | H |
| IV-1320 | c-Pr | (triazolyl-NH) | F | H | F | H | H | Me | H |
| IV-1321 | c-Pr | Me(C=O)NHNH | F | H | F | H | H | Me | H |
| IV-1322 | c-Pr | (Me)(Ac)NNH | F | H | F | H | H | Me | H |
| IV-1323 | c-Pr | Me(SO$_2$)NHNH | F | H | F | H | H | Me | H |
| IV-1324 | c-Pr | MeOC(=O)NHNH | F | H | F | H | H | Me | H |
| IV-1325 | c-Pr | (2-pyridinyl-N(Ac)-NH) | F | H | F | H | H | Me | H |

TABLE 4-continued

Inventive compounds of the formula (I) in which X represents C(R¹³)(R¹⁴)

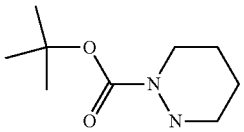

(I)

| No. | R¹ | R² | R³ | R⁴ | R⁵ | R⁶ | R⁷ | R¹³ | R¹⁴ |
|---|---|---|---|---|---|---|---|---|---|
| IV-1326 | c-Pr | 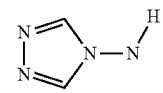 | F | H | F | H | H | Me | H |
| IV-1327 | c-Pr | Me₂NC(=O)NHNH | F | H | F | H | H | Me | H |
| IV-1328 | c-Pr | Me2C=NNH | F | H | F | H | H | Me | H |
| IV-1329 | c-Pr | H₂NNH | F | H | F | H | H | Me | Me |
| IV-1330 | c-Pr | MeNHNH | F | H | F | H | H | Me | Me |
| IV-1331 | c-Pr | H₂NN(Me) | F | H | F | H | H | Me | Me |
| IV-1332 | c-Pr | Me₂NNH | F | H | F | H | H | Me | Me |
| IV-1333 | c-Pr | Me₂NN(Me) | F | H | F | H | H | Me | Me |
| IV-1334 | c-Pr | PhNHNH | F | H | F | H | H | Me | Me |
| IV-1335 | c-Pr | (2-Pyridinyl)NHNH | F | H | F | H | H | Me | Me |
| IV-1336 | c-Pr | 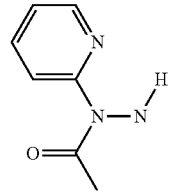 | F | H | F | H | H | Me | Me |
| IV-1337 | c-Pr | Me(C=O)NHNH | F | H | F | H | H | Me | Me |
| IV-1338 | c-Pr | (Me)(Ac)NNH | F | H | F | H | H | Me | Me |
| IV-1339 | c-Pr | Me(SO₂)NHNH | F | H | F | H | H | Me | Me |
| IV-1340 | c-Pr | MeOC(=O)NHNH | F | H | F | H | H | Me | Me |
| IV-1341 | c-Pr | 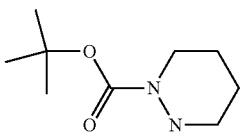 | F | H | F | H | H | Me | Me |
| IV-1342 | c-Pr | 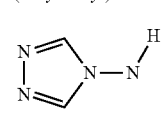 | F | H | F | H | H | Me | Me |
| IV-1343 | c-Pr | Me₂NC(=O)NHNH | F | H | F | H | H | Me | Me |
| IV-1344 | c-Pr | Me2C=NNH | F | H | F | H | H | Me | Me |
| IV-1345 | c-Pr | H₂NNH | F | H | F | H | H | CO₂Et | H |
| IV-1346 | c-Pr | MeNHNH | F | H | F | H | H | CO₂Et | H |
| IV-1347 | c-Pr | H₂NN(Me) | F | H | F | H | H | CO₂Et | H |
| IV-1348 | c-Pr | Me₂NNH | F | H | F | H | H | CO₂Et | H |
| IV-1349 | c-Pr | Me₂NN(Me) | F | H | F | H | H | CO₂Et | H |
| IV-1350 | c-Pr | PhNHNH | F | H | F | H | H | CO₂Et | H |
| IV-1351 | c-Pr | (2-Pyridinyl)NHNH | F | H | F | H | H | CO₂Et | H |
| IV-1352 | c-Pr | 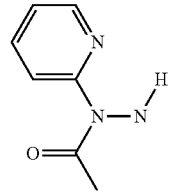 | F | H | F | H | H | CO₂Et | H |
| IV-1353 | c-Pr | Me(C=O)NHNH | F | H | F | H | H | CO₂Et | H |
| IV-1354 | c-Pr | (Me)(Ac)NNH | F | H | F | H | H | CO₂Et | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1355 | c-Pr | Me(SO$_2$)NHNH | F | H | F | H | H | CO$_2$Et | H |
| IV-1356 | c-Pr | MeOC(=O)NHNH | F | H | F | H | H | CO$_2$Et | H |
| IV-1357 | c-Pr | [2-pyridinyl-N(Ac)-NH] | F | H | F | H | H | CO$_2$Et | H |
| IV-1358 | c-Pr | [Boc-piperidazine] | F | H | F | H | H | CO$_2$Et | H |
| IV-1359 | c-Pr | Me$_2$NC(=O)NHNH | F | H | F | H | H | CO$_2$Et | H |
| IV-1360 | c-Pr | Me2C=NNH | F | H | F | H | H | CO$_2$Et | H |
| IV-1361 | c-Pr | H$_2$NNH | F | H | F | H | H | CN | H |
| IV-1362 | c-Pr | MeNHNH | F | H | F | H | H | CN | H |
| IV-1363 | c-Pr | H$_2$NN(Me) | F | H | F | H | H | CN | H |
| IV-1364 | c-Pr | Me$_2$NNH | F | H | F | H | H | CN | H |
| IV-1365 | c-Pr | Me$_2$NN(Me) | F | H | F | H | H | CN | H |
| IV-1366 | c-Pr | PhNHNH | F | H | F | H | H | CN | H |
| IV-1367 | c-Pr | (2-Pyridinyl)NHNH | F | H | F | H | H | CN | H |
| IV-1368 | c-Pr | [triazolyl-NH] | F | H | F | H | H | CN | H |
| IV-1369 | c-Pr | Me(C=O)NHNH | F | H | F | H | H | CN | H |
| IV-1370 | c-Pr | (Me)(Ac)NNH | F | H | F | H | H | CN | H |
| IV-1371 | c-Pr | Me(SO$_2$)NHNH | F | H | F | H | H | CN | H |
| IV-1372 | c-Pr | MeOC(=O)NHNH | F | H | F | H | H | CN | H |
| IV-1373 | c-Pr | [2-pyridinyl-N(Ac)-NH] | F | H | F | H | H | CN | H |
| IV-1374 | c-Pr | [Boc-piperidazine] | F | H | F | H | H | CN | H |
| IV-1375 | c-Pr | Me$_2$NC(=O)NHNH | F | H | F | H | H | CN | H |
| IV-1376 | c-Pr | Me2C=NNH | F | H | F | H | H | CN | H |
| IV-1377 | c-Pr | H$_2$NNH | F | H | H | F | H | Me | H |
| IV-1378 | c-Pr | MeNHNH | F | H | H | F | H | Me | H |
| IV-1379 | c-Pr | H$_2$NN(Me) | F | H | H | F | H | Me | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1380 | c-Pr | Me$_2$NNH | F | H | H | F | H | Me | H |
| IV-1381 | c-Pr | Me$_2$NN(Me) | F | H | H | F | H | Me | H |
| IV-1382 | c-Pr | PhNHNH | F | H | H | F | H | Me | H |
| IV-1383 | c-Pr | (2-Pyridinyl)NHNH | F | H | H | F | H | Me | H |
| IV-1384 | c-Pr | ![triazolyl-NH] | F | H | H | F | H | Me | H |
| IV-1385 | c-Pr | Me(C=O)NHNH | F | H | H | F | H | Me | H |
| IV-1386 | c-Pr | (Me)(Ac)NNH | F | H | H | F | H | Me | H |
| IV-1387 | c-Pr | Me(SO$_2$)NHNH | F | H | H | F | H | Me | H |
| IV-1388 | c-Pr | MeOC(=O)NHNH | F | H | H | F | H | Me | H |
| IV-1389 | c-Pr | ![pyridinyl-N(Ac)-NH] | F | H | H | F | H | Me | H |
| IV-1390 | c-Pr | ![Boc-piperidazine] | F | H | H | F | H | Me | H |
| IV-1391 | c-Pr | Me$_2$NC(=O)NHNH | F | H | H | F | H | Me | H |
| IV-1392 | c-Pr | Me2C=NNH | F | H | H | F | H | Me | H |
| IV-1393 | c-Pr | H$_2$NNH | F | H | H | F | H | Me | Me |
| IV-1394 | c-Pr | MeNHNH | F | H | H | F | H | Me | Me |
| IV-1395 | c-Pr | H$_2$NN(Me) | F | H | H | F | H | Me | Me |
| IV-1396 | c-Pr | Me$_2$NNH | F | H | H | F | H | Me | Me |
| IV-1397 | c-Pr | Me$_2$NN(Me) | F | H | H | F | H | Me | Me |
| IV-1398 | c-Pr | PhNHNH | F | H | H | F | H | Me | Me |
| IV-1399 | c-Pr | (2-Pyridinyl)NHNH | F | H | H | F | H | Me | Me |
| IV-1400 | c-Pr | ![triazolyl-NH] | F | H | H | F | H | Me | Me |
| IV-1401 | c-Pr | Me(C=O)NHNH | F | H | H | F | H | Me | Me |
| IV-1402 | c-Pr | (Me)(Ac)NNH | F | H | H | F | H | Me | Me |
| IV-1403 | c-Pr | Me(SO$_2$)NHNH | F | H | H | F | H | Me | Me |
| IV-1404 | c-Pr | MeOC(=O)NHNH | F | H | H | F | H | Me | Me |
| IV-1405 | c-Pr | ![pyridinyl-N(Ac)-NH] | F | H | H | F | H | Me | Me |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1406 | c-Pr | tert-butyl piperidin-1-yl carboxylate (hexahydropyridazine-1-carboxylate) | F | H | H | F | H | Me | Me |
| IV-1407 | c-Pr | Me$_2$NC(=O)NHNH | F | H | H | F | H | Me | Me |
| IV-1408 | c-Pr | Me2C=NNH | F | H | H | F | H | Me | Me |
| IV-1409 | c-Pr | H$_2$NNH | F | H | H | F | H | CO$_2$Et | H |
| IV-1410 | c-Pr | MeNHNH | F | H | H | F | H | CO$_2$Et | H |
| IV-1411 | c-Pr | H$_2$NN(Me) | F | H | H | F | H | CO$_2$Et | H |
| IV-1412 | c-Pr | Me$_2$NNH | F | H | H | F | H | CO$_2$Et | H |
| IV-1413 | c-Pr | Me$_2$NN(Me) | F | H | H | F | H | CO$_2$Et | H |
| IV-1414 | c-Pr | PhNHNH | F | H | H | F | H | CO$_2$Et | H |
| IV-1415 | c-Pr | (2-Pyridinyl)NHNH | F | H | H | F | H | CO$_2$Et | H |
| IV-1416 | c-Pr | 1,2,4-triazol-1-yl-NH | F | H | H | F | H | CO$_2$Et | H |
| IV-1417 | c-Pr | Me(C=O)NHNH | F | H | H | F | H | CO$_2$Et | H |
| IV-1418 | c-Pr | (Me)(Ac)NNH | F | H | H | F | H | CO$_2$Et | H |
| IV-1419 | c-Pr | Me(SO$_2$)NHNH | F | H | H | F | H | CO$_2$Et | H |
| IV-1420 | c-Pr | MeOC(=O)NHNH | F | H | H | F | H | CO$_2$Et | H |
| IV-1421 | c-Pr | N-(pyridin-2-yl)-N-acetylhydrazinyl | F | H | H | F | H | CO$_2$Et | H |
| IV-1422 | c-Pr | tert-butyl piperidin-1-yl carboxylate | F | H | H | F | H | CO$_2$Et | H |
| IV-1423 | c-Pr | Me$_2$NC(=O)NHNH | F | H | H | F | H | CO$_2$Et | H |
| IV-1424 | c-Pr | Me2C=NNH | F | H | H | F | H | CO$_2$Et | H |
| IV-1425 | c-Pr | H$_2$NNH | F | H | H | F | H | CN | H |
| IV-1426 | c-Pr | MeNHNH | F | H | H | F | H | CN | H |
| IV-1427 | c-Pr | H$_2$NN(Me) | F | H | H | F | H | CN | H |
| IV-1428 | c-Pr | Me$_2$NNH | F | H | H | F | H | CN | H |
| IV-1429 | c-Pr | Me$_2$NN(Me) | F | H | H | F | H | CN | H |
| IV-1430 | c-Pr | PhNHNH | F | H | H | F | H | CN | H |
| IV-1431 | c-Pr | (2-Pyridinyl)NHNH | F | H | H | F | H | CN | H |
| IV-1432 | c-Pr | 1,2,4-triazol-1-yl-NH | F | H | H | F | H | CN | H |
| IV-1433 | c-Pr | Me(C=O)NHNH | F | H | H | F | H | CN | H |
| IV-1434 | c-Pr | (Me)(Ac)NNH | F | H | H | F | H | CN | H |

TABLE 4-continued

Inventive compounds of the formula (I) in which X represents C($R^{13}$) ($R^{14}$)

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1435 | c-Pr | Me(SO$_2$)NHNH | F | H | H | F | H | CN | H |
| IV-1436 | c-Pr | MeOC(=O)NHNH | F | H | H | F | H | CN | H |
| IV-1437 | c-Pr | [2-pyridinyl-N(Ac)-NH] | F | H | H | F | H | CN | H |
| IV-1438 | c-Pr | [Boc-piperidazine] | F | H | H | F | H | CN | H |
| IV-1439 | c-Pr | Me$_2$NC(=O)NHNH | F | H | H | F | H | CN | H |
| IV-1440 | c-Pr | Me2C=NNH | F | H | H | F | H | CN | H |
| IV-1441 | c-Pr | H$_2$NNH | F | H | H | H | F | Me | H |
| IV-1442 | c-Pr | MeNHNH | F | H | H | H | F | Me | H |
| IV-1443 | c-Pr | H$_2$NN(Me) | F | H | H | H | F | Me | H |
| IV-1444 | c-Pr | Me$_2$NNH | F | H | H | H | F | Me | H |
| IV-1445 | c-Pr | Me$_2$NN(Me) | F | H | H | H | F | Me | H |
| IV-1446 | c-Pr | PhNHNH | F | H | H | H | F | Me | H |
| IV-1447 | c-Pr | (2-Pyridinyl)NHNH | F | H | H | H | F | Me | H |
| IV-1448 | c-Pr | [triazolyl-NH] | F | H | H | H | F | Me | H |
| IV-1449 | c-Pr | Me(C=O)NHNH | F | H | H | H | F | Me | H |
| IV-1450 | c-Pr | (Me)(Ac)NNH | F | H | H | H | F | Me | H |
| IV-1451 | c-Pr | Me(SO$_2$)NHNH | F | H | H | H | F | Me | H |
| IV-1452 | c-Pr | MeOC(=O)NHNH | F | H | H | H | F | Me | H |
| IV-1453 | c-Pr | [2-pyridinyl-N(Ac)-NH] | F | H | H | H | F | Me | H |
| IV-1454 | c-Pr | [Boc-piperidazine] | F | H | H | H | F | Me | H |
| IV-1455 | c-Pr | Me$_2$NC(=O)NHNH | F | H | H | H | F | Me | H |
| IV-1456 | c-Pr | Me2C=NNH | F | H | H | H | F | Me | H |
| IV-1457 | c-Pr | H$_2$NNH | F | H | H | H | F | Me | Me |
| IV-1458 | c-Pr | MeNHNH | F | H | H | H | F | Me | Me |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1459 | c-Pr | H₂NN(Me) | F | H | H | H | F | Me | Me |
| IV-1460 | c-Pr | Me₂NNH | F | H | H | H | F | Me | Me |
| IV-1461 | c-Pr | Me₂NN(Me) | F | H | H | H | F | Me | Me |
| IV-1462 | c-Pr | PhNHNH | F | H | H | H | F | Me | Me |
| IV-1463 | c-Pr | (2-Pyridinyl)NHNH | F | H | H | H | F | Me | Me |
| IV-1464 | c-Pr | [1,2,4-triazol-1-yl-NH] | F | H | H | H | F | Me | Me |
| IV-1465 | c-Pr | Me(C=O)NHNH | F | H | H | H | F | Me | Me |
| IV-1466 | c-Pr | (Me)(Ac)NNH | F | H | H | H | F | Me | Me |
| IV-1467 | c-Pr | Me(SO₂)NHNH | F | H | H | H | F | Me | Me |
| IV-1468 | c-Pr | MeOC(=O)NHNH | F | H | H | H | F | Me | Me |
| IV-1469 | c-Pr | [2-pyridinyl-N(Ac)-NH] | F | H | H | H | F | Me | Me |
| IV-1470 | c-Pr | [tBuO-C(=O)-piperidazinyl] | F | H | H | H | F | Me | Me |
| IV-1471 | c-Pr | Me₂NC(=O)NHNH | F | H | H | H | F | Me | Me |
| IV-1472 | c-Pr | Me2C=NNH | F | H | H | H | F | Me | Me |
| IV-1473 | c-Pr | H₂NNH | F | H | H | H | F | CO₂Et | H |
| IV-1474 | c-Pr | MeNHNH | F | H | H | H | F | CO₂Et | H |
| IV-1475 | c-Pr | H₂NN(Me) | F | H | H | H | F | CO₂Et | H |
| IV-1476 | c-Pr | Me₂NNH | F | H | H | H | F | CO₂Et | H |
| IV-1477 | c-Pr | Me₂NN(Me) | F | H | H | H | F | CO₂Et | H |
| IV-1478 | c-Pr | PhNHNH | F | H | H | H | F | CO₂Et | H |
| IV-1479 | c-Pr | (2-Pyridinyl)NHNH | F | H | H | H | F | CO₂Et | H |
| IV-1480 | c-Pr | [1,2,4-triazol-1-yl-NH] | F | H | H | H | F | CO₂Et | H |
| IV-1481 | c-Pr | Me(C=O)NHNH | F | H | H | H | F | CO₂Et | H |
| IV-1482 | c-Pr | (Me)(Ac)NNH | F | H | H | H | F | CO₂Et | H |
| IV-1483 | c-Pr | Me(SO₂)NHNH | F | H | H | H | F | CO₂Et | H |
| IV-1484 | c-Pr | MeOC(=O)NHNH | F | H | H | H | F | CO₂Et | H |
| IV-1485 | c-Pr | [2-pyridinyl-N(Ac)-NH] | F | H | H | H | F | CO₂Et | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1486 | c-Pr | *tert-butyl piperidin-1-yl-carbamate* | F | H | H | H | F | CO$_2$Et | H |
| IV-1487 | c-Pr | Me$_2$NC(=O)NHNH | F | H | H | H | F | CO$_2$Et | H |
| IV-1488 | c-Pr | Me2C=NNH | F | H | H | H | F | CO$_2$Et | H |
| IV-1489 | c-Pr | H$_2$NNH | F | H | H | H | F | CN | H |
| IV-1490 | c-Pr | MeNHNH | F | H | H | H | F | CN | H |
| IV-1491 | c-Pr | H$_2$NN(Me) | F | H | H | H | F | CN | H |
| IV-1492 | c-Pr | Me$_2$NNH | F | H | H | H | F | CN | H |
| IV-1493 | c-Pr | Me$_2$NN(Me) | F | H | H | H | F | CN | H |
| IV-1494 | c-Pr | PhNHNH | F | H | H | H | F | CN | H |
| IV-1495 | c-Pr | (2-Pyridinyl)NHNH | F | H | H | H | F | CN | H |
| IV-1496 | c-Pr | *1,2,4-triazol-1-yl-NH* | F | H | H | H | F | CN | H |
| IV-1497 | c-Pr | Me(C=O)NHNH | F | H | H | H | F | CN | H |
| IV-1498 | c-Pr | (Me)(Ac)NNH | F | H | H | H | F | CN | H |
| IV-1499 | c-Pr | Me(SO$_2$)NHNH | F | H | H | H | F | CN | H |
| IV-1500 | c-Pr | MeOC(=O)NHNH | F | H | H | H | F | CN | H |
| IV-1501 | c-Pr | *N-acetyl-N-(2-pyridinyl)hydrazinyl* | F | H | H | H | F | CN | H |
| IV-1502 | c-Pr | *tert-butyl piperidin-1-yl-carbamate* | F | H | H | H | F | CN | H |
| IV-1503 | c-Pr | Me$_2$NC(=O)NHNH | F | H | H | H | F | CN | H |
| IV-1504 | c-Pr | Me2C=NNH | F | H | H | H | F | CN | H |
| IV-1505 | c-Pr | H$_2$NNH | Cl | F | H | H | H | Me | H |
| IV-1506 | c-Pr | MeNHNH | Cl | F | H | H | H | Me | H |
| IV-1507 | c-Pr | H$_2$NN(Me) | Cl | F | H | H | H | Me | H |
| IV-1508 | c-Pr | Me$_2$NNH | Cl | F | H | H | H | Me | H |
| IV-1509 | c-Pr | Me$_2$NN(Me) | Cl | F | H | H | H | Me | H |
| IV-1510 | c-Pr | PhNHNH | Cl | F | H | H | H | Me | H |
| IV-1511 | c-Pr | (2-Pyridinyl)NHNH | Cl | F | H | H | H | Me | H |
| IV-1512 | c-Pr | *1,2,4-triazol-1-yl-NH* | Cl | F | H | H | H | Me | H |
| IV-1513 | c-Pr | Me(C=O)NHNH | Cl | F | H | H | H | Me | H |
| IV-1514 | c-Pr | (Me)(Ac)NNH | Cl | F | H | H | H | Me | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1515 | c-Pr | Me(SO$_2$)NHNH | Cl | F | H | H | H | Me | H |
| IV-1516 | c-Pr | MeOC(=O)NHNH | Cl | F | H | H | H | Me | H |
| IV-1517 | c-Pr | (2-pyridinyl-N(Ac)NH) | Cl | F | H | H | H | Me | H |
| IV-1518 | c-Pr | (Boc-piperidazinyl) | Cl | F | H | H | H | Me | H |
| IV-1519 | c-Pr | Me$_2$NC(=O)NHNH | Cl | F | H | H | H | Me | H |
| IV-1520 | c-Pr | Me2C=NNH | Cl | F | H | H | H | Me | H |
| IV-1521 | c-Pr | H$_2$NNH | Cl | F | H | H | H | Me | Me |
| IV-1522 | c-Pr | MeNHNH | Cl | F | H | H | H | Me | Me |
| IV-1523 | c-Pr | H$_2$NN(Me) | Cl | F | H | H | H | Me | Me |
| IV-1524 | c-Pr | Me$_2$NNH | Cl | F | H | H | H | Me | Me |
| IV-1525 | c-Pr | Me$_2$NN(Me) | Cl | F | H | H | H | Me | Me |
| IV-1526 | c-Pr | PhNHNH | Cl | F | H | H | H | Me | Me |
| IV-1527 | c-Pr | (2-Pyridinyl)NHNH | Cl | F | H | H | H | Me | Me |
| IV-1528 | c-Pr | (1,2,4-triazolyl-NH) | Cl | F | H | H | H | Me | Me |
| IV-1529 | c-Pr | Me(C=O)NHNH | Cl | F | H | H | H | Me | Me |
| IV-1530 | c-Pr | (Me)(Ac)NNH | Cl | F | H | H | H | Me | Me |
| IV-1531 | c-Pr | Me(SO$_2$)NHNH | Cl | F | H | H | H | Me | Me |
| IV-1532 | c-Pr | MeOC(=O)NHNH | Cl | F | H | H | H | Me | Me |
| IV-1533 | c-Pr | (2-pyridinyl-N(Ac)NH) | Cl | F | H | H | H | Me | Me |
| IV-1534 | c-Pr | (Boc-piperidazinyl) | Cl | F | H | H | H | Me | Me |
| IV-1535 | c-Pr | Me$_2$NC(=O)NHNH | Cl | F | H | H | H | Me | Me |
| IV-1536 | c-Pr | Me2C=NNH | Cl | F | H | H | H | Me | Me |
| IV-1537 | c-Pr | H$_2$NNH | Cl | F | H | H | H | CO$_2$Et | H |
| IV-1538 | c-Pr | MeNHNH | Cl | F | H | H | H | CO$_2$Et | H |
| IV-1539 | c-Pr | H$_2$NN(Me) | Cl | F | H | H | H | CO$_2$Et | H |

TABLE 4-continued

Inventive compounds of the formula (I) in which X represents C(R¹³)(R¹⁴)

| No. | R¹ | R² | R³ | R⁴ | R⁵ | R⁶ | R⁷ | R¹³ | R¹⁴ |
|---|---|---|---|---|---|---|---|---|---|
| IV-1540 | c-Pr | Me₂NNH | Cl | F | H | H | H | CO₂Et | H |
| IV-1541 | c-Pr | Me₂NN(Me) | Cl | F | H | H | H | CO₂Et | H |
| IV-1542 | c-Pr | PhNHNH | Cl | F | H | H | H | CO₂Et | H |
| IV-1543 | c-Pr | (2-Pyridinyl)NHNH | Cl | F | H | H | H | CO₂Et | H |
| IV-1544 | c-Pr | [triazolyl-NH] | Cl | F | H | H | H | CO₂Et | H |
| IV-1545 | c-Pr | Me(C=O)NHNH | Cl | F | H | H | H | CO₂Et | H |
| IV-1546 | c-Pr | (Me)(Ac)NNH | Cl | F | H | H | H | CO₂Et | H |
| IV-1547 | c-Pr | Me(SO₂)NHNH | Cl | F | H | H | H | CO₂Et | H |
| IV-1548 | c-Pr | MeOC(=O)NHNH | Cl | F | H | H | H | CO₂Et | H |
| IV-1549 | c-Pr | [2-pyridinyl-N(Ac)-NH] | Cl | F | H | H | H | CO₂Et | H |
| IV-1550 | c-Pr | [Boc-piperidazinyl] | Cl | F | H | H | H | CO₂Et | H |
| IV-1551 | c-Pr | Me₂NC(=O)NHNH | Cl | F | H | H | H | CO₂Et | H |
| IV-1552 | c-Pr | Me2C=NNH | Cl | F | H | H | H | CO₂Et | H |
| IV-1553 | c-Pr | H₂NNH | Cl | F | H | H | H | CN | H |
| IV-1554 | c-Pr | MeNHNH | Cl | F | H | H | H | CN | H |
| IV-1555 | c-Pr | H₂NN(Me) | Cl | F | H | H | H | CN | H |
| IV-1556 | c-Pr | Me₂NNH | Cl | F | H | H | H | CN | H |
| IV-1557 | c-Pr | Me₂NN(Me) | Cl | F | H | H | H | CN | H |
| IV-1558 | c-Pr | PhNHNH | Cl | F | H | H | H | CN | H |
| IV-1559 | c-Pr | (2-Pyridinyl)NHNH | Cl | F | H | H | H | CN | H |
| IV-1560 | c-Pr | [triazolyl-NH] | Cl | F | H | H | H | CN | H |
| IV-1561 | c-Pr | Me(C=O)NHNH | Cl | F | H | H | H | CN | H |
| IV-1562 | c-Pr | (Me)(Ac)NNH | Cl | F | H | H | H | CN | H |
| IV-1563 | c-Pr | Me(SO₂)NHNH | Cl | F | H | H | H | CN | H |
| IV-1564 | c-Pr | MeOC(=O)NHNH | Cl | F | H | H | H | CN | H |
| IV-1565 | c-Pr | [2-pyridinyl-N(Ac)-NH] | Cl | F | H | H | H | CN | H |

TABLE 4-continued

Inventive compounds of the formula (I) in which X represents C(R$^{13}$)(R$^{14}$)

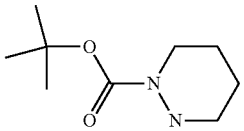

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1566 | c-Pr | 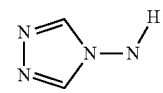 | Cl | F | H | H | H | CN | H |
| IV-1567 | c-Pr | Me$_2$NC(=O)NHNH | Cl | F | H | H | H | CN | H |
| IV-1568 | c-Pr | Me2C=NNH | Cl | F | H | H | H | CN | H |
| IV-1569 | c-Pr | H$_2$NNH | Cl | H | F | H | H | Me | H |
| IV-1570 | c-Pr | MeNHNH | Cl | H | F | H | H | Me | H |
| IV-1571 | c-Pr | H$_2$NN(Me) | Cl | H | F | H | H | Me | H |
| IV-1572 | c-Pr | Me$_2$NNH | Cl | H | F | H | H | Me | H |
| IV-1573 | c-Pr | Me$_2$NN(Me) | Cl | H | F | H | H | Me | H |
| IV-1574 | c-Pr | PhNHNH | Cl | H | F | H | H | Me | H |
| IV-1575 | c-Pr | (2-Pyridinyl)NHNH | Cl | H | F | H | H | Me | H |
| IV-1576 | c-Pr | 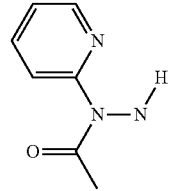 | Cl | H | F | H | H | Me | H |
| IV-1577 | c-Pr | Me(C=O)NHNH | Cl | H | F | H | H | Me | H |
| IV-1578 | c-Pr | (Me)(Ac)NNH | Cl | H | F | H | H | Me | H |
| IV-1579 | c-Pr | Me(SO$_2$)NHNH | Cl | H | F | H | H | Me | H |
| IV-1580 | c-Pr | MeOC(=O)NHNH | Cl | H | F | H | H | Me | H |
| IV-1581 | c-Pr | 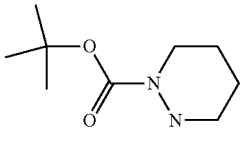 | Cl | H | F | H | H | Me | H |
| IV-1582 | c-Pr | 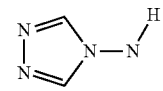 | Cl | H | F | H | H | Me | H |
| IV-1583 | c-Pr | Me$_2$NC(=O)NHNH | Cl | H | F | H | H | Me | H |
| IV-1584 | c-Pr | Me2C=NNH | Cl | H | F | H | H | Me | H |
| IV-1585 | c-Pr | H$_2$NNH | Cl | H | F | H | H | Me | Me |
| IV-1586 | c-Pr | MeNHNH | Cl | H | F | H | H | Me | Me |
| IV-1587 | c-Pr | H$_2$NN(Me) | Cl | H | F | H | H | Me | Me |
| IV-1588 | c-Pr | Me$_2$NNH | Cl | H | F | H | H | Me | Me |
| IV-1589 | c-Pr | Me$_2$NN(Me) | Cl | H | F | H | H | Me | Me |
| IV-1590 | c-Pr | PhNHNH | Cl | H | F | H | H | Me | Me |
| IV-1591 | c-Pr | (2-Pyridinyl)NHNH | Cl | H | F | H | H | Me | Me |
| IV-1592 | c-Pr | | Cl | H | F | H | H | Me | Me |
| IV-1593 | c-Pr | Me(C=O)NHNH | Cl | H | F | H | H | Me | Me |
| IV-1594 | c-Pr | (Me)(Ac)NNH | Cl | H | F | H | H | Me | Me |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1595 | c-Pr | Me(SO$_2$)NHNH | Cl | H | F | H | H | Me | Me |
| IV-1596 | c-Pr | MeOC(=O)NHNH | Cl | H | F | H | H | Me | Me |
| IV-1597 | c-Pr | (2-pyridinyl-N(Ac)NH) | Cl | H | F | H | H | Me | Me |
| IV-1598 | c-Pr | (Boc-hexahydropyridazinyl) | Cl | H | F | H | H | Me | Me |
| IV-1599 | c-Pr | Me$_2$NC(=O)NHNH | Cl | H | F | H | H | Me | Me |
| IV-1600 | c-Pr | Me2C=NNH | Cl | H | F | H | H | Me | Me |
| IV-1601 | c-Pr | H$_2$NNH | Cl | H | F | H | H | CO$_2$Et | H |
| IV-1602 | c-Pr | MeNHNH | Cl | H | F | H | H | CO$_2$Et | H |
| IV-1603 | c-Pr | H$_2$NN(Me) | Cl | H | F | H | H | CO$_2$Et | H |
| IV-1604 | c-Pr | Me$_2$NNH | Cl | H | F | H | H | CO$_2$Et | H |
| IV-1605 | c-Pr | Me$_2$NN(Me) | Cl | H | F | H | H | CO$_2$Et | H |
| IV-1606 | c-Pr | PhNHNH | Cl | H | F | H | H | CO$_2$Et | H |
| IV-1607 | c-Pr | (2-Pyridinyl)NHNH | Cl | H | F | H | H | CO$_2$Et | H |
| IV-1608 | c-Pr | (1,2,4-triazol-1-yl)NH | Cl | H | F | H | H | CO$_2$Et | H |
| IV-1609 | c-Pr | Me(C=O)NHNH | Cl | H | F | H | H | CO$_2$Et | H |
| IV-1610 | c-Pr | (Me)(Ac)NNH | Cl | H | F | H | H | CO$_2$Et | H |
| IV-1611 | c-Pr | Me(SO$_2$)NHNH | Cl | H | F | H | H | CO$_2$Et | H |
| IV-1612 | c-Pr | MeOC(=O)NHNH | Cl | H | F | H | H | CO$_2$Et | H |
| IV-1613 | c-Pr | (2-pyridinyl-N(Ac)NH) | Cl | H | F | H | H | CO$_2$Et | H |
| IV-1614 | c-Pr | (Boc-hexahydropyridazinyl) | Cl | H | F | H | H | CO$_2$Et | H |
| IV-1615 | c-Pr | Me$_2$NC(=O)NHNH | Cl | H | F | H | H | CO$_2$Et | H |
| IV-1616 | c-Pr | Me2C=NNH | Cl | H | F | H | H | CO$_2$Et | H |
| IV-1617 | c-Pr | H$_2$NNH | Cl | H | F | H | H | CN | H |
| IV-1618 | c-Pr | MeNHNH | Cl | H | F | H | H | CN | H |

TABLE 4-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| IV-1619 | c-Pr | H₂NN(Me) | Cl | H | F | H | H | CN | H |
| IV-1620 | c-Pr | Me₂NNH | Cl | H | F | H | H | CN | H |
| IV-1621 | c-Pr | Me₂NN(Me) | Cl | H | F | H | H | CN | H |
| IV-1622 | c-Pr | PhNHNH | Cl | H | F | H | H | CN | H |
| IV-1623 | c-Pr | (2-Pyridinyl)NHNH | Cl | H | F | H | H | CN | H |
| IV-1624 | c-Pr | [1,2,4-triazol-1-yl-NH] | Cl | H | F | H | H | CN | H |
| IV-1625 | c-Pr | Me(C=O)NHNH | Cl | H | F | H | H | CN | H |
| IV-1626 | c-Pr | (Me)(Ac)NNH | Cl | H | F | H | H | CN | H |
| IV-1627 | c-Pr | Me(SO₂)NHNH | Cl | H | F | H | H | CN | H |
| IV-1628 | c-Pr | MeOC(=O)NHNH | Cl | H | F | H | H | CN | H |
| IV-1629 | c-Pr | [2-pyridinyl-N(Ac)-NH] | Cl | H | F | H | H | CN | H |
| IV-1630 | c-Pr | [tBuO-C(=O)-piperidazin-1-yl] | Cl | H | F | H | H | CN | H |
| IV-1631 | c-Pr | Me₂NC(=O)NHNH | Cl | H | F | H | H | CN | H |
| IV-1632 | c-Pr | Me2C=NNH | Cl | H | F | H | H | CN | H |
| IV-1633 | c-Pr | H₂NNH | Cl | H | H | F | H | Me | H |
| IV-1634 | c-Pr | MeNHNH | Cl | H | H | F | H | Me | H |
| IV-1635 | c-Pr | H₂NN(Me) | Cl | H | H | F | H | Me | H |
| IV-1636 | c-Pr | Me₂NNH | Cl | H | H | F | H | Me | H |
| IV-1637 | c-Pr | Me₂NN(Me) | Cl | H | H | F | H | Me | H |
| IV-1638 | c-Pr | PhNHNH | Cl | H | H | F | H | Me | H |
| IV-1639 | c-Pr | (2-Pyridinyl)NHNH | Cl | H | H | F | H | Me | H |
| IV-1640 | c-Pr | [1,2,4-triazol-1-yl-NH] | Cl | H | H | F | H | Me | H |
| IV-1641 | c-Pr | Me(C=O)NHNH | Cl | H | H | F | H | Me | H |
| IV-1642 | c-Pr | (Me)(Ac)NNH | Cl | H | H | F | H | Me | H |
| IV-1643 | c-Pr | Me(SO₂)NHNH | Cl | H | H | F | H | Me | H |
| IV-1644 | c-Pr | MeOC(=O)NHNH | Cl | H | H | F | H | Me | H |
| IV-1645 | c-Pr | [2-pyridinyl-N(Ac)-NH] | Cl | H | H | F | H | Me | H |

TABLE 4-continued

Inventive compounds of the formula (I) in which X represents C(R¹³)(R¹⁴)

$$(I)$$

| No. | R¹ | R² | R³ | R⁴ | R⁵ | R⁶ | R⁷ | R¹³ | R¹⁴ |
|---|---|---|---|---|---|---|---|---|---|
| IV-1646 | c-Pr | *tert-butyl piperidin-1-yl-carboxylate (N-N linked)* | Cl | H | H | F | H | Me | H |
| IV-1647 | c-Pr | Me₂NC(=O)NHNH | Cl | H | H | F | H | Me | H |
| IV-1648 | c-Pr | Me2C=NNH | Cl | H | H | F | H | Me | H |
| IV-1649 | c-Pr | H₂NNH | Cl | H | H | F | H | Me | Me |
| IV-1650 | c-Pr | MeNHNH | Cl | H | H | F | H | Me | Me |
| IV-1651 | c-Pr | H₂NN(Me) | Cl | H | H | F | H | Me | Me |
| IV-1652 | c-Pr | Me₂NNH | Cl | H | H | F | H | Me | Me |
| IV-1653 | c-Pr | Me₂NN(Me) | Cl | H | H | F | H | Me | Me |
| IV-1654 | c-Pr | PhNHNH | Cl | H | H | F | H | Me | Me |
| IV-1655 | c-Pr | (2-Pyridinyl)NHNH | Cl | H | H | F | H | Me | Me |
| IV-1656 | c-Pr | *1,2,4-triazol-4-yl-NH* | Cl | H | H | F | H | Me | Me |
| IV-1657 | c-Pr | Me(C=O)NHNH | Cl | H | H | F | H | Me | Me |
| IV-1658 | c-Pr | (Me)(Ac)NNH | Cl | H | H | F | H | Me | Me |
| IV-1659 | c-Pr | Me(SO₂)NHNH | Cl | H | H | F | H | Me | Me |
| IV-1660 | c-Pr | MeOC(=O)NHNH | Cl | H | H | F | H | Me | Me |
| IV-1661 | c-Pr | *N-acetyl-N-(pyridin-2-yl)hydrazinyl* | Cl | H | H | F | H | Me | Me |
| IV-1662 | c-Pr | *tert-butyl piperidin-1-yl-carboxylate (N-N linked)* | Cl | H | H | F | H | Me | Me |
| IV-1663 | c-Pr | Me₂NC(=O)NHNH | Cl | H | H | F | H | Me | Me |
| IV-1664 | c-Pr | Me2C=NNH | Cl | H | H | F | H | Me | Me |
| IV-1665 | c-Pr | H₂NNH | Cl | H | H | F | H | CO₂Et | H |
| IV-1666 | c-Pr | MeNHNH | Cl | H | H | F | H | CO₂Et | H |
| IV-1667 | c-Pr | H₂NN(Me) | Cl | H | H | F | H | CO₂Et | H |
| IV-1668 | c-Pr | Me₂NNH | Cl | H | H | F | H | CO₂Et | H |
| IV-1669 | c-Pr | Me₂NN(Me) | Cl | H | H | F | H | CO₂Et | H |
| IV-1670 | c-Pr | PhNHNH | Cl | H | H | F | H | CO₂Et | H |
| IV-1671 | c-Pr | (2-Pyridinyl)NHNH | Cl | H | H | F | H | CO₂Et | H |
| IV-1672 | c-Pr | *1,2,4-triazol-4-yl-NH* | Cl | H | H | F | H | CO₂Et | H |
| IV-1673 | c-Pr | Me(C=O)NHNH | Cl | H | H | F | H | CO₂Et | H |
| IV-1674 | c-Pr | (Me)(Ac)NNH | Cl | H | H | F | H | CO₂Et | H |

TABLE 4-continued

Inventive compounds of the formula (I) in which X represents $C(R^{13})(R^{14})$

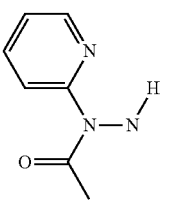

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1675 | c-Pr | Me(SO$_2$)NHNH | Cl | H | H | F | H | CO$_2$Et | H |
| IV-1676 | c-Pr | MeOC(=O)NHNH | Cl | H | H | F | H | CO$_2$Et | H |
| IV-1677 | c-Pr | 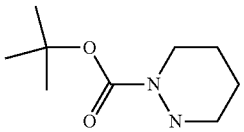 | Cl | H | H | F | H | CO$_2$Et | H |
| IV-1678 | c-Pr | 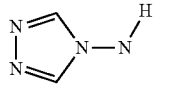 | Cl | H | H | F | H | CO$_2$Et | H |
| IV-1679 | c-Pr | Me$_2$NC(=O)NHNH | Cl | H | H | F | H | CO$_2$Et | H |
| IV-1680 | c-Pr | Me2C=NNH | Cl | H | H | F | H | CO$_2$Et | H |
| IV-1681 | c-Pr | H$_2$NNH | Cl | H | H | F | H | CN | H |
| IV-1682 | c-Pr | MeNHNH | Cl | H | H | F | H | CN | H |
| IV-1683 | c-Pr | H$_2$NN(Me) | Cl | H | H | F | H | CN | H |
| IV-1684 | c-Pr | Me$_2$NNH | Cl | H | H | F | H | CN | H |
| IV-1685 | c-Pr | Me$_2$NN(Me) | Cl | H | H | F | H | CN | H |
| IV-1686 | c-Pr | PhNHNH | Cl | H | H | F | H | CN | H |
| IV-1687 | c-Pr | (2-Pyridinyl)NHNH | Cl | H | H | F | H | CN | H |
| IV-1688 | c-Pr | 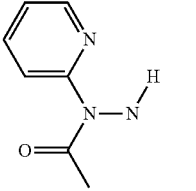 | Cl | H | H | F | H | CN | H |
| IV-1689 | c-Pr | Me(C=O)NHNH | Cl | H | H | F | H | CN | H |
| IV-1690 | c-Pr | (Me)(Ac)NNH | Cl | H | H | F | H | CN | H |
| IV-1691 | c-Pr | Me(SO$_2$)NHNH | Cl | H | H | F | H | CN | H |
| IV-1692 | c-Pr | MeOC(=O)NHNH | Cl | H | H | F | H | CN | H |
| IV-1693 | c-Pr | 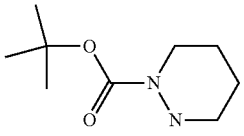 | Cl | H | H | F | H | CN | H |
| IV-1694 | c-Pr |  | Cl | H | H | F | H | CN | H |
| IV-1695 | c-Pr | Me$_2$NC(=O)NHNH | Cl | H | H | F | H | CN | H |
| IV-1696 | c-Pr | Me2C=NNH | Cl | H | H | F | H | CN | H |
| IV-1697 | c-Pr | H$_2$NNH | Cl | H | H | H | F | Me | H |
| IV-1698 | c-Pr | MeNHNH | Cl | H | H | H | F | Me | H |
| IV-1699 | c-Pr | H$_2$NN(Me) | Cl | H | H | H | F | Me | H |
| IV-1700 | c-Pr | Me$_2$NNH | Cl | H | H | H | F | Me | H |

TABLE 4-continued

Inventive compounds of the formula (I) in which X represents C(R$^{13}$)(R$^{14}$)

| No. | R$^1$ | R$^2$ | R$^3$ | R$^4$ | R$^5$ | R$^6$ | R$^7$ | R$^{13}$ | R$^{14}$ |
| --- | --- | --- | --- | --- | --- | --- | --- | --- | --- |
| IV-1701 | c-Pr | Me$_2$NN(Me) | Cl | H | H | H | F | Me | H |
| IV-1702 | c-Pr | PhNHNH | Cl | H | H | H | F | Me | H |
| IV-1703 | c-Pr | (2-Pyridinyl)NHNH | Cl | H | H | H | F | Me | H |
| IV-1704 | c-Pr | (1,2,4-triazol-1-yl)-NH | Cl | H | H | H | F | Me | H |
| IV-1705 | c-Pr | Me(C=O)NHNH | Cl | H | H | H | F | Me | H |
| IV-1706 | c-Pr | (Me)(Ac)NNH | Cl | H | H | H | F | Me | H |
| IV-1707 | c-Pr | Me(SO$_2$)NHNH | Cl | H | H | H | F | Me | H |
| IV-1708 | c-Pr | MeOC(=O)NHNH | Cl | H | H | H | F | Me | H |
| IV-1709 | c-Pr | N-(2-pyridinyl)-N-acetylhydrazino | Cl | H | H | H | F | Me | H |
| IV-1710 | c-Pr | tert-butoxycarbonyl-hexahydropyridazinyl | Cl | H | H | H | F | Me | H |
| IV-1711 | c-Pr | Me$_2$NC(=O)NHNH | Cl | H | H | H | F | Me | H |
| IV-1712 | c-Pr | Me2C=NNH | Cl | H | H | H | F | Me | H |
| IV-1713 | c-Pr | H$_2$NNH | Cl | H | H | H | F | Me | Me |
| IV-1714 | c-Pr | MeNHNH | Cl | H | H | H | F | Me | Me |
| IV-1715 | c-Pr | H$_2$NN(Me) | Cl | H | H | H | F | Me | Me |
| IV-1716 | c-Pr | Me$_2$NNH | Cl | H | H | H | F | Me | Me |
| IV-1717 | c-Pr | Me$_2$NN(Me) | Cl | H | H | H | F | Me | Me |
| IV-1718 | c-Pr | PhNHNH | Cl | H | H | H | F | Me | Me |
| IV-1719 | c-Pr | (2-Pyridinyl)NHNH | Cl | H | H | H | F | Me | Me |
| IV-1720 | c-Pr | (1,2,4-triazol-1-yl)-NH | Cl | H | H | H | F | Me | Me |
| IV-1721 | c-Pr | Me(C=O)NHNH | Cl | H | H | H | F | Me | Me |
| IV-1722 | c-Pr | (Me)(Ac)NNH | Cl | H | H | H | F | Me | Me |
| IV-1723 | c-Pr | Me(SO$_2$)NHNH | Cl | H | H | H | F | Me | Me |
| IV-1724 | c-Pr | MeOC(=O)NHNH | Cl | H | H | H | F | Me | Me |
| IV-1725 | c-Pr | N-(2-pyridinyl)-N-acetylhydrazino | Cl | H | H | H | F | Me | Me |

TABLE 4-continued

Inventive compounds of the formula (I) in which X represents C(R¹³)(R¹⁴)

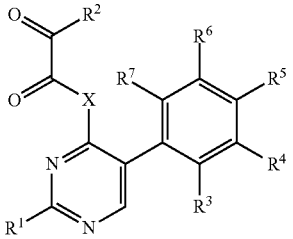

(I)

| No. | R¹ | R² | R³ | R⁴ | R⁵ | R⁶ | R⁷ | R¹³ | R¹⁴ |
|---|---|---|---|---|---|---|---|---|---|
| IV-1726 | c-Pr | 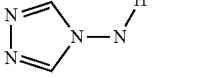 | Cl | H | H | H | F | Me | Me |
| IV-1727 | c-Pr | Me₂NC(=O)NHNH | Cl | H | H | H | F | Me | Me |
| IV-1728 | c-Pr | Me2C=NNH | Cl | H | H | H | F | Me | Me |
| IV-1729 | c-Pr | H₂NNH | Cl | H | H | H | F | CO₂Et | H |
| IV-1730 | c-Pr | MeNHNH | Cl | H | H | H | F | CO₂Et | H |
| IV-1731 | c-Pr | H₂NN(Me) | Cl | H | H | H | F | CO₂Et | H |
| IV-1732 | c-Pr | Me₂NNH | Cl | H | H | H | F | CO₂Et | H |
| IV-1733 | c-Pr | Me₂NN(Me) | Cl | H | H | H | F | CO₂Et | H |
| IV-1734 | c-Pr | PhNHNH | Cl | H | H | H | F | CO₂Et | H |
| IV-1735 | c-Pr | (2-Pyridinyl)NHNH | Cl | H | H | H | F | CO₂Et | H |
| IV-1736 | c-Pr | 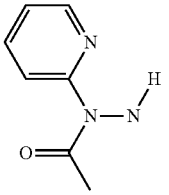 | Cl | H | H | H | F | CO₂Et | H |
| IV-1737 | c-Pr | Me(C=O)NHNH | Cl | H | H | H | F | CO₂Et | H |
| IV-1738 | c-Pr | (Me)(Ac)NNH | Cl | H | H | H | F | CO₂Et | H |
| IV-1739 | c-Pr | Me(SO₂)NHNH | Cl | H | H | H | F | CO₂Et | H |
| IV-1740 | c-Pr | MeOC(=O)NHNH | Cl | H | H | H | F | CO₂Et | H |
| IV-1741 | c-Pr | 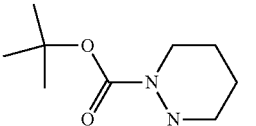 | Cl | H | H | H | F | CO₂Et | H |
| IV-1742 | c-Pr | 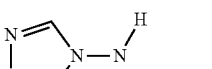 | Cl | H | H | H | F | CO₂Et | H |
| IV-1743 | c-Pr | Me₂NC(=O)NHNH | Cl | H | H | H | F | CO₂Et | H |
| IV-1744 | c-Pr | Me2C=NNH | Cl | H | H | H | F | CO₂Et | H |
| IV-1745 | c-Pr | H₂NNH | Cl | H | H | H | F | CN | H |
| IV-1746 | c-Pr | MeNHNH | Cl | H | H | H | F | CN | H |
| IV-1747 | c-Pr | H₂NN(Me) | Cl | H | H | H | F | CN | H |
| IV-1748 | c-Pr | Me₂NNH | Cl | H | H | H | F | CN | H |
| IV-1749 | c-Pr | Me₂NN(Me) | Cl | H | H | H | F | CN | H |
| IV-1750 | c-Pr | PhNHNH | Cl | H | H | H | F | CN | H |
| IV-1751 | c-Pr | (2-Pyridinyl)NHNH | Cl | H | H | H | F | CN | H |
| IV-1752 | c-Pr | | Cl | H | H | H | F | CN | H |
| IV-1753 | c-Pr | Me(C=O)NHNH | Cl | H | H | H | F | CN | H |
| IV-1754 | c-Pr | (Me)(Ac)NNH | Cl | H | H | H | F | CN | H |

TABLE 4-continued

Inventive compounds of the formula (I) in which X represents C($R^{13}$)($R^{14}$)

(I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1755 | c-Pr | Me(SO$_2$)NHNH | Cl | H | H | H | F | CN | H |
| IV-1756 | c-Pr | MeOC(=O)NHNH | Cl | H | H | H | F | CN | H |
| IV-1757 | c-Pr | (2-pyridinyl-N(Ac)-NH) | Cl | H | H | H | F | CN | H |
| IV-1758 | c-Pr | (tert-butoxycarbonyl piperidazinyl) | Cl | H | H | H | F | CN | H |
| IV-1759 | c-Pr | Me$_2$NC(=O)NHNH | Cl | H | H | H | F | CN | H |
| IV-1760 | c-Pr | Me2C=NNH | Cl | H | H | H | F | CN | H |
| IV-1761 | c-Pr | H$_2$NNH | Cl | Cl | H | H | H | Me | H |
| IV-1762 | c-Pr | MeNHNH | Cl | Cl | H | H | H | Me | H |
| IV-1763 | c-Pr | H$_2$NN(Me) | Cl | Cl | H | H | H | Me | H |
| IV-1764 | c-Pr | Me$_2$NNH | Cl | Cl | H | H | H | Me | H |
| IV-1765 | c-Pr | Me$_2$NN(Me) | Cl | Cl | H | H | H | Me | H |
| IV-1766 | c-Pr | PhNHNH | Cl | Cl | H | H | H | Me | H |
| IV-1767 | c-Pr | (2-Pyridinyl)NHNH | Cl | Cl | H | H | H | Me | H |
| IV-1768 | c-Pr | (1,2,4-triazolyl-NH) | Cl | Cl | H | H | H | Me | H |
| IV-1769 | c-Pr | Me(C=O)NHNH | Cl | Cl | H | H | H | Me | H |
| IV-1770 | c-Pr | (Me)(Ac)NNH | Cl | Cl | H | H | H | Me | H |
| IV-1771 | c-Pr | Me(SO$_2$)NHNH | Cl | Cl | H | H | H | Me | H |
| IV-1772 | c-Pr | MeOC(=O)NHNH | Cl | Cl | H | H | H | Me | H |
| IV-1773 | c-Pr | (2-pyridinyl-N(Ac)-NH) | Cl | Cl | H | H | H | Me | H |
| IV-1774 | c-Pr | (tert-butoxycarbonyl piperidazinyl) | Cl | Cl | H | H | H | Me | H |
| IV-1775 | c-Pr | Me$_2$NC(=O)NHNH | Cl | Cl | H | H | H | Me | H |
| IV-1776 | c-Pr | Me2C=NNH | Cl | Cl | H | H | H | Me | H |
| IV-1777 | c-Pr | H$_2$NNH | Cl | Cl | H | H | H | Me | Me |
| IV-1778 | c-Pr | MeNHNH | Cl | Cl | H | H | H | Me | Me |
| IV-1779 | c-Pr | H$_2$NN(Me) | Cl | Cl | H | H | H | Me | Me |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1780 | c-Pr | Me$_2$NNH | Cl | Cl | H | H | H | Me | Me |
| IV-1781 | c-Pr | Me$_2$NN(Me) | Cl | Cl | H | H | H | Me | Me |
| IV-1782 | c-Pr | PhNHNH | Cl | Cl | H | H | H | Me | Me |
| IV-1783 | c-Pr | (2-Pyridinyl)NHNH | Cl | Cl | H | H | H | Me | Me |
| IV-1784 | c-Pr | (1,2,4-triazol-4-yl)NH | Cl | Cl | H | H | H | Me | Me |
| IV-1785 | c-Pr | Me(C=O)NHNH | Cl | Cl | H | H | H | Me | Me |
| IV-1786 | c-Pr | (Me)(Ac)NNH | Cl | Cl | H | H | H | Me | Me |
| IV-1787 | c-Pr | Me(SO$_2$)NHNH | Cl | Cl | H | H | H | Me | Me |
| IV-1788 | c-Pr | MeOC(=O)NHNH | Cl | Cl | H | H | H | Me | Me |
| IV-1789 | c-Pr | N-(2-pyridinyl)-N-acetylhydrazinyl | Cl | Cl | H | H | H | Me | Me |
| IV-1790 | c-Pr | 1-(tert-butoxycarbonyl)hexahydropyridazin-2-yl | Cl | Cl | H | H | H | Me | Me |
| IV-1791 | c-Pr | Me$_2$NC(=O)NHNH | Cl | Cl | H | H | H | Me | Me |
| IV-1792 | c-Pr | Me2C=NNH | Cl | Cl | H | H | H | Me | Me |
| IV-1793 | c-Pr | H$_2$NNH | Cl | Cl | H | H | H | CO$_2$Et | H |
| IV-1794 | c-Pr | MeNHNH | Cl | Cl | H | H | H | CO$_2$Et | H |
| IV-1795 | c-Pr | H$_2$NN(Me) | Cl | Cl | H | H | H | CO$_2$Et | H |
| IV-1796 | c-Pr | Me$_2$NNH | Cl | Cl | H | H | H | CO$_2$Et | H |
| IV-1797 | c-Pr | Me$_2$NN(Me) | Cl | Cl | H | H | H | CO$_2$Et | H |
| IV-1798 | c-Pr | PhNHNH | Cl | Cl | H | H | H | CO$_2$Et | H |
| IV-1799 | c-Pr | (2-Pyridinyl)NHNH | Cl | Cl | H | H | H | CO$_2$Et | H |
| IV-1800 | c-Pr | (1,2,4-triazol-4-yl)NH | Cl | Cl | H | H | H | CO$_2$Et | H |
| IV-1801 | c-Pr | Me(C=O)NHNH | Cl | Cl | H | H | H | CO$_2$Et | H |
| IV-1802 | c-Pr | (Me)(Ac)NNH | Cl | Cl | H | H | H | CO$_2$Et | H |
| IV-1803 | c-Pr | Me(SO$_2$)NHNH | Cl | Cl | H | H | H | CO$_2$Et | H |
| IV-1804 | c-Pr | MeOC(=O)NHNH | Cl | Cl | H | H | H | CO$_2$Et | H |
| IV-1805 | c-Pr | N-(2-pyridinyl)-N-acetylhydrazinyl | Cl | Cl | H | H | H | CO$_2$Et | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1806 | c-Pr | *tert-butyl piperidine-1-carboxylate (hydrazide linkage)* | Cl | Cl | H | H | H | CO$_2$Et | H |
| IV-1807 | c-Pr | Me$_2$NC(=O)NHNH | Cl | Cl | H | H | H | CO$_2$Et | H |
| IV-1808 | c-Pr | Me2C=NNH | Cl | Cl | H | H | H | CO$_2$Et | H |
| IV-1809 | c-Pr | H$_2$NNH | Cl | Cl | H | H | H | CN | H |
| IV-1810 | c-Pr | MeNHNH | Cl | Cl | H | H | H | CN | H |
| IV-1811 | c-Pr | H$_2$NN(Me) | Cl | Cl | H | H | H | CN | H |
| IV-1812 | c-Pr | Me$_2$NNH | Cl | Cl | H | H | H | CN | H |
| IV-1813 | c-Pr | Me$_2$NN(Me) | Cl | Cl | H | H | H | CN | H |
| IV-1814 | c-Pr | PhNHNH | Cl | Cl | H | H | H | CN | H |
| IV-1815 | c-Pr | (2-Pyridinyl)NHNH | Cl | Cl | H | H | H | CN | H |
| IV-1816 | c-Pr | *1,2,4-triazol-1-yl-NH* | Cl | Cl | H | H | H | CN | H |
| IV-1817 | c-Pr | Me(C=O)NHNH | Cl | Cl | H | H | H | CN | H |
| IV-1818 | c-Pr | (Me)(Ac)NNH | Cl | Cl | H | H | H | CN | H |
| IV-1819 | c-Pr | Me(SO$_2$)NHNH | Cl | Cl | H | H | H | CN | H |
| IV-1820 | c-Pr | MeOC(=O)NHNH | Cl | Cl | H | H | H | CN | H |
| IV-1821 | c-Pr | *N-(pyridin-2-yl)-N-acetyl-hydrazide* | Cl | Cl | H | H | H | CN | H |
| IV-1822 | c-Pr | *tert-butyl piperidine-1-carboxylate (hydrazide linkage)* | Cl | Cl | H | H | H | CN | H |
| IV-1823 | c-Pr | Me$_2$NC(=O)NHNH | Cl | Cl | H | H | H | CN | H |
| IV-1824 | c-Pr | Me2C=NNH | Cl | Cl | H | H | H | CN | H |
| IV-1825 | c-Pr | H$_2$NNH | Cl | H | Cl | H | H | Me | H |
| IV-1826 | c-Pr | MeNHNH | Cl | H | Cl | H | H | Me | H |
| IV-1827 | c-Pr | H$_2$NN(Me) | Cl | H | Cl | H | H | Me | H |
| IV-1828 | c-Pr | Me$_2$NNH | Cl | H | Cl | H | H | Me | H |
| IV-1829 | c-Pr | Me$_2$NN(Me) | Cl | H | Cl | H | H | Me | H |
| IV-1830 | c-Pr | PhNHNH | Cl | H | Cl | H | H | Me | H |
| IV-1831 | c-Pr | (2-Pyridinyl)NHNH | Cl | H | Cl | H | H | Me | H |
| IV-1832 | c-Pr | *1,2,4-triazol-1-yl-NH* | Cl | H | Cl | H | H | Me | H |
| IV-1833 | c-Pr | Me(C=O)NHNH | Cl | H | Cl | H | H | Me | H |
| IV-1834 | c-Pr | (Me)(Ac)NNH | Cl | H | Cl | H | H | Me | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1835 | c-Pr | Me(SO$_2$)NHNH | Cl | H | Cl | H | H | Me | H |
| IV-1836 | c-Pr | MeOC(=O)NHNH | Cl | H | Cl | H | H | Me | H |
| IV-1837 | c-Pr | (2-pyridinyl-N(Ac)NH) | Cl | H | Cl | H | H | Me | H |
| IV-1838 | c-Pr | (Boc-hexahydropyridazine) | Cl | H | Cl | H | H | Me | H |
| IV-1839 | c-Pr | Me$_2$NC(=O)NHNH | Cl | H | Cl | H | H | Me | H |
| IV-1840 | c-Pr | Me2C=NNH | Cl | H | Cl | H | H | Me | H |
| IV-1841 | c-Pr | H$_2$NNH | Cl | H | Cl | H | H | Me | Me |
| IV-1842 | c-Pr | MeNHNH | Cl | H | Cl | H | H | Me | Me |
| IV-1843 | c-Pr | H$_2$NN(Me) | Cl | H | Cl | H | H | Me | Me |
| IV-1844 | c-Pr | Me$_2$NNH | Cl | H | Cl | H | H | Me | Me |
| IV-1845 | c-Pr | Me$_2$NN(Me) | Cl | H | Cl | H | H | Me | Me |
| IV-1846 | c-Pr | PhNHNH | Cl | H | Cl | H | H | Me | Me |
| IV-1847 | c-Pr | (2-Pyridinyl)NHNH | Cl | H | Cl | H | H | Me | Me |
| IV-1848 | c-Pr | (1,2,4-triazol-4-yl-NH) | Cl | H | Cl | H | H | Me | Me |
| IV-1849 | c-Pr | Me(C=O)NHNH | Cl | H | Cl | H | H | Me | Me |
| IV-1850 | c-Pr | (Me)(Ac)NNH | Cl | H | Cl | H | H | Me | Me |
| IV-1851 | c-Pr | Me(SO$_2$)NHNH | Cl | H | Cl | H | H | Me | Me |
| IV-1852 | c-Pr | MeOC(=O)NHNH | Cl | H | Cl | H | H | Me | Me |
| IV-1853 | c-Pr | (2-pyridinyl-N(Ac)NH) | Cl | H | Cl | H | H | Me | Me |
| IV-1854 | c-Pr | (Boc-hexahydropyridazine) | Cl | H | Cl | H | H | Me | Me |
| IV-1855 | c-Pr | Me$_2$NC(=O)NHNH | Cl | H | Cl | H | H | Me | Me |
| IV-1856 | c-Pr | Me2C=NNH | Cl | H | Cl | H | H | Me | Me |
| IV-1857 | c-Pr | H$_2$NNH | Cl | H | Cl | H | H | CO$_2$Et | H |
| IV-1858 | c-Pr | MeNHNH | Cl | H | Cl | H | H | CO$_2$Et | H |
| IV-1859 | c-Pr | H$_2$NN(Me) | Cl | H | Cl | H | H | CO$_2$Et | H |

TABLE 4-continued

Inventive compounds of the formula (I) in which X represents $C(R^{13})(R^{14})$ ![Formula (I) structure showing pyrimidine ring with R¹, linked to phenyl with R³-R⁷ substituents, and X group bearing C(=O)R² and another C=O]

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1860 | c-Pr | Me₂NNH | Cl | H | Cl | H | H | CO₂Et | H |
| IV-1861 | c-Pr | Me₂NN(Me) | Cl | H | Cl | H | H | CO₂Et | H |
| IV-1862 | c-Pr | PhNHNH | Cl | H | Cl | H | H | CO₂Et | H |
| IV-1863 | c-Pr | (2-Pyridinyl)NHNH | Cl | H | Cl | H | H | CO₂Et | H |
| IV-1864 | c-Pr | (1,2,4-triazol-1-yl)NH | Cl | H | Cl | H | H | CO₂Et | H |
| IV-1865 | c-Pr | Me(C=O)NHNH | Cl | H | Cl | H | H | CO₂Et | H |
| IV-1866 | c-Pr | (Me)(Ac)NNH | Cl | H | Cl | H | H | CO₂Et | H |
| IV-1867 | c-Pr | Me(SO₂)NHNH | Cl | H | Cl | H | H | CO₂Et | H |
| IV-1868 | c-Pr | MeOC(=O)NHNH | Cl | H | Cl | H | H | CO₂Et | H |
| IV-1869 | c-Pr | 2-Pyridinyl-N(Ac)-NH | Cl | H | Cl | H | H | CO₂Et | H |
| IV-1870 | c-Pr | N-Boc-hexahydropyridazin-1-yl | Cl | H | Cl | H | H | CO₂Et | H |
| IV-1871 | c-Pr | Me₂NC(=O)NHNH | Cl | H | Cl | H | H | CO₂Et | H |
| IV-1872 | c-Pr | Me₂C=NNH | Cl | H | Cl | H | H | CO₂Et | H |
| IV-1873 | c-Pr | H₂NNH | Cl | H | Cl | H | H | CN | H |
| IV-1874 | c-Pr | MeNHNH | Cl | H | Cl | H | H | CN | H |
| IV-1875 | c-Pr | H₂NN(Me) | Cl | H | Cl | H | H | CN | H |
| IV-1876 | c-Pr | Me₂NNH | Cl | H | Cl | H | H | CN | H |
| IV-1877 | c-Pr | Me₂NN(Me) | Cl | H | Cl | H | H | CN | H |
| IV-1878 | c-Pr | PhNHNH | Cl | H | Cl | H | H | CN | H |
| IV-1879 | c-Pr | (2-Pyridinyl)NHNH | Cl | H | Cl | H | H | CN | H |
| IV-1880 | c-Pr | (1,2,4-triazol-1-yl)NH | Cl | H | Cl | H | H | CN | H |
| IV-1881 | c-Pr | Me(C=O)NHNH | Cl | H | Cl | H | H | CN | H |
| IV-1882 | c-Pr | (Me)(Ac)NNH | Cl | H | Cl | H | H | CN | H |
| IV-1883 | c-Pr | Me(SO₂)NHNH | Cl | H | Cl | H | H | CN | H |
| IV-1884 | c-Pr | MeOC(=O)NHNH | Cl | H | Cl | H | H | CN | H |
| IV-1885 | c-Pr | 2-Pyridinyl-N(C(Me)=CH₂)-NH | Cl | H | Cl | H | H | CN | H |

TABLE 4-continued

Inventive compounds of the formula (I) in which X represents C(R$^{13}$)(R$^{14}$)

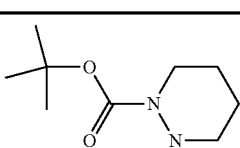

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-1886 | c-Pr | 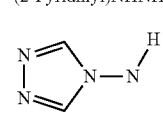 | Cl | H | Cl | H | H | CN | H |
| IV-1887 | c-Pr | Me$_2$NC(=O)NHNH | Cl | H | Cl | H | H | CN | H |
| IV-1888 | c-Pr | Me2C=NNH | Cl | H | Cl | H | H | CN | H |
| IV-1889 | c-Pr | H$_2$NNH | Cl | H | H | Cl | H | Me | H |
| IV-1890 | c-Pr | MeNHNH | Cl | H | H | Cl | H | Me | H |
| IV-1891 | c-Pr | H$_2$NN(Me) | Cl | H | H | Cl | H | Me | H |
| IV-1892 | c-Pr | Me$_2$NNH | Cl | H | H | Cl | H | Me | H |
| IV-1893 | c-Pr | Me$_2$NN(Me) | Cl | H | H | Cl | H | Me | H |
| IV-1894 | c-Pr | PhNHNH | Cl | H | H | Cl | H | Me | H |
| IV-1895 | c-Pr | (2-Pyridinyl)NHNH | Cl | H | H | Cl | H | Me | H |
| IV-1896 | c-Pr | 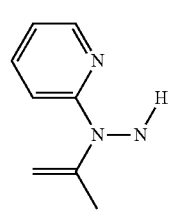 | Cl | H | H | Cl | H | Me | H |
| IV-1897 | c-Pr | Me(C=O)NHNH | Cl | H | H | Cl | H | Me | H |
| IV-1898 | c-Pr | (Me)(Ac)NNH | Cl | H | H | Cl | H | Me | H |
| IV-1899 | c-Pr | Me(SO$_2$)NHNH | Cl | H | H | Cl | H | Me | H |
| IV-1900 | c-Pr | MeOC(=O)NHNH | Cl | H | H | Cl | H | Me | H |
| IV-1901 | c-Pr | 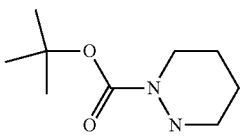 | Cl | H | H | Cl | H | Me | H |
| IV-1902 | c-Pr | 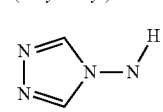 | Cl | H | H | Cl | H | Me | H |
| IV-1903 | c-Pr | Me$_2$NC(=O)NHNH | Cl | H | H | Cl | H | Me | H |
| IV-1904 | c-Pr | Me2C=NNH | Cl | H | H | Cl | H | Me | H |
| IV-1905 | c-Pr | H$_2$NNH | Cl | H | H | Cl | H | Me | Me |
| IV-1906 | c-Pr | MeNHNH | Cl | H | H | Cl | H | Me | Me |
| IV-1907 | c-Pr | H$_2$NN(Me) | Cl | H | H | Cl | H | Me | Me |
| IV-1908 | c-Pr | Me$_2$NNH | Cl | H | H | Cl | H | Me | Me |
| IV-1909 | c-Pr | Me$_2$NN(Me) | Cl | H | H | Cl | H | Me | Me |
| IV-1910 | c-Pr | PhNHNH | Cl | H | H | Cl | H | Me | Me |
| IV-1911 | c-Pr | (2-Pyridinyl)NHNH | Cl | H | H | Cl | H | Me | Me |
| IV-1912 | c-Pr |  | Cl | H | H | Cl | H | Me | Me |
| IV-1913 | c-Pr | Me(C=O)NHNH | Cl | H | H | Cl | H | Me | Me |
| IV-1914 | c-Pr | (Me)(Ac)NNH | Cl | H | H | Cl | H | Me | Me |

TABLE 4-continued

Inventive compounds of the formula (I) in which X represents C(R¹³)(R¹⁴)

(I)

| No. | R¹ | R² | R³ | R⁴ | R⁵ | R⁶ | R⁷ | R¹³ | R¹⁴ |
|---|---|---|---|---|---|---|---|---|---|
| IV-1915 | c-Pr | Me(SO₂)NHNH | Cl | H | H | Cl | H | Me | Me |
| IV-1916 | c-Pr | MeOC(=O)NHNH | Cl | H | H | Cl | H | Me | Me |
| IV-1917 | c-Pr | (1-(2-pyridinyl)-1-methylethylidene)hydrazino | Cl | H | H | Cl | H | Me | Me |
| IV-1918 | c-Pr | tert-butyl tetrahydropyridazine-1-carboxylate | Cl | H | H | Cl | H | Me | Me |
| IV-1919 | c-Pr | Me₂NC(=O)NHNH | Cl | H | H | Cl | H | Me | Me |
| IV-1920 | c-Pr | Me2C=NNH | Cl | H | H | Cl | H | Me | Me |
| IV-1921 | c-Pr | H₂NNH | Cl | H | H | Cl | H | CO₂Et | H |
| IV-1922 | c-Pr | MeNHNH | Cl | H | H | Cl | H | CO₂Et | H |
| IV-1923 | c-Pr | H₂NN(Me) | Cl | H | H | Cl | H | CO₂Et | H |
| IV-1924 | c-Pr | Me₂NNH | Cl | H | H | Cl | H | CO₂Et | H |
| IV-1925 | c-Pr | Me₂NN(Me) | Cl | H | H | Cl | H | CO₂Et | H |
| IV-1926 | c-Pr | PhNHNH | Cl | H | H | Cl | H | CO₂Et | H |
| IV-1927 | c-Pr | (2-Pyridinyl)NHNH | Cl | H | H | Cl | H | CO₂Et | H |
| IV-1928 | c-Pr | (1,2,4-triazol-4-yl)NH | Cl | H | H | Cl | H | CO₂Et | H |
| IV-1929 | c-Pr | Me(C=O)NHNH | Cl | H | H | Cl | H | CO₂Et | H |
| IV-1930 | c-Pr | (Me)(Ac)NNH | Cl | H | H | Cl | H | CO₂Et | H |
| IV-1931 | c-Pr | Me(SO₂)NHNH | Cl | H | H | Cl | H | CO₂Et | H |
| IV-1932 | c-Pr | MeOC(=O)NHNH | Cl | H | H | Cl | H | CO₂Et | H |
| IV-1933 | c-Pr | (1-(2-pyridinyl)-1-methylethylidene)hydrazino | Cl | H | H | Cl | H | CO₂Et | H |
| IV-1934 | c-Pr | tert-butyl tetrahydropyridazine-1-carboxylate | Cl | H | H | Cl | H | CO₂Et | H |
| IV-1935 | c-Pr | Me₂NC(=O)NHNH | Cl | H | H | Cl | H | CO₂Et | H |
| IV-1936 | c-Pr | Me2C=NNH | Cl | H | H | Cl | H | CO₂Et | H |
| IV-1937 | c-Pr | H₂NNH | Cl | H | H | Cl | H | CN | H |
| IV-1938 | c-Pr | MeNHNH | Cl | H | H | Cl | H | CN | H |
| IV-1939 | c-Pr | H₂NN(Me) | Cl | H | H | Cl | H | CN | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1940 | c-Pr | Me$_2$NNH | Cl | H | H | Cl | H | CN | H |
| IV-1941 | c-Pr | Me$_2$NN(Me) | Cl | H | H | Cl | H | CN | H |
| IV-1942 | c-Pr | PhNHNH | Cl | H | H | Cl | H | CN | H |
| IV-1943 | c-Pr | (2-Pyridinyl)NHNH | Cl | H | H | Cl | H | CN | H |
| IV-1944 | c-Pr | (1,2,4-triazol-4-yl)NH | Cl | H | H | Cl | H | CN | H |
| IV-1945 | c-Pr | Me(C=O)NHNH | Cl | H | H | Cl | H | CN | H |
| IV-1946 | c-Pr | (Me)(Ac)NNH | Cl | H | H | Cl | H | CN | H |
| IV-1947 | c-Pr | Me(SO$_2$)NHNH | Cl | H | H | Cl | H | CN | H |
| IV-1948 | c-Pr | MeOC(=O)NHNH | Cl | H | H | Cl | H | CN | H |
| IV-1949 | c-Pr | N-(2-pyridinyl)-N-acetylhydrazinyl | Cl | H | H | Cl | H | CN | H |
| IV-1950 | c-Pr | N-Boc-hexahydropyridazin-1-yl | Cl | H | H | Cl | H | CN | H |
| IV-1951 | c-Pr | Me$_2$NC(=O)NHNH | Cl | H | H | Cl | H | CN | H |
| IV-1952 | c-Pr | Me2C=NNH | Cl | H | H | Cl | H | CN | H |
| IV-1953 | c-Pr | H$_2$NNH | Cl | H | H | H | Cl | Me | H |
| IV-1954 | c-Pr | MeNHNH | Cl | H | H | H | Cl | Me | H |
| IV-1955 | c-Pr | H$_2$NN(Me) | Cl | H | H | H | Cl | Me | H |
| IV-1956 | c-Pr | Me$_2$NNH | Cl | H | H | H | Cl | Me | H |
| IV-1957 | c-Pr | Me$_2$NN(Me) | Cl | H | H | H | Cl | Me | H |
| IV-1958 | c-Pr | PhNHNH | Cl | H | H | H | Cl | Me | H |
| IV-1959 | c-Pr | (2-Pyridinyl)NHNH | Cl | H | H | H | Cl | Me | H |
| IV-1960 | c-Pr | (1,2,4-triazol-4-yl)NH | Cl | H | H | H | Cl | Me | H |
| IV-1961 | c-Pr | Me(C=O)NHNH | Cl | H | H | H | Cl | Me | H |
| IV-1962 | c-Pr | (Me)(Ac)NNH | Cl | H | H | H | Cl | Me | H |
| IV-1963 | c-Pr | Me(SO$_2$)NHNH | Cl | H | H | H | Cl | Me | H |
| IV-1964 | c-Pr | MeOC(=O)NHNH | Cl | H | H | H | Cl | Me | H |
| IV-1965 | c-Pr | N-(2-pyridinyl)-N-acetylhydrazinyl | Cl | H | H | H | Cl | Me | H |

TABLE 4-continued

Inventive compounds of the formula (I) in which X represents C(R¹³)(R¹⁴)

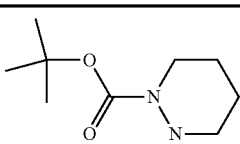

(I)

| No. | R¹ | R² | R³ | R⁴ | R⁵ | R⁶ | R⁷ | R¹³ | R¹⁴ |
|---|---|---|---|---|---|---|---|---|---|
| IV-1966 | c-Pr | 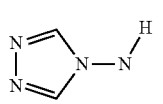 | Cl | H | H | H | Cl | Me | H |
| IV-1967 | c-Pr | Me$_2$NC(=O)NHNH | Cl | H | H | H | Cl | Me | H |
| IV-1968 | c-Pr | Me2C=NNH | Cl | H | H | H | Cl | Me | H |
| IV-1969 | c-Pr | H$_2$NNH | Cl | H | H | H | Cl | Me | Me |
| IV-1970 | c-Pr | MeNHNH | Cl | H | H | H | Cl | Me | Me |
| IV-1971 | c-Pr | H$_2$NN(Me) | Cl | H | H | H | Cl | Me | Me |
| IV-1972 | c-Pr | Me$_2$NNH | Cl | H | H | H | Cl | Me | Me |
| IV-1973 | c-Pr | Me$_2$NN(Me) | Cl | H | H | H | Cl | Me | Me |
| IV-1974 | c-Pr | PhNHNH | Cl | H | H | H | Cl | Me | Me |
| IV-1975 | c-Pr | (2-Pyridinyl)NHNH | Cl | H | H | H | Cl | Me | Me |
| IV-1976 | c-Pr | 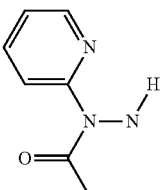 | Cl | H | H | H | Cl | Me | Me |
| IV-1977 | c-Pr | Me(C=O)NHNH | Cl | H | H | H | Cl | Me | Me |
| IV-1978 | c-Pr | (Me)(Ac)NNH | Cl | H | H | H | Cl | Me | Me |
| IV-1979 | c-Pr | Me(SO$_2$)NHNH | Cl | H | H | H | Cl | Me | Me |
| IV-1980 | c-Pr | MeOC(=O)NHNH | Cl | H | H | H | Cl | Me | Me |
| IV-1981 | c-Pr | 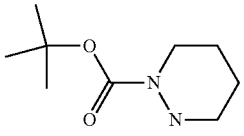 | Cl | H | H | H | Cl | Me | Me |
| IV-1982 | c-Pr | 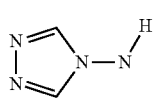 | Cl | H | H | H | Cl | Me | Me |
| IV-1983 | c-Pr | Me$_2$NC(=O)NHNH | Cl | H | H | H | Cl | Me | Me |
| IV-1984 | c-Pr | Me2C=NNH | Cl | H | H | H | Cl | Me | Me |
| IV-1985 | c-Pr | H$_2$NNH | Cl | H | H | H | Cl | CO$_2$Et | H |
| IV-1986 | c-Pr | MeNHNH | Cl | H | H | H | Cl | CO$_2$Et | H |
| IV-1987 | c-Pr | H$_2$NN(Me) | Cl | H | H | H | Cl | CO$_2$Et | H |
| IV-1988 | c-Pr | Me$_2$NNH | Cl | H | H | H | Cl | CO$_2$Et | H |
| IV-1989 | c-Pr | Me$_2$NN(Me) | Cl | H | H | H | Cl | CO$_2$Et | H |
| IV-1990 | c-Pr | PhNHNH | Cl | H | H | H | Cl | CO$_2$Et | H |
| IV-1991 | c-Pr | (2-Pyridinyl)NHNH | Cl | H | H | H | Cl | CO$_2$Et | H |
| IV-1992 | c-Pr | 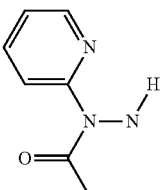 | Cl | H | H | H | Cl | CO$_2$Et | H |
| IV-1993 | c-Pr | Me(C=O)NHNH | Cl | H | H | H | Cl | CO$_2$Et | H |
| IV-1994 | c-Pr | (Me)(Ac)NNH | Cl | H | H | H | Cl | CO$_2$Et | H |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-1995 | c-Pr | Me(SO$_2$)NHNH | Cl | H | H | H | Cl | CO$_2$Et | H |
| IV-1996 | c-Pr | MeOC(=O)NHNH | Cl | H | H | H | Cl | CO$_2$Et | H |
| IV-1997 | c-Pr | (2-pyridinyl-N(Ac)-NH) | Cl | H | H | H | Cl | CO$_2$Et | H |
| IV-1998 | c-Pr | (tBuO-C(=O)-piperidazinyl) | Cl | H | H | H | Cl | CO$_2$Et | H |
| IV-1999 | c-Pr | Me$_2$NC(=O)NHNH | Cl | H | H | H | Cl | CO$_2$Et | H |
| IV-2000 | c-Pr | Me2C=NNH | Cl | H | H | H | Cl | CO$_2$Et | H |
| IV-2001 | c-Pr | H$_2$NNH | Cl | H | H | H | Cl | CN | H |
| IV-2002 | c-Pr | MeNHNH | Cl | H | H | H | Cl | CN | H |
| IV-2003 | c-Pr | H$_2$NN(Me) | Cl | H | H | H | Cl | CN | H |
| IV-2004 | c-Pr | Me$_2$NNH | Cl | H | H | H | Cl | CN | H |
| IV-2005 | c-Pr | Me$_2$NN(Me) | Cl | H | H | H | Cl | CN | H |
| IV-2006 | c-Pr | PhNHNH | Cl | H | H | H | Cl | CN | H |
| IV-2007 | c-Pr | (2-Pyridinyl)NHNH | Cl | H | H | H | Cl | CN | H |
| IV-2008 | c-Pr | (1,2,4-triazolyl-NH) | Cl | H | H | H | Cl | CN | H |
| IV-2009 | c-Pr | Me(C=O)NHNH | Cl | H | H | H | Cl | CN | H |
| IV-2010 | c-Pr | (Me)(Ac)NNH | Cl | H | H | H | Cl | CN | H |
| IV-2011 | c-Pr | Me(SO$_2$)NHNH | Cl | H | H | H | Cl | CN | H |
| IV-2012 | c-Pr | MeOC(=O)NHNH | Cl | H | H | H | Cl | CN | H |
| IV-2013 | c-Pr | (2-pyridinyl-N(Ac)-NH) | Cl | H | H | H | Cl | CN | H |
| IV-2014 | c-Pr | (tBuO-C(=O)-piperidazinyl) | Cl | H | H | H | Cl | CN | H |
| IV-2015 | c-Pr | Me$_2$NC(=O)NHNH | Cl | H | H | H | Cl | CN | H |
| IV-2016 | c-Pr | Me2C=NNH | Cl | H | H | H | Cl | CN | H |
| IV-2017 | c-Pr | H$_2$NNH | Me | H | H | H | H | Me | H |
| IV-2018 | c-Pr | MeNHNH | Me | H | H | H | H | Me | H |
| IV-2019 | c-Pr | H$_2$NN(Me) | Me | H | H | H | H | Me | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-2020 | c-Pr | Me$_2$NNH | Me | H | H | H | H | Me | H |
| IV-2021 | c-Pr | Me$_2$NN(Me) | Me | H | H | H | H | Me | H |
| IV-2022 | c-Pr | PhNHNH | Me | H | H | H | H | Me | H |
| IV-2023 | c-Pr | (2-Pyridinyl)NHNH | Me | H | H | H | H | Me | H |
| IV-2024 | c-Pr | (1,2,4-triazolyl-NH) | Me | H | H | H | H | Me | H |
| IV-2025 | c-Pr | Me(C=O)NHNH | Me | H | H | H | H | Me | H |
| IV-2026 | c-Pr | (Me)(Ac)NNH | Me | H | H | H | H | Me | H |
| IV-2027 | c-Pr | Me(SO$_2$)NHNH | Me | H | H | H | H | Me | H |
| IV-2028 | c-Pr | MeOC(=O)NHNH | Me | H | H | H | H | Me | H |
| IV-2029 | c-Pr | (2-pyridinyl-N(Ac)-NH) | Me | H | H | H | H | Me | H |
| IV-2030 | c-Pr | (Boc-piperidazinyl) | Me | H | H | H | H | Me | H |
| IV-2031 | c-Pr | Me$_2$NC(=O)NHNH | Me | H | H | H | H | Me | H |
| IV-2032 | c-Pr | Me2C=NNH | Me | H | H | H | H | Me | H |
| IV-2033 | c-Pr | H$_2$NNH | Me | H | H | H | H | Me | Me |
| IV-2034 | c-Pr | MeNHNH | Me | H | H | H | H | Me | Me |
| IV-2035 | c-Pr | H$_2$NN(Me) | Me | H | H | H | H | Me | Me |
| IV-2036 | c-Pr | Me$_2$NNH | Me | H | H | H | H | Me | Me |
| IV-2037 | c-Pr | Me$_2$NN(Me) | Me | H | H | H | H | Me | Me |
| IV-2038 | c-Pr | PhNHNH | Me | H | H | H | H | Me | Me |
| IV-2039 | c-Pr | (2-Pyridinyl)NHNH | Me | H | H | H | H | Me | Me |
| IV-2040 | c-Pr | (1,2,4-triazolyl-NH) | Me | H | H | H | H | Me | Me |
| IV-2041 | c-Pr | Me(C=O)NHNH | Me | H | H | H | H | Me | Me |
| IV-2042 | c-Pr | (Me)(Ac)NNH | Me | H | H | H | H | Me | Me |
| IV-2043 | c-Pr | Me(SO$_2$)NHNH | Me | H | H | H | H | Me | Me |
| IV-2044 | c-Pr | MeOC(=O)NHNH | Me | H | H | H | H | Me | Me |
| IV-2045 | c-Pr | (2-pyridinyl-N(Ac)-NH) | Me | H | H | H | H | Me | Me |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-2046 | c-Pr | *tert-butyl piperidazine-1-carboxylate* | Me | H | H | H | H | Me | Me |
| IV-2047 | c-Pr | Me$_2$NC(=O)NHNH | Me | H | H | H | H | Me | Me |
| IV-2048 | c-Pr | Me2C=NNH | Me | H | H | H | H | Me | Me |
| IV-2049 | c-Pr | H$_2$NNH | Me | H | H | H | H | Me | H |
| IV-2050 | c-Pr | MeNHNH | Me | H | H | H | H | CO$_2$Et | H |
| IV-2051 | c-Pr | H$_2$NN(Me) | Me | H | H | H | H | CO$_2$Et | H |
| IV-2052 | c-Pr | Me$_2$NNH | Me | H | H | H | H | CO$_2$Et | H |
| IV-2053 | c-Pr | Me$_2$NN(Me) | Me | H | H | H | H | CO$_2$Et | H |
| IV-2054 | c-Pr | PhNHNH | Me | H | H | H | H | CO$_2$Et | H |
| IV-2055 | c-Pr | (2-Pyridinyl)NHNH | Me | H | H | H | H | CO$_2$Et | H |
| IV-2056 | c-Pr | *1,2,4-triazol-1-yl-NH* | Me | H | H | H | H | CO$_2$Et | H |
| IV-2057 | c-Pr | Me(C=O)NHNH | Me | H | H | H | H | CO$_2$Et | H |
| IV-2058 | c-Pr | (Me)(Ac)NNH | Me | H | H | H | H | CO$_2$Et | H |
| IV-2059 | c-Pr | Me(SO$_2$)NHNH | Me | H | H | H | H | CO$_2$Et | H |
| IV-2060 | c-Pr | MeOC(=O)NHNH | Me | H | H | H | H | CO$_2$Et | H |
| IV-2061 | c-Pr | *N-(2-pyridinyl)-N-acetyl-hydrazinyl* | Me | H | H | H | H | CO$_2$Et | H |
| IV-2062 | c-Pr | *tert-butyl piperidazine-1-carboxylate* | Me | H | H | H | H | CO$_2$Et | H |
| IV-2063 | c-Pr | Me$_2$NC(=O)NHNH | Me | H | H | H | H | CO$_2$Et | H |
| IV-2064 | c-Pr | Me2C=NNH | Me | H | H | H | H | CO$_2$Et | H |
| IV-2065 | c-Pr | H$_2$NNH | Me | H | H | H | H | CN | H |
| IV-2066 | c-Pr | MeNHNH | Me | H | H | H | H | CN | H |
| IV-2067 | c-Pr | H$_2$NN(Me) | Me | H | H | H | H | CN | H |
| IV-2068 | c-Pr | Me$_2$NNH | Me | H | H | H | H | CN | H |
| IV-2069 | c-Pr | Me$_2$NN(Me) | Me | H | H | H | H | CN | H |
| IV-2070 | c-Pr | PhNHNH | Me | H | H | H | H | CN | H |
| IV-2071 | c-Pr | (2-Pyridinyl)NHNH | Me | H | H | H | H | CN | H |
| IV-2072 | c-Pr | *1,2,4-triazol-1-yl-NH* | Me | H | H | H | H | CN | H |
| IV-2073 | c-Pr | Me(C=O)NHNH | Me | H | H | H | H | CN | H |
| IV-2074 | c-Pr | (Me)(Ac)NNH | Me | H | H | H | H | CN | H |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-2075 | c-Pr | $Me(SO_2)NHNH$ | Me | H | H | H | H | CN | H |
| IV-2076 | c-Pr | $MeOC(=O)NHNH$ | Me | H | H | H | H | CN | H |
| IV-2077 | c-Pr | 2-pyridinyl-N(Ac)-NH | Me | H | H | H | H | CN | H |
| IV-2078 | c-Pr | N-Boc-hexahydropyridazinyl | Me | H | H | H | H | CN | H |
| IV-2079 | c-Pr | $Me_2NC(=O)NHNH$ | Me | H | H | H | H | CN | H |
| IV-2080 | c-Pr | $Me2C=NNH$ | Me | H | H | H | H | CN | H |
| IV-2081 | c-Pr | $H_2NNH$ | $CF_3$ | H | H | H | H | Me | H |
| IV-2082 | c-Pr | $MeNHNH$ | $CF_3$ | H | H | H | H | Me | H |
| IV-2083 | c-Pr | $H_2NN(Me)$ | $CF_3$ | H | H | H | H | Me | H |
| IV-2084 | c-Pr | $Me_2NNH$ | $CF_3$ | H | H | H | H | Me | H |
| IV-2085 | c-Pr | $Me_2NN(Me)$ | $CF_3$ | H | H | H | H | Me | H |
| IV-2086 | c-Pr | $PhNHNH$ | $CF_3$ | H | H | H | H | Me | H |
| IV-2087 | c-Pr | (2-Pyridinyl)NHNH | $CF_3$ | H | H | H | H | Me | H |
| IV-2088 | c-Pr | 1,2,4-triazol-1-yl-NH | $CF_3$ | H | H | H | H | Me | H |
| IV-2089 | c-Pr | $Me(C=O)NHNH$ | $CF_3$ | H | H | H | H | Me | H |
| IV-2090 | c-Pr | $(Me)(Ac)NNH$ | $CF_3$ | H | H | H | H | Me | H |
| IV-2091 | c-Pr | $Me(SO_2)NHNH$ | $CF_3$ | H | H | H | H | Me | H |
| IV-2092 | c-Pr | $MeOC(=O)NHNH$ | $CF_3$ | H | H | H | H | Me | H |
| IV-2093 | c-Pr | 2-pyridinyl-N(Ac)-NH | $CF_3$ | H | H | H | H | Me | H |
| IV-2094 | c-Pr | N-Boc-hexahydropyridazinyl | $CF_3$ | H | H | H | H | Me | H |
| IV-2095 | c-Pr | $Me_2NC(=O)NHNH$ | $CF_3$ | H | H | H | H | Me | H |
| IV-2096 | c-Pr | $Me2C=NNH$ | $CF_3$ | H | H | H | H | Me | H |
| IV-2097 | c-Pr | $H_2NNH$ | $CF_3$ | H | H | H | H | Me | Me |
| IV-2098 | c-Pr | $MeNHNH$ | $CF_3$ | H | H | H | H | Me | Me |
| IV-2099 | c-Pr | $H_2NN(Me)$ | $CF_3$ | H | H | H | H | Me | Me |

TABLE 4-continued

Inventive compounds of the formula (I) in which X represents $C(R^{13})(R^{14})$

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-2100 | c-Pr | Me₂NNH | CF₃ | H | H | H | H | Me | Me |
| IV-2101 | c-Pr | Me₂NN(Me) | CF₃ | H | H | H | H | Me | Me |
| IV-2102 | c-Pr | PhNHNH | CF₃ | H | H | H | H | Me | Me |
| IV-2103 | c-Pr | (2-Pyridinyl)NHNH | CF₃ | H | H | H | H | Me | Me |
| IV-2104 | c-Pr | (1,2,4-triazol-1-yl)NH | CF₃ | H | H | H | H | Me | Me |
| IV-2105 | c-Pr | Me(C=O)NHNH | CF₃ | H | H | H | H | Me | Me |
| IV-2106 | c-Pr | (Me)(Ac)NNH | CF₃ | H | H | H | H | Me | Me |
| IV-2107 | c-Pr | Me(SO₂)NHNH | CF₃ | H | H | H | H | Me | Me |
| IV-2108 | c-Pr | MeOC(=O)NHNH | CF₃ | H | H | H | H | Me | Me |
| IV-2109 | c-Pr | N-(2-pyridinyl)-N-acetyl-hydrazino | CF₃ | H | H | H | H | Me | Me |
| IV-2110 | c-Pr | 1-(tert-butoxycarbonyl)hexahydropyridazin-2-yl | CF₃ | H | H | H | H | Me | Me |
| IV-2111 | c-Pr | Me₂NC(=O)NHNH | CF₃ | H | H | H | H | Me | Me |
| IV-2112 | c-Pr | Me2C=NNH | CF₃ | H | H | H | H | Me | Me |
| IV-2113 | c-Pr | H₂NNH | CF₃ | H | H | H | H | CO₂Et | H |
| IV-2114 | c-Pr | MeNHNH | CF₃ | H | H | H | H | CO₂Et | H |
| IV-2115 | c-Pr | H₂NN(Me) | CF₃ | H | H | H | H | CO₂Et | H |
| IV-2116 | c-Pr | Me₂NNH | CF₃ | H | H | H | H | CO₂Et | H |
| IV-2117 | c-Pr | Me₂NN(Me) | CF₃ | H | H | H | H | CO₂Et | H |
| IV-2118 | c-Pr | PhNHNH | CF₃ | H | H | H | H | CO₂Et | H |
| IV-2119 | c-Pr | (2-Pyridinyl)NHNH | CF₃ | H | H | H | H | CO₂Et | H |
| IV-2120 | c-Pr | (1,2,4-triazol-1-yl)NH | CF₃ | H | H | H | H | CO₂Et | H |
| IV-2121 | c-Pr | Me(C=O)NHNH | CF₃ | H | H | H | H | CO₂Et | H |
| IV-2122 | c-Pr | (Me)(Ac)NNH | CF₃ | H | H | H | H | CO₂Et | H |
| IV-2123 | c-Pr | Me(SO₂)NHNH | CF₃ | H | H | H | H | CO₂Et | H |
| IV-2124 | c-Pr | MeOC(=O)NHNH | CF₃ | H | H | H | H | CO₂Et | H |
| IV-2125 | c-Pr | N-(2-pyridinyl)-N-acetyl-hydrazino | CF₃ | H | H | H | H | CO₂Et | H |

TABLE 4-continued

Inventive compounds of the formula (I) in which X represents $C(R^{13})(R^{14})$ (I)

| No. | $R^1$ | $R^2$ | $R^3$ | $R^4$ | $R^5$ | $R^6$ | $R^7$ | $R^{13}$ | $R^{14}$ |
|---|---|---|---|---|---|---|---|---|---|
| IV-2126 | c-Pr | *t*-BuO-C(O)-(hexahydropyridazin-1-yl) | $CF_3$ | H | H | H | H | $CO_2Et$ | H |
| IV-2127 | c-Pr | $Me_2NC(=O)NHNH$ | $CF_3$ | H | H | H | H | $CO_2Et$ | H |
| IV-2128 | c-Pr | $Me_2C=NNH$ | $CF_3$ | H | H | H | H | $CO_2Et$ | H |
| IV-2129 | c-Pr | $H_2NNH$ | $CF_3$ | H | H | H | H | CN | H |
| IV-2130 | c-Pr | MeNHNH | $CF_3$ | H | H | H | H | CN | H |
| IV-2131 | c-Pr | $H_2NN(Me)$ | $CF_3$ | H | H | H | H | CN | H |
| IV-2132 | c-Pr | $Me_2NNH$ | $CF_3$ | H | H | H | H | CN | H |
| IV-2133 | c-Pr | $Me_2NN(Me)$ | $CF_3$ | H | H | H | H | CN | H |
| IV-2134 | c-Pr | PhNHNH | $CF_3$ | H | H | H | H | CN | H |
| IV-2135 | c-Pr | (2-Pyridinyl)NHNH | $CF_3$ | H | H | H | H | CN | H |
| IV-2136 | c-Pr | (1,2,4-triazol-4-yl)NH | $CF_3$ | H | H | H | H | CN | H |
| IV-2137 | c-Pr | Me(C=O)NHNH | $CF_3$ | H | H | H | H | CN | H |
| IV-2138 | c-Pr | (Me)(Ac)NNH | $CF_3$ | H | H | H | H | CN | H |
| IV-2139 | c-Pr | $Me(SO_2)NHNH$ | $CF_3$ | H | H | H | H | CN | H |
| IV-2140 | c-Pr | MeOC(=O)NHNH | $CF_3$ | H | H | H | H | CN | H |
| IV-2141 | c-Pr | N-(2-pyridinyl)-N-acetylhydrazino | $CF_3$ | H | H | H | H | CN | H |
| IV-2142 | c-Pr | *t*-BuO-C(O)-(hexahydropyridazin-1-yl) | $CF_3$ | H | H | H | H | CN | H |
| IV-2143 | c-Pr | $Me_2NC(=O)NHNH$ | $CF_3$ | H | H | H | H | CN | H |
| IV-2144 | c-Pr | $Me_2C=NNH$ | $CF_3$ | H | H | H | H | CN | H |
| IV-2145 | c-Pr | $H_2NNH$ | MeO | H | H | H | H | Me | H |
| IV-2146 | c-Pr | MeNHNH | MeO | H | H | H | H | Me | H |
| IV-2147 | c-Pr | $H_2NN(Me)$ | MeO | H | H | H | H | Me | H |
| IV-2148 | c-Pr | $Me_2NNH$ | MeO | H | H | H | H | Me | H |
| IV-2149 | c-Pr | $Me_2NN(Me)$ | MeO | H | H | H | H | Me | H |
| IV-2150 | c-Pr | PhNHNH | MeO | H | H | H | H | Me | H |
| IV-2151 | c-Pr | (2-Pyridinyl)NHNH | MeO | H | H | H | H | Me | H |
| IV-2152 | c-Pr | (1,2,4-triazol-4-yl)NH | MeO | H | H | H | H | Me | H |
| IV-2153 | c-Pr | Me(C=O)NHNH | MeO | H | H | H | H | Me | H |
| IV-2154 | c-Pr | (Me)(Ac)NNH | MeO | H | H | H | H | Me | H |

TABLE 4-continued

Inventive compounds of the formula (I) in which X represents C(R$^{13}$)(R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-2155 | c-Pr | Me(SO$_2$)NHNH | MeO | H | H | H | H | Me | H |
| IV-2156 | c-Pr | MeOC(=O)NHNH | MeO | H | H | H | H | Me | H |
| IV-2157 | c-Pr | [2-pyridinyl-N(C(=O)Me)-NH] | MeO | H | H | H | H | Me | H |
| IV-2158 | c-Pr | [tBuO-C(=O)-piperidazinyl] | MeO | H | H | H | H | Me | H |
| IV-2159 | c-Pr | Me$_2$NC(=O)NHNH | MeO | H | H | H | H | Me | H |
| IV-2160 | c-Pr | Me2C=NNH | MeO | H | H | H | H | Me | H |
| IV-2161 | c-Pr | H$_2$NNH | MeO | H | H | H | H | Me | Me |
| IV-2162 | c-Pr | MeNHNH | MeO | H | H | H | H | Me | Me |
| IV-2163 | c-Pr | H$_2$NN(Me) | MeO | H | H | H | H | Me | Me |
| IV-2164 | c-Pr | Me$_2$NNH | MeO | H | H | H | H | Me | Me |
| IV-2165 | c-Pr | Me$_2$NN(Me) | MeO | H | H | H | H | Me | Me |
| IV-2166 | c-Pr | PhNHNH | MeO | H | H | H | H | Me | Me |
| IV-2167 | c-Pr | (2-Pyridinyl)NHNH | MeO | H | H | H | H | Me | M |
| IV-2168 | c-Pr | [1,2,4-triazol-1-yl-NH] | MeO | H | H | H | H | Me | Me |
| IV-2169 | c-Pr | Me(C=O)NHNH | MeO | H | H | H | H | Me | Me |
| IV-2170 | c-Pr | (Me)(Ac)NNH | MeO | H | H | H | H | Me | Me |
| IV-2171 | c-Pr | Me(SO$_2$)NHNH | MeO | H | H | H | H | Me | Me |
| IV-2172 | c-Pr | MeOC(=O)NHNH | MeO | H | H | H | H | Me | Me |
| IV-2173 | c-Pr | [2-pyridinyl-N(C(=O)Me)-NH] | MeO | H | H | H | H | Me | Me |
| IV-2174 | c-Pr | [tBuO-C(=O)-piperidazinyl] | MeO | H | H | H | H | Me | Me |
| IV-2175 | c-Pr | Me$_2$NC(=O)NHNH | MeO | H | H | H | H | Me | Me |
| IV-2176 | c-Pr | Me2C=NNH | MeO | H | H | H | H | Me | Me |
| IV-2177 | c-Pr | H$_2$NNH | MeO | H | H | H | H | Me | H |
| IV-2178 | c-Pr | MeNHNH | MeO | H | H | H | H | CO$_2$Et | H |

TABLE 4-continued

Inventive compounds of the formula (I) in which X represents C(R$^{13}$) (R$^{14}$)

(I)

| No. | R$^1$ | R$^2$ | R$^3$ | R$^4$ | R$^5$ | R$^6$ | R$^7$ | R$^{13}$ | R$^{14}$ |
|---|---|---|---|---|---|---|---|---|---|
| IV-2179 | c-Pr | H$_2$NN(Me) | MeO | H | H | H | H | CO$_2$Et | H |
| IV-2180 | c-Pr | Me$_2$NNH | MeO | H | H | H | H | CO$_2$Et | H |
| IV-2181 | c-Pr | Me$_2$NN(Me) | MeO | H | H | H | H | CO$_2$Et | H |
| IV-2182 | c-Pr | PhNHNH | MeO | H | H | H | H | CO$_2$Et | H |
| IV-2183 | c-Pr | (2-Pyridinyl)NHNH | MeO | H | H | H | H | CO$_2$Et | H |
| IV-2184 | c-Pr | [triazolyl-NH] | MeO | H | H | H | H | CO$_2$Et | H |
| IV-2185 | c-Pr | Me(C=O)NHNH | MeO | H | H | H | H | CO$_2$Et | H |
| IV-2186 | c-Pr | (Me)(Ac)NNH | MeO | H | H | H | H | CO$_2$Et | H |
| IV-2187 | c-Pr | Me(SO$_2$)NHNH | MeO | H | H | H | H | CO$_2$Et | H |
| IV-2188 | c-Pr | MeOC(=O)NHNH | MeO | H | H | H | H | CO$_2$Et | H |
| IV-2189 | c-Pr | [2-pyridinyl-N(Ac)-NH] | MeO | H | H | H | H | CO$_2$Et | H |
| IV-2190 | c-Pr | [N-Boc-piperidazinyl] | MeO | H | H | H | H | CO$_2$Et | H |
| IV-2191 | c-Pr | Me$_2$NC(=O)NHNH | MeO | H | H | H | H | CO$_2$Et | H |
| IV-2192 | c-Pr | Me2C=NNH | MeO | H | H | H | H | CO$_2$Et | H |
| IV-2193 | c-Pr | H$_2$NNH | MeO | H | H | H | H | CN | H |
| IV-2194 | c-Pr | MeNHNH | MeO | H | H | H | H | CN | H |
| IV-2195 | c-Pr | H$_2$NN(Me) | MeO | H | H | H | H | CN | H |
| IV-2196 | c-Pr | Me$_2$NNH | MeO | H | H | H | H | CN | H |
| IV-2197 | c-Pr | Me$_2$NN(Me) | MeO | H | H | H | H | CN | H |
| IV-2198 | c-Pr | PhNHNH | MeO | H | H | H | H | CN | H |
| IV-2199 | c-Pr | (2-Pyridinyl)NHNH | MeO | H | H | H | H | CN | H |
| IV-2200 | c-Pr | [triazolyl-NH] | MeO | H | H | H | H | CN | H |
| IV-2201 | c-Pr | Me(C=O)NHNH | MeO | H | H | H | H | CN | H |
| IV-2202 | c-Pr | (Me)(Ac)NNH | MeO | H | H | H | H | CN | H |
| IV-2203 | c-Pr | Me(SO$_2$)NHNH | MeO | H | H | H | H | CN | H |
| IV-2204 | c-Pr | MeOC(=O)NHNH | MeO | H | H | H | H | CN | H |

NMR Data of Selected Examples

NMR Peak List Method

The 1H NMR data of selected examples are noted in the form of 1H NMR peak lists. For each signal peak, first the δ value in ppm and then the signal intensity in round brackets are listed. The δ value/signal intensity number pairs for different signal peaks are listed with separation from one another by semicolons.

The peak list for one example therefore takes the form of:

$\delta_1$(intensity$_1$); $\delta_2$(intensity$_2$); . . . ; $\delta_i$(intensity$_i$); . . . ; $\delta_n$(intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

For calibration of the chemical shift of 1H NMR spectra we use tetramethylsilane and/or the chemical shift of the solvent, particularly in the case of spectra measured in DMSO. Therefore, the tetramethylsilane peak may but need not occur in NMR peak lists.

The lists of the 1H NMR peaks are similar to the conventional 1H NMR printouts and thus usually contain all peaks listed in a conventional NMR interpretation.

In addition, like conventional 1H NMR printouts, they may show solvent signals, signals of stereoisomers of the target compounds, which likewise form part of the subject matter of the invention, and/or peaks of impurities.

In the reporting of compound signals in the delta range of solvents and/or water, our lists of 1H NMR peaks show the usual solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in conventional 1H NMR interpretation.

Further details of 1H NMR peak lists can be found in the Research Disclosure Database Number 564025.

I-137: $^1$H-NMR(400.6 MHz, CDCl3):
δ = 15.9527 (1.5); 8.2222 (15.2); 7.5255 (2.5); 7.5215 (4.0); 7.5191 (1.9); 7.5079 (2.8); 7.5060 (3.1); 7.5029 (3.9); 7.4135 (1.4); 7.4087 (1.9); 7.3950 (4.0); 7.3901 (3.9); 7.3767 (6.2); 7.3717 (4.4); 7.3710 (4.1); 7.3584 (4.6); 7.3545 (4.1); 7.3398 (1.8); 7.3359 (1.5); 7.2711 (0.6); 7.2686 (0.8); 7.2678 (0.9); 7.2670 (1.0); 7.2661 (1.1); 7.2607 (273.0); 7.2564 (7.1); 7.2555 (6.5); 7.2539 (7.1); 7.2532 (6.7); 7.2516 (3.5); 7.2492 (4.7); 7.2473 (4.0); 7.2452 (1.4); 7.2436 (1.1); 7.2420 (0.9); 7.2404 (1.0); 7.2396 (1.0); 7.2388 (1.1); 7.2356 (4.4); 7.2307 (3.1); 6.9970 (2.3); 6.1433 (16.0); 5.4241 (1.0); 2.2220 (0.6); 2.2101 (1.4); 2.2019 (1.4); 2.1961 (0.7); 2.1903 (2.5); 2.1814 (1.0); 2.1780 (1.5); 2.1699 (1.6); 2.1579 (0.8); 1.5509 (4.0); 1.3331 (0.5); 1.3197 (1.4); 1.3109 (1.4); 1.3038 (2.7); 1.2989 (3.3); 1.2951 (3.2); 1.2917 (2.9); 1.2891 (2.6); 1.2837 (2.7); 1.2729 (0.8); 1.2569 (1.8); 1.2544 (2.2); 1.2447 (4.3); 1.2381 (2.5); 1.2342 (1.8); 1.2247 (4.0); 1.2176 (2.8); 1.2108 (1.5); 1.2039 (0.7); 0.0080 (4.3); −0.0002 (170.5); −0.0085 (5.6); −0.0133 (0.9)

I-139: $^1$H-NMR(400.6 MHz, CDCl3):
δ = 8.0295 (6.2); 7.4951 (1.2); 7.4905 (1.6); 7.4782 (1.1); 7.4757 (1.2); 7.4721 (1.6); 7.3856 (0.6); 7.3805 (0.8); 7.3671 (1.7); 7.3619 (1.9); 7.3532 (1.4); 7.3493 (1.7); 7.3477 (1.7); 7.3429 (1.6); 7.3349 (1.9); 7.3308 (1.8); 7.3164 (0.8); 7.3123 (0.6); 7.2687 (4.0); 7.2566 (1.7); 7.2522 (1.2); 7.2498 (1.1); 7.2392 (1.5); 7.2335 (1.0); 5.3291 (7.2); 4.1305 (1.0); 4.1127 (1.1); 3.1090 (2.3); 3.1043 (16.0); 2.9565 (2.4); 2.9519 (14.7); 2.1336 (0.6); 2.1252 (0.6); 2.1136 (1.2); 2.1016 (0.7); 2.0932 (0.7); 2.0454 (5.1); 1.3163 (0.5); 1.3102 (1.2); 1.3041 (2.1); 1.3002 (1.1); 1.2982 (1.0); 1.2960 (1.2); 1.2925 (1.7); 1.2843 (0.9); 1.2769 (1.6); 1.2591 (3.3); 1.2550 (0.6); 1.2413 (1.6); 1.2377 (0.7); 1.2353 (0.6); 1.2282 (1.6); 1.2213 (1.1); 1.2170 (1.0); 1.2083 (1.8); 1.2010 (1.2); 1.1973 (0.7); −0.0002 (2.9)

I-146: $^1$H-NMR(400.6 MHz, CDCl3):
δ = 15.8625 (1.3); 8.3673 (1.3); 8.0941 (14.7); 7.4950 (2.9); 7.4896 (3.2); 7.4786 (2.3); 7.4755 (2.6); 7.4718 (4.1); 7.3803 (1.1); 7.3751 (1.5); 7.3698 (0.5); 7.3618 (3.6); 7.3565 (4.3); 7.3511 (3.9); 7.3449 (6.4); 7.3378 (3.6); 7.3331 (4.3); 7.3287 (4.0); 7.3146 (1.6); 7.3102 (1.1); 7.2790 (2.9); 7.2605 (4.3); 7.2557 (2.7); 7.2526 (2.3); 7.2434 (2.9); 7.2372 (2.6); 5.6792 (16.0); 4.1108 (0.6); 3.7816 (0.7); 3.7689 (1.5); 3.7525 (3.3); 3.7464 (1.6); 3.7347 (2.5); 3.7309 (2.8); 3.7140 (1.9); 3.7017 (1.0); 3.5133 (4.3); 3.4959 (6.8); 3.4797 (3.5); 2.1794 (0.7); 2.1675 (1.4); 2.1591 (1.5); 2.1550 (0.9); 2.1475 (3.0); 2.1385 (1.1); 2.1355 (1.6); 2.1271 (1.6); 2.1153 (0.8); 2.0437 (1.3); 1.9454 (0.5); 1.9390 (0.9); 1.9290 (1.2); 1.9219 (2.1); 1.9082 (3.8); 1.8927 (4.2); 1.8798 (3.1); 1.8664 (3.2); 1.8505 (3.5); 1.8365 (1.7); 1.8343 (1.8); 1.8306 (1.3); 1.8199 (0.6); 1.3371 (0.6); 1.3079 (1.6); 1.3021 (1.9); 1.2959 (3.4); 1.2896 (6.0); 1.2857 (4.2); 1.2820 (4.1); 1.2780 (5.0); 1.2697 (3.8); 1.2617 (3.6); 1.2579 (3.1); 1.2434 (1.2); 1.2316 (0.8); 1.2243 (1.5); 1.2212 (1.4); 1.2149 (4.4); 1.2080 (3.0); 1.2037 (2.5); 1.1949 (4.7); 1.1877 (3.1); 1.1840 (1.6); 1.1777 (0.8); 1.1749 (0.8); 1.0720 (0.5); 1.0523 (0.7); 0.8973 (1.5); 0.8804 (4.6); 0.8628 (1.9); 0.0755 (0.9); −0.0002 (2.1)

I-147: $^1$H-NMR(400.6 MHz, CDCl3):
δ = 15.9068 (0.6); 8.2224 (0.6); 8.0425 (9.2); 7.5057 (1.7); 7.5011 (2.5); 7.4885 (1.6); 7.4862 (1.8); 7.4826 (2.3); 7.3986 (0.8); 7.3937 (1.2); 7.3801 (2.4); 7.3751 (2.6); 7.3654 (2.0); 7.3623 (2.4); 7.3600 (2.4); 7.3559 (2.2); 7.3471 (2.8); 7.3430 (2.6); 7.3286 (1.2); 7.3244 (0.9); 7.2641 (25.0); 7.2589 (2.6); 7.2545 (2.0); 7.2521 (1.8); 7.2413 (2.3); 7.2358 (1.7); 6.1423 (0.6); 5.3679 (10.8); 5.3000 (16.0); 3.7022 (2.3); 3.6733 (3.9); 3.6333 (1.1); 3.6218 (1.5); 3.6095 (1.4); 2.1231 (0.8); 2.1148 (0.9); 2.1032 (1.8); 2.0944 (0.6); 2.0912 (0.9); 2.0829 (1.0); 1.3258 (0.7); 1.3196 (0.8); 1.3133 (1.7); 1.3071 (3.1); 1.3030 (1.6); 1.3014 (1.6); 1.2989 (1.8); 1.2955 (2.6); 1.2873 (1.3); 1.2595 (0.9); 1.2496 (0.5); 1.2430 (1.1); 1.2411 (1.0); 1.2339 (2.3); 1.2268 (1.6); 1.2213 (1.6); 1.2140 (2.6); 1.2066 (1.8); 1.2026 (0.9); 1.1956 (0.5); 1.1937 (0.5); −0.0002 (14.4)

I-547: $^1$H-NMR(400.6 MHz, CDCl3):
δ = 15.8263 (0.5); 7.9951 (6.1); 7.2687 (7.8); 7.2592 (1.5); 7.2527 (1.6); 7.2498 (1.4); 7.2381 (1.5); 7.2349 (1.5); 7.2318 (1.7); 7.2284 (1.8); 7.2135 (1.6); 7.0931 (1.1); 7.0867 (1.0); 7.0733 (1.2); 7.0720 (1.1); 7.0668 (1.1); 7.0656 (0.9); 7.0521 (0.8); 7.0456 (0.8); 5.3008 (11.2); 3.1314 (1.4); 3.1070 (16.0); 2.9594 (14.9); 2.1246 (0.6); 2.1163 (0.6); 2.1047 (1.2); 2.0926 (0.6); 2.0843 (0.7); 1.3075 (1.0); 1.3018 (2.0); 1.2991 (1.2); 1.2942 (1.3); 1.2901 (1.6); 1.2822 (0.9); 1.2413 (0.6); 1.2379 (0.5); 1.2319 (1.6); 1.2249 (1.1); 1.2210 (0.8); 1.2184 (0.8); 1.2120 (1.7); 1.2046 (1.2); 1.2002 (0.6); −0.0002 (4.7)

I-688: $^1$H-NMR(400.0 MHz, CDCl3):
δ = 8.1801 (13.8); 7.2848 (3.5); 7.2785 (3.9); 7.2614 (24.8); 7.2575 (4.4); 7.2443 (3.2); 7.2295 (2.9); 7.2229 (3.6); 7.2082 (3.5); 7.1113 (2.3); 7.1049 (2.1); 7.0915 (2.7); 7.0901 (2.3); 7.0851 (2.4); 7.0837 (2.0); 7.0702 (1.7); 7.0638 (1.6); 6.1127 (16.0); 5.9049 (0.7); 5.8908 (1.5); 5.8792 (0.9); 5.8768 (0.8); 5.8652 (1.7); 5.8620 (0.9); 5.8511 (0.9); 5.8479 (1.8); 5.8363 (1.0); 5.8340 (1.0); 5.8223 (1.9); 5.8083 (0.9); 5.2996 (3.8); 5.2561 (1.0); 5.2521 (2.6); 5.2487 (2.7); 5.2446 (1.1); 5.2132 (0.9); 5.2092 (2.3); 5.2058 (2.4); 5.2017 (1.0); 5.1832 (1.2); 5.1797 (3.0); 5.1764 (2.9); 5.1730 (1.0); 5.1575 (1.0); 5.1541 (2.8); 5.1508 (2.7); 5.1474 (1.0); 3.9765 (1.6); 3.9727 (2.8); 3.9689 (1.8); 3.9616 (2.8); 3.9580 (4.8); 3.9545 (2.8); 3.9472 (1.7); 3.9434 (2.8); 3.9396 (1.6); 2.2232 (0.5); 2.2112 (1.2); 2.2034 (1.3);

-continued 2.1936 (1.8); 2.1917 (1.8); 2.1827 (0.9); 2.1792 (1.3); 2.1713 (1.4); 2.1591 (0.7); 2.0464 (0.7); 1.3327 (3.0); 1.3181 (1.6); 1.3155 (1.7); 1.3105 (3.2); 1.3072 (3.2); 1.3040 (3.5); 1.2990 (3.3); 1.2958 (2.3); 1.2926 (2.3); 1.2846 (4.7); 1.2809 (3.2); 1.2732 (4.2); 1.2662 (2.8); 1.2536 (5.7); 1.2461 (2.7); 1.2373 (0.7); 1.2316 (1.0); 0.8799 (0.5); 0.0080 (0.7); −0.0002 (30.2); −0.0085 (1.1)

II-003: $^1$H-NMR(400.0 MHz, CDCl3):
δ = 15.6674 (2.0); 15.4327 (0.6); 8.3695 (9.4); 8.3105 (2.1); 7.5152 (0.5); 7.5121 (1.0); 7.5071 (1.4); 7.5030 (0.9); 7.4963 (1.3); 7.4903 (4.3); 7.4859 (2.3); 7.4798 (1.4); 7.4760 (2.2); 7.4724 (4.7); 7.4705 (3.3); 7.4661 (1.2); 7.4639 (1.7); 7.4597 (3.1); 7.4557 (2.1); 7.4491 (0.9); 7.4423 (2.3); 7.4331 (0.6); 7.4274 (0.5); 7.4238 (0.7); 7.3904 (0.9); 7.3865 (1.2); 7.3737 (0.5); 7.3697 (1.0); 7.3634 (4.2); 7.3592 (4.9); 7.3537 (1.4); 7.3472 (2.0); 7.3430 (3.8); 7.3395 (2.9); 7.2601 (41.0); 6.5015 (11.1); 6.4188 (2.3); 4.3343 (2.2); 4.3164 (7.2); 4.2986 (7.4); 4.2808 (2.4); 2.2280 (1.0); 2.2198 (1.0); 2.2137 (0.6); 2.2080 (1.8); 2.1992 (0.8); 2.1959 (1.2); 2.1876 (1.2); 2.1758 (0.8); 1.5523 (1.8); 1.3639 (7.6); 1.3460 (16.0); 1.3282 (7.7); 1.3040 (0.6); 1.2962 (0.6); 1.2823 (1.4); 1.2783 (1.3); 1.2688 (4.2); 1.2633 (5.0); 1.2621 (5.1); 1.2570 (3.8); 1.2542 (3.4); 1.2500 (3.6); 1.2422 (1.8); 1.2298 (0.8); 1.2220 (1.0); 1.2164 (1.7); 1.2082 (3.5); 1.2013 (2.6); 1.1961 (2.2); 1.1880 (3.8); 1.1810 (2.4); 1.1740 (0.8); 1.1676 (0.8); 1.1364 (0.6); 1.1162 (0.6); 0.8986 (1.2); 0.8817 (3.9); 0.8640 (1.6); 0.0080 (0.7); −0.0002 (23.2); −0.0084 (1.0)

II-086: $^1$H-NMR(400.0 MHz, CDCl3):
δ = 15.6668 (1.3); 8.3371 (5.0); 7.3400 (1.5); 7.3346 (0.8); 7.3268 (1.7); 7.3236 (1.0); 7.3214 (1.0); 7.3180 (2.2); 7.3105 (0.9); 7.3049 (2.1); 7.2629 (9.4); 7.2111 (2.2); 7.2057 (0.7); 7.1942 (0.8); 7.1896 (3.4); 7.1844 (0.8); 7.1731 (0.6); 7.1678 (1.5); 6.4157 (5.6); 5.2986 (0.6); 3.8543 (16.0); 2.2279 (0.5); 2.2199 (0.6); 2.2117 (0.6); 2.2080 (0.9); 2.1957 (0.6); 2.1878 (0.6); 1.2683 (1.3); 1.2613 (1.7); 1.2548 (1.9); 1.2496 (1.6); 1.2420 (0.9); 1.2386 (0.6); 1.2277 (1.3); 1.2208 (1.5); 1.2138 (1.2); 1.2082 (1.0); 1.2003 (1.7); 1.1936 (1.1); −0.0002 (5.4)

II-097: $^1$H-NMR(400.0 MHz, d$_6$-DMSO):
δ = 14.7341 (0.5); 8.5214 (16.0); 8.3976 (0.9); 7.6824 (4.2); 7.6782 (5.2); 7.6628 (4.4); 7.6594 (5.9); 7.5689 (1.8); 7.5639 (2.3); 7.5505 (5.0); 7.5454 (5.3); 7.5324 (6.6); 7.5264 (5.2); 7.5146 (5.9); 7.5107 (5.7); 7.4963 (2.9); 7.4924 (2.3); 7.4863 (0.6); 7.4687 (6.6); 7.4641 (4.5); 7.4508 (4.2); 7.4453 (3.1); 5.8902 (13.4); 2.6769 (0.7); 2.6721 (1.0); 2.6675 (0.7); 2.5256 (2.8); 2.5210 (3.6); 2.5121 (58.0); 2.5076 (128.8); 2.5030 (180.6); 2.4985 (127.5); 2.4939 (57.4); 2.4635 (0.6); 2.3629 (0.7); 2.3512 (1.6); 2.3401 (1.9); 2.3307 (4.0); 2.3250 (1.8); 2.3198 (2.2); 2.3112 (1.7); 2.2993 (0.8); 2.2171 (3.0); 1.2373 (1.4); 1.2265 (3.7); 1.2188 (6.1); 1.2111 (3.9); 1.2063 (3.6); 1.1987 (5.4); 1.1911 (2.5); 1.1811 (0.6); 1.1747 (0.6); 1.1688 (0.6); 1.1550 (0.7); 1.1440 (2.5); 1.1366 (5.6); 1.1252 (6.9); 1.1179 (4.6); 1.1073 (1.4); 1.0896 (0.6); 1.0694 (0.6); 1.0631 (0.6); 0.0080 (2.7); −0.0002 (99.6); −0.0085 (3.0)

II-098: $^1$H-NMR(400.0 MHz, CDCl3):
δ = 15.4957 (1.0); 8.3379 (5.0); 7.5483 (0.9); 7.5441 (1.3); 7.5306 (1.0); 7.5286 (1.1); 7.5254 (1.3); 7.4320 (0.6); 7.4182 (1.3); 7.4133 (1.3); 7.3999 (2.1); 7.3950 (1.6); 7.3816 (1.5); 7.3777 (1.3); 7.3630 (0.6); 7.2608 (14.2); 7.2543 (1.2); 7.2523 (1.0); 7.2406 (1.3); 7.2356 (0.9); 6.0982 (5.8); 3.8347 (16.0); 2.2465 (0.5); 2.2347 (0.9); 2.2224 (0.5); 2.2143 (0.6); 1.5480 (2.3); 1.3021 (0.5); 1.2898 (1.1); 1.2831 (1.6); 1.2755 (1.5); 1.2712 (1.9); 1.2632 (1.4); 1.2546 (0.6); 1.2409 (0.8); 1.2383 (0.6); 1.2326 (1.4); 1.2257 (1.0); 1.2207 (0.7); 1.2186 (0.6); 1.2124 (1.5); 1.2052 (1.0); 0.8817 (1.2); 0.0079 (0.5); −0.0002 (16.7); −0.0085 (0.6)

II-481: $^1$H-NMR(400.0 MHz, CDCl3):
δ = 8.3063 (1.3); 8.1229 (13.2); 7.5191 (1.6); 7.3127 (3.7); 7.3064 (3.7); 7.2918 (3.6); 7.2855 (3.8); 7.2602 (301.6); 7.2547 (4.9); 7.2397 (3.3); 7.2331 (4.3); 7.2184 (3.9); 7.1415 (2.9); 7.1351 (2.7); 7.1219 (3.2); 7.1154 (2.8); 7.1005 (1.9); 7.0941 (1.7); 6.9962 (1.7); 6.0523 (1.6); 5.9673 (16.0); 3.8456 (4.2); 2.1588 (0.6); 2.1473 (1.4); 2.1392 (1.4); 2.1276 (2.5); 2.1156 (1.4); 2.1072 (1.8); 2.1038 (5.8); 2.0559 (0.7); 2.0453 (1.0); 1.5437 (2.5); 1.4323 (1.6); 1.4029 (1.4); 1.3956 (2.8); 1.3851 (3.8); 1.3737 (2.9); 1.3438 (1.6); 1.3315 (4.8); 1.3240 (3.4); 1.3119 (4.0); 1.3048 (2.8); 1.2597 (0.8); 1.2420 (0.8); 0.1461 (0.9); 0.0080 (8.4); −0.0002 (293.8); −0.0085 (8.4); −0.1500 (0.9)

II-542: $^1$H-NMR(400.0 MHz, CDCl3):
δ = 15.4340 (0.8); 8.2827 (5.1); 7.4795 (2.4); 7.4770 (2.7); 7.4586 (4.0); 7.4575 (4.3); 7.3844 (2.2); 7.3663 (1.6); 7.3622 (1.3); 7.3441 (1.1); 7.2629 (27.2); 5.9425 (6.1); 5.3021 (3.4); 3.8404 (16.0); 2.2491 (0.8); 2.2289 (0.5); 1.3107 (1.0); 1.3036 (1.3); 1.2987 (1.0); 1.2958 (1.0); 1.2916 (1.4); 1.2839 (0.7); 1.2641 (0.5); 1.2590 (0.9); 1.2509 (1.6); 1.2441 (0.9); 1.2390 (0.8); 1.2307 (1.4); 1.2237 (1.0); −0.0002 (16.0)

IV-137: $^1$H-NMR(400.6 MHz, CDCl3):
δ = 8.7372 (1.3); 8.2124 (6.9); 7.5189 (1.0); 7.5146 (1.1); 7.4992 (1.0); 7.4958 (1.4); 7.3883 (1.0); 7.3834 (1.1); 7.3705 (1.6); 7.3656 (1.4); 7.3526 (1.3); 7.3488 (1.2); 7.3340 (0.5); 7.2625 (20.7); 7.2497 (1.4); 7.2452 (1.1); 7.2318 (1.2); 7.2266 (1.0); 6.1133 (6.3); 3.1625 (1.4); 3.1512 (16.0); 2.1897 (0.6); 2.1815 (0.6); 2.1700 (1.1); 2.1578 (0.7); 2.1496 (0.7); 1.4609 (2.4); 1.4413 (8.0); 1.3228 (0.6); 1.3024 (1.7); 1.2982 (1.6); 1.2915 (1.4); 1.2869 (1.4); 1.2771 (1.0); 1.2641 (2.2); 1.2604 (2.2); 1.2504 (2.1); 1.2435 (1.3); 1.2302 (1.8); 1.2233 (1.1); 1.2159 (0.6); 0.8987 (1.0); 0.8818 (3.4); 0.8641 (1.4); −0.0002 (12.6)

IV-138: $^1$H-NMR(400.0 MHz, CDCl3):
δ = 8.9957 (2.7); 8.2165 (8.8); 7.5371 (1.4); 7.5331 (1.6); 7.5173 (1.7); 7.5139 (2.1); 7.4306 (0.7); 7.4259 (0.8); 7.4119 (1.8); 7.4071 (1.8); 7.3930 (1.7); 7.3904 (1.8); 7.3875 (2.0); 7.3718 (2.1); 7.3681 (2.0); 7.3532 (1.0); 7.3495 (0.9); 7.2621 (60.7); 7.2570 (2.5); 7.2527 (1.7); 7.2387 (1.8); 7.2337 (1.6); 6.1027 (7.9); 5.2999 (3.4); 4.1308 (1.0); 4.1130 (1.0); 3.3356 (0.7); 3.3103 (0.5); 3.1614 (15.9); 2.1814 (1.1); 2.1736 (1.2); 2.1620 (1.4); 2.1497 (0.9); 2.1415 (0.8); 2.1309 (0.7); 2.0824 (2.7); 2.0451 (4.9); 2.0320 (16.0); 1.3554 (0.5); 1.3477 (0.8); 1.3408 (1.8); 1.3332 (4.4); 1.3210 (1.7); 1.2951 (1.2); 1.2844 (5.8); 1.2773 (3.2); 1.2647 (2.9); 1.2593 (4.9); 1.2415 (1.8); 1.1986 (0.7); 1.1808 (1.3); 1.1629 (0.7); 1.1362 (0.7); 1.1184 (1.4); 1.1005 (0.7); 0.0079 (1.0); −0.0002 (35.8); −0.0085 (1.1)

IV-140: $^1$H-NMR(400.0 MHz, CDCl3):
δ = 8.9607 (1.5); 8.2148 (5.1); 7.5353 (0.9); 7.5309 (1.2); 7.5176 (0.9); 7.5155 (1.0); 7.5121 (1.3); 7.4206 (0.6); 7.4068 (1.3); 7.4019 (1.3); 7.3890 (1.5); 7.3846 (1.2); 7.3827 (1.1); 7.3713 (1.4); 7.3674 (1.2); 7.3527 (0.6); 7.2608 (15.4); 7.2576 (1.6); 7.2529 (1.0); 7.2509 (0.9); 7.2395 (1.2); 7.2341 (0.9); 6.0435 (5.7); 5.2998 (0.6); 3.2570 (16.0); 3.0206 (15.0); 2.1659 (0.8); 2.1454 (0.5); 1.3328 (0.9); 1.3256 (1.0); 1.3204 (1.2); 1.3178 (1.1); 1.3139 (1.0); 1.3062 (1.1); 1.2890 (0.8); 1.2843 (0.9); 1.2795 (1.5); 1.2728 (1.0); 1.2689 (0.8); 1.2591 (1.7); 1.2526 (1.1); 0.0079 (0.5); −0.0002 (20.0); −0.0085 (0.6)

Compounds of the invention can be prepared by the methods specified in schemes below.

The starting compounds of the 4-methyl-5-arylpyrimidine type can be prepared from 5-bromopyrimidines or 5-iodopyrimidines by a method described for 2,4-dimethyl-5-phenylpyrimidine in Kondo et al, *Chem. Pharm. Bull.* 37 (1989) 2814.

The starting compounds of the 4-halo-5-arylpyrimidine (halogen=chlorine, bromine, iodine) can be prepared from the suitable 4-hydroxy-5-arylpyrimidines, for example by chlorination with phosphorus oxychloride. Such methods are described, for example, for the preparation of 4-chloro-5-(4-chlorophenyl)-2-phenylpyrimidine in Shestakov et al, *Tetrahedron* 73 (2017) 3939.

First of all, by known methods, for example, an amidine or a salt of an amidine is condensed with an enol ester or a 3-hydroxyacryloyl derivative, optionally together with an inorganic, organic or organometallic base, for example potassium carbonate, sodium ethoxide or a hexamethyldisilazide, in a suitable solvent at reaction temperatures between −30 and 180 degrees Celsius (WO2008156726, WO2012171863):

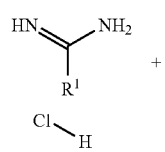

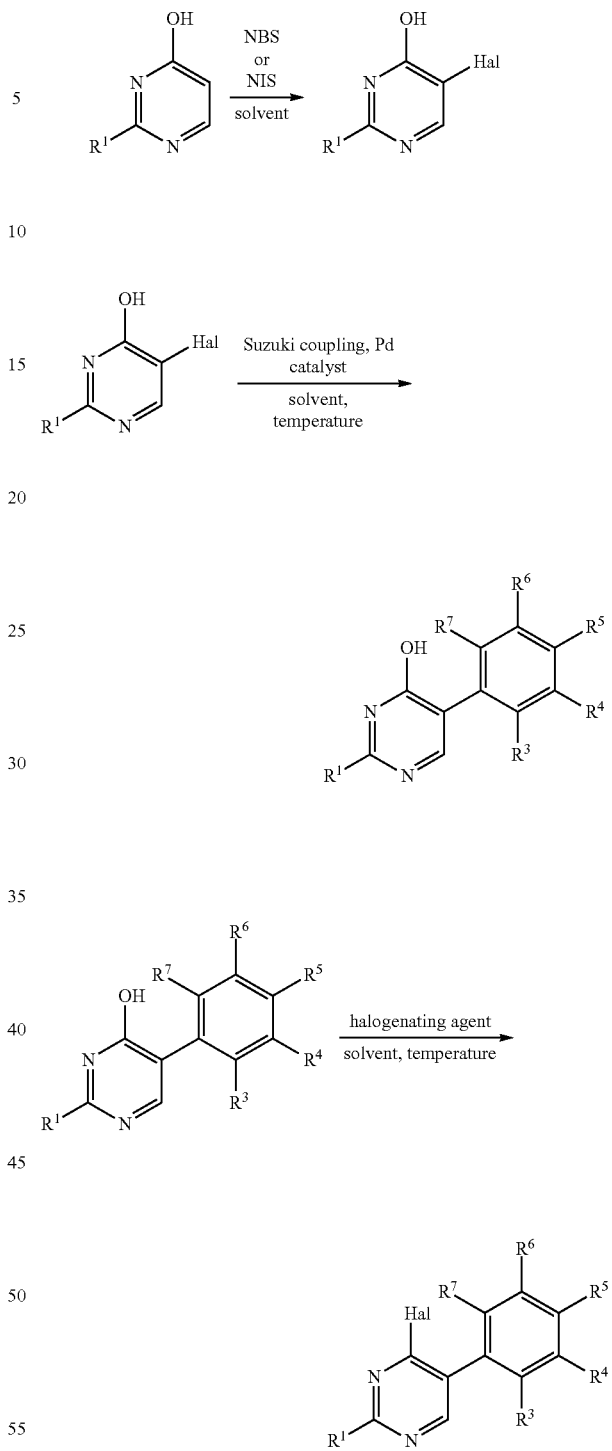

Subsequently, the pyrimidine can be halogenated by known methods in the 5 position with halogenating agents, for example N-iodo- or N-bromosuccinimide or bromine (*J. Med. Chem.* 51 (2008) 5766): Thereafter, it is possible to conduct a cross-coupling reaction, for example a Suzuki coupling (WO2014081617, WO2007146824), a Stille coupling (*J. Org. Chem.* 74 (2009) 5599), a Kumada coupling (*J. Org. Chem.* 73 (2008) 162) or a Negishi coupling (*Synthesis* 48 (2016) 504).

The pyrimidone can subsequently be converted to a 4-halopyrimidine, for example by means of known halogenating agents, for example phosphorus oxychloride or thionyl bromide. This is followed by a Heck coupling (*Tetrahedron Lett.* 28 (1987) 3039) under metal catalysis to give the alkenyloxy acrylate, which is then hydrolyzed to the pyruvate (*J. Org. Chem.* 80 (2015) 2554).

Rather than the 4-halopyridine, it is also possible to use the corresponding triflate or diazonium salt.

A possible alternative reaction regime is shown in the two schemes that follow:

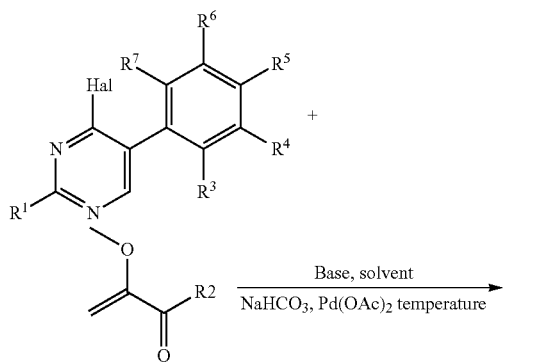

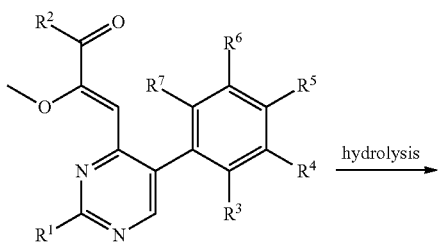

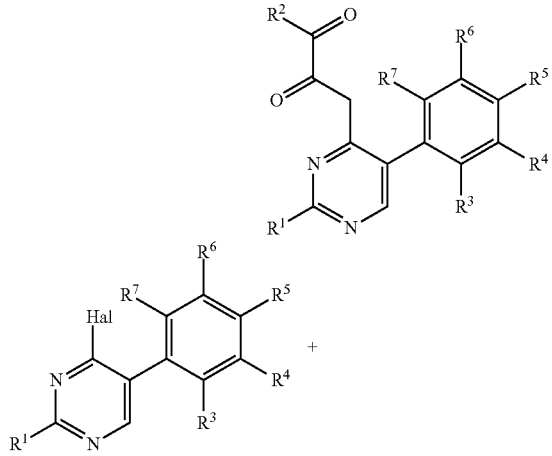

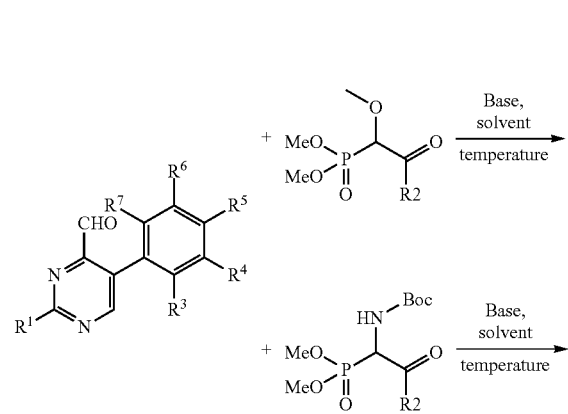

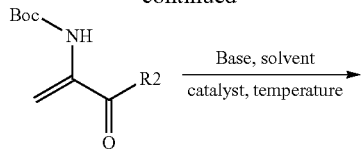

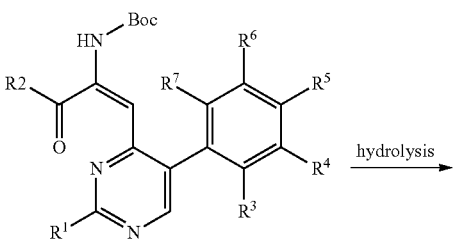

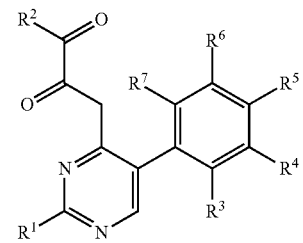

If, rather than the 2-methoxyacrylate, the corresponding 2-enamino acrylate (*Acta. Chem. Scand.* 50 (1996) 316; *Synthesis* 1989, 414) is used in a suitable solvent within temperature ranges between −78 degrees Celsius and 180 degrees Celsius, the enamino ester is obtained as intermediate, which is in turn hydrolyzable to the pyruvate (*J. Org. Chem.* 80 (2015) 2554).

A further alternative proceeds from the pyrimidine-4-carbaldehyde, which is converted via a Wittig-Horner reaction to the alkenyloxy acrylate or to the enamino acrylate and can be hydrolyzed as described above (*J. Org. Chem.* 80 (2015) 2554).

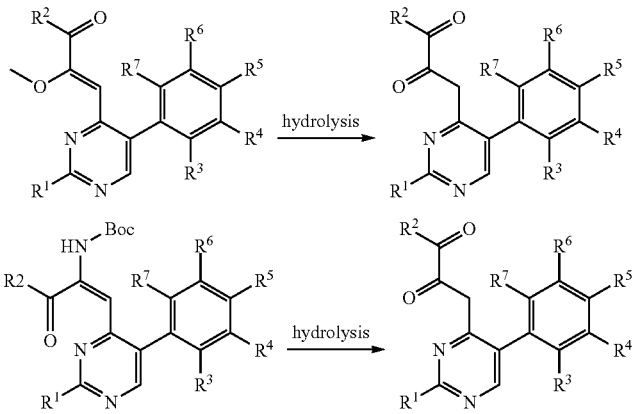

It is additionally possible to prepare the 2-keto acids or esters or amides via an iron-catalyzed addition from the corresponding 4-alkylpyrimidine (*Tetrahedron* 70 (2014) 3056) with subsequent oxidation, for example with the Dess-Martin reagent (*J. Org. Chem.* 81 (2016) 3890) or with the aid of copper acetate (*J. Org. Chem.* 79 (2014) 11735) or by a Swern oxidation (WO 2013057468).

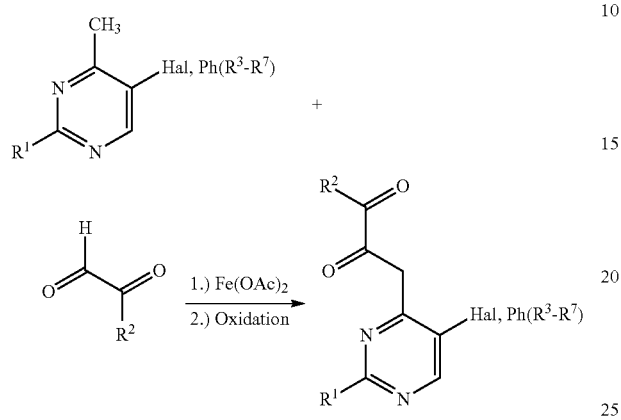

In addition, it is possible to deprotonate pyrimidine alkyl compounds with strong bases, for example lithium diisopropylamide, and react them with oxalic ester derivatives (*Journal of Organic Chemistry* 80 (2015) 2554, *Bioorg. Med. Chem.* 14 (2006) 8420).

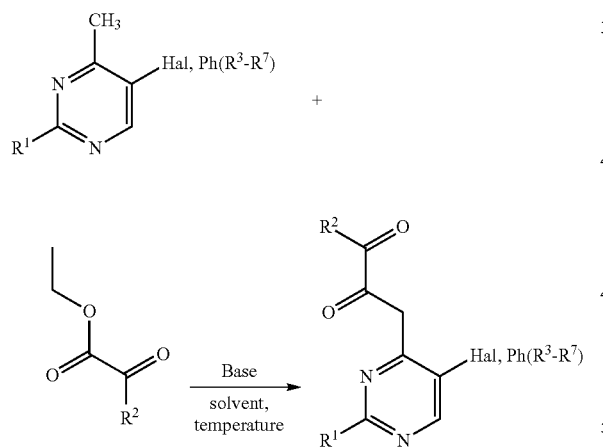

In addition, it is possible to convert the compounds of the invention to the desired target compounds (I) by reacting with an oxalic ester derivative, for example with the following orthoester (J. C. Medina et al., *Tetrahedron Lett.* 49 (2008) 1768; J. Scherkenbeck et al., *J. Org. Chem.* 80 (2015) 2554-2561):

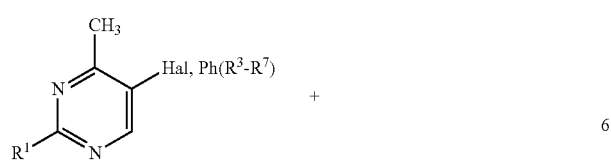

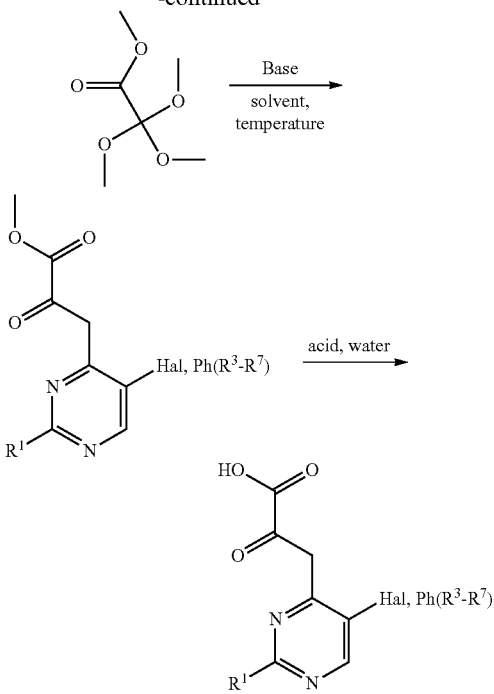

Inventive carboxamide derivatives, carbohydrazides, methylidene hydrazides and optionally substituted N-hydroxycarboxamides (I) are synthesized from the corresponding acids by reaction with a coupling reagent, a base and the respective amine or hydrazine derivative.

A wide variety of different methods are available in the literature for this purpose (*Tetrahedron* 61 (2005) 10827; WO2006/105051, page 8).

Alkylidene hydrazides can be prepared, for example, by heating the primary hydrazide with an appropriate carbonyl compound (*Arch. Pharm. Chem. Life Sci.* 350 (2017) e1600256).

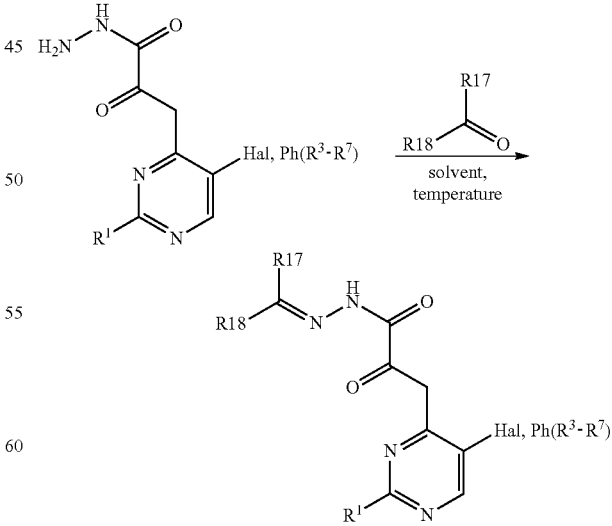

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Gunther Jung), Wiley, 1999, on pages 1 to 34.

The inventive compounds of the formula (I) (and/or salts thereof), referred to collectively as "compounds of the invention" hereinafter, have excellent herbicidal efficacy against a broad spectrum of economically important monocotyledonous and dicotyledonous annual harmful plants.

The present invention therefore also provides a method for controlling unwanted plants or for regulating the growth of plants, preferably in plant crops, in which one or more compound(s) of the invention is/are applied to the plants (for example harmful plants such as monocotyledonous or dicotyledonous weeds or unwanted crop plants), the seed (for example grains, seeds or vegetative propagules such as tubers or shoot parts with buds) or the area on which the plants grow (for example the area under cultivation). The compounds of the invention can be deployed, for example, prior to sowing (if appropriate also by incorporation into the soil), prior to emergence or after emergence. Specific examples of some representatives of the monocotyledonous and dicotyledonous weed flora which can be controlled by the compounds of the invention are as follows, though the enumeration is not intended to impose a restriction to particular species.

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds of the invention are applied to the soil surface before germination, either the weed seedlings are prevented completely from emerging or the weeds grow until they have reached the cotyledon stage, but then stop growing.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

The compounds of the invention can be selective in crops of useful plants and can also be employed as non-selective herbicides.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain active compounds used in agroindustry, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further particular properties lie in tolerance or resistance to abiotic stress factors, for example heat, cold, drought, salinity and ultraviolet radiation.

Preference is given to using the inventive compounds of the formula (I) or salts thereof in economically important transgenic crops of useful and ornamental plants.

The compounds of the formula (I) can be used as herbicides in crops of useful plants which are resistant, or have been made resistant by genetic engineering, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods (see, for example, EP 0221044, EP 0131624). What has been described are, for example, several cases of genetic modifications of crop plants for the purpose of modifying the starch synthesized in the plants (e.g. WO 92/011376 A, WO 92/014827 A, WO 91/019806 A), transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soya with the trade name or the designation Optimum™ GAT™ (Glyphosate ALS Tolerant), transgenic crop plants, for example cotton, capable of producing *Bacillus thuringiensis* toxins (Bt toxins), which make the plants resistant to particular pests (EP 0142924 A, EP 0193259 A), transgenic crop plants having a modified fatty acid composition (WO 91/013972 A), genetically modified crop plants having novel constituents or secondary metabolites, for example novel phytoalexins, which cause an increase in disease resistance (EP 0309862 A, EP 0464461 A), genetically modified plants having reduced photorespiration, which have higher yields and higher stress tolerance (EP 0305398 A), transgenic crop plants which produce pharmaceutically or diagnostically important proteins ("molecular pharming"), transgenic crop plants which feature higher yields or better quality, transgenic crop plants which are distinguished by a combination, for example of the abovementioned novel properties ("gene stacking").

Numerous molecular biology techniques which can be used to produce novel transgenic plants with modified properties are known in principle; see, for example, I.

Potrykus and G. Spangenberg (eds), Gene Transfer to Plants, Springer Lab Manual (1995), Springer Verlag Berlin, Heidelberg or Christou, "Trends in Plant Science" 1 (1996) 423-431).

For such genetic manipulations, nucleic acid molecules which allow mutagenesis or sequence alteration by recombination of DNA sequences can be introduced into plasmids. With the aid of standard methods, it is possible, for example, to undertake base exchanges, remove part sequences or add natural or synthetic sequences. To join the DNA fragments with one another, adapters or linkers can be placed onto the fragments, see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., *Plant J.* 1 (1991), 95-106). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants. Thus, transgenic plants can be obtained whose properties are altered by overexpression, suppression or inhibition of homologous (=natural) genes or gene sequences or expression of heterologous (=foreign) genes or gene sequences.

The compounds (I) of the invention can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds, or to any desired combinations of these active compounds.

The compounds of the invention can be used with particular preference in transgenic crop plants which are resistant to a combination of glyphosates and glufosinates, glyphosates and sulfonylureas or imidazolinones. Most preferably, the compounds of the invention can be used in transgenic crop plants such as corn or soya with the trade name or the designation Optimum™ GAT™ (glyphosate ALS tolerant), for example.

When the active compounds of the invention are employed in transgenic crops, not only do the effects towards harmful plants observed in other crops occur, but frequently also effects which are specific to the application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the inventive compounds of the formula (I) as herbicides for controlling harmful plants in transgenic crop plants.

The compounds of the invention can be applied in the form of wettable powders, emulsifiable concentrates, sprayable solutions, dusting products or granules in the customary formulations. The invention therefore also provides herbicidal and plant-growth-regulating compositions which comprise the compounds of the invention.

The compounds of the invention can be formulated in various ways, according to the biological and/or physico-chemical parameters required. Possible formulations include, for example; wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes. These individual formulation types are known in principle and are described, for example, in: Winnacker-Küchler, "Chemische Technologic [Chemical Technology]", Volume 7, C. Hanser Verlag Munich, 4th Ed. 1986, Wade van Valkenburg, "Pesticide Formulations", Marcel Dekker, N.Y., 1973, K. Martens, "Spray Drying" Handbook, 3rd Ed. 1979, G. Goodwin Ltd. London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologic", volume 7, C. Hanser Verlag Munich, 4th Ed. 1986.

On the basis of these formulations, it is also possible to produce combinations with other active compounds, for example insecticides, acaricides, herbicides, fungicides, and also with safeners, fertilizers and/or growth regulators, for example in the form of a finished formulation or as a tank mix.

Active compounds which can be employed in combination with the compounds of the invention in mixed formulations or in the tank mix are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II or protoporphyrinogen oxidase, as are described in, for example, Weed Research 26 (1986) 441-445 or "The Pesticide Manual", 16th edition, The British Crop Protection Council and the Royal Soc. of Chemistry, 2006 and the literature cited therein. Known herbicides or plant growth regulators which can be combined with the compounds of the invention are, for example, the following, where said active compounds are designated either with their "common name" in accordance with the International Organization for Standardization (ISO) or with the chemical name or with the code number. They always encompass all the use forms, such as, for example, acids, salts, esters and also all isomeric forms such as stereoisomers and optical isomers, even if they are not mentioned explicitly.

Examples of such herbicidal mixing partners are:

acetochlor, acifluorfen, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyron, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthal-dimethyl, chlorsulfuron, cinidon, cinidon-ethyl, cinmethylin, cinosulfuron, clacyfos, clethodim, clodinafop, clodinafop-propargyl, clomazone, clomeprop, clopyralid, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D, 2,4-D-butotyl, -butyl, -dimethylammonium, -diolamin, -ethyl, 2-ethylhexyl, -isobutyl, -isooctyl, -isopropylammonium, -potassium, -triisopropanolammonium and -trolamine, 2,4-DB, 2,4-DB-butyl, -dimethylammonium, isooctyl, -potassium and -sodium, daimuron (dymron), dalapon, dazomet, n-decanol, desmedipham, detosylpyrazolate (DTP), dicamba, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromid, dithiopyr, diuron, DNOC, endothal, EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-9600, F-5231, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimi-dine-2,4(1H,3H)-dione, fenoxaprop, fenoxaprop-P, fenoxaprop-ethyl, fenoxaprop-P-ethyl, fenoxasulfone, fenquinotrione, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropanate, flupyrsulfuron, flupyrsulfuron-methyl-sodium, fluridone, flurochloridone, fluroxypyr, fluroxypyr-meptyl, flurtamone, fluthiacet, fluthiacet-methyl, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)-O-ethyl isopropylphosphoramidothioate, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxyniloctanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, lenacil, linuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, -dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-5950, i.e. N-[3-chloro-4-(1-methylethyl)phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, SL-261, sulcotrion, sulfentrazone, sulfometuron, sulfometuron-methyl, sulfosulfuron, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-dichloro-N-{2-[(4,6-dimethoxypyrimidin-2-yl)oxy] benzyl}aniline, and the following compounds:

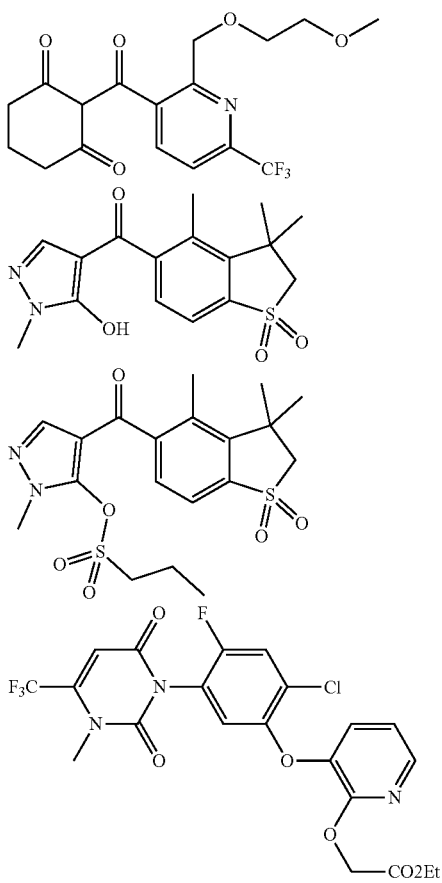

Examples of plant growth regulators as possible mixing partners are:

acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indole-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4 [(2-phenylethyl)amino]butyric acid, paclobutrazole, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Safeners which can be employed in combination with the inventive compounds of the formula (I) and optionally in combination with further active compounds such as insecticides, acaricides, herbicides, fungicides as listed above are preferably selected from the group consisting of:

S1) Compounds of the Formula (S1),

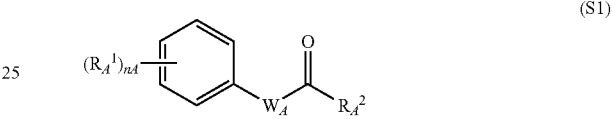

(S1)

where the symbols and indices are defined as follows:

$n_A$ represents a natural number from 0 to 5, preferably from 0 to 3;

$R_A^1$ represents halogen, $(C_1-C_4)$-alkyl, $(C_1-C_4)$-alkoxy, nitro or $(C_1-C_4)$-haloalkyl;

$W_A$ represents an unsubstituted or substituted divalent heterocyclic radical from the group of the partially unsaturated or aromatic five-membered heterocycles having 1 to 3 ring heteroatoms from the N and O group, where at least one nitrogen atom and at most one oxygen atom is present in the ring, preferably a radical from the group of $(W_A^1)$ to $(W_A^4)$,

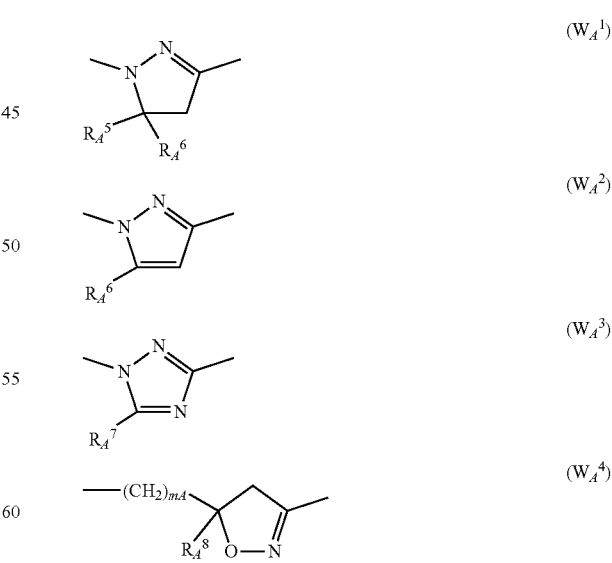

$m_A$ represents 0 or 1;

$R_A^2$ represents $OR_A^3$, $SR_A^3$ or $NR_A^3R_A^4$ or a saturated or unsaturated 3- to 7-membered heterocycle having at least one nitrogen atom and up to 3 heteroatoms, preferably from the group consisting of O and S, which is joined to the carbonyl group in (S1) via the nitrogen atom and is unsubstituted or substituted by radicals from the group consisting of $(C_1-C_4)$-alkyl, $(C_1-C_4)$-alkoxy or optionally substituted phenyl, preferably a radical of the formula $OR_A^3$, $NHR_A^4$ or $N(CH_3)_2$, especially of the formula $OR_A^3$;

$R_A^3$ represents hydrogen or an unsubstituted or substituted aliphatic hydrocarbon radical, preferably having a total of 1 to 18 carbon atoms;

$R_A^4$ represents hydrogen, $(C_1-C_6)$-alkyl, $(C_1-C_6)$-alkoxy or substituted or unsubstituted phenyl;

$R_A^5$ represents H, $(C_1-C_8)$-alkyl, $(C_1-C_8)$-haloalkyl, $(C_1-C_4)$-alkoxy-$(C_1-C_8)$-alkyl, cyano or $COOR_A^9$, where $R_A^9$ represents hydrogen, $(C_1-C_6)$-alkyl, $(C_1-C_8)$-haloalkyl, $(C_1-C_4)$-alkoxy-$(C_1-C_4)$-alkyl, $(C_1-C_6)$-hydroxyalkyl, $(C_3-C_{12})$-cycloalkyl or tri-$(C_1-C_4)$-alkylsilyl;

$R_A^6$, $R_A^7$, $R_A^8$ are identical or different and represent hydrogen, $(C_1-C_8)$-alkyl, $(C_1-C_8)$-haloalkyl, $(C_3-C_{12})$-cycloalkyl or substituted or unsubstituted phenyl;

preferably:

a) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

b) derivatives of dichlorophenylpyrazolecarboxylic acid (S1$^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxy late (S1-3), ethyl 1-(2,4-dichlorophenyl)-5-(1,1-dimethylethyl) pyrazole-3-carboxylate (S1-4) and related compounds as described in EP-A-333 131 and EP-A-269 806;

c) derivatives of 1,5-diphenylpyrazole-3-carboxylic acid (SP), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (S1-6) and related compounds as described in EP-A-268 554, for example;

d) compounds of the triazolecarboxylic acid type (S1$^d$), preferably compounds such as fenchlorazole (-ethyl ester), i.e. ethyl 1-(2,4-dichlorophenyl)-5-trichloromethyl-(1H)-1,2,4-triazole-3-carboxylate (S1-7), and related compounds as described in EP-A-174 562 and EP-A-346 620;

e) compounds of the 5-benzyl- or 5-phenyl-2-isoxazoline-3-carboxylic acid or of the 5,5-diphenyl-2-isoxazoline-3-carboxylic acid type (SP), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazoline-3-carboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Quinoline Derivatives of the Formula (S2), where the symbols and indices are defined as follows:

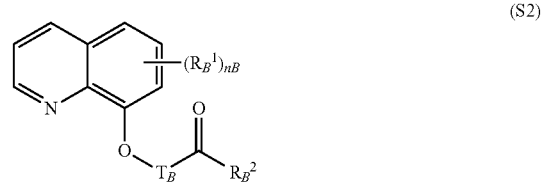

(S2)

$R_B^1$ represents halogen, $(C_1-C_4)$-alkyl, $(C_1-C_4)$-alkoxy, nitro or $(C_1-C_4)$-haloalkyl;

$n_B$ represents a natural number from 0 to 5, preferably from 0 to 3;

$R_B^2$ represents $OR_B^3$, $SR_B^3$ or $NR_B^3R_B^4$ or a saturated or unsaturated 3- to 7-membered heterocycle having at least one nitrogen atom and up to 3 heteroatoms, preferably from the group of O and S, which is joined via the nitrogen atom to the carbonyl group in (S2) and is unsubstituted or substituted by radicals from the group of $(C_1-C_4)$-alkyl, $(C_1-C_4)$-alkoxy or optionally substituted phenyl, preferably a radical of the formula $OR_B^3$, $NHR_B^4$ or $N(CH_3)_2$, especially of the formula $OR_B^3$;

$R_B^3$ represents hydrogen or an unsubstituted or substituted aliphatic hydrocarbon radical, preferably having a total of 1 to 18 carbon atoms;

$R_B^4$ represents hydrogen, $(C_1-C_6)$-alkyl, $(C_1-C_6)$-alkoxy or substituted or unsubstituted phenyl;

$T_B$ represents a $(C_1$ or $C_2)$-alkanediyl chain which is unsubstituted or substituted by one or two $(C_1-C_4)$-alkyl radicals or by [$(C_1-C_3)$-alkoxy]carbonyl;

preferably:

a) compounds of the 8-quinolinoxy acetic acid type (S2$^a$), preferably
1-methylhexyl (5-chloro-8-quinolinoxy)acetate ("cloquintocet-mexyl") (S2-1),
(1,3-dimethylbut-1-yl) (5-chloro-8-quinolinoxy)acetate (S2-2),
4-allyloxybutyl (5-chloro-8-quinolinoxy)acetate (S2-3),
1-allyloxyprop-2-yl (5-chloro-8-quinolinoxy)acetate (S2-4),
ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminoxy)-1-ethyl (5-chloro-8-quinolinoxy)acetate (S2-8), 2-oxoprop-1-yl (5-chloro-8-quinolinoxy)acetate (S2-9) and related compounds, as described in EP-A-86 750, EP-A-94 349 and EP-A-191 736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

b) compounds of the (5-chloro-8-quinolinoxy)malonic acid type (S2$^b$), preferably compounds such as diethyl (5-chloro-8-quinolinoxy)malonate, diallyl (5-chloro-8-quinolinoxy)malonate, methyl ethyl (5-chloro-8-quinolinoxy) malonate and related compounds, as described in EP-A-0 582 198.

S3) Compounds of the Formula (S3)

(S3)

where the symbols and indices are defined as follows:

$R_C^1$ represents $(C_1-C_4)$-alkyl, $(C_1-C_4)$-haloalkyl, $(C_2-C_4)$-alkenyl, $(C_2-C_4)$-haloalkenyl, $(C_3-C_7)$-cycloalkyl, preferably dichloromethyl;

$R_C^2$, $R_C^3$ are identical or different and represent hydrogen, $(C_1-C_4)$alkyl, $(C_2-C_4)$alkenyl, $(C_2-C_4)$alkynyl, $(C_1-C_4)$haloalkyl, $(C_2-C_4)$haloalkenyl, $(C_1-C_4)$alkylcarbamoyl-$(C_1-C_4)$alkyl, $(C_2-C_4)$alkenylcarbamoyl-$(C_1-C_4)$alkyl, $(C_1-C_4)$alkoxy-$(C_1-C_4)$alkyl, dioxolanyl-$(C_1-C_4)$alkyl, thiazolyl, furyl, furylalkyl, thienyl, piperidyl, substituted or unsubstituted phenyl, or $R_C^2$ and $R_C^3$ together form a substituted or unsubstituted heterocyclic ring, preferably an oxazolidine, thiazolidine, piperidine, morpholine, hexahydropyrimidine or benzoxazine ring;

preferably:

active compounds of the dichloroacetamide type, which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonon) or "BAS145138" or "LAB145138" (S3-9)

((RS)-1-dichloroacetyl-3,3,8a-trimethylperhydropyrrolo[1,2-a]pyrimidin-6-one) from BASF, "furilazole" or "MON 13900" ((RS)-3-dichloroacetyl-5-(2-furyl)-2,2-dimethyloxazolidine) (S3-10); and the (R) isomer thereof (S3-11).

S4) N-Acylsulfonamides of the Formula (S4) and Salts Thereof,

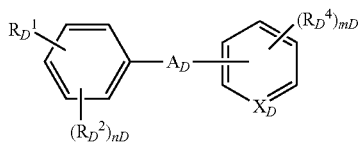

(S4)

in which the symbols and indices are defined as follows:
$A_D$ represents $SO_2—NR_D^3—CO$ or $CO—NR_D^3—SO_2$
$X_D$ represents CH or N;
$R_D^1$ represents $CO—NR_D^5R_D^6$ or $NHCO—R_D^7$;
$R_D^2$ represents halogen, $(C_1-C_4)$-haloalkyl, $(C_1-C_4)$-haloalkoxy, nitro, $(C_1-C_4)$-alkyl, $(C_1-C_4)$-alkoxy, $(C_1-C_4)$-alkylsulfonyl, $(C_1-C_4)$-alkoxycarbonyl or $(C_1-C_4)$-alkylcarbonyl;
$R_D^3$ represents hydrogen, $(C_1-C_4)$-alkyl, $(C_2-C_4)$-alkenyl or $(C_2-C_4)$-alkynyl;
$R_D^4$ represents halogen, nitro, $(C_1-C_4)$-alkyl, $(C_1-C_4)$-haloalkyl, $(C_1-C_4)$-haloalkoxy, $(C_3-C_6)$-cycloalkyl, phenyl, $(C_1-C_4)$-alkoxy, cyano, $(C_1-C_4)$-alkylthio, $(C_1-C_4)$-alkylsulfinyl, $(C_1-C_4)$-alkylsulfonyl, $(C_1-C_4)$-alkoxycarbonyl or $(C_1-C_4)$-alkylcarbonyl;

$R_D^5$ represents hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl, phenyl or 3- to 6-membered heterocyclyl containing $v_D$ heteroatoms from the group consisting of nitrogen, oxygen and sulfur, where the seven latter radicals are substituted by $v_D$ substituents from the group consisting of halogen, $(C_1-C_6)$-alkoxy, $(C_1-C_6)$-haloalkoxy, $(C_1-C_2)$-alkylsulfinyl, $(C_1-C_2)$-alkylsulfonyl, $(C_3-C_6)$-cycloalkyl, $(C_1-C_4)$-alkoxycarbonyl, $(C_1-C_4)$-alkylcarbonyl and phenyl and, in the case of cyclic radicals, also $(C_1-C_4)$-alkyl and $(C_1-C_4)$-haloalkyl;

$R_D^6$ represents hydrogen, $(C_1-C_6)$-alkyl, $(C_2-C_6)$-alkenyl or $(C_2-C_6)$-alkynyl, where the three latter radicals are substituted by $v_D$ radicals from the group consisting of halogen, hydroxyl, $(C_1-C_4)$-alkyl, $(C_1-C_4)$-alkoxy and $(C_1-C_4)$-alkylthio, or $R_D^5$ and $R_D^6$ together with the nitrogen atom carrying them form a pyrrolidinyl or piperidinyl radical;

$R_D^7$ represents hydrogen, $(C_1-C_4)$-alkylamino, di-$(C_1-C_4)$-alkylamino, $(C_1-C_6)$-alkyl, $(C_3-C_6)$-cycloalkyl, where the 2 latter radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;

$n_D$ represents 0, 1 or 2;
$m_D$ represents 1 or 2;
$v_D$ represents 0, 1, 2 or 3;

among these, preference is given to compounds of the N-acylsulfonamide type, for example of the formula (S4$^a$) below, which are known, for example, from WO-A-97/45016

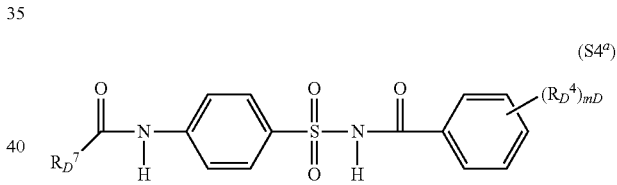

(S4$^a$)

in which
$R_D^7$ represents $(C_1-C_6)$-alkyl, $(C_3-C_6)$-cycloalkyl, where the 2 latter radicals are substituted by $v_D$ substituents from the group consisting of halogen, $(C_1-C_4)$-alkoxy, $(C_1-C_6)$-haloalkoxy and $(C_1-C_4)$-alkylthio and, in the case of cyclic radicals, also $(C_1-C_4)$-alkyl and $(C_1-C_4)$-haloalkyl;
$R_D^4$ represents halogen, $(C_1-C_4)$-alkyl, $(C_1-C_4)$-alkoxy, $CF_3$;
$m_D$ represents 1 or 2;
$v_D$ represents 0, 1, 2 or 3;
and also
acylsulfamoylbenzamides, for example of the formula (S4$^b$) below, which are known, for example, from WO-A-99/16744,

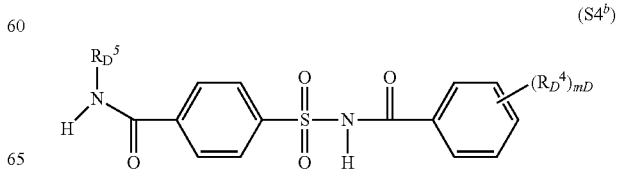

(S4$^b$)

e.g. those in which
$R_D^5$=cyclopropyl and $(R_D^4)$=2-OMe ("cyprosulfamide", S4-1),
$R_D^5$=cyclopropyl and $(R_D^4)$=5-Cl-2-OMe (S4-2),
$R_D^5$=ethyl and $(R_D^4)$=2-OMe (S4-3),
$R_D^5$=isopropyl and $(R_D^4)$=5-Cl-2-OMe (S4-4) and
$R_D^5$=isopropyl and $(R_D^4)$=2-OMe (S4-5)
and also
compounds of the N-acylsulfamoylphenylurea type, of the formula (S4c), which are known, for example, from EP-A-365484,

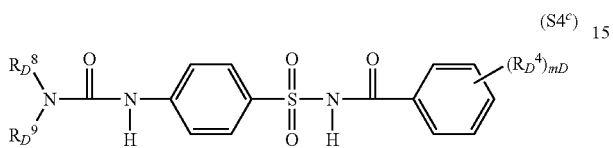
(S4$^c$)

in which
$R_D^8$ and $R_D^9$ independently of one another represent hydrogen, $(C_1-C_8)$-alkyl, $(C_3-C_8)$-cycloalkyl, $(C_3-C_6)$-alkenyl, $(C_3-C_6)$-alkynyl,
$R_D^4$ represents halogen, $(C_1-C_4)$-alkyl, $(C_1-C_4)$-alkoxy, $CF_3$,
$m_D$ represents 1 or 2;
for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea,
and also
N-phenylsulfonylterephthalamides of the formula (S4$^d$), which are known, for example, from CN 101838227,

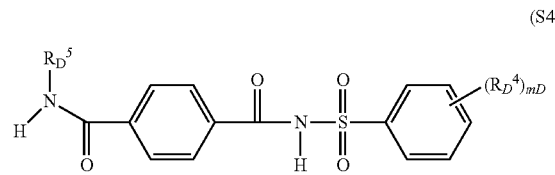
(S4$^d$)

e.g. those in which
$R_D^4$ represents halogen, $(C_1-C_4)$-alkyl, $(C_1-C_4)$-alkoxy, $CF_3$;
$m_D$ represents 1 or 2;
$R_D^5$ represents hydrogen, $(C_1-C_6)$-alkyl, $(C_3-C_6)$-cycloalkyl, $(C_2-C_6)$-alkenyl, $(C_2-C_6)$-alkynyl, $(C_5-C_6)$-cycloalkenyl.

S5) Active compounds from the class of the hydroxyaromatics and the aromatic-aliphatic carboxylic acid derivatives (S5), for example
ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicylic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example
1-methyl-3-(2-thienyl)-1,2-dihydroquinoxalin-2-one,
1-methyl-3-(2-thienyl)-1,2-dihydroquinoxaline-2-thione,
1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds of the formula (S7), as described in WO-A-1998/38856,

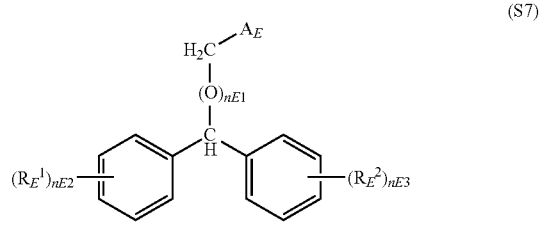
(S7)

in which the symbols and indices are defined as follows:
$R_E^1$, $R_E^2$ independently of one another are halogen, $(C_1-C_4)$-alkyl, $(C_1-C_4)$-alkoxy, $(C_1-C_4)$-haloalkyl, $(C_1-C_4)$-alkylamino, di-$(C_1-C_4)$-alkylamino, nitro;
$A_E$ represents $COOR_E^3$ or $COSR_E^4$
$R_E^3$, $R_E^4$ independently of one another represent hydrogen, $(C_1-C_4)$-alkyl, $(C_2-C_6)$-alkenyl, $(C_2-C_4)$-alkynyl, cyanoalkyl, $(C_1-C_4)$-haloalkyl, phenyl, nitrophenyl, benzyl, halobenzyl, pyridinylalkyl and alkylammonium,
$n_E^1$ represents 0 or 1
$n_E^2$, $n_E^3$ independently of one another represent 0, 1 or 2, preferably:
diphenylmethoxyacetic acid,
ethyl diphenylmethoxyacetate,
methyl diphenylmethoxyacetate (CAS reg. no. 41858-19-9) (S7-1).

S8) Compounds of the formula (S8), as described in WO-A-98/27049,

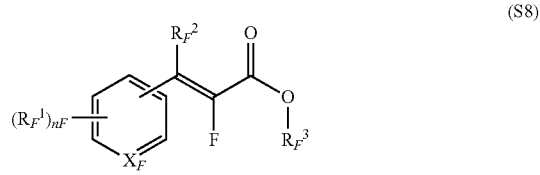
(S8)

in which
$X_F$ represents CH or N,
$n_F$ in the case that $X_F$=N represents an integer from 0 to 4 and
in the case that $X_F$=CH represents an integer from 0 to 5,
$R_F^1$ represents halogen, $(C_1-C_4)$-alkyl, $(C_1-C_4)$-haloalkyl, $(C_1-C_4)$-alkoxy, $(C_1-C_4)$-haloalkoxy, nitro, $(C_1-C_4)$-alkylthio, $(C_1-C_4)$-alkylsulfonyl, $(C_1-C_4)$-alkoxycarbonyl, optionally substituted phenyl, optionally substituted phenoxy,
$R_F^2$ represents hydrogen or $(C_1-C_4)$-alkyl,
$R_F^3$ represents hydrogen, $(C_1-C_8)$-alkyl, $(C_2-C_4)$-alkenyl, $(C_2-C_4)$-alkynyl or aryl, where each of the abovementioned carbon-containing radicals is unsubstituted or substituted by one or more, preferably up to three identical or different radicals from the group consisting of halogen and alkoxy; or salts thereof, preferably compounds in which $X_F$ represents CH, $n_F$ represents an integer from 0 to 2, $R_F^1$ represents halogen, ($C_1$-$C_4$)-alkyl, ($C_1$-$C_4$)-haloalkyl, ($C_1$-$C_4$)-alkoxy, ($C_1$-$C_4$)-haloalkoxy, $R_F^2$ represents hydrogen or ($C_1$-$C_4$)-alkyl, $R_F^3$ represents hydrogen, ($C_1$-$C_8$)-alkyl, ($C_2$-$C_4$)-alkenyl, ($C_2$-$C_4$)-alkynyl or aryl, where each of the abovementioned carbon-containing radicals is unsubstituted or substituted by one or more, preferably up to three identical or different radicals from the group consisting of halogen and alkoxy, or salts thereof.

S9) Active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS reg. no. 219479-18-2), 1,2-dihydro-4-hydroxy-1-methyl-3-(5-tetrazolylcarbonyl)-2-quinolone (CAS Reg. No. 95855-00-8), as described in WO-A-1999/000020.

S10) Compounds of the formulae (S10$^a$) or (S10$^b$) as described in WO-A-2007/023719 and WO-A-2007/023764

(S10$^a$)

(S10$^b$)

in which $R_G^1$ represents halogen, ($C_1$-$C_4$)-alkyl, methoxy, nitro, cyano, $CF_3$, $OCF_3$, $Y_G$, $Z_G$ independently of one another represent O or S, $n_G$ represents an integer from 0 to 4, $R_G^2$ represents ($C_1$-$C_{16}$)-alkyl, ($C_2$-$C_6$)-alkenyl, ($C_3$-$C_6$)-cycloalkyl, aryl; benzyl, halobenzyl, $R_G^3$ represents hydrogen or ($C_1$-$C_6$)-alkyl.

S11) Active compounds of the oxyimino compounds type (S11), which are known as seed-dressing agents, for example "oxabetrinil" ((Z)-1,3-dioxolan-2-ylmethoxyimino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone 0-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino (phenyl)acetonitrile) (S11-3), which is known as a seed-dressing safener for millet/sorghum against metolachlor damage.

S12) Active compounds from the class of the isothiochromanones (S12), for example methyl [(3-oxo-1H-2-benzothiopyran-4 (3H)-ylidene)methoxy]acetate (CAS Reg. No. 205121-04-6) (512-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (513-2), which is known as a safener for pretilachlor in sown rice, "flurazole" (benzyl 2-chloro-4-trifluoromethyl-1,3-thiazole-5-carboxy late) (S13-3), which is known as a seed-dressing safener for millet/sorghum against alachlor and metolachlor damage, "CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS Reg. No. 96420-72-3) (2-dichloromethyl-2-methyl-1,3-dioxolane) (513-5) from Nitrokemia, which is known as a safener for corn, "MG 838" (CAS Reg. No. 133993-74-5) (2-propenyl 1-oxa-4-azaspiro[4.5]decane-4-carbodithioate) (S13-6) from Nitrokemia, "disulfoton" (O,O-diethyl S-2-ethylthioethylphosphorodithioate) (S13-7), "dietholate" (O,O-diethyl O-phenyl phosphorothioate) (513-8), "mephenate" (4-chlorophenyl methylcarbamate) (S13-9).

S14) Active compounds which, in addition to herbicidal action against harmful plants, also have safener action on crop plants such as rice, for example "dimepiperate" or "MY 93" (S-1-methyl 1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as a safener for rice against damage by the herbicide imazosulfuron, "cumyluron"="JC 940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof (S15)

as described in WO-A-2008/131861 and WO-A-2008/131860 in which $R_H^1$ represents a ($C_1$-$C_6$)-haloalkyl radical and $R_H^2$ represents hydrogen or halogen and $R_H^3$, $R_H^4$ independently of one another represent hydrogen, ($C_1$-$C_{16}$)-alkyl, ($C_2$-$C_{16}$)-alkenyl or ($C_2$-$C_{16}$)-alkynyl, where each of the 3 latter radicals is unsubstituted or substituted by one or more radicals from the group of halogen, hydroxyl, cyano, ($C_1$-$C_4$)-alkoxy, ($C_1$-$C_4$)-haloalkoxy, ($C_1$-$C_4$)-alkylthio, ($C_1$-$C_4$)-alkylamino, di[($C_1$-

$C_4$)-alkyl]amino, [($C_1$-$C_4$)-alkoxy]carbonyl, [($C_1$-$C_4$)-haloalkoxy]carbonyl, ($C_3$-$C_6$)-cycloalkyl which is unsubstituted or substituted, phenyl which is unsubstituted or substituted, and heterocyclyl which is unsubstituted or substituted, or ($C_3$-$C_6$)-cycloalkyl, ($C_4$-$C_6$)-cycloalkenyl, ($C_3$-$C_6$)-cycloalkyl fused on one side of the ring to a 4 to 6-membered saturated or unsaturated carbocyclic ring, or ($C_4$-$C_6$)-cycloalkenyl fused on one side of the ring to a 4 to 6-membered saturated or unsaturated carbocyclic ring, where each of the 4 latter radicals is unsubstituted or substituted by one or more radicals from the group consisting of halogen, hydroxyl, cyano, ($C_1$-$C_4$)-alkyl, ($C_1$-$C_4$)-haloalkyl, ($C_1$-$C_4$)-alkoxy, ($C_1$-$C_4$)-haloalkoxy, ($C_1$-$C_4$)-alkylthio, ($C_1$-$C_4$)-alkylamino, di[($C_1$-$C_4$)-alkyl]amino, [($C_1$-$C_4$)-alkoxy]carbonyl, [($C_1$-$C_4$)-haloalkoxy]carbonyl, ($C_3$-$C_6$)-cycloalkyl which is unsubstituted or substituted, phenyl which is unsubstituted or substituted, and heterocyclyl which is unsubstituted or substituted, or $R_H^3$ represents ($C_1$-$C_4$)-alkoxy, ($C_2$-$C_4$)-alkenyloxy, ($C_2$-$C_6$)-alkynyloxy or ($C_2$-$C_4$)-haloalkoxy and $R_H^4$ represents hydrogen or ($C_1$-$C_4$)-alkyl or $R_H^3$ and $R_H^4$ together with the directly attached nitrogen atom represent a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, ($C_1$-$C_4$)-alkyl, ($C_1$-$C_4$)-haloalkyl, ($C_1$-$C_4$)-alkoxy, ($C_1$-$C_4$)-haloalkoxy and ($C_1$-$C_4$)-alkylthio.

S16) Active compounds which are used primarily as herbicides but also have safener action on crop plants, for example (2,4-dichlorophenoxy)acetic acid (2,4-D),
(4-chlorophenoxy)acetic acid,
(R,S)-2-(4-chloro-o-tolyloxy)propionic acid (mecoprop),
4-(2,4-dichlorophenoxy)butyric acid (2,4-DB),
(4-chloro-o-tolyloxy)acetic acid (MCPA),
4-(4-chloro-o-tolyloxy)butyric acid,
4-(4-chlorophenoxy)butyric acid,
3,6-dichloro-2-methoxybenzoic acid (dicamba),
1-(ethoxycarbonyl)ethyl 3,6-dichloro-2-methoxybenzoate (lactidichlor-ethyl).

Particularly preferred safeners are mefenpyr-diethyl, cyprosulfamide, isoxadifen-ethyl, cloquintocet-mexyl and dichlormid.

Wettable powders are preparations uniformly dispersible in water which, in addition to the active compound and apart from a diluent or inert substance, also comprise surfactants of ionic and/or nonionic type (wetting agent, dispersant), e.g. polyethoxylated alkylphenols, polyethoxylated fatty alcohols, polyethoxylated fatty amines, fatty alcohol polyglycolethersulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatuses such as hammer mills, blower mills and air jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan esters, for example sorbitan fatty acid esters, or polyoxyethylene sorbitan esters, for example polyoxyethylene sorbitan fatty esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active compound onto granular inert material capable of adsorption or by applying active compound concentrates to the surface of carrier substances, such as sand, kaolinites or granular inert material, by means of adhesives, for example polyvinyl alcohol, sodium polyacrylate or mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray-Drying Handbook" 3rd Ed. 1979, G. Goodwin Ltd., London, I. E. Browning, "Agglomeration", Chemical and Engineering 1967, pages 147 ff.; "Perry's Chemical Engineer's Handbook", 5th Ed., McGraw-Hill, New York 1973, pp. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations contain generally 0.1 to 99% by weight, especially 0.1 to 95% by weight, of compounds of the invention. In wettable powders, the active compound concentration is, for example, about 10 to 90% by weight, the remainder to 100% by weight consisting of customary formulation constituents. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound;

sprayable solutions contain about 0.05% to 80% by weight, preferably 2% to 50% by weight of active compound. In the case of water-dispersible granules, the active compound content depends partially on whether the active compound is in liquid or solid form and on which granulation auxiliaries, fillers, etc., are used. In the water-dispersible granules, the content of active compound is, for example, between 1 and 95% by weight, preferably between 10 and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and also with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The required application rate of the compounds of the formula (I) varies with the external conditions, including, inter alia, temperature, humidity and the type of herbicide used. It can vary within wide limits, for example between 0.001 and 1.0 kg/ha or more of active substance, but it is preferably between 0.005 and 750 g/ha.

A carrier is a natural or synthetic, organic or inorganic substance with which the active compounds are mixed or combined for better applicability, in particular for application to plants or plant parts or seed. The carrier, which may be solid or liquid, is generally inert and should be suitable for use in agriculture. Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. It is likewise possible to use mixtures of such carriers. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Suitable liquefied gaseous extenders or carriers are liquids which are gaseous at standard temperature and under atmospheric pressure, for example aerosol propellants such as halogenated hydrocarbons, or else butane, propane, nitrogen and carbon dioxide.

In the formulations, it is possible to use tackifiers such as carboxymethylcellulose, natural and synthetic polymers in the form of powders, granules or latices, such as gum arabic, polyvinyl alcohol and polyvinyl acetate, or else natural phospholipids such as cephalins and lecithins, and synthetic phospholipids. Further additives may be mineral and vegetable oils.

When the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The compositions of the invention may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is necessary if one of the active compounds and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active compounds can be combined with any solid or liquid additive commonly used for formulation purposes. In general, the compositions and formulations of the invention contain between 0.05 and 99% by weight, 0.01 and 98% by weight, preferably between 0.1 and 95% by weight, more preferably between 0.5 and 90% active compound, most preferably between 10 and 70 percent by weight. The active compounds or compositions of the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, sprayable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be produced in a manner known per se, for example by mixing the active compounds with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The compositions of the invention include not only formulations which are already ready for use and can be deployed with a suitable apparatus onto the plant or the seed, but also commercial concentrates which have to be diluted with water prior to use.

The active compounds of the invention may be present as such or in their (commercial standard) formulations, or else in the use forms prepared from these formulations as a mixture with other (known) active compounds, such as insecticides, attractants, sterilants, bactericides, acaricides, nematicides, fungicides, growth regulators, herbicides, fertilizers, safeners or semiochemicals.

The inventive treatment of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

As also described below, the treatment of transgenic seed with the active compounds or compositions of the invention is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis.*

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, when treating the seed, it has to be ensured that the amount of the composition of the invention and/or further additives applied to the seed is chosen such that the germination of the seed is not impaired and the plant which arises therefrom is not damaged. This has to be ensured particularly in the case of active compounds which can exhibit phytotoxic effects at certain application rates.

The compositions of the invention can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. Nos. 4,272,417 A, 4,245,432 A, 4,808,430, 5,876,739, US 2003/0176428 A1, WO 2002/080675 A1, WO 2002/028186 A2.

The active compounds of the invention can be converted to the customary seed-dressing formulations, such as solutions, emulsions, suspensions, powders, foams, slurries or other coating compositions for seed, and also ULV formulations.

These formulations are produced in a known manner, by mixing the active compounds with customary additives, for example customary extenders and solvents or diluents, dyes, wetting agents, dispersants, emulsifiers, antifoams, preservatives, secondary thickeners, adhesives, gibberellins, and also water. Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C. I. Solvent Red 1.

Useful wetting agents which may be present in the seed-dressing formulations usable in accordance with the invention are all substances which promote wetting and which are customary for the formulation of agrochemically active compounds. Alkyl naphthalenesulfonates, such as diisopropyl or diisobutyl naphthalenesulfonates, can be used with preference.

Suitable dispersants and/or emulsifiers which may be present in the seed-dressing formulations usable in accordance with the invention are all nonionic, anionic and cationic dispersants customary for the formulation of agrochemically active compounds. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances usable for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

The seed-dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For the treatment of seed with the seed-dressing formulations usable in accordance with the invention or with the preparations prepared therefrom by addition of water, useful equipment is all mixing units usable customarily for seed dressing. Specifically, the seed dressing procedure is to place the seed into a mixer, to add the particular desired amount of seed-dressing formulations, either as such or after prior dilution with water, and to mix them until the formulation is distributed homogeneously on the seed. If appropriate, this is followed by a drying operation.

The active compounds of the invention, given good plant compatibility, favorable homeotherm toxicity and good environmental compatibility, are suitable for protection of plants and plant organs, for increasing harvest yields, and for improving the quality of the harvested crop. They can preferably be used as crop protection agents. They are active against normally sensitive and resistant species and also against all or specific stages of development.

Plants which can be treated in accordance with the invention include the following main crop plants: corn, soya bean, cotton, *Brassica* oil seeds such as *Brassica napus* (e.g. Canola), *Brassica rapa, B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example *Rosaceae* sp. (for example pome fruits such as apples and pears, but also stone fruits such as apricots, cherries, almonds and peaches, and berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes, potatoes, peppers, aubergines), *Liliaceae* sp., *Compositae* sp. (for example lettuce, artichokes and chicory including root chicory, endive or common chicory), *Umbelliferae* sp. (for example carrots, parsley, celery and celeriac), *Cucurbitaceae* sp. (for example cucumbers including gherkins, pumpkins, watermelons, calabashes and melons), *Alliaceae* sp. (for example leeks and onions), *Cruciferae* sp. (for example white cabbage, red cabbage, broccoli, cauliflower, Brussels sprouts, pak choi, kohlrabi, radishes, horseradish, cress and chinese cabbage), *Leguminosae* sp. (for example peanuts, peas, and beans for example runner beans and broad beans), *Chenopodiaceae* sp. (for example Swiss chard, fodder beet, spinach, beetroot), *Malvaceae* (for example okra), *Asparagaceae* (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding techniques, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") which have been grown by conventional breeding, by mutagenesis or by recombinant DNA techniques. They may be cultivars, varieties, biotypes and genotypes.

The treatment method of the invention can be used for the treatment of genetically modified organisms (GMOs), e.g. plants or seeds. Genetically modified plants (or transgenic plants) are plants in which a heterologous gene has been stably integrated into the genome. The term "heterologous gene" means essentially a gene which is provided or assembled outside the plant and which, upon introduction into the nuclear genome, the chloroplast genome or the mitochondrial genome, imparts to the transformed plant novel or improved agronomical or other traits because it expresses a protein or polypeptide of interest or another gene which is present in the plant, or other genes which are present in the plant are down-regulated or switched off (for example by means of antisense technology, co-suppression technologies or RNAi technologies [RNA interference]). A heterologous gene that is located in the genome is also called a transgene. A transgene that is defined by its specific presence in the plant genome is called a transformation or transgenic event.

Depending on the plant species or plant cultivars, their location and growth conditions (soils, climate, vegetation period, diet), the inventive treatment may also result in superadditive ("synergistic") effects.

For example, the following effects which exceed the effects actually to be expected are possible: reduced application rates and/or widened spectrum of activity and/or increased efficacy of the active compounds and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf color, earlier flowering, higher quality and/or a higher nutritional value of the harvested products, higher sugar concentration within the fruits, better storage stability and/or processability of the harvested products.

Plants and plant cultivars which are preferably treated in accordance with the invention include all plants which have genetic material which imparts particularly advantageous, useful traits to these plants (whether obtained by breeding and/or biotechnological means).

Examples of nematode-resistant plants are described, for example, in the following U.S. patent application Ser. Nos. 11/765,491, 11/765,494, 10/926,819, 10/782,020, 12/032, 479, 10/783,417, 10/782,096, 11/657,964, 12/192,904, 11/396,808, 12/166,253, 12/166,239, 12/166,124, 12/166, 209, 11/762,886, 12/364,335, 11/763,947, 12/252,453, 12/209,354, 12/491,396 and 12/497,221.

Plants that may be treated according to the invention are hybrid plants that already express the characteristics of heterosis, or hybrid effect, which results in generally higher yield, vigor, better health and resistance towards biotic and abiotic stress factors. Such plants are typically produced by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in corn) be produced by detasselling (i.e. the mechanical removal of the male reproductive organs or male flowers) but, more typically, male sterility is the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male crossbreeding parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. Thus, for example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, *Science*, 221, 370-371), the CP4 gene of the bacterium *Agrobacterium* sp. (Barry et al., 1992, *Curr. Topics Plant Physiol.* 7, 139-145), the genes encoding a *Petunia* EP SPS (Shah et al., 1986, *Science* 233, 478-481), a tomato EPSPS (Gasser et al., 1988, *J. Biol. Chem.* 263, 4280-4289) or an *Eleusine* EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally-occurring mutations of the abovementioned genes. Plants which express EPSPS genes which impart glyphosate tolerance have been described. Plants which express other genes which impart glyphosate tolerance, for example decarboxylase genes, have been described.

Other herbicide-resistant plants are for example plants made tolerant to herbicides inhibiting the enzyme glutamine synthase, such as bialaphos, phosphinothricin or glufosinate. Such plants can be obtained by expressing an enzyme detoxifying the herbicide or a mutant of the glutamine synthase enzyme that is resistant to inhibition. One example of such an effective detoxifying enzyme is an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite inhibition of the native HPPD enzyme by the HPPD inhibitor. Such plants are described in WO 99/34008 and WO 02/36787. Tolerance of plants to HPPD inhibitors can also be improved by transforming plants with a gene encoding a prephenate dehydrogenase enzyme in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Other herbicide-resistant plants are plants which have been rendered tolerant to acetolactate synthase (ALS) inhibitors. Known ALS inhibitors include, for example, sulfonylurea, imidazolinone, triazolopyrimidines, pyrimidinyloxy (thio)benzoates, and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed *Science* 2002, 50, 700-712). The production of sulfonylurea-tolerant plants and imidazolinone-tolerant plants has been described. Further sulfonylurea- and imidazolinone-tolerant plants have also been described.

Further plants tolerant to imidazolinones and/or sulfonylureas can be obtained by induced mutagenesis, by selection in cell cultures in the presence of the herbicide or by mutation breeding (cf., for example, for soya beans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;

b. plants which contain a stress tolerance-enhancing transgene capable of reducing the expression and/or the activity of the PARG-encoding genes of the plants or plant cells;

c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage stability of the harvested product and/or altered properties of specific components of the harvested product such as, for example:

1) Transgenic plants which synthesize a modified starch which, in its physicochemical characteristics, in particular the amylose content or the amylose/amylopectin ratio, the degree of branching, the average chain length, the side chain distribution, the viscosity behavior, the gelling strength, the starch granule size and/or the starch granule morphology, is changed in comparison with the synthesized starch in wild-type plant cells or plants, so that this modified starch is better suited to specific applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

4) Transgenic plants or hybrid plants such as onions with particular properties, such as "high soluble solids content", "low pungency" (LP) and/or "long storage" (LS).

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;

b) plants, such as cotton plants, which contain an altered form of rsw2 or rsw3 homologous nucleic acids, such as cotton plants with an increased expression of sucrose phosphate synthase;

c) plants, such as cotton plants, with increased expression of sucrose synthase;

d) plants, such as cotton plants, wherein the timing of the plasmodesmatal gating at the base of the fiber cell is altered, for example through downregulation of fiber-selective β-1, 3-glucanase;

e) plants, such as cotton plants, which have fibers with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil characteristics and include:

a) plants, such as oilseed rape plants, which produce oil having a high oleic acid content;

b) plants, such as oilseed rape plants, which produce oil having a low linolenic acid content;

c) plants, such as oilseed rape plants, which produce oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/notreg.html. At the filing date of this application, the petitions with the following information were either granted or pending at APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which non-regulated status is being requested.

APHIS documents: Various documents which have been published by APHIS with regard to the petition or can be obtained from APHIS on request.

Particularly useful transgenic plants which can be treated in accordance with the invention are plants which comprise one or more genes which code for one or more toxins, for example the transgenic plants which are sold under the following trade names: YIELD GARD® (for example corn, cotton, soya beans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants include corn varieties, cotton varieties and soya bean varieties which are available under the following trade names: Roundup Ready® (tolerance to glyphosates, for example corn, cotton, soya beans), Liberty Link® (tolerance to phosphinothricin, for example oilseed rape), IMI® (tolerance to imidazolinone) and SCS® (tolerance to sulfonylurea), for example corn. Herbicide-resistant plants (plants bred in a conventional manner for herbicide tolerance) which may be mentioned include the varieties sold under the name Clearfield® (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gmc.

org/index.php?evidcode=&hstIDXCode=&gType=&Abbr-Code=&atCode=&stCode=&colDCode=&action=gm_crop_database&mode=Submit).

The examples which follow elucidate more particularly the invention.

A. CHEMICAL EXAMPLES

Preparation of ethyl 3-[5-(2-chlorophenyl)-2-cyclopropylpyrimidin-4-yl]-2-oxopropanoate (Example II-099)

300 mg (1.22 mmol) of 5-(2-chlorophenyl)-2-cyclopropyl-4-methylpyrimidine and 230 mg (1.59 mmol) of diethyl oxalate are dissolved in THF (8 ml) under nitrogen. Subsequently, at a temperature of 0-10° C., 1.59 ml of 1 molar LiHDMS solution (1.59 mmol) is added. After 2 h at 20° C., the reaction mixture is worked up by means of extraction with ethyl acetate and water. After separation on silica gel, 63 mg of the desired product is obtained as a yellowish solid. $^1$H-NMR (CDCl$_3$, 400 MHz): 8.33 (s, 1H), 7.55-7.20 (m, 4H), 6.11 (s, 1H), 4.3 (q, 2H), 2.23 (m, 1H), 1.35 (t, 3H), 1.30-1.2 (m, 4H).

Preparation of 3-[5-(2-chlorophenyl)-2-cyclopropylpyrimidin-4-yl]-N,N-dimethyl-2-oxopropanamide (Example I-139)

To an initial charge of 300 mg (1.23 mmol) of 5-(2-chlorophenyl)-2-cyclopropyl-4-methylpyrimidine and 214 mg (1.41 mmol) of ethyl (dimethylamino)(oxo)acetate in 4 ml of DMF under nitrogen was added 108 mg (2.70 mmol) of 60% sodium hydride. After stirring at room temperature for 12 h, the reaction is hydrolyzed with 221 mg (3.68 mmol) of acetic acid, diluted with water and extracted with ethyl acetate. After the organic phase has been dried over sodium sulfate and purified using silica gel, 67 mg of 3-[5-(2-chlorophenyl)-2-cyclopropylpyrimidin-4-yl]-N,N-dimethyl-2-oxopropanamide are obtained.

Preparation of tert-butyl 2-{3-[5-(2-chlorophenyl)-2-cyclopropylpyrimidin-4-yl]-2-oxopropanoyl}-1-methylhydrazinecarboxylate (Example IV-137)

An initial charge of 362 mg (1.4 mmol) of tert-butyl 2-[ethoxy(oxo)acetyl]-1-methylhydrazinecarboxylate and 300 mg (1.2 mmol) of 5-(2-chlorophenyl)-2-cyclopropyl-4-methylpyrimidine in 8 ml of dry THF is cooled down to 0° C. under nitrogen, and 4.045 ml (4 mmol) of a 1 molar lithium hexamethyldisilazide solution is added. After the reaction has ended, 0.281 ml (4.9 mmol) of glacial acetic acid is added, and the mixture is diluted with ethyl acetate and washed with water. After column chromatography purification, 329 mg of the desired target compound is obtained in solid form.

Preparation of 3-[5-(2-chloro-6-fluorophenyl)-2-cyclopropylpyrimidin-4-yl]-1-(piperidin-1-yl)propane-1,2-dione (Example I-146)

Analogously to example IV-137, 80 mg (0.30 mmol) of 5-(2-chloro-6-fluorophenyl)-2-cyclopropyl-4-methylpyrimidine and 75 mg (98%; 0.39 mmol) of ethyl oxo(piperidin-1-yl)acetate, after column chromatography purification on silica gel, give 45 mg of the desired target compound as a yellowish oil. (CDCl$_3$, 400 MHz): 8.03 (s, 1H), 7.39-7.08 (m, 3H), 5.3 (s, 1H), 3.55-3.50 (m, 4H), 2.15-2.08 (m, 1H), 1.67-1.55 (m, 6H), 1.30-1.22 (m, 4H).

Preparation of methyl 3-[2-cyclopropyl-5-(2,6-dichlorophenyl)pyrimidin-4-yl]-2-oxopropanoate (Example II-542)

To 230 mg (0.82 mmol) of 2-cyclopropyl-5-(2,6-dichlorophenyl)-4-methylpyrimidine under nitrogen is added 1.0 ml (0.98 mmol) of lithium hexamethylsisilazide at −78° C., and the mixture is warmed to −30° C. and reacted with 149 mg (0.90 mmol) of methyl trimethoxyacetate. After the reaction has ended, hydrolysis is effected at that temperature with 0.19 ml (3.29 mmol) of glacial acetic acid, and the mixture is washed with sodium chloride solution and dried. After column chromatography purification, 150 mg of the desired product is obtained in a purity of 90%.

Preparation of 3-[5-(2-chlorophenyl)-2-cyclopropylpyrimidin-4-yl]-2-oxopropanoic Acid (Example II-097)

To 390 mg (1.17 mmol) of methyl 3-[5-(2-chlorophenyl)-2-cyclopropylpyrimidin-4-yl]-2-oxopropanoate (prepared analogously to method II-542) in 5 ml THF at 0° C. under nitrogen was added 1.18 ml of 2 N sodium hydroxide solution, and the mixture was stirred at room temperature. Acidification with 2 N hydrochloric acid and extraction with dichloromethane affords a crude product that can be purified by crystallization to give 100 mg of the desired target compound.

Preparation of 5-(2-chlorophenyl)-2-cyclopropyl-4-methylpyrimidine (Intermediate)

To an initial charge of 9400 mg (38.7 mmol) of 3-(2-chlorophenyl)-4-(dimethylamino)but-3-en-2-one in 40 ml of n-butanol under nitrogen is added 6060 mg (50.3 mmol) of cyclopropanecarboximide amide hydrochloride (1:1), followed by condensation with 9.307 ml of 5.4 molar sodium methoxide solution in methanol. The mixture is heated for 7 h and volatiles are distilled off After the reaction has ended, the solvents are removed under reduced pressure, and the residue is taken up in ethyl acetate and washed with water. After the organic phase has been dried over sodium sulfate, 10.17 mg of orange liquid is obtained, which is chromatographed for further purification using silica gel. 6863 mg of yellowish oil of 86% purity is obtained.
$^1$H-NMR (CDCl$_3$, 400 MHz): 8.3 (s, 1H), 7.51-7.18 (m, 4H), 2.30 (s, 3H), 2.30-2.20 (m, 1H), 1.2-1.0 (m, 4H).

Preparation of 3-(2-chlorophenyl)-4-(dimethylamino)but-3-en-2-one (Intermediate)

To an initial charge of 5000 mg (29.65 mmol) of 1-(2-chlorophenyl)acetone under nitrogen was added 5300 mg (44.48 mmol) of 1,1-dimethoxy-N,N-dimethylmethanamine, and the mixture is heated at reflux for 3 h, during which methanol is distilled off After the reaction has ended, the mixture is cooled to room temperature, diluted with a heptane:ethyl acetate mixture=2:1, and washed with water. Drying over sodium sulfate affords 7020 mg (95%) of a red-brown oil. $^1$H-NMR (CDCl$_3$, 400 MHz): 7.65 (s, 1H), 7.5-7.15 (m, 4H), 2.73 (bs, 6H), 1.9 (s, 3H).

B. FORMULATION EXAMPLES

1. Dusting Products

A dusting product is obtained by mixing 10 parts by weight of a compound of the formula (I) and 90 parts by weight of talc as an inert substance and comminuting the mixture in a hammer mill.

2. Dispersible Powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

3. Dispersion Concentrate

A readily water-dispersible dispersion concentrate is obtained by mixing 20 parts by weight of a compound of the formula (I), 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to more than 277° C.) and grinding the mixture in a friction ball mill to a fineness of below 5 microns.

4. Emulsifiable Concentrate

An emulsifiable concentrate is obtained from 15 parts by weight of a compound of the formula (I), 75 parts by weight of cyclohexanone as a solvent and 10 parts by weight of ethoxylated nonylphenol as an emulsifier.

5. Water-Dispersible Granules

Water-dispersible granules are obtained by mixing 75 parts by weight of a compound of the formula (I),
10 parts by weight of calcium lignosulfonate,
5 parts by weight of sodium laurylsulfate, -continued 3 parts by weight of polyvinyl alcohol and
7 parts by weight of kaolin, grinding the mixture in a pinned-disk mill, and granulating the powder in a fluidized bed by spray application of water as a granulating liquid.

Water-dispersible granules are also obtained by homogenizing and precomminuting, in a colloid mill, 25 parts by weight of a compound of the formula (I),
5 parts by weight of sodium 2,2'-dinaphthylmethane-6,6'-disulfonate,
2 parts by weight of sodium oleoylmethyltaurinate,
1 parts by weight of polyvinyl alcohol,
17 parts by weight of calcium carbonate and
50 parts by weight of water, then grinding the mixture in a bead mill and atomizing and drying the suspension thus obtained in a spray tower by means of a one-phase nozzle.

C. BIOLOGICAL EXAMPLES

In the tables below, the following abbreviations are used:
ABUTH: *Abufilon theophrast* AGSTE: *Agrostis tenuis*
ALOMY: *Alopecurus myosuroides*
AMARE: *Amaranthus retroflexus* AVEFA: *Avena fatua*
DIGSA: *Digitaria sanguinalis* ECHCG: *Echinochloa crus-galli*
HORMU: *Hordeum murinum* LOLPE: *Lolium perenne*
LOLRI: *Lolium rigidum* MATCH: *Matricaria* chamonilla
MATIN: *Matricaria inodora* POAAN: *Poa annua*
POLCO: *Polygonum convolvulus*
SETVI: *Setaria viridis* STEME: *Stellaria media*
VERPE: *Veronica persica*

Trial Descriptions

Method A: Post-Emergence Herbicidal Action and Crop Plant Compatibility

Seeds of monocotyledonous and dicotyledonous weeds and crop plants are placed in sandy loam in plastic or organic planting pots, covered with soil and cultivated in a greenhouse under controlled growth conditions. 2 to 3 weeks after sowing, the test plants are treated at the one-leaf stage. The compounds of the invention, formulated in the form of wettable powders (WP) or as emulsion concentrates (EC), are then sprayed onto the green parts of the plants as aqueous suspension or emulsion with addition of 0.5% additive at a water application rate of 600l/ha (converted). After the test plants have been kept in the greenhouse under optimum growth conditions for about 3 weeks, the activity of the preparations is rated visually in comparison to untreated controls. For example, 100% activity=the plants have died, 0% activity=like control plants.

TABLE A

| | | Post-emergence action at 320 g/ha | | | | | | | |
|---|---|---|---|---|---|---|---|---|---|
| Example number | Dosage [g/ha] | ALOMY | AVEFA | DIGSA | ECHCG | LOLRI | POLCO | STEME | HORMU |
| II-099 | 320 | 90 | 90 | | 90 | 100 | 90 | 100 | 80 |
| I-139 | 320 | 100 | 90 | | 90 | 100 | 90 | 80 | 90 |
| I-137 | 320 | 90 | | 80 | | 90 | 80 | 90 | 80 |
| II-098 | 320 | 90 | | | 80 | 90 | | 90 | |

As the results show, compounds of the invention, for example compound Nos. 11-099, 1-139, 1-137, II-098 and other compounds from table A, when applied post-emergence, have very good herbicidal efficacy against harmful plants. For example, compound Nos. 11-099 or 1-139 when applied post-emergence have very good herbicidal action (80% to 100% herbicidal action) against harmful plants such as *Alopecurus myosuroides, Avena fatua, Echinochloa crus-galli, Hordeum murinum, Lolium rigidum, Polygonum convolvulus* and *Stellaria media*, at an application rate of 0.32 kg of active substance or less per hectare. At the same time, some of the compounds of the invention leave Gramineae crops such as barley, wheat, rye, millet/sorghum, corn, rice or sugar cane virtually undamaged when applied post-emergence, even at high active compound dosages. In addition, some substances are also harmless to dicotyledonous crops such as soya, cotton, oilseed rape or sugar beet.

Some of the compounds of the invention have high selectivity and are therefore suitable for controlling unwanted vegetation in agricultural crops by the post-emergence method.

Method B: Pre-Emergence Herbicidal Action and Crop Plant Compatibility

Seeds of monocotyledonous and dicotyledonous weed plants and crop plants are placed in plastic or organic planting pots and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate of 600l/ha (converted). After the treatment, the pots are placed in a greenhouse and kept under good growth conditions for the trial plants. After about 3 weeks, the effect of the preparations is scored visually in comparison with untreated controls as percentages. For example, 100% activity=the plants have died, 0% activity=like control plants.

TABLE C

| | | Post-emergence action at 1280 g/ha | | | | |
|---|---|---|---|---|---|---|
| Example number | Dosage [g/ha] | ECHCG | LOLRI | POAAN | MATIN | STEME |
| I-137 | 1280 | 100 | 100 | 100 | 90 | 100 |
| II-098 | 1280 | 100 | 100 | 100 | | 100 |
| IV-137 | 1280 | 100 | 100 | 100 | | 100 |

TABLE B

| | | Pre-emergence action at 320 g/ha | | | | | | | | | | |
|---|---|---|---|---|---|---|---|---|---|---|---|---|
| Example number | Dosage [g/ha] | ALOMY | AVEFA | DIGSA | ECHCG | LOLRI | ABUTH | AMARE | MATIN | POLCO | STEME | HORMU |
| II-099 | 320 | 100 | 90 | 90 | 100 | 100 | 80 | | | 90 | 100 | 90 |
| I-139 | 320 | 100 | 80 | 100 | 100 | 100 | 80 | | | 90 | 100 | 90 |
| I-137 | 320 | 100 | | 90 | 100 | 100 | | 80 | 100 | 90 | 100 | 90 |
| II-098 | 320 | 100 | | | 90 | 90 | | | 80 | 90 | 100 | |

As the results show, compounds of the invention, for example compound Nos. 11-099, 1-139, 1-137 and 11-09 and other compounds from table B, when applied pre-emergence, have very good herbicidal efficacy against harmful plants. For example, compound Nos. 11-099 and 1-139 when applied pre-emergence have very good herbicidal action (80% to 100% herbicidal action) against harmful plants such as *Abutilon theophrasti, Alopecurus myosuroides, Avena fatua, Echinochloa crus-galli, Hordeum murinum, Lolium rigidum, Polygonum convolvulus* and *Stellaria media*, at an application rate of 0.32 kg of active substance or less per hectare. At the same time, some of the compounds of the invention leave Gramineae crops such as barley, wheat, rye, millet/sorghum, corn, rice or sugar cane virtually undamaged when applied pre-emergence, even at high active compound dosages. In addition, some substances are also harmless to dicotyledonous crops such as soya, cotton, oilseed rape or sugar beet.

Some of the compounds of the invention exhibit high selectivity and are therefore suitable for controlling unwanted vegetation in agricultural crops by the pre-emergence method.

Method C: Herbicidal Post-Emergence Action

Seeds of mono- and dicotyledonous weed plants are placed in plastic pots in sandy loam soil (doubly sown with one species each of mono- or dicotyledonous weed plants per pot), covered with soil and cultivated in a greenhouse under controlled growth conditions. 2 to 3 weeks after sowing, the test plants are treated at the one-leaf stage. The compounds of the invention, formulated in the form of wettable powders (WP) or as emulsion concentrates (EC), are applied to the green parts of the plants as aqueous suspension or emulsion with addition of 0.5% additive at a water application rate equivalent to 600 liters per hectare. After the test plants have been kept in the greenhouse under optimum growth conditions for about 3 weeks, the activity of the preparations is rated visually in comparison to untreated controls. For example, 100% activity=the plants have died, 0% activity=like control plants.

As the results show, compounds of the invention, for example compound Nos. I-137, IV-137 and II-098 and other compounds from table C, when applied post-emergence, have very good herbicidal efficacy against harmful plants. For example, compound No. 1-137 when applied post-emergence has very good herbicidal action (80% to 100% herbicidal action) against harmful plants such as *Echinochloa crus-galli, Lolium rigidum, Matricaria inodora, Poa annua*, and *Stellaria media*, and compound II-098 when applied post-emergence has very good herbicidal action (80% to 100% herbicidal action) against harmful plants such as *Echinochloa crus-galli, Lolium rigidum, Poa annua*, and *Stellaria media*, at an application rate of 1.28 kg of active substance or less per hectare.

Method D: Herbicidal Pre-Emergence Action

Seeds of mono- and dicotyledonous weed plants are placed in plastic pots in sandy loam soil (doubly sown with one species each of mono- or dicotyledonous weed plants per pot) and covered with soil. The compounds of the invention, formulated in the form of wettable powders (WP) or as emulsion concentrates (EC), are then applied onto the surface of the covering soil as aqueous suspension or emulsion with addition of 0.5% additive at a water application rate of 600 liters per hectare (converted). After the treatment, the pots are placed in a greenhouse and kept under good growth conditions for the trial plants. After about 3 weeks, the effect of the preparations is scored visually in comparison with untreated controls as percentages. For example, 100% activity=the plants have died, 0% activity=like control plants.

TABLE D

| | | Pre-emergence action at 1280 g/ha | | | | | | |
|---|---|---|---|---|---|---|---|---|
| Example number | Dosage [g/ha] | ECHCG | LOLRI | POAAN | SETVI | ABUTH | MATIN | STEME |
| IV-137 | 1280 | 90 | 90 | 100 | 90 | 90 | 90 | 100 |
| I-137 | 1280 | 100 | 100 | 100 | | 90 | | 100 |
| II-098 | 1280 | | 100 | | | | | 100 |

As the results show, compounds of the invention, for example compound Nos. IV-137, I-137 and II-098 and other compounds from table D, when applied pre-emergence, have very good herbicidal efficacy against harmful plants. For example, compound Nos. I-137 and IV-137 when applied pre-emergence have very good herbicidal action (80% to 100% herbicidal action) against harmful plants such as *Abufilon theophrast, Echinochloa crus-galli, Lolium rigidum, Poa annua* and *Stellaria media*, at an application rate of 1.28 kg of active substance or less per hectare.

Method E: Herbicidal Early Post-Emergence Action

Seeds of monocotyledonous or dicotyledonous weed plants are placed in 96-well microtiter plates in quartz sand and grown in a climatized chamber under controlled growth conditions. 5 to 7 days after sowing, the test plants are treated at the cotyledon stage. The compounds of the invention, formulated in the form of emulsion concentrates (EC), are applied with a water application rate of the equivalent of 2200 liters per hectare. After the test plants had been left to stand in the climatized chamber for 9 to 12 days under optimum growth conditions, the effect of the preparations is scored visually in comparison to untreated controls. For example, 100% activity=the plants have died, 0% activity=like control plants.

TABLE E

| | | Early post-emergence action at 1900 g/ha | | | | | |
|---|---|---|---|---|---|---|---|
| Example number | Dosage [g/ha] | AGSTE | LOLPE | POAAN | MATCH | STEME | VERPE |
| I-137 | 1900 | 80 | 80 | 100 | 80 | 80 | 80 |
| I-147 | 1900 | 100 | 80 | 100 | 80 | 100 | |
| IV-140 | 1900 | 100 | 100 | 100 | 80 | 80 | |
| I-139 | 1900 | 100 | 80 | 100 | 100 | 100 | |
| II-098 | 1900 | 80 | 80 | 100 | 80 | 100 | |
| I-137 | 1900 | 100 | 80 | 100 | 80 | 100 | |
| I-146 | 1900 | 80 | 80 | 80 | 80 | 80 | |
| IV-137 | 1900 | 100 | 80 | 80 | 80 | 100 | |
| I-547 | 1900 | 100 | 80 | 100 | 80 | 80 | |
| IV-138 | 1900 | 80 | 80 | 100 | 80 | 80 | |
| II-099 | 1900 | 100 | | 100 | 100 | | |
| I-688 | 1900 | 100 | | 100 | 80 | | |
| II-481 | 1900 | 80 | | 100 | | | |

As the results show, compounds of the invention, for example compound Nos. I-147, I-547, II-099 or IV-137 and other compounds from table E, when applied in early post-emergence, have very good herbicidal efficacy against harmful plants. For example, compound Nos. I-147, I-547 or IV-137 when applied post-emergence have very good herbicidal action (80% to 100% herbicidal action) against harmful plants such as *Agrostis tenuis, Lolium perenne, Matricaria chamonilla, Poa annua*, and *Stellaria media*, and compounds II-099 and I-688 when applied post-emergence have very good herbicidal action (80% to 100% herbicidal action) against harmful plants such as *Agrostis tenuis, Matricaria chamonilla* and *Poa annua*, at an application rate of 1900 g of active substance or less per hectare.

The invention claimed is:
1. A compound of formula (I)

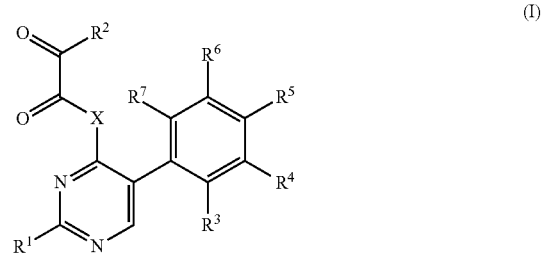

(I)

And/or an agrochemically acceptable salt thereof, wherein

X represents $C(R^{13})(R^{14})$ $R^1$ represents $(C_3-C_6)$-cycloalkyl, $(C_3-C_6)$-cycloalkenyl or heterocyclyl, where these three aforementioned radicals are each substituted by s radicals from the group consisting of halogen, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkenyl, halo-$(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, halo-$(C_3-C_6)$-cycloalkyl-$(C_1-C_6)$-alkyl, halo-$(C_3-C_6)$-cycloalkenyl-$(C_1-C_6)$-alkyl, $R^8(O)C$, $R^8O(O)C$, $(R^8)_2N(O)C$, $R^8O$, $(R^8)_2N$, $R^9(O)_nS$, phenyl, heteroaryl, heterocyclyl, phenyl-$(C_1-C_6)$-alkyl, heteroaryl-$(C_1-C_6)$-alkyl and heterocyclyl-$(C_1-C_6)$-alkyl, where the six latter radicals are substituted by m radicals from the group consisting of $(C_1-C_6)$-alkyl, halo-$(C_1-C_6)$-alkyl, $(C_1-C_6)$-alkoxy, halo-$(C_1-C_6)$-alkoxy and halogen, and where cycloalkyl, cycloalkenyl and heterocyclyl each independently bear n oxo groups, $R^2$ represents hydroxy, $(C_1-C_6)$-alkoxy, $(C_2-C_6)$-alkenyloxy, $(C_2-C_6)$-alkynyloxy, $(C_1-C_6)$-haloalkoxy, $(C_2-C_6)$-haloalkenyloxy, $(C_2-C_6)$-haloalkynyloxy, where the 6 latter radicals are each substituted by s radicals from the group consisting of cyano, $(C_3-C_6)$-cycloalkyl, $(C_3-C_6)$-cycloalkenyl, halo-$(C_3-C_6)$-cycloalkyl, halo-$(C_3-C_6)$-cycloalkenyl, $R^8(O)C$, $R^8(R^8ON=)C$, $R^8O(O)C$, $R^9S(O)C$, $(R^8)_2N(O)C$, $R^8(R^8O)N(O)C$, $(R^8)_2N(R^8)N(O)C$, $R^8(O)C(R^8)N(O)C$, $R^9O(O)C(R^8)N(O)C$, $(R^8)_2N(O)C(R^8)N(O)C$, $R^9(O)_2S(R^8)N(O)C$, $R^8O(O)_2S(R^8)N(O)C$, $(R^8)_2N(O)_2S(R^8)N(O)C$, $R^8O$, $R^8(O)CO$, $R^9(O)_2SO$, $R^9O(O)CO$, $(R^8)_2N(O)CO$, $(R^8)_2N$, $R^8(O)C(R^8)N$, $R^9(O)_2S(R^8)N$, $R^9O(O)C(R^8)N$, $(R^8)_2N(O)C(R^8)N$, $R^8O(O)_2S(R^8)N$, $(R^8)_2N(O)_2S(R^8)N$, $R^9(O)_nS$, $R^8O(O)_2S$, $(R^8)_2N(O)_2S$, $R^8(O)C(R^8)N(O)_2S$, $R^9O(O)C(R^8)N(O)_2S$, $(R^8)_2N(O)C(R^8)N(O)_2S$, $R^{11}_3Si$, $(R^{12}O)_2(O)P$, phenyl, heteroaryl and heterocyclyl, where the three latter radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl, or $R^2$ represents $(C_3-C_6)$-cycloalkoxy, $(C_3-C_6)$-cycloalkenyloxy, phenyloxy, heteroaryloxy or heterocyclyloxy, where these five aforementioned radicals are each substituted by s radicals from the group consisting of halogen, cyano, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, halo-$(C_3-C_6)$-cycloalkyl, halo-$(C_3-C_6)$-cycloalkenyl, $R^8(O)C$, $R^8(R^8ON=)C$, $R^8O(O)C$, $R^9S(O)C$, $(R^8)_2N(O)C$, $R^8(R^8O)N(O)C$, $(R^8)_2N(R^8)N(O)C$, $R^8(O)C(R^8)N(O)C$, $R^9O(O)C(R^8)N(O)C$, $(R^8)_2N(O)C(R^8)N(O)C$, $R^9(O)_2S(R^8)N(O)C$, $R^8O(O)_2S(R^8)N(O)C$, $(R^8)_2N(O)_2S(R^8)N(O)C$, $R^8O$, $R^8(O)CO$, $R^9(O)_2SO$, $R^9O(O)CO$, $(R^8)_2N(O)CO$, $(R^8)_2N$, $R^8(O)C(R^8)N$, $R^9(O)_2S(R^8)N$, $R^9O(O)C(R^8)N$, $(R^8)_2N(O)C(R^8)N$, $R^8O(O)_2S(R^8)N$, $(R^8)_2N(O)_2S(R^8)N$, $R^9(O)_nS$, $R^8O(O)_2S$, $(R^8)_2N(O)_2S$, $R^8(O)C(R^8)N(O)_2S$, $R^9O(O)C(R^8)N(O)_2S$, $(R^8)_2N(O)C(R^8)N(O)_2S$, $R^{11}_3Si$, $(R^{12}O)_2(O)P$, phenyl, heteroaryl and heterocyclyl, where the three latter radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{11}O$, $(R^{10})_2N$, $R^{11}(O)_2S$, $R^{10}O(O)_2S$, $(R^{10})_2N(O)_2S$ and $R^{10}O$—$(C_1-C_6)$-alkyl, and where $(C_3-C_6)$-cycloalkyl, $(C_3-C_6)$-cycloalkenyl, heterocyclyl, $(C_3-C_6)$-cycloalkoxy, $(C_3-C_6)$-cycloalkenyloxy and heterocyclyloxy each independently bear n oxo groups, or $R^2$ represents $R^8(O)CO$, $R^9(O)_2SO$ or $R^{15}R^{16}C=N$-0 or $(R^8)_2N$—O, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})(R^{18})N(R^{19})N$, or $R^2$ represents $R^{17}R^{18}C=N$—$(R^{19})N$—

$R^3$, $R^4$, $R^5$, $R^6$ and $R^7$ each independently represent hydrogen, nitro, halogen, cyano, thiocyano, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^8(O)C$, $R^8(R^8ON=)C$, $R^8O(O)C$, $(R^8)_2N(O)C$, $R^8(R^8O)N(O)C$, $(R^8)_2N(R^8)N(O)C$, $R^8(O)C(R^8)N(O)C$, $R^9O(O)C(R^8)N(O)C$, $(R^8)_2N(O)C(R^8)N(O)C$, $R^9(O)_2S(R^8)N(O)C$, $R^8O(O)_2S(R^8)N(O)C$, $(R^8)_2N(O)_2S(R^8)N(O)C$, $R^8O$, $R^8(O)CO$, $R^9(O)_2SO$, $R^9O(O)CO$, $(R^8)_2N(O)CO$, $(R^8)_2N$, $R^8(O)C(R^8)N$, $R^9(O)_2S(R^8)N$, $R^9O(O)C(R^8)N$, $(R^8)_2N(O)C(R^8)N$, $R^8O(O)_2S(R^8)N$, $(R^8)_2N(O)_2S(R^8)N$, $R^9(O)_nS$, $R^8O(O)_2S$, $(R^8)_2N(O)_2S$, $R^8(O)C(R^8)N(O)_2S$, $R^9O(O)C(R^8)N(O)_2S$, $(R^8)_2N(O)C(R^8)N(O)_2S$, $(R^{12}O)_2(O)P$, $R^8(O)C$—$(C_1-C_6)$-alkyl, $R^8O(O)C$—$(C_1-C_6)$-alkyl, $(R^8)_2N(O)C$—$(C_1-C_6)$-alkyl, $(R^8O)(R^8)N(O)C$—$(C_1-C_6)$-alkyl, $(R^8)_2N(R^8)N(O)C$—$(C_1-C_6)$-alkyl, $R^8(O)C(R^8)N(O)C$—$(C_1-C_6)$-alkyl, $R^9O(O)C(R^8)N(O)C$—$(C_1-C_6)$-alkyl, $(R^8)_2N(O)C(R^8)N(O)C$—$(C_1-C_6)$-alkyl, $R^9(O)_2S(R^8)N(O)C$—$(C_1-C_6)$-alkyl, $R^8O(O)_2S(R^8)N(O)C$—$(C_1-C_6)$-alkyl, $(R^8)_2N(O)_2S(R^8)N(O)C$—$(C_1-C_6)$-alkyl, NC—$(C_1-C_6)$-alkyl, $R^8O$—$(C_1-C_6)$-alkyl, $R^8(O)CO$—$(C_1-C_6)$-alkyl, $R^9(O)_2SO$—$(C_1-C_6)$-alkyl, $R^9O(O)CO$—$(C_1-C_6)$-alkyl, $(R^8)_2N(O)CO$—$(C_1-C_6)$-alkyl, $(R^8)_2N$—$(C_1-C_6)$-alkyl, $R^8(O)C(R^8)N$—$(C_1-C_6)$-alkyl, $R^9(O)_2S(R^8)N$—$(C_1-C_6)$-alkyl, $R^9O(O)C(R^8)N$—$(C_1-C_6)$-alkyl, $(R^8)_2N(O)C(R^8)N$—$(C_1-C_6)$-alkyl, $R^8O(O)_2S(R^8)N$—$(C_1-C_6)$-alkyl, $(R^8)_2N(O)_2S(R^8)N$—$(C_1-C_6)$-alkyl, $R^9(O)_2S$—$(C_1-C_6)$-alkyl, $R^8O(O)_2S$—$(C_1-C_6)$-alkyl, $(R^8)_2N(O)_2S$—$(C_1-C_6)$-alkyl, $R^8(O)C(R^8)N(O)_2S$—$(C_1-C_6)$-alkyl, $R^9O(O)C(R^8)N(O)_2S$—$(C_1-C_6)$-alkyl, $(R^8)_2N(O)C(R^8)N(O)_2S$—$(C_1-C_6)$-alkyl, $(R^{12}O)_2(O)P$—$(C_1-C_6)$-alkyl, phenyl, heteroaryl, heterocyclyl, phenyl-$(C_1-C_6)$-alkyl, heteroaryl-$(C_1-C_6)$-alkyl or heterocyclyl-$(C_1-C_6)$-alkyl, where the six latter radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $R^8O(O)C$, $(R^8)_2N(O)C$, $R^8O$, $(R^8)_2N$, $R^9(O)_nS$, $R^8O(O)_2S$, $(R^8)_2N(O)_2S$ and $R^8O$—$(C_1-C_6)$-alkyl, and where cycloalkyl and heterocyclyl each independently bear n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, $(C_1-C_6)$-alkyl-O—$(C_1-C_6)$-alkyl, $(C_1-C_6)$-alkyl-O—$(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, $(C_3-C_6)$-cycloalkenyl-$(C_1-C_6)$-alkyl-O—$(C_1-C_6)$-alkyl or $(C_1-C_6)$-alkylthio-$(C_1-C_6)$-alkyl, where the twelve latter radicals bear s halogen atoms, or $R^8$ represents phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N$(R^{10})$—$(C_1-C_6)$-alkyl, heteroaryl-N$(R^{10})$—$(C_1-C_6)$-alkyl, heterocyclyl-N$(R^{10})$—$(C_1-C_6)$-alkyl, phenyl-S$(O)_n$—$(C_1-C_6)$-alkyl, heteroaryl-S$(O)_n$—$(C_1-C_6)$-alkyl or heterocyclyl-S$(O)_n$—$(C_1-C_6)$-alkyl, where the radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl, and where $(C_3-C_6)$-cycloalkyl, $(C_3-C_6)$-cycloalkenyl and heterocyclyl each independently bear n oxo groups, or the $R^8$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclyl-heteroaryl or heterocyclenylheteroaryl, where each of these rings in turn is substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O(R^{10})_2N$, $R^{11}(O)_nS$, $R^{10}O(O)_2S$, $(R^{10})_2N(O)_2S$ and $R^{10}O$—$(C_1-C_6)$-alkyl and oxo, $R^9$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, $(C_3-C_6)$-cycloalkyl-$(C_1-C_6)$-alkyl, $(C_3-C_6)$-cycloalkenyl-$(C_1-C_6)$-alkyl, $(C_1-C_6)$-alkyl-O—$(C_1-C_6)$-alkyl, $(C_1-C_6)$-alkyl-O—$(C_1-C_6)$-alkyl-O—$(C_1-C_6)$-alkyl, $(C_3-C_6)$-cycloalkyl-$(C_1-C_6)$-alkyl-O—$(C_1-C_6)$-alkyl, $(C_3-C_6)$-cycloalkenyl-$(C_1-C_6)$-alkyl-O—$(C_1-C_6)$-alkyl or $(C_1-C_6)$-alkylthio-$(C_1-C_6)$-alkyl, where the radicals bear s halogen atoms, or $R^9$ represents phenyl, phenyl-$(C_1-C_6)$-alkyl, heteroaryl, heteroaryl-$(C_1-C_6)$-alkyl, heterocyclyl, heterocyclyl-$(C_1-C_6)$-alkyl, phenyl-O—$(C_1-C_6)$-alkyl, heteroaryl-O—$(C_1-C_6)$-alkyl, heterocyclyl-O—$(C_1-C_6)$-alkyl, phenyl-N($R^{10}$)—$(C_1-C_6)$-alkyl, heteroaryl-N($R^{10}$)—$(C_1-C_6)$-alkyl, heterocyclyl-N($R^{10}$)—$(C_1-C_6)$-alkyl, phenyl-S(O)$_n$—$(C_1-C_6)$-alkyl, heteroaryl-S(O)$_n$—$(C_1-C_6)$-alkyl or heterocyclyl-S(O)$_n$—$(C_1-C_6)$-alkyl, where the radicals are each substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl, and where $(C_3-C_6)$-cycloalkyl, $(C_3-C_6)$-cycloalkenyl and heterocyclyl each independently bear n oxo groups, $R^{10}$ represents hydrogen, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{11}$ represents $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{12}$ represents hydrogen or $(C_1-C_4)$-alkyl, $R^{13}$ and $R^{14}$ each independently represent hydrogen, $(C_1-C_6)$-alkyl, hydroxy, $(C_1-C_6)$-alkoxy, $(R^8)_2N$, halo-$(C_1-C_6)$-alkoxy, halogen, halo-$(C_1-C_6)$-alkyl, cyano, $R^8O(O)C$ or $(R^8)_2N(O)C$, or $R^{13}$ and $R^{14}$ together with the carbon atom to which they are bonded form a $(C_3-C_8)$-cycloalkyl group, $R^{15}$ and $R^{16}$ each independently represent $(C_1-C_6)$-alkyl, phenyl, (C3-C6)-cycloalkyl, heteroaryl or heterocyclyl, $R^{17}$ and $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$, or the $R^{17}$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, thiocyano, $(C_1-C_6)$-alkyl, halo-$(C_1-C_6)$-alkyl, $(C_3-C_6)$-cycloalkyl, $(C_3-C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl and oxo, m represents 0, 1, 2, 3, 4 or 5, n represents 0, 1 or 2, s represents 0, 1, 2, 3, 4, 5, 6, 7, 8, 9, 10 or 11.

2. A compound as claimed in claim 1, wherein

X represents $C(R^{13})(R^{14})$, $R^1$ represents $(C_3-C_6)$-cycloalkyl, $(C_3-C_6)$-cycloalkenyl or heterocyclyl, where these three radicals are each substituted by s radicals from the group consisting of halogen, $(C_1-C_6)$-alkyl and halo-$(C_1-C_6)$-alkyl and where cycloalkyl, cycloalkenyl and heterocyclyl each independently bear n oxo groups, $R^2$ represents hydroxy, $(C_1-C_6)$-alkoxy, $(C_2-C_6)$-alkenyloxy, $(C_2-C_6)$-alkynyloxy, $(C_1-C_6)$-haloalkoxy, $(C_2-C_6)$-haloalkenyloxy, $(C_2-C_6)$-haloalkynyloxy, where the 6 latter radicals are substituted by s radicals from the group consisting of cyano, $R^8(O)C$, $R^8O(O)C$, $(R^8)_2N(O)C$, $R^8(R^8O)N(O)C$, $(R^8)_2N(R^8)N(O)C$, $R^8O$, $R^8(O)CO$, $R^9(O)_2SO$, $(R^8)_2N$, $R^9(O)_nS$, phenyl, heteroaryl and heterocyclyl, where the three latter radicals are each substituted by m radicals from the group consisting of nitro, halogen, cyano, $(C_1-C_6)$-alkyl, halo-$(C_1-C_6)$-alkyl, $(C_3-C_6)$-cycloalkyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl, and where $(C_3-C_6)$-cycloalkyl and heterocyclyl each independently bear n oxo groups, or $R^2$ represents $(C_3-C_6)$-cycloalkoxy, $(C_3-C_6)$-cycloalkenyloxy, phenyloxy, heteroaryloxy or heterocyclyloxy, where these five aforementioned radicals are each substituted by s radicals from the group consisting of halogen, cyano, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkenyl, halo-$(C_3-C_6)$-cycloalkyl, halo-$(C_3-C_6)$-cycloalkenyl, $R^8(O)C$, $R^8O(O)C$, $(R^8)_2N(O)C$, $R^8(R^8O)N(O)C$, $(R^8)_2N(R^8)N(O)C$, $R^8O$, $R^8(O)CO$, $R^9(O)_2SO$, $(R^8)_2N$, $R^9(O)_nS$, phenyl, heteroaryl and heterocyclyl, where the three latter radicals are each substituted by m radicals from the group consisting of nitro, halogen, cyano, $(C_1-C_6)$-alkyl, halo-$(C_1-C_6)$-alkyl, $(C_3-C_6)$-cycloalkyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1-C_6)$-alkyl, and where $(C_3-C_6)$-cycloalkoxy, $(C_3-C_6)$-cycloalkyl and heterocyclyl each independently bear n oxo groups, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})(R^{18})N(R^{19})N$, or $R^2$ represents $R^{17}R^{18}C=N$—$(R^{19})N$—

$R^3$, $R^4$, $R^5$, $R^6$ and $R^7$ each independently represent hydrogen, nitro, halogen, cyano, $(C_1-C_6)$-alkyl, halo-$(C_1-C_6)$-alkyl, $(C_2-C_6)$-alkenyl, $(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $R^8(O)C$, $R^8(R^8ON=)C$, $R^8O(O)C$, $(R^8)_2N(O)C$, $R^8O$, $(R^8)_2N$, $R^8(O)C(R^8)N$, $R^9(O)_2S(R^8)N$, $R^9O(O)C(R^8)N$, $(R^8)_2N(O)C(R^8)N$, $R^9(O)_nS$, $R^8O(O)_2S$, $(R^8)_2N(O)_2S$, $(R^{12}O)_2(O)P$, $R^8(O)C$—$(C_1-C_6)$-alkyl, $R^8O(O)C$—$(C_1-C_6)$-alkyl, $(R^8)_2N(O)C$—$(C_1-C_6)$-alkyl, NC—$(C_1-C_6)$-alkyl, $R^8O$—$(C_1-C_6)$-alkyl, $(R^8)_2N$—$(C_1-C_6)$-alkyl, $R^8(O)C(R^8)N$—$(C_1-C_6)$-alkyl, $R^9(O)_2S(R^8)N$—$(C_1-C_6)$-alkyl, $R^9O(O)C(R^8)N$—$(C_1-$ $C_6$)-alkyl, $(R^8)_2N(O)C(R^8)N$—($C_1$-$C_6$)-alkyl, $R^9(O)_2$S—($C_1$-$C_6$)-alkyl, $R^8O(O)_2S$—($C_1$-$C_6$)-alkyl, $(R^8)_2N(O)_2S$—($C_1$-$C_6$)-alkyl, $(R^{12}O)_2(O)P$—($C_1$-$C_6$)-alkyl, phenyl, heteroaryl, heterocyclyl, phenyl-($C_1$-$C_6$)-alkyl, heteroaryl-($C_1$-$C_6$)-alkyl, heterocyclyl-($C_1$-$C_6$)-alkyl, where the six latter radicals are each substituted by m radicals from the group consisting of nitro, halogen, cyano, ($C_1$-$C_6$)-alkyl, halo-($C_1$-$C_6$)-alkyl, $R^8O$, $(R^8)_2N$, $R^9(O)_nS$, $R^8O(O)_2S$, $(R^8)_2N(O)_2S$ and $R^8O$—($C_1$-$C_6$)-alkyl, and where heterocyclyl bears n oxo groups, $R^8$ is hydrogen, ($C_1$-$C_6$)-alkyl, ($C_3$-$C_6$)-cycloalkyl-($C_1$-$C_6$)-alkyl, ($C_1$-$C_6$)-alkyl-O—($C_1$-$C_6$)-alkyl, ($C_3$-$C_6$)-cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl or heterocyclyl-O—($C_1$-$C_6$)-alkyl, where the nine latter radicals are each substituted by m radicals from the group consisting of nitro, halogen, ($C_1$-$C_6$)-alkyl, halo-($C_1$-$C_6$)-alkyl, $R^{10}O(O)C$, $(R^{10})_2N(O)C$, $R^{10}O$, $(R^{10})_2N$, $R^{11}(O)_nS$ and $R^{10}O$—($C_1$-$C_6$)-alkyl, and where heterocyclyl bears n oxo groups, or the two $R^8$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of halogen, cyano, ($C_1$-$C_6$)-alkyl, halo-($C_1$-$C_6$)-alkyl, ($C_3$-$C_6$)-cycloalkyl, ($C_3$-$C_6$)-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—($C_1$-$C_6$)-alkyl and oxo, $R^9$ represents ($C_1$-$C_6$)-alkyl, ($C_3$-$C_6$)-cycloalkyl-($C_1$-$C_6$)-alkyl, ($C_1$-$C_6$)-alkyl-O—($C_1$-$C_6$)-alkyl, ($C_3$-$C_6$)-cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl or heterocyclyl-O—($C_1$-$C_6$)-alkyl, where the nine latter radicals are each substituted by m radicals from the group consisting of nitro, halogen, ($C_1$-$C_6$)-alkyl, halo-($C_1$-$C_6$)-alkyl, $R^{10}O(O)C$, $(R^{10})_2N(O)C$, $R^{10}O$, $(R^{10})_2N$, $R^{11}(O)_nS$ and $R^{10}O$—($C_1$-$C_6$)-alkyl, and where heterocyclyl bears n oxo groups, $R^{10}$ represents hydrogen or ($C_1$-$C_6$)-alkyl, $R^{11}$ represents ($C_1$-$C_6$)-alkyl, $R^{12}$ represents ($C_1$-$C_4$)-alkyl, $R^{13}$ and $R^{14}$ each independently represent hydrogen, ($C_1$-$C_6$)-alkyl, hydroxy, ($C_1$-$C_6$)-alkoxy, $(R^8)_2N$, halo-($C_1$-$C_6$)-alkoxy, halogen, halo-($C_1$-$C_6$)-alkyl, cyano, $R^8O(O)C$ or $(R^8)_2N(O)C$, or $R^{13}$ and $R^{14}$ together with the carbon atom to which they are bonded form a ($C_3$-$C_8$)-cycloalkyl group, $R^{15}$ and $R^{16}$ each independently represent ($C_1$-$C_6$)-alkyl, phenyl, ($C_3$-$C_6$)-cycloalkyl, heteroaryl or heterocyclyl, $R^{17}$, $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$ or the ($R^{17}$ and $R^{18}$) or ($R^{17}$ and $R^{19}$) radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of halogen, cyano, ($C_1$-$C_6$)-alkyl, halo-($C_1$-$C_6$)-alkyl, ($C_3$-$C_6$)-cycloalkyl, ($C_3$-$C_6$)-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—($C_1$-$C_6$)-alkyl and oxo, m represents 0, 1, 2, 3, 4 or 5, n represents 0, 1 or 2, s represents 0, 1, 2, 3, 4, 5, 6, 7, 8, 9, 10 or 11.

3. A compound as claimed in claim 1, wherein

X represents $C(R^{13})(R^{14})$, $R^1$ represents ($C_3$-$C_6$)-cycloalkyl, where this cycloalkyl group is substituted by s radicals from the group consisting of halogen, ($C_1$-$C_6$)-alkyl and halo-($C_1$-$C_6$)-alkyl, $R^2$ represents hydroxy, ($C_1$-$C_6$)-alkoxy, ($C_1$-$C_6$)-haloalkoxy, ($C_2$-$C_6$)-alkenyloxy, ($C_2$-$C_6$)-haloalkenyloxy, ($C_2$-$C_6$)-alkynyloxy, where the five latter radicals are each substituted by a radical from the group of $R^8(O)C$, $R^8O(O)C$, $(R^8)_2N(O)C$, $R^8(R^8O)N(O)C$, $(R^8)_2N(R^8)N(O)C$, $R^8O$ and phenyl, where the latter radical is substituted in each case by m radicals from the group consisting of nitro, halogen, cyano, ($C_1$-$C_6$)-alkyl, halo-($C_1$-$C_6$)-alkyl and ($C_3$-$C_6$)-cycloalkyl, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})$ $(R^{18})$ $N(R^{19})N$, or $R^2$ represents $R^{17}R^{18}C=N$—$(R^{19})N$—

$R^3$, $R^4$, $R^5$, $R^6$ and $R^7$ each independently represent hydrogen, nitro, halogen, cyano, ($C_1$-$C_6$)-alkyl, halo-($C_1$-$C_6$)-alkyl, ($C_3$-$C_6$)-cycloalkyl, $R^8O(O)C$, $R^8O$ or $R^9(O)_2S$, $R^8$ represents hydrogen, ($C_1$-$C_6$)-alkyl, ($C_3$-$C_6$)-cycloalkyl-($C_1$-$C_6$)-alkyl, ($C_1$-$C_6$)-alkyl-O—($C_1$-$C_6$)-alkyl, ($C_3$-$C_6$)-cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)-alkyl, heterocyclyl, heterocyclyl-($C_1$-$C_6$)-alkyl, phenyl-O—($C_1$-$C_6$)-alkyl, heteroaryl-O—($C_1$-$C_6$)-alkyl or heterocyclyl-O—($C_1$-$C_6$)-alkyl, where the nine latter radicals are each substituted by m radicals from the group consisting of nitro, halogen, ($C_1$-$C_6$)-alkyl, halo-($C_1$-$C_6$)-alkyl, $R^{10}O(O)C$, $(R^{10})_2N(O)C$, $R^{10}O$, $(R^{10})_2N$, $R^{11}(O)_nS$ and $R^{10}O$—($C_1$-$C_6$)-alkyl, and where heterocyclyl bears n oxo groups, or the two $R^8$ radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, ($C_1$-$C_6$)-alkyl, halo-($C_1$-$C_6$)-alkyl, ($C_3$-$C_6$)-cycloalkyl, ($C_3$-$C_6$)-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2 N(O)_2S$ and $R^{10}O$—($C_1$-$C_6$)-alkyl and oxo, $R^9$ represents ($C_1$-$C_6$)-alkyl, ($C_3$-$C_6$)-cycloalkyl-($C_1$-$C_6$)-alkyl, ($C_1$-$C_6$)-alkyl-O—($C_1$-$C_6$)-alkyl, ($C_3$-$C_6$)-cycloalkyl-($C_1$-$C_6$)-alkyl-O—($C_1$-$C_6$)-alkyl, phenyl, phenyl-($C_1$-$C_6$)-alkyl, heteroaryl, heteroaryl-($C_1$-$C_6$)- alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl or heterocyclyl-O—$(C_1$-$C_6)$-alkyl, where the nine latter radicals are each substituted by m radicals from the group consisting of nitro, halogen, $(C_1$-$C_6)$-alkyl, halo-$(C_1$-$C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1$-$C_6)$-alkyl, and where heterocyclyl bears n oxo groups, $R^{10}$ represents hydrogen or $(C_1$-$C_6)$-alkyl, $R^{11}$ represents $(C_1$-$C_6)$-alkyl, $R^{12}$ represents $(C_1$-$C_4)$-alkyl, $R^{13}$ and $R^{14}$ each independently represent hydrogen, $(C_1$-$C_6)$-alkyl, cyano, $R^8O(O)C$ or $(R^8)_2N(O)C$, $R^{15}$ and $R^{16}$ each independently represent $(C_1$-$C_6)$-alkyl, phenyl, $(C_3$-$C_6)$-cycloalkyl, heteroaryl or heterocyclyl, $R^{17}$, $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$, or the ($R^{17}$ and $R^{18}$) or ($R^{17}$ and $R^{19}$) radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1$-$C_6)$-alkyl, halo-$(C_1$-$C_6)$-alkyl, $(C_3$-$C_6)$-cycloalkyl, $(C_3$-$C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1$-$C_6)$-alkyl and oxo, m represents 0 or 1, 2, 3, 4 or 5, n represents 0, 1 or 2, s represents 0, 1, 2, 3, 4, 5, 6, 7, 8, 9, 10 or 11.

4. A compound as claimed in claim 1, wherein

X represents $CH_2$, $R^1$ represents cyclopropyl, where the cyclopropyl group is substituted by s radicals from the group consisting of halogen, $(C_1$-$C_6)$-alkyl and halo-$(C_1$-$C_6)$-alkyl, $R^2$ represents hydroxy, $(C_1$-$C_6)$-alkoxy, $(C_1$-$C_6)$-haloalkoxy, $(C_2$-$C_6)$-alkenyloxy, $(C_2$-$C_6)$-haloalkenyloxy, $(C_2$-$C_6)$-alkynyloxy, or $R^2$ represents $(R^8)_2N$, $R^8(O)C(R^8)N$, $R^9O(O)C(R^8)N$, $(R^8)_2N(O)C(R^8)N$, $R^9(O)_2S(R^8)N$, $R^8O(O)_2S(R^8)N$, $(R^8)_2N(O)_2S(R^8)N$, or $R^2$ represents $R^8(R^8O)N$ or $R^2$ represents $(R^{17})$ $(R^{18})N(R^{19})N$, or $R^2$ represents $R^{17}R^{18}C=N$—$(R^{19})N$— or or the ($R^{17}$ and $R^{18}$) or ($R^{17}$ and $R^{19}$) radicals form a ring with the heteroatom or the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1$-$C_6)$-alkyl, halo-$(C_1$-$C_6)$-alkyl, $(C_3$-$C_6)$-cycloalkyl, $(C_3$-$C_6)$-cycloalkenyl, $R^{10}O(O)C$, $(R^{10})_2N(O)C$, $R^{10}O$, $(R^{10})_2N$, $R^{11}(O)_nS$, $R^{10}O(O)_2S$, $(R^{10})_2N(O)_2S$ and $R^{10}O$—$(C_1$-$C_6)$-alkyl and oxo, $R^3$ represents cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methylsulfonyl, $R^4$, $R^5$, $R^6$ and $R^7$ each independently represent hydrogen, cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methyl sulfonyl, $R^8$ represents hydrogen, $(C_1$-$C_6)$-alkyl, $(C_3$-$C_6)$-cycloalkyl-$(C_1$-$C_6)$-alkyl, $(C_1$-$C_6)$-alkyl-O—$(C_1$-$C_6)$-alkyl, $(C_3$-$C_6)$-cycloalkyl-$(C_1$-$C_6)$-alkyl-O—$(C_1$-$C_6)$-alkyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl or heterocyclyl-O—$(C_1$-$C_6)$-alkyl, where the nine latter radicals are each substituted by m radicals from the group consisting of nitro, halogen, $(C_1$-$C_6)$-alkyl, halo-$(C_1$-$C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1$-$C_6)$-alkyl, and where heterocyclyl bears n oxo groups, or the two $R^8$ radicals form a ring with the heteroatom or the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of nitro, halogen, cyano, $(C_1$-$C_6)$-alkyl, halo-$(C_1$-$C_6)$-alkyl, $(C_3$-$C_6)$-cycloalkyl, $(C_3$-$C_6)$-cycloalkenyl, $R^{10}O(O)C$, $(R^{10})_2 N(O)C$, $R^{10}O(R^{10})_2N$, $R^{11}(O)_nS$, $R^{10}O(O)_2S$, $(R^{10})_2N (O)_2 S$ and $R^{10}O$—$(C_1$-$C_6)$-alkyl and oxo, $R^9$ represents $(C_1$-$C_6)$-alkyl, $(C_3$-$C_6)$-cycloalkyl-$(C_1$-$C_6)$-alkyl, $(C_1$-$C_6)$-alkyl-O—$(C_1$-$C_6)$-alkyl, $(C_3$-$C_6)$-cycloalkyl-$(C_1$-$C_6)$-alkyl-O—$(C_1$-$C_6)$-alkyl, phenyl, phenyl-$(C_1$-$C_6)$-alkyl, heteroaryl, heteroaryl-$(C_1$-$C_6)$-alkyl, heterocyclyl, heterocyclyl-$(C_1$-$C_6)$-alkyl, phenyl-O—$(C_1$-$C_6)$-alkyl, heteroaryl-O—$(C_1$-$C_6)$-alkyl or heterocyclyl-O—$(C_1$-$C_6)$-alkyl, where the nine latter radicals are each substituted by m radicals from the group consisting of nitro, halogen, $(C_1$-$C_6)$-alkyl, halo-$(C_1$-$C_6)$-alkyl, $R^{10}O(O)C$, $(R^{10})_2N(O)C$, $R^{10}O$, $(R^{10})_2N$, $R^{11}(O)_nS$ and $R^{10}O$—$(C_1$-$C_6)$-alkyl, and where heterocyclyl bears n oxo groups, $R^{10}$ represents hydrogen or $(C_1$-$C_6)$-alkyl, $R^{11}$ represents $(C_1$-$C_6)$-alkyl, $R^{12}$ represents $(C_1$-$C_4)$-alkyl, $R^{13}$ and $R^{14}$ each independently represent hydrogen, $(C_1$-$C_6)$-alkyl, cyano, $R^8O(O)C$ or $(R^8)_2N(O)C$, $R^{15}$ and $R^{16}$ each independently represent $(C_1$-$C_6)$-alkyl, phenyl, $(C_3$-$C_6)$-cycloalkyl, heteroaryl or heterocyclyl, $R^{17}$, $R^{18}$ and $R^{19}$ independently represent $R^8$ or $R^9S(O)_2$, $(R^8)_2NS(O)_2$, $R^8OS(O)_2$, $R^9C(O)$, $(R^8)_2NC(O)$, $(R^8)_2NC(S)$, $R^8OC(O)$, $R^8OC(O)C(O)$, $(R^8)_2NC(O)C(O)$, or the ($R^{17}$ and $R^{18}$) or ($R^{17}$ and $R^{19}$) radicals form a ring with the heteroatom or with the heteroatoms via which they are bonded, specifically a heterocyclyl, heterocyclenyl, heteroaryl, arylheterocyclyl, arylheterocyclenyl, heteroarylheterocyclyl, heteroarylheterocyclenyl, heterocyclylheteroaryl or heterocyclenylheteroaryl, where each of these rings in turn is substituted by m radicals from the group consisting of halogen, cyano, $(C_1$-$C_6)$-alkyl, halo-$(C_1$-$C_6)$-alkyl, $(C_3$-$C_6)$-cycloalkyl, $(C_3$-$C_6)$-cycloalkenyl, $R^{10}O(O)C$, $(R^{10})_2N(O)C$, $R^{10}O$, $(R^{10})_2N$, $R^{11}(O)_nS$, $R^{10}O (O)_2S$, $(R^{10})_2N(O)_2S$ and $R^{10}O$—$(C_1$-$C_6)$-alkyl and oxo, m represents 0, 1, 2 or 3, n represents 0, 1 or 2, s represents 0, 1, 2, 3, 4 or 5.

5. A compound as claimed in claim 1, wherein

X represents $CH_2$, $R^1$ represents cyclopropyl, where the cyclopropyl group is substituted by s radicals from the group consisting of halogen, ($C_1$-$C_6$)-alkyl and halo-($C_1$-$C_6$)-alkyl, $R^2$ represents hydroxy, ($C_1$-$C_6$)-alkoxy, ($C_1$-$C_6$)-haloalkoxy, ($C_2$-$C_6$)-alkenyloxy, ($C_2$-$C_6$)-haloalkenyloxy, ($C_2$-$C_6$)-alkynyloxy, $R^3$ represents cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methylsulfonyl, $R^4$, $R^5$, $R^6$ and $R^7$ each independently represent hydrogen, cyano, fluorine, chlorine, bromine, methyl, ethyl, trifluoromethyl, difluoromethyl, cyclopropyl, hydroxycarbonyl, methoxycarbonyl, ethoxycarbonyl, methoxy, ethoxy, methylsulfanyl, methylsulfinyl or methyl sulfonyl, m represents 0, 1, 2 or 3, n represents 0, 1 or 2, s represents 0, 1, 2, 3, 4 or 5.

6. An herbicidal composition comprising at least one compound as claimed in claim 1 mixed with one or more formulation auxiliaries.

7. The herbicidal composition as claimed in claim 6, comprising at least one pesticidally active substance from the group of insecticides, acaricides, herbicides, fungicides, safeners and growth regulators.

8. A method for controlling one or more unwanted plants, comprising applying an effective amount of at least one compound as claimed in claim 1 or of an herbicidal composition thereof to the plants and/or a site of unwanted vegetation.

9. A product comprising a compound as claimed in claim 1 or of an herbicidal composition thereof for controlling one or more unwanted plants.

10. The method as claimed in claim 8, wherein the compound is used for controlling one or more unwanted plants in one or more crops of one or more useful plants.

11. The method as claimed in claim 10, wherein the useful plants are transgenic useful plants.

* * * * *